US012433952B2

(12) United States Patent
Rich et al.

(10) Patent No.: US 12,433,952 B2
(45) Date of Patent: Oct. 7, 2025

(54) ANTIBODY-DRUG CONJUGATES TARGETING FOLATE RECEPTOR ALPHA AND METHODS OF USE

(71) Applicant: ZYMEWORKS BC INC., Vancouver (CA)

(72) Inventors: James R. Rich, Vancouver (CA); Stuart Daniel Barnscher, Vancouver (CA); Mark Edmund Petersen, Vancouver (CA); Raffaele Colombo, Vancouver (CA); Michael G. Brant, Vancouver (CA); Manuel Michel Auguste Lasalle, Vancouver (CA); Rupert H. Davies, Seattle, WA (US); Dunja Urosev, Vancouver (CA); Sukhbir Singh Kang, Vancouver (CA); Peter Wing Yiu Chan, Vancouver (CA); Samir Das, Vancouver (CA); Andrea Hernandez Rojas, Vancouver (CA); Robert William Gene, Vancouver (CA); Ada G. H. Young, Vancouver (CA); Samuel Oliver Lawn, Vancouver (CA); Danny Chui, Vancouver (CA); Duncan Browman, Vancouver (CA); Brandon Clavette, Vancouver (CA)

(73) Assignee: Zymeworks BC Inc., Vancouver (CA)

( * ) Notice: Subject to any disclaimer, the term of this patent is extended or adjusted under 35 U.S.C. 154(b) by 0 days.

(21) Appl. No.: 18/677,564

(22) Filed: May 29, 2024

(65) Prior Publication Data

US 2024/0424125 A1 Dec. 26, 2024

Related U.S. Application Data

(63) Continuation of application No. PCT/CA2023/050406, filed on Mar. 24, 2023.

(60) Provisional application No. 63/450,607, filed on Mar. 7, 2023, provisional application No. 63/417,250, filed on Oct. 18, 2022, provisional application No. 63/324,003, filed on Mar. 25, 2022.

(51) Int. Cl.

| | |
|---|---|
| *A61K 47/68* | (2017.01) |
| *A61P 35/00* | (2006.01) |
| *C07K 16/28* | (2006.01) |

(52) U.S. Cl.

CPC .... *A61K 47/68037* (2023.08); *A61K 47/6849* (2017.08); *A61K 47/6889* (2017.08); *A61P 35/00* (2018.01); *C07K 16/28* (2013.01)

(58) Field of Classification Search

None

See application file for complete search history.

(56) References Cited

U.S. PATENT DOCUMENTS

| | | | |
|---|---|---|---|
| 10,808,039 B2 | 10/2020 | Doronina et al. | |
| 2022/0133711 A1 | 5/2022 | Chari et al. | |
| 2024/0269309 A1 * | 8/2024 | Petersen ............ | A61K 47/6889 |

FOREIGN PATENT DOCUMENTS

| | | |
|---|---|---|
| CN | 110128501 A | 8/2019 |
| JP | 2002255821 A | 9/2002 |
| WO | 1995022549 A1 | 8/1995 |
| WO | 2012058768 A1 | 5/2012 |
| WO | 2013063702 A1 | 5/2013 |
| WO | 2018175994 A1 | 9/2018 |
| WO | 2019195665 A1 | 10/2019 |
| WO | 2019236954 A1 | 12/2019 |
| WO | 2020200880 A1 | 10/2020 |
| WO | 2020219287 A1 | 10/2020 |
| WO | 2021212638 A1 | 10/2021 |
| WO | 2022078524 A2 | 4/2022 |
| WO | 2022170971 A1 | 8/2022 |
| WO | 2022246576 A1 | 12/2022 |
| WO | 2023178451 A1 | 9/2023 |

OTHER PUBLICATIONS

Burke, Patrick J et al. "Design, synthesis, and biological evaluation of antibody-drug conjugates comprised of potent camptothecin analogues." Bioconjugate chemistry vol. 20,6 (2009): 1242-1250.

(Continued)

*Primary Examiner* — Phuong Huynh

(74) *Attorney, Agent, or Firm* — Goodwin Procter LLP

(57) ABSTRACT

Antibody-drug conjugates (ADCs) comprising an antibody construct that binds specifically binds human folate receptor alpha (FRα) (an anti-FRα antibody construct) conjugated to a camptothecin analogue of Formula (I). The ADCs are useful as therapeutics, in particular in the treatment of cancer.

(I)

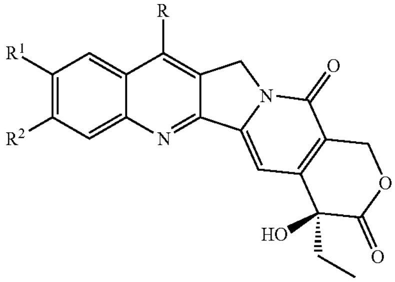

30 Claims, 63 Drawing Sheets

Specification includes a Sequence Listing.

(56) References Cited

OTHER PUBLICATIONS

Furuuchi, Keiji et al. "Antibody-drug conjugate MORAb-202 exhibits long-lasting antitumor efficacy in TNBC PDx models." Cancer science vol. 112,6 (2021): 2467-80.
Guiotto, Andrea et al. "Efficient and chemoselective N-acylation of 10-amino-7-ethyl camptothecin with poly (ethylene glycol)." Bioorganic & medicinal chemistry letters vol. 14,7 (2004): 1803-1805.
Guiotto, Andrea et al. "Synthesis, characterization, and preliminary in vivo tests of new poly(ethylene glycol) conjugates of the antitumor agent 10-amino-7-ethylcamptothecin." Journal of medicinal chemistry vol. 47,5 (2004): 1280-1289.
Heo, Young-A. "Mirvetuximab Soravtansine: First Approval." Drugs vol. 83,3 (2023): 265-73.
Li, Wei et al. "Synthesis and Evaluation of Camptothecin Antibody—Drug Conjugates." ACS medicinal chemistry letters vol. 10,10 (2019): 1386-92.
Li, X., et al., Abstract 1782: Discovery and activity of STRO-002, a novel ADC targeting folate receptor alpha for ovarian and endometrial cancer. Cancer Res Jul. 1, 2018; 78 (13_Supplement): 1782.
O'Shannessy, Daniel J et al. "Characterization of the human folate receptor alpha via novel antibody-based probes." Oncotarget vol. 2,12 (2011): 1227-43.
Song, Y-L., et al., Flexible Molecular Docking Studies of Antineoplastic Camptothecin Derivatives on DNA-topoisomerase I Complex. Acta Chimica Sinica, 2003; 61:1860-1866.
Wang, Yongjun et al. "Disulfide bond bridge insertion turns hydrophobic anticancer prodrugs into self-assembled nanomedicines." Nano letters vol. 14, 10 (2014): 5577-8.
Zhao, B., et al., Abstract 1085: PRO1184, a novel folate receptor alpha-directed antibody-drug conjugate, demonstrates robust antitumor activity in mouse carcinoma models. Cancer Res Jun. 15, 2022; 82 (12_Supplement): 1085.
"Topo1i ADC Platform: from concept to pipeline," World ADC Summit, London, UK, Mar. 31, 2022.
"Zymeworks Topoisomerase 1 Inhibitor ADC Platform: From Concept to Pipeline," PEGS Summit, Boston, MA, May 1, 2022.
"Topo1i ADC Platform: from concept to pipeline," Antibody Drug Conjugates, Digital Conference, Aug. 10, 2022.
"Zymeworks Topoisomerase 1 Inhibitor ADC Platform: From Concept to Pipeline," World ADC Summit, San Diego, CA, Sep. 9, 2022.
"Zymeworks Early Research & Development Day," New York Stock Exchange, NY, Oct. 20, 2022.
"Pairing Zymeworks' Topoisomerase 1-Inhibitor Linker-Payload with the Appropriate ADC Target, Antibody, and Indication," 2nd ADC Target Selection Summit, Boston, MA, Dec. 7, 2022.
"ZW191: A Potential Best-in-Class TOPO1i ADC for Treatment of FRa-Expressing Solid Tumors," World ADC Summit, London, UK, Mar. 15-16, 2023.
Furuuchi, K., et al., "Antibody-drug conjugate MORAb-202 exhibits long-lasting antitumor efficiacy in TNBC PDx models", Cancer Science, Jun. 2021, vol. 112, No. 6, pp. 2467-2480.
International Search Report and Written Opinion for PCT/CA2023/050405, 10 pages.
U.S. Appl. No. 18/850,293, Anti-Folate Receptor Alpha Antibodies and Methods of Use, filed Sep. 24, 2024.
U.S. Appl. No. 18/562,049, Camptothecin Analogues, Conjugates and Methods of Use, filed Nov. 17, 2023.

* cited by examiner

1A Heavy Chain

EVQLLESGGGLVQPGGSLRLSCAAS *GFSLSSYGVS* WVRQAPGKGLEWVS *AVNSGGSAY*
YADSVKGRFTISRDNSKNTLYLQMNSLRAEDTAVYYCAK *SGSGYPMDYLAI* WGQGTLVTVSS

FIG. 1A

1B Light Chain

DIQMTQSPSSLSASVGDRVTITC *QASQSIGDWLA* WYQQKPGKAPKLLIY *EASTLAS*
GVPSRFSGSGSGTDFTLTISSLQPEDFATYYC *QQGYGRSNVDNI* FGGGTKVEIK

FIG. 1B

OVCAR-3

Internalization 24 Hours 37C

OVCAR-3

Internalization 6 Hours 37C

```
         5          10         15         20         25         30         35         40         45         50
  1 RIAWA RTELL NVCMN AKHHK EKPGP EDKLH EQCRP WRKNA CCSTN TSQEA
         55         60         65         70         75         80         85         90         95        100
 51 HKDVS YLYRF NWNHC GEMAP ACKRH FIQDT CLYEC SPNLG PWIQQ VDQSW
        105        110        115        120        125        130        135        140        145        150
101 RKERV LNVPL CKEDC EQWWE DCRTS YTCKS NWHKG WNWTS GFNKC AVGAA
        155        160        165        170        175        180        185        190        195        200
151 CQPFH FYFPT PTVLC NEIWT HSYKV SNYSR GSGRC IQMWF DPAQG NPNEE
        205        210        215        220        225
201 VARFY AAAMG GGSGG GSHHH HHHHH HH
```

FIG. 7

CDR Sequences of Anti-FRα Antibodies

| Variant | Numbering System | Heavy Chain CDR | Sequence | SEQ ID NO | Light Chain CDR | Sequence | SEQ ID NO |
|---|---|---|---|---|---|---|---|
| v23924<br>v30618 | IMGT | HCDR1 | GFSLSSYG | 20 | LCDR1 | QSIGDW | 40 |
| | | HCDR2 | VNSGGSA | 21 | LCDR2 | EAS | 41 |
| | | HCDR3 | ARSGSGYPMDYLAI | 22 | LCDR3 | QQGYGRSNVDNI | 42 |
| | Chothia | HCDR1 | GFSLSSY | 23 | LCDR1 | QASQSIGDWLA | 43 |
| | | HCDR2 | NSGGS | 24 | LCDR2 | EASTLAS | 44 |
| | | HCDR3 | SGSGYPMDYLAI | 25 | LCDR3 | QQGYGRSNVDNI | 42 |
| | Kabat | HCDR1 | SYGVS | 26 | LCDR1 | QASQSIGDWLA | 43 |
| | | HCDR2 | AVNSGGSAYYANWAKS | 27 | LCDR2 | EASTLAS | 44 |
| | | HCDR3 | SGSGYPMDYLAI | 25 | LCDR3 | QQGYGRSNVDNI | 42 |
| | Contact | HCDR1 | SSYGVS | 28 | LCDR1 | GDWLAWY | 45 |
| | | HCDR2 | WIGAVNSGGSAY | 29 | LCDR2 | LLIYEASTLA | 46 |
| | | HCDR3 | ARSGSGYPMDYLA | 30 | LCDR3 | QQGYGRSNVDN | 47 |
| | AbM | HCDR1 | GFSLSSYGVS | 31 | LCDR1 | QASQSIGDWLA | 43 |
| | | HCDR2 | AVNSGGSAY | 32 | LCDR2 | EASTLAS | 44 |
| | | HCDR3 | SGSGYPMDYLAI | 25 | LCDR3 | QQGYGRSNVDNI | 42 |
| v30384<br>v30389<br>v31422<br>v31423<br>v31424<br>v31425<br>v31426<br>v36675 | IMGT | HCDR1 | GFSLSSYG | 20 | LCDR1 | QSIGDW | 40 |
| | | HCDR2 | VNSGGSA | 21 | LCDR2 | EAS | 41 |
| | | HCDR3 | ARSGSGYPMDYLAI | 22 | LCDR3 | QQGYGRSNVDNI | 42 |
| | Chothia | HCDR1 | GFSLSSY | 23 | LCDR1 | RASQSIGDWLA | 65 |
| | | HCDR2 | NSGGS | 24 | LCDR2 | EASTLAS | 44 |
| | | HCDR3 | SGSGYPMDYLAI | 25 | LCDR3 | QQGYGRSNVDNI | 42 |
| | Kabat | HCDR1 | SYGVS | 26 | LCDR1 | RASQSIGDWLA | 65 |
| | | HCDR2 | AVNSGGSAYYADSVKG | 51 | LCDR2 | EASTLAS | 44 |
| | | HCDR3 | SGSGYPMDYLAI | 25 | LCDR3 | QQGYGRSNVDNI | 42 |
| | Contact | HCDR1 | SSYGVS | 28 | LCDR1 | GDWLAWY | 45 |
| | | HCDR2 | WIGAVNSGGSAY | 29 | LCDR2 | LLIYEASTLA | 46 |
| | | HCDR3 | ARSGSGYPMDYLA | 30 | LCDR3 | QQGYGRSNVDN | 47 |
| | AbM | HCDR1 | GFSLSSYGVS | 31 | LCDR1 | RASQSIGDWLA | 65 |

FIG.11

| Variant | Numbering System | Heavy Chain CDR | Sequence | SEQ ID NO | Light Chain CDR | Sequence | SEQ ID NO |
|---|---|---|---|---|---|---|---|
| | | HCDR2 | AVNSGGSAY | 32 | LCDR2 | EASTLAS | 44 |
| | | HCDR3 | SGSGYPMDYLAI | 25 | LCDR3 | QQGYGRSNVDNI | 42 |
| v30394 v30399 | IMGT | HCDR1 | GFSLSSYG | 20 | LCDR1 | QSIGDW | 40 |
| | | HCDR2 | VNSGGSA | 21 | LCDR2 | EAS | 41 |
| | | HCDR3 | ARSGSGYPMDYLAI | 22 | LCDR3 | QQGYGRSNVDNI | 42 |
| | Chothia | HCDR1 | GFSLSSY | 23 | LCDR1 | RASQSIGDWLA | 65 |
| | | HCDR2 | NSGGS | 24 | LCDR2 | EASTLAS | 44 |
| | | HCDR3 | SGSGYPMDYLAI | 25 | LCDR3 | QQGYGRSNVDNI | 42 |
| | Kabat | HCDR1 | SYGVS | 26 | LCDR1 | RASQSIGDWLA | 65 |
| | | HCDR2 | AVNSGGSAYYADWAKG | 58 | LCDR2 | EASTLAS | 44 |
| | | HCDR3 | SGSGYPMDYLAI | 25 | LCDR3 | QQGYGRSNVDNI | 42 |
| | Contact | HCDR1 | SSYGVS | 28 | LCDR1 | GDWLAWY | 45 |
| | | HCDR2 | WIGAVNSGGSAY | 29 | LCDR2 | LLIYEASTLA | 46 |
| | | HCDR3 | ARSGSGYPMDYLA | 30 | LCDR3 | QQGYGRSNVDN | 47 |
| | AbM | HCDR1 | GFSLSSYGVS | 31 | LCDR1 | RASQSIGDWLA | 65 |
| | | HCDR2 | AVNSGGSAY | 32 | LCDR2 | EASTLAS | 44 |
| | | HCDR3 | SGSGYPMDYLAI | 25 | LCDR3 | QQGYGRSNVDNI | 42 |
| v35305 | IMGT | HCDR1 | GFSLSLYG | 92 | LCDR1 | QSIWYW | 125 |
| | | HCDR2 | VNSGGSA | 21 | LCDR2 | EAS | 41 |
| | | HCDR3 | ARSGSGYPMDYLAI | 22 | LCDR3 | QQGYGRSNVDNI | 42 |
| | Chothia | HCDR1 | GFSLSLY | 93 | LCDR1 | RASQSIWYWLA | 126 |
| | | HCDR2 | NSGGS | 24 | LCDR2 | EASTLAS | 44 |
| | | HCDR3 | SGSGYPMDYLAI | 25 | LCDR3 | QQGYGRSNVDNI | 42 |
| | Kabat | HCDR1 | LYGVS | 94 | LCDR1 | RASQSIWYWLA | 126 |
| | | HCDR2 | AVNSGGSAYYADSVKG | 51 | LCDR2 | EASTLAS | 44 |
| | | HCDR3 | SGSGYPMDYLAI | 25 | LCDR3 | QQGYGRSNVDNI | 42 |
| | Contact | HCDR1 | SLYGVS | 95 | LCDR1 | WYWLAWY | 127 |
| | | HCDR2 | WIGAVNSGGSAY | 29 | LCDR2 | LLIYEASTLA | 46 |
| | | HCDR3 | ARSGSGYPMDYLA | 30 | LCDR3 | QQGYGRSNVDN | 47 |

FIG. 11 (cont.)

| Variant | Numbering System | Heavy Chain CDR | Sequence | SEQ ID NO | Light Chain CDR | Sequence | SEQ ID NO |
|---|---|---|---|---|---|---|---|
| | AbM | HCDR1 | GFSLSLYGVS | 96 | LCDR1 | RASQSIWYWLA | 126 |
| | | HCDR2 | AVNSGGSAY | 32 | LCDR2 | EASTLAS | 44 |
| | | HCDR3 | SGSGYPMDYLAI | 25 | LCDR3 | QQGYGRSNVDNI | 42 |
| v35342 | IMGT | HCDR1 | GFSLSLYG | 92 | LCDR1 | QSIWYW | 125 |
| | | HCDR2 | LNSGGSA | 100 | LCDR2 | EAS | 41 |
| | | HCDR3 | ARSGSGYPMDYLAI | 22 | LCDR3 | QQGYGRWHILNI | 120 |
| | Chothia | HCDR1 | GFSLSLY | 93 | LCDR1 | RASQSIWYWLA | 126 |
| | | HCDR2 | NSGGS | 24 | LCDR2 | EASTLAS | 44 |
| | | HCDR3 | SGSGYPMDYLAI | 25 | LCDR3 | QQGYGRWHILNI | 120 |
| | Kabat | HCDR1 | LYGVS | 94 | LCDR1 | RASQSIWYWLA | 126 |
| | | HCDR2 | SLNSGGSAYYADSVKG | 101 | LCDR2 | EASTLAS | 44 |
| | | HCDR3 | SGSGYPMDYLAI | 25 | LCDR3 | QQGYGRWHILNI | 120 |
| | Contact | HCDR1 | SLYGVS | 95 | LCDR1 | WYWLAWY | 127 |
| | | HCDR2 | WIGSLNSGGSAY | 102 | LCDR2 | LLIYEASTLA | 46 |
| | | HCDR3 | ARSGSGYPMDYLA | 30 | LCDR3 | QQGYGRWHILN | 121 |
| | AbM | HCDR1 | GFSLSLYGVS | 96 | LCDR1 | RASQSIWYWLA | 126 |
| | | HCDR2 | SLNSGGSAY | 103 | LCDR2 | EASTLAS | 44 |
| | | HCDR3 | SGSGYPMDYLAI | 25 | LCDR3 | QQGYGRWHILNI | 120 |
| v35347 | IMGT | HCDR1 | GFSLSLYG | 92 | LCDR1 | QSIGDW | 40 |
| | | HCDR2 | VNSGGSA | 21 | LCDR2 | EAS | 41 |
| | | HCDR3 | ARSGSGYPMDYHPI | 107 | LCDR3 | QQGYGRSNVDNI | 42 |
| | Chothia | HCDR1 | GFSLSLY | 93 | LCDR1 | RASQSIGDWLA | 65 |
| | | HCDR2 | NSGGS | 24 | LCDR2 | EASTLAS | 44 |
| | | HCDR3 | SGSGYPMDYHPI | 108 | LCDR3 | QQGYGRSNVDNI | 42 |
| | Kabat | HCDR1 | LYGVS | 94 | LCDR1 | RASQSIGDWLA | 65 |
| | | HCDR2 | AVNSGGSAYYADSFKG | 109 | LCDR2 | EASTLAS | 44 |
| | | HCDR3 | SGSGYPMDYHPI | 108 | LCDR3 | QQGYGRSNVDNI | 42 |
| | Contact | HCDR1 | SLYGVS | 95 | LCDR1 | GDWLAWY | 45 |
| | | HCDR2 | WIGAVNSGGSAY | 29 | LCDR2 | LLIYEASTLA | 46 |

FIG. 11 (cont.)

| Variant | Numbering System | Heavy Chain CDR | Sequence | SEQ ID NO | Light Chain CDR | Sequence | SEQ ID NO |
|---|---|---|---|---|---|---|---|
| | | HCDR3 | ARSGSGYPMDYHP | 110 | LCDR3 | QQGYGRSNVDN | 47 |
| | AbM | HCDR1 | GFSLSLYGVS | 96 | LCDR1 | RASQSIGDWLA | 65 |
| | | HCDR2 | AVNSGGSAY | 32 | LCDR2 | EASTLAS | 44 |
| | | HCDR3 | SGSGYPMDYHPI | 108 | LCDR3 | QQGYGRSNVDNI | 42 |
| v35348 | IMGT | HCDR1 | GFSLSLYG | 92 | LCDR1 | QSIGDW | 40 |
| | | HCDR2 | VNSGGSA | 21 | LCDR2 | EAS | 41 |
| | | HCDR3 | ARSGSGYPMDYHPI | 107 | LCDR3 | QQGYGRWHILNI | 120 |
| | Chothia | HCDR1 | GFSLSLY | 93 | LCDR1 | RASQSIGDWLA | 65 |
| | | HCDR2 | NSGGS | 24 | LCDR2 | EASTLAS | 44 |
| | | HCDR3 | SGSGYPMDYHPI | 108 | LCDR3 | QQGYGRWHILNI | 120 |
| | Kabat | HCDR1 | LYGVS | 94 | LCDR1 | RASQSIGDWLA | 65 |
| | | HCDR2 | AVNSGGSAYYADSFKG | 109 | LCDR2 | EASTLAS | 44 |
| | | HCDR3 | SGSGYPMDYHPI | 108 | LCDR3 | QQGYGRWHILNI | 120 |
| | Contact | HCDR1 | SLYGVS | 95 | LCDR1 | GDWLAWY | 45 |
| | | HCDR2 | WIGAVNSGGSAY | 29 | LCDR2 | LLIYEASTLA | 46 |
| | | HCDR3 | ARSGSGYPMDYHP | 110 | LCDR3 | QQGYGRWHILN | 121 |
| | AbM | HCDR1 | GFSLSLYGVS | 96 | LCDR1 | RASQSIGDWLA | 65 |
| | | HCDR2 | AVNSGGSAY | 32 | LCDR2 | EASTLAS | 44 |
| | | HCDR3 | SGSGYPMDYHPI | 108 | LCDR3 | QQGYGRWHILNI | 120 |
| v35350 | IMGT | HCDR1 | GFSLSLYG | 92 | LCDR1 | QSIWYW | 125 |
| | | HCDR2 | VNSGGSA | 21 | LCDR2 | EAS | 41 |
| | | HCDR3 | ARSGSGYPMDYHPI | 107 | LCDR3 | QQGYGRWHILNI | 120 |
| | Chothia | HCDR1 | GFSLSLY | 93 | LCDR1 | RASQSIWYWLA | 126 |
| | | HCDR2 | NSGGS | 24 | LCDR2 | EASTLAS | 44 |
| | | HCDR3 | SGSGYPMDYHPI | 108 | LCDR3 | QQGYGRWHILNI | 120 |
| | Kabat | HCDR1 | LYGVS | 94 | LCDR1 | RASQSIWYWLA | 126 |
| | | HCDR2 | AVNSGGSAYYADSFKG | 109 | LCDR2 | EASTLAS | 44 |
| | | HCDR3 | SGSGYPMDYHPI | 108 | LCDR3 | QQGYGRWHILNI | 120 |
| | Contact | HCDR1 | SLYGVS | 95 | LCDR1 | WYWLAWY | 127 |

FIG. 11 (cont.)

| Variant | Numbering System | Heavy Chain CDR | Sequence | SEQ ID NO | Light Chain CDR | Sequence | SEQ ID NO |
|---|---|---|---|---|---|---|---|
| | | HCDR2 | WIGAVNSGGSAY | 29 | LCDR2 | LLIYEASTLA | 46 |
| | | HCDR3 | ARSGSGYPMDYHP | 110 | LCDR3 | QQGYGRWHILN | 121 |
| | AbM | HCDR1 | GFSLSLYGVS | 96 | LCDR1 | RASQSIWYWLA | 126 |
| | | HCDR2 | AVNSGGSAY | 32 | LCDR2 | EASTLAS | 44 |
| | | HCDR3 | SGSGYPMDYHPI | 108 | LCDR3 | QQGYGRWHILNI | 120 |
| v35354 | IMGT | HCDR1 | GFSLSLYG | 92 | LCDR1 | QSIWYW | 125 |
| | | HCDR2 | VNSGGSA | 21 | LCDR2 | EAS | 41 |
| | | HCDR3 | ARSGSGYPMDYLAI | 22 | LCDR3 | QQGYGRWHILNI | 120 |
| | Chothia | HCDR1 | GFSLSLY | 93 | LCDR1 | RASQSIWYWLA | 126 |
| | | HCDR2 | NSGGS | 24 | LCDR2 | EASTLAS | 44 |
| | | HCDR3 | SGSGYPMDYLAI | 25 | LCDR3 | QQGYGRWHILNI | 120 |
| | Kabat | HCDR1 | LYGVS | 94 | LCDR1 | RASQSIWYWLA | 126 |
| | | HCDR2 | AVNSGGSAYYADSFKG | 109 | LCDR2 | EASTLAS | 44 |
| | | HCDR3 | SGSGYPMDYLAI | 25 | LCDR3 | QQGYGRWHILNI | 120 |
| | Contact | HCDR1 | SLYGVS | 95 | LCDR1 | WYWLAWY | 127 |
| | | HCDR2 | WIGAVNSGGSAY | 29 | LCDR2 | LLIYEASTLA | 46 |
| | | HCDR3 | ARSGSGYPMDYLA | 30 | LCDR3 | QQGYGRWHILN | 121 |
| | AbM | HCDR1 | GFSLSLYGVS | 96 | LCDR1 | RASQSIWYWLA | 126 |
| | | HCDR2 | AVNSGGSAY | 32 | LCDR2 | EASTLAS | 44 |
| | | HCDR3 | SGSGYPMDYLAI | 25 | LCDR3 | QQGYGRWHILNI | 120 |
| v35356 | IMGT | HCDR1 | GFSLSSYG | 20 | LCDR1 | QSIGDW | 40 |
| | | HCDR2 | VNSGGSA | 21 | LCDR2 | EAS | 41 |
| | | HCDR3 | ARSGSGYPMDYHPI | 107 | LCDR3 | QQGYGRWHILNI | 120 |
| | Chothia | HCDR1 | GFSLSSY | 23 | LCDR1 | RASQSIGDWLA | 65 |
| | | HCDR2 | NSGGS | 24 | LCDR2 | EASTLAS | 44 |
| | | HCDR3 | SGSGYPMDYHPI | 108 | LCDR3 | QQGYGRWHILNI | 120 |
| | Kabat | HCDR1 | SYGVS | 26 | LCDR1 | RASQSIGDWLA | 65 |
| | | HCDR2 | AVNSGGSAYYADSFKG | 109 | LCDR2 | EASTLAS | 44 |
| | | HCDR3 | SGSGYPMDYHPI | 108 | LCDR3 | QQGYGRWHILNI | 120 |

FIG. 11 (cont.)

| Variant | Numbering System | Heavy Chain CDR | Sequence | SEQ ID NO | Light Chain CDR | Sequence | SEQ ID NO |
|---|---|---|---|---|---|---|---|
| | Contact | HCDR1 | SSYGVS | 28 | LCDR1 | GDWLAWY | 45 |
| | | HCDR2 | WIGAVNSGGSAY | 29 | LCDR2 | LLIYEASTLA | 46 |
| | | HCDR3 | ARSGSGYPMDYHP | 110 | LCDR3 | QQGYGRWHILN | 121 |
| | AbM | HCDR1 | GFSLSSYGVS | 31 | LCDR1 | RASQSIGDWLA | 65 |
| | | HCDR2 | AVNSGGSAY | 32 | LCDR2 | EASTLAS | 44 |
| | | HCDR3 | SGSGYPMDYHPI | 108 | LCDR3 | QQGYGRWHILNI | 120 |
| v35358 | IMGT | HCDR1 | GFSLSSYG | 20 | LCDR1 | QSIWYW | 125 |
| | | HCDR2 | VNSGGSA | 21 | LCDR2 | EAS | 41 |
| | | HCDR3 | ARSGSGYPMDYHPI | 107 | LCDR3 | QQGYGRWHILNI | 120 |
| | Chothia | HCDR1 | GFSLSSY | 23 | LCDR1 | RASQSIWYWLA | 126 |
| | | HCDR2 | NSGGS | 24 | LCDR2 | EASTLAS | 44 |
| | | HCDR3 | SGSGYPMDYHPI | 108 | LCDR3 | QQGYGRWHILNI | 120 |
| | Kabat | HCDR1 | SYGVS | 26 | LCDR1 | RASQSIWYWLA | 126 |
| | | HCDR2 | AVNSGGSAYYADSFKG | 109 | LCDR2 | EASTLAS | 44 |
| | | HCDR3 | SGSGYPMDYHPI | 108 | LCDR3 | QQGYGRWHILNI | 120 |
| | Contact | HCDR1 | SSYGVS | 28 | LCDR1 | WYWLAWY | 127 |
| | | HCDR2 | WIGAVNSGGSAY | 29 | LCDR2 | LLIYEASTLA | 46 |
| | | HCDR3 | ARSGSGYPMDYHP | 110 | LCDR3 | QQGYGRWHILN | 121 |
| | AbM | HCDR1 | GFSLSSYGVS | 31 | LCDR1 | RASQSIWYWLA | 126 |
| | | HCDR2 | AVNSGGSAY | 32 | LCDR2 | EASTLAS | 44 |
| | | HCDR3 | SGSGYPMDYHPI | 108 | LCDR3 | QQGYGRWHILNI | 120 |
| v36167 | IMGT | HCDR1 | GFSLSSYG | 20 | LCDR1 | QSIWYW | 125 |
| | | HCDR2 | VNSGGSA | 21 | LCDR2 | EAS | 41 |
| | | HCDR3 | ARSGSGYPMDYLAI | 22 | LCDR3 | QQGYGRWHILNI | 120 |
| | Chothia | HCDR1 | GFSLSSY | 23 | LCDR1 | RASQSIWYWLA | 126 |
| | | HCDR2 | NSGGS | 24 | LCDR2 | EASTLAS | 44 |
| | | HCDR3 | SGSGYPMDYLAI | 25 | LCDR3 | QQGYGRWHILNI | 120 |
| | Kabat | HCDR1 | SYGVS | 26 | LCDR1 | RASQSIWYWLA | 126 |
| | | HCDR2 | AVNSGGSAYYADSFKG | 109 | LCDR2 | EASTLAS | 44 |

FIG. 11 (cont.)

| Variant | Numbering System | Heavy Chain CDR | Sequence | SEQ ID NO | Light Chain CDR | Sequence | SEQ ID NO |
|---|---|---|---|---|---|---|---|
| | | HCDR3 | SGSGYPMDYLAI | 25 | LCDR3 | QQGYGRWHILNI | 120 |
| | Contact | HCDR1 | SSYGVS | 28 | LCDR1 | WYWLAWY | 127 |
| | | HCDR2 | WIGAVNSGGSAY | 29 | LCDR2 | LLIYEASTLA | 46 |
| | | HCDR3 | ARSGSGYPMDYLA | 30 | LCDR3 | QQGYGRWHILN | 121 |
| | AbM | HCDR1 | GFSLSSYGVS | 31 | LCDR1 | RASQSIWYWLA | 126 |
| | | HCDR2 | AVNSGGSAY | 32 | LCDR2 | EASTLAS | 44 |
| | | HCDR3 | SGSGYPMDYLAI | 25 | LCDR3 | QQGYGRWHILNI | 120 |
| v36168 | IMGT | HCDR1 | GFSLSLYG | 92 | LCDR1 | QSIWYW | 125 |
| | | HCDR2 | VNSGGSA | 21 | LCDR2 | EAS | 41 |
| | | HCDR3 | ARSGSGYPMDYLAI | 22 | LCDR3 | QQGYGRWHILNI | 120 |
| | Chothia | HCDR1 | GFSLSLY | 93 | LCDR1 | RASQSIWYWLA | 126 |
| | | HCDR2 | NSGGS | 24 | LCDR2 | EASTLAS | 44 |
| | | HCDR3 | SGSGYPMDYLAI | 25 | LCDR3 | QQGYGRWHILNI | 120 |
| | Kabat | HCDR1 | LYGVS | 94 | LCDR1 | RASQSIWYWLA | 126 |
| | | HCDR2 | SVNSGGSAYYADSVKG | 137 | LCDR2 | EASTLAS | 44 |
| | | HCDR3 | SGSGYPMDYLAI | 25 | LCDR3 | QQGYGRWHILNI | 120 |
| | Contact | HCDR1 | SLYGVS | 95 | LCDR1 | WYWLAWY | 127 |
| | | HCDR2 | WIGSVNSGGSAY | 138 | LCDR2 | LLIYEASTLA | 46 |
| | | HCDR3 | ARSGSGYPMDYLA | 30 | LCDR3 | QQGYGRWHILN | 121 |
| | AbM | HCDR1 | GFSLSLYGVS | 96 | LCDR1 | RASQSIWYWLA | 126 |
| | | HCDR2 | SVNSGGSAY | 139 | LCDR2 | EASTLAS | 44 |
| | | HCDR3 | SGSGYPMDYLAI | 25 | LCDR3 | QQGYGRWHILNI | 120 |

FIG. 11 (cont.)

VH and VL Sequences of Anti-FRα Antibodies

| Variant | Region | Sequence | SEQ ID NO |
|---|---|---|---|
| v23924 v30618 | VH | QSVKESEGGLFKPTDTLTLTCTVSGFSLSSYGVSWVRQAPGNGLEWIGAVNSGGSAYYANWAKSRSTITRNTNLFTVTLKMTSLAVADTATYFCARSGSGYPMDYLAIWGPGTLVTVSS | 19 |
| v30384 v36675 | VH | EVQLLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSS | 50 |
| v30389 | VH | EVQVLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSS | 54 |
| v30394 | VH | EVQLLESGGGLVQPGGSLRLSCAVSGFSLSSYGVSWVRQAPGKGLEWIGAVNSGGSAYYADWAKGRSTISRDNSKNTVYLQMNSLRAEDTAVYYCARSGSGYPMDYLAIWGQGTLVTVSS | 57 |
| v30399 | VH | EVQVLESGGGLVQPGGSLRLSCAVSGFSLSSYGVSWVRQAPGKGLEWIGAVNSGGSAYYADWAKGRSTISRDNSKNTVYLQMNSLRAEDTAVYYCARSGSGYPMDYLAIWGQGTLVTVSS | 61 |
| v31422 | VH | EVQLLESGGGLFQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSS | 76 |
| v31423 | VH | EVQLLESGGGLVQPGGSLRLSCAVSGFSLSSYGVSWVRQAPGKGLEWIGAVNSGGSAYYADSVKGRSTISRDTSKNTVYLQMNSLRAEDTAVYYCARSGSGYPMDYLAIWGQGTLVTVSS | 79 |
| v31424 | VH | EVQLLESGGGLVQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSS | 82 |
| v31425 | VH | EVQLLESGGGLFQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSS | 85 |
| v31426 | VH | QQLLESGGGLFQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSS | 88 |
| v35305 | VH | EVQLLESGGGLVQPGGSLRLSCAVSGFSLSLYGVSWVRQAPGKGLEWIGAVNSGGSAYYADSVKGRSTISRDNSKNTVYLQMNSLRAEDTAVYYCARSGSGYPMDYLAIWGQGTLVTVSS | 91 |

FIG. 12

| Variant | Region | Sequence | SEQ ID NO |
|---|---|---|---|
| v35342 | VH | EVQLLESGGGLVQPGGSLRLSCAVSGFSLSLYGVSWVRQAPGKGLEWIGSLNSGGSAYYADSVKGRSTISRDNSKNTVYLQMNSLRAEDTAVYYCARSGSGYPMDYLAIWGQGTLVTVSS | 99 |
| v35347<br>v35348<br>v35350 | VH | EVQLLESGGGLVQPGGSLRLSCAVSGFSLSLYGVSWVRQAPGKGLEWIGAVNSGGSAYYADSFKGRSTISRDNSKNTVYLQMNSLRAEDTAVYYCARSGSGYPMDYHPIWGQGTLVTVSS | 106 |
| v35354 | VH | EVQLLESGGGLVQPGGSLRLSCAVSGFSLSLYGVSWVRQAPGKGLEWIGAVNSGGSAYYADSFKGRSTISRDNSKNTVYLQMNSLRAEDTAVYYCARSGSGYPMDYLAIWGQGTLVTVSS | 113 |
| v35356<br>v35358 | VH | EVQLLESGGGLVQPGGSLRLSCAVSGFSLSSYGVSWVRQAPGKGLEWIGAVNSGGSAYYADSFKGRSTISRDNSKNTVYLQMNSLRAEDTAVYYCARSGSGYPMDYHPIWGQGTLVTVSS | 116 |
| v36167 | VH | EVQLLESGGGLVQPGGSLRLSCAVSGFSLSSYGVSWVRQAPGKGLEWIGAVNSGGSAYYADSFKGRSTISRDNSKNTVYLQMNSLRAEDTAVYYCARSGSGYPMDYLAIWGQGTLVTVSS | 133 |
| v36168 | VH | EVQLLESGGGLVQPGGSLRLSCAVSGFSLSLYGVSWVRQAPGKGLEWIGSVNSGGSAYYADSVKGRSTISRDNSKNTVYLQMNSLRAEDTAVYYCARSGSGYPMDYLAIWGQGTLVTVSS | 136 |
| v23924<br>v30618 | VL | AYDMTQTPASVEVAVGGTVTIKCQASQSIGDWLAWYQQKPGQPPRLLIYEASTLASGVPSRFSGSGSGTQFTLTISGVECADAATYYCQQGYGRSNVDNIFGGGTEVVVK | 39 |
| v30384<br>v30389<br>v30394<br>v30399<br>v31422<br>v31423<br>v31424<br>v31425<br>v31426<br>v35347<br>v36675 | VL | DYQMTQSPSSVSASVGDRVTITCRASQSIGDWLAWYQQKPGKAPKLLIYEASTLASGVPSRFSGSGSGTDFTLTISSVQPEDAATYYCQQGYGRSNVDNIFGGGTKVEVK | 64 |
| v35348<br>v35356 | VL | DYQMTQSPSSVSASVGDRVTITCRASQSIGDWLAWYQQKPGKAPKLLIYEASTLASGVPSRFSGSGSGTDFTLTISSVQPEDAATYYCQQGYGRWHILNIFGGGTKVEVK | 119 |

FIG.12 (cont.)

| Variant | Region | Sequence | SEQ ID NO |
|---|---|---|---|
| v35305 | VL | DYQMTQSPSSVSASVGDRVTITCRASQSIWYWLAWYQQKPGKAPKLLIYEASTLASGVPSRFSGSGSGTDFTLTISSVQPEDAATYYCQQGYGRSNVDNIFGGGTKVEVK | 124 |
| v35342<br>v35350<br>v35354<br>v35358<br>v36167<br>v36168 | VL | DYQMTQSPSSVSASVGDRVTITCRASQSIWYWLAWYQQKPGKAPKLLIYEASTLASGVPSRFSGSGSGTDFTLTISSVQPEDAATYYCQQGYGRWHILNIFGGGTKVEVK | 130 |

FIG. 12 (cont.)

Table 8
| Name | Structure |
|---|---|
| **DL:** MT-GGFG-Compound 104 | 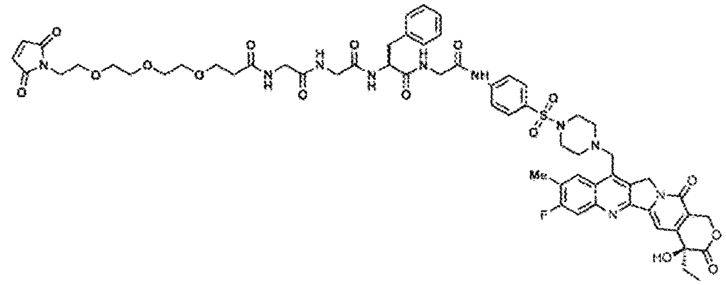 |
| **DL:** MT-GGFG-Compound 108 | 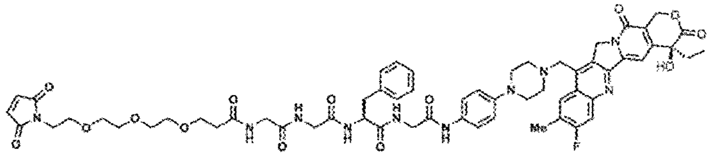 |
| **DL:** MT-GGFG-Compound 127 | 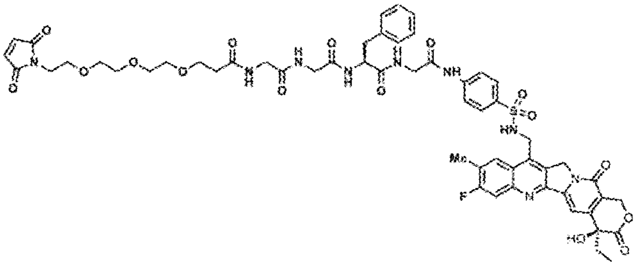 |
| **DL:** MT-GGFG-AM-Compound 136 | 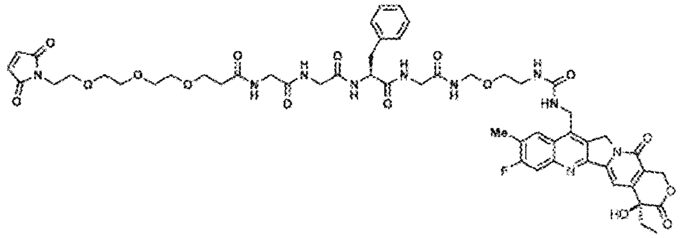 |
FIG. 13

Table 8 (cont.)
| Name | Structure |
|---|---|
| **DL:** MT-GGFG-AM-Compound 139 | 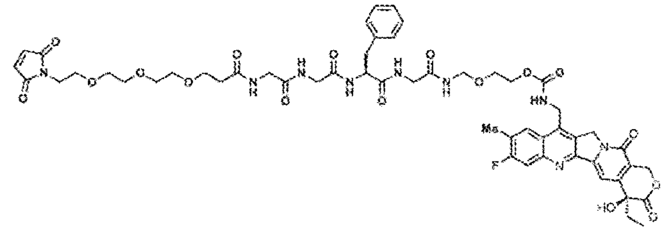 |
| **DL:** MT-GGFG-AM-Compound 129 | 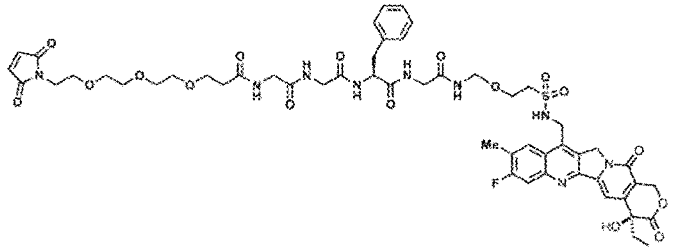 |
| **DL:** MT-GGFG-AM-Compound 113 | 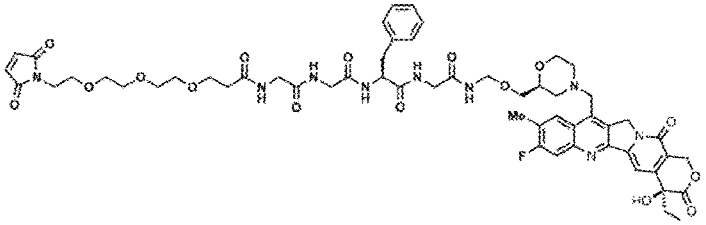 |
| **DL:** MT-GGFG-AM-Compound 141 | 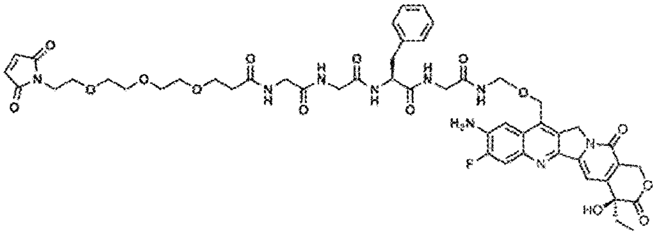 |
FIG. 13 (cont.)

Table 8 (cont.)
| Name | Structure |
|---|---|
| **DL:** MC-GGFG-AM-Compound 141 | 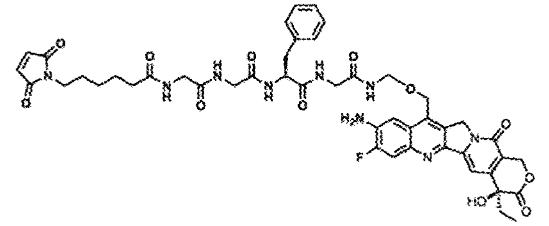 |
| **DL:** MT-GGFG-AM-Compound 117 | 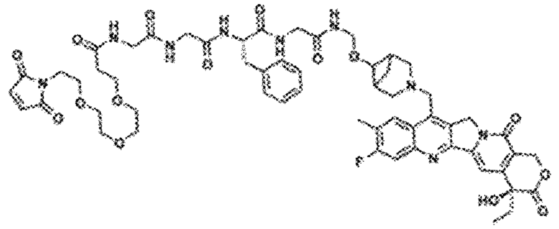 |
| **DL:** MT-GGFG-AM-Compound 118 | 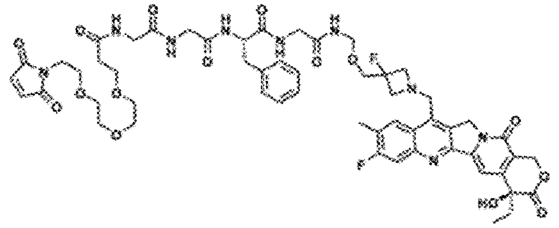 |
| **DL:** MC-GGFG-AM-Compound 139 | 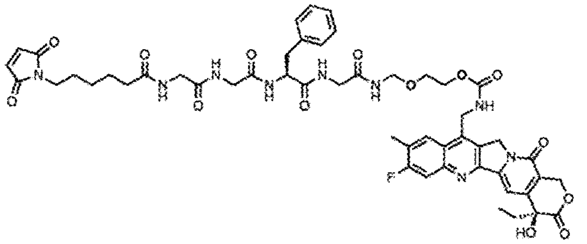 |
| **DL:** DiS-Compound 145 | 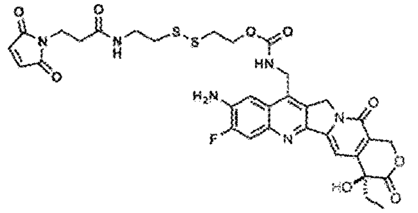 |
FIG. 13 (cont.)

Table 9
| Name | Structure |
|---|---|
| **DL:** MT-GGFG-Compound 140 | 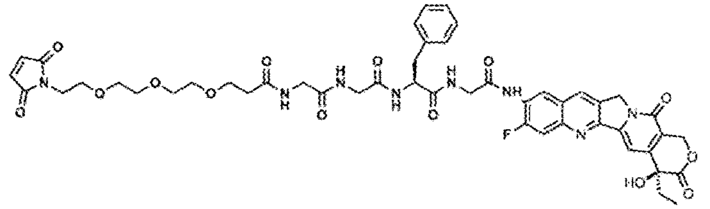 |
| **DL:** MT-GGFG-Compound 141 | 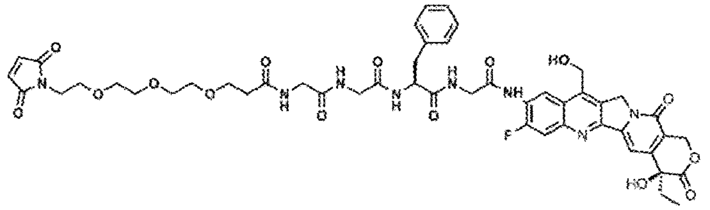 |
| **DL:** MT-GGFG-Compound 145 | 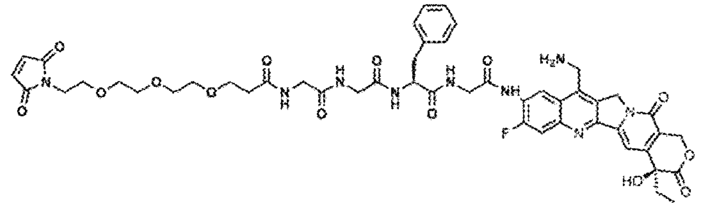 |
| **DL:** MT-GGFG-Compound 148 | 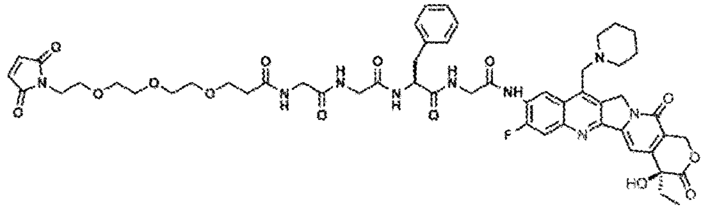 |
| **DL:** MC-GGFG-Compound 140 | 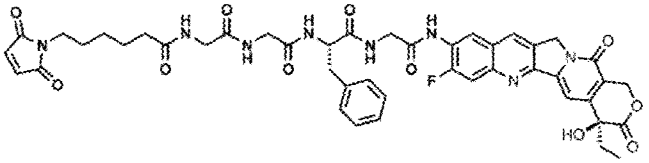 |
FIG. 14

Table 9 (cont.)
| Name | Structure |
|---|---|
| **DL:** MT-GGFG-Compound 142 | 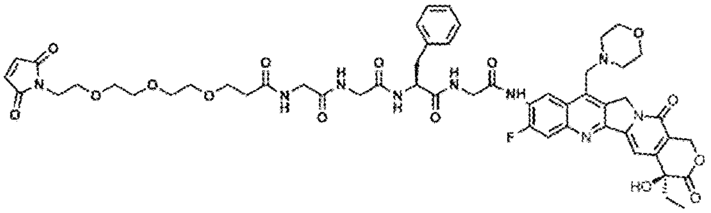 |
| **DL:** MC-GGFG-Compound 141 | 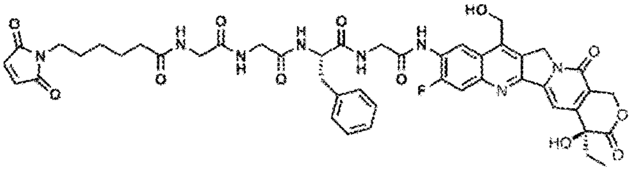 |
| **DL:** MC-VA-Compound 140 (DL: 201) | 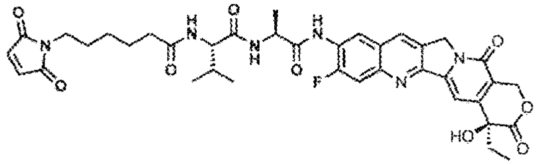 |
| **DL:** NHC-C-VA-Compound 140 | 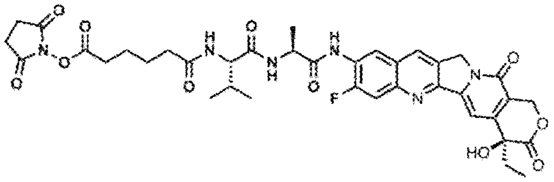 |
| **DL:** Azido-PEG8-VA-Compound 140 | 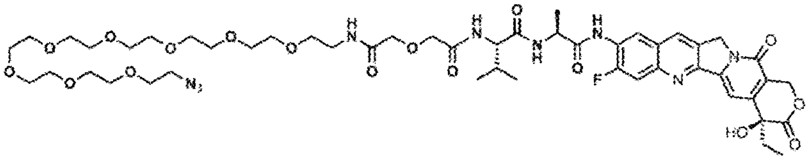 |
FIG. 14 (cont.)

Table 10
| Name | Structure |
|---|---|
| DL: 200 | 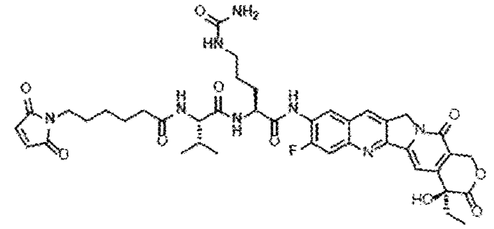 |
| DL: 202 | 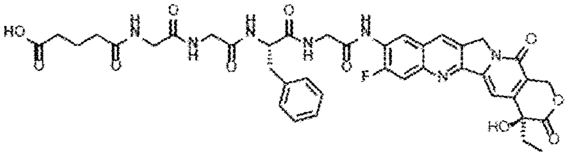 |
| DL: 203 | 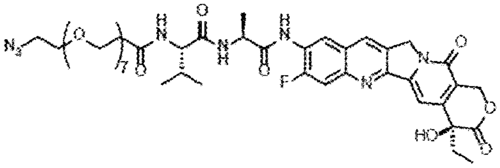 |
| DL: 204 | 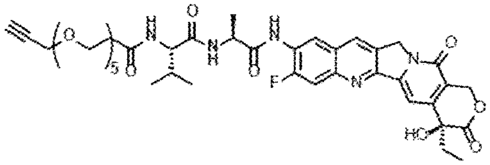 |
FIG. 15

Table 10 (cont.)
| Name | Structure |
|---|---|
| DL: 205 | 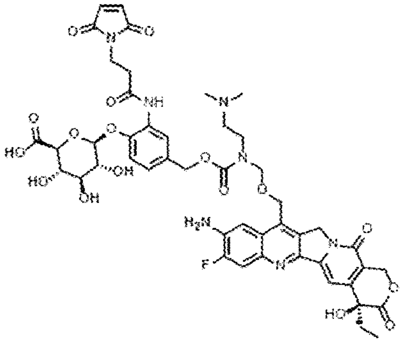 |
| DL: 206 | 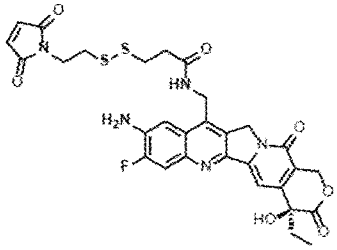 |
| DL: 207 | 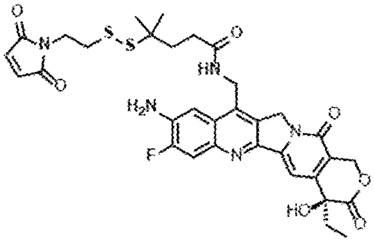 |
| DL: 208 | 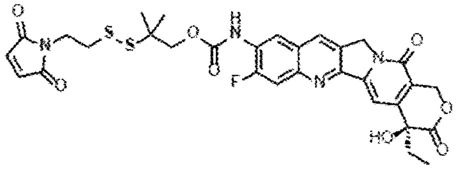 |
FIG. 15 (cont.)

Table 10 (cont.)
| Name | Structure |
| --- | --- |
| DL: 209 | 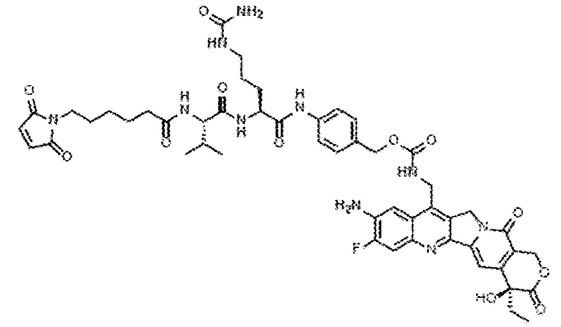 |
| DL: 210 | 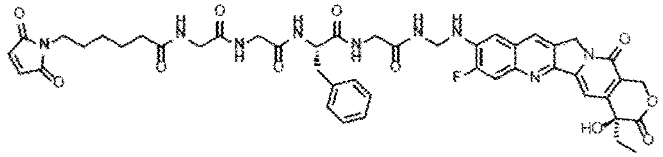 |
FIG. 15 (cont.)

Table 11
| Name | Structure |
| --- | --- |
| **DC:** MT-GGFG-Compound 104 | 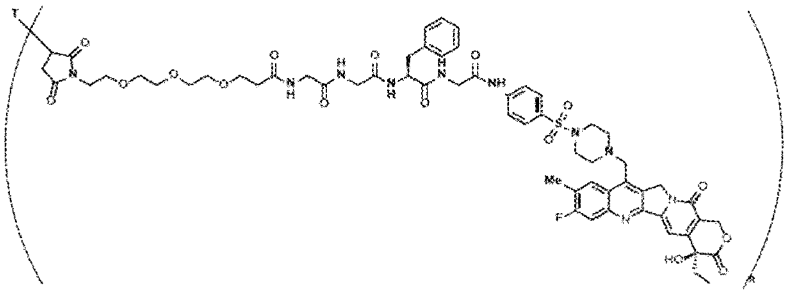 |
| **DC:** MT-GGFG-Compound 108 | 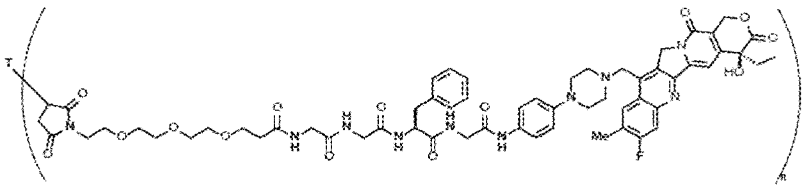 |
| **DC:** MT-GGFG-Compound 127 | 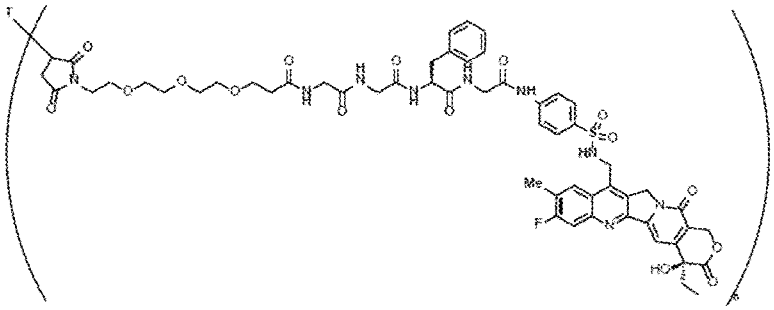 |
FIG. 16

Table 11 (cont.)
| Name | Structure |
|---|---|
| **DC:** MT-GGFG-AM-Compound 136 | 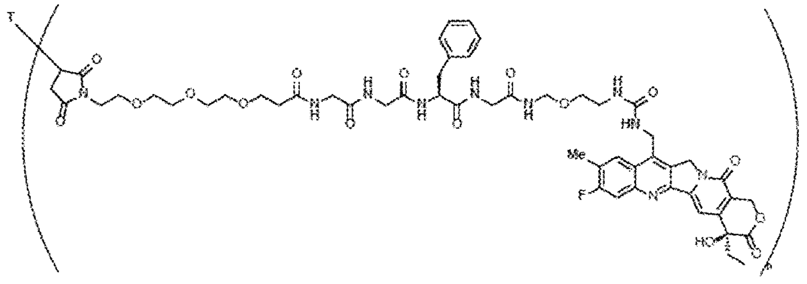 |
| **DC:** MT-GGFG-AM-Compound 139 | 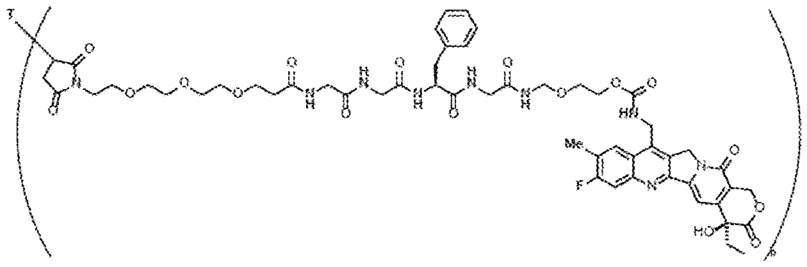 |
| **DC:** MT-GGFG-AM-Compound 129 | 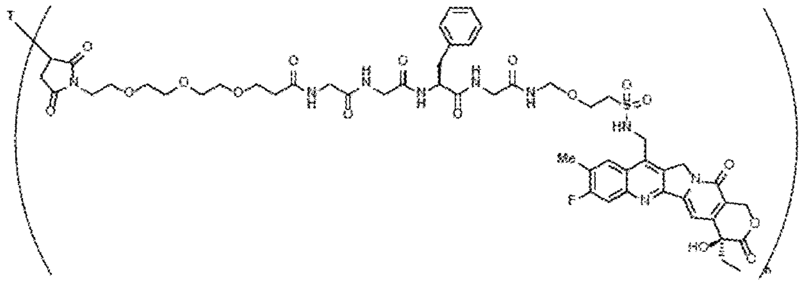 |
FIG. 16 (cont.)

Table 11 (cont.)
| Name | Structure |
|---|---|
| **DC**: MT-GGFG-AM-Compound 113 | 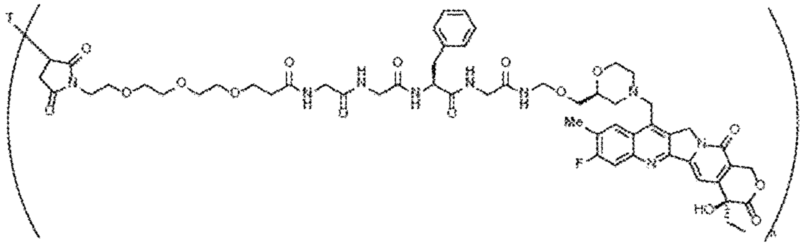 |
| **DC**: MT-GGFG-AM-Compound 141 | 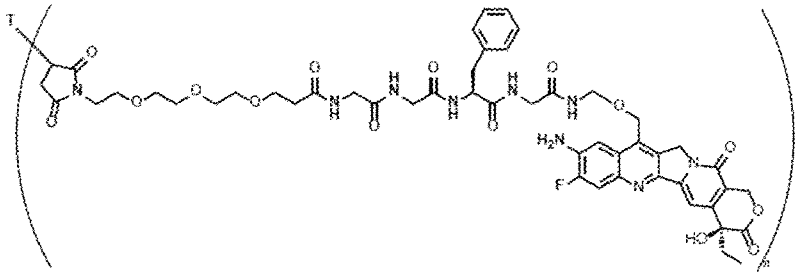 |
| **DC**: MC-GGFG-AM-Compound 141 | 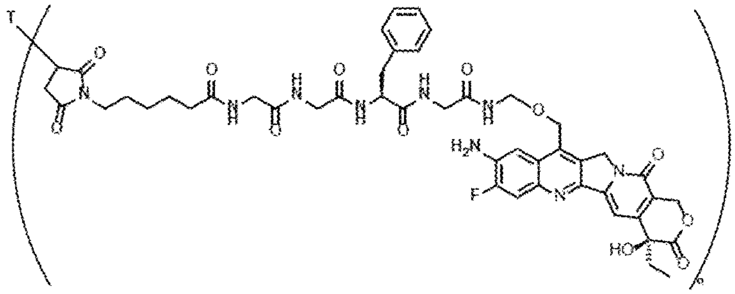 |
FIG. 16 (cont.)

Table 11 (cont.)
| Name | Structure |
| --- | --- |
| **DC:** MT-GGFG-AM-Compound 117 | 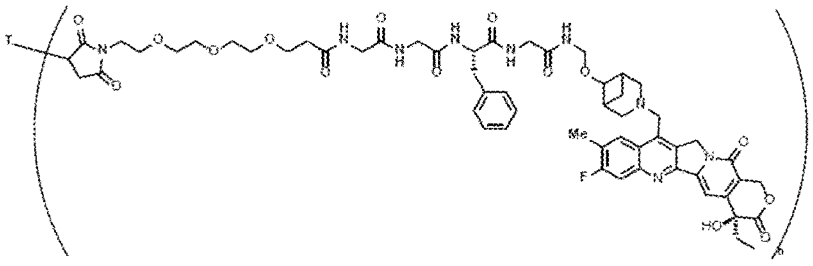 |
| **DC:** MT-GGFG-AM-Compound 118 | 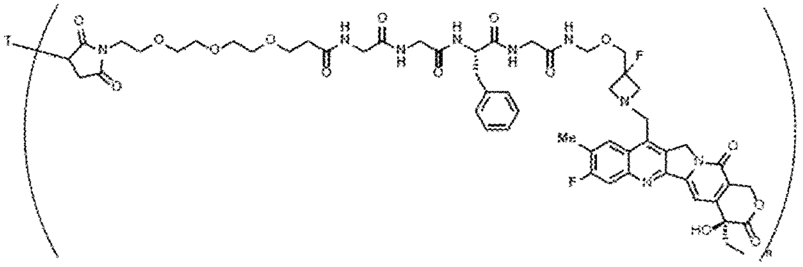 |
| **DC:** MC-GGFG-AM-Compound 139 | 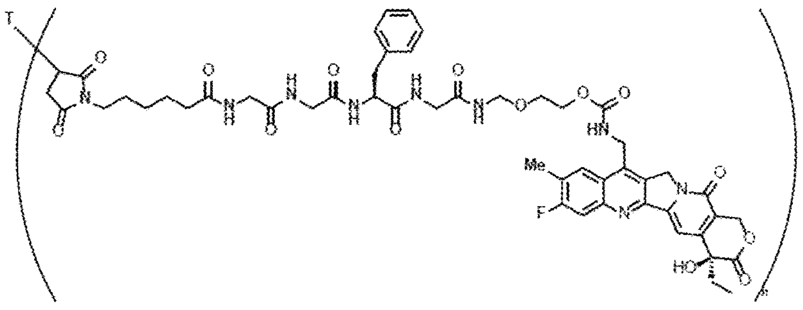 |
| Name | Structure |
| --- | --- |
| **DC:** DiS-Compound 145 | 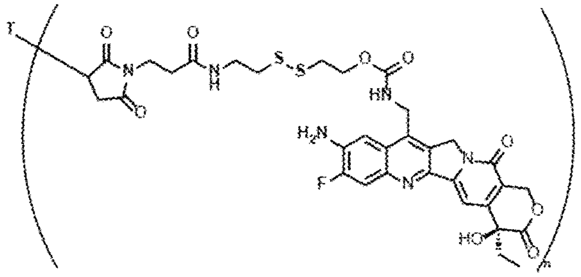 |
FIG. 16 (cont.)

Table 12
| Name | Structure |
|---|---|
| **DC:** MT-GGFG-Compound 140 | 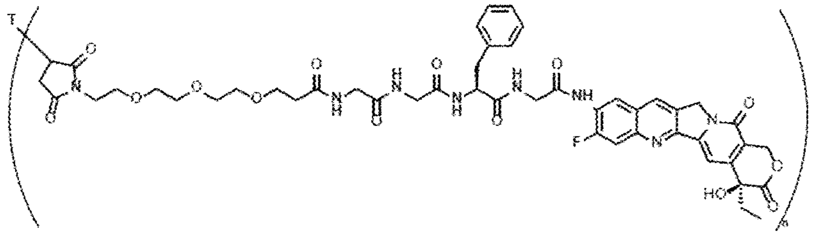 |
| **DC:** MT-GGFG-Compound 141 | 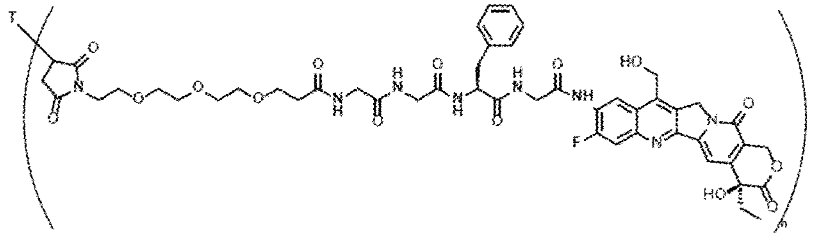 |
| **DC:** MT-GGFG-Compound 145 | 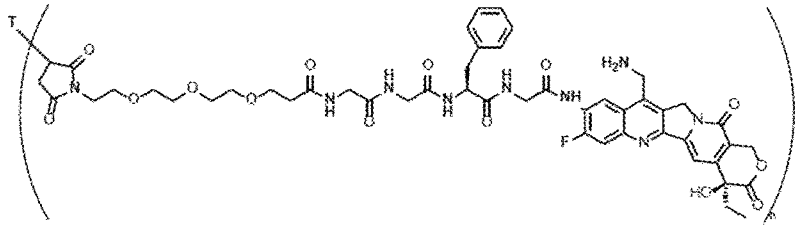 |
| **DC:** MT-GGFG-Compound 148 | 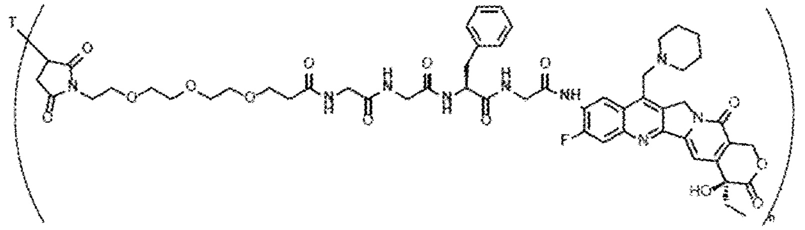 |
FIG. 17

Table 12 (cont.)
| Name | Structure |
|---|---|
| **DC:** MT-GGFG-Compound 142 | 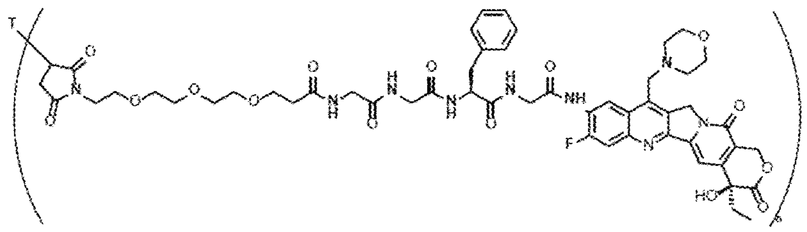 |
| **DC:** MC-GGFG-Compound 140 | 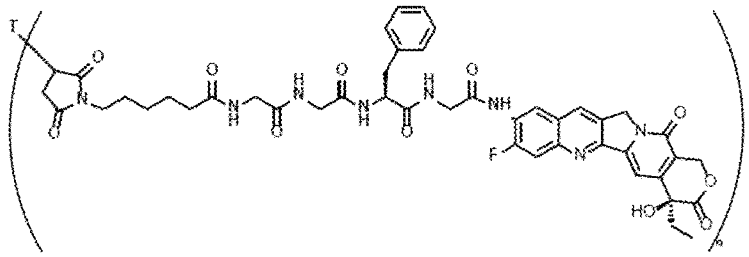 |
| **DC:** MC-GGFG-Compound 141 | 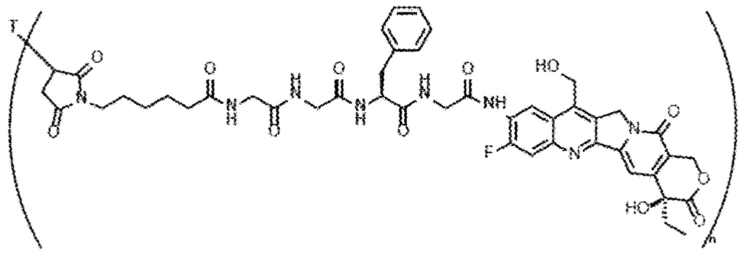 |
FIG. 17 (cont.)

Table 12 (cont.)
| Name | Structure |
|---|---|
| **DC:** MC-VA-Compound 140 (DC: 301) | 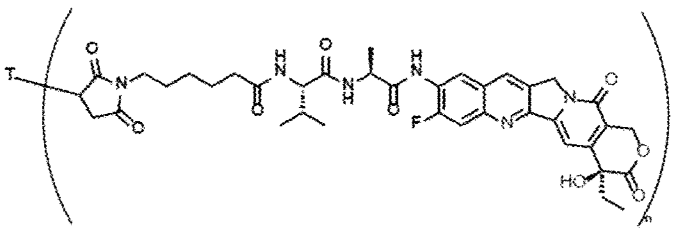 |
| **DC:** NHC-C-VA-Compound 140 | 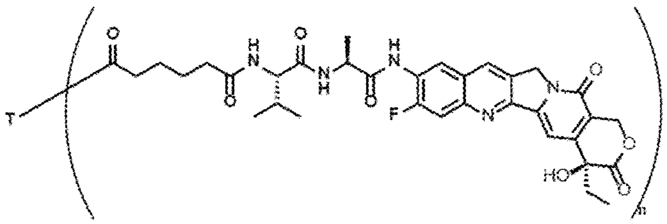 |
| **DC:** Azido-PEG8-VA-Compound 140 | 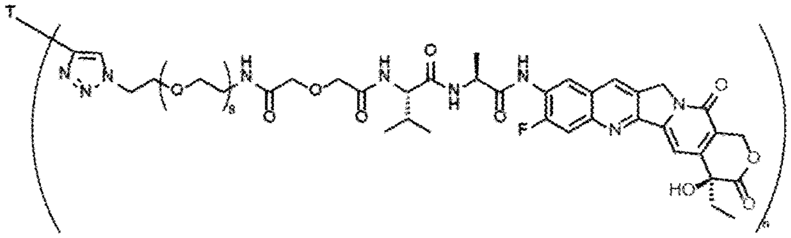 |
FIG. 17 (cont.)

Table 13
| Name | Structure |
| --- | --- |
| DC: 300 | 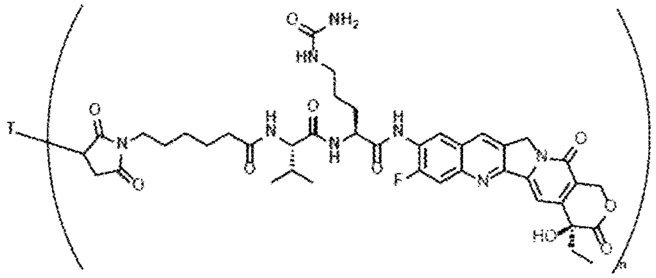 |
| DC: 302 | 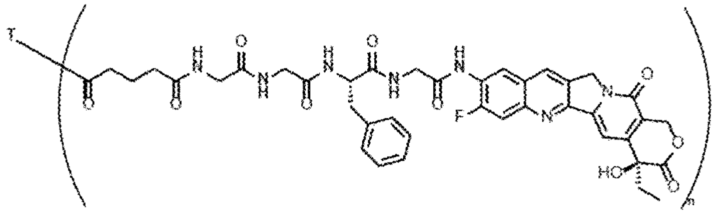 |
| DC: 303a | 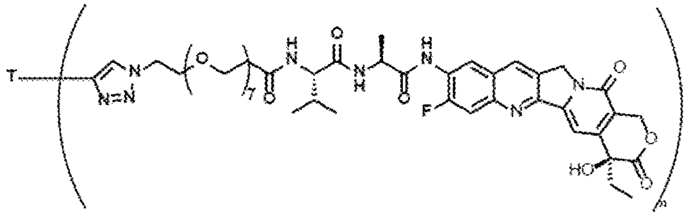 |
FIG. 18

Table 13 (cont.)
| Name | Structure |
|---|---|
| DC: 303b | 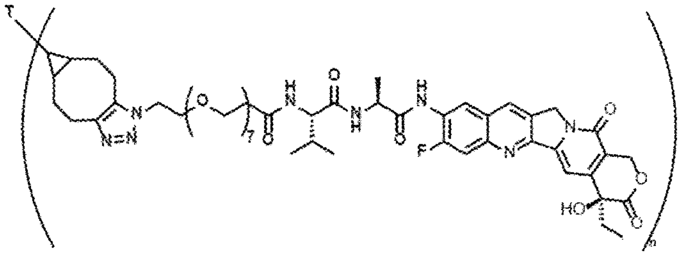 |
| DC: 304 | 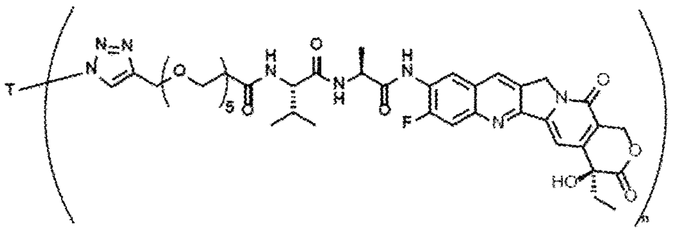 |
| DC: 305 | 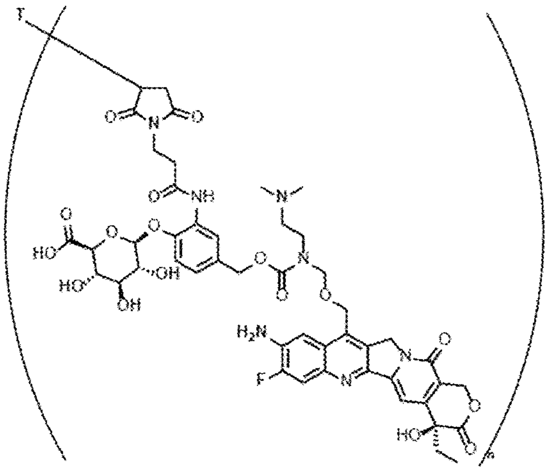 |
FIG. 18 (cont.)

Table 13 (cont.)
| Name | Structure |
|---|---|
| DC: 306 | 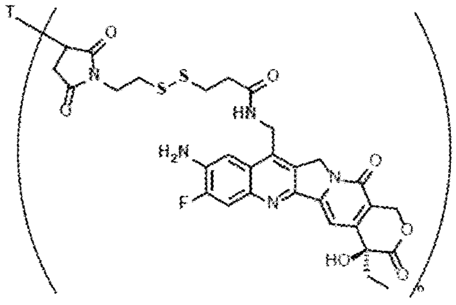 |
| DC: 307 | 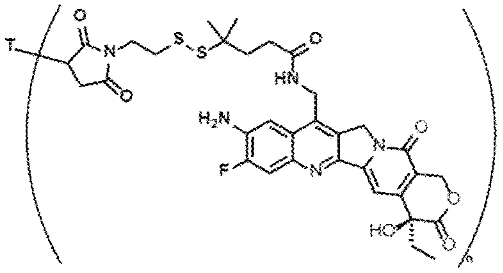 |
| DC: 308 | 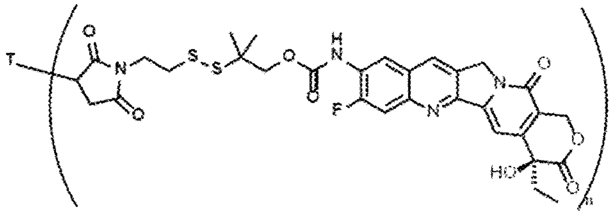 |
FIG. 18 (cont.)

Table 13 (cont.)
| Name | Structure |
|---|---|
| DC: 309 | 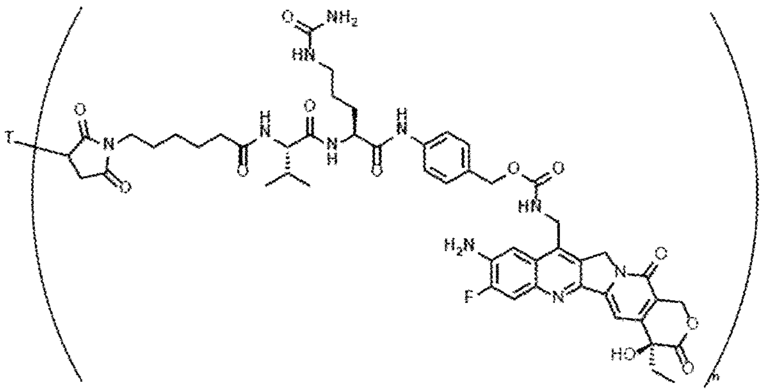 |
| DC: 310 | 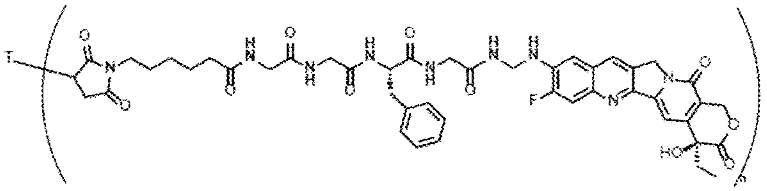 |
FIG. 18 (cont.)

4 hours 24 hours 48 hours 96 hours

ANTIBODY-DRUG CONJUGATES TARGETING FOLATE RECEPTOR ALPHA AND METHODS OF USE

CROSS REFERENCE TO RELATED APPLICATIONS

This application is a continuation of International Application No. PCT/CA2023/050406, filed Mar. 24, 2023, which claims priority to and the benefit of U.S. Provisional Application No. 63/324,003, filed Mar. 25, 2022, U.S. Provisional Application No. 63/417,250, filed Oct. 18, 2022, and U.S. Provisional Application No. 63/450,607, filed Mar. 7, 2023, each of which is hereby incorporated in its entirety by reference.

SEQUENCE LISTING

The instant application contains a Sequence Listing which is hereby incorporated by reference in its entirety. Said XML copy, created on May 1, 2025 is named 2025 05 01 Amended ZYME082US1 XML Sequence Listing.xml, and is 232,094 bytes in size.

FIELD

The present disclosure relates to the field of immunotherapeutics and, in particular, to antibody-drug conjugates targeting human folate receptor alpha (hFRα).

BACKGROUND

Folate receptor alpha (FRα) is a glycosyl-phosphatidylinositol (GPI)-anchored cell-surface protein encoded by FOLR1 and is one of a family of high-affinity FRs that also includes FRβ (FOLR2), FRγ (FOLR3) and FRδ (FOLR4). FRα has been identified as a highly relevant cancer therapy target as it is overexpressed in a variety of cancers including ovarian cancer, triple-negative breast cancer (TNBC), endometrial cancer, mesothelioma and lung cancer, with minimal expression in non-malignant tissues.

Several clinical studies involving FRα-targeted agents in the treatment of cancer are currently ongoing, including the anti-FRα antibody, farletuzumab, and the FRα-targeted antibody-drug conjugates (ADCs), mirvetuximab soravtansine (ImmunoGen, Inc.), MORAb-202 (Eisai Inc.) and STRO-002 (Sutro Biopharma, Inc.).

Camptothecin analogues have been developed as payloads for antibody-drug conjugates (ADCs). Two such ADCs have been approved for treatment of cancer. Trastuzumab deruxtecan (Enhertu™) in which the camptothecin analogue, deruxtecan (Dxd), is conjugated to the anti-HER2 antibody, trastuzumab, via a cleavable tetrapeptide-based linker, and sacituzumab govitecan (Trodelvy™) in which the camptothecin analogue, SN-38, is conjugated to the anti-Trop-2 antibody, sacituzumab, via a hydrolysable, pH-sensitive linker.

Other camptothecin analogues and derivatives, as well as ADCs comprising them have been described. See, for example, International (PCT) Publication Nos. WO 2019/195665; WO 2019/236954; WO 2020/200880 and WO 2020/219287.

This background information is provided for the purpose of making known information believed by the applicant to be of possible relevance to the present disclosure. No admission is necessarily intended, nor should be construed, that any of the preceding information constitutes prior art against the claimed invention.

SUMMARY

Described herein are antibody-drug conjugates (ADCs) targeting human FRα and methods of use. One aspect of the present disclosure relates to an antibody-drug conjugate having Formula (X):

$$T\text{-}[L\text{-}(D)_m]_n \qquad (X)$$

wherein:

m is between 1 and 4;

n is between 1 and 10;

T is an anti-FRα antibody construct comprising an antigen-binding domain that specifically binds to an epitope within human folate receptor alpha (hFRα) comprising amino acid residues E120, D121, R123, T124, S125 and Y126 of SEQ ID NO: 15;

L is a linker, and

D is a compound of Formula I:

(I)

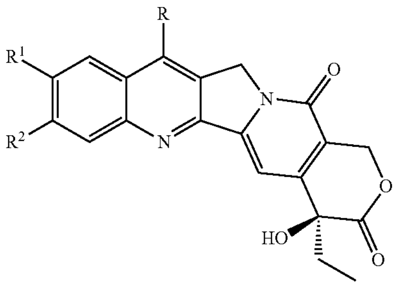

wherein:

$R^1$ is selected from: —H, —$CH_3$, —$CHF_2$, —$CF_3$, —F, —Br, —Cl, —OH, —$OCH_3$, —$OCF_3$ and —$NH_2$, and $R^2$ is selected from: —H, —$CH_3$, —$CF_3$, —F, —Br, —Cl, —OH, —$OCH_3$ and —$OCF_3$, and wherein:

when $R^1$ is —$NH_2$, then R is $R^3$ or $R^4$, and when $R^1$ is other than —$NH_2$, then R is $R^4$;

$R^3$ is selected from: —H, —$C_1$-$C_6$ alkyl, —$C_3$-$C_8$ cycloalkyl, —($C_1$-$C_6$ alkyl)-O—$R^5$,

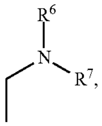

—$CO_2R^8$, -aryl, -heteroaryl and —($C_1$-$C_6$ alkyl)-aryl;

$R^4$ is selected from:

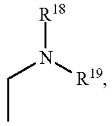

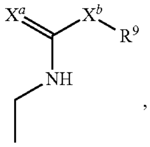

,

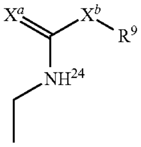

,

-continued

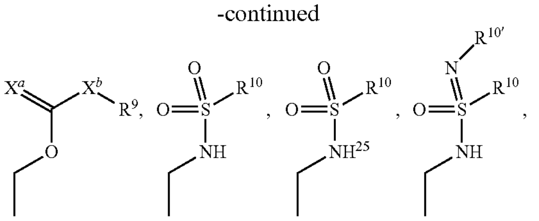

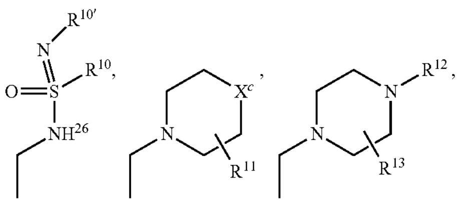

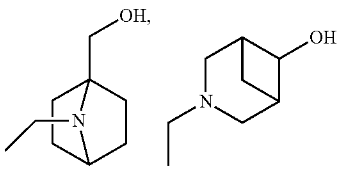

and

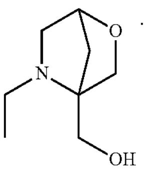

R$^5$ is selected from: —H, —$C_1$-$C_6$ alkyl, —$C_3$-$C_8$ cycloalkyl, -aryl, -heteroaryl, -aryl and —($C_1$-$C_6$ alkyl)-aryl;

R$^6$ and R$^7$ are each independently selected from: —H, —$C_1$-$C_6$ alkyl, —$C_3$-$C_8$ cycloalkyl, —($C_1$-$C_6$ alkyl)-O—R$^5$, —$C_3$-$C_8$ heterocycloalkyl and —C(O)R$^{17}$;

R$^8$ is selected from: —H, —$C_1$-$C_6$ alkyl, —$C_3$-$C_8$ cycloalkyl and —$C_3$-$C_8$ heterocycloalkyl;

each R$^9$ is independently selected from: —H, —$C_1$-$C_6$ alkyl, —$C_3$-$C_8$ cycloalkyl, -aryl, -heteroaryl and —($C_1$-$C_6$ alkyl)-aryl;

each R$^{10}$ is independently selected from: —$C_1$-$C_6$ alkyl, —$C_3$-$C_8$ cycloalkyl, —NR$^{14}$R$^{14'}$, -aryl, -heteroaryl and —($C_1$-$C_6$ alkyl)-aryl;

R$^{10'}$ is selected from: —H, —$C_1$-$C_6$ alkyl, —$C_3$-$C_8$ cycloalkyl, -aryl, -heteroaryl, and —($C_1$-$C_6$ alkyl)-aryl;

R$^{11}$ is selected from: —H and —$C_1$-$C_6$ alkyl;

R$^{12}$ is selected from: —H, —$C_1$-$C_6$ alkyl, —$CO_2R^8$, -aryl, -heteroaryl,—($C_1$-$C_6$ alkyl)-aryl, —S(O)$_2$R$^{16}$ and

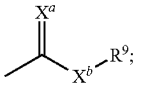

R$^{13}$ is selected from: —H and —$C_1$-$C_6$ alkyl;

R$^{14}$ and R$^{14'}$ are each independently selected from: —H, $C_1$-$C_6$ alkyl, —$C_3$-$C_8$ cycloalkyl and —$C_3$-$C_8$ heterocycloalkyl;

R$^{16}$ is selected from: —$C_1$-$C_6$ alkyl, —$C_3$-$C_8$ cycloalkyl, -aryl, -heteroaryl and —($C_1$-$C_6$ alkyl)-aryl;

R$^{17}$ is selected from: —$C_1$-$C_6$ alkyl, —$C_3$-$C_8$ cycloalkyl, —$C_3$-$C_8$ heterocycloalkyl, —($C_1$-$C_6$ alkyl)-$C_3$-$C_8$ heterocycloalkyl, -aryl, -heteroaryl and —($C_1$-$C_6$ alkyl)-aryl;

R$^{18}$ and R$^{19}$ taken together with the N atom to which they are bonded form a 4-, 5-, 6- or 7-membered ring having 0 to 3 substituents selected from: halogen, —$C_1$-$C_6$ alkyl, —$C_3$-$C_8$ cycloalkyl and —($C_1$-$C_6$ alkyl)-O—R$^5$;

R$^{24}$, R$^{25}$ and R$^{26}$ are each —$C_1$-$C_6$ alkyl;

X$^a$ and X$^b$ are each independently selected from: NH, O and S, and

X$^c$ is selected from; O, S and S(O)$_2$, with the proviso that the compound is other than (S)-9-amino-11-butyl-4-ethyl-4-hydroxy-1,12-dihydro-14H-pyrano[3',4':6,7]indolizino[1,2-b]quinoline-3,14(4H)-dione.

Another aspect of the present disclosure relates to an antibody-drug conjugate having a structure selected from:

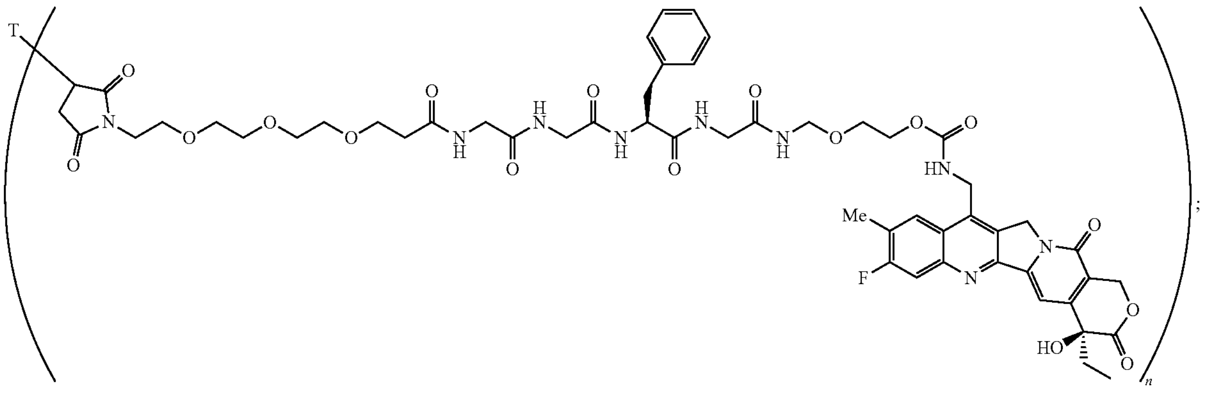

-continued
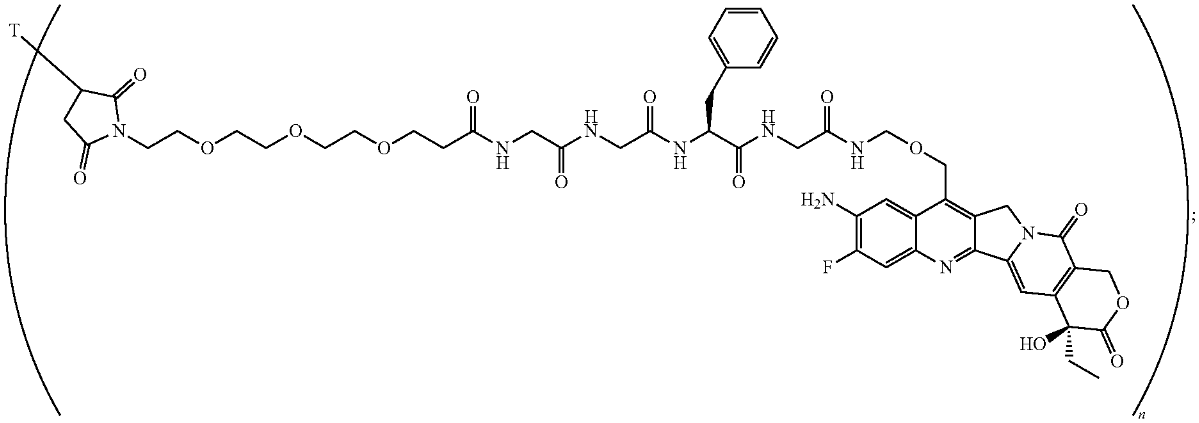
;
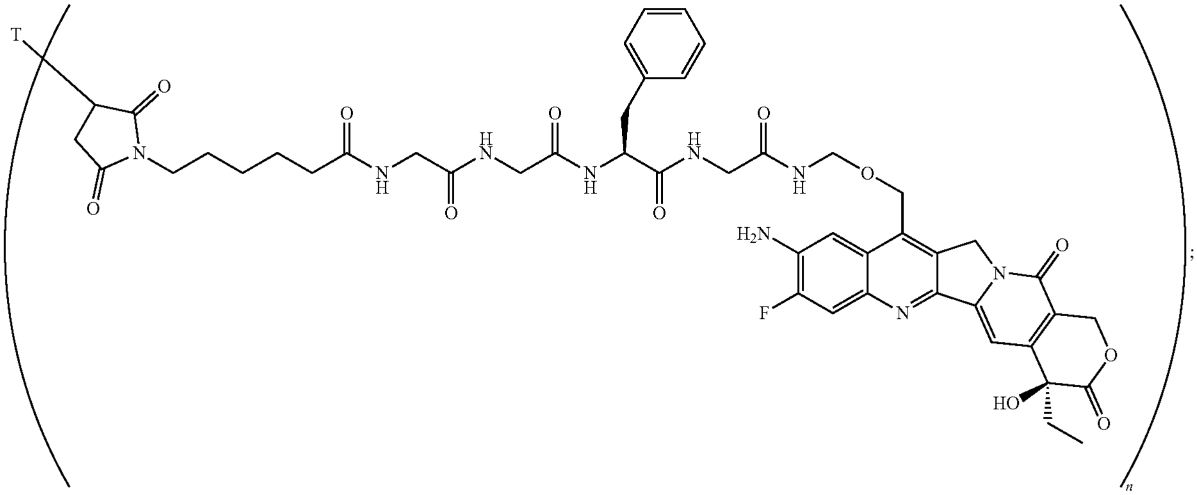
;
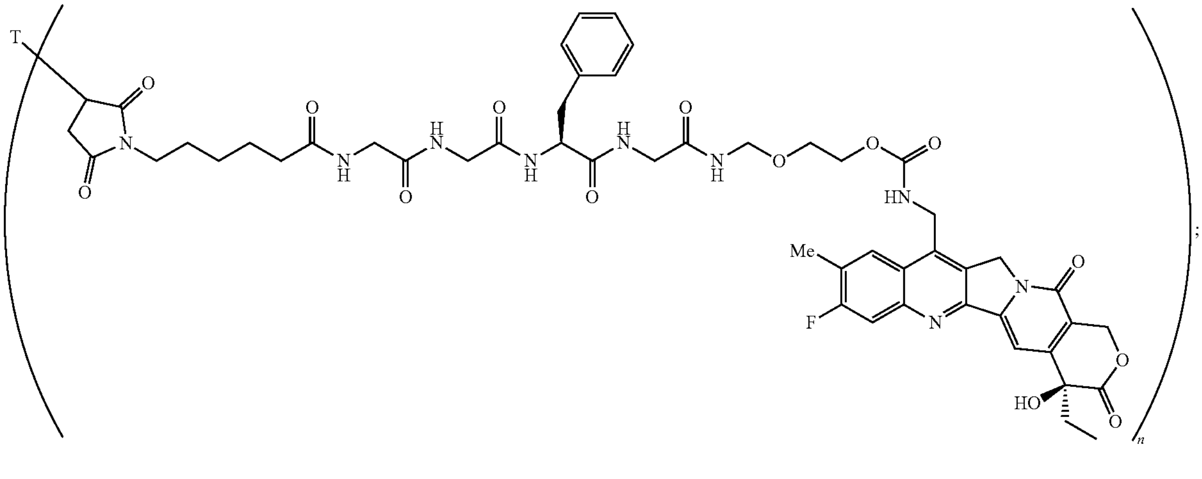
;

-continued

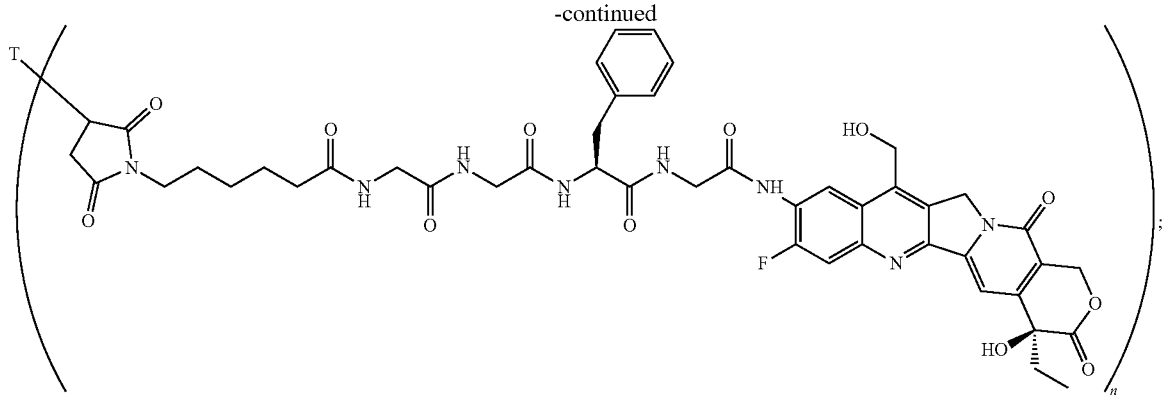

; and

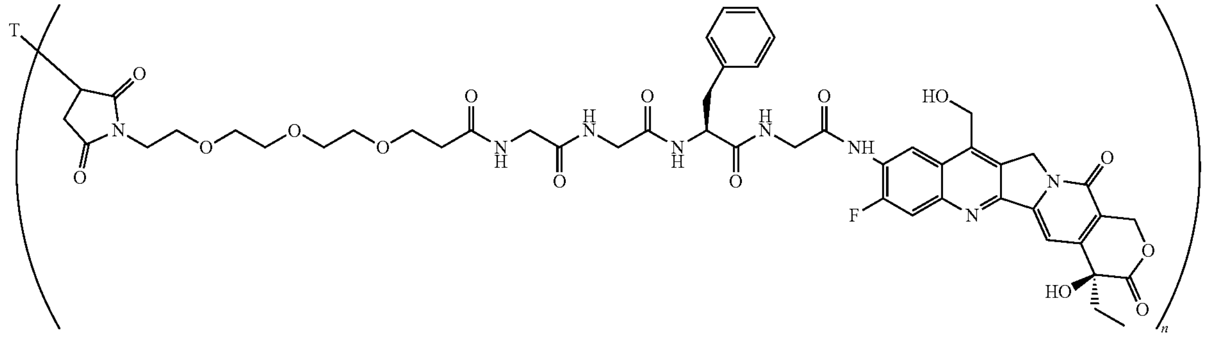

wherein:

T is an anti-FRα antibody construct comprising two antigen-binding domains operably linked to an IgG Fc region, each of the antigen-binding domains comprising:

(a) a VL amino acid sequence as set forth in SEQ ID NO: 39, and a VH amino acid sequence as set forth in SEQ ID NO: 19; or (b) a VL amino acid sequence as set forth in SEQ ID NO: 124, and a VH amino acid sequence as set forth in SEQ ID NO: 91; or (c) a VL amino acid sequence as set forth in SEQ ID NO: 64, and (i) a VH amino acid sequence as set forth in SEQ ID NO: 50, or (ii) a VH amino acid sequence as set forth in SEQ ID NO: 54, or (iii) a VH amino acid sequence as set forth in SEQ ID NO: 57, or (iv) a VH amino acid sequence as set forth in SEQ ID NO: 61, or (v) a VH amino acid sequence as set forth in SEQ ID NO: 76, or (vi) a VH amino acid sequence as set forth in SEQ ID NO: 79, or (vii) a VH amino acid sequence as set forth in SEQ ID NO: 82, or (viii) a VH amino acid sequence as set forth in SEQ ID NO: 85, or (ix) a VH amino acid sequence as set forth in SEQ ID NO: 88, or (x) a VH amino acid sequence as set forth in SEQ ID NO: 106; or (d) a VL amino acid sequence as set forth in SEQ ID NO: 130, and (i) a VH amino acid sequence as set forth in SEQ ID NO: 99, or (ii) a VH amino acid sequence as set forth in SEQ ID NO: 106, or (iii) a VH amino acid sequence as set forth in SEQ ID NO: 113, or (iv) a VH amino acid sequence as set forth in SEQ ID NO: 116, or (v) a VH amino acid sequence as set forth in SEQ ID NO: 133, or (vi) a VH amino acid sequence as set forth in SEQ ID NO: 136; or (e) a VL amino acid sequence as set forth in SEQ ID NO: 119, and (i) a VH amino acid sequence as set forth in SEQ ID NO: 106, or (ii) a VH amino acid sequence as set forth in SEQ ID NO: 116, and wherein n is between 4 and 8.

Another aspect of the present disclosure relates to a pharmaceutical composition comprising an antibody-drug conjugate as described herein, and a pharmaceutically acceptable carrier or diluent.

Another aspect of the present disclosure relates to a method of inhibiting the proliferation of cancer cells comprising contacting the cells with an effective amount of the antibody-drug conjugate as described herein.

Another aspect of the present disclosure relates to a method of killing cancer cells comprising contacting the cells with an effective amount of the antibody-drug conjugate as described herein.

Another aspect of the present disclosure relates to a method of treating cancer in a subject in need thereof comprising administering to the subject an effective amount of the antibody-drug conjugate as described herein.

Another aspect of the present disclosure relates to an antibody-drug conjugate as described herein for use in therapy.

Another aspect of the present disclosure relates to an antibody-drug conjugate as described herein for use in the treatment of cancer.

Another aspect of the present disclosure relates to a use of an antibody-drug conjugate as described herein in the manufacture of a medicament for the treatment of cancer.

BRIEF DESCRIPTION OF THE DRAWINGS

FIG. 1A & 1B shows the sequence of the rabbit heavy chain variable domain CDRs of the chimeric anti-FRα antibody v23924 ported onto a human VH framework (IGHV3-23*01) (SEQ ID NO: 155) (1A), and the sequence of the rabbit light chain variable domain CDRs of chimeric antibody v23924 ported onto a human VL framework (IG-KVI-39*01) (SEQ ID NO: 156) (1B). The CDRs were assigned with the AbM definition and marked in bold italic font.

FIG. 2A & 2C show the profiles from electrophoresis under non-reducing (NR) and reducing (R) conditions after preparative SEC purification (post prep-SEC) or after Protein A purification (post-pA) of parental chimeric anti-FRα antibody v23924 (2A) and purified representative humanized variant v30384 (2C), FIG. 2B & 2D show the UPLC-SEC profiles of parental chimeric anti-FRα antibody v23924 after preparative SEC purification (2B) and purified representative humanized variant v30384 after Protein A purification (2D).

FIG. 7 shows the coverage of the hFRα sequence (SEQ ID NO: 15) by peptides generated by pepsin digestion of hFRα. Each bar below the sequence represents a peptide.

FIG. 11 presents a table showing the CDR sequences of representative anti-FRα antibodies as defined by IMGT, Chothia, Kabat, Contact and AbM definitions.

FIG. 12 presents a table showing the VH and VL sequences of representative anti-FRα antibodies.

FIG. 13 shows exemplary drug-linker (DL) structures comprising camptothecin analogues of Formula (I) with a C7 linkage (Table 8).

FIG. 14 shows exemplary drug-linker (DL) structures comprising camptothecin analogues of Formula (I) with a C10 linkage (Table 9).

FIG. 15 shows exemplary drug-linker (DL) structures comprising camptothecin analogues of Formula (I) with either a C7 or C10 linkage (Table 10).

FIG. 16 shows exemplary conjugate (DC) structures comprising camptothecin analogues of Formula (I) with a C7 linkage (Table 11).

FIG. 17 shows exemplary conjugate (DC) structures comprising camptothecin analogues of Formula (I) with a C10 linkage (Table 12).

FIG. 18 shows exemplary conjugate (DC) structures comprising camptothecin analogues of Formula (I) with either a C7 or C10 linkage (Table 13).

FIG. 22A, 22B, 22C, 22D, 19B, & 22E shows the in vivo anti-tumor activities of ADCs comprising the anti-FRα humanized antibody variant v36675 conjugated to the camptothecin analogues Compound 139 or Compound 141, each at DAR 4 or DAR 8, in an OV90 CDX xenograft model (22A, B); conjugated to the camptothecin analogues Compound 140 or Compound 141, each at DAR 4 or DAR 8, in an OVCAR3 CDX xenograft model (22C); conjugated to the camptothecin analogue Compound 139 at DAR 8 in a GTG-2025 PDX xenograft model (22D), and conjugated to the camptothecin analogue Compound 139 at DAR 8 in a GTG-0958 PDX xenograft model (22E).

FIG. 23A, 23B, 23C, 19B, & 23D shows the total antibody serum concentrations of ADCs comprising the anti-FRα humanized antibody v36675 in blood samples collected after a first dose in a cynomolgus monkey toxicity study; ADCs comprising v36675 conjugated to Compound 139 or Compound 141 at DAR 8 administered at 30 mg/kg (23A), ADCs comprising v36675 conjugated to Compound 139 or Compound 141 at DAR 4 administered at 60 mg/kg (23B), ADCs comprising v36675 conjugated to Compound 139 or Compound 141 at DAR 8 administered at 80 mg/kg (23C), and ADCs comprising v36675 conjugated to Compound 139 or Compound 141 at DAR 4 or DAR 8 administered at 120 mg/kg (23D).

FIG. 25A, 25B, 25C, 19B, & 25D shows penetration of the anti-FRα humanized antibody variant v36675 into JEG-3 cell spheroids compared to mirvetuximab and negative control, palivizumab, at 4 hours (25A), 24 hours (25B), 48 hours (25C), and 96 hours (25D).

FIG. 27A, 27B, 27C, 27D, 27E, 27F, 27G, 27H, 19B, & 27I show the in vivo anti-tumor activities of an ADC comprising the anti-FRα humanized antibody variant v36675 conjugated to Compound 139 at DAR 8 (v36675-MC-GGFG-AM-Compound 139) and a control ADC, mirvetuximab-DM4 DAR 4, in patient derived xenograft (PDX) models of ovarian cancer when dosed at 6 mg/kg: CTG-0703 PDX model (27A), CTG-1301 PDX model (27B), CTG-2025 PDX model (27C), CTG-3383 PDX model (27D), CTG-0947 PDX model (27E), CTG-0958 PDX model (27F), CTG-3718 PDX model (27G), CTG-1703 PDX model (27H), and CTG-1602 PDX model (27I).

DETAILED DESCRIPTION

Figure 2A:
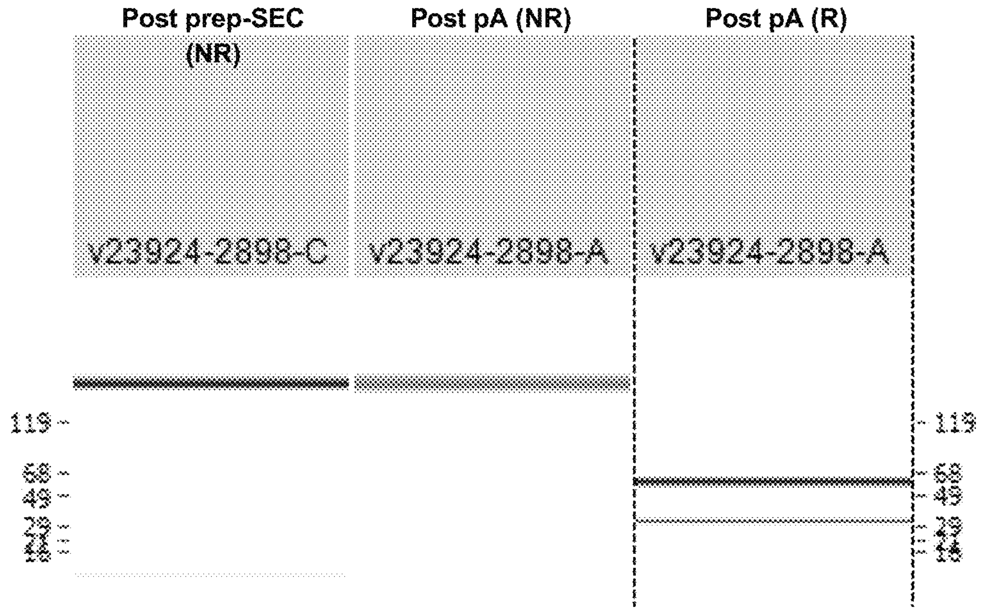
FIG. 2A, 2B, 2C, & 2D show the profiles of purified parental chimeric anti-FRα antibody v23924 and purified representative humanized variant v30384 as analyzed by electrophoresis and UPLC-SEC.

The present disclosure relates to antibody-drug conjugates (ADCs) comprising an antibody construct that specifically binds human folate receptor alpha (FRα) (an anti-FRα antibody construct) conjugated to a camptothecin analogue of Formula (I) as described herein. In particular, the present disclosure relates to ADCs having Formula (X):

$$T\text{-}[L\text{-}(D)_m]_n \quad (X)$$

wherein:

T is an anti-FRα antibody construct as described herein;

L is a linker;

D is a camptothecin analogue of Formula (I) as described herein;

m is between 1 and 4, and n is between 1 and 10.

The ADCs of the present disclosure may find use, for example, as therapeutics, in particular in the treatment of cancer.

Definitions

Unless defined otherwise, all technical and scientific terms used herein have the same meaning as commonly understood by one of ordinary skill in the art.

As used herein, the term "about" refers to an approximately +/−10% variation from a given value. It is to be understood that such a variation is always included in any given value provided herein, whether or not it is specifically referred to.

The use of the word "a" or "an" when used herein in conjunction with the term "comprising" may mean "one," but it is also consistent with the meaning of "one or more," "at least one" and "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

A "complementarity determining region" or "CDR[11] is an amino acid sequence that contributes to antigen-binding specificity and affinity. "Framework" regions (FR) can aid in maintaining the proper conformation of the CDRs to promote binding between the antigen-binding region and an antigen. From N-terminus to C-terminus, both the light chain variable region (VL) and the heavy chain variable region (VH) of an antibody typically comprise the domains FR1, CDR1, FR2, CDR2, FR3, CDR3, and FR4. The three heavy chain CDRs are referred to herein as HCDR1, HCDR2, and HCDR3, and the three light chain CDRs are referred to as LCDR1, LCDR2, and LCDR3. CDRs provide the majority of contact residues for the binding of the antibody to the antigen or epitope. Often, the three heavy chain CDRs and the three light chain CDRs are required to bind antigen. However, in some instances, even a single variable domain can confer binding specificity to the antigen. Furthermore, as is known in the art, in some cases, antigen-binding may also occur through a combination of a minimum of one or more CDRs selected from the VH and/or VL domains, for example HCDR3.

A number of different definitions of the CDR sequences are in common use, including those described by Kabat et al. (1983, *Sequences of Proteins of Immunological Interest*, NIH Publication No. 369-847, Bethesda, MD), by Chothia et al. (1987, *J Mol Biol*, 196:901-917), as well as the IMGT, AbM (University of Bath) and Contact (MacCallum, et al., 1996, *J Mol Biol*, 262(5):732-745) definitions. By way of example, CDR definitions according to Kabat, Chothia, IMGT, AbM and Contact are provided in Table 1 below. Accordingly, as would be readily apparent to one skilled in the art, the exact numbering and placement of CDRs may differ based on the numbering system employed. However, it is to be understood that the disclosure herein of a VH includes the disclosure of the associated (inherent) heavy chain CDRs (HCDRs) as defined by any of the known numbering systems. Similarly, disclosure herein of a VL includes the disclosure of the associated (inherent) light chain CDRs (LCDRs) as defined by any of the known numbering systems.

TABLE 1

Common CDR Definitions[1]

| Definition | Heavy Chain CDR1[2] | Heavy Chain CDR2 | Heavy Chain CDR3 | Light Chain CDR1 | Light Chain CDR2 | Light Chain CDR3 |
|---|---|---|---|---|---|---|
| Kabat | H31-H35B | H50-H65 | H95-H102 | L24-L34 | L50-L56 | L89-L97 |
| Chothia | H26-H32, H33 or H34 | H52-H56 | H95-H102 | L24-L34 | L50-L56 | L89-L97 |
| IMGT | H26-H33, H34, H35, H35A or H35B | H51-H57 | H93-H102 | L27-L32 | L50-L52 | L89-L97 |
| AbM | H26-H35B | H50-H58 | H95-H102 | L24-L34 | L50-L56 | L89-L97 |
| Contact | H30-H35B | H47-H58 | H93-H101 | L30-L36 | L46-L55 | L89-L96 |

[1]Either the Kabat or Chothia numbering system may be used for HCDR2, HCDR3 and the light chain CDRs for all definitions except Contact, which uses Chothia numbering
[2]Using Kabat numbering. The position in the Kabat numbering scheme that demarcates the end of the Chothia and IMGT CDR-H1 loop varies depending on the length of the loop because Kabat places insertions outside of those CDR definitions at positions 35A and 35B. However, the IMGT and Chothia CDR-H1 loop can be unambiguously defined using Chothia numbering. CDR-H1 definitions using Chothia numbering: Kabat H31-H35, Chothia H26-H32, AbM H26-H35, IMGT H26-H33, Contact H30-H35.

The term "identical" in the context of two or more polynucleotide or polypeptide sequences, refers to two or more sequences or subsequences that are the same. Sequences are "substantially identical" if they have a percentage of amino acid residues or nucleotides that are the same (for example, about 80%, about 85%, about 90%, about 95%, or about 98% identity, over a specified region) when compared and aligned for maximum correspondence over a comparison window or over a designated region as measured using one of the commonly used sequence comparison algorithms as known to persons of ordinary skill in the art or by manual alignment and visual inspection. For sequence comparison, typically test sequences are compared to a designated reference sequence. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window" refers to a segment of a sequence comprising contiguous amino acid or nucleotide positions which may be, for example, from about 10 to 600 contiguous amino acid or nucleotide positions, or from about 10 to about 200, or from about 10 to about 150 contiguous amino acid or nucleotide positions over which a test sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, for example, by the local homology algorithm of Smith & Waterman, 1970, *Adv. Appl. Math.*, 2:482c; by the homology alignment algorithm of Needleman & Wunsch, 1970, *J. Mol. Biol.*, 48:443; by the search for similarity method of Pearson & Lipman, 1988, *Proc. Natl. Acad. Sci. USA*, 85:2444, or by computerized implementations of these algorithms (for example, GAP, BESTFIT, FASTA or TFASTA in the Wisconsin Genetics Software Package, Genetics Computer Group, Madison, WI), or by manual alignment and visual inspection (see, for example, Ausubel et al., Current Protocols in Molecular Biology, (1995 supplement), Cold Spring Harbor Laboratory Press).

Examples of available algorithms suitable for determining percent sequence identity are the BLAST and BLAST 2.0 algorithms, which are described in Altschul et al., 1997, *Nuc. Acids Res.*, 25:3389-3402, and Altschul et al., 1990, *J. Mol. Biol.*, 215:403-410, respectively. Software for performing BLAST analyses is publicly available through the website for the National Center for Biotechnology Information (NCBI).

The term "acyl," as used herein, refers to the group —C(O)R, where R is hydrogen, alkyl, aryl, heteroaryl, cycloalkyl or heterocycloalkyl.

The term "acyloxy" refers to the group —OC(O)R, where R is alkyl.

The term "alkoxy," as used herein, refers to the group —OR, where R is alkyl, aryl, heteroaryl, cycloalkyl or cycloheteroalkyl.

The term "alkyl," as used herein, refers to a straight chain or branched saturated hydrocarbon group containing the specified number of carbon atoms. Examples of alkyl include, but are not limited to, methyl, ethyl, n-propyl, isopropyl, n-butyl, sec-butyl, isobutyl, t-butyl, pentyl, isopentyl, t-pentyl, neo-pentyl, 1-methylbutyl, 2-methylbutyl, n-hexyl, and the like.

The term "alkylaminoaryl," as used herein, refers to an alkyl group as defined herein substituted with one aminoaryl group as defined herein.

The term "alkylheterocycloalkyl," as used herein, refers to an alkyl group as defined herein substituted with one heterocycloalkyl group as defined herein.

The term "alkylthio," as used herein, refers to the group —SR, where R is an alkyl group.

The term "amido," as used herein, refers to the group —C(O)NRR$^1$, where R and R$^1$ are independently hydrogen, alkyl, aryl, heteroaryl, cycloalkyl or heterocycloalkyl.

The term "amino," as used herein, refers to the group —NRR$^1$, where R and R$^1$ are independently hydrogen, alkyl, aryl, heteroaryl, cycloalkyl or heterocycloalkyl.

The term "aminoalkyl," as used herein, refers to an alkyl group as defined herein substituted with one or more amino groups, for example, one, two or three amino groups.

The term "aminoaryl," as used herein, refers to an aryl group as defined herein substituted with one amino group.

The term "aryl," as used herein, refers to a 6- to 12-membered mono- or bicyclic hydrocarbon ring system in which at least one ring is aromatic. Examples of aryl include, but are not limited to, phenyl, naphthalenyl, 1,2,3,4-tetrahydronaphthalenyl, 5,6,7,8-tetrahydro-naphthalenyl, indanyl, and the like.

The term "carboxy," as used herein, refers to the group —C(O)OR, where R is H, alkyl, aryl, heteroaryl, cycloalkyl or cycloheteroalkyl.

The term "cyano," as used herein, refers to the group —CN.

The term "cycloalkyl," as used herein, refers to a mono- or bicyclic saturated hydrocarbon containing the specified number of carbon atoms. Examples of cycloalkyl include, but are not limited to, cyclopropyl, cyclobutyl, cyclopentyl, cyclohexyl, cycloheptane, bicyclo [2.2.1]heptane, bicyclo [3.1.1]heptane, and the like.

The term "haloalkyl," as used herein, refers to an alkyl group as defined herein substituted with one or more halogen atoms.

The terms "halogen" and "halo," as used herein, refer to fluorine (F), bromine (Br), chlorine (Cl) and iodine (I).

The term "heteroaryl," as used herein, refers to a 6- to 12-membered mono- or bicyclic ring system in which at least one ring atom is a heteroatom and at least one ring is aromatic.

Examples of heteroatoms include, but are not limited to, O, S and N. Examples of heteroaryl include, but are not limited to: pyridyl, benzofuranyl, pyrazinyl, pyridazinyl, pyrimidinyl, triazinyl, quinolinyl, benzoxazolyl, benzothiazolyl, isoquinolinyl, quinazolinyl, quinoxalinyl, pyrrolyl, indolyl, and the like.

The term "heterocycloalkyl," as used herein, refers to a mono- or bicyclic non-aromatic ring system containing the specified number of atoms and in which at least one ring atom is a heteroatom, for example, O, S or N. A heterocyclyl substituent can be attached via any of its available ring atoms, for example, a ring carbon, or a ring nitrogen. Examples of heterocycloalkyl include, but are not limited to, aziridinyl, azetidinyl, piperidinyl, morpholinyl, piperazinyl, pyrrolidinyl, and the like.

The terms "hydroxy" and "hydroxyl," as used herein, refer to the group —OH.

The term "hydroxyalkyl," as used herein, refers to an alkyl group as defined herein substituted with one or more hydroxy groups.

The term "nitro," as used herein, refers to the group —$NO_2$.

The term "sulfonyl," as used herein, refers to the group —$S(O)_2R$, where R is H, alkyl or aryl.

The term "sulfonamido," as used herein, refers to the group —NH—$S(O)_2R$, where R is H, alkyl or aryl.

The terms "thio" and "thiol," as used herein, refer to the group —SH.

Unless specifically stated as being "unsubstituted," any alkyl, cycloalkyl, heterocycloalkyl, aryl or heteroaryl group referred to herein is understood to be "optionally substituted," i.e. each such reference includes both unsubstituted and substituted versions of these groups. For example, reference to a "—$C_1$-$C_6$ alkyl" includes both unsubstituted —$C_1$-$C_6$ alkyl and —$C_1$-$C_6$ alkyl substituted with one or more substituents. Examples of substituents include, but are not limited to, halogen, acyl, acyloxy, alkoxy, carboxy, hydroxy, amino, amido, nitro, cyano, azido, alkylthio, thio, sulfonyl, sulfonamido, alkyl, cycloalkyl, heterocycloalkyl, aryl or heteroaryl. In certain embodiments, each alkyl, cycloalkyl, heterocycloalkyl, aryl or heteroaryl group referred to herein is optionally substituted with one or more substituents selected from: halogen, acyl, acyloxy, alkoxy, carboxy, hydroxy, amino, amido, nitro, cyano, azido, alkylthio, thio, sulfonyl and sulfonamido.

A chemical group described herein as "substituted," may include one substituent or a plurality of substituents up to the full valence of substitution for that group. For example, a methyl group may include 1, 2, or 3 substituents, and a phenyl group may include 1, 2, 3, 4, or 5 substituents. When a group is substituted with more than one substituent, the substituents may be the same or they may be different.

The term "subject," as used herein, refers to an animal, in some embodiments a mammal, which is the object of treatment, observation or experiment. The animal may be a human, a non-human primate, a companion animal (for example, dog, cat, or the like), farm animal (for example, cow, sheep, pig, horse, or the like) or a laboratory animal (for example, rat, mouse, guinea pig, non-human primate, or the like). In certain embodiments, the subject is a human.

It is contemplated that any embodiment discussed herein can be implemented with respect to any method, use or composition disclosed herein, and vice versa.

Particular features, structures and/or characteristics described in connection with an embodiment disclosed herein may be combined with features, structures and/or characteristics described in connection with another embodiment disclosed herein in any suitable manner to provide one or more further embodiments.

It is also to be understood that the positive recitation of a feature in one embodiment, serves as a basis for excluding the feature in an alternative embodiment. For example, where a list of options is presented for a given embodiment or claim, it is to be understood that one or more option may be deleted from the list and the shortened list may form an alternative embodiment, whether or not such an alternative embodiment is specifically referred to.

Anti-FRα Antibody Constructs

The ADCs of the present disclosure comprise an anti-FRα antibody construct. In this context, the term "antibody construct" refers to a polypeptide or a set of polypeptides that comprises one or more antigen-binding domains, where each of the one or more antigen-binding domains specifically binds to an epitope or antigen. Where the antibody construct comprises two or more antigen-binding domains, each of the antigen-binding domains may bind the same epitope or antigen (i.e. the antibody construct is monospecific) or they may bind to different epitopes or antigens (i.e. the antibody construct is bispecific or multispecific). The antibody construct may further comprise a scaffold and the one or more antigen-binding domains can be fused or covalently attached to the scaffold, optionally via a linker, as described herein.

In accordance with the present disclosure, the anti-FRα antibody construct comprises at least one antigen-binding domain that specifically binds to human FRα (hFRα). By "specifically binds" to hFRα, it is meant that the antibody construct binds to hFRα but does not exhibit significant binding to any of human folate receptor beta (FOLR2), gamma (FOLR3) or delta (FOLR4). In certain embodiments, the anti-FRα antibody constructs of the present disclosure may be capable of binding to an FRα from one or more non-human species. In certain embodiments, the anti-FRα antibody constructs of the present disclosure are capable of binding to cynomolgus monkey FRα.

Human FRα is also known as "human folate receptor 1" or "FOLR1." The protein sequences of hFRα from various sources are known in the art and readily available from publicly accessible databases, such as GenBank or UniProtKB. Examples of hFRα sequences include for example those provided under NCBI reference numbers P15328, AAX29268.1, AAX37119.1, NP_057937.1 and NP_057936.1. An exemplary hFRα protein sequence is provided in Table 2 as SEQ ID NO: 1 (NCBI Reference Sequence: NP_057936.1). An exemplary cynomolgus monkey FRα protein sequence is also provided in Table 2 (SEQ ID NO: 2; NCBI Reference Sequence: XP_005579002.2).

TABLE 2

| Organism | Sequence | SEQ ID NO |
|---|---|---|
| Human | MAQRMTTQLLLLLVWVAVVG EAQTRIAWARTELLNVCMNA KHHKEKPGPEDKLHEQCRPW RKNACCSTNTSQEAHKDVSY LYRFNWNHCGEMAPACKRHF IQDTCLYECSPNLGPWIQQV DQSWRKERVLNVPLCKEDCE QWWEDCRTSYTCKSNWHKGW NWTSGFNKCAVGAACQPFHF YFPTPTVLCNEIWTHSYKVS NYSRGSGRCIQMWFDPAQGN PNEEVARFYAAAMSGAGPWA AWPFLLSLALMLLWLLS | 1 |
| Cynomolgus Monkey | MAQRMTTQLLLLLVWVAVVG EAQTRTTRARTELLNVCMNA KHHKEKPGPEDKLHEQCRPW KKNACCSTNTSQEAHKDVSY LYRFNWNHCGEMAPACKRHF IQDTCLYECSPNLGPWIQQV DQSWRKERVLNVPLCKEDCE QWWEDCRTSYTCKSNWHKGW NWTSGFNKCPVGAACQPFHF YFPTPTVLCNEIWTYSYKVS NYSRGSGRCIQMWFDPAQGN PNEEVARFYAAAMSGAGPWA AWPLLLSLALTLLWLLS | 2 |

Human and Cynomolgus Monkey FRα Protein Sequences

Specific binding of an antigen-binding domain to a target antigen or epitope may be measured, for example, through an enzyme-linked immunosorbent assay (ELISA), a surface plasmon resonance (SPR) technique (employing, for example, a BIAcore instrument) (Liljeblad et al., 2000, *Glyco J,* 17:323-329), flow cytometry or a traditional binding assay (Heeley, 2002, *Endocr Res,* 28:217-229). In certain embodiments, specific binding may be defined as the extent of binding to a non-target protein (such as FOLR2, FOLR3 or FOLR4) being less than about 10% of the binding to hFRα as measured by ELISA or flow cytometry, for example. In certain embodiments, specific binding of an antibody construct for FRα may be defined by a dissociation constant ($K_D$) of ≤1 μM, for example, ≤500 nM, ≤250 nM, ≤100 nM, ≤50 nM, or ≤10 nM. In certain embodiments, specific binding of an antibody construct for a particular antigen or an epitope may be defined by a dissociation constant ($K_D$) of $10^{-6}$ M or less, for example, $10^{-7}$ M or less, or $10^{-8}$ M or less. In some embodiments, specific binding of an antibody construct for a particular antigen or an epitope may be defined by a dissociation constant ($K_D$) between $10^{-6}$ M and $10^{-9}$ M, for example, between $10^{-7}$ M and $10^{-9}$ M.

In certain embodiments, the anti-FRα antibody constructs of the present disclosure show higher internalization into FRα-expressing cells than the reference antibodies mirvetuximab (huMov19 or huFR107) and farletuzumab (MORAb-003).

Antibody internalization may be measured using art-known methods, for example, by a direct internalization method according to the protocol detailed in Schmidt, M. et al., 2008, *Cancer Immunol. Immunother.,* 57:1879-1890, or using commercially available fluorescent dyes such as the pHAb Dyes (Promega Corporation, Madison, WI), pHrodo iFL and Deep Red Dyes (ThermoFisher Scientific Corporation, Waltham, MA) and Incucyte® Fabfluor-pH Antibody Labeling Reagent (Sartorius AG, Göttingen, Germany), and analysis techniques such as microscopy, FACS, high content imaging or other plate-based assays.

In certain embodiments, the anti-FRα antibody construct is considered to demonstrate a higher internalization into FRα-expressing cells than a corresponding reference antibody (mirvetuximab or farletuzumab) when the amount of anti-FRα antibody construct internalized into the FRα-expressing cells is at least 1.2 times greater than the amount of reference antibody internalized into the same FRα-expressing cells under the same test conditions. In certain embodiments, the amount of internalized antibody is determined using an appropriate fluorescent dye and high content imaging. In some embodiments, the amount of internalized antibody is determined in cells that express FRα at a high level. In some embodiments, the amount of internalized antibody is determined in IGROV-1 cells or cells that express FRα at a similar level to IGROV-1 cells. In some embodiments, the amount of internalized antibody is determined after a 6-hour incubation period. In some embodiments, the amount of internalized antibody is determined after a 24-hour incubation period.

In certain embodiments, the anti-FRα antibody construct is considered to demonstrate a higher internalization into FRα-expressing cells than a corresponding reference antibody (mirvetuximab or farletuzumab) when the amount of anti-FRα antibody construct internalized into the FRα-expressing cells is at least 1.3 times greater, at least 1.4 times greater, at least 1.5 times greater, 1.6 times greater, 1.7 times greater, 1.8 times greater, 1.9 times greater, or 2.0 times greater, than the amount of reference antibody internalized into the same FRα-expressing cells under the same test conditions. In certain embodiments, the amount of internalized antibody is determined using an appropriate fluorescent dye and high content imaging. In some embodiments, the amount of internalized antibody is determined in cells that express FRα at a high level. In some embodiments, the amount of internalized antibody is determined in IGROV-1 cells or cells that express FRα at a similar level to IGROV-1 cells. In some embodiments, the amount of internalized antibody is determined after a 6-hour incubation period. In some embodiments, the amount of internalized antibody is determined after a 24-hour incubation period.

Antigen-Binding Domains

The anti-FRα antibody constructs of the present disclosure comprise at least one antigen-binding domain that is capable of binding to hFRα. The at least one antigen-binding domain capable of binding to hFRα typically is an immunoglobulin-based binding domain, such as an antigen-binding antibody fragment. Examples of an antigen-binding antibody fragment include, but are not limited to, a Fab fragment, a Fab' fragment, a single chain Fab (scFab), a single chain Fv (scFv) and a single domain antibody (sdAb).

A "Fab fragment" contains the constant domain of the light chain (CL) and the first constant domain of the heavy chain (CH1) along with the variable domains of the light and heavy chains (VL and VH, respectively). Fab' fragments differ from Fab fragments by the addition of a few amino acid residues at the C-terminus of the heavy chain CH1 domain, including one or more cysteines from the antibody hinge region. A Fab fragment may also be a single-chain Fab molecule, i.e. a Fab molecule in which the Fab light chain and the Fab heavy chain are connected by a peptide linker to form a single peptide chain. For example, the C-terminus of the Fab light chain may be connected to the N-terminus of the Fab heavy chain in the single-chain Fab molecule.

An "scFv" includes a heavy chain variable domain (VH) and alight chain variable domain (VL) of an antibody in a single polypeptide chain. The scFv may optionally further comprise a polypeptide linker between the VH and VL domains which enables the scFv to form a desired structure for antigen binding. For example, an scFv may include a VL connected from its C-terminus to the N-terminus of a VH by a polypeptide linker. Alternately, an scFv may comprise a VH connected through its C-terminus to the N-terminus of a VL by a polypeptide linker (see review in Pluckthun in *The Pharmacology of Monoclonal Antibodies*, vol. 113, Rosenburg and Moore eds., Springer-Verlag, New York, pp. 269-315 (1994)).

An "sdAb" format refers to a single immunoglobulin domain. The sdAb may be, for example, of camelid origin. Camelid antibodies lack light chains and their antigen-binding sites consist of a single domain, termed a "VHH." An sdAb comprises three CDR/hypervariable loops that form the antigen-binding site: CDR1, CDR2 and CDR3. sdAbs are fairly stable and easy to express, for example, as a fusion with the Fc chain of an antibody (see, for example, Harmsen & De Haard, 2007*, Appl. Microbiol Biotechnol.,* 77(1):13-22).

In those embodiments in which the anti-FRα antibody constructs comprise two or more antigen-binding domains, each additional antigen-binding domain may independently be an immunoglobulin-based domain, such as an antigen-binding antibody fragment, or a non-immunoglobulin-based domain, such as a non-immunoglobulin-based antibody mimetic, or other polypeptide or small molecule capable of specifically binding to its target, for example, a natural or engineered ligand. Non-immunoglobulin-based antibody mimetic formats include, for example, anticalins, fynomers, affimers, alphabodies, DARPins and avimers.

The present disclosure describes herein the identification of an antibody that specifically binds hFRα (variant v23924), as well as representative humanized versions of this antibody (variants v30384, v30389, v30394, v30399, v31422, v31423, v31424, v31425 and v31426) and representative affinity-matured versions of this antibody (variants v35305, v35342, v35347, v35348, v35350, v35354, v35356, v35358, v36167, v36168 and v36675) (see Examples and Sequence Tables). Epitope mapping using the hFRα sequence shown in FIG. 7 (SEQ ID NO: 15) determined that the epitope within the hFRα protein bound by variant v23924 comprises the amino acid residues E120, D121, R123, T124, S125 and Y126 of SEQ ID NO: 15 (see Example 13).

In certain embodiments, the at least one antigen-binding domain that binds hFRα comprised by the anti-FRα antibody constructs of the present disclosure binds an epitope within the hFRα protein that comprises the amino acid residues E120, D121, R123, T124, S125 and Y126 of SEQ ID NO: 15. In some embodiments, the hFRα epitope bound by the anti-FRα antibody constructs is a non-linear (or discontinuous) epitope comprising the amino acid residues E120, D121, R123, T124, S125 and Y126 of SEQ ID NO: 15. In certain embodiments, the anti-FRα antibody constructs of the present disclosure comprise an antigen-binding domain that competes for binding to hFRα with an antibody that binds to an epitope within the hFRα protein comprising the amino acid residues E120, D121, R123, T124, S125 and Y126. In certain embodiments, the anti-FRα antibody constructs of the present disclosure comprise an antigen-binding domain that competes for binding to hFRα with antibody v23924 described herein.

One can determine whether an antibody construct competes for binding to hFRα with an antibody that binds to an epitope within the hFRα protein comprising the amino acid residues E120, D121, R123, T124, S125 and Y126 or with antibody v23924 using competition assays known in the art. For example, the antibody that binds to an epitope within the hFRα protein comprising the amino acid residues E120, D121, R123, T124, S125 and Y126 or antibody v23924 (the reference antibody) is first allowed to bind to hFRα under saturating conditions and then the ability of the test antibody construct to bind to hFRα is measured. If the test antibody construct is able to bind to hFRα at the same time as the reference antibody, then the test antibody construct is considered to bind to a different epitope than the reference antibody. Conversely, if the test antibody construct is not able to bind to hFRα at the same time as the reference antibody, then the test antibody construct is considered to bind to the same epitope, to an overlapping epitope, or to an epitope that is in close proximity to the epitope bound by the reference antibody. Competition assays may also be run in which the binding order of the reference and test antibodies is reversed, that is, the test antibody is first allowed to bind to hFRα under saturating conditions and then the ability of the reference antibody construct to bind to hFRα is measured.

Such competition assays can be performed using techniques such as ELISA, radioimmunoassay, surface plasmon resonance (SPR), bio-layer interferometry, flow cytometry and the like. An "antibody that competes with" a reference antibody refers to an antibody that blocks binding of the reference antibody to its epitope in a competition assay by 50% or more.

In certain embodiments, the anti-FRα antibody constructs of the present disclosure comprise at least one antigen-binding domain that specifically binds to hFRα, where the antigen-binding domain comprises a set of CDRs based on the CDRs of antibody variant v23924 described herein. The CDR sequences of the antibody v23924 and representative humanized or affinity-matured versions of this antibody are shown in FIG. 11. Analysis of the CDR sequences from the parental and affinity-matured anti-FRα antibodies identified a minimal amino acid sequence present in each CDR as defined by any one of the IMGT, Chothia, Kabat, Contact or AbM numbering systems. These amino acid sequences are represented by the minimal consensus CDR sequences provided in Table 3. Extended versions of these CDR consensus sequences based on CDR sequences defined by the AbM numbering system are shown in Table 4.

TABLE 3

Minimal CDR Consensus Sequences of Anti-FRα Antibodies

| CDR | Sequence | Variable (X) | SEQ ID NO |
|---|---|---|---|
| Heavy Chain | | | |
| HCDR1 | $X^1$YGVS | $X^1$ is S or L | 3 |
| HCDR2 | NSGGS | | 4 |
| HCDR3 | SGSGYPM DY$X^2X^3$I | $X^2$ is L or H<br>$X^3$ is A or P | 5 |
| Light Chain | | | |
| LCDR1 | QSI$X^4X^5$W | $X^4$ is G or W<br>$X^5$ is D or Y | 6 |

TABLE 3-continued

| Minimal CDR Consensus Sequences of Anti-FRα Antibodies | | | |
|---|---|---|---|
| CDR | Sequence | Variable (X) | SEQ ID NO |
| LCDR2 | EAS | | 7 |
| LCDR3 | QQGYGRX$^{6}$ X$^{7}$X$^{8}$X$^{9}$N | X$^{6}$ is S or W<br>X$^{7}$ is N or H<br>X$^{8}$ is V or I<br>X$^{9}$ is D or L | 8 |

TABLE 4

| CDR Consensus Sequences of Anti-FRα Antibodies based on AbM Numbering System | | | |
|---|---|---|---|
| CDR | Sequence | Variable | SEQ ID NO |
| Heavy Chain | | | |
| HCDR1 | GFSLSX$^{10}$YGVS | X$^{10}$ is S or L | 9 |
| HCDR2 | X$^{11}$X$^{12}$NSGGSAY | X$^{11}$ is S or A<br>X$^{12}$ is V or L | 10 |
| HCDR3 | SGSGYPMDY X$^{13}$X$^{14}$I | X$^{13}$ is L or H<br>X$^{14}$ $^{14}$ is A or P | 11 |
| Light Chain | | | |
| LCDR1 | X$^{15}$ASQSIX$^{16}$ X$^{17}$WLA | X$^{15}$ is R or Q<br>X$^{16}$ is G or W<br>X$^{17}$ is D or Y | 12 |
| LCDR2 | EASTLAS | | 13 |
| LCDR3 | QQGYGRX$^{18}$X$^{19}$ X$^{20}$X$^{21}$NI | X$^{18}$ is S or W<br>X$^{19}$ is N or H<br>X$^{20}$ is V or I<br>X$^{21}$ is D or L | 14 |

In certain embodiments, the anti-FRα antibody constructs of the present disclosure comprise an antigen-binding domain having heavy chain CDR amino acid sequences (HCDR1, HCDR2 and HCDR3) comprising the sequences as set forth in SEQ ID NOs: 3, 4 and 5, and light chain CDR amino acid sequences (LCDR1, LCDR2 and LCDR3) comprising the sequences as set forth in SEQ ID NOs: 6, 7 and 8.

In certain embodiments, the anti-FRα antibody constructs of the present disclosure comprise an antigen-binding domain having:

(i) an HCDR1 amino acid sequence as set forth in SEQ ID NO: 3; an HCDR2 amino acid sequence as set forth in SEQ ID NO: 4, and an HCDR3 amino acid sequence as set forth in SEQ ID NO: 5, where $X^2$ is L and $X^3$ is A, or $X^2$ is H and $X^3$ is P, and (ii) an LCDR1 amino acid sequence as set forth in SEQ ID NO: 6, where $X^4$ is G and $X^5$ is D, or $X^4$ is W and $X^5$ is Y; an LCDR2 amino acid sequence as set forth in SEQ ID NO: 7, and an LCDR3 amino acid sequence as set forth in SEQ ID NO: 8, where $X^6$ is S, $X^7$ is N, $X^8$ is V and $X^9$ is D, or $X^6$ is W, $X^7$ is H, $X^8$ is I and $X^9$ is L.

In certain embodiments, the anti-FRα antibody constructs of the present disclosure comprise an antigen-binding domain having heavy chain CDR amino acid sequences (HCDR1, HCDR2 and HCDR3) comprising the sequences as set forth in SEQ ID NOs: 9, 10 and 11, and light chain CDR amino acid sequences (LCDR1, LCDR2 and LCDR3) comprising the sequences as set forth in SEQ ID NOs: 12, 13 and 14.

In certain embodiments, the anti-FRα antibody constructs of the present disclosure comprise an antigen-binding domain having:

(i) an HCDR1 amino acid sequence as set forth in SEQ ID NO: 9; an HCDR2 amino acid sequence as set forth in SEQ ID NO: 10, where $X^{11}$ is S or A and $X^{12}$ is V, or $X^{11}$ is S and $X^{12}$ is L, and an HCDR3 amino acid sequence as set forth in SEQ ID NO: 11, where $X^{13}$ is L and $X^{14}$ is A, or $X^{13}$ is H and $X^{14}$ is P, and (ii) an LCDR1 amino acid sequence as set forth in SEQ ID NO: 12, where $X^{15}$ is R or Q, $X^{16}$ is G and $X^{17}$ is D, or $X^{15}$ is R, $X^{16}$ is W and $X^{17}$ is Y; an LCDR2 amino acid sequence as set forth in SEQ ID NO: 13, and an LCDR3 amino acid sequence as set forth in SEQ ID NO: 14, where $X^{18}$ is S, $X^{19}$ is N, $X^{20}$ is V and $X^{21}$ is D, or $X^{18}$ is W, $X^{19}$ is H, $X^{20}$ is I and $X^{21}$ is L.

In certain embodiments, the anti-FRα antibody constructs of the present disclosure comprise an antigen-binding domain having:

(i) an HCDR1 amino acid sequence selected from the HCDR1 amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675; an HCDR2 amino acid sequence selected from the HCDR2 amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, and an HCDR3 amino acid sequence selected from the HCDR3 amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, and (ii) a LCDR1 amino acid sequence selected from the LCDR1 amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675; a LCDR2 amino acid sequence selected from the LCDR2 amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, and a LCDR3 amino acid sequence selected from the LCDR3 amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, where the CDR amino acid sequences are as defined by any one of the IMGT, Chothia, Kabat, Contact or AbM numbering systems (see FIG. 11).

In certain embodiments, the anti-FRα antibody constructs of the present disclosure comprise an antigen-binding domain having heavy chain CDR amino acid sequences (HCDR1, HCDR2 and HCDR3) selected from the heavy chain CDR amino acid sequences (HCDR1, HCDR2 and HCDR3) of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, as defined by any one of the IMGT, Chothia, Kabat, Contact or AbM numbering systems, and light chain CDR amino acid sequences (LCDR1, LCDR2 and LCDR3) selected from the light chain CDR amino acid sequences (LCDR1, LCDR2 and LCDR3) of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, as defined by any one of the IMGT, Chothia, Kabat, Contact or AbM numbering systems.

In certain embodiments, the anti-FRα antibody constructs of the present disclosure comprise an antigen-binding domain comprising heavy chain CDR amino acid sequences (HCDR1, HCDR2 and HCDR3) and light chain CDR amino acid sequences (LCDR1, LCDR2 and LCDR3) of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, as defined by any one of the IMGT, Chothia, Kabat, Contact or AbM numbering systems.

In certain embodiments, the anti-FRα antibody constructs of the present disclosure comprise an antigen-binding domain comprising the CDR sequences of the VH domain of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675. In certain embodiments, the anti-FRα antibody constructs of the present disclosure comprise an antigen-binding domain comprising the CDR sequences of the VL domain of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675. The VH and VL sequences of v23924, v30618, v30384, v30389, v30394, v30399, v31422, v31423, v31424, v31425, v31426, v35305, v35342, v35347, v35348, v35350, v35354, v35356, v35358, v36167, v36168 and v36675 are provided in FIG. 12.

In certain embodiments, the anti-FRα antibody constructs of the present disclosure comprise an antigen-binding domain comprising a VH amino acid sequence selected from the VH amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675. In certain embodiments, the anti-FRα antibody constructs of the present disclosure comprise an antigen-binding domain comprising a VL amino acid sequence selected from the VL amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675.

In certain embodiments, the anti-FRα antibody constructs of the present disclosure comprise an antigen-binding domain comprising a VH amino acid sequence and a VL amino acid sequence selected from the VH and VL amino acid sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675.

One skilled in the art will appreciate that a limited number of amino acid substitutions may be introduced into the CDR sequences or into the VH or VL sequences of known antibodies without the antibody losing its ability to bind its target. Candidate amino acid substitutions may be identified by computer modeling or by art-known techniques such as alanine scanning, with the resulting variants being tested for binding activity by standard techniques. Accordingly, in certain embodiments, the anti-FRα antibody constructs of the present disclosure comprise an antigen-binding domain that comprises a set of CDRs (i.e. heavy chain HCDR1, HCDR2 and HCDR3, and light chain LCDR1, LCDR2 and LCDR3) that have 90% or greater, 95% or greater, 98% or greater, 99% or greater, or 100% sequence identity to a set of CDRs of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, where the % sequence identity is calculated across all six CDRs and where the antigen-binding domain retains the ability to bind hFRα.

In certain embodiments, the anti-FRα antibody constructs of the present disclosure comprise an antigen-binding domain that comprises a variant of the set of CDR sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, where the variant comprises between 1 and 10 amino acid substitutions across the set of CDRs (i.e. the CDRs may be modified by up to 10 amino acid substitutions with any combination of the six CDRs being modified), and where the antigen-binding domain retains the ability to bind hFRα. In some embodiments, the anti-FRα antibody constructs of the present disclosure comprise an antigen-binding domain that comprises a variant of the set of CDR sequences of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, where the variant comprises between 1 and 7 amino acid substitutions, between 1 and 5 amino acid substitutions, between 1 and 4 amino acid substitutions, between 1 and 3 amino acid substitutions, between 1 and 2 amino acid substitutions, or 1 amino acid substitution, across the set of CDRs, and where the antigen-binding domain retains the ability to bind hFRα.

In certain embodiments, the anti-FRα antibody constructs of the present disclosure comprise an antigen-binding domain that comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, where the antigen-binding domain retains the ability to bind hFRα. In certain embodiments, the anti-FRα antibody constructs of the present disclosure comprise an antigen-binding domain that comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence of any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, where the antigen-binding domain retains the ability to bind hFRα.

In certain embodiments, the anti-FRα antibody constructs of the present disclosure comprise an antigen-binding domain having:

(i) an HCDR1 amino acid sequence selected from the amino acid sequences as set forth in any one of SEQ ID NOs: 20, 23, 26, 28, 31, 92, 93, 94, 95 or 96; an HCDR2 amino acid sequence selected from the amino acid sequences as set forth in any one of SEQ ID NOs: 21, 24, 27, 29, 32, 51, 58, 100, 101, 102, 103, 109, 137, 138 or 139, and an HCDR3 amino acid sequence selected from the amino acid sequences as set forth in any one of SEQ ID NOs: 22, 25, 30, 107, 108 or 110, and (ii) a LCDR1 amino acid sequence selected from the amino acid sequences as set forth in any one of SEQ ID NOs: 40, 43, 45, 65, 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42, 47, 120 or 121.

In certain embodiments, the anti-FRα antibody constructs of the present disclosure comprise an antigen-binding domain comprising the CDR sequences of the VH domain having a sequence as set forth in any one of SEQ ID NOs: 19, 50, 54, 57, 61, 76, 79, 82, 85, 88, 91, 99, 106, 113, 116, 133 or 136. In certain embodiments, the anti-FRα antibody constructs of the present disclosure comprise an antigen-binding domain comprising the CDR sequences of the VL domain having a sequence as set forth in any one of SEQ ID NOs: 39, 64, 119, 124 or 130.

In certain embodiments, the anti-FRα antibody constructs of the present disclosure comprise an antigen-binding domain having:

(a) a LCDR1 amino acid sequence selected from the amino acid sequences as set forth in any one of SEQ ID NOs: 40, 43 or 45; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, and an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 27, 29 or 32; an HCDR3 amino acid sequence selected from the amino acid sequences as set forth in any one of SEQ ID NOs: 22, 25 or 30;

(b) a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, and an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 51; an HCDR3 amino acid sequence selected from the amino acid sequences as set forth in any one of SEQ ID NOs: 22, 25 or 30;

(c) a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, and (i) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 51; an HCDR3 amino acid sequence selected from the amino acid sequences as set forth in any one of SEQ ID NOs: 22, 25 or 30, or (ii) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 58; an HCDR3 amino acid sequence selected from the amino acid sequences as set forth in any one of SEQ ID NOs: 22, 25 or 30, or (iii) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 24, 100, 101, 102 or 103; an HCDR3 amino acid sequence selected from the amino acid sequences as set forth in any one of SEQ ID NOs: 22, 25 or 30; or (d) a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, and (i) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 24, 100, 101, 102 or 103; an HCDR3 amino acid sequence selected from the amino acid sequences as set forth in any one of SEQ ID NOs: 22, 25 or 30, or (ii) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110, or (iii) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 22, 25 or 30, or (iv) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110, or (v) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 22, 25 or 30, or (vi) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 137, 138 or 139; an HCDR3 amino acid sequence selected from the amino acid sequences as set forth in any one of SEQ ID NOs: 22, 25 or 30; or (e) a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, and (i) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110, or (ii) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110.

In certain embodiments, the anti-FRα antibody constructs of the present disclosure comprise an antigen-binding domain having:

(a) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 27, 29 or 32; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 40, 43 or 45; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, or (b) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 51; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, or (c) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 58; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, or (d) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 51; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, or (e) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 24, 100, 101, 102 or 103; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (f) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110; a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 42 or 47, or (g) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110; a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (h) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (i) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (j) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110; a LCDR1 amino acid sequence selected from the amino acid sequences as set forth in any one of SEQ ID NOs: 40, 45 or 65; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (k) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 107, 108 or 110; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (l) an HCDR1 amino acid sequence selected from the amino acid sequences as set forth in any one of SEQ ID NOs: 20, 23, 26, 28 or 31; an HCDR2 amino acid sequence selected from the amino acid sequences as set forth in any one of SEQ ID NOs: 21, 24, 29, 32 or 109; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121, or (m) an HCDR1 amino acid sequence selected from the amino acid sequences as set forth in any one of SEQ ID NOs: 92, 93, 94, 95 or 96; an HCDR2 amino acid sequence selected from the amino acid sequences as set forth in any one of SEQ ID NOs: 21, 24, 137, 138 or 139; an HCDR3 amino acid sequence selected from the amino acid sequences as set forth in any one of SEQ ID NOs: 22, 25 or 30; a LCDR1 amino acid sequence selected from the amino acid sequences as set forth in any one of SEQ ID NOs: 125, 126 or 127; a LCDR2 amino acid sequence selected from the amino acid sequences as set forth in any one of SEQ ID NOs: 41, 44 or 46, and a LCDR3 amino acid sequence selected from the amino acid sequences as set forth in any one of SEQ ID NOs: 120 or 121.

In certain embodiments, the anti-FRα antibody constructs of the present disclosure comprise an antigen-binding domain comprising a VH amino acid sequence selected from the VH amino acid sequences as set forth in any one of SEQ ID NOs: 19, 50, 54, 57, 61, 76, 79, 82, 85, 88, 91, 99, 106, 113, 116, 133 or 136. In certain embodiments, the anti-FRα antibody constructs of the present disclosure comprise an antigen-binding domain comprising a VL amino acid sequence selected from the VL amino acid sequences as set forth in any one of SEQ ID NOs: 39, 64, 119, 124 or 130.

In certain embodiments, the anti-FRα antibody constructs of the present disclosure comprise an antigen-binding domain comprising a VH amino acid sequence selected from the VH amino acid sequences as set forth in any one of SEQ ID NOs: 19, 50, 54, 57, 61, 76, 79, 82, 85, 88, 91, 99, 106, 113, 116, 133 or 136, and a VL amino acid sequence selected from the VL amino acid sequences as set forth in any one of SEQ ID NOs: 39, 64, 119, 124 or 130.

In certain embodiments, the anti-FRα antibody constructs of the present disclosure comprise an antigen-binding domain comprising:

(a) a VL amino acid sequence as set forth in SEQ ID NO: 39, and a VH amino acid sequence as set forth in SEQ ID NO: 19; or (b) a VL amino acid sequence as set forth in SEQ ID NO: 124, and a VH amino acid sequence as set forth in SEQ ID NO: 91; or
(c) a VL amino acid sequence as set forth in SEQ ID NO: 64, and
  (i) a VH amino acid sequence as set forth in SEQ ID NO: 50, or
  (ii) a VH amino acid sequence as set forth in SEQ ID NO: 54, or
  (iii) a VH amino acid sequence as set forth in SEQ ID NO: 57, or
  (iv) a VH amino acid sequence as set forth in SEQ ID NO: 61, or
  (v) a VH amino acid sequence as set forth in SEQ ID NO: 76, or
  (vi) a VH amino acid sequence as set forth in SEQ ID NO: 79, or
  (vii) a VH amino acid sequence as set forth in SEQ ID NO: 82, or
  (viii) a VH amino acid sequence as set forth in SEQ ID NO: 85, or
  (ix) a VH amino acid sequence as set forth in SEQ ID NO: 88, or
  (x) a VH amino acid sequence as set forth in SEQ ID NO: 106; or
(d) a VL amino acid sequence as set forth in SEQ ID NO: 130, and
  (i) a VH amino acid sequence as set forth in SEQ ID NO: 99, or
  (ii) a VH amino acid sequence as set forth in SEQ ID NO: 106, or
  (iii) a VH amino acid sequence as set forth in SEQ ID NO: 113, or
  (iv) a VH amino acid sequence as set forth in SEQ ID NO: 116, or
  (v) a VH amino acid sequence as set forth in SEQ ID NO: 133, or
  (vi) a VH amino acid sequence as set forth in SEQ ID NO: 136; or
(e) a VL amino acid sequence as set forth in SEQ ID NO: 119, and
  (i) a VH amino acid sequence as set forth in SEQ ID NO: 106, or
  (ii) a VH amino acid sequence as set forth in SEQ ID NO: 116.

In certain embodiments, the anti-FRα antibody constructs of the present disclosure comprise an antigen-binding domain comprising:
(i) a VH amino acid sequence as set forth in SEQ ID NO: 19, and a VL amino acid sequence as set forth in SEQ ID NO: 39, or
(ii) a VH amino acid sequence as set forth in SEQ ID NO: 50, and a VL amino acid sequence as set forth in SEQ ID NO: 64, or
(iii) a VH amino acid sequence as set forth in SEQ ID NO: 54, and a VL amino acid sequence as set forth in SEQ ID NO: 64, or
(iv) a VH amino acid sequence as set forth in SEQ ID NO: 57, and a VL amino acid sequence as set forth in SEQ ID NO: 64, or
(v) a VH amino acid sequence as set forth in SEQ ID NO: 61, and a VL amino acid sequence as set forth in SEQ ID NO: 64, or
(vi) a VH amino acid sequence as set forth in SEQ ID NO: 76, and a VL amino acid sequence as set forth in SEQ ID NO: 64, or
(vii) a VH amino acid sequence as set forth in SEQ ID NO: 79, and a VL amino acid sequence as set forth in SEQ ID NO: 64, or
(viii) a VH amino acid sequence as set forth in SEQ ID NO: 82, and a VL amino acid sequence as set forth in SEQ ID NO: 64, or
(ix) a VH amino acid sequence as set forth in SEQ ID NO: 85, and a VL amino acid sequence as set forth in SEQ ID NO: 64, or
(x) a VH amino acid sequence as set forth in SEQ ID NO: 88, and a VL amino acid sequence as set forth in SEQ ID NO: 64, or
(xi) a VH amino acid sequence as set forth in SEQ ID NO: 91, and a VL amino acid sequence as set forth in SEQ ID NO: 124, or
(xii) a VH amino acid sequence as set forth in SEQ ID NO: 99, and a VL amino acid sequence as set forth in SEQ ID NO: 130, or
(xiii) a VH amino acid sequence as set forth in SEQ ID NO: 106, and a VL amino acid sequence as set forth in SEQ ID NO: 64, or
(xiv) a VH amino acid sequence as set forth in SEQ ID NO: 106, and a VL amino acid sequence as set forth in SEQ ID NO: 119, or
(xv) a VH amino acid sequence as set forth in SEQ ID NO: 106, and a VL amino acid sequence as set forth in SEQ ID NO: 130, or
(xvi) a VH amino acid sequence as set forth in SEQ ID NO: 113, and a VL amino acid sequence as set forth in SEQ ID NO: 130, or
(xvii) a VH amino acid sequence as set forth in SEQ ID NO: 116, and a VL amino acid sequence as set forth in SEQ ID NO: 119 or
(xviii) a VH amino acid sequence as set forth in SEQ ID NO: 116, and a VL amino acid sequence as set forth in SEQ ID NO: 130, or
(xix) a VH amino acid sequence as set forth in SEQ ID NO: 133, and a VL amino acid sequence as set forth in SEQ ID NO: 130, or
(xx) a VH amino acid sequence as set forth in SEQ ID NO: 136, and a VL amino acid sequence as set forth in SEQ ID NO: 130.

Formats

The anti-FRα antibody constructs may have various formats. The minimal component of the anti-FRα antibody construct is an antigen-binding domain that binds to hFRα. The anti-FRα antibody constructs may further optionally comprise one or more additional antigen-binding domains and/or a scaffold. In those embodiments in which the anti-FRα antibody construct comprises two or more antigen-binding domains, each additional antigen-binding domain may bind to the same epitope within hFRα, may bind to a different epitope within hFRα, or may bind to a different antigen. Thus, the anti-FRα antibody construct may be, for example, monospecific, biparatopic, bispecific or multispecific.

In certain embodiments, the anti-FRα antibody construct comprises at least one antigen-binding domain that binds to hFRα and a scaffold, where the antigen-binding domain is operably linked to the scaffold. The term "operably linked," as used herein, means that the components described are in a relationship permitting them to function in their intended manner. Examples of suitable scaffolds are described below.

In certain embodiments, the anti-FRα antibody construct comprises two antigen-binding domains optionally operably linked to a scaffold. In some embodiments, the anti-FRα antibody construct may comprise three or four antigen-binding domains and optionally a scaffold. In these formats, when comprising a scaffold, at least a first antigen-binding domain is operably linked to the scaffold and the remaining antigen-binding domain(s) may each independently be operably linked to the scaffold or to the first antigen-binding domain or, when more than two antigen-binding domains are present, to another antigen-binding domain.

Anti-FRα antibody constructs that lack a scaffold may comprise a single antigen-binding domain in an appropriate format, such as an sdAb, or they may comprise two or more antigen-binding domains optionally operably linked by one or more linkers. In such anti-FRα antibody constructs, the antigen-binding domains may be in the form of scFvs, Fabs, sdAbs, or a combination thereof. For example, using scFvs as the antigen-binding domains, formats such as a tandem scFv ($(scFv)_2$ or taFv) may be constructed, in which the scFvs are connected together by a flexible linker. scFvs may also be used to construct diabody formats, which comprise two scFvs connected by a short linker (usually about 5 amino acids in length). The restricted length of the linker results in dimerization of the scFvs in a head-to-tail manner. In any of the preceding formats, the scFvs may be further stabilized by inclusion of an interdomain disulfide bond. For example, a disulfide bond may be introduced between VL and VH through introduction of an additional cysteine residue in each chain (for example, at position 44 in VH and position 100 in VL) (see, for example, Fitzgerald et al., 1997, *Protein Engineering,* 10:1221-1225), or a disulfide bond may be introduced between two VHs to provide a construct having a DART format (see, for example, Johnson et al., 2010, *J Mol. Biol.,* 399:436-449).

Similarly, formats comprising two sdAbs, such as VHs or VHHs, connected together through a suitable linker may be employed in some embodiments. Other examples of anti-FRα antibody construct formats that lack a scaffold include those based on Fab fragments, for example, $Fab_2$ and $F(ab')_2$ formats, in which the Fab fragments are connected through a linker or an IgG hinge region.

Combinations of antigen-binding domains in different forms may also be employed to generate alternative scaffold-less formats. For example, an scFv or a sdAb may be fused to the C-terminus of either or both of the light and heavy chain of a Fab fragment resulting in a bivalent (Fab-scFv/sdAb) construct.

In certain embodiments, the anti-FRα antibody construct may be in an antibody format that is based on an immunoglobulin (Ig). In certain embodiments, the anti-FRα antibody construct may be based on an IgG class immunoglobulin, for example, an IgG1, IgG2, IgG3 or IgG4 immunoglobulin. In some embodiments, the anti-FRα antibody construct may be based on an IgG1 immunoglobulin. In the context of the present disclosure, when an anti-FRα antibody construct is based on a specified immunoglobulin isotype, it is meant that the anti-FRα antibody construct comprises all or a portion of the constant region of the specified immunoglobulin isotype. For example, an anti-FRα antibody construct based on a given Ig isotype may comprise at least one antigen-binding domain operably linked to an Ig scaffold, where the scaffold comprises an Fc region from the given isotype and optionally an Ig hinge region from the same or a different isotype. It is to be understood that the anti-FRα antibody constructs may also comprise hybrids of isotypes and/or subclasses in some embodiments. It is also to be understood that the Fc region and/or hinge region may optionally be modified to impart one or more desirable functional properties as is known in the art.

In some embodiments, the anti-FRα antibody constructs may be derived from two or more immunoglobulins that are from different species, for example, the anti-FRα antibody construct may be a chimeric antibody or a humanized antibody. The terms "chimeric antibody" and "humanized antibody" both refer generally to antibodies that combine immunoglobulin regions or domains from more than one species.

A "chimeric antibody" typically comprises at least one variable domain from a non-human antibody, such as a rabbit or rodent (for example, murine) antibody, and at least one constant domain from a human antibody. The human constant domain of a chimeric antibody need not be of the same isotype as the non-human constant domain it replaces. Chimeric antibodies are discussed, for example, in Morrison et al., 1984, *Proc. Natl. Acad. Sci. USA,* 81:6851-55, and U.S. Pat. No. 4,816,567.

A "humanized antibody" is a type of chimeric antibody that contains minimal sequence derived from a non-human antibody. Generally, humanized antibodies are human immunoglobulins (recipient antibody) in which residues from a hypervariable region (CDR) of the recipient are replaced by residues from a hypervariable region (CDR) of a non-human species (donor antibody), such as mouse, rat, rabbit or non-human primate, having the desired specificity and affinity for a target antigen. This technique for creating humanized antibodies is often referred to as "CDR grafting."

In some instances, additional modifications may be made to a humanized antibody to further refine antibody performance. For example, framework region (FR) residues of the human immunoglobulin are replaced by corresponding non-human residues, or the humanized antibodies may comprise residues that are not found in either the recipient antibody or the donor antibody. In general, a variable domain in a humanized antibody will comprise all or substantially all of the hypervariable regions from a non-human immunoglobulin and all or substantially all of the FRs from a human immunoglobulin sequence. Humanized antibodies are described in more detail in Jones, et al., 1986, *Nature,* 321:522-525; Riechmann, et al., 1988, *Nature,* 332:323-329, and Presta, 1992, *Curr. Op. Struct. Biol.,* 2:593-596, for example.

A number of approaches are known in the art for selecting the most appropriate human frameworks in which to graft the non-human CDRs. Early approaches used a limited subset of well-characterised human antibodies, irrespective of the sequence identity to the non-human antibody providing the CDRs (the "fixed frameworks" approach). More recent approaches have employed variable regions with high amino acid sequence identity to the variable regions of the non-human antibody providing the CDRs ("homology matching" or "best-fit" approach). An alternative approach is to select fragments of the framework sequences within each light or heavy chain variable region from several different human antibodies. CDR-grafting may in some cases result in a partial or complete loss of affinity of the grafted molecule for its target antigen. In such cases, affinity can be restored by back-mutating some of the residues of human origin to the corresponding non-human ones. Methods for preparing humanized antibodies by these approaches are well-known in the art (see, for example, Tsurushita & Vasquez, 2004, *Humanization of Monoclonal Antibodies*, Molecular Biology of B Cells, 533-545, Elsevier Science (USA); Jones et al., 1986, *Nature,* 321:522-525; Riechmann et al., 1988, *Nature,* 332:323-329; Presta et al., 1997, *Cancer Res,* 57(20):4593-4599).

Alternatively, or in addition to, these traditional approaches, more recent technologies may be employed to further reduce the immunogenicity of a CDR-grafted humanized antibody. For example, frameworks based on human germline sequences or consensus sequences may be employed as acceptor human frameworks rather than human frameworks with somatic mutation(s). Another technique that aims to reduce the potential immunogenicity of non-human CDRs is to graft only specificity-determining residues (SDRs). In this approach, only the minimum CDR residues required for antigen-binding activity (the "SDRs") are grafted into a human germline framework. This method improves the "humanness" (i.e. the similarity to human germline sequence) of the humanized antibody and thus may help reduce the risk of immunogenicity of the variable region. These techniques have been described in various publications (see, for example, Almagro & Fransson, 2008, *Front Biosci,* 13:1619-1633; Tan, et al., 2002, *J Immunol,* 169:1119-1125; Hwang, et al., 2005, *Methods,* 36:35-42; Pelat, et al., 2008, *J Mol Biol,* 384:1400-1407; Tamura, et al., 2000, *J Immunol,* 164:1432-1441; Gonzales, et al., 2004, *Mol Immunol,* 1:863-872, and Kashmiri, et al., 2005, *Methods,* 36:25-34).

In certain embodiments, the anti-FRα antibody construct of the present disclosure comprises humanized antibody sequences, for example, one or more humanized variable domains. In some embodiments, the anti-FRα antibody construct can be a humanized antibody. Non-limiting examples of humanized antibodies based on the anti-FRα antibody v23924 are described herein (v30384, v30389, v30394, v30399, v31422, v31423, v31424, v31425 and v31426; see Examples and Sequence Tables).

Scaffolds

In certain embodiments, the anti-FRα antibody constructs comprise one or more antigen-binding domains operably linked to a scaffold. The antigen-binding domain(s) may be in one or a combination of the forms described above (for example, scFvs, Fabs and/or sdAbs). Examples of suitable scaffolds are described in more detail below and include, but are not limited to, immunoglobulin Fc regions, albumin, albumin analogues and derivatives, heterodimerizing peptides (such as leucine zippers, heterodimer-forming "zipper" peptides derived from Jun and Fos, IgG CH1 and CL domains or barnase-barstar toxins), cytokines, chemokines or growth factors. Other examples include antibodies based on the DOCK-AND-LOCK™ (DNL™) technology developed by IBC Pharmaceuticals, Inc. and Immunomedics, Inc. (see, for example, Chang, et al., 2007, *Clin. Cancer Res.,* 13:5586s-5591s).

A scaffold may be a peptide, polypeptide, polymer, nanoparticle or other chemical entity. Where the scaffold is a polypeptide, each antigen-binding domain of the anti-FRα antibody construct may be linked to either the N- or C-terminus of the polypeptide scaffold. Anti-FRα antibody constructs comprising a polypeptide scaffold in which one or more of the antigen-binding domains are linked to a region other than the N- or C-terminus, for example, via the side chain of an amino acid with or without a linker, are also contemplated in certain embodiments.

In embodiments where the anti-FRα antibody construct comprises a scaffold that is a peptide or polypeptide, the antigen-binding domain(s) may be linked to the scaffold by genetic fusion or chemical conjugation. Typically, when the scaffold is a peptide or polypeptide, the antigen-binding domain(s) are linked to the scaffold by genetic fusion. In some embodiments, where the scaffold is a polymer or nanoparticle, the antigen-binding domain(s) may be linked to the scaffold by chemical conjugation.

A number of protein domains are known in the art that comprise selective pairs of two different polypeptides and may be used to form a scaffold. An example is leucine zipper domains such as Fos and Jun that selectively pair together (Kostelny, et al., J Immunol, 148:1547-53 (1992); Wranik, et al., J. Biol. Chem., 287: 43331-43339 (2012)). Other selectively pairing molecular pairs include, for example, the barnase-barstar pair (Deyev, et al., Nat Biotechnol, 21:1486-1492 (2003)), DNA strand pairs (Chaudri, et al., FEBS Letters, 450(1-2):23-26 (1999)) and split fluorescent protein pairs (International Patent Application Publication No. WO 2011/135040).

Other examples of protein scaffolds include immunoglobulin Fc regions, albumin, albumin analogues and derivatives, toxins, cytokines, chemokines and growth factors. The use of protein scaffolds in combination with antigen-binding moieties has been described (see, for example, Muller et al., 2007, *J. Biol. Chem.,* 282:12650-12660; McDonaugh et al., 2012, *Mol. Cancer Ther.,* 11:582-593; Vallera et al., 2005, *Clin. Cancer Res.,* 11:3879-3888; Song et al., 2006, *Biotech. Appl. Biochem.,* 45:147-154, and U.S. Patent Application Publication No. 2009/0285816).

For example, fusing antigen-binding moieties such as scFvs, diabodies or single chain diabodies to albumin has been shown to improve the serum half-life of the antigen-binding moieties (Muller et al., ibid.). Antigen-binding moieties may be fused at the N- and/or C-termini of albumin, optionally via a linker.

Derivatives of albumin in the form of heteromultimers that comprise two transporter polypeptides obtained by segmentation of an albumin protein such that the transporter polypeptides self-assemble to form quasi-native albumin have been described (see International Patent Application Publication Nos. WO 2012/116453 and WO 2014/012082). As a result of the segmentation of albumin, the heteromultimer includes four termini and thus can be fused to up to four different antigen-binding moieties, optionally via linkers.

In certain embodiments, the anti-FRα antibody construct may comprise a protein scaffold.

In some embodiments, the anti-FRα antibody construct may comprise a protein scaffold that is based on an immunoglobulin Fc region, an albumin or an albumin analogue or derivative. In some embodiments, the anti-FRα antibody construct may comprise a protein scaffold that is based on an immunoglobulin Fc region, for example, an IgG Fc region.

Fc Regions

The terms "Fe region," "Fc" or "Fc domain" as used herein refer to a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, MD (1991).

In certain embodiments, the anti-FRα antibody constructs may comprise a scaffold that is based on an immunoglobulin Fc region. The Fc region may be dimeric and composed of two Fc polypeptides or alternatively, the Fc region may be composed of a single polypeptide.

An "Fe polypeptide" in the context of a dimeric Fc refers to one of the two polypeptides forming the dimeric Fc domain, i.e. a polypeptide comprising one or more C-terminal constant regions of an immunoglobulin heavy chain that is capable of stable self-association. When referring to the polypeptides forming a dimeric Fc region, the terms "first Fc polypeptide" and "second Fc polypeptide" may be used interchangeably provided that the Fc region comprises one first Fc polypeptide and one second Fc polypeptide.

An Fc region may comprise a CH3 domain or it may comprise both a CH3 and a CH2 domain. For example, in certain embodiments, an Fc polypeptide of a dimeric IgG Fc region may comprise an IgG CH2 domain sequence and an IgG CH3 domain sequence. In such embodiments, the CH3 domain comprises two CH3 sequences, one from each of the two Fc polypeptides of the dimeric Fc region, and the CH2 domain comprises two CH2 sequences, one from each of the two Fc polypeptides of the dimeric Fc region.

In some embodiments, the anti-FRα antibody construct may comprise a scaffold that is based on an IgG Fc region. In some embodiments, the anti-FRα antibody construct may comprise a scaffold that is based on a human IgG Fc region. In some embodiments, the anti-FRα antibody construct may comprise a scaffold based on an IgG1 Fc region. In some embodiments, the anti-FRα antibody construct may comprise a scaffold based on a human IgG1 Fc region.

In certain embodiments, the anti-FRα antibody construct may comprise a scaffold based on an IgG Fc region, which is a homodimeric Fc region, comprising a first Fc polypeptide and a second Fc polypeptide, each comprising a CH3 sequence, and optionally a CH2 sequence and in which the amino acid sequences of the first and second Fc polypeptides are the same.

In certain embodiments, the anti-FRα antibody construct may comprise a scaffold based on an IgG Fc region, which is a heterodimeric Fc region, comprising a first Fc polypeptide and a second Fc polypeptide, each comprising a CH3 sequence, and optionally a CH2 sequence and in which the amino acid sequences of the first and second Fc polypeptides are different. In some embodiments, the anti-FRα antibody construct may comprise a scaffold based on an Fc region which comprises two CH3 sequences, at least one of which comprises one or more amino acid modifications. In some embodiments, the anti-FRα antibody construct may comprise a scaffold based on an Fc region which comprises two CH3 sequences and two CH2 sequences, at least one of the CH2 sequences comprising one or more amino acid modifications.

In some embodiments, the anti-FRα antibody construct may comprise a heterodimeric Fc region comprising a modified CH3 domain, where the modified CH3 domain is an asymmetrically modified CH3 domain comprising one or more asymmetric amino acid modifications. As used herein, an "asymmetric amino acid modification" refers to a modification, such as a substitution or an insertion, in which an amino acid at a specific position on a first CH3 or CH2 sequence is different to the amino acid on a second CH3 or CH2 sequence at the same position. These asymmetric amino acid modifications can be a result of modification of only one of the two amino acids at the same respective amino acid position on each sequence, or different modifications of both amino acids at the same respective position on each of the first and second CH3 or CH2 sequences. Each of the first and second CH3 or CH2 sequences of a heterodimeric Fc may comprise one or more than one asymmetric amino acid modification.

In some embodiments, the anti-FRα antibody construct may comprise a heterodimeric Fc comprising a modified CH3 domain, where the modified CH3 domain comprises one or more amino acid modifications that promote formation of the heterodimeric Fc over formation of a homodimeric Fc. In some embodiments, one or more of the amino acid modifications are asymmetric amino acid modifications.

Amino acid modifications that may be made to the CH3 domain of an Fc in order to promote formation of a heterodimeric Fc are known in the art and include, for example, those described in International Publication No. WO 96/027011 ("knobs into holes"), Gunasekaran et al., 2010, *J Biol Chem,* 285, 19637-46 ("electrostatic steering"), Davis et al., 2010, *Prot Eng Des Sel,* 23(4):195-202 (strand exchange engineered domain (SEED) technology) and Labrijn et al., 2013, *Proc Natl Acad Sci USA,* 110(13):5145-50 (Fab-arm exchange). Other examples include approaches combining positive and negative design strategies to produce stable asymmetrically modified Fc regions as described in International Publication Nos. WO 2012/058768 and WO 2013/063702. In certain embodiments, the anti-FRα antibody construct may comprise a scaffold based on a modified Fc region as described in International Publication No. WO 2012/058768 or WO 2013/063702.

Table 5 provides the amino acid sequence of the human IgG1 Fc sequence (SEQ ID NO:16), corresponding to amino acids 231 to 447 of the full-length human IgG1 heavy chain. The CH3 sequence comprises amino acids 341-447 of the full-length human IgG1 heavy chain. Also shown in Table 5 are CH3 domain amino acid modifications that promote formation of a heterodimeric Fc as described in in International Patent Application Publication Nos. WO 2012/058768 and WO 2013/063702.

In certain embodiments, the anti-FRα antibody construct may comprise a heterodimeric Fc scaffold having a modified CH3 domain comprising the modifications of any one of Variant 1, Variant 2, Variant 3, Variant 4 or Variant 5, as shown in Table 5.

TABLE 5

| Human IgG1 Fc Sequence[1] and CH3 Domain Amino Acid Modifications Promoting Heterodimer Formation | | |
|---|---|---|
| APELLGGPSVFLFPPKPKDTLMISRTPEV TCVVVDVSHEDPEVKFNWYVDGVEVHNAK TKPREEQYNSTYRVVSVLTVLHQDWLNGK EYKCKVSNKALPAPIEKTISKAKGQPREP QVYTLPPSRDELTKNQVSLTCLVKGFYPS DIAVEWESNGQPENNYKTTPPVLDSDGSF FLYSKLTVDKSRWQQGNVFSCSVMHEALH NHYTQKSLSLSPGK (SEQ ID NO: 16) | | |
| Variant No | Chain | Mutations |
| 1 | A | L351Y_F405A_Y407V |
| | B | T366L_K392M_T394W |
| 2 | A | L351Y_F405A_Y407V |
| | B | T366L_K392L_T394W |
| 3 | A | T350V_L351Y_F405A_Y407V |
| | B | T350V_T366L_K392L_T394W |
| 4 | A | T350V_L351Y_F405A_Y407V |
| | B | T350V_T366L_K392M_T394W |
| 5 | A | T350V_L351Y_S400E_F405A_Y407V |
| | B | T350V_T366L_N390R_K392M_T394W |

[1]Sequence from positions 231-447 (EU numbering)

In some embodiments, the anti-FRα antibody construct may comprise a scaffold based on an Fc region comprising two CH3 sequences and two CH2 sequences, at least one of the CH2 sequences comprising one or more amino acid modifications. Modifications in the CH2 domain can affect the binding of Fc receptors (FcRs) to the Fc, such as receptors of the FcγRI, FcγRII and FcγRIII subclasses.

In some embodiments, the anti-FRα antibody construct comprises a scaffold based on an IgG Fc having a modified CH2 domain, wherein the modification of the CH2 domain results in altered binding to one or more of the FcγRI, FcγRII and FcγRIII receptors.

A number of amino acid modifications to the CH2 domain that selectively alter the affinity of the Fc for different Fcγ receptors are known in the art. Amino acid modifications that result in increased binding and amino acid modifications that result in decreased binding can each be useful in certain indications. For example, increasing binding affinity of an Fc for FcγRIIIa (an activating receptor) may result in increased antibody dependent cell-mediated cytotoxicity (ADCC), which in turn results in increased lysis of the target cell. Decreased binding to FcγRIIb (an inhibitory receptor) likewise may be beneficial in some circumstances. In certain indications, a decrease in, or elimination of, ADCC and complement-mediated cytotoxicity (CDC) may be desirable. In such cases, modified CH2 domains comprising amino acid modifications that result in increased binding to FcγRIIb or amino acid modifications that decrease or eliminate binding of the Fc region to all of the Fcγ receptors ("knock-out" variants) may be useful.

Examples of amino acid modifications to the CH2 domain that alter binding of the Fc by Fcγ receptors include, but are not limited to, the following: S298A/E333A/K334A and S298A/E333A/K334A/K326A (increased affinity for FcγRIIIa) (Lu, et al., 2011, *J Immunol Methods,* 365(1-2): 132-41); F243L/R292P/Y300L/V305I/P396 μL (increased affinity for FcγRIIIa) (Stavenhagen, et al., 2007, *Cancer Res,* 67(18):8882-90); F243L/R292P/Y300L/L235V/P396L (increased affinity for FcγRIIIa) (Nordstrom J L, et al., 2011, *Breast Cancer Res,* 13(6):R[123]); F243 μL (increased affinity for FcγRIIIa) (Stewart, et al., 2011, *Protein Eng Des Sel.,* 24(9):671-8); S298A/E333A/K334A (increased affinity for FcγRIIIa) (Shields, et al., 2001, *J Biol Chem,* 276(9):6591-604); S239D/I332E/A330 μL and S239D/I332E (increased affinity for FcγRIIIa) (Lazar, et al., 2006, *Proc Natl Acad Sci USA,* 103(11):4005-10), and S239D/S267E and S267E/L328F (increased affinity for FcγRIIb) (Chu, et al., 2008, *Mol Immunol,* 45(15):3926-33). Various amino acid modifications to the CH2 domain that alter binding of the Fc by FcγRIIb are described in International Publication No. WO 2021/232162. Additional modifications that affect Fc binding to Fcγ receptors are described in Therapeutic Antibody Engineering (Strohl & Strohl, Woodhead Publishing series in Biomedicine No 11, ISBN 1 907568 37 9, Oct 2012, page 283).

In certain embodiments, the anti-FRα antibody construct comprises a scaffold based on an IgG Fc having a modified CH2 domain, in which the modified CH2 domain comprises one or more amino acid modifications that result in decreased or eliminated binding of the Fc region to all of the Fcγ receptors (i.e. a "knock-out" variant).

Various publications describe strategies that have been used to engineer antibodies to produce "knock-out" variants (see, for example, Strohl, 2009, *Curr Opin Biotech* 20:685-691, and Strohl & Strohl, "*Antibody Fc engineering for optimal antibody performance*" In Therapeutic Antibody Engineering, Cambridge: Woodhead Publishing, 2012, pp 225-249). These strategies include reduction of effector function through modification of glycosylation, use of IgG2/IgG4 scaffolds, or the introduction of mutations in the hinge or CH2 domain of the Fc (see also, U.S. Patent Publication No. 2011/0212087, International Publication No. WO 2006/105338, U.S. Patent Publication No. 2012/0225058, U.S. Patent Publication No. 2012/0251531 and Strop et al., 2012, *J. Mol. Biol.,* 420: 204-219).

Examples of mutations that may be introduced into the hinge or CH2 domain to produce a "knock-out" variant include the amino acid modifications L234A/L235A, and L234A/L235A/D265S.

In certain embodiments, the anti-FRα antibody constructs described herein may comprise a scaffold based on an IgG Fc in which native glycosylation has been modified. As is known in the art, glycosylation of an Fc may be modified to increase or decrease effector function. For example, mutation of the conserved asparagine residue at position 297 to alanine, glutamine, lysine or histidine (i.e. N297A, Q, K or H) results in an aglycoslated Fc that lacks all effector function (Bolt et al., 1993, *Eur. J. Immunol.,* 23:403-411; Tao & Morrison, 1989, *J. Immunol.,* 143:2595-2601).

Conversely, removal of fucose from heavy chain N297-linked oligosaccharides has been shown to enhance ADCC, based on improved binding to FcγRIIIa (see, for example, Shields et al., 2002, *J Biol Chem.,* 277:26733-26740, and Niwa et al., 2005, *J. Immunol. Methods,* 306:151-160). Such low fucose antibodies may be produced, for example in knockout Chinese hamster ovary (CHO) cells lacking fucosyltransferase (FUT8) (Yamane-Ohnuki et al., 2004, *Biotechnol. Bioeng.,* 87:614-622); in the variant CHO cell line, Lee 13, that has a reduced ability to attach fucose to N297-linked carbohydrates (International Publication No. WO 03/035835), or in other cells that generate afucosylated antibodies (see, for example, Li et al., 2006, *Nat Biotechnol,* 24:210-215; Shields et al., 2002, ibid, and Shinkawa et al., 2003, *J. Biol. Chem.,* 278:3466-3473). In addition, International Publication No. WO 2009/135181 describes the addition of fucose analogues to culture medium during antibody production to inhibit incorporation of fucose into the carbohydrate on the antibody.

Other methods of producing antibodies with little or no fucose on the Fc glycosylation site (N297) are well known in the art. For example, the GlymaX® technology (ProBioGen AG) (see von Horsten et al., 2010, *Glycobiology,* 20(12):1607-1618 and U.S. Pat. No. 8,409,572).

Other glycosylation variants include those with bisected oligosaccharides, for example, variants in which a biantennary oligosaccharide attached to the Fc region of the antibody is bisected by N-acetylglucosamine (GlcNAc). Such glycosylation variants may have reduced fucosylation and/or improved ADCC function (see, for example, International Publication No. WO 2003/011878, U.S. Pat. No. 6,602,684 and US Patent Application Publication No. US 2005/0123546). Useful glycosylation variants also include those having at least one galactose residue in the oligosaccharide attached to the Fc region, which may have improved CDC function (see, for example, International Publication Nos. WO 1997/030087, WO 1998/58964 and WO 1999/22764).

In certain embodiments, the anti-FRα antibody constructs have the format of a full-size antibody (FSA). In some embodiments, the anti-FRα antibody constructs have the format of an IgG FSA, for example, an IgG1 FSA. In some embodiments, the anti-FRα antibody construct is a FSA comprising a first heavy chain sequence (H1), a second heavy chain sequence (H2), a first light chain sequence (L1) and a second light chain sequence (L2). In some embodiments, the anti-FRα antibody construct is a monospecific FSA with a homodimeric Fc and comprises H1, H2, L1 and L2 sequence, where H1 and H2 have the same amino acid sequence, and L1 and L2 have the same amino acid sequence. In some embodiments, the anti-FRα antibody construct is a monospecific FSA with a heterodimeric Fc and comprises H1, H2, L1 and L2 sequences, where H1 and H2 have different amino acid sequences, and L1 and L2 have the same amino acid sequence. In some embodiments, the anti-FRα antibody construct is a bispecific or biparatopic FSA with a heterodimeric Fc and comprises H1, H2, L1 and L2 sequences, where H1 and H2 have different amino acid sequences, and L1 and L2 have different amino acid sequences.

In certain embodiments, the anti-FRα antibody construct is a FSA having a set of H1, H2, L1 and L2 sequences comprising the H1, H2, L1 and L2 amino acid sequences as set forth in Tables A & B for any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675. As is known in the art, expression of antibody heavy chain sequences in certain cell lines or from certain expression vector may result in the inclusion of a C-terminal lysine residue on one or both of the heavy chains. Accordingly, certain embodiments of the present disclosure relate to anti-FRα antibody constructs that are FSAs having a set of H1, H2, L1 and L2 sequences comprising the H1, H2, L1 and L2 amino acid sequences as set forth in Tables A & B for any one of variants v23924, v30618, v30384, v30389, v30394, v30399, v31422, v31423, v31424, v31425, v31426, v35305, v35342, v35347, v35348, v35350, v35354, v35356, v35358, v36167, v36168 or v36675, in which one or both of the H1 and H2 sequences comprise a C-terminal lysine (see, for example, SEQ ID NO: 157).

Preparation of Anti-FRα Antibody Constructs

The anti-FRα antibody constructs described herein may be produced using standard recombinant methods known in the art (see, for example, U.S. Pat. No. 4,816,567 and "*Antibodies: A Laboratory Manual,*" 2nd Edition, Ed. Greenfield, Cold Spring Harbor Laboratory Press, New York, 2014).

Typically, for recombinant production of an antibody construct, a polynucleotide or set of polynucleotides encoding the anti-FRα antibody construct is generated and inserted into one or more vectors for further cloning and/or expression in a host cell. Polynucleotide(s) encoding the anti-FRα antibody construct may be produced by standard methods known in the art (see, for example, Ausubel et al., *Current Protocols in Molecular Biology*, John Wiley & Sons, New York, 1994 & update, and "*Antibodies: A Laboratory Manual,*" 2nd Edition, Ed. Greenfield, Cold Spring Harbor Laboratory Press, New York, 2014). As would be appreciated by one of skill in the art, the number of polynucleotides required for expression of the anti-FRα antibody construct will be dependent on the format of the construct, including whether or not the antibody construct comprises a scaffold. For example, when an anti-FRα antibody construct is in a mAb format with a homodimeric Fc, two polynucleotides each encoding one polypeptide chain will be required, whereas when an anti-FRα antibody construct is in a mAb format with a heterodimeric Fc, three polynucleotides each encoding one polypeptide chain will be required. When multiple polynucleotides are required, they may be incorporated into one vector or into more than one vector.

Generally, for expression, the polynucleotide or set of polynucleotides is incorporated into an expression vector or vectors together with one or more regulatory elements, such as transcriptional elements, which are required for efficient transcription of the polynucleotide. Examples of such regulatory elements include, but are not limited to, promoters, enhancers, terminators, and polyadenylation signals. One skilled in the art will appreciate that the choice of regulatory elements is dependent on the host cell selected for expression of the antibody construct and that such regulatory elements may be derived from a variety of sources, including bacterial, fungal, viral, mammalian or insect genes. The expression vector may optionally further contain heterologous nucleic acid sequences that facilitate expression or purification of the expressed protein. Examples include, but are not limited to, signal peptides and affinity tags such as metal-affinity tags, histidine tags, avidin/streptavidin encoding sequences, glutathione-S-transferase (GST) encoding sequences and biotin encoding sequences. The expression vector may be an extrachromosomal vector or an integrating vector.

Suitable host cells for cloning or expression of the anti-FRα antibody constructs include various prokaryotic or eukaryotic cells as known in the art. Eukaryotic host cells include, for example, mammalian cells, plant cells, insect cells and yeast cells (such as *Saccharomyces* or *Pichia* cells). Prokaryotic host cells include, for example, *E. coli, A. salmonicida* or *B. subtilis* cells.

In certain embodiments, the anti-FRα antibody construct may be produced in bacteria, in particular when glycosylation and Fc effector function are not needed, as described for example in U.S. Pat. Nos. 5,648,237; 5,789,199, and 5,840,523, and in Charlton, Methods in Molecular Biology, Vol. 248, pp. 245-254, B. K. C. Lo, ed., Humana Press, Totowa, N.J., 2003.

Eukaryotic microbes such as filamentous fungi or yeast may be suitable expression host cells in certain embodiments, in particular fungi and yeast strains whose glycosylation pathways have been "humanized" resulting in the production of an antibody construct with a partially or fully human glycosylation pattern (see, for example, Gerngross, 2004, *Nat. Biotech.* 22:1409-1414, and Li et al., 2006, *Nat. Biotech.* 24:210-215).

Suitable host cells for the expression of glycosylated anti-FRα antibody constructs are usually eukaryotic cells. For example, U.S. Pat. Nos. 5,959,177, 6,040,498, 6,420,548, 7,125,978 and 6,417,429 describe PLANTIBODIES™ technology for producing antigen-binding constructs in transgenic plants. Mammalian cell lines adapted to grow in suspension may be particularly useful for expression of antibody constructs. Examples include, but are not limited to, monkey kidney CV1 line transformed by SV40 (COS-7), human embryonic kidney (HEK) line 293 or 293 cells (see, for example, Graham et al., 1977, *J. Gen Virol.*, 36:59), baby hamster kidney cells (BHK), mouse sertoli TM4 cells (see, for example, Mather, 1980. *Biol Reprod,* 23:243-251), monkey kidney cells (CV1), African green monkey kidney cells (VERO-76), human cervical carcinoma (HeLa) cells, canine kidney cells (MDCK), buffalo rat liver cells (BRL 3A), human lung cells (W138), human liver cells (Hep G2), mouse mammary tumour (MMT 060562), TRI cells (see, for example, Mather et al., 1982, *Annals N.Y. Acad Sci,* 383:44-68), MRC 5 cells, FS4 cells, Chinese hamster ovary (CHO) cells (including $DHFR^-$ CHO cells, see Urlaub et al., 1980, *Proc Natl Acad Sci USA,* 77:4216), and myeloma cell lines (such as Y0, NSO and Sp2/0). Exemplary mammalian host cell lines suitable for production of antibody constructs are reviewed in Yazaki & Wu, Methods in Molecular Biology, Vol. 248, pp. 255-268 (B. K. C. Lo, ed., Humana Press, Totowa, N.J., 2003).

In certain embodiments, the host cell may be a transient or stable higher eukaryotic cell line, such as a mammalian cell line. In some embodiments, the host cell may be a mammalian HEK293T, CHO, HeLa, NSO or COS cell line, or a cell line derived from any one of these cell lines. In some embodiments, the host cell may be a stable cell line that allows for mature glycosylation of the antibody construct.

The host cells comprising the expression vector(s) encoding the anti-FRα antibody construct may be cultured using routine methods to produce the anti-FRα antibody construct. Alternatively, in some embodiments, host cells comprising the expression vector(s) encoding the anti-FRα antibody construct may be used therapeutically or prophylactically to deliver the anti-FRα antibody construct to a subject, or polynucleotides or expression vectors may be administered to a cell from a subject ex vivo and the cell then returned to the body of the subject.

Typically, the anti-FRα antibody constructs are purified after expression. Proteins may be isolated or purified in a variety of ways known to those skilled in the art (see, for example, *Protein Purification: Principles and Practice,* $3^{rd}$ Ed., Scopes, Springer-Verlag, NY, 1994). Standard purification methods include chromatographic techniques, including ion exchange, hydrophobic interaction, affinity, sizing or gel filtration, and reverse-phase, carried out at atmospheric pressure or at high pressure using systems such as FPLC and HPLC. Additional purification methods include electrophoretic, immunological, precipitation, dialysis and chromatofocusing techniques. Ultrafiltration and diafiltration techniques, in conjunction with protein concentration, are also useful. As is well known in the art, a variety of natural proteins bind Fc and antibodies, and these proteins may be used for purification of certain antibody constructs. For example, the bacterial proteins A and G bind to the Fc region. Likewise, the bacterial protein L binds to the Fab region of some antibodies. Purification may also be enabled by a particular fusion partner. For example, antibodies may be purified using glutathione resin if a GST fusion is employed, $Ni^{+2}$ affinity chromatography if a His-tag is employed or immobilized anti-flag antibody if a flag-tag is used. The degree of purification necessary will vary depending on the use of the anti-FRα antibody constructs. In some instances, no purification may be necessary.

In certain embodiments, the anti-FRα antibody constructs are substantially pure. The term “substantially pure” (or “substantially purified”) when used in reference to an anti-FRα antibody construct described herein, means that the antibody construct is substantially or essentially free of components that normally accompany or interact with the protein as found in its naturally occurring environment, such as a native cell, or a host cell in the case of recombinantly produced construct. In certain embodiments, an anti-FRα antibody construct that is substantially pure is a protein preparation having less than about 30%, less than about 25%, less than about 20%, less than about 15%, less than about 10%, or less than about 5% (by dry weight) of contaminating protein.

Certain embodiments of the present disclosure relate to a method of making an anti-FRα antibody construct comprising culturing a host cell into which one or more polynucleotides encoding the anti-FRα antibody construct, or one or more expression vectors encoding the anti-FRα antibody construct, have been introduced, under conditions suitable for expression of the anti-FRα antibody construct, and optionally recovering the anti-FRα antibody construct from the host cell (or from host cell culture medium).

Post-Translational Modifications

In certain embodiments, the anti-FRα antibody constructs described herein may comprise one or more post-translational modifications. Such post-translational modifications may occur in vivo, or they be conducted in vitro after isolation of the anti-FRα antibody construct from the host cell.

Post-translational modifications include various modifications as are known in the art (see, for example, *Proteins—Structure and Molecular Properties,* 2nd Ed., T. E. Creighton, W. H. Freeman and Company, New York, 1993; *Post-Translational Covalent Modification of Proteins*, B. C. Johnson, Ed., Academic Press, New York, pgs. 1-12, 1983; Seifter et al., 1990, *Meth. Enzymol.,* 182:626-646, and Rattan et al., 1992, *Ann. N.Y. Acad. Sci.,* 663:48-62). In those embodiments in which the anti-FRα antibody construct comprises one or more post-translational modifications, the construct may comprise the same type of modification at one or several sites, or it may comprise different modifications at different sites.

Examples of post-translational modifications include glycosylation, acetylation, phosphorylation, amidation, derivatization by known protecting/blocking groups, formylation, oxidation, reduction, proteolytic cleavage or specific chemical cleavage by cyanogen bromide, trypsin, chymotrypsin, papain, V8 protease or $NaBH_4$.

Other examples of post-translational modifications include, for example, addition or removal of N-linked or O-linked carbohydrate chains, chemical modifications of N-linked or β-linked carbohydrate chains, processing of N-terminal or C-terminal ends, attachment of chemical moieties to the amino acid backbone, and addition or deletion of an N-terminal methionine residue resulting from prokaryotic host cell expression. Post-translational modifications may also include modification with a detectable label, such as an enzymatic, fluorescent, luminescent, isotopic or affinity label to allow for detection and isolation of the protein. Examples of suitable enzyme labels include, but are not limited to, horseradish peroxidase, alkaline phosphatase, beta-galactosidase and acetylcholinesterase. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, rhodamine, dichlorotriazinylamine fluorescein, dansyl chloride and phycoerythrin. Examples of luminescent materials include luminol, and bioluminescent materials such as luciferase, luciferin and aequorin. Examples of suitable radioactive materials include iodine, carbon, sulfur, tritium, indium, technetium, thallium, gallium, palladium, molybdenum, xenon and fluorine.

Additional examples of post-translational modifications include acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, gamma-carboxylation, GPI anchor formation, hydroxylation, iodination, methylation, myristylation, pegylation, prenylation, racemization, selenoylation, sulfation, transfer-RNA mediated addition of amino acids to proteins such as arginylation, and ubiquitination.

Camptothecin Analogues

The camptothecin analogue comprised by the ADCs of the present disclosure is a compound having Formula (I):

(I)

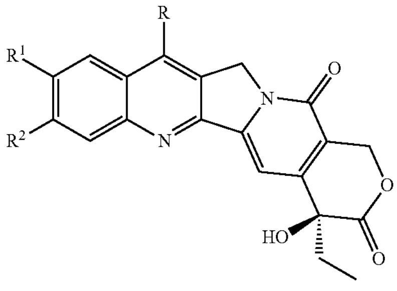

wherein:

$R^1$ is selected from: —H, —$CH_3$, —$CHF_2$, —$CF_3$, —F, —Br, —Cl, —OH, —$OCH_3$, —$OCF_3$ and —$NH_2$, and $R^2$ is selected from: —H, —$CH_3$, —$CF_3$, —F, —Br, —Cl, —OH, —$OCH_3$ and —$OCF_3$, and wherein:

when $R^1$ is —$NH_2$, then R is $R^3$ or $R^4$, and when $R^1$ is other than —$NH_2$, then R is $R^4$;

$R^3$ is selected from: —H, —$C_1$-$C_6$ alkyl, —$C_3$-$C_8$ cycloalkyl, —($C_1$-$C_6$ alkyl)-O—$R^5$,

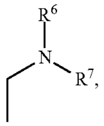

—$CO_2R^8$, -aryl, -heteroaryl and —($C_1$-$C_6$ alkyl)-aryl;

$R^4$ is selected from:

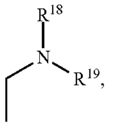

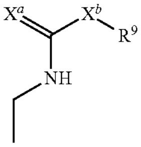

,

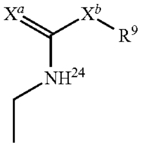

,

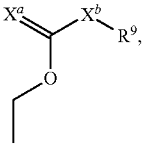

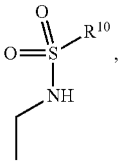

,

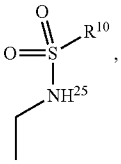

,

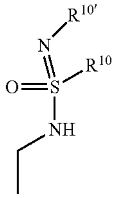

,

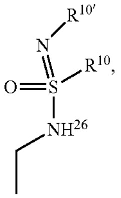

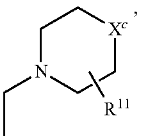

,

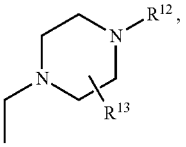

-continued

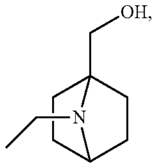

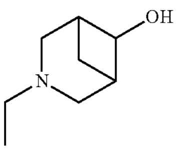

and

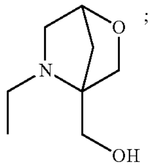

;

$R^5$ is selected from: —H, —$C_1$-$C_6$ alkyl, —$C_3$-$C_8$ cycloalkyl, -aryl, -heteroaryl, -aryl and —($C_1$-$C_6$ alkyl)-aryl;

$R^6$ and $R^7$ are each independently selected from: —H, —$C_1$-$C_6$ alkyl, —$C_3$-$C_8$ cycloalkyl, —($C_1$-$C_6$ alkyl)-O—$R^5$, —$C_3$-$C_8$ heterocycloalkyl and —C(O)$R^{17}$;

$R^8$ is selected from: —H, —$C_1$-$C_6$ alkyl, —$C_3$-$C_8$ cycloalkyl and —$C_3$-$C_8$ heterocycloalkyl;

each $R^9$ is independently selected from: —H, —$C_1$-$C_6$ alkyl, —$C_3$-$C_8$ cycloalkyl, -aryl, -heteroaryl and —($C_1$-$C_6$ alkyl)-aryl;

each $R^{10}$ is independently selected from: —$C_1$-$C_6$ alkyl, —$C_3$-$C_8$ cycloalkyl, —$NR^{14}R^{14'}$, -aryl, -heteroaryl and —($C_1$-$C_6$ alkyl)-aryl;

$R^{10'}$ is selected from: —H, —$C_1$-$C_6$ alkyl, —$C_3$-$C_8$ cycloalkyl, -aryl, -heteroaryl, and —($C_1$-$C_6$ alkyl)-aryl;

$R^{11}$ is selected from: —H and —$C_1$-$C_6$ alkyl;

$R^{12}$ is selected from: —H, —$C_1$-$C_6$ alkyl, —$CO_2R^8$, -aryl, -heteroaryl,—($C_1$-$C_6$ alkyl)-aryl, —$S(O)_2R^{16}$ and

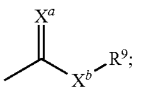

$R^{13}$ is selected from: —H and —$C_1$-$C_6$ alkyl;

$R^{14}$ and $R^{14'}$ are each independently selected from: —H, $C_1$-$C_6$ alkyl, —$C_3$-$C_8$ cycloalkyl and —$C_3$-$C_8$ heterocycloalkyl;

$R^{16}$ is selected from: —$C_1$-$C_6$ alkyl, —$C_3$-$C_8$ cycloalkyl, -aryl, -heteroaryl and —($C_1$-$C_6$ alkyl)-aryl;

$R^{17}$ is selected from: —$C_1$-$C_6$ alkyl, —$C_3$-$C_8$ cycloalkyl, —$C_3$-$C_8$ heterocycloalkyl, —($C_1$-$C_6$alkyl)-$C_3$-$C_8$ heterocycloalkyl, -aryl, -heteroaryl and —($C_1$-$C_6$ alkyl)-aryl;

$R^{18}$ and $R^{19}$ taken together with the N atom to which they are bonded form a 4-, 5-, 6- or 7-membered ring having 0 to 3 substituents selected from: halogen, —$C_1$-$C_6$ alkyl, —$C_3$-$C_8$ cycloalkyl and —($C_1$-$C_6$ alkyl)-O—$R^5$;

$R^{24}$, $R^{25}$ and $R^{26}$ are each —$C_1$-$C_6$ alkyl;

$X^a$ and $X^b$ are each independently selected from: NH, O and S, and $X^c$ is selected from; O, S and $S(O)_2$, with the proviso that the compound is other than (S)-9-amino-11-butyl-4-ethyl-4-hydroxy-1,12-dihydro-14H-pyrano[3',4':6,7]indolizino[1,2-b]quinoline-3,14(4H)-dione.

In some embodiments, the camptothecin analogues are compounds of Formula (I), with the proviso that when $R^1$ is $NH_2$, $R^2$ is other than H.

In some embodiments, in compounds of Formula (I), $R^1$ is selected from: —$CH_3$, —$CF_3$, —$OCH_3$, —$OCF_3$ and $NH_2$.

In some embodiments, in compounds of Formula (I), $R^1$ is $NH_2$.

In some embodiments, in compounds of Formula (I), $R^1$ is selected from: —H, —$CH_3$, —$CF_3$, —F, —Br, —Cl, —OH, —$OCH_3$ and —$OCF_3$.

In some embodiments, in compounds of Formula (I), $R^1$ is selected from: —$CH_3$, —$CF_3$, —$OCH_3$ and —$OCF_3$.

In some embodiments, in compounds of Formula (I), $R^2$ is selected from: —H, —$CH_3$, —$CF_3$, —F, —Cl, —$OCH_3$ and —$OCF_3$.

In some embodiments, in compounds of Formula (I), $R^2$ is selected from: —$CH_3$, —$CF_3$, —F, —Cl, —$OCH_3$ and —$OCF_3$.

In some embodiments, in compounds of Formula (I), $R^2$ is selected from: —H, —F, —Br and —Cl.

In some embodiments, in compounds of Formula (I), $R^2$ is selected from: —F, —Br and —Cl.

In some embodiments, in compounds of Formula (I), $R^3$ is selected from: —H, unsubstituted —$C_1$-$C_6$ alkyl, —$C_1$-$C_6$ haloalkyl, —$C_1$-$C_6$ hydroxyalkyl, —$C_3$-$C_8$ cycloalkyl, —($C_1$-$C_6$ alkyl)-O—$R^5$,

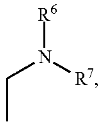

—$CO_2R^8$, unsubstituted -aryl, -aminoaryl, -heteroaryl and —($C_1$-$C_6$ alkyl)-aminoaryl.

In some embodiments, in compounds of Formula (I), $R^4$ is selected from:

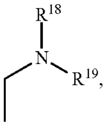 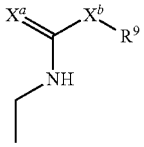 , 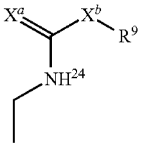 ,

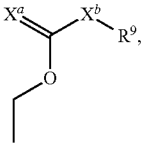 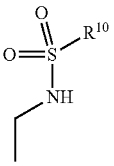 , 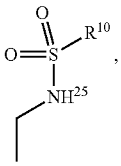 , 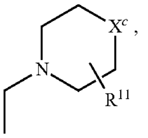

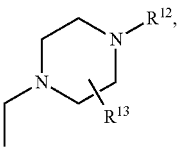 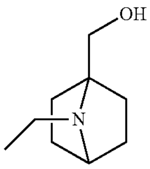 , 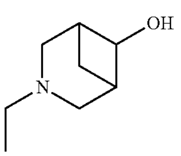 and

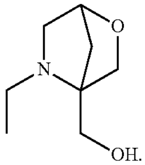

In some embodiments, in compounds of Formula (I), $R^5$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (I), $R^6$ and $R^7$ are each independently selected from: —H, unsubstituted —$C_1$-$C_6$ alkyl, —$C_1$-$C_6$ haloalkyl, —$C_1$-$C_6$ hydroxyalkyl, —$C_3$-$C_8$ cycloalkyl, —($C_1$-$C_6$ alkyl)-O—$R^5$, —$C_3$-$C_8$ heterocycloalkyl and —C(O)$R^{17}$.

In some embodiments, in compounds of Formula (I), $R^8$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (I), each $R^9$ is independently selected from: —$C_1$-$C_6$ alkyl, —$C_3$-$C_8$ cycloalkyl, -aryl and —($C_1$-$C_6$ alkyl)-aryl.

In some embodiments, in compounds of Formula (I), each $R^9$ is independently selected from: —$C_1$-$C_6$ alkyl and —($C_1$-$C_6$ alkyl)-aryl.

In some embodiments, in compounds of Formula (I), each $R^9$ is independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (I), each $R^{10}$ is independently selected from: —$C_1$-$C_6$ alkyl, —$C_3$-$C_8$ cycloalkyl, —$NR^{14}R^{14'}$, -aryl and —($C_1$-$C_6$ alkyl)-aryl.

In some embodiments, in compounds of Formula (I), each $R^{10}$ is independently selected from: —$C_1$-$C_6$ alkyl, —$NR^{14}R^{14'}$, -aryl and —($C_1$-$C_6$ alkyl)-aryl.

In some embodiments, in compounds of Formula (I), each $R^{10}$ is independently selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, —$NR^{14}R^{14'}$, unsubstituted -aryl, -aminoaryl, -heteroaryl and —($C_1$-$C_6$ alkyl)-aryl.

In some embodiments, in compounds of Formula (I), $R^{10'}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aryl.

In some embodiments, in compounds of Formula (I), $R^{11}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (I), $R^{12}$ is selected from: —H, —$C_1$-$C_6$ alkyl, —$CO_2R^8$, -aryl, —($C_1$-$C_6$ alkyl)-aryl and —$S(O)_2R^{16}$.

In some embodiments, in compounds of Formula (I), $R^{12}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$CO_2R^8$, unsubstituted -aryl,-aminoaryl, -heteroaryl,—($C_1$-$C_6$ alkyl)-aminoaryl, —$S(O)_2R^{16}$ and

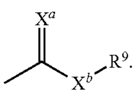

In some embodiments, in compounds of Formula (I), $R^{13}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (I), $R^{14}$ and $R^{14'}$ are each independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (I), $R^{16}$ is selected from: -aryl, -heteroaryl and —($C_1$-$C_6$ alkyl)-aryl.

In some embodiments, in compounds of Formula (I), $R^{16}$ is selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted aryl, -aminoaryl, -heteroaryl and —($C_1$-$C_6$ alkyl)-aminoaryl.

In some embodiments, in compounds of Formula (I), $R^{17}$ is selected from: unsubstituted $C_1$-$C_6$ alkyl, —$C_1$-$C_6$ hydroxyalkyl, —$C_3$-$C_8$ cycloalkyl, —$C_3$-$C_8$ heterocycloalkyl, —($C_1$-$C_6$ alkyl)-$C_3$-$C_8$ heterocycloalkyl, unsubstituted aryl, -hydroxyaryl, -aminoaryl, -heteroaryl and —($C_1$-$C_6$ alkyl)-aminoaryl.

In some embodiments, in compounds of Formula (I), $R^{18}$ and $R^{19}$ taken together with the N atom to which they are bonded form a 4-, 5-, 6- or 7-membered ring having 0 to 3 substituents selected from: halogen, unsubstituted $C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —($C_1$-$C_6$ alkyl)-O—$R^5$.

In some embodiments, in compounds of Formula (I), $X^a$ and $X^b$ are each independently selected from: NH and O.

Combinations of any of the foregoing embodiments for compounds of Formula (I) are also contemplated and each combination forms a separate embodiment for the purposes of the present disclosure.

In certain embodiments, the compound of Formula (I) has Formula (II):

(II)

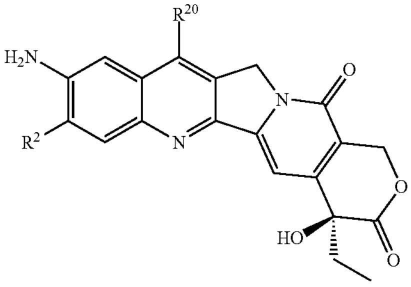

wherein:

$R^2$ is selected from: —H, —$CH_3$, —$CF_3$, —F, —Br, —Cl, —OH, —$OCH_3$ and —$OCF_3$;

$R^{20}$ is selected from: —H, —$C_1$-$C_6$ alkyl, —$C_3$-$C_8$ cycloalkyl, —($C_1$-$C_6$ alkyl)-O—$R^5$,

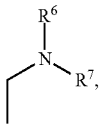

$CO_2R^8$, -aryl, -heteroaryl,—($C_1$-$C_6$ alkyl)-aryl,

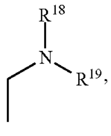 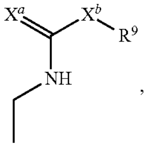 , 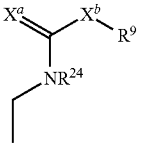 ,

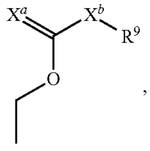 , 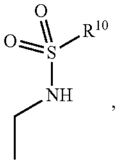 , 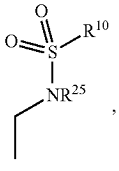 ,

-continued

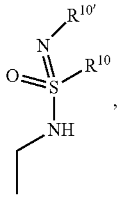 , 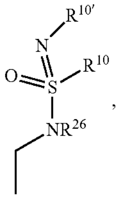 , 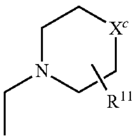 ,

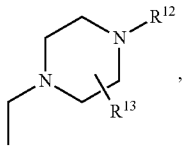 , 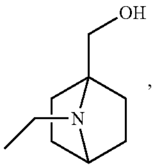 , 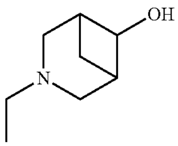 and

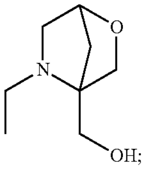

$R^5$ is selected from: —H, —$C_1$-$C_6$ alkyl, —$C_3$-$C_8$ cycloalkyl, -aryl, -heteroaryl and —($C_1$-$C_6$ alkyl)-aryl;

$R^6$ and $R^7$ are each independently selected from: —H, —$C_1$-$C_6$ alkyl, —$C_3$-$C_8$ cycloalkyl, —($C_1$-$C_6$ alkyl)-O—$R^5$, —$C_3$-$C_8$ heterocycloalkyl and —C(O)$R^{17}$;

$R^8$ is selected from: —H, —$C_1$-$C_6$ alkyl, —$C_3$-$C_8$ cycloalkyl and —$C_3$-$C_8$ heterocycloalkyl;

each $R^9$ is independently selected from: —H, —$C_1$-$C_6$ alkyl, —$C_3$-$C_8$ cycloalkyl, -aryl, -heteroaryl and —($C_1$-$C_6$ alkyl)-aryl;

each $R^{10}$ is independently selected from: —$C_1$-$C_6$ alkyl, —$C_3$-$C_8$ cycloalkyl, —$NR^{14}R^{14'}$-aryl, -heteroaryl and —($C_1$-$C_6$ alkyl)-aryl;

$R^{10'}$ is selected from: —H, —$C_1$-$C_6$ alkyl, —$C_3$-$C_8$ cycloalkyl, -aryl, -heteroaryl, and —($C_1$-$C_6$ alkyl)-aryl;

$R^{11}$ is selected from: —H and —$C_1$-$C_6$ alkyl;

$R^{12}$ is selected from: —H, —$C_1$-$C_6$ alkyl, —$CO_2R^8$, -aryl, -heteroaryl, —($C_1$-$C_6$ alkyl)-aryl, —$S(O)_2R^{16}$ and

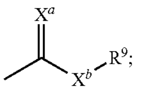

$R^{13}$ is selected from: —H and —$C_1$-$C_6$ alkyl;

$R^{14}$ and $R^{14'}$ are each independently selected from: —H, $C_1$-$C_6$ alkyl, —$C_3$-$C_8$ cycloalkyl and —$C_3$-$C_8$ heterocycloalkyl;

$R^{16}$ is selected from: —$C_1$-$C_6$ alkyl, —$C_3$-$C_8$ cycloalkyl, -aryl, -heteroaryl and —($C_1$-$C_6$ alkyl)-aryl;

$R^{17}$ is selected from: —$C_1$-$C_6$ alkyl, —$C_3$-$C_8$ cycloalkyl, —$C_3$-$C_8$ heterocycloalkyl, —($C_1$-$C_6$alkyl)-$C_3$-$C_8$ heterocycloalkyl, -aryl, -heteroaryl and —($C_1$-$C_6$ alkyl)-aryl;

$R^{18}$ and $R^{19}$ taken together with the N atom to which they are bonded form a 4-, 5-, 6-, or 7-membered ring having 0 to 3 substituents selected from: halogen, —$C_1$-$C_6$ alkyl, —$C_3$-$C_8$ cycloalkyl and —($C_1$-$C_6$ alkyl)-O—$R^5$;

$R^{24}$, $R^{25}$ and $R^{26}$ are each —$C_1$-$C_6$ alkyl; $X^a$ and $X^b$ are each independently selected from: NH, O and S, and $X^c$ is selected from: O, S and $S(O)_2$, with the proviso that the compound is other than (S)-9-amino-11-butyl-4-ethyl-4-hydroxy-1,12-dihydro-14H-pyrano[3',4':6,7]indolizino[1,2-b]quinoline-3,14(4H)-dione.

In some embodiments, in compounds of Formula (II), $R^2$ is selected from: —$CH_3$, —$CF_3$, —F, —Br, —Cl, —OH, —$OCH_3$ and —$OCF_3$.

In some embodiments, in compounds of Formula (II), $R^2$ is selected from: —$CH_3$, —$CF_3$, —F, —Cl, —$OCH_3$ and —$OCF_3$.

In some embodiments, in compounds of Formula (II), $R^2$ is selected from F and Cl.

In some embodiments, in compounds of Formula (II), $R^{20}$ is selected from: —H, —$C_1$-$C_6$ alkyl,—($C_1$-$C_6$ alkyl)-O—$R^5$,

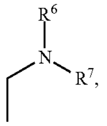

—($C_1$-$C_6$ alkyl)-aryl,

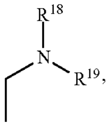 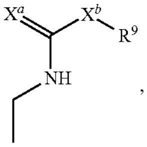 , 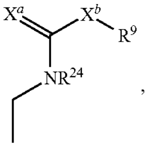 ,

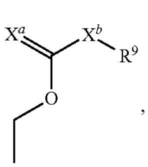 , 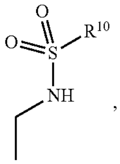 , 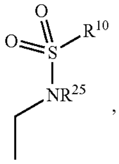 ,

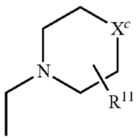 , 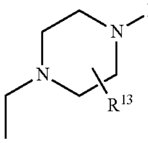 , 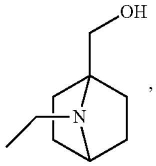 ,

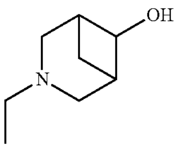 and 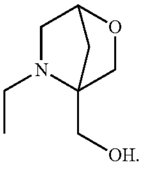

In some embodiments, in compounds of Formula (II), $R^{20}$ is selected from: —H, —$C_1$-$C_6$ alkyl,—($C_1$-$C_6$ alkyl)-O—$R^5$,

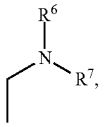

—($C_1$-$C_6$ alkyl)-aryl,

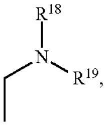 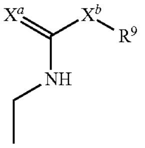 , 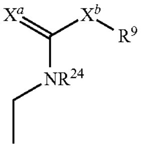 ,

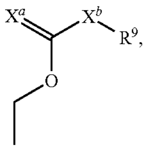 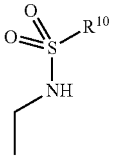 , 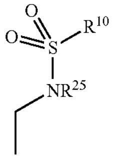 ,

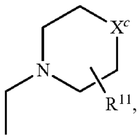 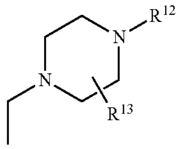 and

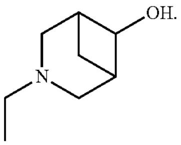

In some embodiments, in compounds of Formula (II), $R^{20}$ is selected from: —H, —$C_1$-$C_6$ alkyl,—($C_1$-$C_6$ alkyl)-O—$R^5$,

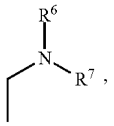 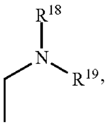 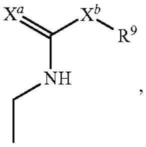 , 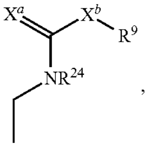 ,

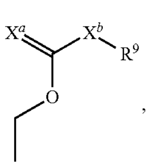 , 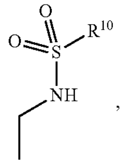 , 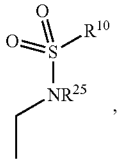 ,

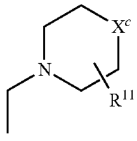 , 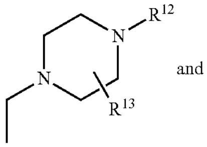 and

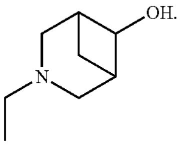

In some embodiments, in compounds of Formula (II), $R^{20}$ is selected from: —H, unsubstituted-$C_1$-$C_6$ alkyl,—$C_1$-$C_6$ haloalkyl,—$C_1$-$C_6$ hydroxyalkyl,—$C_3$-$C_8$ cycloalkyl,—($C_1$-$C_6$ alkyl)-O—$R^5$,

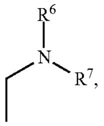

—$CO_2R^8$, unsubstituted aryl, -aminoaryl, -heteroaryl, —($C_1$-$C_6$ alkyl)-aminoaryl,

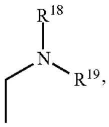 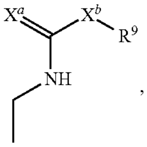 , 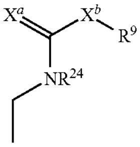 ,

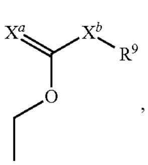 , 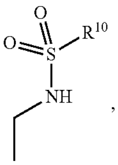 , 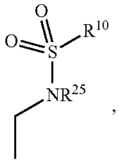 ,

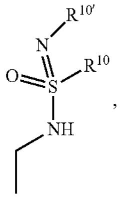 , 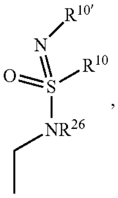 , 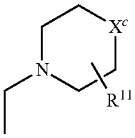 ,

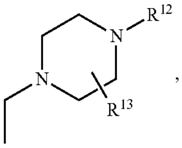 , 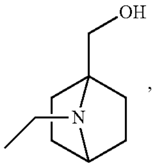 , 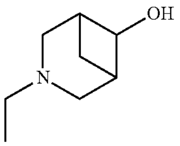 and

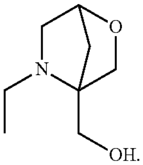

In some embodiments, in compounds of Formula (II), $R^2$ is selected from: —$CH_3$, —$CF_3$, —F, —Br, —Cl, —OH, —$OCH_3$ and —$OCF_3$, and $R^{20}$ is selected from: —H, —$C_1$-$C_6$ alkyl, —($C_1$-$C_6$ alkyl)-O—$R^5$

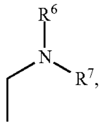

—($C_1$-$C_6$ alkyl)-aryl,

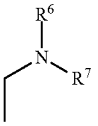 , 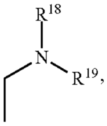 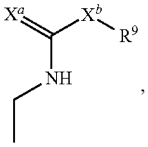 , 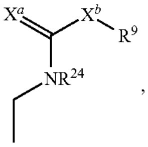 ,

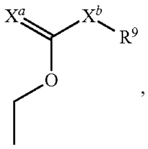 , 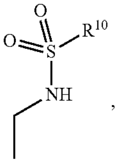 , 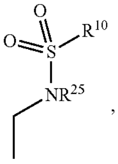 ,

-continued

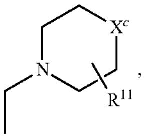 , 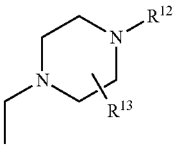 , 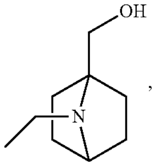 ,

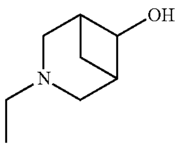 and 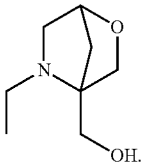

In some embodiments, in compounds of Formula (II), $R^2$ is selected from: —$CH_3$, —$CF_3$, —F, —Br, —Cl, —OH, —$OCH_3$ and —$OCF_3$, and $R^{20}$ is selected from: —H, —$C_1$-$C_6$ alkyl, —($C_1$-$C_6$ alkyl)-O—$R^5$,

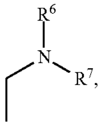

—($C_1$-$C_6$ alkyl)-aryl,

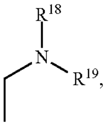 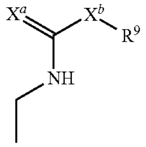 , 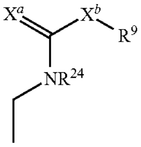 ,

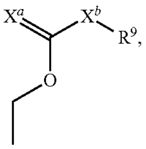 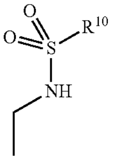 , 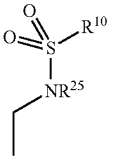 ,

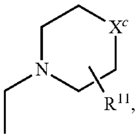 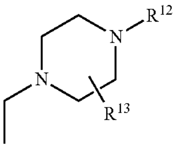 and

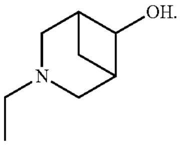

In some embodiments, in compounds of Formula (II), $R^2$ is selected from: —$CH_3$, —$CF_3$, —F, —Br, —Cl, —OH, —$OCH_3$ and —$OCF_3$, and $R^{20}$ is selected from: —H, —$C_1$-$C_6$ alkyl, —($C_1$-$C_6$ alkyl)-O—$R^5$,

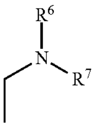 , 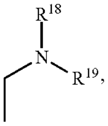 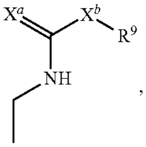 , 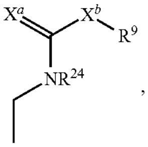 ,

-continued

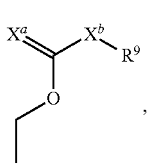,
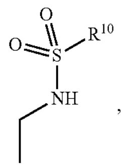,
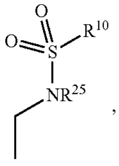,
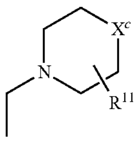,
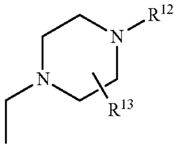 and
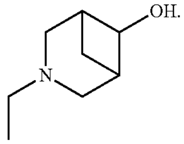

In some embodiments, in compounds of Formula (II), $R^5$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (II), $R^6$ and $R^7$ are each independently selected from: —H, —$C_1$-$C_6$ alkyl, —$C_3$-$C_8$ cycloalkyl and —C(O)$R^{17}$.

In some embodiments, in compounds of Formula (II), $R^6$ is H, and $R^7$ is selected from: —H, —$C_1$-$C_6$ alkyl, —$C_3$-$C_8$ cycloalkyl, —($C_1$-$C_6$ alkyl)-O—$R^5$, —$C_3$-$C_8$ heterocycloalkyl and —C(O)$R^{17}$.

In some embodiments, in compounds of Formula (II), $R^6$ is H, and $R^7$ is selected from: —H, —$C_1$-$C_6$ alkyl, —$C_3$-$C_8$ cycloalkyl and —C(O)$R^{17}$.

In some embodiments, in compounds of Formula (II), $R^6$ and $R^7$ are each independently selected from: —H, unsubstituted —$C_1$-$C_6$ alkyl, —$C_1$-$C_6$ haloalkyl, —$C_1$-$C_6$ hydroxyalkyl, —$C_3$-$C_8$ cycloalkyl, —($C_1$-$C_6$ alkyl)-O—$R^5$, —$C_3$-$C_8$ heterocycloalkyl and —C(O)$R^{17}$.

In some embodiments, in compounds of Formula (II), $R^8$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (II), each $R^9$ is independently selected from: —$C_1$-$C_6$ alkyl, —$C_3$-$C_8$ cycloalkyl, -aryl and —($C_1$-$C_6$ alkyl)-aryl.

In some embodiments, in compounds of Formula (II), each $R^9$ is independently selected from: —$C_1$-$C_6$ alkyl and —($C_1$-$C_6$ alkyl)-aryl.

In some embodiments, in compounds of Formula (II), each $R^9$ is independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (II), each $R^{10}$ is independently selected from: —$C_1$-$C_6$ alkyl, —$C_3$-$C_8$ cycloalkyl, —$NR^{14}R^{14'}$, -aryl and —($C_1$-$C_6$ alkyl)-aryl.

In some embodiments, in compounds of Formula (II), each $R^{10}$ is independently selected from: —$C_1$-$C_6$ alkyl, —$NR^{14}R^{14'}$, -aryl and —($C_1$-$C_6$ alkyl)-aryl.

In some embodiments, in compounds of Formula (II), each $R^{10}$ is independently selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, —$NR^{14}R^{14'}$, unsubstituted -aryl, -aminoaryl, -heteroaryl and —($C_1$-$C_6$ alkyl)-aryl.

In some embodiments, in compounds of Formula (II), $R^{10'}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aryl.

In some embodiments, in compounds of Formula (II), $R^{11}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (II), $R^{12}$ is selected from: —H, —$C_1$-$C_6$ alkyl, —$CO_2R^8$, -aryl, —($C_1$-$C_6$ alkyl)-aryl and —$S(O)_2R^{16}$.

In some embodiments, in compounds of Formula (II), $R^{12}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$CO_2R^8$, unsubstituted -aryl,-aminoaryl, -heteroaryl,—($C_1$-$C_6$ alkyl)-aminoaryl, —$S(O)_2R^{16}$ and

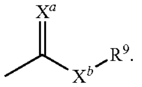

In some embodiments, in compounds of Formula (II), $R^{13}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (II), $R^{14}$ and $R^{14'}$ are each independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (II), $R^{16}$ is selected from: -aryl, -heteroaryl and —($C_1$-$C_6$ alkyl)-aryl.

In some embodiments, in compounds of Formula (II), $R^{16}$ is selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (II), $R^{17}$ is —$C_1$-$C_6$ alkyl.

In some embodiments, in compounds of Formula (II), $R^{17}$ is selected from: unsubstituted $C_1$-$C_6$ alkyl, —$C_1$-$C_6$ hydroxyalkyl, —$C_3$-$C_8$ cycloalkyl, —$C_3$-$C_8$ heterocycloalkyl, —($C_1$-$C_6$ alkyl)-$C_3$-$C_8$ heterocycloalkyl, unsubstituted aryl, -hydroxyaryl, -aminoaryl, -heteroaryl and —($C_1$-$C_6$ alkyl)-aminoaryl.

In some embodiments, in compounds of Formula (II), $R^{18}$ and $R^{19}$ taken together with the N atom to which they are bonded form a 4-, 5-, 6- or 7-membered ring having 0 to 3 substituents selected from: halogen, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —($C_1$-$C_6$ alkyl)-O—$R^5$.

In some embodiments, in compounds of Formula (II), $X^a$ and $X^b$ are each independently selected from: NH and O.

Combinations of any of the foregoing embodiments for compounds of Formula (II) are also contemplated and each combination forms a separate embodiment for the purposes of the present disclosure.

In certain embodiments, the compound of Formula (I) has Formula (III):

(III)

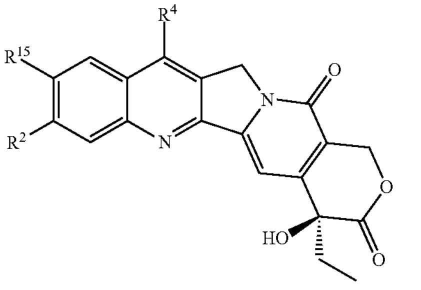

wherein:

$R^2$ is selected from: —H, —$CH_3$, —$CF_3$, —F, —Br, —Cl, —OH, —$OCH_3$ and —$OCF_3$;

$R^{15}$ is selected from: —H, —$CH_3$, —$CHF_2$, —$CF_3$, —F, —Br, —Cl, —OH, —$OCH_3$ and —$OCF_3$;

$R^4$ is selected from:

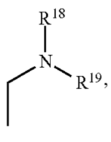 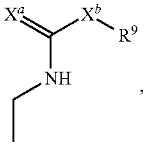 , 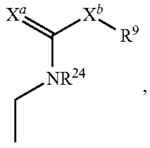 ,

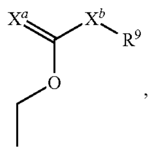 , 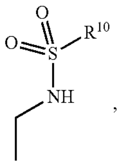 , 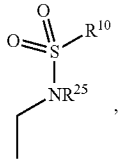 ,

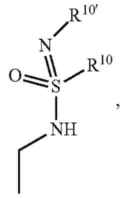 , 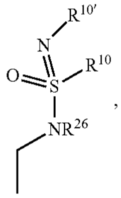 , 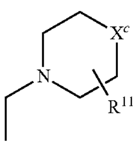 ,

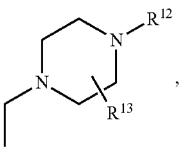 , 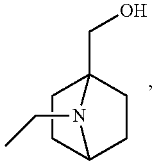 , 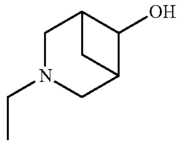 and

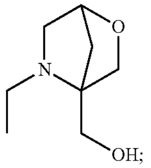

$R^5$ is selected from: —H, —$C_1$-$C_6$ alkyl, —$C_3$-$C_8$ cycloalkyl, -aryl, -heteroaryl and —($C_1$-$C_6$ alkyl)-aryl;

$R^8$ is selected from: —H, —$C_1$-$C_6$ alkyl, —$C_3$-$C_8$ cycloalkyl and —$C_3$-$C_8$ heterocycloalkyl;

each $R^9$ is independently selected from: —H, —$C_1$-$C_6$ alkyl, —$C_3$-$C_8$ cycloalkyl, -aryl, -heteroaryl and —($C_1$-$C_6$ alkyl)-aryl;

each $R^{10}$ is independently selected from: —$C_1$-$C_6$ alkyl, —$C_3$-$C_8$ cycloalkyl, —$NR^{14}R^{14'}$, -aryl, -heteroaryl and —($C_1$-$C_6$ alkyl)-aryl;

$R^{10'}$ is selected from: —H, —$C_1$-$C_6$ alkyl, —$C_3$-$C_8$ cycloalkyl, -aryl, -heteroaryl and —($C_1$-$C_6$alkyl)-aryl;

$R^{11}$ is selected from: —H and —$C_1$-$C_6$ alkyl;

$R^{12}$ is selected from: —H, —$C_1$-$C_6$ alkyl, —$CO_2R^8$, -aryl, -heteroaryl, —($C_1$-$C_6$ alkyl)-aryl, —$S(O)_2R^{16}$ and

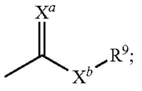

$R^{13}$ is selected from: —H and —$C_1$-$C_6$ alkyl;

$R^{14}$ and $R^{14'}$ are each independently selected from: —H, $C_1$-$C_6$ alkyl, —$C_3$-$C_8$ cycloalkyl and —$C_3$-$C_8$ heterocycloalkyl;

$R^{16}$ is selected from: —$C_1$-$C_6$ alkyl, —$C_3$-$C_8$ cycloalkyl, -aryl, -heteroaryl and —($C_1$-$C_6$ alkyl)-aryl;

$R^{18}$ and $R^{19}$ taken together with the N atom to which they are bonded form a 4-, 5-, 6-, or 7-membered ring having 0 to 3 substituents selected from: halogen, —$C_1$-$C_6$ alkyl, —$C_3$-$C_8$ cycloalkyl and —($C_1$-$C_6$ alkyl)-O—$R^5$;

$R^{24}$, $R^{25}$ and $R^{26}$ are each —$C_1$-$C_6$ alkyl; $X^a$ and $X^b$ are each independently selected from: NH, O and S, and $X^c$ is selected from: O, S and $S(O)_2$.

In some embodiments, in compounds of Formula (III), $R^2$ is selected from: —H, —$CH_3$, —$CF_3$, —F, —Cl, —$OCH_3$ and —$OCF_3$.

In some embodiments, in compounds of Formula (III), $R^2$ is selected from: —H, —F and —Cl.

In some embodiments, in compounds of Formula (III), $R^{15}$ is selected from: —$CH_3$, —$CF_3$, —$OCH_3$ and —$OCF_3$.

In some embodiments, in compounds of Formula (III), $R^{15}$ is selected from: —$CH_3$ and —$OCH_3$.

In some embodiments, in compounds of Formula (III), $R^2$ is selected from: —H, —F and —Cl, and $R^{15}$ is selected from: —$CH_3$, —$CF_3$, —$OCH_3$ and —$OCF_3$.

In some embodiments, in compounds of Formula (III), $R^2$ is selected from: —H, —F and —Cl, and $R^{15}$ is selected from: —$CH_3$ and —$OCH_3$.

In some embodiments, in compounds of Formula (III), $R^4$ is selected from:

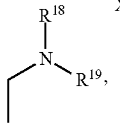 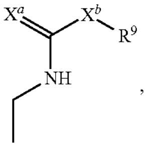 , 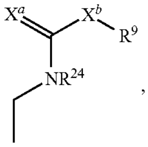 ,

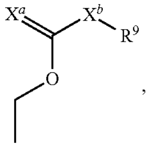 , 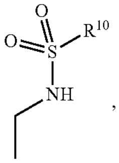 , 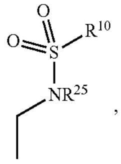 ,

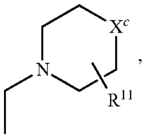 , 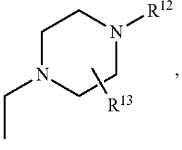 ,

-continued

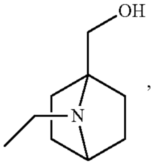

,

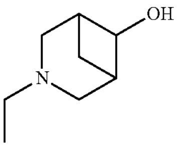

and

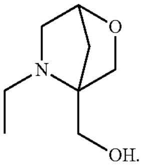

In some embodiments, in compounds of Formula (III), $R^5$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (III), $R^8$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (III), each $R^9$ is independently selected from: —$C_1$-$C_6$ alkyl, —$C_3$-$C_8$ cycloalkyl, -aryl and —($C_1$-$C_6$ alkyl)-aryl.

In some embodiments, in compounds of Formula (III), each $R^9$ is independently selected from: —$C_1$-$C_6$ alkyl and —($C_1$-$C_6$ alkyl)-aryl.

In some embodiments, in compounds of Formula (III), each $R^9$ is independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (III), each $R^{10}$ is independently selected from: —$C_1$-$C_6$ alkyl, —$C_3$-$C_8$ cycloalkyl, —$NR^{14}R^{14'}$, -aryl and —($C_1$-$C_6$ alkyl)-aryl.

In some embodiments, in compounds of Formula (III), each $R^{10}$ is independently selected from: —$C_1$-$C_6$ alkyl, —$NR^{14}R^{14'}$, -aryl and —($C_1$-$C_6$ alkyl)-aryl.

In some embodiments, in compounds of Formula (III), each $R^{10}$ is independently selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, —$NR^{14}R^{14'}$, unsubstituted -aryl, -aminoaryl, -heteroaryl and —($C_1$-$C_6$ alkyl)-aryl.

In some embodiments, in compounds of Formula (III), $R^{10'}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aryl.

In some embodiments, in compounds of Formula (III), $R^{11}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (III), $R^{12}$ is selected from: —H, —$C_1$-$C_6$ alkyl, —$CO_2R^8$, -aryl, —($C_1$-$C_6$ alkyl)-aryl and —$S(O)_2R^{16}$.

In some embodiments, in compounds of Formula (III), $R^{12}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$CO_2R^8$, unsubstituted -aryl, -aminoaryl, -heteroaryl, —($C_1$-$C_6$ alkyl)-aminoaryl, —$S(O)_2R^{16}$ and

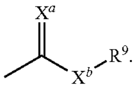

In some embodiments, in compounds of Formula (III), $R^{13}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (III), $R^{14}$ and $R^{14'}$ are each independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (III), $R^{16}$ is selected from: -aryl, -heteroaryl and —($C_1$-$C_6$ alkyl)-aryl.

In some embodiments, in compounds of Formula (III), $R^{16}$ is selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (III), $R^{18}$ and $R^{19}$ taken together with the N atom to which they are bonded form a 4-, 5-, 6- or 7-membered ring having 0 to 3 substituents selected from: halogen, unsubstituted $C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —($C_1$-$C_6$ alkyl)-O—$R^5$.

In some embodiments, in compounds of Formula (III), $X^a$ and $X^b$ are each independently selected from: NH and O.

Combinations of any of the foregoing embodiments for compounds of Formula (III) are also contemplated and each combination forms a separate embodiment for the purposes of the present disclosure.

In certain embodiments, each alkyl, cycloalkyl, heterocycloalkyl, aryl and heteroaryl group as defined in any one of Formulae (I), (II) or (III) is optionally substituted with one or more substituents selected from: halogen, acyl, acyloxy, alkoxy, carboxy, hydroxy, amino, amido, nitro, cyano, azido, alkylthio, thio, sulfonyl, sulfonamido, alkyl, cycloalkyl, heterocycloalkyl, aryl and heteroaryl. In some embodiments, each alkyl, cycloalkyl, heterocycloalkyl, aryl and heteroaryl group as defined in any one of Formulae (I), (II) or (III) is optionally substituted with one or more substituents selected from: halogen, acyl, acyloxy, alkoxy, carboxy, hydroxy, amino, amido, nitro, cyano, azido, alkylthio, thio, sulfonyl and sulfonamido.

In certain embodiments, the camptothecin analogue comprised by the ADC according to the present disclosure is a compound having Formula (I) and is selected from the compounds shown in Tables 6 and 7.

In certain embodiments, the camptothecin analogue is a compound having Formula (II).

In some embodiments, the camptothecin analogue is a compound having Formula (II), in which $R^2$ is F, and $R^{20}$ is H, —($C_1$-$C_6$)—O—$R^5$ or

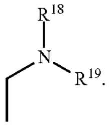

In some embodiments, the camptothecin analogue is a compound having Formula (II), in which $R^2$ is F; $R^{20}$ is H, —($C_1$-$C_6$)—O—$R^5$ or

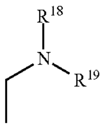

$R^5$ is H, and $R^{18}$ and $R^{19}$ taken together with the N atom to which they are bonded form an unsubstituted 4-, 5-, 6-, or 7-membered ring. In some embodiments, the camptothecin analogue is a compound having Formula (II), in which $R^2$ is F; $R^{20}$ is —($C_1$-$C_6$)—O—$R^5$, and $R^5$ is H. In certain embodiments, the camptothecin analogue is a compound having Formula (II) and is selected from the compounds shown in Table 6.

In certain embodiments, the camptothecin analogue is a compound having Formula (III). In certain embodiments, the camptothecin analogue is a compound having Formula (III), in which $R^2$ is F; $R^{15}$ is —$CH_3$; $R^4$ is

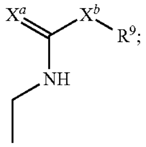

$R^9$ is —$C_1$-$C_6$ hydroxyalkyl, and $X^a$ and $X^b$ are each O. In certain embodiments, the camptothecin analogue is a compound having Formula (III) and is selected from the compounds shown in Table 7.

In certain embodiments, the camptothecin analogue comprised by the ADC according to the present disclosure is Compound 139, Compound 140, Compound 141 or Compound 148. In some embodiments, the camptothecin analogue comprised by the ADC according to the present disclosure is Compound 139 or Compound 141.

TABLE 6

Exemplary Camptothecin Analogues of Formula (II)

| Structure | Compound Name | Compound Number |
|---|---|---|
| 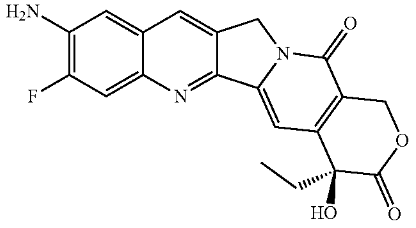 [SMILES: CC[C@@]1(O)C(=O)OCc2c1cc1n(c2=O)Cc2cc3cc(N)c(F)cc3nc2-1] | (S)-9-amino-4-ethyl-8-fluoro-4-hydroxy-1,12-dihydro-14H-pyrano[3',4':6,7]indolizino[1,2-b]quinoline-3,14(4H)-dione | Compound 140 |
| 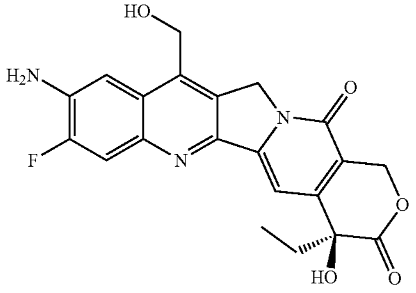 [SMILES: CC[C@@]1(O)C(=O)OCc2c1cc1n(c2=O)Cc2c-1nc1cc(F)c(N)cc1c2CO] | (S)-9-amino-4-ethyl-8-fluoro-4-hydroxy-11-(hydroxymethyl)-1,12-dihydro-14H-pyrano[3',4':6,7]indolizino[1,2-b]quinoline-3,14(4H)-dione | Compound 141 |
| 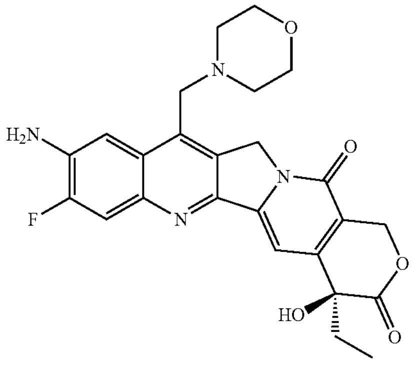 [SMILES: CC[C@@]1(O)C(=O)OCc2c1cc1n(c2=O)Cc2c-1nc1cc(F)c(N)cc1c2CN1CCOCC1] | (S)-9-amino-4-ethyl-8-fluoro-4-hydroxy-11-(morpholinomethyl)-1,12-dihydro-14H-pyrano[3',4':6,7]indolizino[1,2-b]quinoline-3,14(4H)-dione | Compound 142 |

TABLE 6-continued

Exemplary Camptothecin Analogues of Formula (II)

| Structure | Compound Name | Compound Number |
|---|---|---|
| 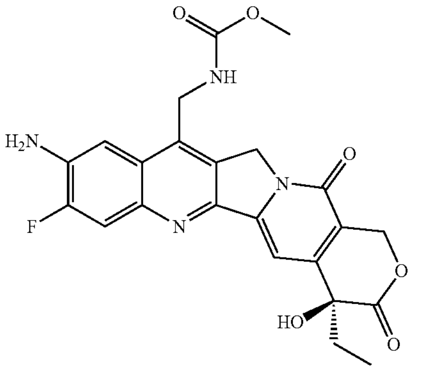 [SMILES: CC[C@@]1(O)C(=O)OCc2c1cc1n(c2=O)Cc2c-1nc1cc(F)c(N)cc1c2CNC(=O)OC] | methyl (S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)carbamate | Compound 143 |
| 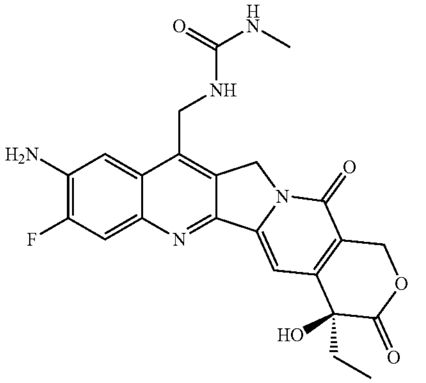 | (S)-1-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-3-methylurea | Compound 144 |
| 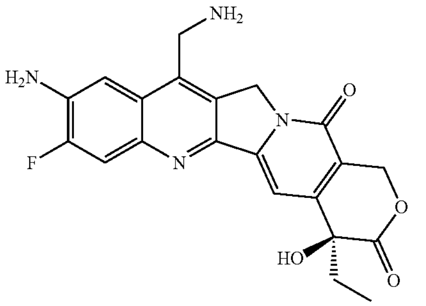 [SMILES: CC[C@@]1(O)C(=O)OCc2c1cc1n(c2=O)Cc2c-1nc1cc(F)c(N)cc1c2CN] | (S)-9-amino-11-(aminomethyl)-4-ethyl-8-fluoro-4-hydroxy-1,12-dihydro-14H-pyrano[3',4':6,7]indolizino[1,2-b]quinoline-3,14(4H)-dione | Compound 145 |
| 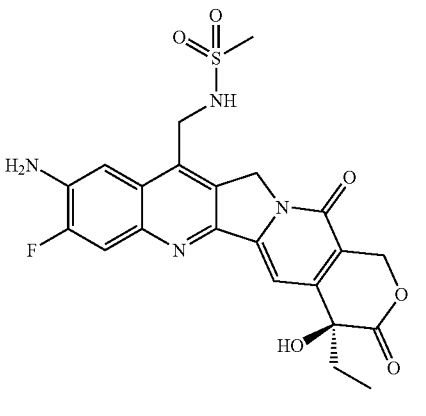 [SMILES: CC[C@@]1(O)C(=O)OCc2c1cc1n(c2=O)Cc2c-1nc1cc(F)c(N)cc1c2CNS(C)(=O)=O] | (S)-N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)methanesulfonamide | Compound 146 |

TABLE 6-continued

Exemplary Camptothecin Analogues of Formula (II)

| Structure | Compound Name | Compound Number |
| --- | --- | --- |
| 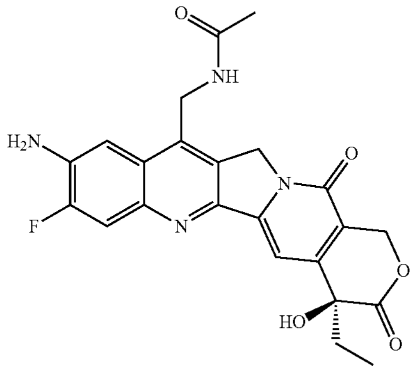 [SMILES: CC[C@@]1(O)C(=O)OCc2c1cc1n(c2=O)Cc2c-1nc1cc(F)c(N)cc1c2CNC(C)=O] | (S)-N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)acetamide | Compound 147 |
| 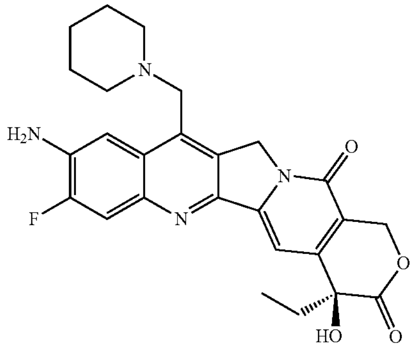 [SMILES: CC[C@@]1(O)C(=O)OCc2c1cc1n(c2=O)Cc2c-1nc1cc(F)c(N)cc1c2CN1CCCCC1] | (S)-9-amino-4-ethyl-8-fluoro-4-hydroxy-11-(piperidin-1-ylmethyl)-1,12-dihydro-14H-pyrano[3',4':6,7]indolizino[1,2-b]quinoline-3,14(4H)-dione | Compound 148 |
| 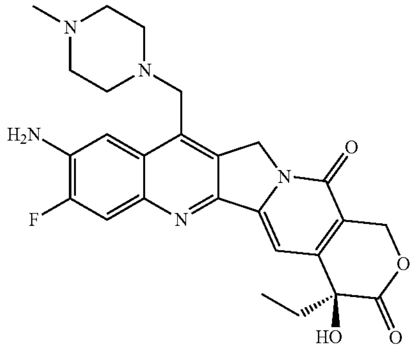 [SMILES: CC[C@@]1(O)C(=O)OCc2c1cc1n(c2=O)Cc2c-1nc1cc(F)c(N)cc1c2CN1CCN(C)CC1] | (S)-9-amino-4-ethyl-8-fluoro-4-hydroxy-11-((4-methylpiperazin-1-yl)methyl)-1,12-dihydro-14H-pyrano[3',4':6,7]indolizino[1,2-b]quinoline-3,14(4H)-dione | Compound 149 |
| 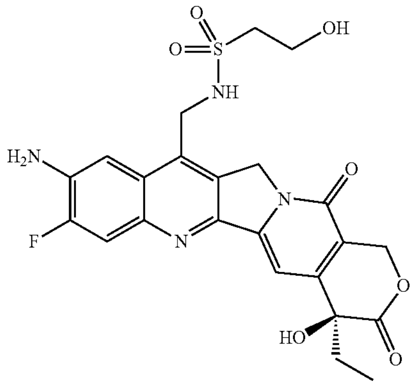 [SMILES: CC[C@@]1(O)C(=O)OCc2c1cc1n(c2=O)Cc2c-1nc1cc(F)c(N)cc1c2CNS(=O)(=O)CCO] | (S)-N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-2-hydroxyethane-1-sulfonamide | Compound 150 |

TABLE 6-continued

Exemplary Camptothecin Analogues of Formula (II)

| Structure | Compound Name | Compound Number |
|---|---|---|
| 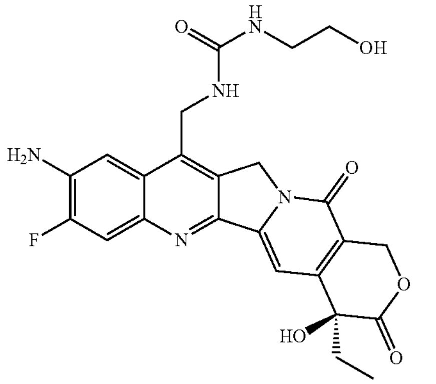 [SMILES: CC[C@@]1(O)C(=O)OCc2c1cc1n(c2=O)Cc2c-1nc1cc(F)c(N)cc1c2CNC(=O)NCCO] | (S)-1-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-3-(2-hydroxyethyl)urea | Compound 151 |
| 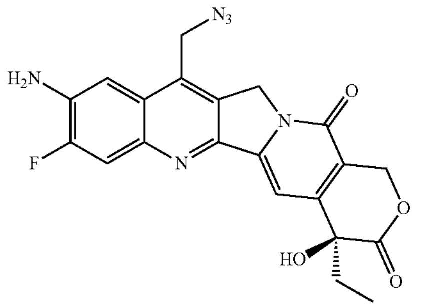 [SMILES: CC[C@@]1(O)C(=O)OCc2c1cc1n(c2=O)Cc2c-1nc1cc(F)c(N)cc1c2CN=[N+]=[N-]] | (S)-9-amino-11-(azidomethyl)-4-ethyl-8-fluoro-4-hydroxy-1,12-dihydro-14H-pyrano[3',4':6,7]indolizino[1,2-b]quinoline-3,14(4H)-dione | Compound 152 |
| 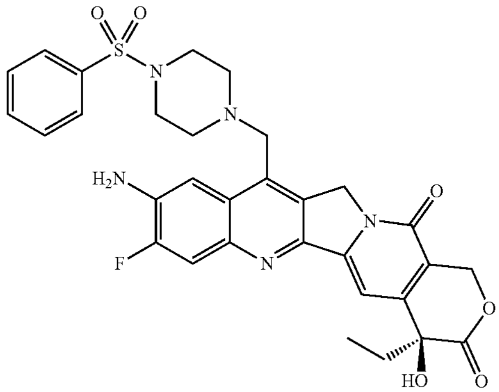 [SMILES: CC[C@@]1(O)C(=O)OCc2c1cc1n(c2=O)Cc2c-1nc1cc(F)c(N)cc1c2CN1CCN(S(=O)(=O)c2ccccc2)CC1] | (S)-9-amino-4-ethyl-8-fluoro-4-hydroxy-11-((4-(phenylsulfonyl)piperazin-1-yl)methyl)-1,12-dihydro-14H-pyrano[3',4':6,7]indolizino[1,2-b]quinoline-3,14(4H)-dion | Compound 153 |
| 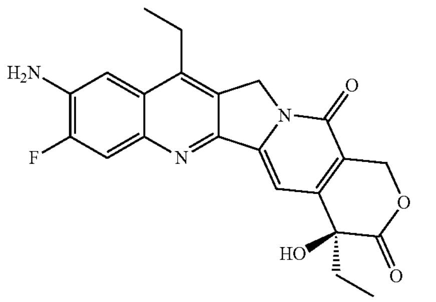 [SMILES: CCc1c2c(nc3cc(F)c(N)cc13)-c1cc3c(c(=O)n1C2)COC(=O)[C@]3(O)CC] | (S)-9-amino-4,11-diethyl-8-fluoro-4-hydroxy-1,12-dihydro-14H-pyrano[3',4':6,7]indolizino[1,2-b]quinoline-3,14(4H)-dione | Compound 154 |

TABLE 6-continued

| Exemplary Camptothecin Analogues of Formula (II) | | |
|---|---|---|
| | Compound | |
| Structure | Name | Number |
| 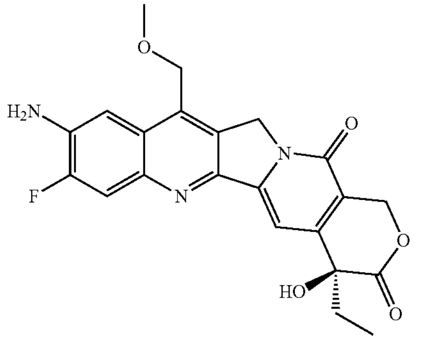 [SMILES: CC[C@@]1(O)C(=O)OCc2c1cc1n(c2=O)Cc2c-1nc1cc(F)c(N)cc1c2COC] | (S)-9-amino-4-ethyl-8-fluoro-4-hydroxy-11-(methoxymethyl)-1,12-dihydro-14H-pyrano[3',4':6,7]indolizino[1,2-b]quinoline-3,14(4H)-dione | Compound 155 |
| 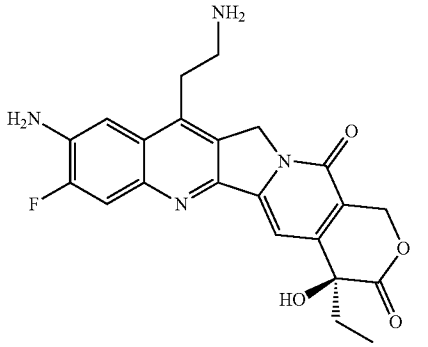 | (S)-9-amino-11-(2-aminoethyl)-4-ethyl-8-fluoro-4-hydroxy-1,12-dihydro-14H-pyrano[3',4':6,7]indolizino[1,2-b]quinoline-3,14(4H)-dione | Compound 156 |
| 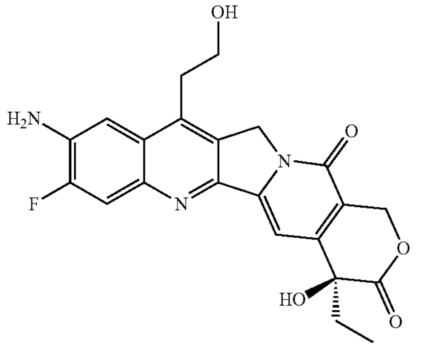 [SMILES: CC[C@@]1(O)C(=O)OCc2c1cc1n(c2=O)Cc2c-1nc1cc(F)c(N)cc1c2CCO] | (S)-9-amino-4-ethyl-8-fluoro-4-hydroxy-11-(2-hydroxyethyl)-1,12-dihydro-14H-pyrano[3',4':6,7]indolizino[1,2-b]quinoline-3,14(4H)-dione | Compound 157 |
| 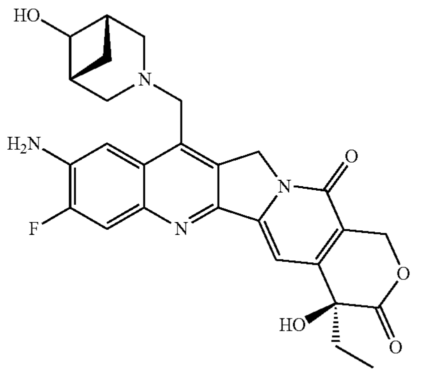 [SMILES: CC[C@@]1(O)C(=O)OCc2c1cc1n(c2=O)Cc2c-1nc1cc(F)c(N)cc1c2CN1C[C@H]2C[C@@H](C1)C2O] | (4S)-9-amino-4-ethyl-8-fluoro-4-hydroxy-11-(((1R,5S)-6-hydroxy-3-azabicyclo[3.1.1]heptan-3-yl)methyl)-1,12-dihydro-14H-pyrano[3',4':6,7]indolizino[1,2-b]quinoline-3,14(4H)-dione | Compound 158 |

TABLE 6-continued

| Exemplary Camptothecin Analogues of Formula (II) | | |
|---|---|---|
| | Compound | |
| Structure | Name | Number |
| 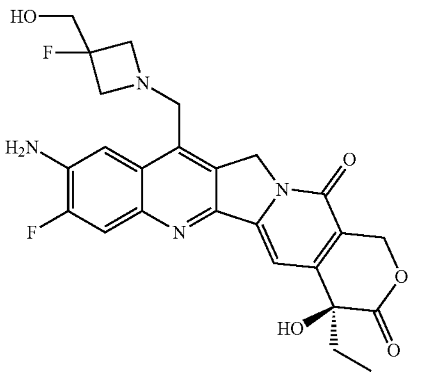 [SMILES: CC[C@@]1(O)C(=O)OCc2c1cc1n(c2=O)Cc2c-1nc1cc(F)c(N)cc1c2CN1CC(F)(CO)C1] | (S)-9-amino-4-ethyl-8-fluoro-11-((3-fluoro-3-(hydroxymethyl)azetidin-1-yl)methyl)-4-hydroxy-1,12-dihydro-14H-pyrano[3',4':6,7]indolizino[1,2-b]quinoline-3,14(4H)-dione | Compound 159 |
| 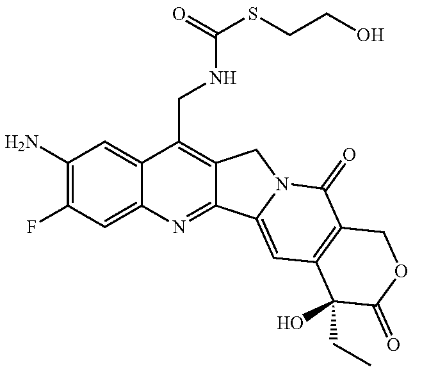 [SMILES: CC[C@@]1(O)C(=O)OCc2c1cc1n(c2=O)Cc2c-1nc1cc(F)c(N)cc1c2CNC(=O)SCCO] | S-(2-hydroxyethyl)(S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)carbamothioate | Compound 160 |
| 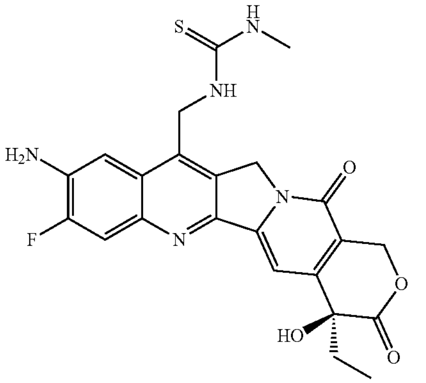 [SMILES: CC[C@@]1(O)C(=O)OCc2c1cc1n(c2=O)Cc2c-1nc1cc(F)c(N)cc1c2CNC(=S)NC] | (S)-1-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-3-methylthiourea | Compound 161 |
| 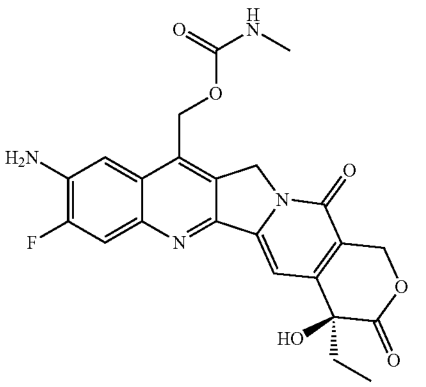 [SMILES: CC[C@@]1(O)C(=O)OCc2c1cc1n(c2=O)Cc2c-1nc1cc(F)c(N)cc1c2COC(=O)NC] | (S)-(9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl methylcarbamate | Compound 162 |

TABLE 6-continued

| Exemplary Camptothecin Analogues of Formula (II) | | |
|---|---|---|
| | Compound | |
| Structure | Name | Number |
| 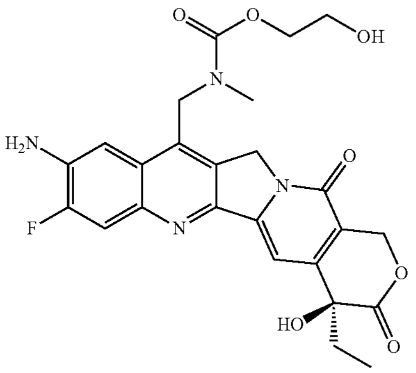 [SMILES: CC[C@@]1(O)C(=O)OCc2c1cc1n(c2=O)Cc2c-1nc1cc(F)c(N)cc1c2CN(C)C(=O)OCCO] | 2-hydroxyethyl (S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)(methyl)carbamate | Compound 163 |
| 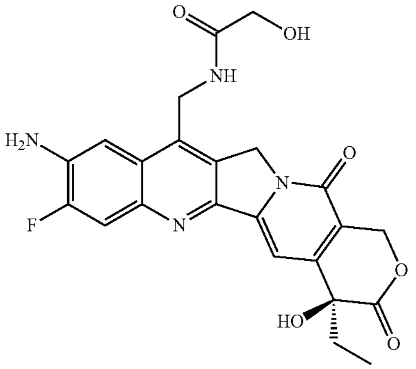 [SMILES: CC[C@@]1(O)C(=O)OCc2c1cc1n(c2=O)Cc2c-1nc1cc(F)c(N)cc1c2CNC(=O)CO] | (S)-N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-2-hydroxyacetamide | Compound 164 |
| 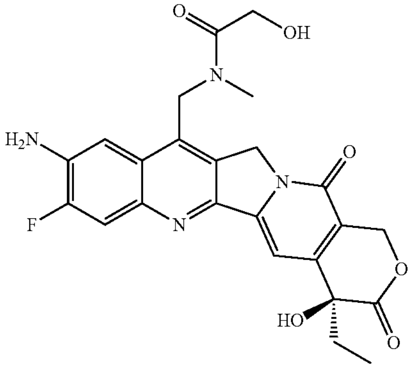 [SMILES: CC[C@@]1(O)C(=O)OCc2c1cc1n(c2=O)Cc2c-1nc1cc(F)c(N)cc1c2CN(C)C(=O)CO] | (S)-N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-2-hydroxy-N-methylacetamide | Compound 165 |
| 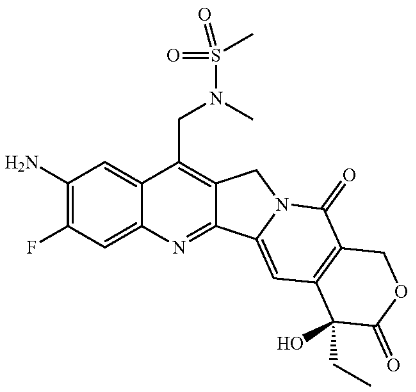 [SMILES: CC[C@@]1(O)C(=O)OCc2c1cc1n(c2=O)Cc2c-1nc1cc(F)c(N)cc1c2CN(C)S(C)(=O)=O] | (S)-N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-N-methylmethanesulfonamide | Compound 166 |

TABLE 6-continued

| Exemplary Camptothecin Analogues of Formula (II) | | |
|---|---|---|
| | Compound | |
| Structure | Name | Number |
| 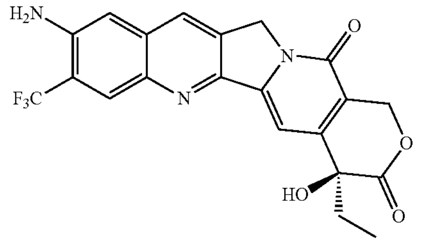 [SMILES: CC[C@@]1(O)C(=O)OCc2c1cc1n(c2=O)Cc2cc3cc(N)c(C(F)(F)F)cc3nc2-1] | (S)-9-amino-4-ethyl-4-hydroxy-8-(trifluoromethyl)-1,12-dihydro-14H-pyrano[3',4':6,7]indolizino[1,2-b]quinoline-3,14(4H)-dione | Compound 167 |
| 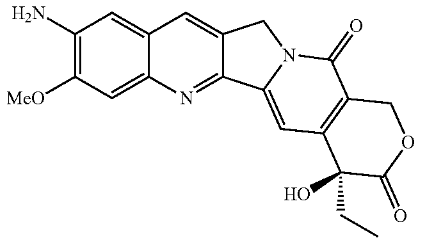 [SMILES: CC[C@@]1(O)C(=O)OCc2c1cc1n(c2=O)Cc2cc3cc(N)c(OC)cc3nc2-1] | (S)-9-amino-4-ethyl-4-hydroxy-8-methoxy-1,12-dihydro-14H-pyrano[3',4':6,7]indolizino[1,2-b]quinoline-3,14(4H)-dione | Compound 168 |
| 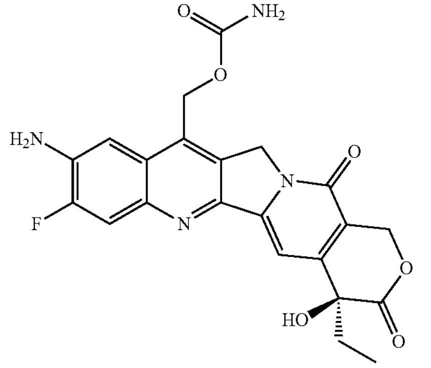 [SMILES: CC[C@@]1(O)C(=O)OCc2c1cc1n(c2=O)Cc2c-1nc1cc(F)c(N)cc1c2COC(N)=O] | (S)-(9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl carbamate | Compound 169 |
| 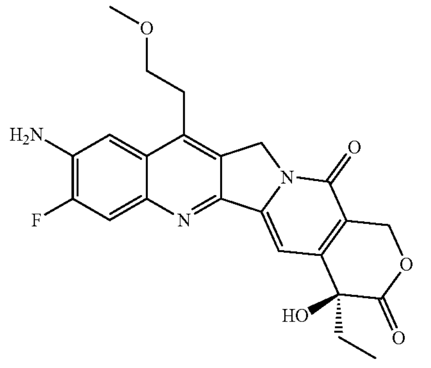 [SMILES: CC[C@@]1(O)C(=O)OCc2c1cc1n(c2=O)Cc2c-1nc1cc(F)c(N)cc1c2CCOC] | (S)-9-amino-4-ethyl-8-fluoro-4-hydroxy-11-(2-methoxyethyl)-1,12-dihydro-14H-pyrano[3',4':6,7]indolizino[1,2-b]quinoline-3,14(4H)-dione | Compound 170 |
| 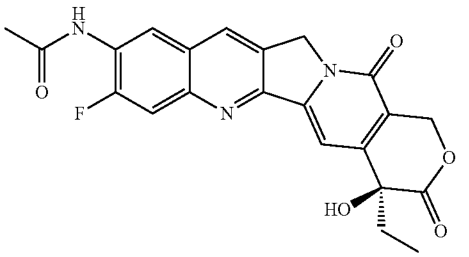 [SMILES: CC[C@@]1(O)C(=O)OCc2c1cc1n(c2=O)Cc2cc3cc(NC(C)=O)c(F)cc3nc2-1] | (S)-N-(4-ethyl-8-fluoro-4-hydroxy-3,14-dioxo-3,4,12,14-tetrahydro-1H-pyrano[3',4':6,7]indolizino[1,2-b]quinolin-9-yl)acetamide | Compound 171 |

TABLE 6-continued

| Exemplary Camptothecin Analogues of Formula (II) | | |
|---|---|---|
| | Compound | |
| Structure | Name | Number |

TABLE 7

| Exemplary Camptothecin Analogues of Formula (III) | | |
|---|---|---|
| | Compound | |
| Structure | Name | Number |
| 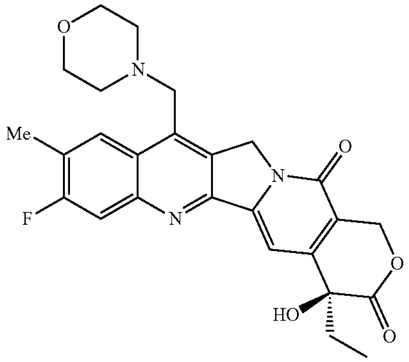 [SMILES: CC[C@@]1(O)C(=O)OCc2c1cc1n(c2=O)Cc2c-1nc1cc(F)c(C)cc1c2CN1CCOCC1] | (S)-4-ethyl-8-fluoro-4-hydroxy-9-methyl-11-(morpholinomethyl)-1,12-dihydro-14H-pyrano[3',4':6,7]indolizino[1,2-b]quinoline-3,14(4H)-dione | Compound 100 |
| 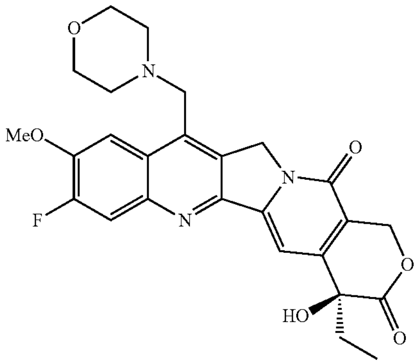 [SMILES: CC[C@@]1(O)C(=O)OCc2c1cc1n(c2=O)Cc2c-1nc1cc(F)c(OC)cc1c2CN1CCOCC1] | (S)-4-ethyl-8-fluoro-4-hydroxy-9-methoxy-11-(morpholinomethyl)-1,12-dihydro-14H-pyrano[3',4':6,7]indolizino[1,2-b]quinoline-3,14(4H)-dione | Compound 101 |
| 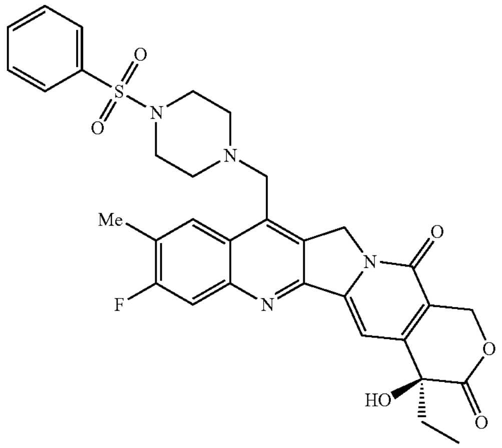 [SMILES: CC[C@@]1(O)C(=O)OCc2c1cc1n(c2=O)Cc2c-1nc1cc(F)c(C)cc1c2CN1CCN(S(=O)(=O)c2ccccc2)CC1] | (S)-4-ethyl-8-fluoro-4-hydroxy-9-methyl-11-((4-(phenylsulfonyl)piperazin-1-yl)methyl)-1,12-dihydro-14H-pyrano[3',4':6,7]indolizino[1,2-b]quinoline-3,14(4H)-dione | Compound 102 |

TABLE 7-continued

| Exemplary Camptothecin Analogues of Formula (III) | | |
|---|---|---|
| | Compound | |
| Structure | Name | Number |
| 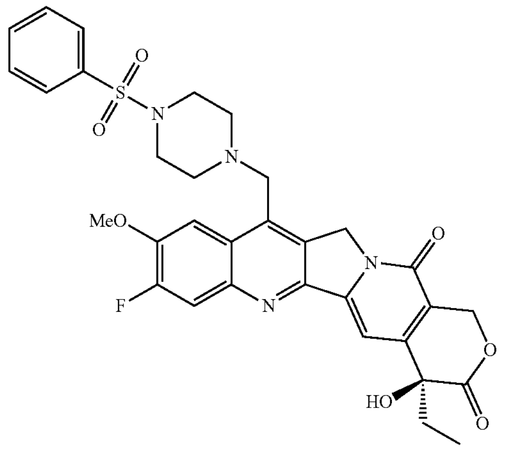 [SMILES: CC[C@@]1(O)C(=O)OCc2c1cc1n(c2=O)Cc2c-1nc1cc(F)c(OC)cc1c2CN1CCN(S(=O)(=O)c2ccccc2)CC1] | (S)-4-ethyl-8-fluoro-4-hydroxy-9-methoxy-11-((4-(phenylsulfonyl)piperazin-1-yl)methyl)-1,12-dihydro-14H-pyrano[3',4':6,7]indolizino[1,2-b]quinoline-3,14(4H)-dione | Compound 103 |
| 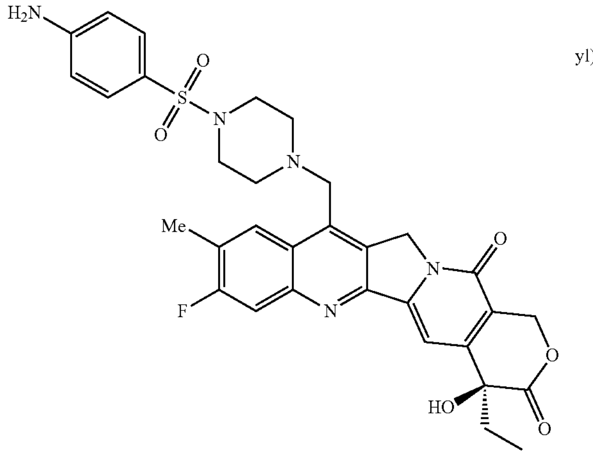 | (S)-11-((4-((4-aminophenyl)sulfonyl)piperazin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione | Compound 104 |
| 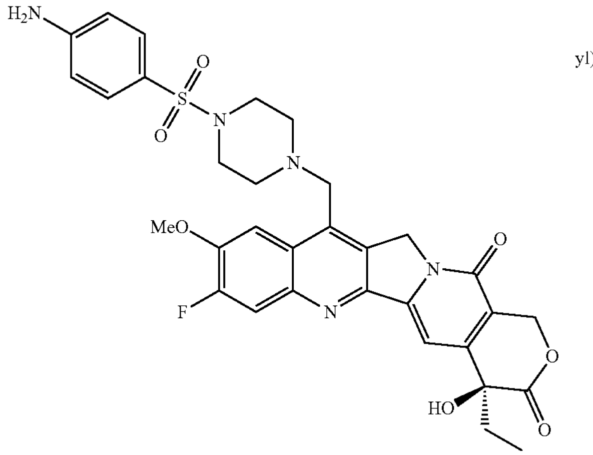 | (S)-11-((4-((4-aminophenyl)sulfonyl)piperazin-1-yl)methyl)-4-ethyl-8-fluoro-4-hydroxy-9-methoxy-1,12-dihydro-14H-pyrano[3',4':6,7]indolizino[1,2-b]quinoline-3,14(4H)-dione | Compound 105 |

TABLE 7-continued

Exemplary Camptothecin Analogues of Formula (III)

| Structure | Compound Name | Compound Number |
|---|---|---|
| 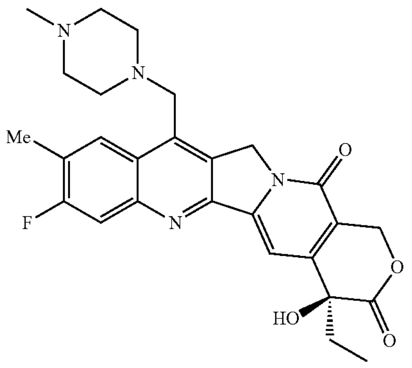 [SMILES: CC[C@@]1(O)C(=O)OCc2c1cc1n(c2=O)Cc2c-1nc1cc(F)c(C)cc1c2CN1CCN(C)CC1] | (S)-4-ethyl-8-fluoro-4-hydroxy-9-methyl-11-((4-methylpiperazin-1-yl)methyl)-1,12-dihydro-14H-pyrano[3',4':6,7]indolizino[1,2-b]quinoline-3,14(4H)-dione | Compound 106 |
| 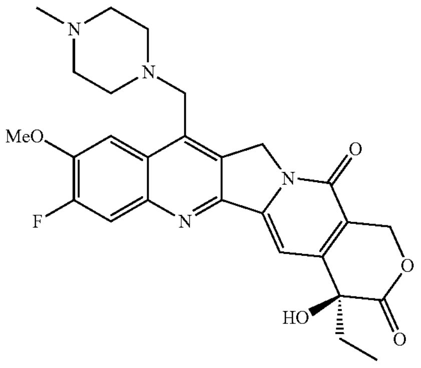 [SMILES: CC[C@@]1(O)C(=O)OCc2c1cc1n(c2=O)Cc2c-1nc1cc(F)c(OC)cc1c2CN1CCN(C)CC1] | (S)-4-ethyl-8-fluoro-4-hydroxy-9-methoxy-11-((4-methylpiperazin-1-yl)methyl)-1,12-dihydro-14H-pyrano[3',4':6,7]indolizino[1,2-b]quinoline-3,14(4H)-dione | Compound 107 |
| 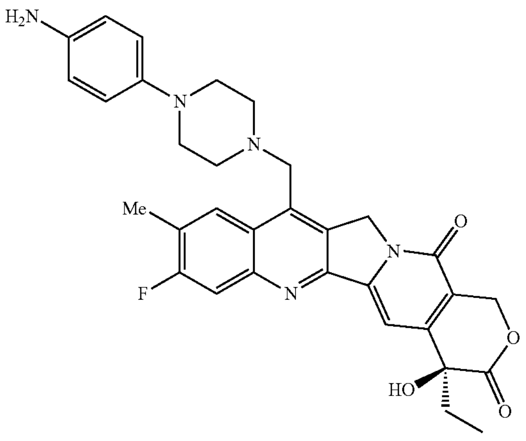 [SMILES: CC[C@@]1(O)C(=O)OCc2c1cc1n(c2=O)Cc2c-1nc1cc(F)c(C)cc1c2CN1CCN(c2ccc(N)cc2)CC1] | (S)-11-((4-(4-aminophenyl)piperazin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione | Compound 108 |

TABLE 7-continued

Exemplary Camptothecin Analogues of Formula (III)

| Structure | Compound Name | Compound Number |
|---|---|---|
| 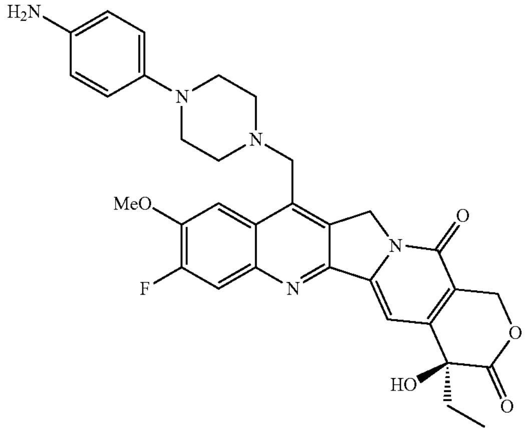 [SMILES: CC[C@@]1(O)C(=O)OCc2c1cc1n(c2=O)Cc2c-1nc1cc(F)c(OC)cc1c2CN1CCN(c2ccc(N)cc2)CC1] | (S)-11-((4-(4-aminophenyl)piperazin-1-yl)methyl)-4-ethyl-8-fluoro-4-hydroxy-9-methoxy-1,12-dihydro-14H-pyrano[3',4':6,7]indolizino[1,2-b]quinoline-3,14(4H)-dione | Compound 109 |
| 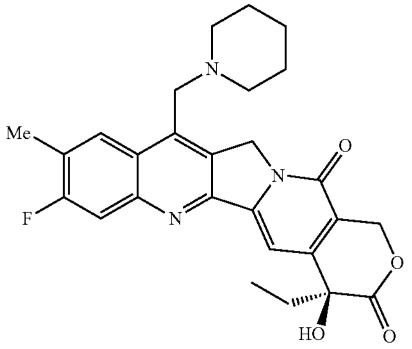 [SMILES: CC[C@@]1(O)C(=O)OCc2c1cc1n(c2=O)Cc2c-1nc1cc(F)c(C)cc1c2CN1CCCCC1] | (S)-4-ethyl-8-fluoro-4-hydroxy-9-methyl-11-(piperidin-1-ylmethyl)-1,12-dihydro-14H-pyrano[3',4':6,7]indolizino[1,2-b]quinoline-3,14(4H)-dione | Compound 110 |
| 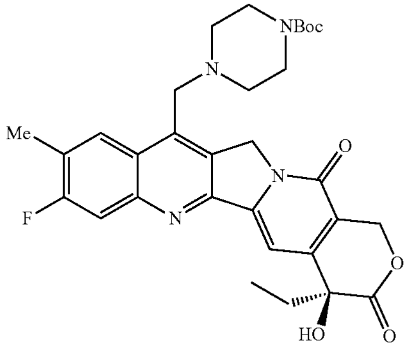 [SMILES: CC[C@@]1(O)C(=O)OCc2c1cc1n(c2=O)Cc2c-1nc1cc(F)c(C)cc1c2CN1CCN(C(=O)OC(C)(C)C)CC1] | tert-butyl (S)-4-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)piperazine-1-carboxylate | Compound 111 |
| 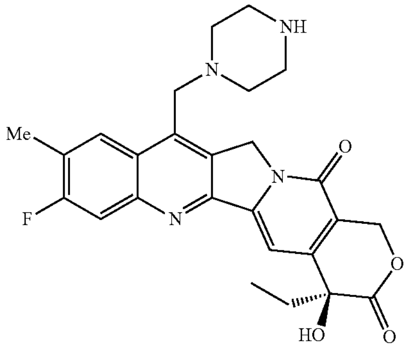 [SMILES: CC[C@@]1(O)C(=O)OCc2c1cc1n(c2=O)Cc2c-1nc1cc(F)c(C)cc1c2CN1CCNCC1] | (S)-4-ethyl-8-fluoro-4-hydroxy-9-methyl-11-(piperazin-1-ylmethyl)-1,12-dihydro-14H-pyrano[3',4':6,7]indolizino[1,2-b]quinoline-3,14(4H)-dione | Compound 112 |

TABLE 7-continued

| Exemplary Camptothecin Analogues of Formula (III) | | |
|---|---|---|
| Structure | Compound Name | Compound Number |
| 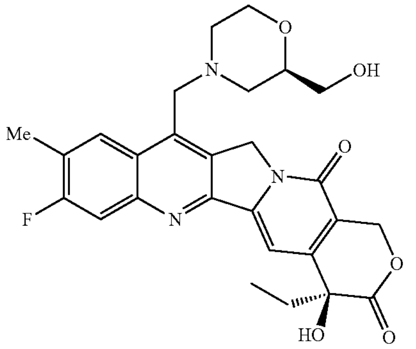 [SMILES: CC[C@@]1(O)C(=O)OCc2c1cc1n(c2=O)Cc2c-1nc1cc(F)c(C)cc1c2CN1CCO[C@@H](CO)C1] | (S)-4-ethyl-8-fluoro-4-hydroxy-11-(((R)-2-(hydroxymethyl)morpholino)methyl)-9-methyl-1,12-dihydro-14H-pyrano[3',4':6,7]indolizino[1,2-b]quinoline-3,14(4H)-dione | Compound 113 |
| 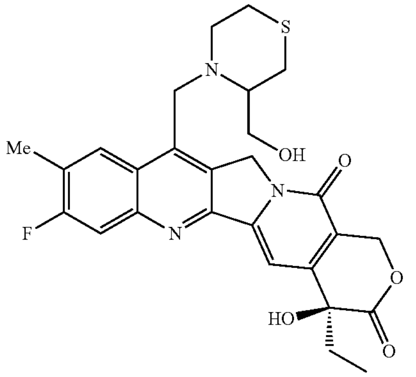 [SMILES: CC[C@@]1(O)C(=O)OCc2c1cc1n(c2=O)Cc2c-1nc1cc(F)c(C)cc1c2CN1CCSCC1CO] | (4S)-4-ethyl-8-fluoro-4-hydroxy-11-((3-(hydroxymethyl)thiomorpholino)methyl)-9-methyl-1,12-dihydro-14H-pyrano[3',4':6,7]indolizino[1,2-b]quinoline-3,14(4H)-dione | Compound 114 |
| 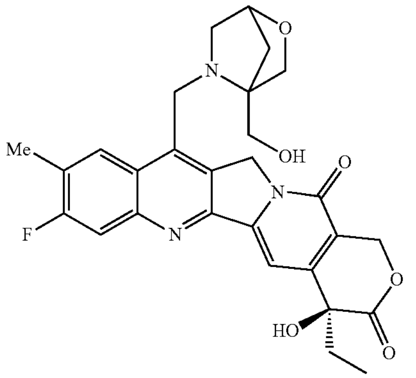 [SMILES: CC[C@@]1(O)C(=O)OCc2c1cc1n(c2=O)Cc2c-1nc1cc(F)c(C)cc1c2CN1CC2CC1(CO)CO2] | (4S)-4-ethyl-8-fluoro-4-hydroxy-11-((4-(hydroxymethyl)-2-oxa-5-azabicyclo[2.2.1]heptan-5-yl)methyl)-9-methyl-1,12-dihydro-14H-pyrano[3',4':6,7]indolizino[1,2-b]quinoline-3,14(4H)-dione | Compound 115 |
| 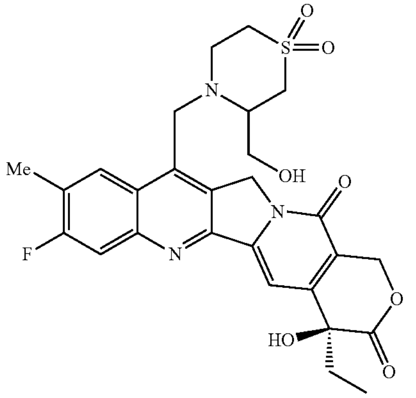 [SMILES: CC[C@@]1(O)C(=O)OCc2c1cc1n(c2=O)Cc2c-1nc1cc(F)c(C)cc1c2CN1CCS(=O)(=O)CC1CO] | (4S)-4-ethyl-8-fluoro-4-hydroxy-11-((3-(hydroxymethyl)-1,1-dioxidothiomorpholino)methyl)-9-methyl-1,12-dihydro-14H-pyrano[3',4':6,7]indolizino[1,2-b]quinoline-3,14(4H)-dione | Compound 116 |

TABLE 7-continued

| Exemplary Camptothecin Analogues of Formula (III) | | |
|---|---|---|
| | Compound | |
| Structure | Name | Number |
| 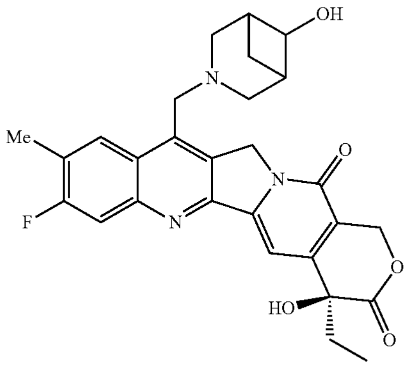 [SMILES: CC[C@@]1(O)C(=O)OCc2c1cc1n(c2=O)Cc2c-1nc1cc(F)c(C)cc1c2CN1CC2CC(C1)C2O] | (4S)-4-ethyl-8-fluoro-4-hydroxy-11-((6-hydroxy-3-azabicyclo[3.1.1]heptan-3-yl)methyl)-9-methyl-1,12-dihydro-14H-pyrano[3',4':6,7]indolizino[1,2-b]quinoline-3,14(4H)-dione | Compound 117 |
| 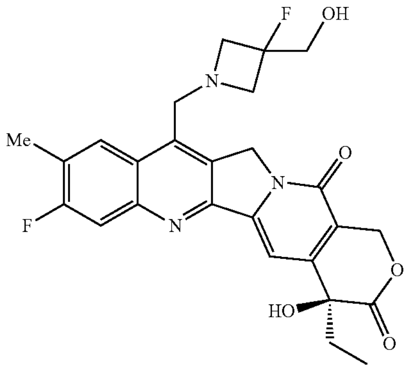 [SMILES: CC[C@@]1(O)C(=O)OCc2c1cc1n(c2=O)Cc2c-1nc1cc(F)c(C)cc1c2CN1CC(F)(CO)C1] | (S)-4-ethyl-8-fluoro-11-((3-fluoro-3-(hydroxymethyl)azetidin-1-yl)methyl)-4-hydroxy-9-methyl-1,12-dihydro-14H-pyrano[3',4':6,7]indolizino[1,2-b]quinoline-3,14(4H)-dione | Compound 118 |
| 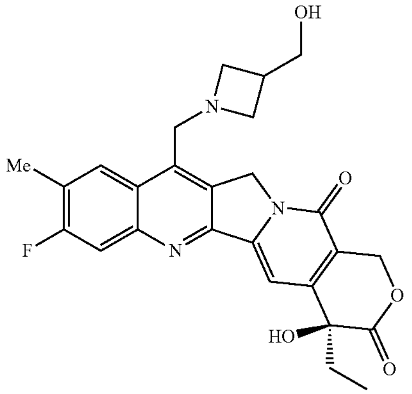 [SMILES: CC[C@@]1(O)C(=O)OCc2c1cc1n(c2=O)Cc2c-1nc1cc(F)c(C)cc1c2CN1CC(CO)C1] | (S)-4-ethyl-8-fluoro-4-hydroxy-11-((3-(hydroxymethyl)azetidin-1-yl)methyl)-9-methyl-1,12-dihydro-14H-pyrano[3',4':6,7]indolizino[1,2-b]quinoline-3,14(4H)-dione | Compound 119 |

TABLE 7-continued

| Exemplary Camptothecin Analogues of Formula (III) | | |
| --- | --- | --- |
| | Compound | |
| Structure | Name | Number |
| 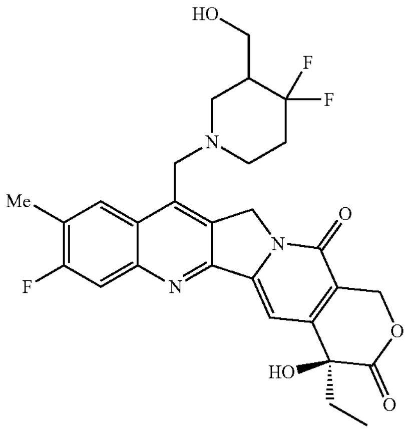 [SMILES: CC[C@@]1(O)C(=O)OCc2c1cc1n(c2=O)Cc2c-1nc1cc(F)c(C)cc1c2CN1CCC(F)(F)C(CO)C1] | (4S)-11-((4,4-difluoro-3-(hydroxymethyl)piperidin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione | Compound 120 |
| 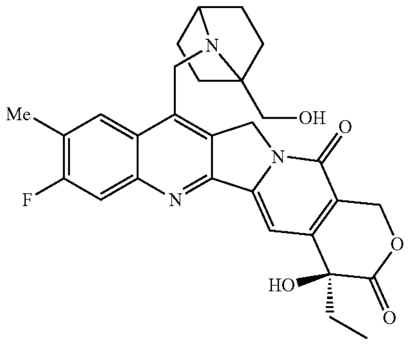 [SMILES: CC[C@@]1(O)C(=O)OCc2c1cc1n(c2=O)Cc2c-1nc1cc(F)c(C)cc1c2CN1C2CCC1(CO)CC2] | (4S)-11-((4,4-difluoro-3-(hydroxymethyl)piperidin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione | Compound 121 |
| 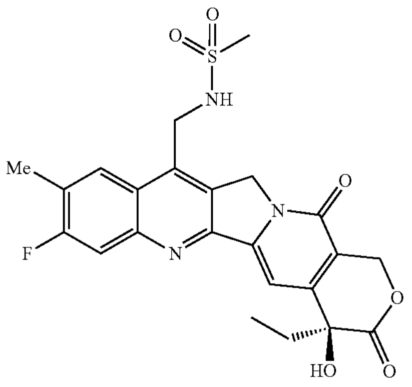 [SMILES: CC[C@@]1(O)C(=O)OCc2c1cc1n(c2=O)Cc2c-1nc1cc(F)c(C)cc1c2CNS(C)(=O)=O] | (S)-N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)methanesulfonamide | Compound 122 |

TABLE 7-continued

| Exemplary Camptothecin Analogues of Formula (III) | | |
|---|---|---|
| | Compound | |
| Structure | Name | Number |
| 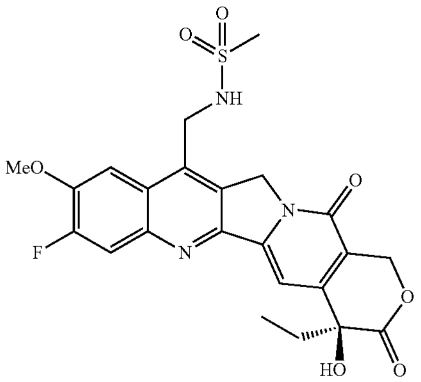 [SMILES: CC[C@@]1(O)C(=O)OCc2c1cc1n(c2=O)Cc2c-1nc1cc(F)c(OC)cc1c2CNS(C)(=O)=O] | (S)-N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)methanesulfonamide | Compound 123 |
| 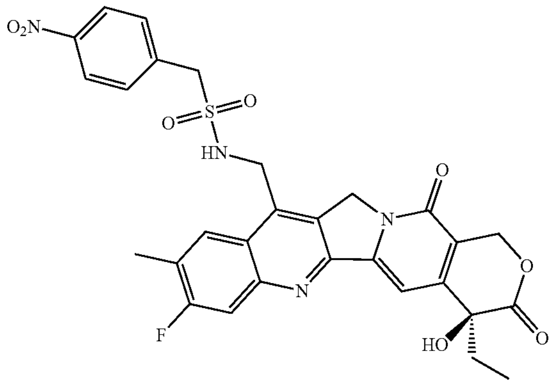 [SMILES: CC[C@@]1(O)C(=O)OCc2c1cc1n(c2=O)Cc2c-1nc1cc(F)c(C)cc1c2CNS(=O)(=O)Cc1ccc([N+](=O)[O-])cc1] | (S)-N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-1-(4-nitrophenyl)methanesulfonamide | Compound 124 |
| 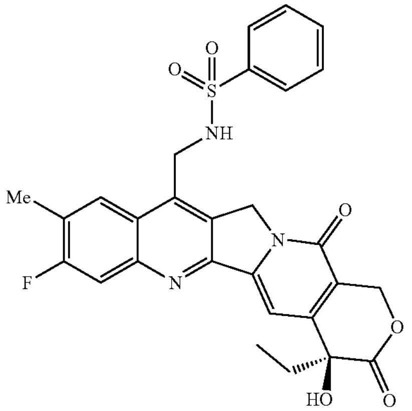 [SMILES: CC[C@@]1(O)C(=O)OCc2c1cc1n(c2=O)Cc2c-1nc1cc(F)c(C)cc1c2CNS(=O)(=O)c1ccccc1] | (S)-N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)benzenesulfonamide | Compound 125 |

TABLE 7-continued

| Exemplary Camptothecin Analogues of Formula (III) | | |
|---|---|---|
| | Compound | |
| Structure | Name | Number |
| 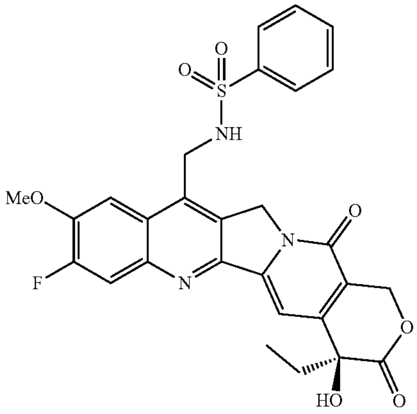 [SMILES: CC[C@@]1(O)C(=O)OCc2c1cc1n(c2=O)Cc2c-1nc1cc(F)c(OC)cc1c2CNS(=O)(=O)c1ccccc1] | (S)-N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)benzenesulfonamide | Compound 126 |
| 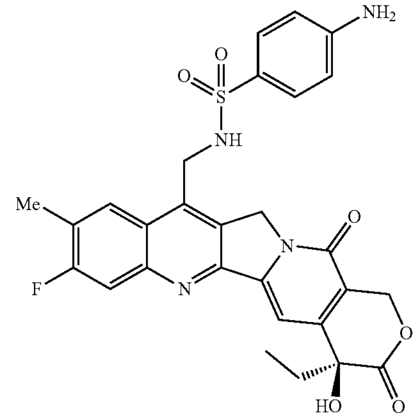 [SMILES: CC[C@@]1(O)C(=O)OCc2c1cc1n(c2=O)Cc2c-1nc1cc(F)c(C)cc1c2CNS(=O)(=O)c1ccc(N)cc1] | (S)-4-amino-N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)benzenesulfonamide | Compound 127 |
| 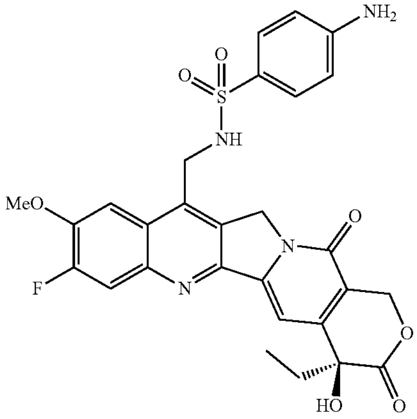 [SMILES: CC[C@@]1(O)C(=O)OCc2c1cc1n(c2=O)Cc2c-1nc1cc(F)c(OC)cc1c2CNS(=O)(=O)c1ccc(N)cc1] | (S)-4-amino-N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)benzenesulfonamide | Compound 128 |

TABLE 7-continued

Exemplary Camptothecin Analogues of Formula (III)

| Structure | Compound Name | Compound Number |
|---|---|---|
| 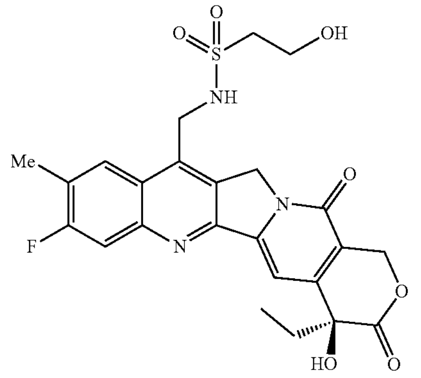 [SMILES: CC[C@@]1(O)C(=O)OCc2c1cc1n(c2=O)Cc2c-1nc1cc(F)c(C)cc1c2CNS(=O)(=O)CCO] | (S)-N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-2-hydroxyethane-1-sulfonamide | Compound 129 |
| 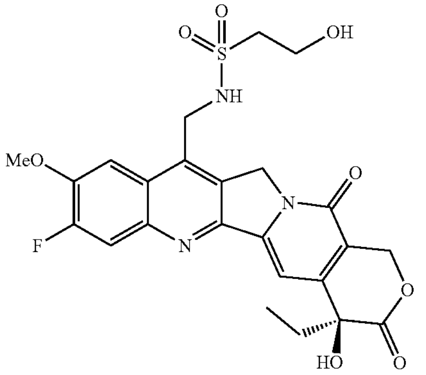 [SMILES: CC[C@@]1(O)C(=O)OCc2c1cc1n(c2=O)Cc2c-1nc1cc(F)c(OC)cc1c2CNS(=O)(=O)CCO] | (S)-N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)-2-hydroxyethane-1-sulfonamide | Compound 130 |
| 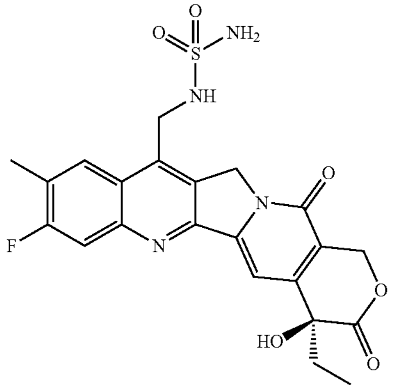 [SMILES: CC[C@@]1(O)C(=O)OCc2c1cc1n(c2=O)Cc2c-1nc1cc(F)c(C)cc1c2CNS(N)(=O)=O] | (S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)sulfamide | Compound 131 |
| 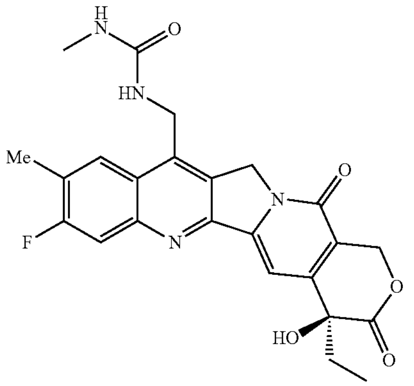 [SMILES: CC[C@@]1(O)C(=O)OCc2c1cc1n(c2=O)Cc2c-1nc1cc(F)c(C)cc1c2CNC(=O)NC] | (S)-1-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-methylurea | Compound 132 |

TABLE 7-continued

| Exemplary Camptothecin Analogues of Formula (III) | | |
|---|---|---|
| | Compound | |
| Structure | Name | Number |
| 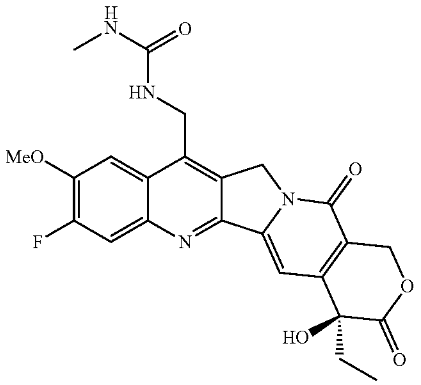 [SMILES: CC[C@@]1(O)C(=O)OCc2c1cc1n(c2=O)Cc2c-1nc1cc(F)c(OC)cc1c2CNC(=O)NC] | (S)-1-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)-3-methylurea | Compound 133 |
| 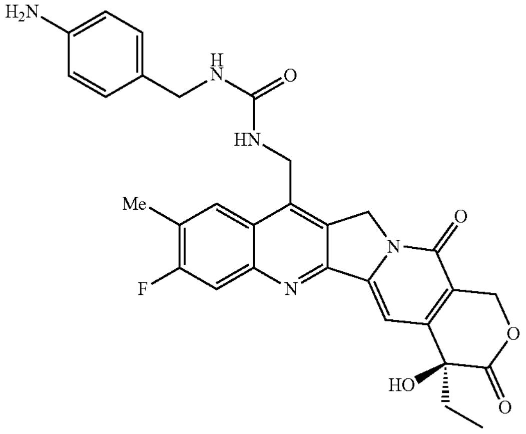 [SMILES: CC[C@@]1(O)C(=O)OCc2c1cc1n(c2=O)Cc2c-1nc1cc(F)c(C)cc1c2CNC(=O)NCc1ccc(N)cc1] | (S)-1-(4-aminobenzyl)-3-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)urea | Compound 134 |
| 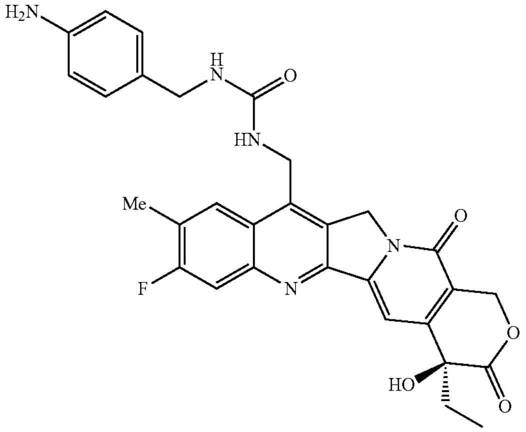 [SMILES: CC[C@@]1(O)C(=O)OCc2c1cc1n(c2=O)Cc2c-1nc1cc(F)c(C)cc1c2CNC(=O)NCc1ccc(N)cc1] | (S)-1-(4-aminobenzyl)-3-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)urea | Compound 135 |

TABLE 7-continued

| Exemplary Camptothecin Analogues of Formula (III) | | |
|---|---|---|
| | Compound | |
| Structure | Name | Number |
| 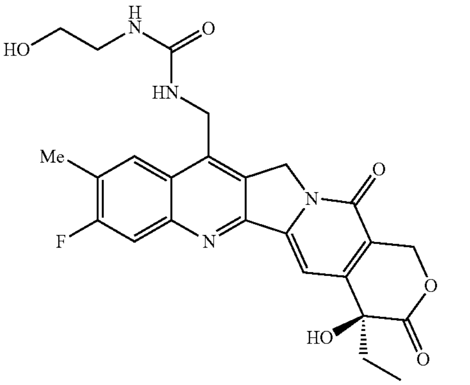 [SMILES: CC[C@@]1(O)C(=O)OCc2c1cc1n(c2=O)Cc2c-1nc1cc(F)c(C)cc1c2CNC(=O)NCCO] | (S)-1-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-(2-hydroxyethyl)urea | Compound 136 |
| 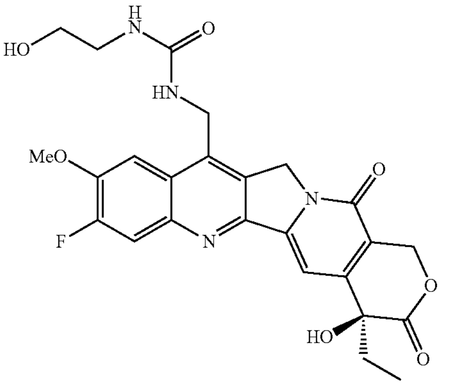 [SMILES: CC[C@@]1(O)C(=O)OCc2c1cc1n(c2=O)Cc2c-1nc1cc(F)c(OC)cc1c2CNC(=O)NCCO] | (S)-1-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)-3-(2-hydroxyethyl)urea | Compound 137 |
| 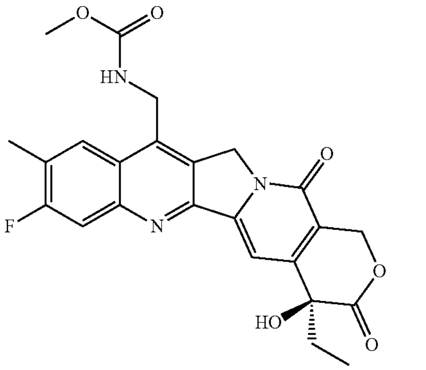 [SMILES: CC[C@@]1(O)C(=O)OCc2c1cc1n(c2=O)Cc2c-1nc1cc(F)c(C)cc1c2CNC(=O)OC] | methyl (S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)carbamate | Compound 138 |
| 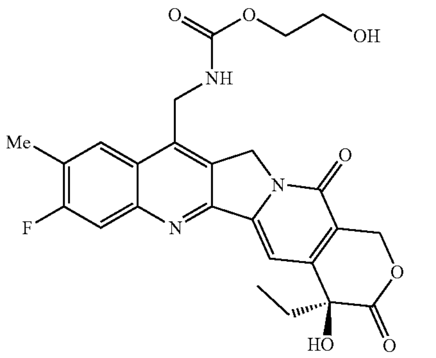 [SMILES: CC[C@@]1(O)C(=O)OCc2c1cc1n(c2=O)Cc2c-1nc1cc(F)c(C)cc1c2CNC(=O)OCCO] | 2-hydroxyethyl (S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)carbamate | Compound 139 |

It is to be understood that reference to compounds of Formula (I) throughout this disclosure, includes in various embodiments, compounds of Formula (II) and Formula (III), as well as the individual compounds shown in Tables 6 and 7, to the same extent as if embodiments reciting each of these Formulae or compounds individually were specifically recited.

Antibody-Drug Conjugates

The present disclosure relates to antibody-drug conjugates (ADCs) comprising an anti-FRα antibody construct conjugated to a camptothecin analogue having Formula (I). In certain embodiments, the ADC has Formula (X):

$$T\text{-}[L\text{-}(D)_m]_n \quad (X)$$

wherein:

T is an anti-FRα antibody construct as described herein;

L is a linker;

D is a camptothecin analogue having Formula (I);

m is between 1 and 4, and n is between 1 and 10.

In certain embodiments, in conjugates of Formula (X), m is between 1 and 2. In some embodiments, m is 1.

In some embodiments, in conjugates of Formula (X), n is between 1 and 8, for example, between 2 and 8. In some embodiments, n is between 4 and 8.

In certain embodiments, in conjugates of Formula (X), m is between 1 and 2, and n is between 2 and 8, or between 4 and 8. In some embodiments, in conjugates of Formula (X), m is 1, and n is between 2 and 8, or between 4 and 8.

As noted above and reflected by parameters m and n in Formula (X), the anti-FRα antibody construct, "T," can be conjugated to more than one compound of Formula (I), "D." Those skilled in the art will appreciate that, while any particular anti-FRα antibody construct T is conjugated to an integer number of compounds D, analysis of a preparation of the conjugate to determine the ratio of compound D to anti-FRα antibody construct T may give a non-integer result, reflecting a statistical average. This ratio of compound D to targeting moiety T may generally be referred to as the drug-to-antibody ratio, or "DAR." Accordingly, conjugate preparations having non-integer DARs are intended to be encompassed by Formula (X).

In certain embodiments, in the conjugates of Formula (X), D is a compound of Formula Formula (II) or Formula (III). In certain embodiments, in the conjugates of Formula (X), D is a compound selected from the compounds shown in Tables 6 and 7. In certain embodiments, in the conjugates of Formula (X), D is Compound 139, Compound 140, Compound 141 or Compound 148. In some embodiments, in the conjugates of Formula (X), D is Compound 139 or Compound 141.

Certain embodiments of the present disclosure relate to ADCs having Formula (X), in which D is a compound of Formula (IV):

(IV)

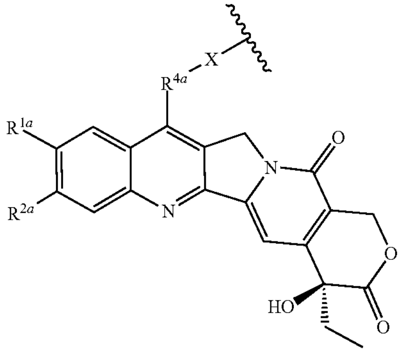

wherein:

$R^{1a}$ is selected from: —H, —$CH_3$, —$CHF_2$, —$CF_3$, —F, —Br, —Cl, —OH, —$OCH_3$, —$OCF_3$ and —$NH_2$;

$R^{2a}$ is selected from: —H, —$CH_3$, —$CF_3$, —F, —Br, —Cl, —OH, —$OCH_3$ and —$OCF_3$;

X is —O—, —S— or —NH—, and $R^{4a}$ is selected from:

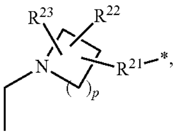 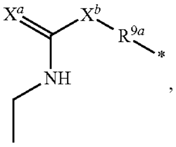, 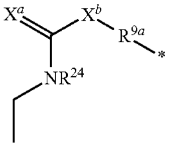,

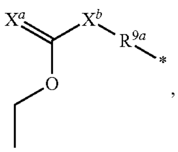, 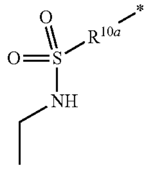, 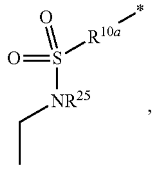,

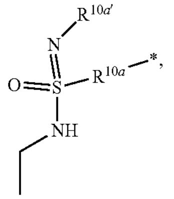, 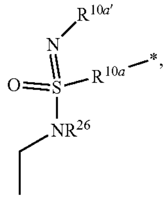, 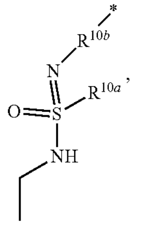,

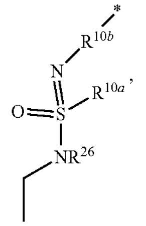, 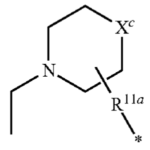 and

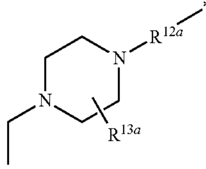

wherein * is the point of attachment to X, and wherein p is 1, 2, 3 or 4; or

X is O, and $R^{4a}$—X— is selected from:

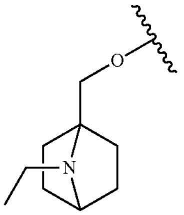
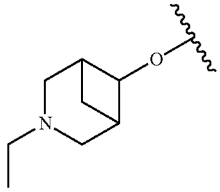
and
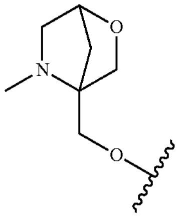
;

$R^{5a}$ is selected from: —$C_1$-$C_6$ alkyl, —$C_3$-$C_8$ cycloalkyl, -aryl, -heteroaryl and —($C_1$-$C_6$ alkyl)-aryl;

$R^{8a}$ is selected from: —$C_1$-$C_6$ alkyl, —$C_3$-$C_8$ cycloalkyl and —$C_3$-$C_8$ heterocycloalkyl;

each $R^{9a}$ is independently selected from: —$C_1$-$C_6$ alkyl, —$C_3$-$C_8$ cycloalkyl, -aryl, -heteroaryl and —($C_1$-$C_6$ alkyl)-aryl; or $R^{9a}$ is absent and $X^b$=X;

each $R^{10a}$ is independently selected from: —$C_1$-$C_6$ alkyl, —$C_3$-$C_8$ cycloalkyl, -aryl, -heteroaryl, —($C_1$-$C_6$ alkyl)-aryl and

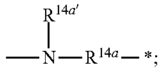
;

each $R^{10a'}$ is independently selected from: —H, —$C_1$-$C_6$ alkyl, —$C_3$-$C_8$ cycloalkyl, -aryl, -heteroaryl and —($C_1$-$C_6$ alkyl)-aryl;

each $R^{10b}$ is independently selected from: —$C_1$-$C_6$ alkyl, —$C_3$-$C_8$ cycloalkyl, -aryl, -heteroaryl and —($C_1$-$C_6$ alkyl)-aryl;

$R^{11a}$ is absent or is —$C_1$-$C_6$ alkyl;

$R^{12a}$ is selected from: —$C_1$-$C_6$ alkyl, —$CO_2R^{8a}$, -aryl, -heteroaryl, —($C_1$-$C_6$ alkyl)-aryl, —$S(O)_2R^{16a}$ and

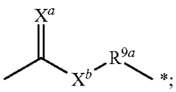
;

$R^{13a}$ is selected from: —H and —$C_1$-$C_6$ alkyl;

$R^{14a}$ is selected from: —$C_1$-$C_6$ alkyl, —$C_3$-$C_8$ cycloalkyl and —$C_3$-$C_8$ heterocycloalkyl;

$R^{14a'}$ is selected from: H, —$C_1$-$C_6$ alkyl, —$C_3$-$C_8$ cycloalkyl and —$C_3$-$C_8$ heterocycloalkyl;

$R^{16a}$ is selected from: —$C_1$-$C_6$ alkyl, —$C_3$-$C_8$ cycloalkyl, -aryl, -heteroaryl and —($C_1$-$C_6$ alkyl)-aryl;

$R^{21}$ is selected from: —$C_1$-$C_6$ alkyl, —$C_3$-$C_8$ cycloalkyl and —($C_1$-$C_6$ alkyl)-O—$R^{5a}$;

$R^{22}$ and $R^{23}$ are each independently selected from: —H, -halogen, —$C_1$-$C_6$ alkyl and —$C_3$-$C_8$ cycloalkyl;

$R^{24}$, $R^{25}$ and $R^{26}$ are each —$C_1$-$C_6$ alkyl;

$X^a$ and $X^b$ are each independently selected from: NH, O and S;

$X^c$ is selected from: O, S and $S(O)_2$, and denotes the point of attachment to linker, L.

In some embodiments, in compounds of Formula (IV), $R^{1a}$ is selected from: —$CH_3$, —$CF_3$, —$OCH_3$, —$OCF_3$ and —$NH_2$.

In some embodiments, in compounds of Formula (IV), $R^{1a}$ is selected from: —$CH_3$, —$CF_3$, —$OCH_3$ and —$OCF_3$.

In some embodiments, in compounds of Formula (IV), $R^{1a}$ is selected from: —$CH_3$, —$OCH_3$ and $NH_2$.

In some embodiments, in compounds of Formula (IV), $R^{1a}$ is selected from: —$CH_3$ and —$OCH_3$.

In some embodiments, in compounds of Formula (IV), $R^{2a}$ is selected from: —H, —$CH_3$, —$CF_3$, —F, —Cl, —$OCH_3$ and —$OCF_3$.

In some embodiments, in compounds of Formula (IV), $R^{2a}$ is selected from: —H, —F and —Cl.

In some embodiments, in compounds of Formula (IV), $R^{2a}$ is —F.

In some embodiments, in compounds of Formula (IV), X is —O—, —S— or —NH—, and $R^{4a}$ is selected from:

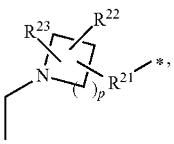
,
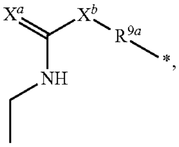
,
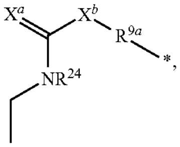
,
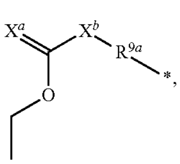
,
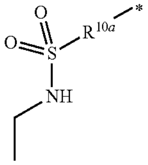
,
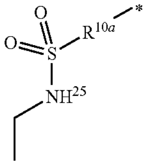
,
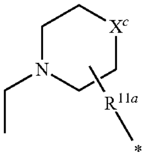
and
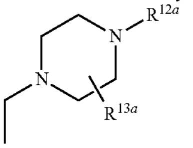
.

In some embodiments, in compounds of Formula (IV), X is —O— or —NH—.

In some embodiments, in compounds of Formula (IV), each $R^{9a}$ is independently selected from: —$C_1$-$C_6$ alkyl, —$C_3$-$C_8$ cycloalkyl, -aryl and —($C_1$-$C_6$ alkyl)-aryl.

In some embodiments, in compounds of Formula (IV), each $R^{9a}$ is independently selected from: —$C_1$-$C_6$ alkyl and —($C_1$-$C_6$ alkyl)-aryl.

In some embodiments, in compounds of Formula (IV), each $R^{10a}$ is independently selected from: —$C_1$-$C_6$ alkyl, —$C_3$-$C_8$ cycloalkyl, -aryl, —($C_1$-$C_6$ alkyl)-aryl and

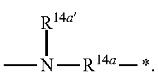
.

In some embodiments, in compounds of Formula (IV), each $R^{10a}$ is independently selected from: —$C_1$-$C_6$ alkyl, -aryl, —($C_1$-$C_6$ alkyl)-aryl and

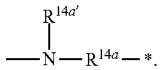

In some embodiments, in compounds of Formula (IV), $R^{12a}$ is selected from: —$C_1$-$C_6$ alkyl, -aryl, —($C_1$-$C_6$ alkyl)-aryl and —$S(O)_2R^{16}$.

In some embodiments, in compounds of Formula (IV), $R^{13a}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (IV), $R^{14a'}$ is selected from: H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (IV), $R^{16a}$ is selected from: -aryl, -heteroaryl and —($C_1$-$C_6$ alkyl)-aryl.

In some embodiments, in compounds of Formula (IV), $R^{22}$ and $R^{23}$ are each independently selected from: —H, -halogen, unsubstituted —$C_1$-$C_6$ alkyl, —$C_1$-$C_6$ haloalkyl, —$C_1$-$C_6$ aminoalkyl, —$C_1$-$C_6$ hydroxyalkyl and —$C_3$-$C_8$ cycloalkyl.

In some embodiments, in compounds of Formula (IV), $X^a$ and $X^b$ are each independently selected from: NH and O.

In some embodiments, in compounds of Formula (IV), $X^a$ and $X^b$ are each O.

In some embodiments, in compounds of Formula (IV), X is O; $R^{4a}$ is

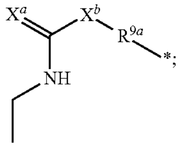

$X^a$ and $X^b$ are each O, and $R^{9a}$ is —$C_1$-$C_6$ alkyl.

In some embodiments, in compounds of Formula (IV), $R^{1a}$ is —$CH_3$ or —$OCH_3$; X is O; $R^{4a}$ is

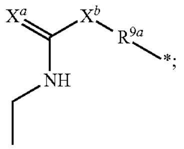

$X^a$ and $X^b$ are each 0; and $R^{9a}$ is —$C_1$-$C_6$ alkyl.

In some embodiments, in compounds of Formula (IV), $R^{1a}$ is —$CH_3$ or —$OCH_3$; $R^{2a}$ is H or F; X is O; $R^{4a}$ is

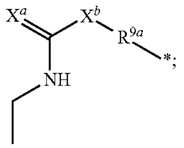

$X^a$ and $X^b$ are each 0; and $R^{9a}$ is —$C_1$-$C_6$ alkyl.

Other combinations of any of the foregoing embodiments for compounds of Formula (IV) are also contemplated and each combination forms a separate embodiment for the purposes of the present disclosure.

Certain embodiments of the present disclosure relate to ADCs having Formula (X), in which D is a compound of Formula (V):

(V)

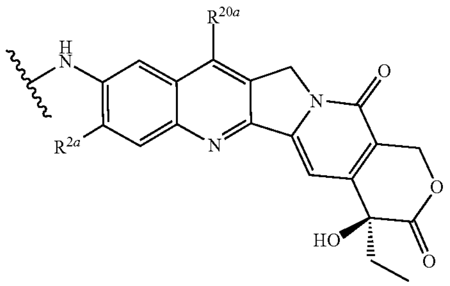

wherein:

$R^{2a}$ is selected from: —$CH_3$, —$CF_3$, —F, —Br, —Cl, —OH, —$OCH_3$ and —$OCF_3$;

$R^{20a}$ is selected from: —H, —$C_1$-$C_6$ alkyl, —$C_3$-$C_8$ cycloalkyl, —($C_1$-$C_6$ alkyl)-O—$R^5$,

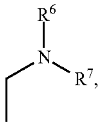

—$CO_2R^8$, -aryl, -heteroaryl,—($C_1$-$C_6$ alkyl)-aryl,

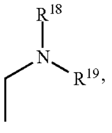 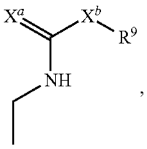, 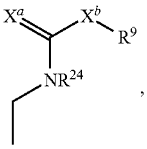,

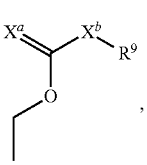, 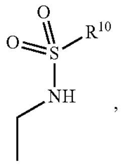, 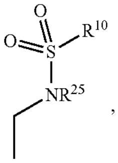,

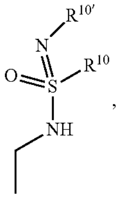, 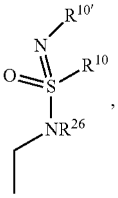, 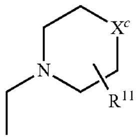,

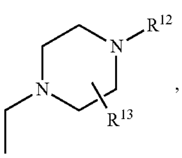, 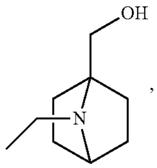, 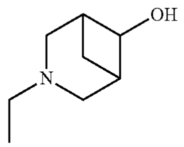 and

-continued

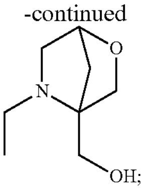

$R^5$ is selected from: —H, —$C_1$-$C_6$ alkyl, —$C_3$-$C_8$ cycloalkyl, -aryl, -heteroaryl and —($C_1$-$C_6$ alkyl)-aryl;

$R^6$ and $R^7$ are each independently selected from: —H, —$C_1$-$C_6$ alkyl, —$C_3$-$C_8$ cycloalkyl, —($C_1$-$C_6$ alkyl)-O—$R^5$, —$C_3$-$C_8$ heterocycloalkyl and —C(O)$R^{17}$;

$R^8$ is selected from: —H, —$C_1$-$C_6$ alkyl, —$C_3$-$C_8$ cycloalkyl and —$C_3$-$C_8$ heterocycloalkyl;

each $R^9$ is independently selected from: —H, —$C_1$-$C_6$ alkyl, —$C_3$-$C_8$ cycloalkyl, -aryl, -heteroaryl and —($C_1$-$C_6$ alkyl)-aryl;

each $R^{10}$ is independently selected from: —$C_1$-$C_6$ alkyl, —$C_3$-$C_8$ cycloalkyl, -aryl, -heteroaryl, —($C_1$-$C_6$ alkyl)-aryl and —$NR^{14}R^{14'}$;

each $R^{10'}$ is independently selected from: —H, —$C_1$-$C_6$ alkyl, —$C_3$-$C_8$ cycloalkyl, -aryl, -heteroaryl and —($C_1$-$C_6$ alkyl)-aryl;

$R^{11}$ is selected from: —H and —$C_1$-$C_6$ alkyl;

$R^{12}$ is selected from: —H, —$C_1$-$C_6$ alkyl, —$CO_2R^8$, -aryl, -heteroaryl, —($C_1$-$C_6$ alkyl)-aryl, —$S(O)_2R^{16}$ and

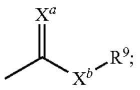

$R^{13}$ is selected from: —H and —$C_1$-$C_6$ alkyl;

$R^{14}$ and $R^{14'}$ are each independently selected from: —H, $C_1$-$C_6$ alkyl, —$C_3$-$C_8$ cycloalkyl and —$C_3$-$C_8$ heterocycloalkyl;

$R^{16}$ is selected from: —$C_1$-$C_6$ alkyl, —$C_3$-$C_8$ cycloalkyl, -aryl, -heteroaryl and —($C_1$-$C_6$ alkyl)-aryl;

$R^{17}$ is selected from: —$C_1$-$C_6$ alkyl, —$C_3$-$C_8$ cycloalkyl, —$C_3$-$C_8$ heterocycloalkyl, —($C_1$-$C_6$alkyl)-$C_3$-$C_8$ heterocycloalkyl, -aryl, -heteroaryl and —($C_1$-$C_6$ alkyl)-aryl;

$R^{18}$ and $R^{19}$ taken together with the N atom to which they are bonded form a 4-, 5-, 6-, or 7-membered ring having 0 to 3 substituents selected from: halogen, —$C_1$-$C_6$ alkyl, —$C_3$-$C_8$ cycloalkyl and —($C_1$-$C_6$ alkyl)-O—$R^5$;

$R^{24}$, $R^{25}$ and $R^{26}$ are each —$C_1$-$C_6$ alkyl;

$X^a$ and $X^b$ are each independently selected from: NH, O and S;

$X^c$ is selected from: O, S and $S(O)_2$, and denotes the point of attachment to linker, L.

In some embodiments, in compounds of Formula (V), $R^{2a}$ is selected from: —$CH_3$, —$CF_3$, —F, —Cl, —$OCH_3$ and —$OCF_3$.

In some embodiments, in compounds of Formula (V), $R^{2a}$ is selected from: —$CF_3$, —F, —Cl and —$OCH_3$.

In some embodiments, in compounds of Formula (V), $R^{2a}$ is F.

In some embodiments, in compounds of Formula (V), $R^{20a}$ is selected from: —H, —$C_1$-$C_6$ alkyl, —$C_3$-$C_8$ cycloalkyl, —($C_1$-$C_6$ alkyl)-O—$R^5$,

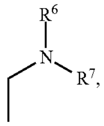

—$CO_2R^8$, -aryl, -heteroaryl,—($C_1$-$C_6$ alkyl)-aryl,

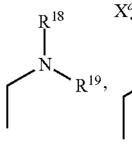 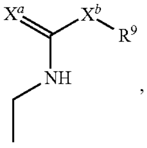, 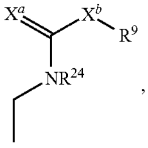,

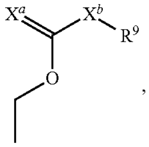, 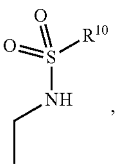, 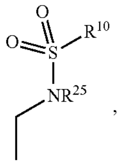,

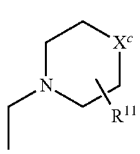, 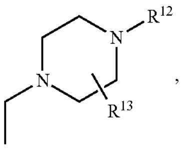,

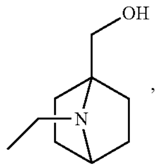, 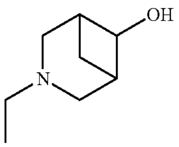 and

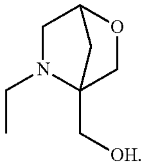

In some embodiments, in compounds of Formula (V), $R^{20a}$ is selected from: —H, —$C_1$-$C_6$ alkyl, —($C_1$-$C_6$ alkyl)-O—$R^5$,

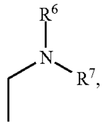

—($C_1$-$C_6$ alkyl)-aryl,

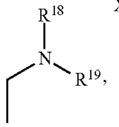 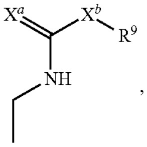, 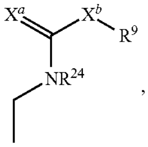,

-continued

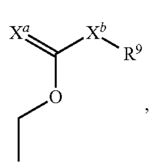, 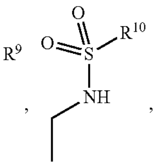, 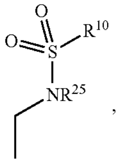,

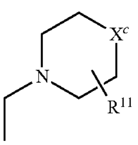, 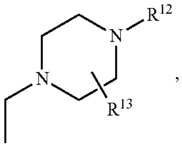,

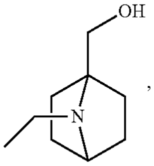, 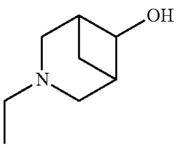 and

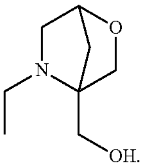

In some embodiments, in compounds of Formula (V), $R^{20a}$ is selected from: —H, —$C_1$-$C_6$ alkyl, —($C_1$-$C_6$ alkyl)-O—$R^5$,

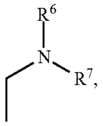

—($C_1$-$C_6$ alkyl)-aryl,

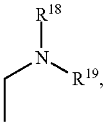 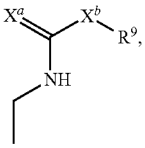 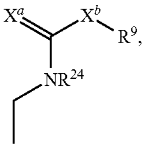

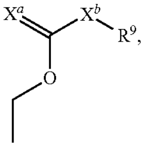 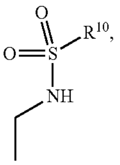 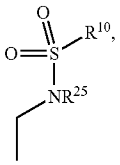

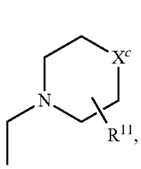 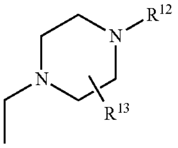 and 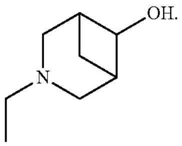

In some embodiments, in compounds of Formula (V), $R^{20a}$ is selected from: —H, —$C_1$-$C_6$ alkyl, —($C_1$-$C_6$ alkyl)-O—$R^5$,

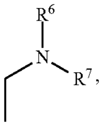 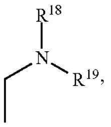 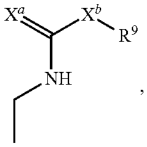, 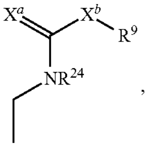,

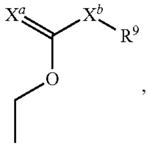, 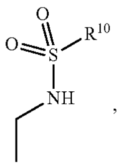, 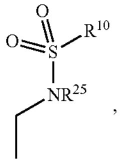,

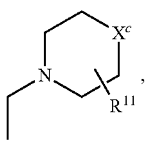, 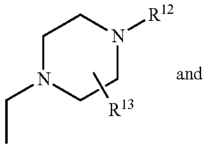 and

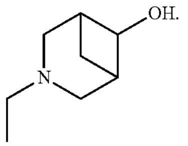

In some embodiments, in compounds of Formula (V), $R^{20a}$ is selected from: —H, unsubstituted —$C_1$-$C_6$ alkyl, —$C_1$-$C_6$ haloalkyl, —$C_1$-$C_6$ hydroxyalkyl, —$C_3$-$C_8$ cycloalkyl, —($C_1$-$C_6$ alkyl)-O—$R^5$,

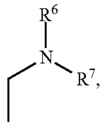

—$CO_2R^8$, unsubstituted -aryl, -aminoaryl, -heteroaryl, —($C_1$-$C_6$ alkyl)-aminoaryl,

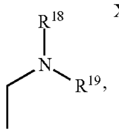 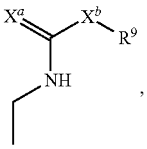, 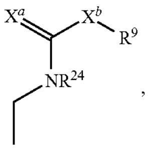,

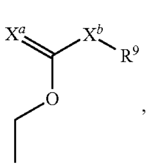, 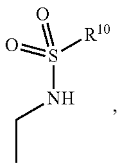, 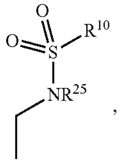,

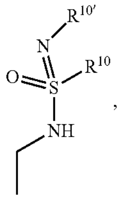, 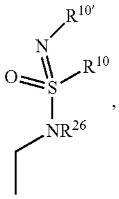, 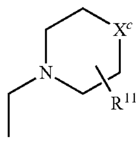,

-continued

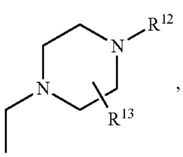 , 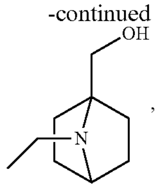 , 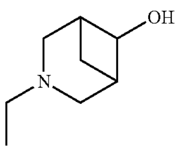 and

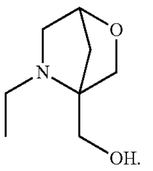

In some embodiments, in compounds of Formula (V), $R^6$ and $R^7$ are each independently selected from: —H, —$C_1$-$C_6$ alkyl, —$C_3$-$C_8$ cycloalkyl and —C(O)$R^{17}$.

In some embodiments, in compounds of Formula (V), $R^6$ is H, and $R^7$ is selected from: —H, —$C_1$-$C_6$ alkyl, —$C_3$-$C_8$ cycloalkyl, —($C_1$-$C_6$ alkyl)-O—$R^5$, —$C_3$-$C_8$ heterocycloalkyl and —C(O)$R^{17}$.

In some embodiments, in compounds of Formula (V), $R^6$ is H, and $R^7$ is selected from: —H, —$C_1$-$C_6$ alkyl, —$C_3$-$C_8$ cycloalkyl and —C(O)$R^{17}$.

In some embodiments, in compounds of Formula (V), $R^6$ and $R^7$ are each independently selected from: —H, unsubstituted —$C_1$-$C_6$ alkyl, —$C_1$-$C_6$ haloalkyl, —$C_1$-$C_6$ hydroxyalkyl, —$C_3$-$C_8$ cycloalkyl, —($C_1$-$C_6$ alkyl)-O—$R^5$, —$C_3$-$C_8$ heterocycloalkyl and —C(O)$R^{17}$.

In some embodiments, in compounds of Formula (V), $R^8$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (V), each $R^9$ is independently selected from: —$C_1$-$C_6$ alkyl, —$C_3$-$C_8$ cycloalkyl, -aryl and —($C_1$-$C_6$ alkyl)-aryl.

In some embodiments, in compounds of Formula (V), each $R^9$ is independently selected from: —$C_1$-$C_6$ alkyl and —($C_1$-$C_6$ alkyl)-aryl.

In some embodiments, in compounds of Formula (V), each $R^9$ is independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (V), each $R^{10}$ is independently selected from: —$C_1$-$C_6$ alkyl, —$C_3$-$C_8$ cycloalkyl, —$NR^{14}R^{14'}$, -aryl and —($C_1$-$C_6$ alkyl)-aryl.

In some embodiments, in compounds of Formula (V), each $R^{10}$ is independently selected from: —$C_1$-$C_6$ alkyl, —$NR^{14}R^{14'}$, -aryl and —($C_1$-$C_6$ alkyl)-aryl.

In some embodiments, in compounds of Formula (V), $R^{11}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (V), $R^{12}$ is selected from: —H, —$C_1$-$C_6$ alkyl, -aryl, —($C_1$-$C_6$ alkyl)-aryl and —$S(O)_2R^{16}$.

In some embodiments, in compounds of Formula (V), $R^{12}$ is selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$CO_2R^8$, unsubstituted -aryl, -aminoaryl, -heteroaryl, —($C_1$-$C_6$ alkyl)-aminoaryl, —$S(O)_2R^{16}$ and

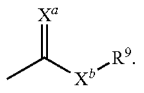

In some embodiments, in compounds of Formula (V), $R^{13}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (V), $R^{14}$ and $R^{14'}$ are each independently selected from: —H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (V), $R^{16}$ is selected from: -aryl, -heteroaryl and —($C_1$-$C_6$ alkyl)-aryl.

In some embodiments, in compounds of Formula (V), $R^{16}$ is selected from: unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl, unsubstituted -aryl, -aminoaryl, -heteroaryl and —($C_1$-$C_6$ alkyl)-aminoaryl.

In some embodiments, in compounds of Formula (V), $R^{17}$ is selected from: unsubstituted —$C_1$-$C_6$ alkyl, —$C_3$-$C_8$ cycloalkyl, —$C_3$-$C_8$ heterocycloalkyl, —($C_1$-$C_6$ alkyl)-$C_3$-$C_5$ heterocycloalkyl, unsubstituted -aryl, -hydroxyaryl, -aminoaryl, -heteroaryl and —($C_1$-$C_6$ alkyl)-aminoaryl.

In some embodiments, in compounds of Formula (V), $R^{18}$ and $R^{19}$ taken together with the N atom to which they are bonded form a 4-, 5-, 6-, or 7-membered ring having 0 to 3 substituents selected from: halogen, unsubstituted —$C_1$-$C_6$ alkyl, —$C_1$-$C_6$ haloalkyl, —$C_1$-$C_6$ aminoalkyl, —$C_1$-$C_6$ hydroxyalkyl, —$C_3$-$C_8$ cycloalkyl and —($C_1$-$C_6$ alkyl)-O—$R^5$.

In some embodiments, in compounds of Formula (V), $R^{17}$ is —$C_1$-$C_6$ alkyl.

In some embodiments, in compounds of Formula (V), $X^a$ and $X^b$ are each independently selected from: NH and O.

In some embodiments, in compounds of Formula (V), $X^a$ and $X^b$ are each O.

In some embodiments, in compounds of Formula (V), $R^{20a}$ is —($C_1$-$C_6$ alkyl)-O—$R^5$.

In some embodiments, in compounds of Formula (V), $R^{20a}$ is —($C_1$-$C_6$ alkyl)-O—$R^5$, and $R^5$ is H.

In some embodiments, in compounds of Formula (V), $R^{2a}$ is F; $R^{20a}$ is —($C_1$-$C_6$ alkyl)-O—$R^5$, and $R^5$ is H.

Other combinations of any of the foregoing embodiments for compounds of Formula (V) are also contemplated and each combination forms a separate embodiment for the purposes of the present disclosure.

Certain embodiments of the present disclosure relate to ADCs having Formula (X), in which D is a compound of Formula (VI):

(VI)

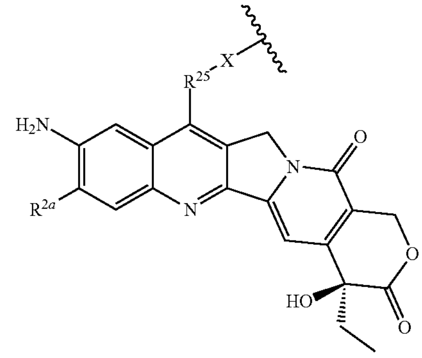

wherein:

$R^{2a}$ is selected from: —H, —$CH_3$, —$CF_3$, —F, —Br, —Cl, —OH, —$OCH_3$ and —$OCF_3$;

X is —O—, —S— or —NH—, and $R^{25}$ is selected from: —$C_1$-$C_6$ alkyl, —($C_1$-$C_6$ alkyl)-O—$R^{5a}$, —$CO_2R^{8a}$, -aryl, -heteroaryl,—($C_1$-$C_6$ alkyl)-aryl,

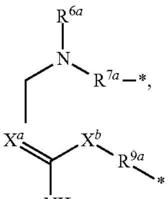,

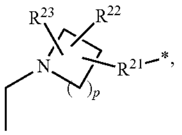, 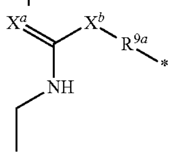, 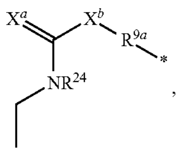,

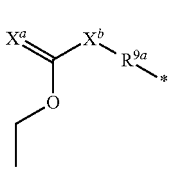, 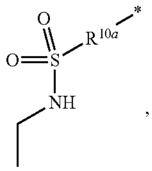, 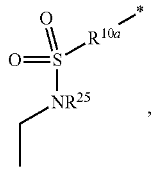,

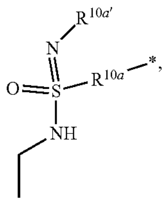, 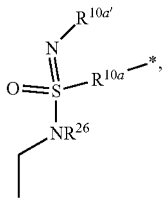, 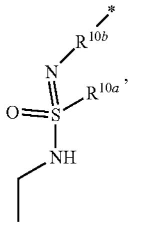,

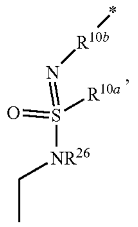, 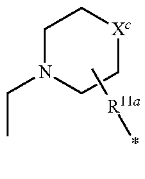 and

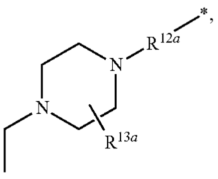, wherein * is the point of attachment to X, and wherein p is 1, 2, 3 or 4; or X is O, and $R^{25}$—X— is selected from:

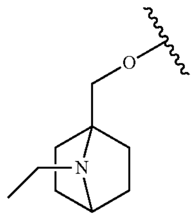 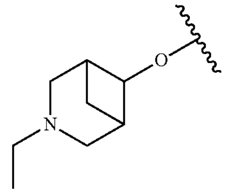 and 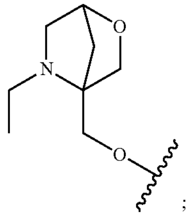;

$R^{5a}$ is selected from: —$C_1$-$C_6$ alkyl, —$C_3$-$C_8$ cycloalkyl, -aryl, -heteroaryl and —($C_1$-$C_6$ alkyl)-aryl;

$R^{6a}$ is selected from: —H, —$C_1$-$C_6$ alkyl, —$C_3$-$C_8$ cycloalkyl and —$C_3$-$C_8$ heterocycloalkyl;

$R^{7a}$ is selected from: —$C_1$-$C_6$ alkyl, —$C_3$-$C_8$ cycloalkyl, —($C_1$-$C_6$ alkyl)-O—$R^{5a}$, —$C_3$-$C_8$ heterocycloalkyl and —C(O)$R^{17a}$;

$R^{8a}$ is selected from: —$C_1$-$C_6$ alkyl, —$C_3$-$C_8$ cycloalkyl and —$C_3$-$C_8$ heterocycloalkyl;

each $R^{9a}$ is independently selected from: —$C_1$-$C_6$ alkyl, —$C_3$-$C_8$ cycloalkyl, -aryl, -heteroaryl and —($C_1$-$C_6$ alkyl)-aryl; or $R^{9a}$ is absent and $X^b$=X;

each $R^{10a}$ is independently selected from: —$C_1$-$C_6$ alkyl, —$C_3$-$C_8$ cycloalkyl, -aryl, -heteroaryl, —($C_1$-$C_6$ alkyl)-aryl and

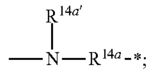;

each $R^{10a'}$ is independently selected from: —H, —$C_1$-$C_6$ alkyl, —$C_3$-$C_8$ cycloalkyl, -aryl, -heteroaryl and —($C_1$-$C_6$ alkyl)-aryl;

each $R^{10b}$ is independently selected from: —$C_1$-$C_6$ alkyl, —$C_3$-$C_8$ cycloalkyl, -aryl, -heteroaryl and —($C_1$-$C_6$ alkyl)-aryl;

$R^{11a}$ is absent or is —$C_1$-$C_6$ alkyl;

$R^{12a}$ is selected from: —$C_1$-$C_6$ alkyl, —$CO_2R^{8a}$, -aryl, -heteroaryl, —($C_1$-$C_6$ alkyl)-aryl, —$S(O)_2R^{16a}$ and

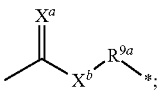;

$R^{13a}$ is selected from: —H and —$C_1$-$C_6$ alkyl;

$R^{14a}$ is selected from: —$C_1$-$C_6$ alkyl, —$C_3$-$C_8$ cycloalkyl and —$C_3$-$C_8$ heterocycloalkyl;

$R^{14a'}$ is selected from: H, —$C_1$-$C_6$ alkyl, —$C_3$-$C_8$ cycloalkyl and —$C_3$-$C_8$ heterocycloalkyl;

$R^{16a}$ is selected from: —$C_1$-$C_6$ alkyl, —$C_3$-$C_8$ cycloalkyl, -aryl, -heteroaryl and —($C_1$-$C_6$ alkyl)-aryl;

$R^{17a}$ is selected from: $—C_1$-$C_6$ alkyl, $—C_3$-$C_8$ cycloalkyl, $—C_3$-$C_8$ heterocycloalkyl, $—(C_1$-$C_6$alkyl)-$C_3$-$C_8$ heterocycloalkyl, -aryl, -heteroaryl and $—(C_1$-$C_6$ alkyl)-aryl;

$R^{21}$ is selected from: $—C_1$-$C_6$ alkyl, $—C_3$-$C_8$ cycloalkyl and $—(C_1$-$C_6$ alkyl)-O—$R^{5a}$;

$R^{22}$ and $R^{23}$ are each independently selected from: —H, -halogen, $—C_1$-$C_6$ alkyl and $—C_3$-$C_8$ cycloalkyl;

$R^{24}$, $R^{25}$ and $R^{26}$ are each $—C_1$-$C_6$ alkyl;

$X^a$ and $X^b$ are each independently selected from: NH, O and S;

$X^c$ is selected from: O, S and $S(O)_2$, and denotes the point of attachment to linker, L.

In some embodiments, in compounds of Formula (VI), $R^{2a}$ is selected from: $—CH_3$, $—CF_3$, —F, —Br, —Cl, —OH, $—OCH_3$ and $—OCF_3$.

In some embodiments, in compounds of Formula (VI), $R^{2a}$ is selected from: $—CH_3$, $—CF_3$, —F, —Cl, $—OCH_3$ and $—OCF_3$.

In some embodiments, in compounds of Formula (VI), $R^{2a}$ is selected from: F and Cl.

In some embodiments, in compounds of Formula (VI), $R^{2a}$ is F.

In some embodiments, in compounds of Formula (VI), X is —O—, —S— or —NH—, and $R^{25}$ is selected from: $—C_1$-$C_6$ alkyl, $—(C_1$-$C_6$ alkyl)-O—$R^{5a}$, $—(C_1$-$C_6$ alkyl)-aryl,

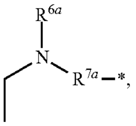

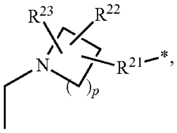

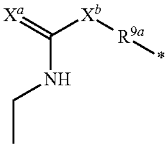
,
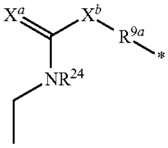
,

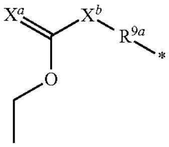
,
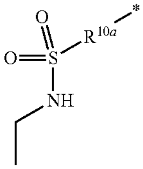
,
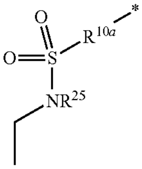
,

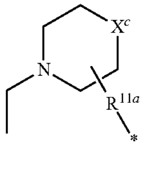
and
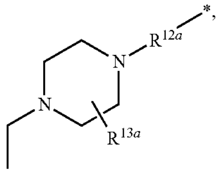

or X is O, and $R^{25}$—X— is selected from:

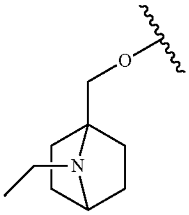

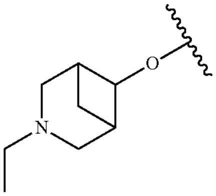
and

-continued

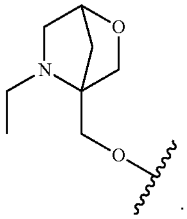

In some embodiments, in compounds of Formula (VI), X is —O—, —S— or —NH—, and $R^{25}$ is selected from: $—C_1$-$C_6$ alkyl, $—(C_1$-$C_6$ alkyl)-O—$R^{5a}$, $—(C_1$-$C_6$ alkyl)-aryl,

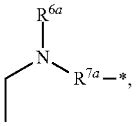

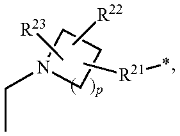

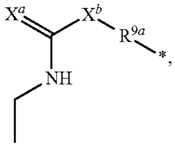

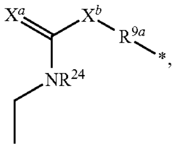

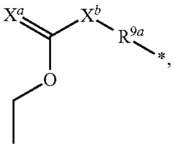

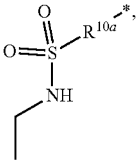

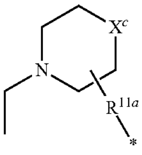
and
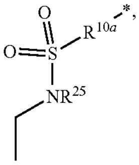

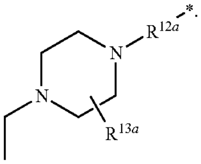

In some embodiments, in compounds of Formula (VI), X is —O—, —S— or —NH—, and $R^{25}$ is selected from: $—C_1$-$C_6$ alkyl, $—(C_1$-$C_6$ alkyl)-O—$R^{5a}$,

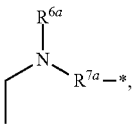

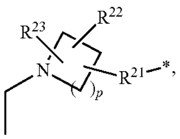

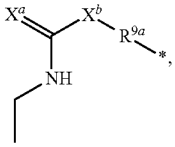

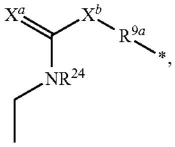

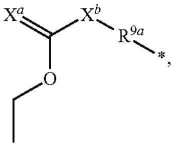

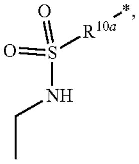

-continued

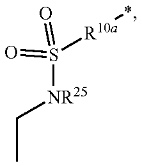,

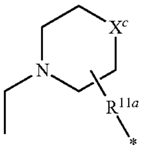

and

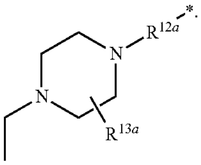.

In some embodiments, in compounds of Formula (VI), X is —O—, —S— or —NH—, and $R^{25}$ is selected from:

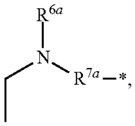,

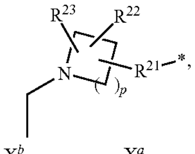,

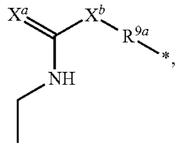,

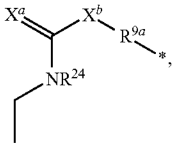,

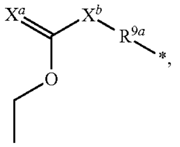,

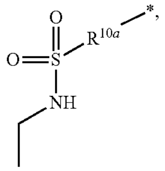,

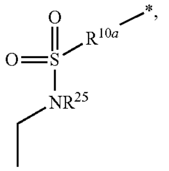, and

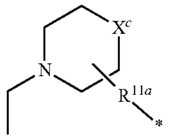

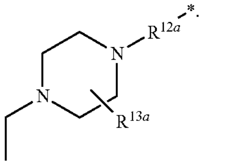.

In some embodiments, in compounds of Formula (VI), X is —O— or —NH—.

In some embodiments, in compounds of Formula (VI), $R^{6a}$ is H.

In some embodiments, in compounds of Formula (VI), $R^{6a}$ is selected from: —H, unsubstituted —$C_1$-$C_6$ alkyl, —$C_1$-$C_6$ haloalkyl, —$C_1$-$C_6$ hydroxyalkyl, —$C_3$-$C_8$ cycloalkyl and —$C_3$-$C_8$ heterocycloalkyl.

In some embodiments, in compounds of Formula (VI), $R^{7a}$ is selected from: —$C_1$-$C_6$ alkyl, —$C_3$-$C_8$ cycloalkyl and —C(O)$R^{17a}$ In some embodiments, in compounds of Formula (VI), each $R^{9a}$ is independently selected from: —$C_1$-$C_6$ alkyl, —$C_3$-$C_8$ cycloalkyl, -aryl and —($C_1$-$C_6$ alkyl)-aryl.

In some embodiments, in compounds of Formula (VI), each $R^{9a}$ is independently selected from: —$C_1$-$C_6$ alkyl and —($C_1$-$C_6$ alkyl)-aryl.

In some embodiments, in compounds of Formula (VI), each $R^{10a}$ is independently selected from: —$C_1$-$C_6$ alkyl, —$C_3$-$C_8$ cycloalkyl, -aryl, —($C_1$-$C_6$ alkyl)-aryl and

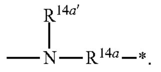.

In some embodiments, in compounds of Formula (VI), each $R^{10a}$ is independently selected from: —$C_1$-$C_6$ alkyl, -aryl,—($C_1$-$C_6$ alkyl)-aryl and

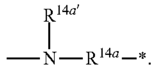.

In some embodiments, in compounds of Formula (VI), $R^{12a}$ is selected from: —$C_1$-$C_6$ alkyl, -aryl, —($C_1$-$C_6$ alkyl)-aryl and —$S(O)_2R^{16a}$ In some embodiments, in compounds of Formula (VI), $R^{13a}$ is selected from: —H, unsubstituted —$C_1$-$C_6$ alkyl, —$C_1$-$C_6$ haloalkyl, —$C_1$-$C_6$ hydroxyalkyl and —$C_1$-$C_6$ aminoalkyl.

In some embodiments, in compounds of Formula (VI), $R^{14a'}$ is selected from: H, unsubstituted —$C_1$-$C_6$ alkyl, —$C_1$-$C_6$ haloalkyl, —$C_1$-$C_6$ hydroxyalkyl, —$C_1$-$C_6$ aminoalkyl, —$C_3$-$C_8$ cycloalkyl and —$C_3$-$C_8$ heterocycloalkyl.

In some embodiments, in compounds of Formula (VI), $R^{16a}$ is selected from: -aryl, -heteroaryl and —($C_1$-$C_6$ alkyl)-aryl.

In some embodiments, in compounds of Formula (VI), $R^{17a}$ is —$C_1$-$C_6$ alkyl.

In some embodiments, in compounds of Formula (VI), $R^{22}$ and $R^{23}$ are each independently selected from: —H, -halogen, unsubstituted —$C_1$-$C_6$ alkyl, —$C_1$-$C_6$ haloalkyl, —$C_1$-$C_6$ hydroxyalkyl, —$C_1$-$C_6$ aminoalkyl and —$C_3$-$C_8$ cycloalkyl.

In some embodiments, in compounds of Formula (VI), $X^a$ and $X^b$ are each independently selected from: NH and O.

In some embodiments, in compounds of Formula (VI), $X^a$ and $X^b$ are each O.

In some embodiments, in compounds of Formula (VI), X is O, and $R^{25}$ is —$C_1$-$C_6$ alkyl.

In some embodiments, in compounds of Formula (VI), $R^{2a}$ is F; X is O, and $R^{25}$ is —$C_1$-$C_6$ alkyl.

Other combinations of any of the foregoing embodiments for compounds of Formula (VI) are also contemplated and each combination forms a separate embodiment for the purposes of the present disclosure.

In certain embodiments, each alkyl, cycloalkyl, heterocycloalkyl, aryl and heteroaryl group as defined in any one of Formulae (IV), (V) or (VI) is optionally substituted with one or more substituents selected from: halogen, acyl, acyloxy, alkoxy, carboxy, hydroxy, amino, amido, nitro, cyano, azido, alkylthio, thio, sulfonyl, sulfonamido, alkyl, cycloalkyl, heterocycloalkyl, aryl and heteroaryl. In some embodiments, each alkyl, cycloalkyl, heterocycloalkyl, aryl and heteroaryl group as defined in any one of Formulae (IV), (V) or (VI) is optionally substituted with one or more substituents selected from: halogen, acyl, acyloxy, alkoxy, carboxy, hydroxy, amino, amido, nitro, cyano, azido, alkylthio, thio, sulfonyl and sulfonamido.

In certain embodiments, in ADCs having Formula (X), D is a compound of Formula (IV), in which $R^{1a}$ is —$CH_3$, and $R^{2a}$ is F. In some embodiments, in ADCs having Formula (X), D is a compound of Formula (IV), in which $R^{1a}$ is —$CH_3$; $R^{2a}$ is F; X is —O—; $R^{4a}$ is

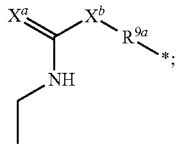

$R^{9a}$ is —$C_1$-$C_6$ alkyl, and $X^a$ and $X^b$ are each 0.

In certain embodiments, in ADCs having Formula (X), D is a compound of Formula (V), in which $R^{2a}$ is F, and $R^{20a}$ is H, —($C_1$-$C_6$)—O—$R^5$ or

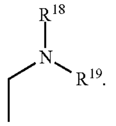

In some embodiments, in ADCs having Formula (X), D is a compound of Formula (V), in which $R^{2a}$ is F; $R^{20a}$ is H, —($C_1$-$C_6$)—O—$R^5$ or

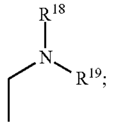

$R^5$ is H, and $R^{18}$ and $R^{19}$ taken together with the N atom to which they are bonded form an unsubstituted 4-, 5-, 6-, or 7-membered ring. In some embodiments, in ADCs having Formula (X), D is a compound of Formula (V), in which $R^{2a}$ is F; $R^{20a}$ is —($C_1$-$C_6$)—O—$R^5$, and $R^5$ is H.

In certain embodiments, in ADCs having Formula (X), D is a compound of Formula (VI), in which $R^{2a}$ is F; X is —O—, and $R^{25}$ is —$C_1$-$C_6$ alkyl.

Linker, L

The conjugates of Formula (X) include a linker, L, which is a bifunctional or multifunctional moiety capable of linking one or more camptothecin analogues, D, to the anti-FRα antibody construct, T. A bifunctional (or monovalent) linker, L, links a single compound D to a single site on the anti-FRα antibody construct, T, whereas a multifunctional (or polyvalent) linker, L, links more than one compound, D, to a single site on the anti-FRα antibody construct, T. A linker that links one compound, D, to more than one site on the anti-FRα antibody construct, T, may also be considered to be multifunctional.

Linker, L, includes a functional group capable of reacting with the target group or groups on the anti-FRα antibody construct, T, and at least one functional group capable of reacting with a target group on the camptothecin analogue, D. Suitable functional groups are known in the art and include those described, for example, in Bioconjugate Techniques (G. T. Hermanson, 2013, Academic Press). Groups on the anti-FRα antibody construct, T, and the camptothecin analogue, D, that may serve as target groups for linker attachment include, but are not limited to, thiol, hydroxyl, carboxyl, amine, aldehyde and ketone groups.

Non-limiting examples of functional groups capable of reacting with thiols include maleimide, haloacetamide, haloacetyl, activated esters (such as succinimide esters, 4-nitrophenyl esters, pentafluorophenyl esters and tetrafluorophenyl esters), anhydrides, acid chlorides, sulfonyl chlorides, isocyanates and isothiocyanates. Also useful in this context are "self-stabilizing" maleimides as described in Lyon et al., 2014, *Nat. Biotechnol.,* 32:1059-1062.

Non-limiting examples of functional groups capable of reacting with amines include activated esters (such as N-hydroxysuccinamide (NHS) esters and sulfo-NHS esters), imido esters (such as Traut's reagent), isothiocyanates, aldehydes and acid anhydrides (such as diethylenetriaminepentaacetic anhydride (DTPA)). Other examples include the use of succinimido-1,1,3,3-tetra-methyluronium tetrafluoroborate (TSTU) or benzotriazol-1-yl-oxytripyrrolidinophosphonium hexafluorophosphate (PyBOP) to convert a carboxylic acid to an activated ester, which may then be reacted with an amine.

Non-limiting examples of functional groups capable of reacting with an electrophilic group such as an aldehyde or ketone carbonyl group include hydrazide, oxime, amino, hydrazine, thiosemicarbazone, hydrazine carboxylate and arylhydrazide.

In certain embodiments, linker, L, may include a functional group that allows for bridging of two interchain cysteines on the anti-FRα antibody construct, such as a ThioBridge™ linker (Badescu et al., 2014, *Bioconjug. Chem.* 25:1124-1136), a dithiomaleimide (DTM) linker (Behrens et al., 2015, *Mol. Pharm.* 12:3986-3998), a dithioaryl(TCEP)pyridazinedione-based linker (Lee et al., 2016, *Chem. Sci.,* 7:799-802) or a dibromopyridazinedione-based linker (Maruani et al., 2015, *Nat. Commun.,* 6:6645).

Alternatively, the anti-FRα antibody construct, T, may be modified to include a non-natural reactive group, such as an azide, that allows for conjugation to the linker via a complementary reactive group on the linker. For example, conjugation of the linker to the anti-FRα antibody construct may make use of click chemistry reactions (see, for example, Chio & Bane, 2020, *Methods Mol. Biol.,* 2078:83-97), such as the azide-alkyne cycloaddition (AAC) reaction, which has been used successfully in the development of antibody-drug conjugates. The AAC reaction may be a copper-catalyzed AAC (CuAAC) reaction, which involves coupling of an azide with a linear alkyne, or a strain-promoted AAC (SPAAC) reaction, which involves coupling of an azide with a cyclooctyne.

Linker, L, may be a cleavable or a non-cleavable linker. A cleavable linker is a linker that is susceptible to cleavage under specific conditions, for example, intracellular conditions (such as in an endosome or lysosome) or within the vicinity of a target cell (such as in the tumor microenvironment). Examples include linkers that are protease-sensitive, acid-sensitive or reduction-sensitive. Non-cleavable linkers by contrast, rely on the degradation of the antibody in the cell, which typically results in the release of an amino acid-linker-drug moiety.

Examples of cleavable linkers include, for example, linkers comprising an amino acid sequence that is a cleavage recognition sequence for a protease. Many such cleavage recognition sequences are known in the art. For conjugates that are not intended to be internalized by a cell, for example, an amino acid sequence that is recognized and cleaved by a protease present in the extracellular matrix in the vicinity of a target cell, such as a cancer cell, may be employed.

Examples of extracellular tumor-associated proteases include, for example, plasmin, matrix metalloproteases (MMPs), elastase and kallikrein-related peptidases.

For conjugates intended to be internalized by a cell, linker, L, may comprise an amino acid sequence that is recognized and cleaved by an endosomal or lysosomal protease. Examples of such proteases include, for example, cathepsins B, C, D, H, L and S, and legumain.

Cleavage recognition sequences may be, for example, dipeptides, tripeptides or tetrapeptides. Non-limiting examples of dipeptide recognition sequences that may be included in cleavable linkers include, but are not limited to, Ala-(D)Asp, Ala-Lys, Ala-Phe, Asn-Lys, Asn-(D)Lys, Asp-Val, His-Val, Ile-Cit, Ile-Pro, Ile-Val, Leu-Cit, $Me_3$Lys-Pro, Met-Lys, Met-(D)Lys, NorVal-(D)Asp, Phe-Arg, Phe-Cit, Phe-Lys, PhenylGly-(D)Lys, Pro-(D)Lys, Trp-Cit, Val-Ala, Val-(D)Asp, Val-Cit, Val-Gly, Val-Gln and Val-Lys. Examples of tri- and tetrapeptide cleavage sequences include, but are not limited to, Ala-Ala-Asn, Ala-Val-Cit, (D)Ala-Phe-Lys, Asp-Val-Ala, Asp-Val-Cit, Gly-Cit-Val, Lys-Val-Ala, Lys-Val-Cit, Met-Cit-Val, (D)Phe-Phe-Lys, Asn-Pro-Val, Ala-Leu-Ala-Leu [SEQ ID NO: 158], Gly-Phe-Leu-Gly [SEQ ID NO: 159], Gly-Gly-Phe-Gly [SEQ ID NO: 160] and Gly-Phe-Gly-Gly [SEQ ID NO: 161].

Additional examples of cleavable linkers include disulfide-containing linkers such as N-succinimydyl-4-(2-pyridyldithio) butanoate (SPDB) and N-succinimydyl-4-(2-pyridyldithio)-2-sulfo butanoate (sulfo-SPDB). Disulfide-containing linkers may optionally include additional groups to provide steric hindrance adjacent to the disulfide bond in order to improve the extracellular stability of the linker, for example, inclusion of a geminal dimethyl group. Other cleavable linkers include linkers hydrolyzable at a specific pH or within a pH range, such as hydrazone linkers. Linkers comprising combinations of these functionalities may also be useful, for example, linkers comprising both a hydrazone and a disulfide are known in the art.

A further example of a cleavable linker is a linker comprising a β-glucuronide, which is cleavable by β-glucuronidase, an enzyme present in lysosomes and tumor interstitium (see, for example, De Graaf et al., 2002, *Curr. Pharm. Des.* 8:1391-1403, and International Patent Publication No. WO 2007/011968). β-glucuronide may also function to improve the hydrophilicity of linker, L.

Another example of a linker that is cleaved internally within a cell and improves hydrophilicity is a linker comprising a pyrophosphate diester moiety (see, for example, Kern et al., 2016, *J Am Chem Soc.,* 138:2430-1445).

In certain embodiments, the linker, L, comprised by the conjugate of Formula (X) is a cleavable linker. In some embodiments, linker, L, comprises a cleavage recognition sequence. In some embodiments, linker, L, may comprise an amino acid sequence that is recognized and cleaved by a lysosomal protease.

Cleavable linkers may optionally further comprise one or more additional functionalities such as self-immolative and self-elimination groups, stretchers or hydrophilic moieties.

Self-immolative and self-elimination groups that find use in linkers include, for example, p-aminobenzyl (PAB) and p-aminobenzyloxycarbonyl (PABC) groups, methylated ethylene diamine (MED) and hemi-aminal groups. Other examples of self-immolative groups include, but are not limited to, aromatic compounds that are electronically similar to the PAB or PABC group such as heterocyclic derivatives, for example 2-aminoimidazol-5-methanol derivatives as described in U.S. Pat. No. 7,375,078. Other examples include groups that undergo cyclization upon amide bond hydrolysis, such as substituted and unsubstituted 4-aminobutyric acid amides (Rodrigues et al., 1995, *Chemistry Biology* 2:223-227) and 2-aminophenylpropionic acid amides (Amsberry, et al., 1990, *J. Org. Chem.* 55:5867-5877). Self-immolative/self-elimination groups are typically attached to an amino or hydroxyl group on the compound, D. Self-immolative/self-elimination groups, alone or in combination are often included in peptide-based linkers, but may also be included in other types of linkers.

Stretchers that find use in linkers for drug conjugates include, for example, alkylene groups and stretchers based on aliphatic acids, diacids, amines or diamines, such as diglycolate, malonate, caproate and caproamide. Other stretchers include, for example, glycine-based stretchers and polyethylene glycol (PEG) or monomethoxy polyethylene glycol (mPEG) stretchers.

PEG and mPEG stretchers can also function as hydrophilic moieties within a linker. For example, PEG or mPEG may be included in a linker either "in-line" or as pendant groups to increase the hydrophilicity of the linker (see, for example, U.S. Patent Application Publication No. US 2016/0310612). Various PEG-containing linkers are commercially available from companies such as Quanta BioDesign, Ltd (Plain City, OH). Other hydrophilic groups that may optionally be incorporated into linker, L, include, for example, β-glucuronide, sulfonate groups, carboxylate groups and pyrophosphate diesters.

In certain embodiments, ADCs of Formula (X) may comprise a cleavable linker. In some embodiments, ADCs of Formula (X) may comprise a peptide-containing linker. In some embodiments, ADCs of Formula (X) may comprise a protease-cleavable linker.

In some embodiments, in ADCs of Formula (X), m is 1, and linker, L, is a cleavable linker having Formula (XI):

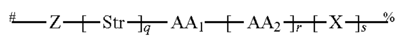

(XI)

wherein:

Z is a functional group capable of reacting with a target group on the anti-FRα antibody construct, T;

Str is a stretcher;

$AA_1$ and $AA_2$ are each independently an amino acid, wherein $AA_1$-$[AA_2]_r$ forms a protease cleavage site;

X is a self-immolative group;

q is 0 or 1;

r is 1, 2 or 3;

s is 0, 1 or 2;

# is the point of attachment to the anti-FRα antibody construct, T, and

% is the point of attachment to the camptothecin analogue, D.

In some embodiments, in linkers of Formula (XI), q is 1.

In some embodiments, in linkers of Formula (XI), s is 1. In some embodiments, in ADCs of Formula (XI), s is 0.

In some embodiments, in linkers of Formula (XI), r is 1. In some embodiments, in ADCs of Formula (XI), r is 3.

In some embodiments, in linkers of Formula (XI): Z is

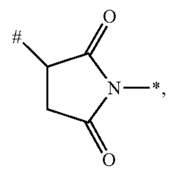

where # is the point of attachment to T, and * is the point of attachment to the remainder of the linker.

In some embodiments, in linkers of Formula (XI), Str is selected from:

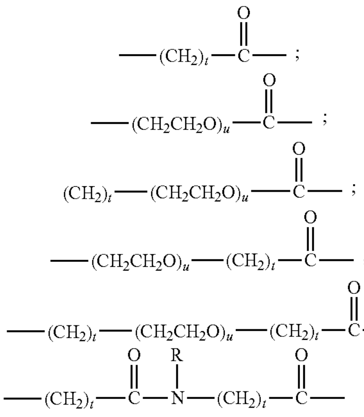

and

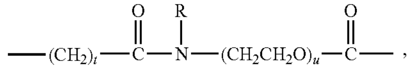

wherein:

R is H or $C_1$-$C_6$ alkyl;

t is an integer between 2 and 10, and u is an integer between 1 and 10.

In some embodiments, in linkers of Formula (XI), Str is selected from:

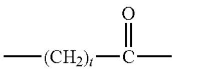

and

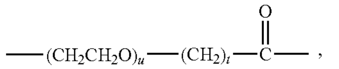

wherein:

t is an integer between 2 and 10, and u is an integer between 1 and 10.

In some embodiments, in linkers of Formula (XI), $AA_1$-$[AA_2]_{r}$ is a dipeptide (i.e. r=1). In some embodiments, in linkers of Formula (XI), $AA_1$-$[AA_2]_{r}$ has a sequence selected from: Ala-(D)Asp, Ala-Lys, Ala-Phe, Asn-Lys, Asn-(D)Lys, Asp-Val, His-Val, Ile-Cit, Ile-Pro, Ile-Val, Leu-Cit, $Me_3$Lys-Pro, Met-Lys, Met-(D)Lys, NorVal-(D)Asp, Phe-Arg, Phe-Cit, Phe-Lys, PhenylGly-(D)Lys, Pro-(D)Lys, Trp-Cit, Val-Ala, Val-(D)Asp, Val-Cit, Val-Gly, Val-Gln and Val-Lys.

In some embodiments, in linkers of Formula (XI), $AA_1$-$[AA_2]_{r}$ is a tripeptide (i.e. r=2). In some embodiments, in linkers of Formula (XI), $AA_1$-$[AA_2]_{r}$ has a sequence selected from: Ala-Ala-Asn, Ala-Val-Cit, (D)Ala-Phe-Lys, Asp-Val-Ala, Asp-Val-Cit, Gly-Cit-Val, Lys-Val-Ala, Lys-Val-Cit, Met-Cit-Val, (D)Phe-Phe-Lys and Asn-Pro-Val.

In some embodiments, in linkers of Formula (XI), $AA_1$-$[AA_2]_{r}$ is a tetrapeptide (i.e. r=3). In some embodiments, in linkers of Formula (XI), $AA_1$-$[AA_2]_{r}$ has a sequence selected from: Ala-Leu-Ala-Leu [SEQ ID NO: 158], Gly-Phe-Leu-Gly [SEQ ID NO: 159], Gly-Gly-Phe-Gly [SEQ ID NO: 160] and Gly-Phe-Gly-Gly [SEQ ID NO: 161].

In certain embodiments, in ADCs of Formula (X), m is 1, and linker, L, is a cleavable linker having Formula (XII):

$$\#-Z-[Str]_q-AA_1-[AA_2]_r-[X]_v-\% \quad \text{(XII)}$$

wherein:

Z is a functional group capable of reacting with a target group on the anti-FRα antibody construct, T;

Str is a stretcher;

$AA_1$ and $AA_2$ are each independently an amino acid, wherein $AA_1$-$[AA_2]_{r}$ forms a protease cleavage site;

Y is —NH—$CH_2$— or —NH—$CH_2$—C(O)—;

q is 0 or 1;

r is 1, 2 or 3;

v is 0 or 1;

# is the point of attachment to the anti-FRα antibody construct, T, and

% is the point of attachment to the camptothecin analogue, D.

In some embodiments, in linkers of Formula (XII), q is 1.

In some embodiments, in linkers of Formula (XII), v is O. In some embodiments, in ADCs of Formula (XII), v is 1.

In some embodiments, in linkers of Formula (XII), r is 1. In some embodiments, in ADCs of Formula (XII), r is 3.

In some embodiments, in linkers of Formula (XII):

Z is

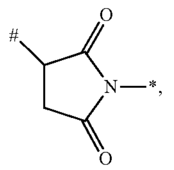

where # is the point of attachment to T, and * is the point of attachment to the remainder of the linker.

In some embodiments, in linkers of Formula (XII), Str is selected from:

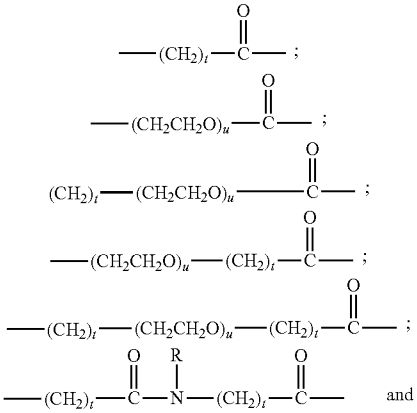

and

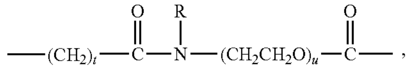

wherein:

R is H or $C_1$-$C_6$ alkyl;

t is an integer between 2 and 10, and u is an integer between 1 and 10.

In some embodiments, in linkers of Formula (XII), Str is selected from:

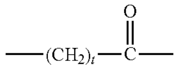

and

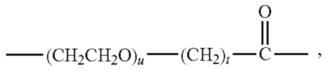

, wherein:

t is an integer between 2 and 10, and u is an integer between 1 and 10.

In some embodiments, in linkers of Formula (XII), $AA_1$-$[AA_2]_r$ is a dipeptide (i.e. r=1).

In some embodiments, in linkers of Formula (XII), $AA_1$-$[AA_2]_r$ has a sequence selected from: Ala-(D)Asp, Ala-Lys, Ala-Phe, Asn-Lys, Asn-(D)Lys, Asp-Val, His-Val, Ile-Cit, Ile-Pro, Ile-Val, Leu-Cit, $Me_3$Lys-Pro, Met-Lys, Met-(D)Lys, NorVal-(D)Asp, Phe-Arg, Phe-Cit, Phe-Lys, PhenylGly-(D)Lys, Pro-(D)Lys, Trp-Cit, Val-Ala, Val-(D)Asp, Val-Cit, Val-Gly, Val-Gln and Val-Lys.

In some embodiments, in linkers of Formula (XII), $AA_1$-$[AA_2]_r$ is a tripeptide (i.e. r=2).

In some embodiments, in linkers of Formula (XII), $AA_1$-$[AA_2]_r$ has a sequence selected from: Ala-Ala-Asn, Ala-Val-Cit, (D)Ala-Phe-Lys, Asp-Val-Ala, Asp-Val-Cit, Gly-Cit-Val, Lys-Val-Ala, Lys-Val-Cit, Met-Cit-Val, (D)Phe-Phe-Lys and Asn-Pro-Val.

In some embodiments, in linkers of Formula (XII), $AA_1$-$[AA_2]_r$ is a tetrapeptide (i.e. r=3). In some embodiments, in linkers of Formula (XII), $AA_1$-$[AA_2]_r$ has a sequence selected from: Ala-Leu-Ala-Leu [SEQ ID NO: 158], Gly-Phe-Leu-Gly [SEQ ID NO: 159], Gly-Gly-Phe-Gly [SEQ ID NO: 160] and Gly-Phe-Gly-Gly [SEQ ID NO: 161].

In some embodiments, in linkers of Formula (XII), Y is —NH—$CH_2$. In some embodiments, in linkers of Formula (XII), v is 1 and Y is —NH—$CH_2$.

In some embodiments, ADCs of Formula (X) may comprise a disulfide-containing linker. In some embodiments, in ADCs of Formula (X), m is 1, and linker, L, is a cleavable linker having Formula (XIII):

(XIII)

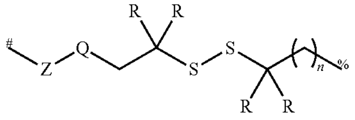

wherein:

Z is a functional group capable of reacting with a target group on the anti-FRα antibody construct, T;

Q is —$(CH_2)_p$— or —$(CH_2CH_2O)_q$—, wherein p and q are each independently an integer between 1 and 10;

each R is independently H or $C_1$-$C_6$ alkyl;

n is 1, 2 or 3;

# is the point of attachment to the anti-FRα antibody construct, T, and

% is the point of attachment to the camptothecin analogue, D.

In some embodiments, ADCs of Formula (X) may comprise a β-glucuronide-containing linker.

Various non-cleavable linkers are known in the art for linking drugs to targeting moieties and may be useful in the ADCs of the present disclosure in certain embodiments. Examples of non-cleavable linkers include linkers having an N-succinimidyl ester or N-sulfosuccinimidyl ester moiety for reaction with the anti-FRα antibody construct, as well as a maleimido- or haloacetyl-based moiety for reaction with the camptothecin analogue, or vice versa. An example of such a non-cleavable linker is based on sulfosuccinimidyl-4-[N-maleimidomethyl]cyclohexane-1-carboxylate (sulfo-SMCC). Sulfo-SMCC conjugation typically occurs via a maleimide group which reacts with sulfhydryls (thiols, SH) on the camptothecin analogue, while the sulfo-NHS ester is reactive toward primary amines (as found in lysine and at the N-terminus of proteins or peptides) on the anti-FRα antibody construct. Other non-limiting examples of such linkers include those based on N-succinimidyl 4-(maleimidomethyl)cyclohexanecarboxylate (SMCC), N-succinimidyl-4-(N-maleimidomethyl)-cyclohexane-1-carboxy-(6-amidocaproate) ("long chain" SMCC or LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N—(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB) and N-(p-maleimidophenyl)isocyanate (PMPI). Other examples include those comprising a haloacetyl-based functional group such as N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP).

Non-limiting examples of drug-linkers comprising camptothecin analogues of Formula (I) are shown in Table 8 (FIG. 13), Table 9 (FIG. 14) and Table 10 (FIG. 15). Non-limiting examples of conjugates comprising these drug-linkers are shown in Table 11 (FIG. 16), Table 12 (FIG. 17) and Table 13 (FIG. 18). In certain embodiments, the ADC of Formula (X) comprises a drug-linker selected from the drug-linkers shown in Tables 8, 9 and 10. In certain embodiments, the ADC of Formula (X) is selected from the conjugates shown in Tables 11, 12 and 13, where T is the anti-FRα antibody construct and n is between 1 and 10. In some embodiments, the ADC of Formula (X) is selected from the conjugates shown in Tables 11, 12 and 13, where T is the anti-FRα antibody construct and n is between 2 and 8. In some embodiments, the ADC of Formula (X) is selected from the conjugates shown in Tables 11, 12 and 13, where T is the anti-FRα antibody construct and n is between 4 and 8.

In certain embodiments, the ADC of Formula (X) comprises a drug-linker (L-$(D)_m$) selected from MT-GGFG-AM-Compound 139, MC-GGFG-AM-Compound 139, MT-GGFG-Compound 140, MC-GGFG-Compound 140, MT-GGFG-AM-Compound 141, MC-GGFG-AM-Compound 141, MT-GGFG-Compound 141, MC-GGFG-Compound 141, MT-GGFG-Compound 148 and MC-GGFG-Compound 148, and n is 4 or 8. In some embodiments, the ADC of Formula (X) comprises a drug-linker (L-$(D)_m$) selected from MT-GGFG-AM-Compound 139, MC-GGFG-AM-Compound 139, MT-GGFG-Compound 140, MC-GGFG-Compound 140, MT-GGFG-AM-Compound 141, MC-GGFG-AM-Compound 141, MT-GGFG-Compound 141, MC-GGFG-Compound 141, MT-GGFG-Compound 148 and MC-GGFG-Compound 148, and n is 8.

Preparation of ADCs

ADCs of Formula (X) may be prepared by standard methods known in the art (see, for example, Bioconjugate Techniques (G. T. Hermanson, 2013, Academic Press)). Various linkers and linker components are commercially available or may be prepared using standard synthetic organic chemistry techniques (see, for example, March's Advanced Organic Chemistry (Smith & March, 2006, Sixth Ed., Wiley); Toki et al., (2002) *J. Org. Chem.* 67:1866-1872; Frisch et al., (1997) *Bioconj. Chem.* 7:180-186; Bioconjugate Techniques (G. T. Hermanson, 2013, Academic Press)). In addition, various antibody drug conjugation services are available commercially from companies such as Lonza Inc. (Allendale, NJ), Abzena PLC (Cambridge, UK), ADC Biotechnology (St. Asaph, UK), Baxter BioPharma Solutions (Baxter Healthcare Corporation, Deerfield, IL) and Piramal Pharma Solutions (Grangemouth, UK).

Typically, preparation of the ADCs comprises first preparing a drug-linker, D-L, comprising one or more camptothecin analogues of Formula (I) and linker L, and then conjugating the drug-linker, D-L, to an appropriate group on the anti-FRα antibody construct, T. Ligation of linker, L, to the anti-FRα antibody construct, T, and subsequent ligation of the anti-FRα antibody construct-linker, T-L, to one or more camptothecin analogues of Formula (I), D, remains however an alternative approach that may be employed in some embodiments.

Suitable groups on compounds of Formula (I), D, for attachment of linker, L, in either of the above approaches include, but are not limited to, thiol groups, amine groups, carboxylic acid groups and hydroxyl groups. In some embodiments of the present disclosure, linker, L, is attached to a compound of Formula (I), D, via a hydroxyl or amine group on the compound.

Suitable groups on the anti-FRα antibody construct, T, for attachment of linker, L, in either of the above approaches include sulfhydryl groups (for example, on the side-chain of cysteine residues), amino groups (for example, on the side-chain of lysine residues), carboxylic acid groups (for example, on the side-chains of aspartate or glutamate residues), and carbohydrate groups.

For example, the anti-FRα antibody construct T may comprise one or more naturally occurring sulfhydryl groups allowing the anti-FRα antibody construct, T, to bond to linker, L, via the sulfur atom of a sulfhydryl group. Alternatively, the anti-FRα antibody construct, T, may comprise one or more lysine residues that can be chemically modified to introduce one or more sulfhydryl groups. Reagents that can be used to modify lysine residues include, but are not limited to, N-succinimidyl S-acetylthioacetate (SATA), N-succinimidyl-3-(2-pyridyldithio)propionate ("SPDP") and 2-iminothiolane hydrochloride (Traut's Reagent). Alternatively, the anti-FRα antibody construct, T, may comprise one or more carbohydrate groups that can be chemically modified to include one or more sulfhydryl groups.

Carbohydrate groups on the anti-FRα antibody construct, T, may also be oxidized to provide an aldehyde (—CHO) group (see, for example, Laguzza et al., 1989, J. Med. Chem. 32(3):548-55), which could subsequently be reacted with linker, L, for example, via a hydrazine or hydroxylamine group on linker, L.

The anti-FRα antibody construct, T, may also be modified to include additional cysteine residues (see, for example, U.S. Pat. Nos. 7,521,541; 8,455,622 and 9,000,130) or non-natural amino acids that provide reactive handles, such as selenomethionine, p-acetylphenylalanine, formylglycine or p-azidomethyl-L-phenylalanine (see, for example, Hofer et al., 2009, *Biochemistry,* 48:12047-12057; Axup et al., 2012, *PNAS,* 109:16101-16106; Wu et al., 2009, *PNAS,* 106:3000-3005; Zimmerman et al., 2014, *Bioconj. Chem.,* 25:351-361), to allow for site-specific conjugation. Alternatively, the anti-FRα antibody construct, T, may be modified to include a non-natural reactive group, such as an azide, that allows for conjugation to the linker via a complementary reactive group on the linker, for example, for example, by click chemistry (see, for example, Chio & Bane, 2020, *Methods Mol. Biol.,* 2078:83-97). A further option is the use of GlycoConnect™ technology (Synaffix BV, Nijmegen, Netherlands), which involves enzymatic remodelling of the antibody glycans to allow for attachment of a linker by metal-free click chemistry (see, for example, European Patent No. EP 2 911 699).

Other protocols for the modification of proteins for the attachment or association of linker, L, are known in the art and include those described in Coligan et al., *Current Protocols in Protein Science*, vol. 2, John Wiley & Sons (2002).

Alternatively, ADCs may be prepared using the enzyme transglutaminase, in particular, bacterial transglutaminase (BTG) from *Streptomyces mobaraensis* (see, for example, Jeger et al., 2010, *Angew. Chem. Int. Ed.,* 49:9995-9997). BTG forms an amide bond between the side chain carboxamide of a glutamine (the amine acceptor, typically on the antibody) and an alkyleneamino group (the amine donor, typically on the drug-linker), which can be, for example, the ε-amino group of a lysine or a 5-amino-n-pentyl group. Antibodies may also be modified to include a glutamine containing peptide, or "tag," which allows BTG conjugation to be used to conjugate the antibody to a drug-linker (see, for example, U.S. Patent Application Publication No. US 2013/0230543 and International (PCT) Publication No. WO 2016/144608).

A similar conjugation approach utilizes the enzyme sortase A. In this approach, the antibody is typically modified to include the sortase A recognition motif (LPXTG, where X is any natural amino acid) and the drug-linker is designed to include an oligoglycine motif (typically GGG) to allow for sortase A-mediated transpeptidation (see, for example, Beerli, et al., 2015, *PLos One,* 10:e0131177; Chen et al., 2016, *Nature:Scientific Reports,* 6:31899).

Once conjugation is complete, the average number of compounds of Formula (I) conjugated to the anti-FRα antibody construct, T, (i.e. the "drug-to-antibody ratio" or DAR) may be determined by standard techniques such as UV/VIS spectroscopic analysis, ELISA-based techniques, chromatography techniques such as hydrophobic interaction chromatography (HIC), UV-MALDI mass spectrometry (MS) and MALDI-TOF MS. In addition, distribution of drug-linked forms (for example, the fraction of the anti-FRα antibody construct, T, containing zero, one, two, three, etc. compounds of Formula (I), D) may also optionally be analyzed. Various techniques are known in the art to measure DAR distribution, including MS (with or without an accompanying chromatographic separation step), hydrophobic interaction chromatography, reverse-phase HPLC or iso-electric focusing gel electrophoresis (IEF) (see, for example, Wakankar et al., 2011, mAbs, 3:161-172).

Pharmaceutical Compositions

For therapeutic uses, the ADCs of the present disclosure are typically formulated as pharmaceutical compositions. Certain embodiments of the present disclosure thus relate to pharmaceutical compositions comprising an ADC as described herein and a pharmaceutically acceptable carrier, diluent, or excipient. Such pharmaceutical compositions may be prepared by known procedures using well-known and readily available ingredients.

Pharmaceutical compositions may be formulated for administration to a subject by, for example, oral (including, for example, buccal or sublingual), topical, parenteral, rectal or vaginal routes, or by inhalation or spray. "Parenteral" administration may be subcutaneous injection, or intradermal, intra-articular, intravenous, intramuscular, intravascular, intrasternal, intrathecal injection or infusion. The pharmaceutical composition will typically be formulated in a format suitable for administration to the subject, for example, as a syrup, elixir, tablet, troche, lozenge, hard or soft capsule, pill, suppository, oily or aqueous suspension, dispersible powder or granule, emulsion, injectable or solution. Pharmaceutical compositions may be provided as unit dosage formulations.

In certain embodiments, the pharmaceutical compositions comprising the ADCs are formulated for parenteral administration, for example as lyophilized formulations or aqueous solutions. Such pharmaceutical compositions may be provided, for example, in a unit dosage injectable form.

Pharmaceutically acceptable carriers are generally nontoxic to recipients at the dosages and concentrations employed. Examples of such carriers include, but are not limited to, buffers such as phosphate, citrate, and other organic acids; antioxidants such as ascorbic acid and methionine; preservatives such as octadecyldimethylbenzyl ammonium chloride, hexamethonium chloride, benzalkonium chloride, benzethonium chloride, phenol, butyl alcohol, benzyl alcohol, alkyl parabens (such as methyl or propyl paraben), catechol, resorcinol, cyclohexanol, 3-pentanol and m-cresol; low molecular weight (less than about 10 residues) polypeptides; proteins such as serum albumin or gelatin; hydrophilic polymers such as polyvinylpyrrolidone; amino acids such as glycine, glutamine, asparagine, histidine, arginine or lysine; monosaccharides, disaccharides, and other carbohydrates such as glucose, mannose or dextrins; chelating agents such as EDTA; sugars such as sucrose, mannitol, trehalose or sorbitol; salt-forming counter-ions such as sodium; metal complexes such as Zn-protein complexes, and non-ionic surfactants such as polyethylene glycol (PEG).

In certain embodiments, the compositions comprising the ADCs may be in the form of a sterile injectable aqueous or oleaginous solution or suspension. Such suspensions may be formulated using suitable dispersing or wetting agents and/or suspending agent that are known in the art. The sterile injectable solution or suspension may comprise the ADC in a non-toxic parentally acceptable diluent or carrier. Acceptable diluents and carriers that may be employed include, for example, 1,3-butanediol, water, Ringer's solution or isotonic sodium chloride solution. In addition, sterile, fixed oils may be employed as a carrier. For this purpose, various bland fixed oils may be employed, including synthetic mono- or diglycerides. In addition, fatty acids such as oleic acid find use in the preparation of injectables. Adjuvants such as local anaesthetics, preservatives and/or buffering agents may also be included in the injectable solution or suspension.

In certain embodiments, the composition comprising the ADC may be formulated for intravenous administration to humans. Typically, compositions for intravenous administration are solutions in sterile isotonic aqueous buffer. Where necessary, the composition may also include a solubilizing agent and/or a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, PA (2000).

Methods of Use

Certain embodiments of the present disclosure relate to the therapeutic use of the ADCs described herein. Some embodiments relate to the use of the ADCs as therapeutic agents.

Certain embodiments of the present disclosure relate to methods of inhibiting abnormal cancer cell or tumor cell growth; inhibiting cancer cell or tumor cell proliferation, or treating cancer in a subject, comprising administering an ADC described herein. In certain embodiments, the ADCs described herein may be used in the treatment of cancer. Some embodiments of the present disclosure thus relate to the use of the ADCs as anti-cancer agents.

Certain embodiments of the present disclosure relate to methods of inhibiting the proliferation of cancer or tumor cells comprising contacting the cells with an ADC as described herein, for example, an ADC of Formula (X). Some embodiments relate to a method of killing cancer or tumor cells comprising contacting the cells with an ADC as described herein, for example, an ADC of Formula (X).

Some embodiments relate to methods of treating a subject having a cancer by administering to the subject an ADC as described herein, for example, an ADC of Formula (X). In this context, treating the subject may result in one or more of a reduction in the size of a tumor, the slowing or prevention of an increase in the size of a tumor, an increase in the disease-free survival time between the disappearance or removal of a tumor and its reappearance, prevention of a subsequent occurrence of a tumor (for example, metastasis), an increase in the time to progression, reduction of one or more adverse symptom associated with a tumor, and/or an increase in the overall survival time of a subject having cancer.

Certain embodiments relate to the use of an ADC as described herein, for example, an ADC of Formula (X), in a method of inhibiting tumor growth in a subject. Some embodiments relate to the use of an ADC as described herein, for example, an ADC of Formula (X), in a method of inhibiting proliferation of and/or killing cancer cells in vitro. Some embodiments relate to the use of an ADC as described herein, for example, an ADC of Formula (X), in a method of inhibiting proliferation of and/or killing cancer cells in vivo in a subject having a cancer.

Examples of cancers which may be treated in certain embodiments are carcinomas, including adenocarcinomas and squamous cell carcinomas; melanomas and sarcomas. Carcinomas and sarcomas are also frequently referred to as "solid tumors." Examples of commonly occurring solid tumors that may be treated in certain embodiments include, but are not limited to, brain cancer, breast cancer, cervical cancer, colon cancer, head and neck cancer, kidney cancer, lung cancer, ovarian cancer, pancreatic cancer, prostate cancer, stomach cancer, uterine cancer, non-small cell lung cancer (NSCLC) and colorectal cancer. Various forms of lymphoma also may result in the formation of a solid tumor and, therefore, may also be considered to be solid tumors in certain situations. Typically, the cancer to be treated is an FRα-expressing cancer.

Certain embodiments relate to methods of inhibiting the growth of FRα-positive tumor cells comprising contacting the cells with an ADC as described herein, for example, an ADC of Formula (X). The cells may be in vitro or in vivo. In certain embodiments, the ADCs may be used in methods of treating an FRα-positive cancer or tumor in a subject.

Cancers that overexpress FRα are typically solid tumors. Examples include, but are not limited to, ovarian cancer, endometrial cancer, lung cancer (such as non-small cell lung cancer (NSCLC)), mesothelioma, breast cancer (including triple negative breast cancer (TNBC)), colorectal cancer, biliary tract cancer, pancreatic cancer and esophageal cancer. Certain embodiments of the present disclosure relate to methods of treating a FRα-positive cancer with an ADC as described herein, for example, an ADC of Formula (X), where the cancer is ovarian cancer, endometrial cancer, lung cancer (such as non-small cell lung cancer (NSCLC)), mesothelioma, breast cancer, colorectal cancer, biliary tract cancer, pancreatic cancer or esophageal cancer. In some embodiments, the ADCs of Formula (X) may be useful in treating triple negative breast cancer (TNBC).

Certain embodiments of the present disclosure relate to methods of treating a FRα-positive cancer with an ADC as described herein, for example, an ADC of Formula (X), where the cancer is a solid tumor that expresses FRα at high levels (an FRα-high solid tumor). Certain embodiments of the present disclosure relate to methods of treating a FRα-positive cancer with an ADC as described herein, for example, an ADC of Formula (X), where the cancer is a solid tumor that expresses FRα at moderate levels (an FRα-mid solid tumor). Certain embodiments of the present disclosure relate to methods of treating a FRα-positive cancer with an ADC as described herein, for example, an ADC of Formula (X), where the cancer is a solid tumor that expresses FRα at moderate to low levels (an FRα-mid/μlow solid tumor). Certain embodiments of the present disclosure relate to methods of treating a FRα-positive cancer with an ADC as described herein, for example, an ADC of Formula (X), where the cancer is a solid tumor that expresses FRα at low levels (an FRα-low solid tumor). In certain embodiments, the solid tumor is breast cancer, ovarian cancer, colorectal cancer, lung cancer (such as NSCLC), pancreatic cancer or endometrial cancer.

Pharmaceutical Kits

Certain embodiments relate to pharmaceutical kits comprising an ADC as described herein, for example, an ADC of Formula (X).

The kit typically will comprise a container holding the ADC and a label and/or package insert on or associated with the container. The label or package insert contains instructions customarily included in commercial packages of therapeutic products, providing information about the indications, usage, dosage, administration, contraindications and/or warnings concerning the use of such therapeutic products. The label or package insert may further include a notice in the form prescribed by a governmental agency regulating the manufacture, use or sale of pharmaceuticals or biological products, which notice reflects approval by the agency of manufacture, for use or sale for human or animal administration. In some embodiments, the container may have a sterile access port. For example, the container may be an intravenous solution bag or a vial having a stopper that may be pierced by a hypodermic injection needle.

In addition to the container holding the ADC, the kit may optionally comprise one or more additional containers comprising other components of the kit. For example, a pharmaceutically acceptable buffer (such as bacteriostatic water for injection (BWFI), phosphate-buffered saline, Ringer's solution or dextrose solution), other buffers or diluents.

Suitable containers include, for example, bottles, vials, syringes, intravenous solution bags, and the like. The containers may be formed from a variety of materials such as glass or plastic. If appropriate, one or more components of the kit may be lyophilized or provided in a dry form, such as a powder or granules, and the kit can additionally contain a suitable solvent for reconstitution of the lyophilized or dried component(s).

The kit may further include other materials desirable from a commercial or user standpoint, such as filters, needles, and syringes.

The following Examples are provided for illustrative purposes and are not intended to limit the scope of the claimed invention in any way.

EXAMPLES

General

Chemistry: Examples 1-3 below illustrate various methods of preparing camptothecin analogues of Formula (I). It is understood that one skilled in the art may be able to make these compounds by similar methods or by combining other methods known in the art. It is also understood that one skilled in the art would be able to make, using the methods described below or similar methods, other compounds of Formula (I) not specifically illustrated below by using the appropriate starting components and modifying the parameters of the synthesis as needed. In general, starting components may be obtained from commercial sources such as Sigma Aldrich (Merck KGaA), Alfa Aesar and Maybridge (Thermo Fisher Scientific Inc.), Matrix Scientific, Tokyo Chemical Industry Ltd. (TCI) and Fluorochem Ltd., or synthesized according to sources known to those skilled in the art (see, for example, *March's Advanced Organic Chemistry: Reactions, Mechanisms, and Structure,* 7th edition, John Wiley & Sons, Inc., 2013) or prepared as described herein.

Biological Assays: Expression levels of FRα in the cell lines and CDX models employed in the Examples was assessed in-house using a research level IHC assay and assigned a relative expression level (high/mid/μlow or strong/moderate/weak). PDX models were assessed similarly using archival tumor samples.

Abbreviations

The following abbreviations are used throughout the Examples section: BCA: bicinchonic acid; Boc: di-tert-butyl dicarbonate; CE-SDS: capillary electrophoresis sodium dodecyl sulfate; DCM: dichloromethane; DTPA: diethylenetriamine pentaacetic acid; DIPEA: N,N-diisopropylethylamine; DMF: dimethylformamide; DMM™: (4-(4,6-dimethoxy-1,3,5-triazin-2-yl)-4-rnethyl-morpholinium chloride; EDC: 1-ethyl-3-(3-dimethylaminopropyl)carbodiimide; Fmoc: fluorenylmethyloxycarbonyl; HATU: hexafluorophosphate azabenzotriazole tetramethyl uronium; HIC: hydrophobic interaction chromatography; HOAt: 1-hydroxy-7-azabenzotriazole; HPLC: high-performance liquid chromatography; LC/MS: liquid chromatography mass spectrometry; MC: maleimidocaproyl; MT: maleimidotriethylene glycolate; NMM: N-methylmorpholine; PNP: p-nitrophenol; RP-UPLC-MS: reversed-phase ultra-high performance chromatography mass spectrometry; SEC: size exclusion chromatography; TCEP: tris(2-carboxyethyl) phosphine; Tfp: tetrafluorophenyl; TLC: thin layer chromatography; TFA: trifluoracetic acid.

General Chemistry Procedures

General Procedure 1: Conversion of chloride to amine

To a stirring solution of chloride compound in dimethylformamide (0.05-0.1 M) was added the appropriate secondary amine (3 eq.). Upon completion (determined by LC/MS, typically 1-3 h), the reaction mixture was purified by reverse-phase HPLC to provide the desired product after lyophilization.

General Procedure 2: Conversion of Amine to Amide

To a stirring solution of amine compound in dimethylformamide (0.05-0.1 M) was added triethylamine (1.2 eq.), the appropriate carboxylic acid (1.1 eq.) followed by a solution of DMM™ (2 eq.) in water (1 M). Upon completion (determined by LC/MS, typically 16 h), the reaction mixture was purified by reverse-phase HPLC to provide the desired product after lyophilization.

General Procedure 3: Conversion of Amine to Sulfonamide

To a stirring solution of amine compound in dimethylformamide (0.05-0.1 M) was added DIPEA (3 eq.) followed by the appropriate sulfonyl chloride. Upon completion (determined by LC/MS, typically 16 h), the reaction mixture was purified by reverse-phase HPLC to provide the desired product after lyophilization.

General Procedure 4: 2-step conversion of amine to urea (Synthetic Scheme IV; FIG. 1D) Step 1: To a stirring solution of amine compound in dichloromethane or dimethylformamide (0.05-0.1 M) was added p-nitrophenyl carbonate (1 eq.) then triethylamine (2 eq.). Upon completion (determined by LC/MS typically 1-4 h), the reaction mixture was concentrated to dryness then purified by reverse-phase HPLC to provide the desired PNP-carbamate intermediate after lyophilization. This intermediate can either used to generate a single analog or be divided into multiple batches in order to generate multiple analogs in the second step. Step 2: To the PNP-carbamate intermediate in dimethylformamide (0.1-0.2 M) was added the appropriate primary amine (3 eq.). Upon completion (determined by LC/MS, typically 1 h), the reaction mixture was purified by reverse-phase HPLC to provide the desired product after lyophilization.

General Procedure 5: Conversion of Amine to Carbamate

To a stirring solution of amine compound in dichloromethane or dimethylformamide (0.05-0.1 M) was added p-nitrophenyl carbonate (1 eq.) then triethylamine (2 eq.). Upon completion (determined by LC/MS, typically 1-4 h), the appropriate alcohol was added to the resultant PNP-carbamate intermediate. Upon completion (determined by LC/MS, typically 1-16 h), the reaction mixture was purified by reverse-phase HPLC to provide the desired product after lyophilization.

General Procedure 6: Removal of Boc Protecting Group

To a stirring solution of the Boc-protected amine compound in dichloromethane (0.1 M) was added TFA (20% by volume). Upon completion (determined by LC/MS, typically 1 h), the reaction mixture was concentrated in vacuo to provide a crude solid or was purified as described in General Procedure 9.

General Procedure 7: Copper-Mediated Amide Coupling

To a rapidly stirring solution of Boc-GGFG-OH (3 eq.) and HOAt (3 eq.) in a 10% v/v mixture of dimethyl formamide in dichloromethane (0.02 M) was added EDC (HCl salt, 3 eq.). After 5 min, a solution of the amine containing payload (1 eq.) in a 10% v/v mixture of dimethyl formamide in dichloromethane (0.02 M) was added, followed immediately by the addition of CuCl2 (4 eq.). Upon completion (determined by LC/MS, typically 1-16 h), the reaction mixture was concentrated in vacuo to provide a crude solid or was purified by preparative HPLC to provide the desired product after lyophilization.

General Procedure 8: MT Installation

To a stirring solution of amine compound (1 eq.) in dimethylformamide (~0.02 M) was added a solution of MT-OTfp (1.2-1.5 eq.) in acetonitrile (~0.02 M) then DIPEA (10 uL, 4 eq.). Upon completion (determined by LC/MS, typically 1-16 h), the reaction mixture was concentrated in vacuo to provide a crude solid which was purified by preparative HPLC to provide the desired product after lyophilization.

General Procedure 9: Compound Purification

Flash Chromatography: Crude reaction products were purified with Biotage® Snap Ultra columns (10, 25, 50, or 100 g) (Biotage, Charlotte, NC), eluting with linear gradients of ethyl acetate/hexanes or methanol/dichloromethane on a Biotage® Isolera™ automated flash system (Biotage, Charlotte, NC). Alternatively, reverse-phase flash purification was conducting using Biotage® Snap Ultra C18 columns (12, 30, 60, or 120 g), eluting with linear gradients of 0.1% TFA in acetonitrile/0.1% TFA in water. Purified compounds were isolated by either removal of organic solvents by rotavap or lyophilization of acetonitrile/water mixtures.

Preparative HPLC: Reverse-phase HPLC of crude compounds was performed using a Luna® 5-μm C18 100 A (150×30 mm) column (Phenomenex, Torrance, CA) on an Agilent 1260 Infinity II preparative LC/MSD system (Agilent Technologies, Inc., Santa Clara, CA), and eluting with linear gradients of 0.1% TFA in acetonitrile/0.1% TFA in water. Purified compounds were isolated by lyophilization of acetonitrile/water mixtures.

General Procedure 10: Compound Analysis

LC/MS: Reactions were monitored for completion and purified compounds were analyzed using a Kinetex® 2.6-μm C18 100 A (30×3 mm) column (Phenomenex, Torrance, CA) on an Agilent 1290 HPLC/6120 single quad LC/MS system (Agilent Technologies, Inc., Santa Clara, CA), eluting with a 10 to 100% linear gradient of 0.1% formic acid in acetonitrile/0.1% formic acid in water.

NMR: $^1H$ NMR spectra were collected with a Bruker AVANCE III 300 Spectrometer (300 MHz) (Bruker Corporation, Billerica, MA). Chemical shifts are reported in parts per million (ppm).

Example 1: Preparation of Camptothecin Analogues Having Methyl at the C10 Position

1.1: (S)-11-(chloromethyl)-4-ethyl-8-fluoro-4-hydroxy-9-methyl-1,12-dihydro-14H-pyrano[3',4':6,7]indolizino[1,2-b]quinoline-3,14(4H)-dione (Compound 1.1)

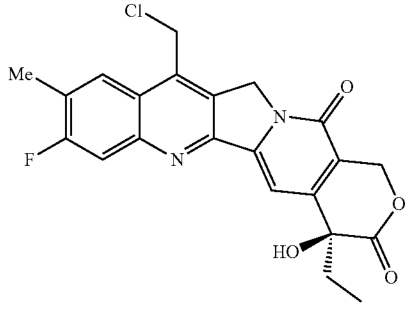 [SMILES: CC[C@@]1(O)C(=O)OCc2c1cc1n(c2=O)Cc2c-1nc1cc(F)c(C)cc1c2CCl]

The title compound was prepared according to the procedure provided in Li, et al., 2019, *ACS Med. Chem. Lett.*, 10(10): 1386-1392.

1.2: (S)-11-(aminomethyl)-4-ethyl-8-fluoro-4-hydroxy-9-methyl-1,12-dihydro-14H-pyrano[3',4':6,7]indolizino[1,2-b]quinoline-3,14(4H)-dione (Compound 1.2)

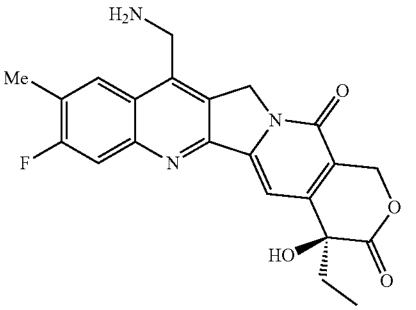 [SMILES: CC[C@@]1(O)C(=O)OCc2c1cc1n(c2=O)Cc2c-1nc1cc(F)c(C)cc1c2CN]

The title compound was prepared according to the procedure provided in Li, et al., 2019, *ACS Med. Chem. Lett.*, 10(10): 1386-1392.

1.3: (S)-4-ethyl-8-fluoro-4-hydroxy-9-methyl-11-(morpholinomethyl)-1,12-dihydro-14H-pyrano[3',4':6,7]indolizino[1,2-b]quinoline-3,14(4H)-dione (Compound 100)

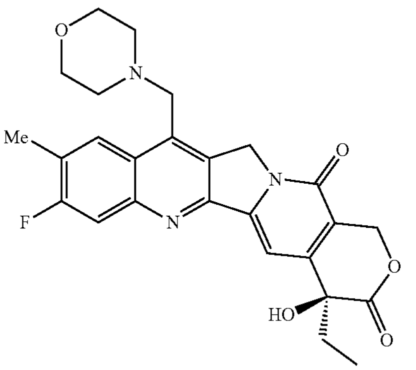 [SMILES: CC[C@@]1(O)C(=O)OCc2c1cc1n(c2=O)Cc2c-1nc1cc(F)c(C)cc1c2CN1CCOCC1]

The title compound was prepared according to General Procedure 1 starting from Compound 1.1 (10 mg) and morpholine. Preparative HPLC purification was accomplished as described in General Procedure 9, eluting with a 20 to 60% $CH_3CN/H_2O$+0.1% TFA gradient to give the title compound as an off-white solid (TFA salt, 3.6 mg, 26% yield).

LC/MS: Calc'd m/z=479.2 for $C_{26}H_{26}FN_3O_5$, found $[M+H]^+$=480.4.

$^1H$ NMR (300 MHz, $CDCl_3$) δ 8.20 (d, J=8.0 Hz, 1H), 7.82 (d, J=10.4 Hz, 1H), 7.67 (s, 1H), 5.77 (d, J=16.4 Hz, 1H), 5.42 (s, 2H), 5.33 (d, J=16.4 Hz, 1H), 4.26 (s, 2H), 3.81 (t, J=4.7 Hz, 4H), 2.82-2.76 (m, 4H), 2.57 (d, J=1.7 Hz, 3H), 1.99-1.82 (m, 2H), 1.06 (t, J=7.4 Hz, 3H).

1.4: (S)-4-ethyl-8-fluoro-4-hydroxy-9-methyl-11-((4-(phenylsulfonyl)piperazin-1-yl)methyl)-1,12-dihydro-14H-pyrano[3',4':6,7]indolizino[1,2-b]quinoline-3,14(4H)-dione (Compound 102)

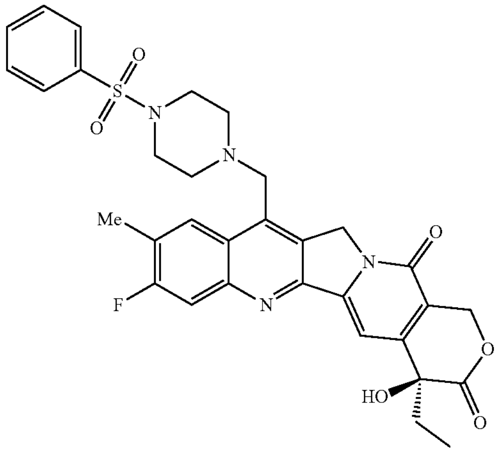 [SMILES: CC[C@@]1(O)C(=O)OCc2c1cc1n(c2=O)Cc2c-1nc1cc(F)c(C)cc1c2CN1CCN(S(=O)(=O)c2ccccc2)CC1]

The title compound was prepared according to General Procedure 1 starting from Compound 1.1 (10 mg) and 1-(phenylsulfonyl)piperazine. Preparative HPLC purification was accomplished as described in General Procedure 9, eluting with a 20 to 60% $CH_3CN/H_2O$+0.1% TFA gradient to give the title compound as an off-white solid (TFA salt, 3.6 mg, 21% yield).

LC/MS: Calc'd m/z=618.2 for $C_{32}H_{31}FN_4O_6$, found $[M+H]^+$=619.4.

$^1H$ NMR (300 MHz, $CDCl_3$) δ 8.07 (d, J=7.9 Hz, 1H), 7.88-7.44 (m, 7H), 5.73 (d, J=16.4 Hz, 1H), 5.33 (s, 2H), 5.33-5.26 (m, 1H), 4.19 (s, 2H), 3.12 (s, 4H), 2.80 (s, 4H), 2.54 (s, 3H), 1.90 (dt, J=11.6, 7.0 Hz, 2H), 1.04 (t, J=7.3 Hz, 3H).

1.5: (S)-11-((4-((4-aminophenyl)sulfonyl)piperazin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione (Compound 104)

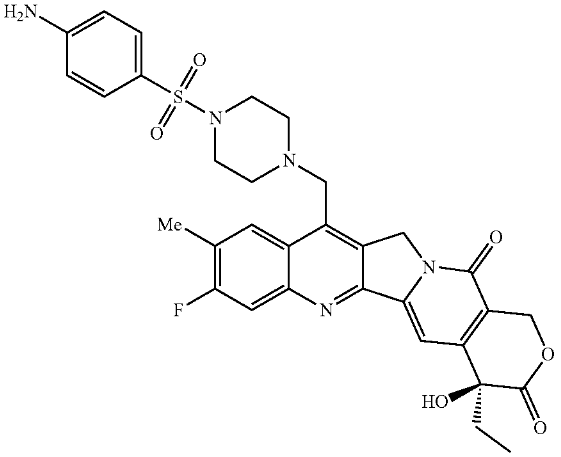 [SMILES: CC[C@@]1(O)C(=O)OCc2c1cc1n(c2=O)Cc2c-1nc1cc(F)c(C)cc1c2CN1CCN(S(=O)(=O)c2ccc(N)cc2)CC1]

The title compound was prepared according to General Procedure 1 starting from Compound 1.1 (10 mg) and 4-(piperazin-1-ylsulfonyl)aniline. Preparative HPLC purification was accomplished as described in General Procedure 9, eluting with a 20 to 60% $CH_3CN/H_2O$+0.1% TFA gradient to give the title compound as an off-white solid (TFA salt, 4.7 mg, 27% yield).

LC/MS: Calc'd m/z=633.2 for $C_{32}H_{32}FN_5O_6$, found $[M+H]^+$=634.4.

$^1$H NMR (300 MHz, MeOD) δ 8.32 (d, J=8.0 Hz, 1H), 7.85 (d, J=10.5 Hz, 1H), 7.65 (s, 1H), 7.46 (d, J=8.7 Hz, 2H), 6.74 (d, J=8.7 Hz, 2H), 5.61 (d, J=16.5 Hz, 1H), 5.44 (s, 2H), 5.41 (d, J=16.5 Hz, 1H), 4.51 (s, 2H), 3.22-3.07 (m, 8H), 2.58 (s, 3H), 2.03-1.93 (m, 2H), 1.02 (t, J=7.3 Hz, 3H).

1.6: (S)-4-ethyl-8-fluoro-4-hydroxy-9-methyl-11-((4-methylpiperazin-1-yl)methyl)-1,12-dihydro-14H-pyrano[3',4':6,7]indolizino[1,2-b]quinoline-3,14(4H)-dione (Compound 106)

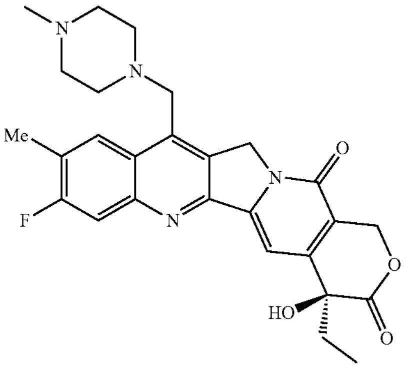 [SMILES: CC[C@@]1(O)C(=O)OCc2c1cc1n(c2=O)Cc2c-1nc1cc(F)c(C)cc1c2CN1CCN(C)CC1]

The title compound was prepared according to General Procedure 1 starting from Compound 1.1 (10 mg) and N-methylpiperazine. Preparative HPLC purification was accomplished as described in General Procedure 9, eluting with a 20 to 50% $CH_3CN/H_2O$+0.1% TFA gradient to give the title compound as an off-white solid (TFA salt, 3.6 mg, 25% yield).

LC/MS: Calc'd m/z=492.2 for $C_{27}H_{29}FN_4O_4$, found $[M+H]^+$=493.4.

1.7: (S)-11-((4-(4-aminophenyl)piperazin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione (Compound 108)

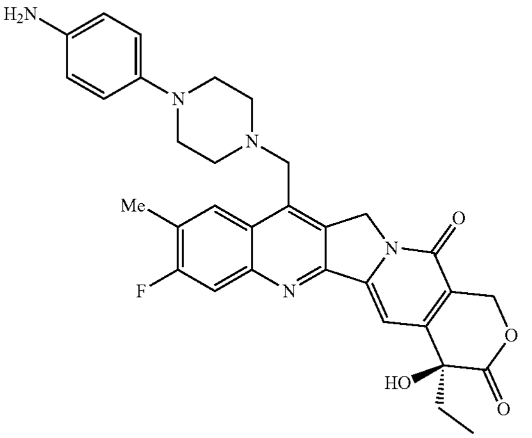 [SMILES: CC[C@@]1(O)C(=O)OCc2c1cc1n(c2=O)Cc2c-1nc1cc(F)c(C)cc1c2CN1CCN(c2ccc(N)cc2)CC1]

The title compound was prepared according to General Procedure 1 starting from Compound 1.1 (10 mg) and 4-(piperazin-1-yl)aniline. Preparative HPLC purification was accomplished as described in General Procedure 9, eluting with a 20 to 50% $CH_3CN/H_2O$+0.1% TFA gradient to give the title compound as an off-white solid (TFA salt, 3.7 mg, 23% yield).

LC/MS: Calc'd m/z=569.2 for $C_{32}H_{32}FN_5O_4$, found $[M+H]^+$=570.4.

$^1$H NMR (300 MHz, MeOD) δ 8.39 (d, J=8.1 Hz, 1H), 7.79 (d, J=10.6 Hz, 1H), 7.21 (d, J=9.0 Hz, 2H), 7.14 (d, J=9.0 Hz, 2H), 5.62 (d, J=16.4 Hz, 1H), 5.49 (s, 2H), 5.41 (d, J=16.4 Hz, 1H), 4.45 (s, 2H), 3.44-3.38 (m, 4H), 3.06-3.00 (m, 4H), 2.58 (d, J=1.8 Hz, 3H), 2.00-1.89 (m, 2H), 1.03 (t, J=7.3 Hz, 3H).

1.8: (S)-4-ethyl-8-fluoro-4-hydroxy-9-methyl-11-(piperidin-1-ylmethyl)-1,12-dihydro-14H-pyrano[3',4':6,7]indolizino[1,2-b]quinoline-3,14(4H)-dione (Compound 110)

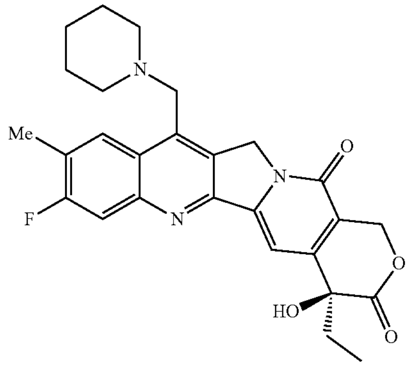 [SMILES: CC[C@@]1(O)C(=O)OCc2c1cc1n(c2=O)Cc2c-1nc1cc(F)c(C)cc1c2CN1CCCCC1]

The title compound was prepared according to General Procedure 1 starting from Compound 1.1 (10 mg) and piperidine. Preparative HPLC purification was accomplished as described in General Procedure 9, eluting with a 10 to 60% $CH_3CN/H_2O$+0.1% TFA gradient to give the title compound as an off-white solid (TFA salt, 1.5 mg, 11% yield).

LC/MS: Calc'd m/z=477.2 for $C_{27}H_{28}FN_3O_4$, found $[M+H]^+$=478.2.

$^1$H NMR (300 MHz, MeOD) δ 8.34 (d, J=7.6 Hz, 1H), 7.94 (d, J=10.3 Hz, 1H), 7.70 (s, 1H), 5.63 (d, J=16.4 Hz, 1H), 5.52 (s, 2H), 5.44 (d, J=16.5 Hz, 1H), 4.99 (s, 2H), 3.73-3.46 (m, 4H), 2.64 (s, 3H), 2.03-1.90 (m, 2H), 1.90-1.84 (m, 6H), 1.03 (t, J=7.4 Hz, 3H).

1.9: tert-butyl (S)-4-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)piperazine-1-carboxylate (Compound 111)

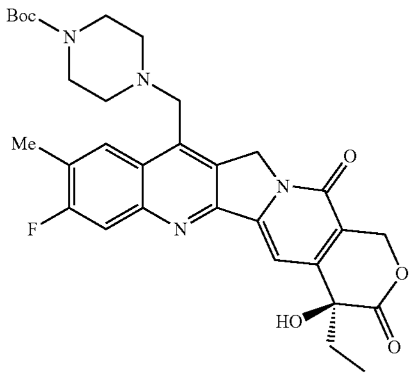 [SMILES: CC[C@@]1(O)C(=O)OCc2c1cc1n(c2=O)Cc2c-1nc1cc(F)c(C)cc1c2CN1CCN(C(=O)OC(C)(C)C)CC1]

The title compound was prepared according to General Procedure 1 starting from Compound 1.1 (10 mg) and tert-butyl piperazine-1-carboxylate. Preparative HPLC purification was accomplished as described in General Procedure 9, eluting with a 10 to 60% $CH_3CN/H_2O$+0.1% TFA gradient to give the title compound as an off-white solid (TFA salt, 6.6 mg, 40% yield).

LC/MS: Calc'd m/z=578.2 for $C_{31}H_{35}FN_4O_6$, found $[M+H]^+$=579.4.

1.10: (S)-4-ethyl-8-fluoro-4-hydroxy-9-methyl-11-(piperazin-1-ylmethyl)-1,12-dihydro-14H-pyrano[3',4':6,7]indolizino[1,2-b]quinoline-3,14(4H)-dione (Compound 112)

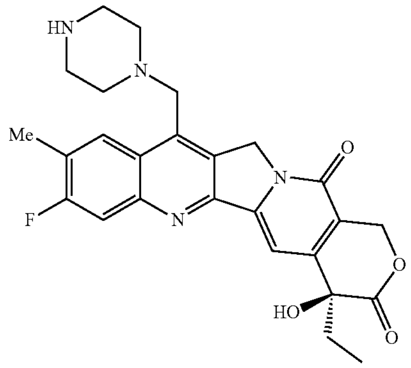 [SMILES: CC[C@@]1(O)C(=O)OCc2c1cc1n(c2=O)Cc2c-1nc1cc(F)c(C)cc1c2CN1CCNCC1]

The title compound was prepared according to General Procedure 6 starting from Compound 111 (5.0 mg) to give the title compound as an off-white solid (TFA salt, 4.4 mg).

LC/MS: Calc'd m/z=478.2 for $C_{26}H_{27}FN_4O_4$, found $[M+H]^+$=479.2.

1.11: (S)-4-ethyl-8-fluoro-4-hydroxy-11-(((R)-2-(hydroxymethyl)morpholino)methyl)-9-methyl-1,12-dihydro-14H-pyrano[3',4':6,7]indolizino[1,2-b]quinoline-3,14(4H)-dione (Compound 113)

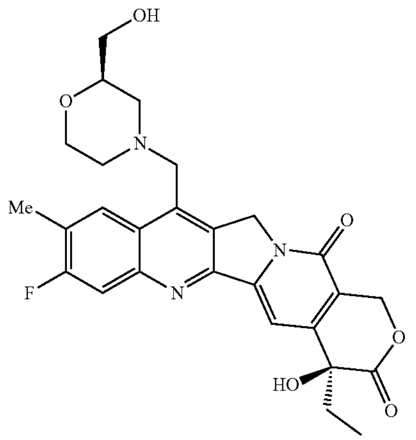 [SMILES: CC[C@@]1(O)C(=O)OCc2c1cc1n(c2=O)Cc2c-1nc1cc(F)c(C)cc1c2CN1CCO[C@@H](CO)C1]

The title compound was prepared according to General Procedure 1 starting from Compound 1.1 (10 mg) and (R)-morpholin-2-yl methanol. Preparative HPLC purification was accomplished as described in General Procedure 9, eluting with a 10 to 60% $CH_3CN/H_2O$+0.1% TFA gradient to give the title compound as an off-white solid (TFA salt, 4.6 mg, 32% yield).

LC/MS: Calc'd m/z=509.2 for $C_{27}H_{28}FN_3O_6$, found $[M+H]^+$=510.4.

1.12: (4S)-4-ethyl-8-fluoro-4-hydroxy-11-((3-(hydroxymethyl)thiomorpholino)methyl)-9-methyl-1,12-dihydro-14H-pyrano[3',4':6,7]indolizino[1,2-b]quinoline-3,14(4H)-dione (Compound 114)

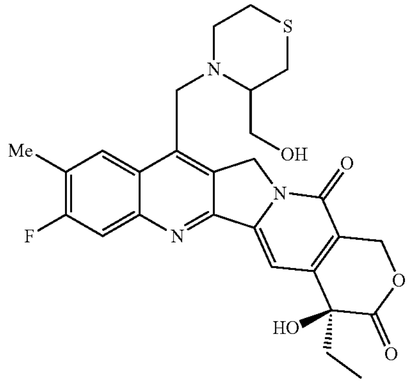 [SMILES: CC[C@@]1(O)C(=O)OCc2c1cc1n(c2=O)Cc2c-1nc1cc(F)c(C)cc1c2CN1CCSCC1CO]

The title compound was prepared according to General Procedure 1 starting from Compound 1.1 (10 mg) and thiomorpholin-3-ylmethanol. Preparative HPLC purification was accomplished as described in General Procedure 9, eluting with a 10 to 60% $CH_3CN/H_2O$+0.1% TFA gradient to give the title compound as an off-white solid (TFA salt, 1.5 mg, 12% yield).

LC/MS: Calc'd m/z=525.6 for $C_{27}H_{28}FN_3O_5S$, found $[M+H]^+$=526.5.

$^1$H NMR (300 MHz, 10% $D_2O/CD_3CN$) 8.36 (d, J=8.1 Hz, 1H), 7.83 (d, J=10.7 Hz, 1H), 7.50 (s, 1H), 5.57 (d, J=16.4 Hz, 1H), 5.52-5.29 (m, 3H), 5.02 (d, J=14.6 Hz, 1H), 4.71-4.54 (m, 1H), 4.27 (dd, J=12.4, 5.0 Hz, 1H), 3.98 (dd, J=12.3, 3.4 Hz, 1H), 3.55 (s, 1H), 3.30-3.03 (m, 4H) 2.97-2.72 (m, 3H), 2.62 (s, 1H), 2.55 (s, 3H), 0.95 (t, J=7.4 Hz, 3H).

1.13: (4S)-4-ethyl-8-fluoro-4-hydroxy-11-((4-(hydroxymethyl)-2-oxa-5-azabicyclo[2.2.1]heptan-5-yl) methyl)-9-methyl-1,12-dihydro-14H-pyrano[3',4':6,7]indolizino[1,2-b]quinoline-3,14(4H)-dione (Compound 115)

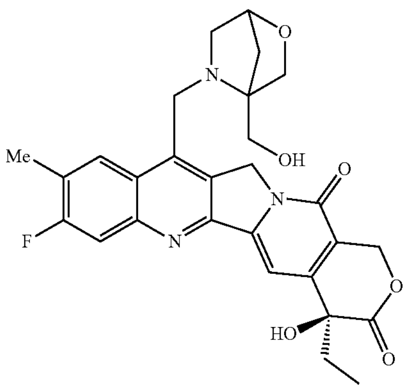 [SMILES: CC[C@@]1(O)C(=O)OCc2c1cc1n(c2=O)Cc2c-1nc1cc(F)c(C)cc1c2CN1CC2CC1(CO)CO2]

The title compound was prepared according to General Procedure 1 starting from Compound 1.1 (10 mg) and 2-oxa-5-azabicyclo[2.2.1]heptan-4-yl methanol. Preparative HPLC purification was accomplished as described in General Procedure 9, eluting with a 10 to 60% $CH_3CN/H_2O$+ 0.1% TFA gradient to give the title compound as an off-white solid (TFA salt, 3.5 mg, 29% yield).

LC/MS: Calc'd m/z=521.5 for $C_{28}H_{28}FN_3O_6$, found $[M+H]^+$=522.5.

$^1$H NMR (300 MHz, 10% $D_2O/CD_3CN$) 6 8.36 (d, J=7.9 Hz, 1H), 7.86 (dd, J=10.6, 5.0 Hz, 1H), 7.50 (d, J=1.8 Hz, 1H), 5.63-5.49 (m, 2H), 5.37 (dd, J=17.8, 14.1 Hz, 2H), 5.05 (s, 2H), 4.63 (d, J=2.5 Hz, 1H), 4.55 (d, J=10.7 Hz, 1H), 4.33 (s, 2H), 3.92 (d, J=10.7 Hz, 1H), 3.36 (s, 2H), 2.57 (s, 3H), 2.41-2.13 (m, 2H), 1.97-1.85 (m, 2H), 0.95 (t, J=7.4 Hz, 3H).

1.14: (4S)-4-ethyl-8-fluoro-4-hydroxy-11-((3-(hydroxymethyl)-1,1-dioxidothiomorpholino) methyl)-9-methyl-1,12-dihydro-14H-pyrano[3',4':6,7]indolizino[1,2-b]quinoline-3,14(4H)-dione (Compound 116)

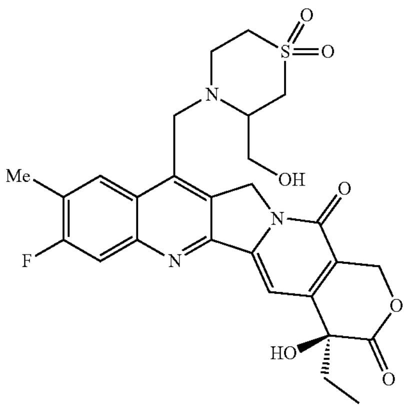 [SMILES: CC[C@@]1(O)C(=O)OCc2c1cc1n(c2=O)Cc2c-1nc1cc(F)c(C)cc1c2CN1CCS(=O)(=O)CC1CO]

The title compound was prepared according to General Procedure 1 starting from Compound 1.1 (10 mg) and 3-(hydroxymethyl)-1λ$^6$-thiomorpholine-1,1-dione. Purification was accomplished as described in General Procedure 9, eluting with a 10 to 60% $CH_3CN/H_2O$+0.1% TFA gradient to give the title compound as an off-white solid (TFA salt, 0.2 mg, 2% yield).

LC/MS: Calc'd m/z=557.6 for $C_{27}H_{28}FN_3O_7S$, found $[M+H]^+$=558.4.

$^1$H NMR (300 MHz, 10% $D_2O/CD_3CN$) 6 8.44 (d, J=8.2 Hz, 1H), 7.80 (d, J=11.0 Hz, 1H), 7.50 (s, 1H), 5.58 (d, J=16.5 Hz, 1H), 5.45-5.26 (m, 3H), 4.60 (d, J=14.9 Hz, 1H), 4.33 (d, J=14.7 Hz, 1H), 3.88 (d, J=4.8 Hz, 2H), 3.41-2.85 (m, 4H), 2.53 (s, 2H), 2.19 (p, J=2.5 Hz, 2H), 1.74 (p, J=2.5 Hz, 2H), 1.27 (s, 2H), 0.95 (t, J=7.4 Hz, 3H).

1.15: (4S)-4-ethyl-8-fluoro-4-hydroxy-11-((6-hydroxy-3-azabicyclo[3.1.1]heptan-3-yl)methyl)-9-methyl-1,12-dihydro-14H-pyrano[3',4':6,7]indolizino[1,2-b]quinoline-3,14(4H)-dione (Compound 117)

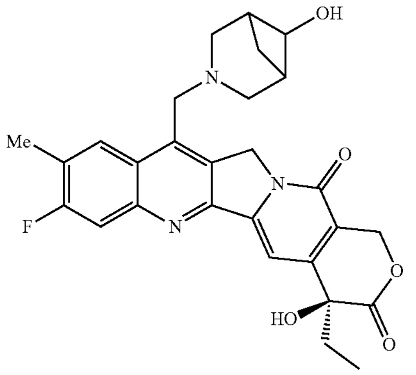 [SMILES: CC[C@@]1(O)C(=O)OCc2c1cc1n(c2=O)Cc2c-1nc1cc(F)c(C)cc1c2CN1CC2CC(C1)C2O]

The title compound was prepared according to General Procedure 1 starting from Compound 1.1 (10 mg) and 3-azabicyclo[3.1.1]heptan-6-ol. Preparative HPLC purification was accomplished as described in General Procedure 9, eluting with a 10 to 60% $CH_3CN/H_2O$+0.1% TFA gradient to give the title compound as an off-white solid (TFA salt, 1.3 mg, 11% yield).

LC/MS: Calc'd m/z=505.5 for $C_{28}H_{28}FN_3O_5$, found $[M+H]^+$=506.6.

$^1$H NMR (300 MHz, 10% $D_2O/CD_3CN$) 6 8.25 (d, J=7.9 Hz, 1H), 7.87 (d, J=10.6 Hz, 1H), 7.50 (s, 1H), 5.65-5.27 (m, 4H), 4.98 (s, 2H), 4.24 (s, 1H), 3.83-3.57 (m, 4H), 2.54 (s, 5H), 2.01-1.86 (m, 2H), 1.70 (s, 2H), 0.95 (t, J=7.3 Hz, 3H).

1.16: (S)-4-ethyl-8-fluoro-11-((3-fluoro-3-(hydroxymethyl)azetidin-1-yl)methyl)-4-hydroxy-9-methyl-1,12-dihydro-14H-pyrano[3',4':6,7]indolizino[1,2-b]quinoline-3,14(4H)-dione (Compound 118)

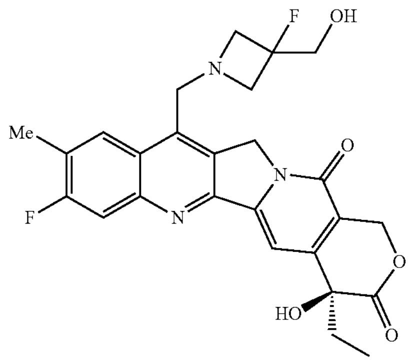 [SMILES: CC[C@@]1(O)C(=O)OCc2c1cc1n(c2=O)Cc2c-1nc1cc(F)c(C)cc1c2CN1CC(F)(CO)C1]

The title compound was prepared according to General Procedure 1 starting from Compound 1.1 (10 mg) and 3-fluoroazetidin-3-yl methanol. Preparative HPLC purification was accomplished as described in General Procedure 9, eluting with a 10 to 60% $CH_3CN/H_2O$+0.1% TFA gradient to give the title compound as an off-white solid (TFA salt, 1.4 mg, 12% yield).

LC/MS: Calc'd m/z=497.5 for $C_{26}H_{25}F_2N_3O_5$, found $[M+H]^+$=498.4.

$^1H$ NMR (300 MHz, 10% $D_2O/CD_3CN$) δ 8.24 (d, J=7.9 Hz, 1H), 7.85 (d, J=10.7 Hz, 1H), 7.50 (s, 1H), 5.57 (d, J=16.5 Hz, 1H), 5.48-5.28 (m, 3H), 4.98 (s, 2H), 4.44-4.14 (m, 4H), 3.78 (d, J=14.9 Hz, 2H), 2.01-1.86 (m, 2H), 0.95 (t, J=7.4 Hz, 3H).

1.17: (S)-4-ethyl-8-fluoro-4-hydroxy-11-((3-(hydroxymethyl)azetidin-1-yl)methyl)-9-methyl-1,12-dihydro-14H-pyrano[3',4':6,7]indolizino[1,2-b]quinoline-3,14(4H)-dione (Compound 119)

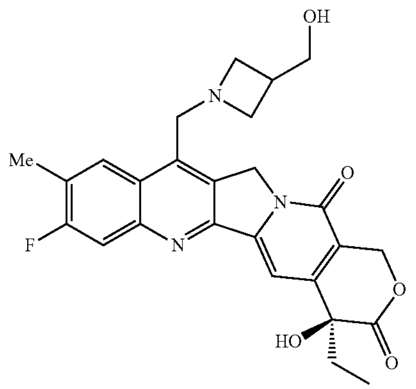 [SMILES: CC[C@@]1(O)C(=O)OCc2c1cc1n(c2=O)Cc2c-1nc1cc(F)c(C)cc1c2CN1CC(CO)C1]

The title compound was prepared according to General Procedure 1 starting from Compound 1.1 (10 mg) and azetidin-3-ylmethanol. Preparative HPLC purification was accomplished as described in General Procedure 9, eluting with a 10 to 60% $CH_3CN/H_2O$+0.1% TFA gradient to give the title compound as an off-white solid (TFA salt, 0.5 mg, 4.5% yield).

LC/MS: Calc'd m/z=479.5 for $C_{26}H_{26}FN_3O_5$, found $[M+H]^+$=480.4.

$^1H$ NMR (300 MHz, 10% $D_2O/CD_3CN$) δ 8.23 (d, J=7.8 Hz, 1H), 7.90 (d, J=10.6 Hz, 1H), 7.53 (s, 1H), 5.58 (d, J=16.5 Hz, 1H), 5.50-5.28 (m, 3H), 5.01 (s, 2H), 4.31-4.17 (m, 2H), 4.15-4.00 (m, 2H), 3.62 (d, J=3.9 Hz, 2H), 2.58 (s, 3H), 2.01-1.86 (m, 2H), 0.96 (t, J=7.4 Hz, 3H).

1.18: (4S)-11-((4,4-difluoro-3-(hydroxymethyl)piperidin-1-yl)methyl)-4-ethyl-8-fluoro-4-hydroxy-9-methyl-1,12-dihydro-14H-pyrano[3',4':6,7]indolizino[1,2-b]quinoline-3,14(4H)-dione (Compound 120)

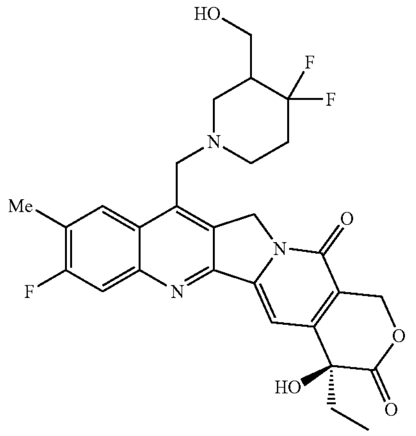 [SMILES: CC[C@@]1(O)C(=O)OCc2c1cc1n(c2=O)Cc2c-1nc1cc(F)c(C)cc1c2CN1CCC(F)(F)C(CO)C1]

The title compound was prepared according to General Procedure 1 starting from Compound 1.1 (10 mg) and 4,4-difluoropiperidin-3-yl methanol. Preparative HPLC purification was accomplished as described in General Procedure 9, eluting with a 10 to 60% $CH_3CN/H_2O$+0.1% TFA gradient to give the title compound as an off-white solid (TFA salt, 4 mg, 32% yield).

LC/MS: Calc'd m/z=543.5 for $C_{28}H_{28}F_3N_3O_5$, found $[M+H]^+$=544.4.

$^1H$ NMR (300 MHz, 10% $D_2O/CD_3CN$) δ 8.25 (d, J=8.0 Hz, 1H), 7.77 (dd, J=10.7, 1.4 Hz, 1H), 7.47 (s, 1H), 5.55 (d, J=16.5 Hz, 1H), 5.42-5.25 (m, 3H), 4.66 (d, J=3.2 Hz, 2H), 3.90-3.77 (m, 1H), 3.71-3.45 (m, 4H), 2.24 (q, J=11.8, 9.2 Hz, 2H), 2.01-1.86 (m, 2H), 0.94 (t, J=7.4 Hz, 3H).

1.19: (S)-4-ethyl-8-fluoro-4-hydroxy-11-((1-(hydroxymethyl)-7-azabicyclo[2.2.1]heptan-7-yl)methyl)-9-methyl-1,12-dihydro-14H-pyrano[3',4':6,7]indolizino[1,2-b]quinoline-3,14(4H)-dione (Compound 121)

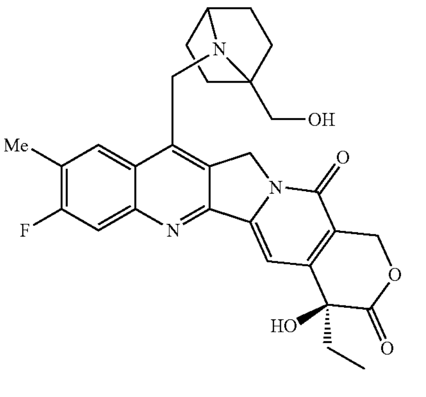 [SMILES: CC[C@@]1(O)C(=O)OCc2c1cc1n(c2=O)Cc2c-1nc1cc(F)c(C)cc1c2CN1C2CCC1(CO)CC2]

The title compound was prepared according to General Procedure 1 starting from Compound 1.1 (10 mg) and 7-azabicyclo[2.2.1]heptan-1-ylmethanol. Preparative HPLC purification was accomplished as described in General Procedure 9, eluting with a 10 to 60% $CH_3CN/H_2O$+0.1% TFA gradient to give the title compound as an off-white solid (TFA salt, 0.8 mg, 6.6% yield).

LC/MS: Calc'd m/z=519.6 for $C_{29}H_{30}FN_3O_5$, found $[M+H]^+$=520.4.

$^1$H NMR (300 MHz, 10% $D_2O/CD_3CN$) 6 8.22 (s, 1H), 7.92 (d, J=10.7 Hz, 1H), 7.54 (s, 1H), 5.59 (dd, J=17.6, 7.6 Hz, 2H), 5.33 (t, J=17.4 Hz, 2H), 4.98-4.81 (m, 1H), 4.67-4.44 (m, 2H), 4.28-3.93 (m, 4H), 2.73 (s, 2H), 2.34-2.03 (m, 4H), 1.91 (d, J=14.0 Hz, 5H), 0.96 (t, J=7.4 Hz, 3H).

1.20: (S)—N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)methanesulfonamide (Compound 122)

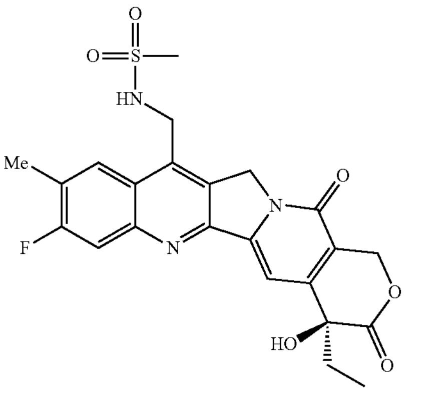 [SMILES: CC[C@@]1(O)C(=O)OCc2c1cc1n(c2=O)Cc2c-1nc1cc(F)c(C)cc1c2CNS(C)(=O)=O]

The title compound was prepared according to General Procedure 3 starting from Compound 1.2 (10 mg) and methane sulfonyl chloride. Preparative HPLC purification was accomplished as described in General Procedure 9, eluting with a 10 to 50% $CH_3CN/H_2O$+0.1% TFA gradient to give the title compound as an off-white solid (0.8 mg, 7% yield).

LC/MS: Calc'd m/z=487.1 for $C_{23}H_{22}FN_3O_6S$, found $[M+H]^+$=488.2.

$^1$H NMR (300 MHz, MeOD) δ 8.33 (d, J=8.1 Hz, 1H), 7.83 (d, J=10.8 Hz, 1H), 7.68 (s, 1H), 5.62 (d, J=16.3 Hz, 1H), 5.52 (s, 2H), 5.42 (d, J=16.4 Hz, 1H), 4.87 (s, 2H), 3.06 (s, 3H), 2.59 (s, 3H), 2.06-1.93 (m, 2H), 1.03 (t, J=7.4 Hz, 3H).

1.21: (S)—N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-1-(4-nitrophenyl) methanesulfonamide (Compound 124)

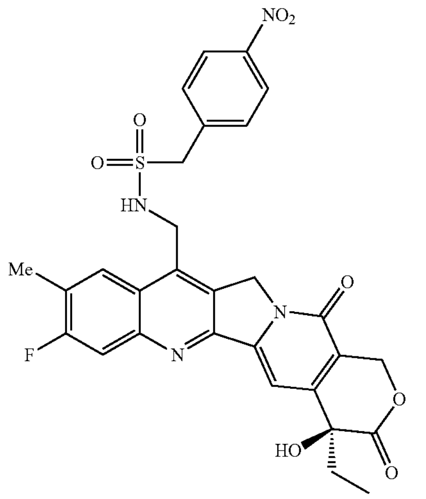 [SMILES: CC[C@@]1(O)C(=O)OCc2c1cc1n(c2=O)Cc2c-1nc1cc(F)c(C)cc1c2CNS(=O)(=O)Cc1ccc([N+](=O)[O-])cc1]

The title compound was prepared according to General Procedure 3 starting from Compound 1.2 (20 mg) and (4-nitrophenyl)methanesulfonyl chloride. Preparative HPLC purification was accomplished as described in General Procedure 9, eluting with a 10 to 50% $CH_3CN/H_2O$+0.1% TFA gradient to give the title compound as an off-white solid (5.0 mg, 17% yield).

LC/MS: Calc'd m/z=608.1 for $C_{29}H_{25}FN_4O_8S$, found $[M+H]^+$=609.2.

$^1$H NMR (300 MHz, $CDCl_3$) δ 8.02-7.92 (m, 3H), 7.74 (d, J=10.5 Hz, 1H), 7.65 (s, 1H), 7.33 (d, J=8.6 Hz, 2H), 5.66 (d, J=16.8 Hz, 1H), 5.28 (d, J=16.5 Hz, 1H), 5.14 (d, J=5.4 Hz, 2H), 4.67 (s, 2H), 4.28 (d, J=6.3 Hz, 2H), 3.39 (s, 3H), 2.03-1.83 (m, 2H), 1.04 (t, J=7.4 Hz, 3H).

1.22: (S)—N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)benzenesulfonamide (Compound 125)

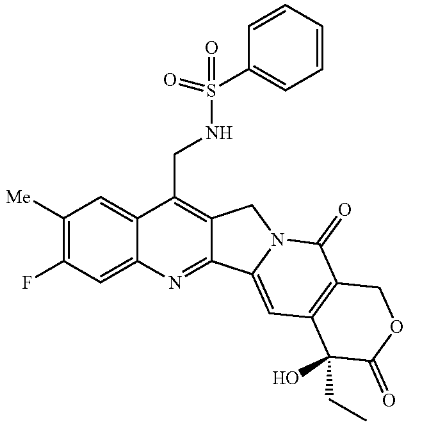 [SMILES: CC[C@@]1(O)C(=O)OCc2c1cc1n(c2=O)Cc2c-1nc1cc(F)c(C)cc1c2CNS(=O)(=O)c1ccccc1]

The title compound was prepared according to General Procedure 3 starting from Compound 1.2 (10 mg) and benzenesulfonyl chloride. Preparative HPLC purification was accomplished as described in General Procedure 9, eluting with a 10 to 50% $CH_3CN/H_2O$+0.1% TFA gradient to give the title compound as an off-white solid (9.8 mg, 73% yield).

LC/MS: Calc'd m/z=549.6 for $C_{28}H_{24}FN_3O_6S$, found $[M+H]^+$=550.6.

$^1$H NMR (300 MHz, DMSO-d6) δ 8.60 (t, J=6.2 Hz, 1H), 8.17 (d, J=8.1 Hz, 1H), 7.83 (d, J=10.8 Hz, 1H), 7.71 (dd, J=7.1, 1.7 Hz, 2H), 7.66-7.48 (m, 2H), 7.46 (dd, J=8.3, 6.8 Hz, 2H), 7.40-7.27 (m, 2H), 7.18 (s, 1H), 7.01 (s, 1H), 5.45 (s, 2H), 5.33 (s, 2H), 4.63 (d, J=6.2 Hz, 2H), 2.48 (s, 3H), 1.98-1.76 (m, 2H), 0.89 (t, J=7.3 Hz, 3H).

1.23: (S)—N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-4-nitrobenzenesulfonamide (Compound 1.23)

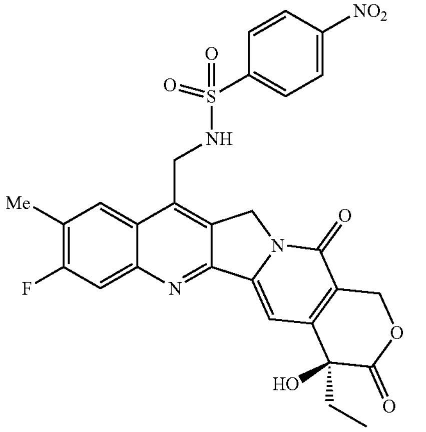 [SMILES: CC[C@@]1(O)C(=O)OCc2c1cc1n(c2=O)Cc2c-1nc1cc(F)c(C)cc1c2CNS(=O)(=O)c1ccc([N+](=O)[O-])cc1]

The title compound was prepared according to General Procedure 3 starting from Compound 1.2 (75 mg) and 4-nitrobenzenesulfonyl chloride. Purification of the title compound was accomplished as described in General Procedure 9, using a 12 g C18 column and eluting with a 5 to 75% $CH_3CN/H_2O$+0.1% TFA gradient to give the title compound as an off-white solid (37.8 mg, 47% yield).

LC/MS: Calc'd m/z=594.6 for $C_{28}H_{23}FN_4O_8S$, found $[M+H]^+$=595.2.

1.24: (S)-4-amino-N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)benzenesulfonamide (Compound 127)

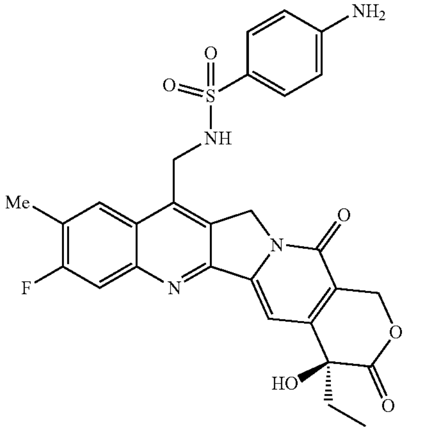 [SMILES: CC[C@@]1(O)C(=O)OCc2c1cc1n(c2=O)Cc2c-1nc1cc(F)c(C)cc1c2CNS(=O)(=O)c1ccc(N)cc1]

To a solution of Compound 1.23 (37.8 mg, 0.064 mmol) in methanol (6.4 mL) was added platinum 1% vanadium 2% on carbon (75 mg). The flask was purged with $H_2$ then stirred at room temperature under an $H_2$ atmosphere for 45 min. The mixture was filtered through a pad of celite, washed with DMF, and the filtrate evaporated to give the title compound as a pale yellow solid (30 mg, 84% yield).

LC/MS: Calc'd m/z=564.6 for $C_{28}H_{24}FN_4O_6S$, found $[M+H]^+$=565.2.

$^1$H NMR (300 MHz, DMSO-d6) δ 8.13 (d, J=8.2 Hz, 1H), 8.02 (t, J=6.2 Hz, 1H), 7.88 (d, J=10.8 Hz, 1H), 7.48-7.35 (m, 2H), 7.31 (d, J=8.4 Hz, 1H), 6.63-6.45 (m, 2H), 5.45 (s, 2H), 5.36 (s, 2H), 4.50 (d, J=6.3 Hz, 2H), 1.98-1.75 (m, 2H), 0.89 (t, J=7.3 Hz, 3H).

1.25: (S)—N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-2-hydroxyethane-1-sulfonamide (Compound 129)

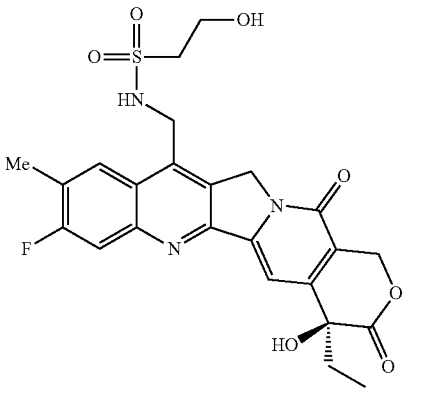 [SMILES: CC[C@@]1(O)C(=O)OCc2c1cc1n(c2=O)Cc2c-1nc1cc(F)c(C)cc1c2CNS(=O)(=O)CCO]

The title compound was prepared according to General Procedure 3 starting from Compound 1.2 (20 mg) and 2-hydroxyethanesulfonyl chloride. Preparative HPLC purification was accomplished as described in General Procedure 9, eluting with a 25 to 50% $CH_3CN/H_2O$+0.1% TFA gradient to give the title compound as an off-white solid (1.3 mg, 13% yield).

LC/MS: Calc'd m/z=517.1 for $C_{24}H_{24}FN_3O_7S$, found $[M+H]^+$=518.2.

$^1H$ NMR (300 MHz, DMSO-d6) δ 8.30 (d, J=8.4 Hz, 1H), 7.91 (d, J=10.9 Hz, 1H), 7.84 (t, J=6.3 Hz, 1H), 7.33 (s, 1H), 5.50-5.33 (m, 4H), 5.07 (t, J=5.4 Hz, 1H), 4.78 (d, J=6.0 Hz, 2H), 4.07 (s, 3H), 3.80 (dt, J=6.3 Hz, J=5.8 Hz, 2H), 1.86 (m, 2H), 0.87 (d, J=7.3 Hz, 3H).

1.26: (S)—N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl) methanesulfamide (Compound 131)

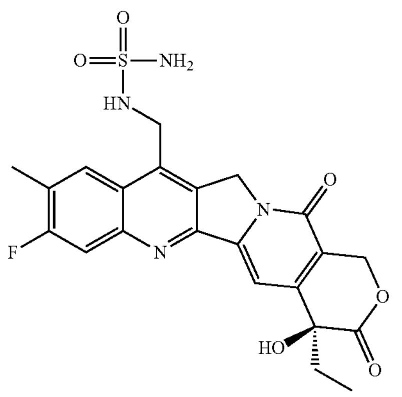 [SMILES: CC[C@@]1(O)C(=O)OCc2c1cc1n(c2=O)Cc2c-1nc1cc(F)c(C)cc1c2CNS(N)(=O)=O]

To a solution of chlorosulfonyl isocyanate (3 uL) in dichloromethane (1 mL) was added tert-butanol (3 uL). This solution was stirred for 1 h, then Compound 1.2 (13 mg) dissolved in dichloromethane (1 mL) was added followed by triethylamine (13 uL). The reaction was stirred for 1 hr then concentrated to dryness. Preparative HPLC purification of the intermediate Boc compound was accomplished as described in General Procedure 9, eluting with a 10 to 50% $CH_3CN/H_2O$+0.1% TFA gradient. To the purified solid in dichloromethane (1 mL) was added trifluoroacetic acid (200 uL). The reaction was stirred for 16 h then concentrated to dryness to provide the title compound as an off-white solid (7.5 mg, 48% yield).

LC/MS: Calc'd m/z=488.1 for $C_{22}H_{21}FN_4O_6S$, found $[M+H]^+$=489.0.

$^1H$ NMR (300 MHz, MeOD) δ 8.25 (d, J=8.1 Hz, 1H), 7.73 (d, J=10.7 Hz, 1H), 7.62 (s, 1H), 5.59 (d, J=16.4 Hz, 1H), 5.45 (s, 2H), 5.39 (d, J=16.4 Hz, 1H), 4.81 (s, 2H), 2.55 (d, J=1.7 Hz, 3H), 2.07-1.89 (m, 2H), 1.03 (t, J=7.4 Hz, 3H).

1.27: 4-nitrophenyl-(S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl) methyl)carbamate (Compound 1.27)

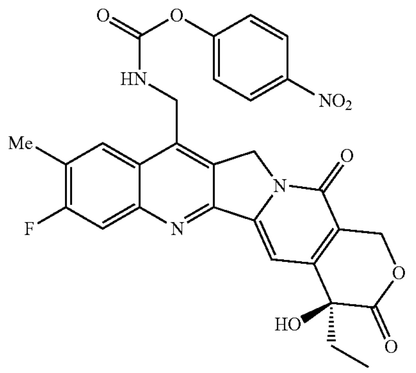 [SMILES: CC[C@@]1(O)C(=O)OCc2c1cc1n(c2=O)Cc2c-1nc1cc(F)c(C)cc1c2CNC(=O)Oc1ccc([N+](=O)[O-])cc1]

The title PNP-carbamate intermediate compound was prepared according to the first step of General Procedure 4 starting from Compound 1.2 (24 mg). Purification was accomplished as described in General Procedure 9, using a 12 g column C18 column and eluting with a 10 to 50% $CH_3CN/H_2O$+0.1% TFA gradient to give the title compound as an off-white solid (14 mg, 53% yield).

LC/MS: Calc'd m/z=574.2 for $C_{29}H_{23}FN_4O_8S$, found $[M+H]^+$=575.2

1.28: (S)-1-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-methyl-urea (Compound 132)

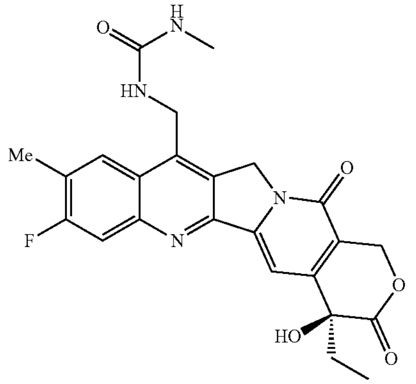 [SMILES: CC[C@@]1(O)C(=O)OCc2c1cc1n(c2=O)Cc2c-1nc1cc(F)c(C)cc1c2CNC(=O)NC]

The title compound was prepared according to General Procedure 4 starting from Compound 1.2 (25 mg) and aqueous methyl amine (500 uL, 40 wt. % in water) as the primary amine. In this instance, the intermediate PNP-carbamate was used crude. Preparative HPLC purification was accomplished as described in General Procedure 9, eluting with a 10 to 50% $CH_3CN/H_2O$+0.1% TFA gradient to give the title compound as an off-white solid (8.9 mg, 31% yield).

LC/MS: Calc'd m/z=466.2 for $C_{24}H_{23}FN_4O_5$, found $[M+H]^+$=467.2.

$^1$H NMR (300 MHz, MeOD) δ 8.26 (d, J=8.2 Hz, 1H), 7.79 (d, J=10.7 Hz, 1H), 7.66 (s, 1H), 5.61 (d, J=16.3 Hz, 1H), 5.48 (s, 2H), 5.41 (d, J=16.4 Hz, 1H), 4.97 (s, 2H), 2.73 (s, 3H), 2.57 (s, 3H), 2.08-1.93 (m, 2H), 1.03 (t, J=7.4 Hz, 3H).

1.29: (S)-1-(4-aminobenzyl)-3-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)urea (Compound 134)

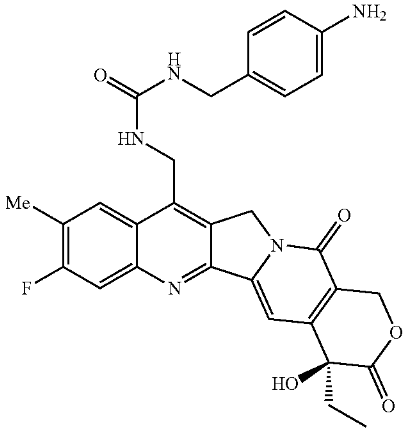 [SMILES: CC[C@@]1(O)C(=O)OCc2c1cc1n(c2=O)Cc2c-1nc1cc(F)c(C)cc1c2CNC(=O)NCc1ccc(N)cc1]

The title compound was prepared according to the second step of General Procedure 4 using Compound 1.27 (4 mg) as the PNP-carbamate and 4-(aminomethyl)aniline as the primary amine. Preparative HPLC purification was accomplished as described in General Procedure 9, eluting with a 20 to 50% $CH_3CN/H_2O$+0.1% TFA gradient to give the title compound as an off-white solid (0.6 mg, 12% yield).

LC/MS: Calc'd m/z=557.2 for $C_{30}H_{28}FN_5O_5$, found $[M+H]^+$=558.4.

$^1$H NMR (300 MHz, MeOD) δ 8.25 (d, J=8.1 Hz, 1H), 7.80 (d, J=10.8 Hz, 1H), 7.67 (s, 1H), 7.43 (d, J=8.2 Hz, 2H), 7.24 (d, J=8.3 Hz, 2H), 5.63 (d, J=16.4 Hz, 1H), 5.48 (s, 2H), 5.43 (d, J=16.4 Hz, 1H), 5.01 (s, 2H), 4.37 (s, 2H), 2.56 (d, J=1.7 Hz, 3H), 2.05-1.94 (m, 2H), 1.03 (t, J=7.3 Hz, 3H).

1.30: (S)-1-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-(2-hydroxyethyl)urea (Compound 136)

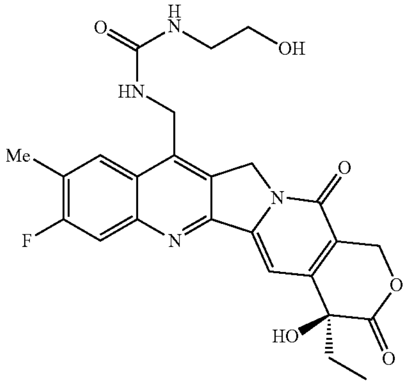 [SMILES: CC[C@@]1(O)C(=O)OCc2c1cc1n(c2=O)Cc2c-1nc1cc(F)c(C)cc1c2CNC(=O)NCCO]

The title compound was prepared according to the second step of General Procedure 4 using Compound 1.27 (4 mg) as the PNP-carbamate and hydroxyethylamine as the primary amine. Preparative HPLC purification was accomplished as described in General Procedure 9, eluting with a 10 to 50% $CH_3CN/H_2O$+0.1% TFA gradient to give the title compound as an off-white solid (2.4 mg, 66% yield).

LC/MS: Calc'd m/z=496.2 for $C_{25}H_{25}FN_4O_6$, found $[M+H]^+$=497.2.

$^1$H NMR (300 MHz, MeOD) δ 8.08 (d, J=8.0 Hz, 1H), 7.74 (d, J=10.5 Hz, 1H), 7.68 (s, 1H), 5.64 (d, J=16.4 Hz, 1H), 5.41 (s, 2H), 5.31 (d, J=16.4 Hz, 1H), 4.96 (s, 2H), 3.63 (t, J=5.2 Hz, 2H), 3.29 (t, J=5.3 Hz, 2H), 2.54 (s, 3H), 1.98-1.87 (m, 2H), 1.01 (t, J=7.4 Hz, 3H).

1.31: Methyl-(S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl) carbamate (Compound 138)

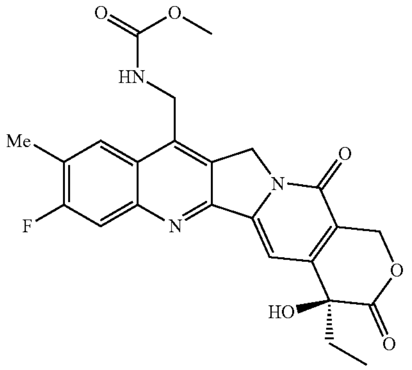 [SMILES: CC[C@@]1(O)C(=O)OCc2c1cc1n(c2=O)Cc2c-1nc1cc(F)c(C)cc1c2CNC(=O)OC]

The title compound was prepared according to General Procedure 5 starting from Compound 1.2 (50 mg) and reacting methanol with the intermediate PNP-carbamate. Preparative HPLC purification was accomplished as described in General Procedure 9, eluting with a 20 to 50% $CH_3CN/H_2O$+0.1% TFA gradient to give the title compound as an off-white solid (3.5 mg, 6% yield).

LC/MS: Calc'd m/z=467.2 for $C_{24}H_{22}FN_3O_6$, found $[M+H]^+$=468.2.

$^1$H NMR (300 MHz, MeOD) δ 8.17 (d, J=8.2 Hz, 1H), 7.77 (d, J=10.5 Hz, 1H), 7.69 (s, 1H), 5.65 (d, J=16.5 Hz, 1H), 5.48 (s, 2H), 5.33 (d, J=16.4 Hz, 1H), 4.86 (d, J=5.6 Hz, 2H), 3.65 (s, 3H), 2.56 (s, 3H), 2.02-1.89 (m, 2H), 1.02 (t, J=7.4 Hz, 3H).

1.32: 2-hydroxyethyl (S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl) methyl)carbamate (Compound 139)

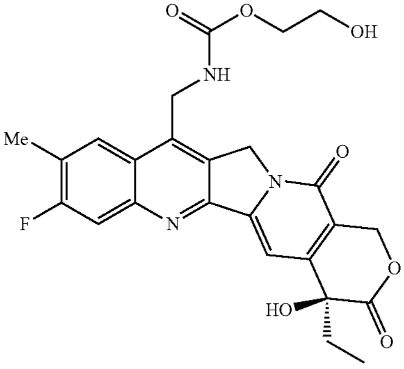 [SMILES: CC[C@@]1(O)C(=O)OCc2c1cc1n(c2=O)Cc2c-1nc1cc(F)c(C)cc1c2CNC(=O)OCCO]

The title compound was prepared according to General Procedure 5 starting from Compound 1.2 (18 mg) and reacting 1,2-ethanediol with the intermediate PNP-carbamate.

Preparative HPLC purification was accomplished as described in General Procedure 9, eluting with a 10 to 60% $CH_3CN/H_2O$+0.1% TFA gradient to give the title compound as an off-white solid (4.2 mg, 19% yield).

LC/MS: Calc'd m/z=497.2 for $C_{25}H_{24}FN_3O_7$, found $[M+H]^+$=498.2.

$^1$H NMR (300 MHz, DMSO) δ 8.23 (d, J=8.2 Hz, 1H), 7.78 (d, J=10.7 Hz, 1H), 7.40 (s, 1H), 5.47 (d, J=16.5 Hz, 1H), 5.42 (s, 2H), 5.34 (d, J=16.4 Hz, 1H), 4.77 (s, 2H), 3.99 (t, J=4.9 Hz, 2H), 3.64-3.38 (m, 2H), 2.48 (s, 3H), 2.02-1.67 (m, 2H), 0.89 (t, J=7.3 Hz, 3H).

Example 2: Preparation of Camptothecin Analogues Having Methoxy at the C10 Position 2.1: 1-(2-amino-4-fluoro-5-methoxyphenyl)-2-chloroethan-1-one (Compound 2.1)

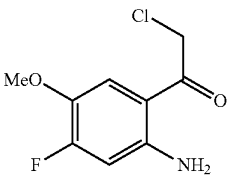 [SMILES: COc1cc(C(=O)CCl)c(N)cc1F]

A solution of 3-fluoro-4-methoxyaniline (10 μg, 71 mmol) in DCM (100 mL) was cooled to 0° C. To this solution was first added a 1 M $BCl_3$ in DCM (71 mL, 71 mmol), followed by a 1 M chloro(diethyl)alumane in DCM (71 mL, 71 mmol), then finally 2-chloroacetonitrile (6.4 μg, 85 mmol). The solution was heated at reflux for 3 h, cooled to room temperature, and quenched by the addition of an aqueous 2 M HCl solution. The resulting heterogenous mixture was heated to reflux for 1 h, cooled to room temperature, then the pH was adjusted to ~12 with $Na_2CO_3$. The layers were separated, and the aqueous layer extracted with DCM (3×100 mL). The combined organic layers were dried over $Na_2SO_4$, concentrated, and flash purified as described in General Procedure 9, eluting with 0 to 20% EtOAc/Hexanes to give the title compound (6 μg, 28 mmol, 39% yield).

LC/MS: Calc'd m/z=217.1 for $C_9H_9ClFNO_2$, found $[M+H]^+$=218.1.

$^1$H NMR (400 MHz, $CDCl_3$) δ 7.19 (d, J=9.2 Hz, 1H), 6.44 (d, J=12.8 Hz, 1H), 4.59 (s, 2H), 3.86 (s, 3H)

2.2: (S)-11-(chloromethyl)-4-ethyl-8-fluoro-4-hydroxy-9-methoxy-1,12-dihydro-14H-pyrano[3',4':6,7]indolizino[1,2-b]quinoline-3,14(4H)-dione (Compound 2.2)

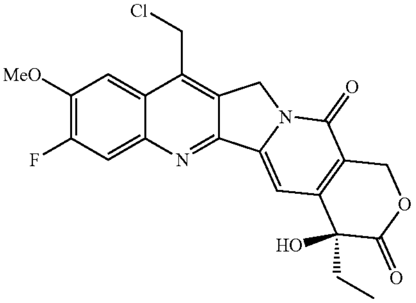 [SMILES: CC[C@@]1(O)C(=O)OCc2c1cc1n(c2=O)Cc2c-1nc1cc(F)c(OC)cc1c2CCl]

To a solution of Compound 2.1 (1.65 μg, 7.6 mmol) and (S)-4-ethyl-4-hydroxy-7,8-dihydro-1H-pyrano[3,4-f]indolizine-3,6,10(4H)-trione (2 μg, 7.6 mmol) in toluene (200 mL) was added toluene-4-sulfonic acid (157 mg, 0.9 mmol). This solution was heated at 140° C. for 3 h then cooled to room temperature. The product as yellow precipitate was collected by filtration to give the title compound (1.27 μg, 2.85 mmol, 37.5% yield).

LC/MS: Calc'd m/z=445.2 for $C_{22}H_{18}C_1FN_2O_5$, found $[M+H]^+$=445.1.

$^1$H NMR (400 MHz, DMSO-d6) δ 7.99 (d, J=12.0 Hz, 1H) 7.80 (d, J=9.2 Hz, 1H) 7.27 (s, 1H), 6.50 (s, 1H), 5.45 (s, 2H), 5.41 (s, 2H), 5.33 (s, 2H) 4.08 (s, 3H), 1.87-1.83 (m, 2H), 0.87 (t, J=7.2 Hz, 3H)

2.3: (S)-4-ethyl-8-fluoro-4-hydroxy-9-methoxy-11-(morpholinomethyl)-1,12-dihydro-14H-pyrano[3',4':6,7]indolizino[1,2-b]quinoline-3,14(4H)-dione (Compound 101)

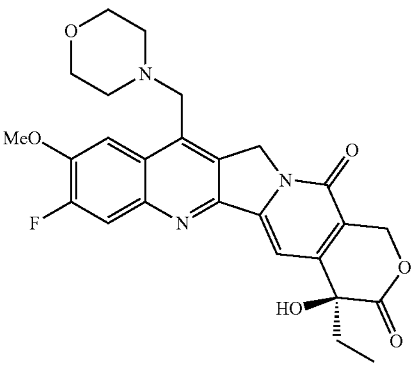 [SMILES: CC[C@@]1(O)C(=O)OCc2c1cc1n(c2=O)Cc2c-1nc1cc(F)c(OC)cc1c2CN1CCOCC1]

The title compound was prepared according to General Procedure 1 starting from Compound 2.2 (10 mg) and morpholine. Preparative HPLC purification was accomplished as described in General Procedure 9, eluting with a 20 to 60% $CH_3CN/H_2O$+0.1% TFA gradient to give the title compound as an off-white solid (5.6 mg, 41% yield).

LC/MS: Calc'd m/z=495.2 for $C_{26}H_{26}FN_3O_6$, found $[M+H]^+$=496.4.

$^1$H NMR (300 MHz, MeOD) δ 7.84-7.70 (m, 2H), 7.59 (s, 1H), 5.62 (d, J=16.3 Hz, 1H), 5.45-5.36 (m, 3H), 4.29 (s, 2H), 4.12 (s, 3H), 3.58-3.48 (m, 2H), 3.28-3.09 (m, 2H), 2.75-2.61 (m, 2H), 2.05-1.91 (m, 2H), 1.02 (t, J=7.4 Hz, 3H).

2.4: (S)-4-ethyl-8-fluoro-4-hydroxy-9-methoxy-11-((4-(phenylsulfonyl)piperazin-1-yl)methyl)-1,12-dihydro-14H-pyrano[3',4':6,7]indolizino[1,2-b]quinoline-3,14(4H)-dione (Compound 103)

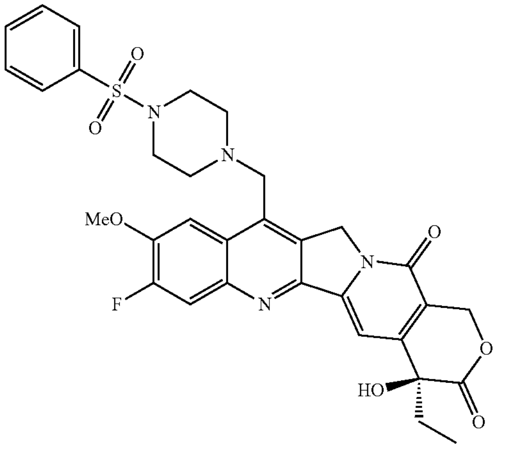 [SMILES: CC[C@@]1(O)C(=O)OCc2c1cc1n(c2=O)Cc2c-1nc1cc(F)c(OC)cc1c2CN1CCN(S(=O)(=O)c2ccccc2)CC1]

The title compound was prepared according to General Procedure 1 starting from Compound 2.2 (10 mg) and 1-(phenylsulfonyl)piperazine. Preparative HPLC purification was accomplished as described in General Procedure 9, eluting with a 20 to 60% $CH_3CN/H_2O$+0.1% TFA gradient to give the title compound as an off-white solid (2.5 mg, 14% yield).

LC/MS: Calc'd m/z=634.2 for $C_{32}H_{31}FN_4O_7S$, found $[M+H]^+$=635.4.

2.5: (S)-11-((4-((4-aminophenyl)sulfonyl)piperazin-1-yl)methyl)-4-ethyl-8-fluoro-4-hydroxy-9-methoxy-1,12-dihydro-14H-pyrano[3',4':6,7]indolizino[1,2-b]quinoline-3,14(4H)-dione (Compound 105)

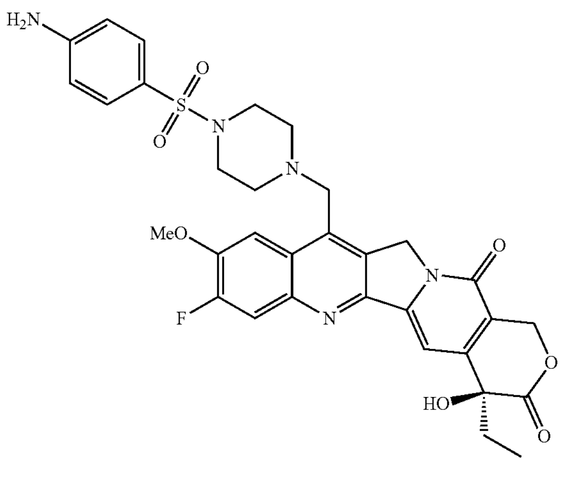 [SMILES: CC[C@@]1(O)C(=O)OCc2c1cc1n(c2=O)Cc2c-1nc1cc(F)c(OC)cc1c2CN1CCN(S(=O)(=O)c2ccc(N)cc2)CC1]

The title compound was prepared according to General Procedure 1 starting from Compound 2.2 (10 mg) and 4-(piperazin-1-ylsulfonyl)aniline. Preparative HPLC purification was accomplished as described in General Procedure 9, eluting with a 20 to 60% $CH_3CN/H_2O$+0.1% TFA gradient to give the title compound as an off-white solid (4.0 mg, 23% yield).

LC/MS: Calc'd m/z=649.2 for $C_{32}H_{32}FN_5O_7S$, found $[M+H]^+$=650.4.

$^1$H NMR (300 MHz, DMSO) δ 8.08 (s, 2H), 7.90-7.67 (m, 2H), 7.35 (s, 1H), 7.32-7.26 (m, 2H), 6.67-6.57 (m, 2H), 5.46 (d, J=16.5 Hz, 1H), 5.33-5.22 (m, 3H), 3.92 (s, 3H), 3.02-2.72 (m, 4H), 2.75-2.58 (m, 4H), 1.97-1.70 (m, 2H), 0.90 (t, J=7.3 Hz, 3H).

2.6: (S)-4-ethyl-8-fluoro-4-hydroxy-9-methoxy-11-((4-methylpiperazin-1-yl)methyl)-1,12-dihydro-14H-pyrano[3',4':6,7]indolizino[1,2-b]quinoline-3,14(4H)-dione (Compound 107)

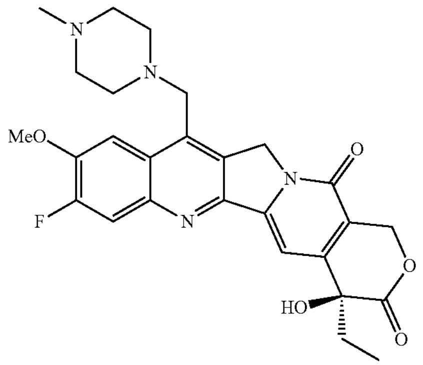 [SMILES: CC[C@@]1(O)C(=O)OCc2c1cc1n(c2=O)Cc2c-1nc1cc(F)c(OC)cc1c2CN1CCN(C)CC1]

The title compound was prepared according to General Procedure 1 starting from Compound 2.2 (10 mg) and N-methylpiperazine. Preparative HPLC purification was accomplished as described in General Procedure 9, eluting with a 20 to 60% $CH_3CN/H_2O$+0.1% TFA gradient to give the title compound as an off-white solid (2.1 mg, 19% yield).

LC/MS: Calc'd m/z=508.2 for $C_{27}H_{29}FN_4O_5$, found $[M+H]^+$=509.4.

2.7: (S)-11-((4-(4-aminophenyl)piperazin-1-yl)methyl)-4-ethyl-8-fluoro-4-hydroxy-9-methoxy-1,12-dihydro-14H-pyrano[3',4':6,7]indolizino[1,2-b]quinoline-3,14(4H)-dione (Compound 109)

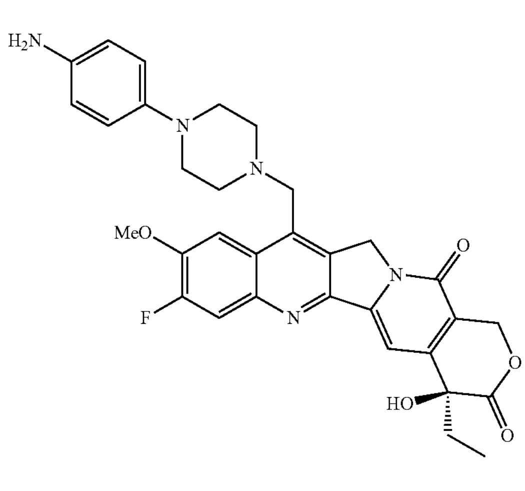 [SMILES: CC[C@@]1(O)C(=O)OCc2c1cc1n(c2=O)Cc2c-1nc1cc(F)c(OC)cc1c2CN1CCN(c2ccc(N)cc2)CC1]

The title compound was prepared according to General Procedure 1 starting from Compound 2.2 (10 mg) and 4-(piperazin-1-yl)aniline. Preparative HPLC purification was accomplished as described in General Procedure 9, eluting with a 20 to 60% $CH_3CN/H_2O$+0.1% TFA gradient to give the title compound as an off-white solid (3.2 mg, 20% yield).

LC/MS: Calc'd m/z=585.2 for $C_{32}H_{32}FN_5O_5$, found $[M+H]^+$=586.4.

$^1$H NMR (300 MHz, MeOD) δ 7.83-7.74 (m, 2H), 7.62 (s, 1H), 7.06 (d, J=8.9 Hz, 2H), 6.98 (d, J=8.9 Hz, 2H), 5.65 (d, J=16.4 Hz, 1H), 5.36 (s, 2H), 5.27 (d, J=16.4 Hz, 1H), 4.13 (s, 2H), 4.06 (s, 3H), 3.26 (br s, 4H), 2.79 (br s, 4H), 1.97-1.83 (m, 2H), 1.00 (t, J=7.4 Hz, 3H).

2.8: (S)-11-(aminomethyl)-4-ethyl-8-fluoro-4-hydroxy-9-methoxy-1,12-dihydro-14H-pyrano[3',4':6,7]indolizino[1,2-b]quinoline-3,14(4H)-dione (Compound 2.8)

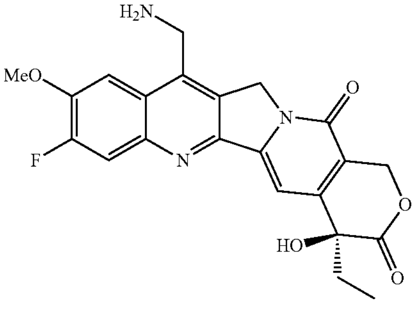 [SMILES: CC[C@@]1(O)C(=O)OCc2c1cc1n(c2=O)Cc2c-1nc1cc(F)c(OC)cc1c2CN]

To a solution of Compound 2.2 (250 mg, 0.56 mmol) in ethanol (7 mL) was added hexamethylenetetramine (236 mg, 1.7 mmol) followed by $iPr_2NEt$ (100 uL, 0.56 mmol). This solution was heated at reflux for 5 h, cooled to room temperature and quenched with 12 M aqueous HCl (60 uL). This solution was concentrated to ½ H volume and 1 M aqueous HCl (1.5 mL) was added, stirred for 5 min, then concentrated to give a brown residue. Purification was accomplished as described in General Procedure 9, using a 12 g C18 flash column and eluting with a 5 to 40% $CH_3CN/H_2O$+0.1% TFA gradient to give the title compound as pale yellow solid (179 mg, 75% yield).

LC/MS: Calc'd m/z=425.4 for $C_{22}H_{20}FN_3O_5$, found $[M+H]^+$=426.2 2.9: (S)—N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)methanesulfonamide (Compound 123)

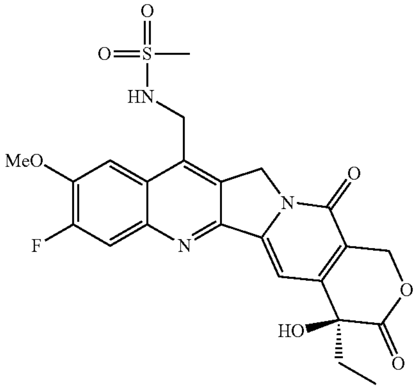 [SMILES: CC[C@@]1(O)C(=O)OCc2c1cc1n(c2=O)Cc2c-1nc1cc(F)c(OC)cc1c2CNS(C)(=O)=O]

The title compound was prepared according to General Procedure 3 starting from Compound 2.8 (10 mg) and methanesulfonyl chloride. Preparative HPLC purification was accomplished as described in General Procedure 9, eluting with a 5 to 65% $CH_3CN/H_2O$+0.1% TFA gradient to give the title compound as an off-white solid (8.5 mg, 91% yield).

LC/MS: Calc'd m/z=503.1 for $C_{23}H_{22}FN_3O_7S$, found $[M+H]^+$=504.2.

$^1$H NMR (300 MHz, DMSO-d6) δ 7.98 (d, J=12.1 Hz, 1H), 7.89 (t, J=6.4 Hz, 1H), 7.80 (d, J=9.1 Hz, 1H), 7.28 (s, 1H), 5.42 (s, 2H), 5.39 (s, 2H), 4.77 (d, J=6.4 Hz, 2H), 4.06 (s, 3H), 3.06 (s, 3H), 1.95-1.73 (m, 2H), 0.88 (d, J=7.3 Hz, 3H).

2.10: (S)—N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)benzenesulfonamide (Compound 126)

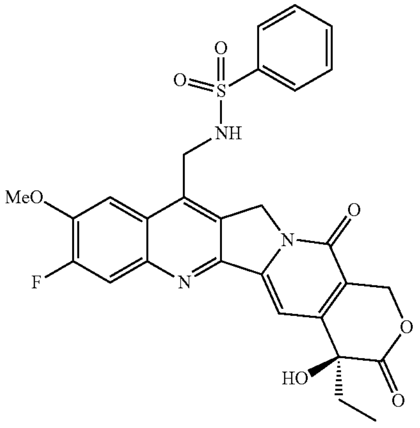 [SMILES: CC[C@@]1(O)C(=O)OCc2c1cc1n(c2=O)Cc2c-1nc1cc(F)c(OC)cc1c2CNS(=O)(=O)c1ccccc1]

The title compound was prepared according to General Procedure 3 starting from Compound 2.8 (7.5 mg) and benzenesulfonyl chloride. Preparative HPLC purification was accomplished as described in General Procedure 9, eluting with a 5 to 70% $CH_3CN/H_2O$+0.1% TFA gradient to give the title compound as an off-white solid (4.6 mg, 46% yield).

LC/MS: Calc'd m/z=565.6 for $C_{28}H_{24}FN_3O_7S$, found $[M+H]^+$=566.2.

$^1$H NMR (300 MHz, DMSO-d6) δ 8.59 (t, J=6.3 Hz, 1H), 7.94 (d, J=12.2 Hz, 1H), 7.82-7.68 (m, 2H), 7.62-7.46 (m,

1H), 7.51-7.40 (m, 1H), 7.28 (d, J=8.3 Hz, 1H), 6.52 (s, 1H), 5.44 (s, 1H), 5.36 (s, 1H), 4.64 (d, J=6.3 Hz, 1H), 4.09 (s, 2H), 1.95-1.81 (m, 1H), 0.89 (t, J=7.3 Hz, 2H).

2.11: (S)—N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)-4-nitrobenzenesulfonamide (Compound 2.11)

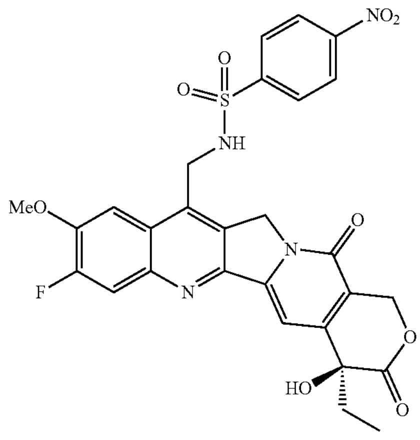

The title compound was prepared according to General Procedure 3 starting from Compound 2.8 (12 mg) and 4-nitrobenzenesulfonyl chloride. Purification was accomplished as described in General Procedure 9 using a 12 g C18 flash column and eluting with a 5 to 75% $CH_3CN/H_2O$+0.1% TFA gradient to give the title compound as pale yellow solid (9.7 mg, 71% yield).

LC/MS: Calc'd m/z=610.6 for $C_{28}H_{23}FN_4O_9S$, found $[M+H]^+$=611.5.

2.12: (S)-4-amino-N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)benzenesulfonamide (Compound 128)

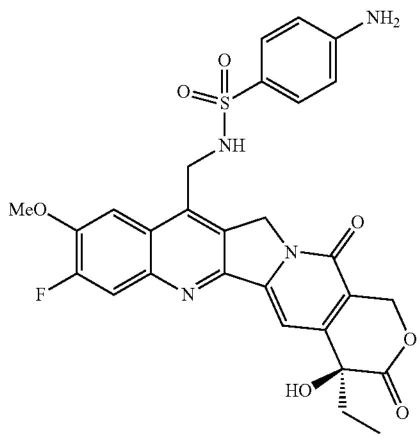 [SMILES: CC[C@@]1(O)C(=O)OCc2c1cc1n(c2=O)Cc2c-1nc1cc(F)c(OC)cc1c2CNS(=O)(=O)c1ccc([N+](=O)[O-])cc1]

To a solution of Compound 2.11 (9.7 mg, 0.016 mmol) in methanol (1.6 mL) was added platinum 1% vanadium 2% on carbon (15 mg). The flask was purged with $H_2$ then stirred at room temperature under an $H_2$ atmosphere for 45 min. The mixture was filtered through a pad of celite, washed with DMF, then the filtrate was evaporated to give the title compound as a pale yellow solid (1.5 mg, 16% yield).

LC/MS: Calc'd m/z=580.6 for $C_{28}H_{25}FN_4O_7S$, found $[M+H]^+$=581.4.

$^1$H NMR (300 MHz, MeOD) δ 7.77 (d, J=11.0 Hz, 1H), 7.58 (s, 1H), 7.48 (d, J=8.6 Hz, 1H), 6.61 (d, J=8.6 Hz, 1H), 5.59 (d, J=16.3 Hz, 1H), 5.39 (d, J=16.4 Hz, 1H), 5.30 (s, 1H), 4.56 (s, 1H), 4.10 (d, J=3.7 Hz, 3H), 2.04-1.91 (m, 2H), 1.31 (s, 1H), 1.02 (t, J=7.3 Hz, 3H), 0.90 (s, 1H).

2.13: (S)—N-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)-2-hydroxyethane-1-sulfonamide (Compound 130)

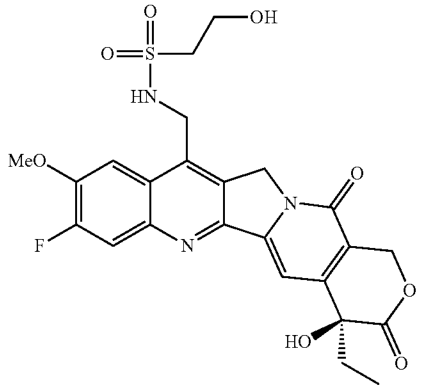 [SMILES: CC[C@@]1(O)C(=O)OCc2c1cc1n(c2=O)Cc2c-1nc1cc(F)c(OC)cc1c2CNS(=O)(=O)CCO]

The title compound was prepared according to General Procedure 3 starting from Compound 2.8 (8 mg) and 2-hydroxyethanesulfonyl chloride. Preparative HPLC purification was accomplished as described in General Procedure 9, eluting with a 15 to 50% $CH_3CN/H_2O$+0.1% TFA gradient to give the title compound as an off-white solid (2.2 mg, 22% yield).

LC/MS: Calc'd m/z=533.1 for $C_{24}H_{24}FN_3O_8S$ found $[M+H]^+$=534.2.

$^1$H NMR (300 MHz, DMSO-d6) δ 7.99 (d, J=12.2 Hz, 1H), 7.89-7.79 (m, 2H), 7.29 (s, 1H), 5.43 (s, 2H), 5.40 (s, 2H), 4.76 (d, J=6.4 Hz, 2H), 4.06 (s, 3H), 3.81 (t, J=6.3 Hz, 2H), 3.34 (t, J=6.3 Hz, 2H), 1.94-1.75 (m, 2H), 0.87 (d, J=7.4 Hz, 3H).

2.14: 4-nitrophenyl-(S)-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl) methyl)carbamate (Compound 2.14)

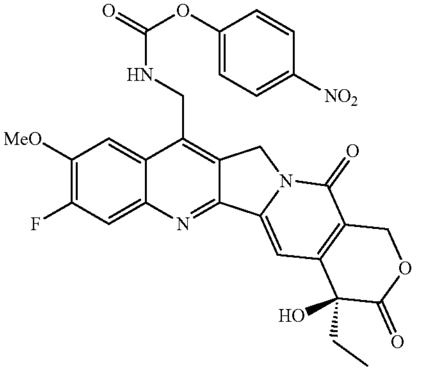 [SMILES: CC[C@@]1(O)C(=O)OCc2c1cc1n(c2=O)Cc2c-1nc1cc(F)c(OC)cc1c2CNC(=O)Oc1ccc([N+](=O)[O-])cc1]

The title PNP-carbamate intermediate compound was prepared according to the first step of General Procedure 4 starting from Compound 2.8 (65 mg) and using a 1:1 mixture of dimethylformamide and dichloromethane as the solvent. Flash purification was accomplished as described in General Procedure 9, using a 12 g $C_{12}$ column and eluting with a 10 to 50% $CH_3CN/H_2O$+0.1% TFA gradient to give the title compound as an off-white solid (61 mg, 86% yield). This intermediate was divided and used to generate the following compounds.

LC/MS: Calc'd m/z=590.1 for $C_{29}H_{23}FN_4O_9$, found $[M+H]^+$=591.2.

2.15: (S)-1-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl) methyl)-3-methylurea (Compound 133)

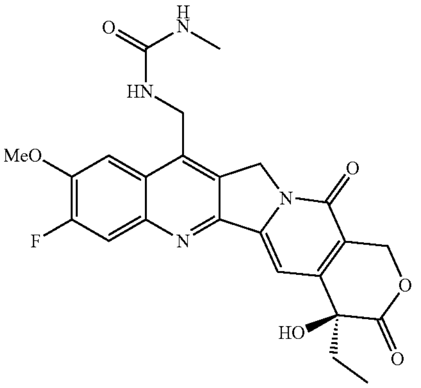 [SMILES: CC[C@@]1(O)C(=O)OCc2c1cc1n(c2=O)Cc2c-1nc1cc(F)c(OC)cc1c2CNC(=O)NC]

The title compound was prepared according to second step of General Procedure 4 using Compound 2.14 (15 mg) as the PNP-carbamate and aqueous methyl amine (500 uL, 40 wt. % in water) as the primary amine. Preparative HPLC purification was accomplished as described in General Procedure 9, eluting with a 20 to 60% $CH_3CN/H_2O$+0.1% TFA gradient to give the title compound as an off-white solid (5.8 mg, 47% yield).

LC/MS: Calc'd m/z=482.2 for $C_{24}H_{23}FN_4O_6$, found $[M+H]^+$=483.2.

$^1H$ NMR (300 MHz, DMSO-d6) δ 8.00-7.87 (m, 2H), 7.31 (s, 1H), 5.48-5.39 (m, 3H), 4.81 (s, 3H), 2.56 (s, 3H), 1.93-1.81 (m, 2H), 0.89 (t, J=7.3 Hz, 3H).

2.16: (S)-1-(4-aminobenzyl)-3-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl)methyl)urea (Compound 135)

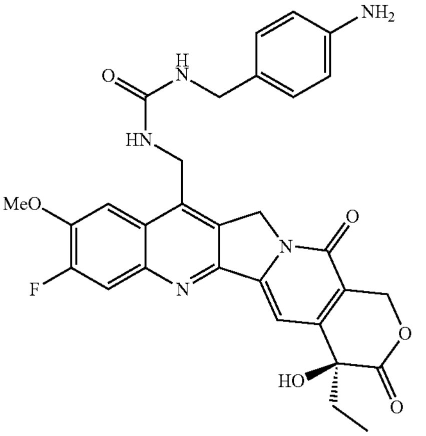 [SMILES: CC[C@@]1(O)C(=O)OCc2c1cc1n(c2=O)Cc2c-1nc1cc(F)c(OC)cc1c2CNC(=O)NCc1ccc(N)cc1]

The title compound was prepared according to the second step of General Procedure 4 using Compound 2.14 (15 mg) as the PNP-carbamate and 4-(aminomethyl)aniline as the primary amine. Preparative HPLC purification was accomplished as described in General Procedure 9, eluting with a 20 to 60% $CH_3CN/H_2O$+0.1% TFA gradient to give the title compound as an off-white solid (TFA salt, 2.1 mg, 12% yield).

LC/MS: Calc'd m/z=573.2 for $C_{30}H_{28}FN_5O_6$, found $[M+H]^+$=574.2.

$^1H$ NMR (300 MHz, MeOD) δ 7.79 (d, J=11.9 Hz, 1H), 7.74 (d, J=9.0 Hz, 1H), 7.59 (s, 1H), 7.43 (d, J=8.2 Hz, 2H), 7.25 (d, J=8.2 Hz, 2H), 5.61 (d, J=16.3 Hz, 1H), 5.52-5.35 (m, 3H), 4.98 (s, 2H), 4.39 (s, 2H), 4.01 (s, 3H), 2.03-1.93 (m, 2H), 1.03 (t, J=7.4 Hz, 3H).

2.17: (S)-1-((4-ethyl-8-fluoro-4-hydroxy-9-methoxy-3,14-dioxo-3,4,12,14-tetrahydro-1H-pyrano[3',4':6,7]indolizino[1,2-b]quinolin-11-yl) methyl)-3-(2-hydroxyethyl)urea (Compound 137)

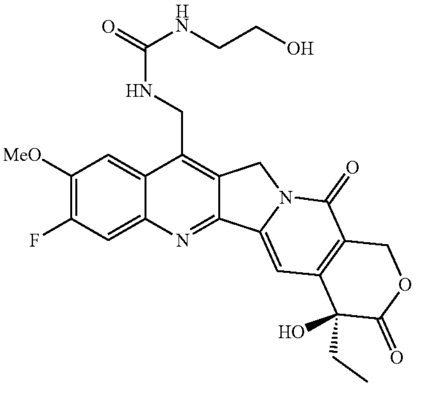 [SMILES: CC[C@@]1(O)C(=O)OCc2c1cc1n(c2=O)Cc2c-1nc1cc(F)c(OC)cc1c2CNC(=O)NCCO]

The title compound was prepared according to the second step of General Procedure 4 using Compound 2.14 (15 mg) as the PNP-carbamate and hydroxyethylamine as the primary amine. Preparative HPLC purification was accomplished as described in General Procedure 9, eluting with a 20 to 60% $CH_3CN/H_2O$+0.1% TFA gradient to give the title compound as an off-white solid (1.5 mg, 12% yield).

LC/MS: Calc'd m/z=512.2 for $C_{25}H_{25}FN_4O_7$, found $[M+H]^+$=513.2.

$^1$H NMR (300 MHz, MeOD) δ 7.93 (d, J=12.1 Hz, 1H), 7.88 (d, J=9.2 Hz, 1H), 7.56 (s, 1H), 5.62 (d, J=16.2 Hz, 1H), 5.52 (s, 2H), 5.45 (d, J=16.3 Hz, 1H), 4.98 (s, 2H), 4.17 (s, 3H), 3.59 (t, J=5.6 Hz, 2H), 3.28 (t, J=5.6 Hz, 2H), 2.10-1.91 (m, 2H), 1.05 (t, J=7.3 Hz, 3H).

Example 3: Preparation of Camptothecin Analogues Having Amino at the C10 Position

3.1: 5-bromo-4-fluoro-2-nitrobenzaldehyde (Compound 3.1)

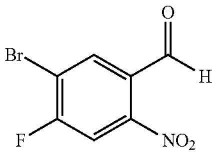

° C. was added 3-bromo-4-fluorobenzaldehyde (180 μg, 1.0 eq.). After the addition was complete, the ice bath was removed, and the reaction was allowed to stir for 5 h at 25° C. The mixture was poured into ice (5 L), filtered and then dried under vacuum. The title compound was obtained as a yellow solid (219 g).

$^1$H NMR (400 MHz, $CDCl_3$) δ 10.39 (s, 1H), 8.23 (d, J=6.8 Hz, 1H), 7.91 (d, J=7.6 Hz, 1H).

3.2: tert-butyl (2-fluoro-5-formyl-4-nitrophenyl)carbamate (Compound 3.2)

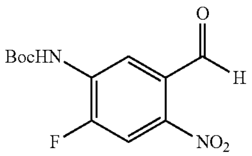 [SMILES: CC(C)(C)OC(=O)Nc1cc(C=O)c([N+](=O)[O-])cc1F]

A mixture of Compound 3.1(219 μg, 1.0 eq.), tert-butyl carbamate (124 μg, 1.2 eq.), $Cs_2CO_3$ (575 μg, 2.0 eq.), $Pd_2(dba)_3$ (40 μg, 0.05 eq.) and XPhos (84 μg, 0.2 eq.) in toluene (2000 mL) was degassed and purged with $N_2$ for three cycles. The mixture was then stirred at 90° C. for 15 h under $N_2$ atmosphere. The reaction mixture was diluted with $H_2O$ (800 mL) and extracted with EtOAc (300 mL×2). The combined organic layers were washed with brine (200 mL×2), then dried over sodium sulfate, filtered and concentrated under reduced pressure. The residue was purified by column chromatography ($SiO_2$, petroleum ether: ethyl acetate=100: 1 to 20:1) to afford the title compound as a yellow solid (140 μg, 56% yield).

$^1$H NMR (400 MHz, DMSO-d6) δ 10.24 (s, 1H), 9.94 (s, 1H), 8.42 (d, J=7.6 Hz, 1H), 8.16 (d, J=10.8 Hz, 1H), 1.50 (s, 9H)

3.3: tert-butyl (4-amino-2-fluoro-5-formylphenyl)carbamate (Compound 3.3)

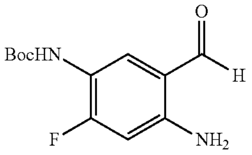 [SMILES: CC(C)(C)OC(=O)Nc1cc(C=O)c(N)cc1F]

To a solution of Compound 3.2 (100 μg, 1.0 eq.) in $H_2O$ (300 mL) and EtOH (1200 mL) was added $NH_4Cl$ (30.5 μg, 1.62 eq.). Iron (78.6 μg, 4.0 eq.) was added in portions at 80° C. The mixture was stirred at 80° C. for 6 h. The mixture was filtered, water was added to the filtrate, and the resulting mixture was extracted with ethyl acetate. The organic layer was washed with brine, dried over sodium sulfate, and concentrated under vacuum. The residue was purified by column chromatography ($SiO_2$, Petroleum ether: ethyl acetate=1: 0 to 0: 1), TLC (petroleum ether) to afford the title compound as a yellow solid (19.0 μg, 21% yield).

LC/MS: Calc'd m/z=254.1 for $C_{12}H_{15}FN_2O_3$, found $[M+H]^+$=255.0.

$^1$H NMR (400 MHz, DMSO-d6) δ 9.73 (s, 1H), 8.57 (s, 1H), 7.58 (d, J=4.8 Hz, 1H), 7.21 (s, 2H), 6.53 (d, J=12.8 Hz, 1H), 1.43 (s, 9H).

3.4: tert-butyl (S)-(4-ethyl-8-fluoro-4-hydroxy-3,14-dioxo-3,4,12,14-tetrahydro-1H-pyrano[3',4':6,7]indolizino[1,2-b]quinolin-9-yl)carbamate (Compound 3.4)

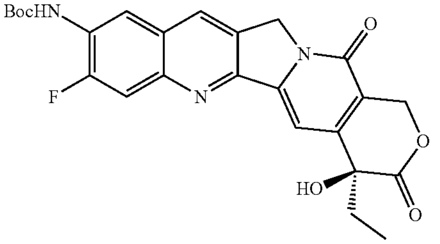 [SMILES: CC[C@@]1(O)C(=O)OCc2c1cc1n(c2=O)Cc2cc3cc(NC(=O)OC(C)(C)C)c(F)cc3nc2-1]

A mixture of Compound 3.3 (4.20 μg, 1.2 eq.), (S)-4-ethyl-4-hydroxy-7,8-dihydro-1H-pyrano[3,4-f]indolizine-3,6,10(4H)-trione (3.5 μg, 1 eq.) and TsOH (monohydrate, 253 mg, 0.1 eq.) in toluene (350 mL) was stirred at 110° C. for 2 hrs. The reaction solution was cooled to 25° C., filtered, the solid was washed with methyl-t-butyl ether (30 mL) and then dried under vacuum.

The title compound was obtained as a yellow solid (4.5 μg, 62% yield).

LC/MS: Calc'd m/z=481.2 for $C_{25}H_{24}FN_3O_6$, found $[M+H]^+$=482.1.

$^1$H NMR (400 MHz, DMSO-d6) δ 9.49 (s, 1H), 8.65 (s, 1H), 8.43 (d, J=8.4 Hz, 1H), 7.95 (d, J=12.0 Hz, 1H), 7.30 (s, 1H), 6.51 (s, 1H), 5.42 (s, 2H), 5.25 (s, 2H), 1.80-1.92 (m, 2H), 1.52 (s, 9H), 0.88 (t, J=7.2 Hz, 3H)

3.5: tert-butyl (S)-(4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl) carbamate (Compound 3.5)

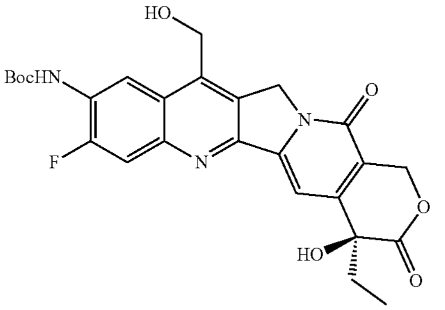 [SMILES: CC[C@@]1(O)C(=O)OCc2c1cc1n(c2=O)Cc2c-1nc1cc(F)c(NC(=O)OC(C)(C)C)cc1c2CO]

To a mixture of Compound 3.4 (4.00 g) in MeOH (360 mL) was added a solution of $FeSO_4$ (heptahydrate, 1.2 g), $H_2SO_4$ (280 L) in $H_2O$ (4 mL). The reaction mixture was heated at 65° C. while $H_2O_2$(24 mL, 30% purity) was added dropwise over 30 min and then stirred 0.5 h. The reaction solution was cooled to 25° C., then filtered to provide the title compound as a yellow solid (1.53 µg, 33.2% yield). To the filtrate was added $H_2O$ (400 mL), then quenched with saturated aqueous $Na_2S203$. The pH was adjusted to 7-8 with saturated aqueous $Na_2CO_3$ then the solution was concentrated and filtered. The solid was triturated with MeOH (30 mL) at 55° C. for 1 h, then filtered, to provide a second batch of the title compound as a brown solid (1.09 µg, 26% yield).

LC/MS: Calc'd m/z=511.2 for $C_{26}H_{26}FN_3O_7$, found $[M+H]^+$=512.2.

$^1$H NMR (300 MHz, d6-DMSO) δ 9.47 (s, 1H), 8.47 (d, J=7.6 Hz, 1H), 7.94 (d, J=12.0 Hz, 1H), 7.29 (d, J=1.6 Hz, 1H), 6.49 (s, 1H), 5.86-5.76 (m, 1H), 5.42 (s, 2H), 5.38 (s, 2H), 5.16 (d, J=4.4 Hz, 2H), 1.90-1.83 (m, 2H), 1.52 (s, 9H), 0.88 (t, J=6.4 Hz, 3H).

3.6: tert-butyl(S)-(4-ethyl-8-fluoro-11-formyl-4-hydroxy-3,14-dioxo-3,4,12,14-tetrahydro-1H-pyrano [3',4':6,7]indolizino[1,2-b]quinolin-9-yl)carbamate (Compound 3.6)

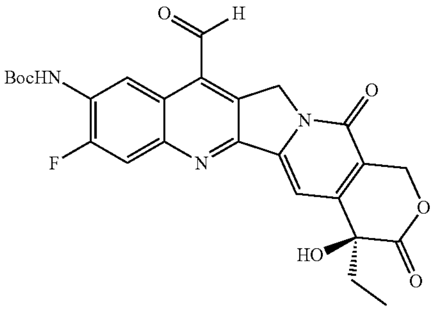 [SMILES: CC[C@@]1(O)C(=O)OCc2c1cc1n(c2=O)Cc2c-1nc1cc(F)c(NC(=O)OC(C)(C)C)cc1c2C=O]

In a 50 mL round-bottom flask containing Compound 3.5 (150 mg, 0.293 mmol) was added DCM (2.9 mL) followed by Dess-Martin periodinane (0.56 µg, 1.32 mmol) and water (15.8 µL, 0.88 mmol). This solution was stirred at room temperature for 18 h then diluted with DCM, washed with saturated aqueous $NaHCO_3$ and brine. The layers were separated, and the combined organic layers were evaporated onto celite. Flash purification was accomplished as described in General Procedure 9, using a 10 g silica column and eluting with 0 to 10% DCM/MeOH to give the title product as an orange powder (42.5 mg, 28%).

LC/MS: Calc'd m/z=509.2 for $C_{26}H_{24}FN_3O_7$, found $[M+H]^+$=510.4.

$^1$H NMR (300 MHz, Acetone-d6) δ 11.10 (s, 1H), 9.68 (d, J=8.6 Hz, 1H), 8.81 (s, 1H), 8.04 (d, J=11.9 Hz, 1H), 7.63 (s, 1H), 5.73 (s, 2H), 5.69 (d, J=16.2 Hz, 1H), 5.42 (d, J=16.2 Hz, 1H), 2.02-1.95 (m, 2H), 8.47 (d, J=7.6 Hz, 1H), 7.94 (d, J=12.0 Hz, 1H), 7.29 (d, J=1.6 Hz, 1H), 6.49 (s, 1H), 5.86-5.76 (m, 1H), 5.42 (s, 2H), 5.38 (s, 2H), 5.16 (d, J=4.4 Hz, 2H), 1.90-1.83 (m, 2H), 1.52 (s, 9H), 0.88 (t, J=6.4 Hz, 3H).

3.7: (S)-9-amino-4-ethyl-8-fluoro-4-hydroxy-1,12-dihydro-14H-pyrano[3',4':6,7]indolizino [1,2-b]quinoline-3,14(4H)-dione (Compound 140)

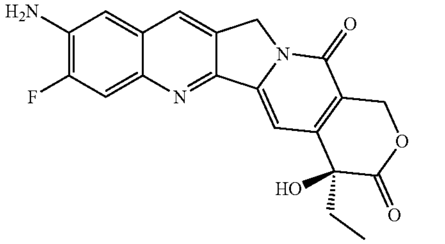 [SMILES: CC[C@@]1(O)C(=O)OCc2c1cc1n(c2=O)Cc2cc3cc(N)c(F)cc3nc2-1]

The title compound was prepared according to General Procedure 6 starting from Compound 3.4 (40 mg) to give the title compound as a red solid (TFA salt, 36 mg, 87% yield).

LC/MS: Calc'd m/z=381.1 for $C_{20}H_{16}FN_3O_4$, found $[M+H]^+$=382.2.

$^1$H NMR (300 MHz, DMSO) δ 8.28 (s, 1H), 7.72 (d, J=12.5 Hz, 1H), 7.21 (d, J=7.3 Hz, 1H), 5.43 (d, J=16.2 Hz, 1H), 5.34 (d, J=16.2 Hz, 1H), 5.17 (s, 2H), 1.92-1.74 (m, 2H), 0.88 (t, J=7.3 Hz, 3H).

3.8: (S)-9-amino-4-ethyl-8-fluoro-4-hydroxy-11-(hydroxymethyl)-1,12-dihydro-14H-pyrano[3',4':6,7] indolizino[1,2-b]quinoline-3,14(4H)-dione (Compound 141)

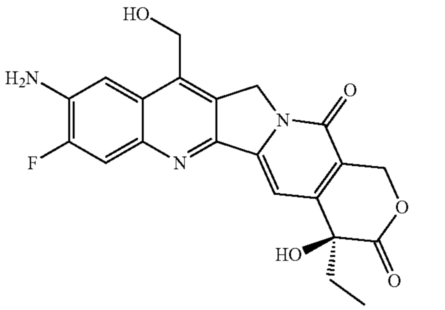 [SMILES: CC[C@@]1(O)C(=O)OCc2c1cc1n(c2=O)Cc2c-1nc1cc(F)c(N)cc1c2CO]

The title compound was prepared according to General Procedure 6 starting from Compound 3.5 (5 mg) to give the title compound as a red solid (TFA salt, 4.1 mg, 78% yield).

LC/MS: Calc'd m/z=411.2 for $C_{21}H_{18}FN_3O_5$, found $[M+H]^+$=412.2.

$^1$H NMR (300 MHz, MeOD) δ 7.71 (d, J=12.2 Hz, 1H), 7.60 (s, 1H), 7.29 (d, J=9.5 Hz, 1H), 5.61 (d, J=16.3 Hz, 1H), 5.47 (s, 2H), 5.40 (d, J=16.3 Hz, 1H), 5.25 (s, 2H), 2.03-1.94 (m, 2H), 1.03 (t, J=7.4 Hz, 3H).

3.9: tert-butyl (S)-(11-(chloromethyl)-4-ethyl-8-fluoro-4-hydroxy-3,14-dioxo-3,4,12,14-tetrahydro-1H-pyrano[3',4':6,7]indolizino[1,2-b]quinolin-9-yl) carbamate (Compound 3.9)

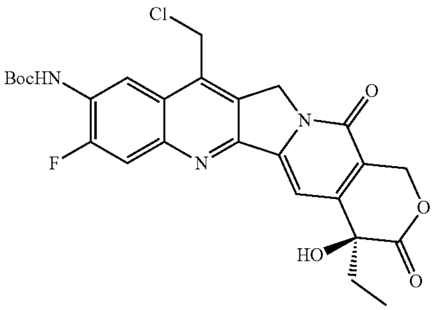 [SMILES: CC[C@@]1(O)C(=O)OCc2c1cc1n(c2=O)Cc2c-1nc1cc(F)c(NC(=O)OC(C)(C)C)cc1c2CCl]

To a stirring solution of Compound 3.5 (100 mg) in dichloromethane (5 mL) was added a solution of thionyl chloride (14 uL) in dichloromethane (0.1 mL). After 1 h, additional thionyl chloride (14 uL) in dichloromethane (0.1 mL) was added. After another 1 h the reaction was diluted with dichloromethane (10 mL) and toluene (1 mL) then concentrated in vacuo to provide the title compound as a red solid that was used in subsequent reactions without additional purification.

LC/MS: Calc'd m/z=529.1 for $C_{26}H_{25}C_1FN_3O_6$, found $[M+H]^+$=530.2.

3.10: tert-butyl (S)-(11-(aminomethyl)-4-ethyl-8-fluoro-4-hydroxy-3,14-dioxo-3,4,12,14-tetrahydro-1H-pyrano[3',4':6,7]indolizino[1,2-b]quinolin-9-yl) carbamate (Compound 3.10)

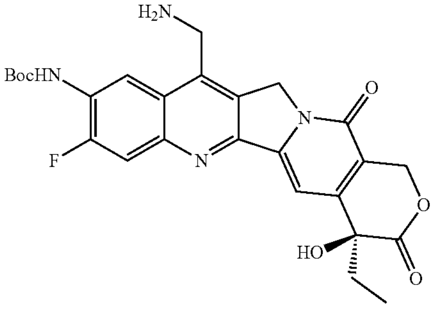 [SMILES: CC[C@@]1(O)C(=O)OCc2c1cc1n(c2=O)Cc2c-1nc1cc(F)c(NC(=O)OC(C)(C)C)cc1c2CN]

To Compound 3.9 (100 mg) in ethanol (500 uL) was added hexamethylenetetramine (79 mg) then DIPEA (99 uL). This solution was heated at 60° C. for 16 h then concentrated to dryness in vacuo. Flash purification was accomplished as described in General Procedure 9, using a 12 g C18 column and eluting with a 10 to 50% $CH_3CN/H_2O$+0.1% TFA gradient to give the title compound as an off-white solid (TFA salt, 29 mg, 24% yield).

LC/MS: Calc'd m/z=510.2 for $C_{26}H_{27}FN_4O_6$, found $[M+H]^+$=511.4.

$^1$H NMR (300 MHz, MeOD) δ 8.88 (d, J=8.2 Hz, 1H), 7.96 (d, J=11.9 Hz, 1H), 7.62 (s, 1H), 5.60 (d, J=16.4 Hz, 1H), 5.48 (s, 2H), 5.41 (d, J=16.4 Hz, 1H), 4.80 (s, 2H), 2.07-1.89 (m, 2H), 1.64 (s, 9H), 1.02 (t, J=7.3 Hz, 3H).

3.11: (S)-9-amino-11-(aminomethyl)-4-ethyl-8-fluoro-4-hydroxy-1,12-dihydro-14H-pyrano[3',4':6,7]indolizino[1,2-b]quinoline-3,14(4H)-dione (Compound 145)

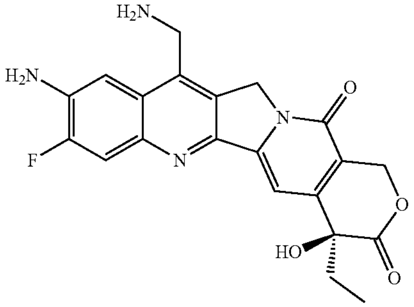 [SMILES: CC[C@@]1(O)C(=O)OCc2c1cc1n(c2=O)Cc2c-1nc1cc(F)c(N)cc1c2CN]

The title compound was prepared according to General Procedure 6 starting from Compound 3.10 (2.1 mg) to give the title compound as a red solid (TFA salt, 1.8 mg, 100% yield).

LC/MS: Calc'd m/z=410.1 for $C_{21}H_{19}FN_4O_4$, found $[M+H]^+$=411.2.

$^1$H NMR (300 MHz, MeOD) δ 7.82 (d, J=12.1 Hz, 1H), 7.60 (s, 1H), 7.37 (d, J=9.1 Hz, 1H), 5.61 (d, J=16.3 Hz, 1H), 5.42 (s, 2H), 5.41 (d, J=16.3 Hz, 1H), 4.69 (s, 2H), 2.08-1.94 (m, 2H), 1.03 (t, J=7.4 Hz, 3H).

Example 3.12: (S)-9-amino-4-ethyl-8-fluoro-4-hydroxy-11-(morpholinomethyl)-1,12-dihydro-14H-pyrano[3',4':6,7]indolizino[1,2-b]quinoline-3,14(4H)-dione (Compound 3.12)

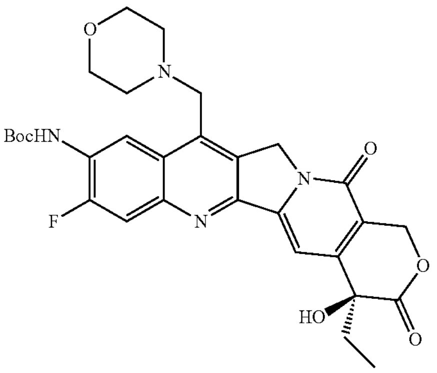 [SMILES: CC[C@@]1(O)C(=O)OCc2c1cc1n(c2=O)Cc2c-1nc1cc(F)c(NC(=O)OC(C)(C)C)cc1c2CN1CCOCC1]

The title compound was prepared according to General Procedure 1 starting from Compound 3.9 (150 mg) and morpholine. Preparative HPLC purification was accomplished as described in General Procedure 9, eluting with a 10 to 60% $CH_3CN/H_2O$+0.1% TFA gradient to give the title compound as a red solid (TFA salt, 103 mg, 52% yield).

LC/MS: Calc'd m/z=580.2 for $C_{30}H_{33}FN_4O_7$, found $[M+H]^+$=581.4.

$^1H$ NMR (300 MHz, MeOD) δ 9.06 (d, J=8.3 Hz, 1H), 7.93 (d, J=12.0 Hz, 1H), 7.66 (s, 1H), 5.63 (d, J=16.3 Hz, 1H), 5.51 (s, 2H), 5.43 (d, J=16.4 Hz, 1H), 4.92 (s, 2H), 3.84 (s, 4H), 3.10 (s, 4H), 1.99 (d, J=5.5 Hz, 2H), 1.63 (s, 9H), 1.03 (t, J=7.4 Hz, 3H).

3.13: (S)-9-amino-4-ethyl-8-fluoro-4-hydroxy-11-(morpholinomethyl)-1,12-dihydro-14H-pyrano[3',4':6,7]indolizino[1,2-b]quinoline-3,14(4H)-dione (Compound 142)

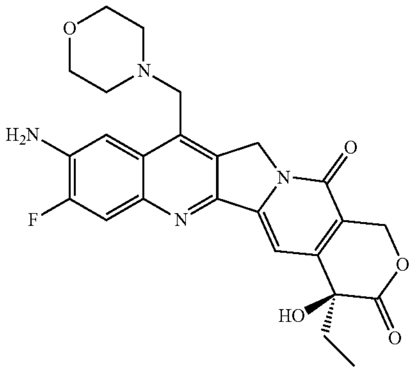 [SMILES: CC[C@@]1(O)C(=O)OCc2c1cc1n(c2=O)Cc2c-1nc1cc(F)c(N)cc1c2CN1CCOCC1]

The title compound was prepared according to General Procedure 6 starting from Compound 3.12 (45 mg) to give the title compound as a red solid (TFA salt, 37 mg, 99% yield).

LC/MS: Calc'd m/z=480.2 for $C_{25}H_{25}FN_4O_5$, found $[M+H]^+$=481.4.

$^1H$ NMR (300 MHz, MeOD) δ 7.73 (d, J=12.0 Hz, 1H), 7.54 (s, 1H), 7.48 (d, J=9.2 Hz, 1H), 5.60 (d, J=16.3 Hz, 1H), 5.47-5.34 (m, 3H), 4.65 (s, 2H), 3.91-3.85 (m, 4H), 3.30-3.24 (m, 4H), 2.08-1.91 (m, 2H), 1.02 (t, J=7.3 Hz, 3H).

3.14: (S)-9-amino-4-ethyl-8-fluoro-4-hydroxy-11-(piperidin-1-ylmethyl)-1,12-dihydro-14H-pyrano[3',4':6,7]indolizino[1,2-b]quinoline-3,14(4H)-dione (Compound 148)

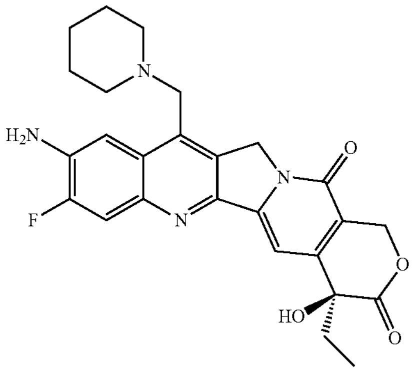 [SMILES: CC[C@@]1(O)C(=O)OCc2c1cc1n(c2=O)Cc2c-1nc1cc(F)c(N)cc1c2CN1CCCCC1]

To a 5 mL flask containing Compound 3.6 (37 mg, 0.067 mmol) was added dichloromethane (1.45 mL) followed by acetic acid (18.69 μL, 0.327 mmol), piperidine (21.52 μL, 0.218 mmol), and sodium triacetoxyborohydride (23.0 mg, 0.109 mmol). This solution was then stirred at room temperature for 2 h, quenched by the addition of water+0.1% TFA and DMF (1:1, 1.0 mL), and partially evaporated. Purification was accomplished as described in General Procedure 9, using a 12 g C18 flash column and eluting with a 5 to 40% $CH_3CN/H_2O$+0.1% TFA gradient to give the Boc-protected intermediate as a yellow powder. This intermediate was then deprotected according to General Procedure 6 to give the title compound as a yellow solid (TFA salt, 32.5 mg, 98% yield).

LC/MS: Calc'd m/z=478.2 for $C_{26}H_{27}FN_4O_4$, found $[M+H]^+$=479.4.

$^1H$ NMR (300 MHz, MeOD) δ 7.78 (d, J=12.1 Hz, 1H), 7.56 (s, 1H), 7.41 (d, J=9.1 Hz, 1H), 5.60 (d, J=16.4 Hz, 1H), 5.47-5.35 (m, 3H), 4.86 (s, 2H), 3.80-3.68 (m, 2H), 3.28-3.19 (m, 2H), 2.02-1.68 (m, 8H), 1.01 (t, J=7.4 Hz, 3H).

3.15: (S)-9-amino-4-ethyl-8-fluoro-4-hydroxy-11-((4-methylpiperazin-1-yl)methyl)-1,12-dihydro-14H-pyrano[3',4':6,7]indolizino[1,2-b]quinoline-3,14(4H)-dione (Compound 149)

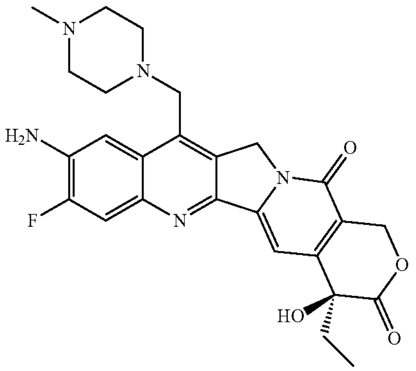 [SMILES: CC[C@@]1(O)C(=O)OCc2c1cc1n(c2=O)Cc2c-1nc1cc(F)c(N)cc1c2CN1CCN(C)CC1]

To a 2 mL vial containing Compound 3.6 (15 mg, 0.029 mmol) was added dichloromethane (0.59 mL), acetic acid (7.58 μL, 0.132 mmol), and N-methylpiperazine (4.90 μL, 0.044 mmol). This solution was stirred at room temperature for 4 h then sodium triacetoxyborohydride (7.8 mg, 0.037 mmol) was then added and stirred for an additional 45 min. Excess hydride was then quenched by the addition of a 0.1% aqueous TFA solution (0.5 mL). Purification was accomplished as described in General Procedure 9 using a 12 g C18 flash column and eluting with a 5 to 40% $CH_3CN/H_2O$+0.1% TFA gradient to give the Boc-protected intermediate as a yellow powder. This intermediate was deprotected according to General Procedure 6 to give the title product as a yellow solid (TFA salt, 1.5 mg, 7.1% yield).

LC/MS: Calc'd m/z=493.2 for $C_{26}H_{28}FN_5O_4$, found $[M+H]^+$=494.4.

$^1H$ NMR (300 MHz, MeOD) δ 7.68 (d, J=12.2 Hz, 1H), 7.56 (s, 1H), 7.53 (d, J=9.5 Hz, 1H), 5.60 (d, J=16.3 Hz, 1H), 5.45-5.30 (m, 3H), 4.15 (s, 2H), 3.55-3.44 (m, 2H), 3.18-3.07 (m, 2H), 2.93 (s, 3H), 2.70-2.51 (m, 2H), 2.03-1.89 (m, 2H), 1.02 (t, J=7.4 Hz, 3H).

3.16: (S)-9-amino-4-ethyl-8-fluoro-4-hydroxy-11-((4-(phenylsulfonyl)piperazin-1-yl)methyl)-1,12-dihydro-14H-pyrano[3',4':6,7]indolizino[1,2-b]quinoline-3,14(4H)-dione (Compound 153)

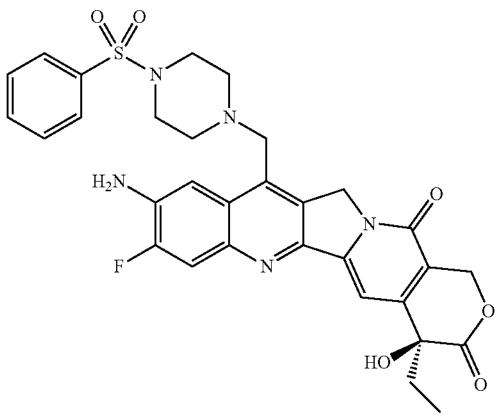 [SMILES: CC[C@@]1(O)C(=O)OCc2c1cc1n(c2=O)Cc2c-1nc1cc(F)c(N)cc1c2CN1CCN(S(=O)(=O)c2ccccc2)CC1]

The Boc-protected precursor of the title compound was prepared according to General Procedure 1 starting from Compound 3.9 (10 mg) and 1-(phenylsulfonyl)piperazine. Preparative HPLC was accomplished as described in General Procedure 9, eluting with a 35 to 44% $CH_3CN/H_2O$+0.1% TFA gradient to give the Boc-protected intermediate as a yellow powder. This intermediate was then deprotected according to General Procedure 6 to give the title compound (TFA salt, 2.4 mg, 17% yield over 2 steps).

LC/MS: Calc'd m/z=619.2 for $C_{31}H_{30}FN_5O_6S$, found $[M+H]^+$=520.4.

$^1H$ NMR (300 MHz, MeOD) δ 7.81-7.60 (m, 7H), 7.34 (s, 1H), 5.51 (d, J=16.4 Hz, 1H), 5.35 (d, J=16.4 Hz, 1H), 5.22 (s, 2H), 4.10 (s, 2H), 3.15-3.02 (m, 4H), 2.79-2.71 (m, 4H), 2.00-1.93 (m, 2H), 1.00 (t, J=7.4 Hz, 3H).

3.17: (S)—N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)acetamide (Compound 147)

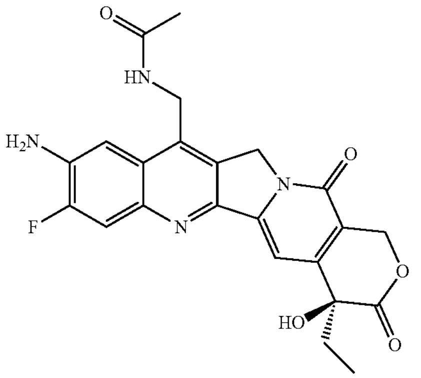 [SMILES: CC[C@@]1(O)C(=O)OCc2c1cc1n(c2=O)Cc2c-1nc1cc(F)c(N)cc1c2CNC(C)=O]

The title compound was prepared according to General Procedure 2 followed by General Procedure 6 starting from Compound 3.10 (8 mg) and acetic acid. Preparative HPLC purification of the intermediate Boc-protected compound was accomplished as described in General Procedure 9, eluting with a 10 to 60% $CH_3CN/H_2O$+0.1% TFA gradient. The title compound was obtained as a red solid (4.0 mg, 56% yield).

LC/MS: Calc'd m/z=452.2 for $C_{23}H_{21}FN_4O_5$, found $[M+H]^+$=453.2.

$^1H$ NMR (300 MHz, MeOD) δ 7.69 (d, J=12.1 Hz, 1H), 7.56 (s, 1H), 7.38 (d, J=9.3 Hz, 1H), 5.59 (d, J=16.3 Hz, 1H), 5.44-5.33 (m, 3H), 4.85 (s, 3H), 2.03 (s, 3H), 2.00-1.84 (m, 2H), 1.03 (t, J=7.4 Hz, 3H).

3.18: (S)—N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)methanesulfonamide (Compound 146)

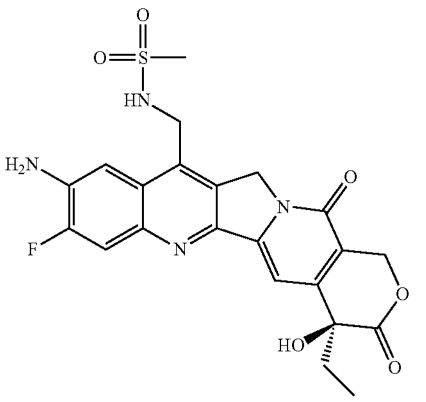 [SMILES: CC[C@@]1(O)C(=O)OCc2c1cc1n(c2=O)Cc2c-1nc1cc(F)c(N)cc1c2CNS(C)(=O)=O]

The title compound was prepared according to General Procedure 3 followed by General Procedure 6 starting from Compound 3.10 (8 mg) and methane sulfonyl chloride. Preparative HPLC purification of the intermediate Boc-protected compound was accomplished as described in General Procedure 9, eluting with a 10 to 60% $CH_3CN/H_2O$+0.1% TFA gradient. The title compound was obtained as a red solid (4.4 mg, 57% yield).

LC/MS: Calc'd m/z=488.1 for $C_{22}H_{21}FN_4O_6S$, found $[M+H]^+$=489.2.

$^1H$ NMR (300 MHz, MeOD) δ 7.74 (d, J=12.2 Hz, 1H), 7.60 (s, 1H), 7.49 (d, J=9.3 Hz, 1H), 5.61 (d, J=16.2 Hz, 1H), 5.45 (s, 2H), 5.40 (d, J=16.2 Hz, 1H), 4.78 (s, 2H), 3.05 (s, 3H), 2.08-1.94 (m, 2H), 1.03 (t, J=7.4 Hz, 3H).

3.19: (S)—N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-2-hydroxyethane-1-sulfonamide (Compound 150)

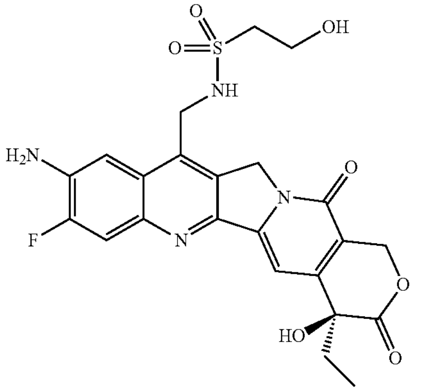 [SMILES: CC[C@@]1(O)C(=O)OCc2c1cc1n(c2=O)Cc2c-1nc1cc(F)c(N)cc1c2CNS(=O)(=O)CCO]

The title compound was prepared according to General Procedure 3 followed by General Procedure 6 starting from Compound 3.10 (6 mg) and 2-hydroxyethanesulfonyl chloride. Preparative HPLC purification of the intermediate Boc-protected compound was accomplished as described in General Procedure 9, eluting with a 10 to 60% $CH_3CN/H_2O$+0.1% TFA gradient. The title compound was obtained as a red solid (1 mg, 16% yield).

LC/MS: Calc'd m/z=518.5 for $C_{23}H_{23}FN_4O_7S$, found $[M+H]^+$=519.5.

$^1H$ NMR (300 MHz, 10% $D_2O/CD_3CN$) 6 7.77-7.61 (m, 1H), 7.48-7.30 (m, 2H), 5.53 (d, J=16.3 Hz, 1H), 5.31 (d, J=15.4 Hz, 3H), 4.69 (s, 2H), 3.97 (dd, J=6.6, 4.9 Hz, 2H), 3.39 (t, J=5.8 Hz, 2H), 2.93 (s, 1H), 1.99-1.83 (m, 2H), 0.94 (t, J=7.3 Hz, 3H).

3.20: 4-nitrophenyl (S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)carbamate (Compound 3.20)

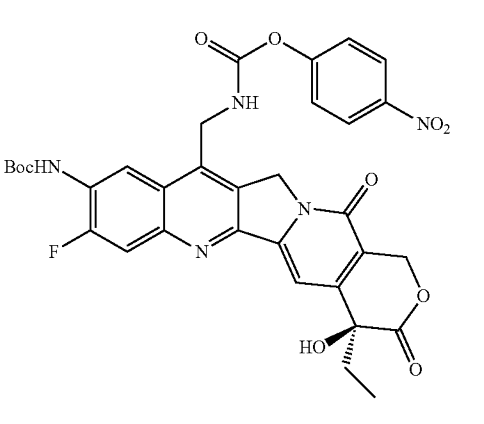 [SMILES: CC[C@@]1(O)C(=O)OCc2c1cc1n(c2=O)Cc2c-1nc1cc(F)c(NC(=O)OC(C)(C)C)cc1c2CNC(=O)Oc1ccc([N+](=O)[O-])cc1]

To a solution of Compound 3.10 (10 mg, 0.02 mmol) in DMF (400 uL, 0.05 M) was added 4-nitrophenyl carbonate (12 mg, 0.04 mmol) and diisopropylethylamine (6.8 uL, 0.04 mmol). This solution was stirred at room temperature for −30 min, then used directly in subsequent reactions.

3.21: Methyl (S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl) carbamate (Compound 143)

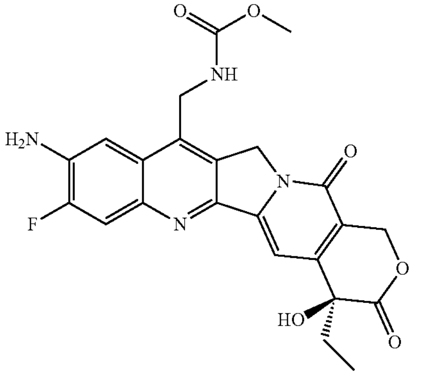 [SMILES: CC[C@@]1(O)C(=O)OCc2c1cc1n(c2=O)Cc2c-1nc1cc(F)c(N)cc1c2CNC(=O)OC]

The title compound was prepared by addition of MeOH (100 uL) to 200 ul of the solution of Compound 3.20. This solution was stirred at room temperature for 30 min. Preparative HPLC purification of the intermediate Boc-protected compound was accomplished as described in General Procedure 9, eluting with a 10 to 60% $CH_3CN/H_2O$+0.1% TFA gradient. The title compound was obtained according to General Procedure 6 as a red solid (2.1 mg, 47% yield).

LC/MS: Calc'd m/z=468.4 for $C_{23}H_{21}FN_4O_6$, found $[M+H]^+$=468.3.

$^1H$ NMR (300 MHz, 10% $D_2O/CD_3CN$) 6 7.72 (d, J=12.2 Hz, 1H), 7.41 (d, J=18.1 Hz, 1H), 6.96 (s, 1H), 5.52 (d, J=3.6 Hz, 1H), 5.39-5.23 (m, 3H), 4.82 (s, 1H), 4.73 (s, 1H), 3.63 (d, J=1.2 Hz, 3H), 1.56 (s, 3H), 1.27 (s, 2H), 0.94 (t, J=7.4 Hz, 3H).

3.22: (S)-1-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-3-methylurea (Compound 144)

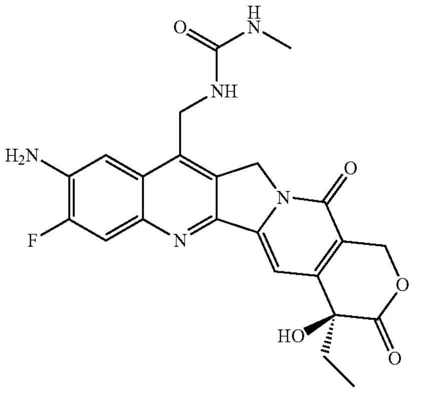 [SMILES: CC[C@@]1(O)C(=O)OCc2c1cc1n(c2=O)Cc2c-1nc1cc(F)c(N)cc1c2CNC(=O)NC]

The title compound was prepared by addition of methylamine hydrochloride (10 mg) to 200 ul of the solution of Compound 3.20, followed by $iPr_2NEt$ (5 uL). This solution was stirred at room temperature for 30 min. Preparative HPLC purification of the intermediate Boc-protected compound was accomplished as described in General Procedure 9, eluting with a 10 to 60% $CH_3CN/H_2O$+0.1% TFA gradient. The title compound was obtained according to General Procedure 6 as a red solid (2.9 mg, 64.5% yield).

LC/MS: Calc'd m/z=467.5 for $C_{23}H_{21}FN_5O_5$, found $[M+H]^+$=468.5.

$^1$H NMR (300 MHz, 10% $D_2O/CD_3CN$) 6 8.13 (d, J=9.2 Hz, 1H), 7.92 (s, 1H), 7.73 (d, J=12.3 Hz, 1H), 7.52-7.35 (m, 2H), 6.94 (d, J=9.2 Hz, 2H), 5.55 (d, J=16.5 Hz, 2H), 5.44-5.27 (m, 4H), 4.85 (s, 2H), 4.78 (s, 1H), 1.56 (d, J=2.5 Hz, 3H), 1.27 (s, 2H), 0.93 (q, J=11.7, 9.5 Hz, 3H).

3.23: (S)-1-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-3-(2-hydroxyethyl)urea (Compound 151)

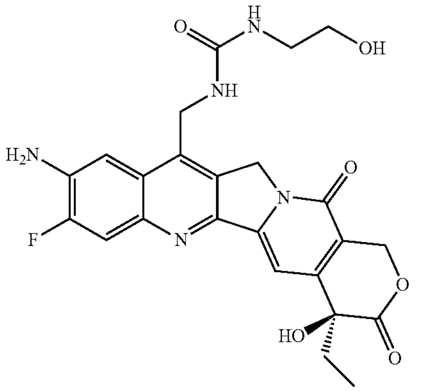 [SMILES: CC[C@@]1(O)C(=O)OCc2c1cc1n(c2=O)Cc2c-1nc1cc(F)c(N)cc1c2CNC(=O)NCCO]

The title compound was prepared by addition of ethanolamine (100 uL) to 200 ul of the solution of Compound 3.20. This solution was stirred at room temperature for 30 min. Preparative HPLC purification of the intermediate Boc-protected compound was accomplished as described in General Procedure 9, eluting with a 10 to 60% $CH_3CN/H_2O$+0.1% TFA gradient. The title compound was obtained according to General Procedure 6 as a red solid (0.5 mg, 8.5% yield).

LC/MS: Calc'd m/z=497.5 for $C_{24}H_{24}FN_5O_6$, found $[M+H]^+$=498.5.

$^1$H NMR (300 MHz, 10% $D_2O/CD_3CN$) 6 7.77-7.61 (m, 1H), 7.48-7.30 (m, 2H), 5.53 (d, J=16.3 Hz, 1H), 5.31 (d, J=15.4 Hz, 1H), 5.19 (s, 2H), 4.69 (s, 2H), 3.97 (dd, J=6.6, 4.9 Hz, 2H), 3.39 (t, J=5.8 Hz, 2H), 2.93 (s, 1H), 2.01-1.83 (m, 2H), 0.94 (t, J=7.3 Hz, 3H).

3.24: (S)-9-amino-11-(azidomethyl)-4-ethyl-8-fluoro-4-hydroxy-1,12-dihydro-14H-pyrano[3',4':6,7]indolizino[1,2-b]quinoline-3,14(4H)-dione (Compound 152)

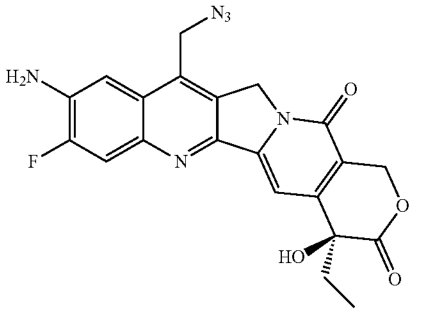 [SMILES: CC[C@@]1(O)C(=O)OCc2c1cc1n(c2=O)Cc2c-1nc1cc(F)c(N)cc1c2CN=[N+]=[N-]]

To a stirring solution of Compound 3.5 (100 mg) in 2 mL dichloromethane was added thionyl chloride (35 μL, 2.5 eq.). The solution was stirred at room temperature for 20 min, then additional thionyl chloride (35 μL, 2.5 eq.) was added. After 20 minutes, toluene (1 mL) was added, and the reaction mixture was concentrated in vacuo. The crude solid was suspended in DMSO (1 mL) and sodium azide (19 mg, 1.5 eq.) was added. This solution was stirred at room temperature for 16 h. Purification was accomplished as described in General Procedure 9, eluting with a 5 to 50% $CH_3CN/H_2O$+0.1% TFA gradient to give the title compound as an off-white solid (20 mg, 23% yield).

LC/MS: Calc'd m/z=436.1 for $C_{21}H_{17}FN_6O_4$, found $[M+H]^+$=437.2.

$^1$H NMR (300 MHz, MeOD) δ 7.75 (d, J=12.2 Hz, 1H), 7.60 (s, 1H), 7.38 (d, J=9.3 Hz, 1H), 5.61 (d, J=16.3 Hz, 1H), 5.46-5.35 (m, 3H), 5.07 (s, 2H), 2.03-1.97 (m, 2H), 1.03 (t, J=7.3 Hz, 3H).

3.25: (S)—N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)acetamide (Compound 164)

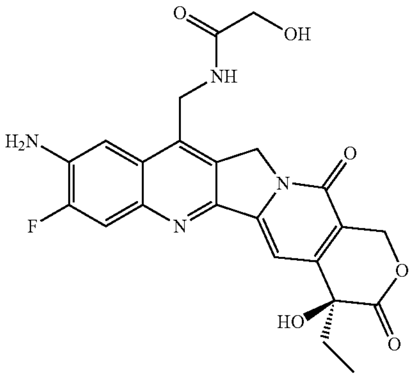 [SMILES: CC[C@@]1(O)C(=O)OCc2c1cc1n(c2=O)Cc2c-1nc1cc(F)c(N)cc1c2CNC(=O)CO]

The title compound was prepared according to General Procedure 2 starting from Compound 145 (10 mg) and glycolic acid. Preparative HPLC purification was accomplished as described in General Procedure 9, eluting with a 10 to 45% $CH_3CN/H_2O$+0.1% TFA gradient.

The title compound was obtained as a yellow solid (6.9 mg, 60% yield).

LC/MS: Calc'd m/z=468.1 for $C_{23}H_{21}FN_4O_6$, found $[M+H]^+$=469.2.

$^1$H NMR (300 MHz, MeOD) 7.70 (d, J=12.2 Hz, 1H), 7.60 (s, 1H), 7.42 (d, J=9.4 Hz, 1H), 5.62 (d, J=16.3 Hz, 1H), 5.43 (s, 2H), 5.36 (d, J=16.2 Hz, 1H), 4.95 (d, J=5.9 Hz, 2H), 4.08 (s, 2H), 2.04-1.90 (m, 1H), 1.03 (t, J=7.4 Hz, 3H).

3.26: (S)-1-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-3-methylthiourea (Compound 161)

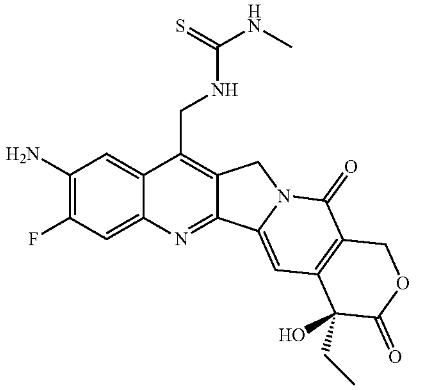 [SMILES: CC[C@@]1(O)C(=O)OCc2c1cc1n(c2=O)Cc2c-1nc1cc(F)c(N)cc1c2CNC(=S)NC]

To a solution of Compound 145 (9 mg, 1.0 eq.) in DMF (1 mL) was added thiocarbonyldiimidazole (6 mg, 1.5 eq.) then DIPEA (8 μL, 2.0 eq.). The resulting solution was stirred at 25° C. for 2 h, after which complete conversion to the isothiocyanate intermediate was observed. Methylammonium chloride (3 mg, 2.0 eq.) was then added and the reaction mixture was heated at 60° C. for 30 min. Preparative HPLC purification was accomplished as described in General Procedure 9, eluting with a 10 to 45% $CH_3CN/H_2O$+0.1% TFA gradient. The title compound was obtained as a yellow solid (2.3 mg, 22% yield).

LC/MS: Calc'd m/z=483.1 for $C_{23}H_{22}FN_5O_4S$ found $[M+H]^+$=484.2.

$^1$H NMR (300 MHz, MeOD) δ 7.70 (d, J=12.0 Hz, 1H), 7.60 (s, 1H), 7.38 (d, J=9.3 Hz, 1H), 5.62 (d, J=16.2 Hz, 1H), 5.36 (s, 2H), 5.31 (d, J=16.2 Hz, 1H), 5.30 (s, 2H), 3.04 (s, 3H), 1.99-1.90 (m, 2H), 1.02 (t, J=7.4 Hz, 3H).

3.27: S-(2-hydroxyethyl)-(S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)carbamothioate (Compound 160)

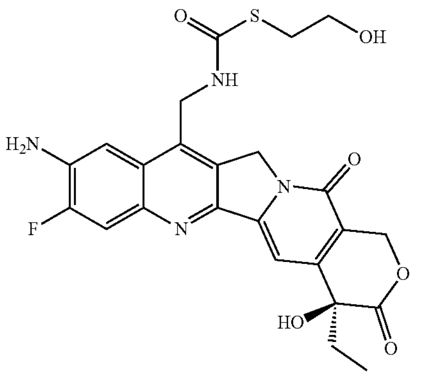 [SMILES: CC[C@@]1(O)C(=O)OCc2c1cc1n(c2=O)Cc2c-1nc1cc(F)c(N)cc1c2CNC(=O)SCCO]

The title compound was prepared according to General Procedure 5 starting from Compound 145 (10 mg) and 2-mercaptoethanol. Preparative HPLC purification was accomplished as described in General Procedure 9, eluting with a 10 to 45% $CH_3CN/H_2O$+0.1% TFA gradient. The title compound was obtained as a yellow solid (4.2 mg, 43% yield).

LC/MS: Calc'd m/z=514.1 for $C_{24}H_{23}FN_4O_6S$ found $[M+H]^+$=515.2.

$^1$H NMR (300 MHz, MeOD) δ 7.71 (d, J=12.1 Hz, 1H), 7.60 (s, 1H), 7.36 (d, J=9.4 Hz, 1H), 5.62 (d, J=16.3 Hz, 1H), 5.42 (s, 2H), 5.35 (d, J=16.2 Hz, 1H), 4.88 (d, J=4.6 Hz, 2H), 3.68 (t, J=6.4 Hz, 2H), 3.03 (t, J=6.5 Hz, 2H), 2.04-1.92 (m, 2H), 1.03 (t, J=7.4 Hz, 3H).

3.28: (S)-9-amino-4,11-diethyl-8-fluoro-4-hydroxy-1,12-dihydro-14H-pyrano[3',4':6,7]indolizino[1,2-b]quinoline-3,14(4H)-dione (Compound 154)

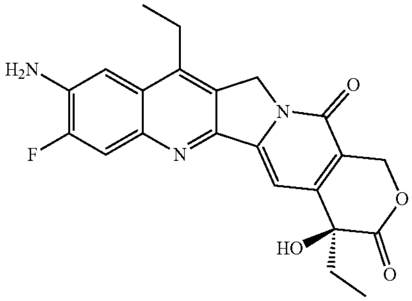 [SMILES: CCc1c2c(nc3cc(F)c(N)cc13)-c1cc3c(c(=O)n1C2)COC(=O)[C@]3(O)CC]

To a 5 mL flask containing Compound 140 (50 mg) was added water (0.72 mL), $FeSO_4$ (heptahydrate, 11.0 mg) and propionaldehyde (74 μL). The obtained suspension was cooled to -° C. using an ice brine bath, then sulfuric acid (0.40 mL) was added dropwise. Hydrogen peroxide (95 μL) was then added dropwise. This mixture was stirred at −15° C. for 10 min then allowed to warm up to room temperature and stirred for 2 h. The reaction mixture was diluted with water (30 mL) and the obtained suspension was extracted with DCM (3×30 mL). The organic phase was then evaporated to dryness. Preparative HPLC purification was accomplished as described in General Procedure 9, eluting with a 25 to 70% $CH_3CN/H_2O$+0.1% TFA gradient to give the title compound as a dark orange solid (2.4 mg, 4.4% yield).

LC/MS: Calc'd m/z=410.1 for $C_{22}H_{20}FN_3O_4$ found $[M+H]^+$=410.2.

$^1$H NMR (300 MHz, MeOD) δ 7.63 (d, J=12.3 Hz, 1H), 7.55 (s, 1H), 7.36 (d, J=9.4 Hz, 1H), 5.57 (d, J=16.4 Hz, 1H), 5.37 (d, J=16.4 Hz, 1H), 5.21 (s, 2H), 3.13 (q, J=7.7 Hz, 2H), 2.02-1.90 (m, 2H), 1.38 (t, J=7.7 Hz, 3H), 1.01 (t, J=7.3 Hz, 3H).

3.29: tert-butyl-(S)-(11-((carbamoyloxy)methyl)-4-ethyl-8-fluoro-4-hydroxy-3,14-dioxo-3,4,12,14-tetrahydro-1H-pyrano[3',4':6,7]indolizino[1,2-b]quinolin-9-yl)carbamate (Compound 3.29)

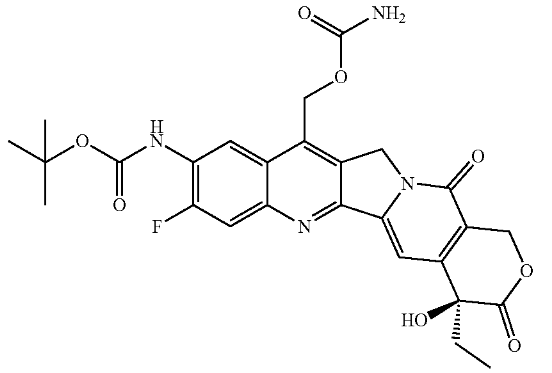 [SMILES: CC[C@@]1(O)C(=O)OCc2c1cc1n(c2=O)Cc2c-1nc1cc(F)c(NC(=O)OC(C)(C)C)cc1c2COC(N)=O]

In a 5 mL conical flask containing a solution of chlorosulfonyl isocyanate (7.7 μL) in dimethylformamide (0.29 mL), at −20° C., was added Compound 3.5 (15 mg). The obtained suspension was stirred at −20° C. for 5 min. Water (59 μL) was added, and the reaction mixture was allowed to warm up to room temperature and stirred for 2 h, then heated at 70° C. for 1 h. The reaction mixture was allowed to cool down to room temperature and partially evaporated. Preparative HPLC purification was accomplished as described in General Procedure 9, eluting with a 40 to 55% $CH_3CN/H_2O$+0.1% TFA gradient to give the title compound as a dark orange solid (5.1 mg, 31% yield).

LC/MS: Calc'd m/z=555.2 for $C_{27}H_{27}FN_4O_8$ found $[M+H]^+$=555.2.

$^1$H NMR (300 MHz, DMSO-d6) δ 9.53 (s, 1H), 8.56 (d, J=8.5 Hz, 1H), 8.00 (d, J=12.0 Hz, 1H), 7.31 (s, 1H), 7.11-6.62 (m, 2H), 6.52 (s, 1H), 5.58 (s, 2H), 5.49-5.27 (m, 4H), 1.94-1.77 (m, 2H), 1.52 (s, 9H), 1.38 (t, J=7.7 Hz, 3H), 0.87 (t, J=7.2 Hz, 3H).

3.30: (S)-(9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl carbamate (Compound 169)

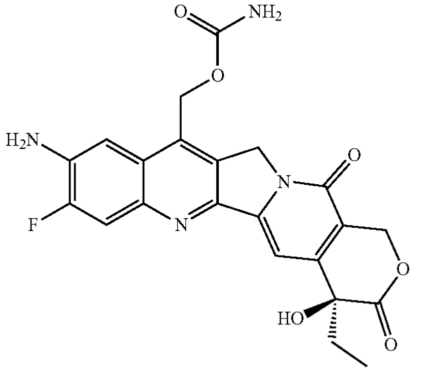 [SMILES: CC[C@@]1(O)C(=O)OCc2c1cc1n(c2=O)Cc2c-1nc1cc(F)c(N)cc1c2COC(N)=O]

The title compound was prepared according to General Procedure 6 starting from Compound 3.29 (5.1 mg) to give the title compound as yellow powder (TFA salt, 3.8 mg, 73% yield).

LC/MS: Calc'd m/z=455.1 for $C_{22}H_{19}FN_4O_6$ found $[M+H]^+$=455.2.

$^1$H NMR (300 MHz, DMSO-d6) δ 7.79 (d, J=12.4 Hz, 1H), 7.29 (d, J=9.7 Hz, 1H), 7.21 (s, 1H), 7.0-6.50 (m, 2H), 5.45 (s, 2H), 5.40 (s, 2H), 5.33 (s, 2H), 1.95-1.77 (m, 2H), 0.87 (t, J=7.3 Hz, 3H).

3.31: ((S)-9-amino-4-ethyl-8-fluoro-4-hydroxy-11-(methoxymethyl)-1,12-dihydro-14H-pyrano[3',4':6,7]indolizino[1,2-b]quinoline-3,14(4H)-dione (Compound 155)

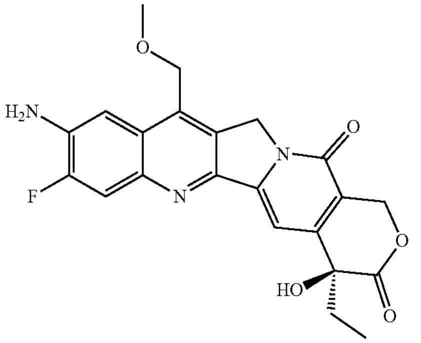 [SMILES: CC[C@@]1(O)C(=O)OCc2c1cc1n(c2=O)Cc2c-1nc1cc(F)c(N)cc1c2COC]

In a 50 mL flask containing Compound 3.5 (30 mg) was added MeOH/Dioxane (1:1) (9.8 mL) and sulfuric acid (0.73 mL). The reaction mixture was then stirred at reflux for 24 h. The reaction mixture was concentrated, poured into water (30 mL), and extracted with DCM (3×50 mL). The organic phases were combined and dried over $MgSO_4$. Preparative HPLC purification was accomplished as described in General Procedure 9, eluting with a 25 to 40% $CH_3CN/H_2O$+0.1% TFA gradient to give the title compound as a dark orange solid (5.1 mg, 16% yield).

LC/MS: Calc'd m/z=426.1 for $C_{22}H_{20}FN_3O_5$ found $[M+H]^+$=426.2.

$^1$H NMR (300 MHz, DMSO-d6) δ 7.75 (d, J=12.3 Hz, 1H), 7.24 (d, J=9.9 Hz, 1H), 7.20 (s, 1H), 6.47 (s, 1H), 6.30-5.92 (brs, 2H), 5.40 (s, 2H), 5.24 (s, 2H), 4.93 (s, 2H), 3.43 (s, 3H), 1.95-1.75 (m, 2H), 0.87 (t, J=7.3 Hz, 3H).

3.32: (4S)-9-amino-4-ethyl-8-fluoro-4-hydroxy-11-(((JR,5S)-6-hydroxy-3-azabicyclo[3.1.1]heptan-3-yl)methyl)-1,12-dihydro-14H-pyrano[3',4':6,7]indolizino[1,2-b]quinoline-3,14(4H)-dione (Compound 158)

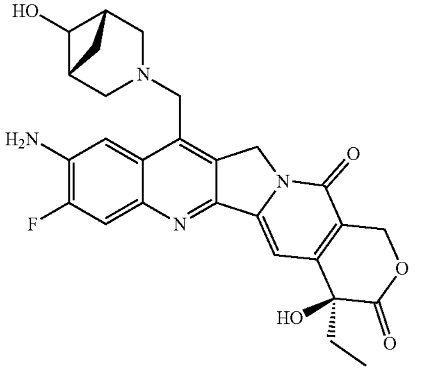 [SMILES: CC[C@@]1(O)C(=O)OCc2c1cc1n(c2=O)Cc2c-1nc1cc(F)c(N)cc1c2CN1C[C@H]2C[C@@H](C1)C2O]

In a 5 mL conical flask containing Compound 3.6 (15 mg) was added dichloromethane (0.6 mL) followed by 3-azabicyclo[3.1.1]heptan-6-ol (10 mg) and acetic acid (7.6 μL). The reaction was stirred at room temperature and sodium triacetoxyborohydride (9.4 mg) was added. After 1 hour at room temperature, the reaction was quenched by addition of water+0.1% TFA and diluted with DMF. The reaction mixture was then partially evaporated. Preparative HPLC purification was accomplished as described in General Procedure 9, eluting with a 20 to 50% $CH_3CN/H_2O$+0.1% TFA gradient to give the Boc-protected title compound as a yellow powder. Deprotection was performed according to General Procedure 6, and the obtained residue was purified by preparative HPLC purification as described in General Procedure 9, eluting with a 20 to 50% $CH_3CN/H_2O$+0.1% TFA gradient to give the title compound as yellow powder (TFA salt, 7.1 mg, 39% yield).

LC/MS: Calc'd m/z=507.2 for $C_{27}H_{27}FN_4O_5$ found $[M+H]^+$=507.4.

$^1$H NMR (300 MHz, DMSO-d6) δ 7.85 (d, J=12.1 Hz, 1H), 7.46 (d, J=9.4 Hz, 1H), 7.23 (s, 1H), 6.64-5.85 (m, 3H), 5.60-5.25 (m, 4H), 4.85 (s, 1H), 4.10-3.95 (m, 1H), 3.68 (s, 2H), 2.45-2.33 (m, 2H), 1.96-1.72 (m, 2H), 0.87 (t, J=7.3 Hz, 3H).

3.33: (S)-9-amino-4-ethyl-8-fluoro-11-((3-fluoro-3-(hydroxymethyl)azetidin-1-yl)methyl)-4-hydroxy-1,12-dihydro-14H-pyrano[3',4':6,7]indolizino[1,2-b]quinoline-3,14(4H)-dione (Compound 159)

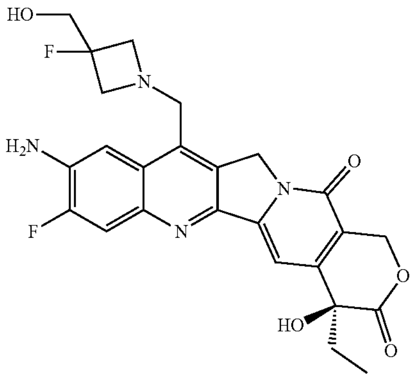 [SMILES: CC[C@@]1(O)C(=O)OCc2c1cc1n(c2=O)Cc2c-1nc1cc(F)c(N)cc1c2CN1CC(F)(CO)C1]

In a 5 mL conical flask containing Compound 3.6 (15 mg) was added dichloromethane (0.6 mL) followed by (3-fluoroazetidin-3-yl)methanol (9.3 mg) and acetic acid (7.6 μL). The reaction was stirred at room temperature and sodium triacetoxyborohydride (9.4 mg) was added. After 1 hour at room temperature, the reaction was quenched by addition of water+0.1% TFA, diluted with DMF, then partially evaporated. Preparative HPLC purification was accomplished as described in General Procedure 9, eluting with a 20 to 50% $CH_3CN/H_2O$+0.1% TFA gradient to give the Boc-protected title compound as a yellow powder. Deprotection was then performed according to General Procedure 6. The obtained residue was purified by preparative HPLC purification as described in General Procedure 9, eluting with a 20 to 50% $CH_3CN/H_2O$+0.1% TFA gradient to give the title compound as yellow powder (TFA salt, 1.8 mg, 10% yield).

LC/MS: Calc'd m/z=499.2 for $C_{25}H_{24}F_2N_4O_5$ found $[M+H]^+$=499.4.

$^1$H NMR (300 MHz, DMSO-d6) δ 7.82 (d, J=12.4 Hz, 1H), 7.45 (d, J=9.5 Hz, 1H), 7.21 (s, 1H), 5.45-5.33 (m, 4H), 3.75-3.61 (m, 2H), 1.93-1.78 (m, 2H), 0.87 (t, J=7.3 Hz, 3H).

3.34: tert-butyl-(S)-(4-ethyl-8-fluoro-4-hydroxy-11-((methylamino)methyl)-3,14-dioxo-3,4,12,14-tetrahydro-1H-pyrano[3',4':6,7]indolizino[1,2-b]quinolin-9-yl)carbamate (Compound 3.34)

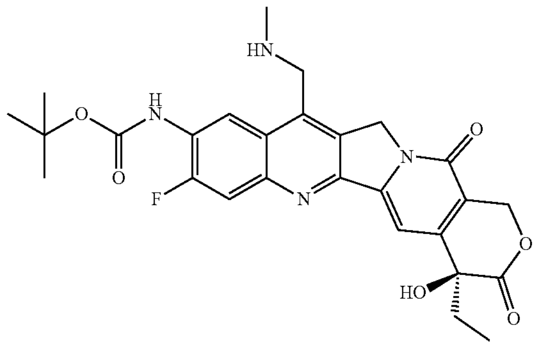 [SMILES: CC[C@@]1(O)C(=O)OCc2c1cc1n(c2=O)Cc2c-1nc1cc(F)c(NC(=O)OC(C)(C)C)cc1c2CNC]

To a stirring solution of Compound 3.9 (210 mg) in DMF (5 mL) was added sodium iodide (5.9 mg) followed by methylammonium chloride (107 mg). The reaction mixture was then stirred at room temperature overnight. Reverse phase purification was accomplished as described in General Procedure 9 using a 30g C18 column and eluting with a 10 to 65% $CH_3CN/H_2O$+0.1% TFA gradient to give the title compound as a yellow solid (15.0 mg, 7.2% yield).

LC/MS: Calc'd m/z=524.2 for $C_{27}H_{29}FN_4O_6$, found $[M+H]^+$=525.4.

3.35: (S)—N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-2-hydroxy-N-methylacetamide (Compound 165)

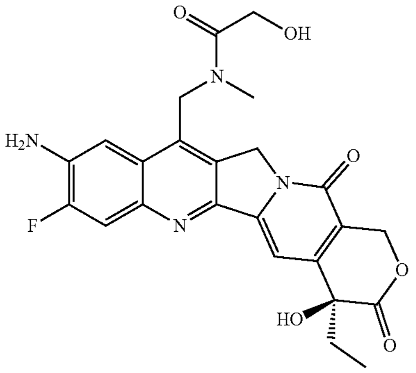 [SMILES: CC[C@@]1(O)C(=O)OCc2c1cc1n(c2=O)Cc2c-1nc1cc(F)c(N)cc1c2CN(C)C(=O)CO]

The Boc-protected version of the title compound was prepared according to General Procedure 2 starting from Compound 3.34 (6.4 mg) and glycolic acid. Preparative HPLC purification was accomplished as described in General Procedure 9, eluting with a 20 to 50% $CH_3CN/H_2O$+0.1% TFA gradient. Deprotection was then performed according to General Procedure 6 to give the title compound as yellow powder (TFA salt, 2.0 mg, 28% yield).

LC/MS: Calc'd m/z=482.2 for $C_{24}H_{23}FN_4O_6$, found $[M+H]^+$=483.2.

$^1$H NMR (300 MHz, DMSO-d6) δ 7.79 (d, J=12.3 Hz, 1H), 7.27 (d, J=9.5 Hz, 1H), 7.22 (s, 1H), 6.48 (s, 1H), 6.28-6.02 (m, 2H), 5.40 (s, 2H), 5.21 (s, 2H), 5.06-4.93 (m, 2H), 4.18 (s, 2H), 2.80 (s, 3H), 1.92-1.78 (m, 2H), 0.87 (t, J=7.3 Hz, 3H).

3.36: (S)—N-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)-N-methyl-methanesulfonamide (Compound 166)

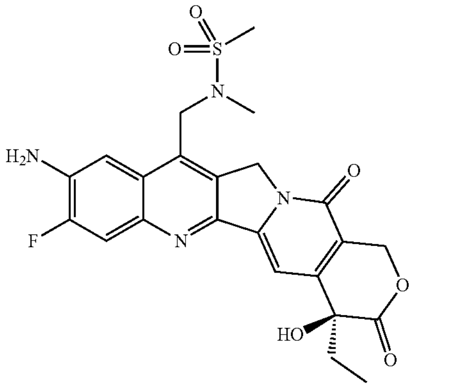 [SMILES: CC[C@@]1(O)C(=O)OCc2c1cc1n(c2=O)Cc2c-1nc1cc(F)c(N)cc1c2CN(C)S(C)(=O)=O]

The Boc-protected version of the title compound was prepared according to General Procedure 3 starting from Compound 3.34 (8.0 mg) and methanesulfonyl chloride. Preparative HPLC purification was accomplished as described in General Procedure 9, eluting with a 10 to 50% $CH_3CN/H_2O$+0.1% TFA gradient. Deprotection was then performed according to General Procedure 6 to give the title compound as yellow powder (TFA salt, 2.6 mg, 34% yield).

LC/MS: Calc'd m/z=502.1 for $C_{23}H_{23}FN_4O_6S$, found $[M+H]^+$=503.2.

$^1$H NMR (300 MHz, DMSO-d6) δ 7.81 (d, J=12.3 Hz, 1H), 7.41 (d, J=9.4 Hz, 1H), 7.23 (s, 1H), 6.63-5.84 (m, 2H), 5.42 (s, 2H), 5.29 (s, 2H), 4.81-4.64 (m, 2H), 3.14 (s, 3H), 2.67 (s, 3H), 1.96-1.76 (m, 2H), 0.88 (t, J=7.3 Hz, 3H).

3.37: (S)-9-amino-4-ethyl-8-fluoro-4-hydroxy-11-(2-methoxyethyl)-1,12-dihydro-14H-pyrano[3',4':6,7]indolizino[1,2-b]quinoline-3,14(4H)-dione (Compound 170)

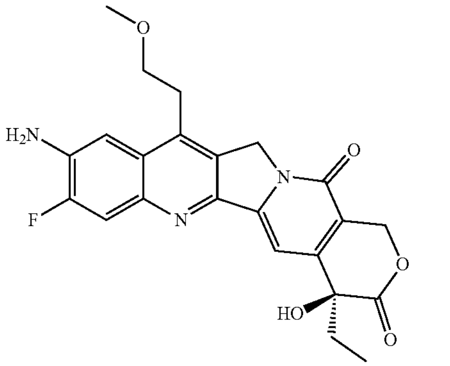 [SMILES: CC[C@@]1(O)C(=O)OCc2c1cc1n(c2=O)Cc2c-1nc1cc(F)c(N)cc1c2CCOC]

To a 10 mL round bottom flask containing Compound 3.4 (62.0 mg) was added water (0.89 mL), $FeSO_4$ (heptahydrate, 18.0 mg), and 3-methoxypropanal (113.0 mg). To the obtained suspension was added sulfuric acid (0.495 mL) dropwise while stirring at −15° C. in an ice salt bath. Hydrogen peroxide (0.118 mL) was then added dropwise. The mixture was stirred at −15° C. for 10 min and was then allowed to warm up to room temperature and stirred for 1 h. The reaction mixture was then diluted with water (30 mL) and the obtained suspension was extracted with DCM (3×30 mL). The organic phase was evaporated to dryness. Preparative HPLC purification was accomplished as described in General Procedure 9, eluting with a 25 to 45% $CH_3CN/H_2O$+0.1% TFA gradient to give the title compound as a dark orange solid (TFA salt, 3.1 mg, 4.4% yield).

LC/MS: Calc'd m/z=440.2 for $C_{23}H_{22}FN_3O_5$, found $[M+H]^+$=440.2.

$^1$H NMR (300 MHz, DMSO-d6) δ 7.75 (d, J=12.4 Hz, 1H), 7.33 (d, J=9.4 Hz, 1H), 7.20 (s, 1H), 6.60-6.42 (m, 2H), 5.40 (s, 2H), 5.25 (s, 2H), 3.69 (t, J=6.5 Hz, 2H), 3.24 (s, 3H), 3.23 (t, J=6.5 Hz, 2H), 1.96-1.76 (m, 2H), 0.88 (t, J=7.3 Hz, 3H).

3.38: (S)—N-(4-ethyl-8-fluoro-4-hydroxy-3,14-dioxo-3,4,12,14-tetrahydro-1H-pyrano[3',4':6,7]indolizino[1,2-b]quinolin-9-yl)acetamide (Compound 171)

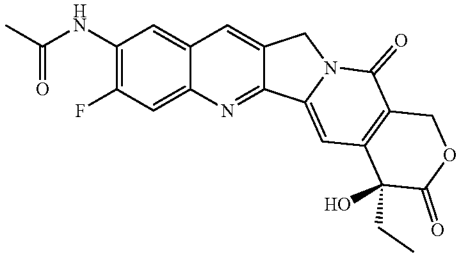 [SMILES: CC[C@@]1(O)C(=O)OCc2c1cc1n(c2=O)Cc2cc3cc(NC(C)=O)c(F)cc3nc2-1]

To a 25 mL round bottom flask containing acetic acid (0.071 mL) in dimethylformamide (0.69 mL) was added N-methylmorpholine (0.343 mL), HOAt (0.142 g), and HATU (0.435 g). After stirring at room temperature for 5 min, this solution was added to a 10 mL cone-shaped flask containing Compound 140 (0.127 g). This solution was stirred at room temperature for 24 h then directly purified by preparative HPLC as described in General Procedure 9, eluting with a 25 to 45% $CH_3CN/H_2O$+0.1% TFA gradient to give the title compound as a bright yellow powder (43.0 mg, 38% yield).

LC/MS: Calc'd m/z=424.1 for $C_{22}H_{18}FN_3O_5$, found $[M+H]^+$=424.2.

$^1$H NMR (300 MHz, DMSO-d6) δ 10.13 (s, 1H), 8.73 (d, J=8.5 Hz, 1H), 8.61 (s, 1H), 7.96 (d, J=912.1 Hz, 1H), 7.29 (s, 1H), 6.60-6.42 (m, 2H), 5.41 (s, 2H), 5.21 (s, 2H), 2.20 (s, 3H), 1.96-1.76 (m, 2H), 0.88 (t, J=7.3 Hz, 3H).

3.39: tert-butyl (5-formyl-2-methoxy-4-nitrophenyl)carbamate (Compound 3.39)

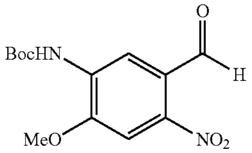 [SMILES: COc1cc([N+](=O)[O-])c(C=O)cc1NC(=O)OC(C)(C)C]

To a solution of Compound 3.2 (1.3 μg, 1.0 eq.) in MeOH (12 mL) at 0° C. was added sodium methoxide (0.74 μg, 3.0 eq.). After the addition was complete, the ice bath was removed and the resulting solution was stirred at room temperature for 72 h. The reaction was then quenched with ice water (50 mL) and extracted with DCM (3×100 mL). The combined organic layers were washed with brine (50 mL), dried over sodium sulfate, filtered, and concentrated in vacuo to yield the title compound as an orange solid (1.2 μg, 89% yield).

LC/MS: Calc'd m/z=296.10 for $C_{13}H_{16}N_2O_6$, found $[M+H]^+$=297.1.

$^1$H NMR (300 MHz, MeOD) δ 10.29 (s, 1H), 8.61 (s, 1H), 7.73 (s, 1H), 4.08 (s, 3H), 1.57 (s, 9H)

3.40: tert-butyl (4-amino-5-formyl-2-methoxyphenyl)carbamate (Compound 3.40)

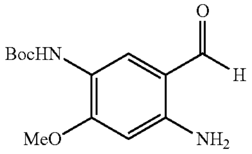

To a solution of Compound 3.39 (500 mg, 1 eq.) in MeOH (10 mL) and $H_2O$ (1 mL) was added $B_2(OH)_4$ (454 mg, 3 eq.). The resulting mixture was cooled to 0° C. and an aqueous 5M NaOH solution (2.75 mL) was added with stirring over the course of 10 min. The reaction mixture was stirred for an additional 5 min then quenched by pouring the solution into ice (40 mL). The resulting mixture was extracted with DCM (3×50 mL), dried over sodium sulfate, filtered, and concentrated in vacuo. Flash purification was accomplished as described in General Procedure 9, using a 25 g silica column and eluting with 10 to 50% hexanes/EtOAc to give the title compound as an orange solid (386 mg, 86%).

LC/MS: Calc'd m/z=266.1 for $C_{13}H_{18}N_2O_4$, found $[M+H]^+$=297.2.

3.41: (S)-9-amino-4-ethyl-8-fluoro-4-hydroxy-1,12-dihydro-14H-pyrano[3',4':6,7]indolizine o[1,2-b]quinoline-3,14(4H)-dione (Compound 168)

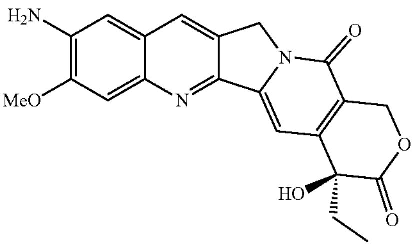 [SMILES: CC[C@@]1(O)C(=O)OCc2c1cc1n(c2=O)Cc2cc3cc(N)c(OC)cc3nc2-1]

A mixture of Compound 3.40 (385 mg, 1.0 eq.) and (S)-4-ethyl-4-hydroxy-7,8-dihydro-1H-pyrano[3,4-f]indolizine-3,6,10(4H)-trione (362 mg, 0.95 eq.), TsOH (monohydrate, 25 mg, 0.1 eq.) and toluene (30 mL) in a 250 mL round bottom flask equipped with a Dean-Stark apparatus was stirred at 110° C. for 2 h. The reaction mixture was then cooled to 25° C. and concentrated in vacuo. Purification was accomplished as described in General Procedure 9, using a 25 g silica column and eluting with a 0 to 50% DCM/MeOH gradient to provide the Boc-protected intermediate as a red solid. This material was then deprotecting according to General Procedure 6 followed by preparative HPLC purification as described in General Procedure 9, eluting with a 20 to 65% $CH_3CN/H_2O$+0.1% TFA gradient to give the title compound as a red solid (TFA salt, 300 mg, 53% yield).

LC/MS: Calc'd m/z=393.2 for $C_{21}H_{19}N_3O_5$, found $[M+H]^+$=393.2.

$^1$H NMR (300 MHz, MeOD) δ 8.27 (s, 1H), 7.62 (s, 1H), 7.42 (s, 1H), 7.11 (s, 1H), 5.61 (d, J=16.2 Hz, 1H), 5.38 (d, J=16.2 Hz, 1H), 5.24 (s, 2H), 4.11 (s, 3H), 2.06-1.91 (m, 2H), 1.04 (t, J=7.4 Hz, 3H).

3.42: 5-bromo-2-nitro-4-(trifluoromethyl)benzaldehyde (Compound 3.42)

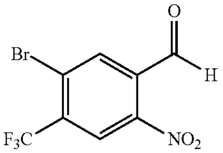

A stirring solution of $HNO_3$ (2.0 g, 1.4 mL, 67% purity, 2 eq.) in $H_2SO_4$ (8 mL) at 0° C. was added 3-bromo-4-(trifluoromethyl)benzaldehyde (4 μg, 1 eq.). After the addition was complete, the ice bath was removed, and the reaction was allowed to stir for 5 h at room temperature. The mixture was poured into ice (100 mL) and the precipitate extracted with DCM (3×100 mL). The combined organic fractions were then washed with brine (50 mL), dried over $Na_2SO_4$, and concentrated in vacuo to yield the title compound as a yellow solid (4.4 μg, 93% yield).

LC/MS: Calc'd m/z=296.90 for $C_8H_3BrF_3NO_3$, found $[M+H]^+$=298.0.

$^1$H NMR (300 MHz, MeOD) δ 10.35 (s, 1H), 8.29 (s, 1H), 8.23 (s, 1H).

3.43: tert-butyl (5-formyl-4-nitro-2-(trifluoromethyl) phenyl)carbamate (Compound 3.43)

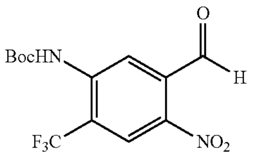

A mixture of Compound 3.42 (800 mg, 1 eq.), tert-butyl carbamate (378 mg, 1.2 eq.), $Cs_2CO_3$ (1.7 μg, 2 eq.), $Pd_2(dba)_3$ (122 mg, 0.05 eq.), and dicyclohexyl[2',4',6'-tris (propan-2-yl)[1,1'-biphenyl]-2-yl]phosphane (XPhos) (256 mg, 0.2 eq.) in toluene (5 mL) was degassed and purged with $N_2$ for three cycles. The mixture was then stirred at 90° C. for 15 h under $N_2$ atmosphere. The reaction mixture was diluted with $H_2O$ (25 mL) and extracted with EtOAc (3×50 mL). The combined organic layers were washed with brine (2×25 mL), dried over sodium sulfate, filtered, and concentrated under reduced pressure. Flash purification was achieved according to General Procedure 9, using a 25 g silica column and eluting with 0 to 25% DCM/MeOH to give the title compound as an orange solid (750 mg, 84% yield).

LC/MS: Calc'd m/z=334.1 for $C_{13}H_{13}FN_2O_5$, found $[M-H]^-$=333.1.

3.44: tert-butyl (4-amino-5-formyl-2-(trifluoromethyl)phenyl)carbamate (Compound 3.44)

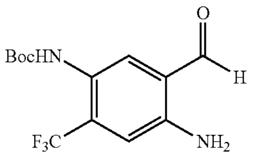

To a solution of Compound 3.43 (750 mg, 1 eq.) in MeOH (16 mL) and $H_2O$ (1.6 mL) was added $B_2(OH)_4$ (603 mg, 3 eq.). The resulting mixture was cooled to 0° C. and an aqueous 5M NaOH solution (2.75 mL) was added with stirring over the course of 10 min. The reaction mixture was stirred for an additional 5 min then quenched by pouring the solution into ice (50 mL). The resulting mixture was extracted with DCM (3×75 mL), dried over sodium sulfate, filtered, and concentrated in vacuo. Flash purification was accomplished as described in General Procedure 9, using a 25 g silica column and eluting with 10 to 50% hexanes/EtOAc to give the title compound as an orange solid (460 mg, 67%).

LC/MS: Calc'd m/z=304.1 for $C_{13}H_{15}F_3N_{203}$, found $[M+H]^+$=305.2

3.45: (S)-9-amino-4-ethyl-4-hydroxy-8-(trifluoromethyl)-1,12-dihydro-14H-pyrano[3',4':6,7]indolizino [1,2-b]quinoline-3,14(4H)-dione (Compound 167)

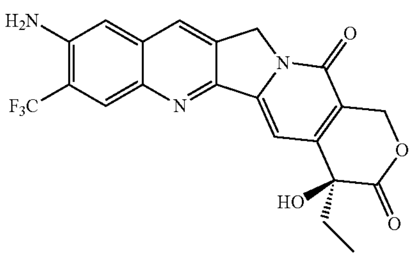 [SMILES: CC[C@@]1(O)C(=O)OCc2c1cc1n(c2=O)Cc2cc3cc(N)c(C(F)(F)F)cc3nc2-1]

A mixture of Compound 3.44 (460 mg, 1 eq.) and (S)-4-ethyl-4-hydroxy-7,8-dihydro-1H-pyrano[3,4-f]indolizine-3,6,10(4H)-trione (378 mg, 0.95 eq.), TsOH (monohydrate, 26 mg, 0.1 eq.) and toluene (35 mL) in a 250 mL round bottom flask equipped with a Dean-Stark apparatus was stirred at 110° C. for 2 h. The reaction mixture was then cooled to 25° C. and concentrated in vacuo. Purification was accomplished as described in General Procedure 9, using a 25 g silica column and eluting with a 0 to 50% DCM/MeOH gradient to provide the Boc-protected intermediate as a red solid. This material was then deprotecting according to General Procedure 6 followed by preparative HPLC purification as described in General Procedure 9, eluting with a 20 to 65% $CH_3CN/H_2O$+0.1% TFA gradient to give the titled compound as a yellow solid (6.2 mg, 48%).

LC/MS: Calc'd m/z=431.1 for $C_{21}H_{16}F_3N_3O_4$, found $[M+H]^+$=432.2.

$^1H$ NMR (300 MHz, MeOD) δ 8.29 (s, 1H), 8.27 (s, 1H), 7.59 (s, 1H), 7.24 (s, 1H), 5.59 (d, J=16.3 Hz, 1H), 5.39 (d, J=16.3 Hz, 1H), 5.28 (s, 2H), 2.00-1.89 (m, 2H), 1.03 (t, J=7.4 Hz, 3H).

Example 4: Preparation of Drug-Linkers 4.1: 2,5-dioxopyrrolidin-1-yl (((9H-fluoren-9-yl) methoxy)carbonyl)glycylglycinate (Compound 4.1)

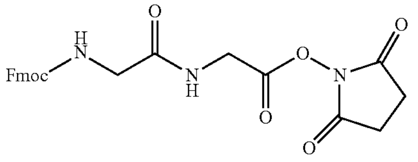

The title compound was prepared according to the procedure described in Chinese Patent Publication No. CN105218644.

4.2: (((9H-fluoren-9-yl)methoxy)carbonyl) glycylglycyl-L-phenylalanine (Fmoc-GGF-OH; Compound 4.2)

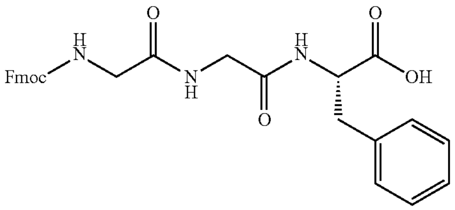

To L-phenylalanine (965 mg) in acetonitrile (10 mL) and dimethyl formamide (0.5 mL) was added DIPEA (1.51 mL) then Compound 4.1 (1.3 g). After 1 h the reaction was concentrated to dryness. Flash purification was accomplished as described in General Procedure 9, eluting with a 10 to 50% $CH_3CN/H_2O$+0.1% TFA gradient to provide the title compound as a white solid (430 mg, 30% yield).

LC/MS: Calc'd m/z=501.2 for $C_{28}H_{71}N_3O_6S$, found $[M+H]^+$=502.4.

$^1$H NMR (300 MHz, DMSO) δ 8.16 (d, J=8.1 Hz, 1H), 8.04 (t, J=5.8 Hz, 1H), 7.90 (d, J=7.5 Hz, 2H), 7.72 (d, J=7.4 Hz, 2H), 7.59 (t, J=6.0 Hz, 1H), 7.54-7.39 (m, 2H), 7.33 (t, J=7.6 Hz, 2H), 7.28-7.13 (m, 5H), 4.44 (td, J=8.5, 5.1 Hz, 1H), 4.33-4.13 (m, 3H), 3.83-3.59 (m, 4H), 3.06 (dd, J=13.7, 5.1 Hz, 1H), 2.88 (dd, J=13.8, 9.0 Hz, 1H).

4.3: 2,3,5,6-tetrafluorophenyl 3-(2-(2-(2-(2,5-dioxo-2,5-dihydro-1H-pyrrol-1-yl)ethoxy) ethoxy)ethoxy) propanoate (MT-OTfp; Compound 4.3)

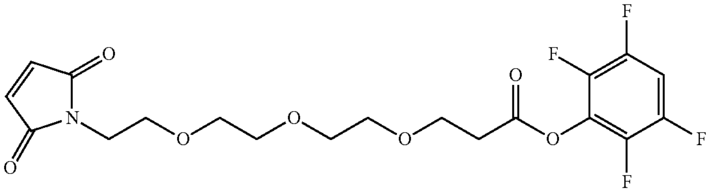 [SMILES: O=C(CCOCCOCCOCCN1C(=O)C=CC1=O)Oc1c(F)c(F)cc(F)c1F]

The title compound was prepared according to the procedure described in International Patent Publication No. WO 2017/054080.

4.4: (3-(2-(2-(2-(2,5-dioxo-2,5-dihydro-1H-pyrrol-1-yl)ethoxy)ethoxy)ethoxy)propanoyl) glycylglycyl-L-phenylalanine (Compound 4.4)

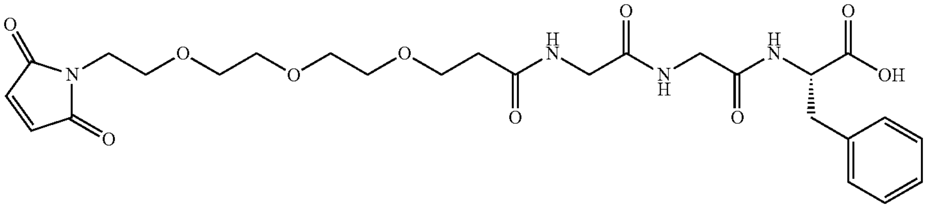 [SMILES: O=C(CCOCCOCCOCCN1C(=O)C=CC1=O)NCC(=O)NCC(=O)N[C@@H](Cc1ccccc1)C(=O)O]

To a solution of Compound 4.3 (1.61 μg, 3.58 mmol) in DMF (35 mL) was added Gly-Gly-Phe (1 μg, 3.58 mmol) as a single portion followed by $iPr_2NEt$ (1.25 mL, 7.2 mmol). This solution was stirred at room temperature for 1 h, then evaporated to dryness. Purification was accomplished as described in General Procedure 9 using a 30 g C18 flash column and eluting with a 10 to 90% $CH_3CN/H_2O$+0.1% TFA gradient to provide the title compound as a white solid (400 mg, 20% yield).

LC/MS: Calc'd m/z=562.6 for $C_{26}H_{34}N_4O_{10}$, found $[M-H]^-$=561.5.

$^1$H NMR (300 MHz, $CDCl_3$) δ 7.60 (t, J=5.6 Hz, 2H), 7.41 (d, J=7.7 Hz, 1H), 7.32-7.07 (m, 5H), 6.70 (s, 2H), 6.33-6.07 (m, 3H), 4.72 (td, J=7.6, 5.3 Hz, 1H), 4.12-3.78 (m, 4H), 3.72 (ddd, J=15.2, 6.9, 4.8 Hz, 5H), 3.60 (dd, J=11.6, 6.1 Hz, I0H), 3.12 (ddd, J=48.2, 14.0, 6.5 Hz, 2H), 2.52 (d, J=11.7 Hz, 2H).

4.5: (S)-11-benzyl-1-(9H-fluoren-9-yl)-3,6,9,12,15-pentaoxo-2-oxa-4,7,10,13,16-pentaazaheptadecan-17-yl acetate (Compound 4.5)

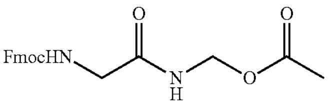

The title compound was prepared according to the procedure described in US Patent Publication No. US 2017/021031.

4.6: (S)-11-benzyl-1-(9H-fluoren-9-yl)-3,6,9,12,15-pentaoxo-2-oxa-4,7,10,13,16-pentaazaheptadecan-17-yl acetate (Compound 4.6)

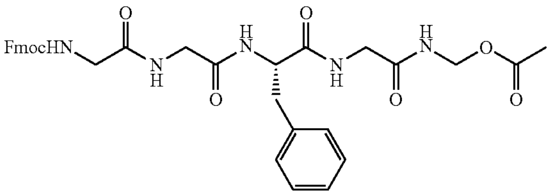

The title compound was prepared according to the procedure described in US Patent Publication No. US 2017/021031 using Fmoc-GGFGG-OH as the starting peptide.

4.7: tert-butyl (2-((2-(((S)-1-((2-((4-((4-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)piperazin-1-yl)sulfonyl)phenyl)amino)-2-oxoethyl)amino)-1-oxo-3-phenylpropan-2-yl)amino)-2-oxoethyl)amino)-2-oxoethyl)carbamate (Compound 4.7)

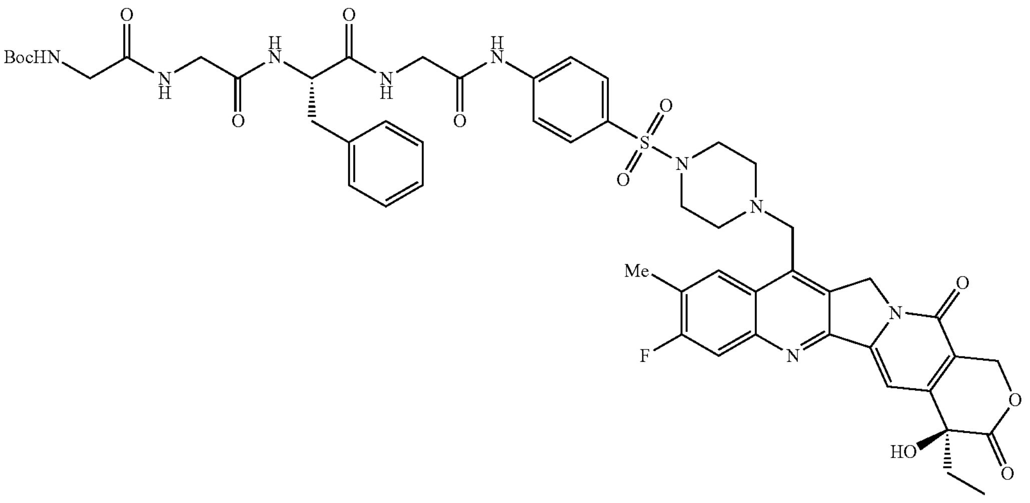 [SMILES: CC[C@@]1(O)C(=O)OCc2c1cc1n(c2=O)Cc2c-1nc1cc(F)c(C)cc1c2CN1CCN(S(=O)(=O)c2ccc(NC(=O)CNC(=O)[C@H](Cc3ccccc3)NC(=O)CNC(=O)CNC(=O)OC(C)(C)C)cc2)CC1]

The title compound was prepared according to General Procedure 7 starting from Compound 104 (20 mg). Preparative HPLC purification was accomplished as described in General Procedure 9, eluting with a 10 to 60% $CH_3CN$/$H_2O$+0.1% TFA gradient to provide the title compound as a white solid (14 mg, 42% yield).

LC/MS: Calc'd m/z=1051.4 for $C_{52}H_{58}N_9O_{12}S$, found $[M+H]^+$=1052.6.

4.8: (S)-2-(1-(2,5-dioxo-2,5-dihydro-1H-pyrrol-1-yl)-12,15-dioxo-3,6,9-trioxa-13,16-diazaoctadecan-18-amido)-N-(2-((4-((4-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)piperazin-1-yl)sulfonyl)phenyl)amino)-2-oxoethyl)-3-phenylpropanamide (MT-GGFG-Compound 104)

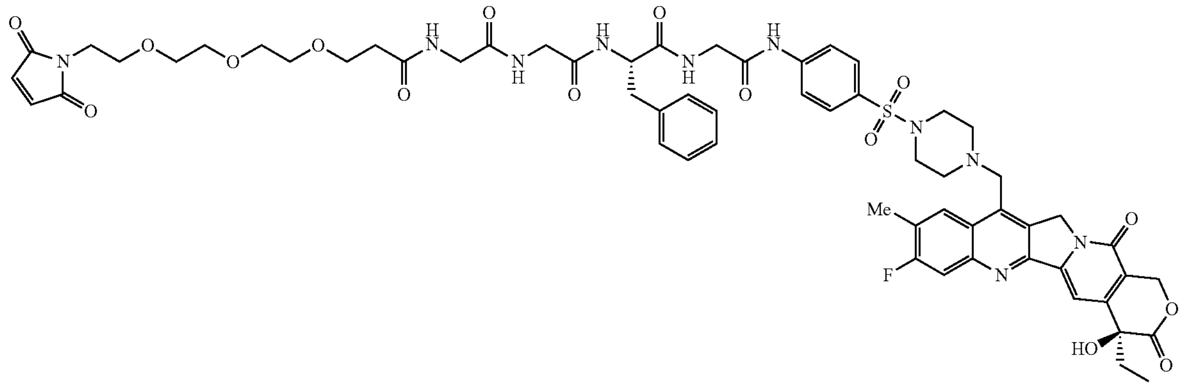 [SMILES: CC[C@@]1(O)C(=O)OCc2c1cc1n(c2=O)Cc2c-1nc1cc(F)c(C)cc1c2CN1CCN(S(=O)(=O)c2ccc(NC(=O)CNC(=O)[C@H](Cc3ccccc3)NC(=O)CNC(=O)CNC(=O)CCOCCOCCOCCN3C(=O)C=CC3=O)cc2)CC1]

The title compound was prepared according to Procedure 6 followed by Procedure 8 starting from Compound 4.7 (14 mg). Preparative HPLC purification was accomplished as described in General Procedure 9, eluting with a 10 to 60% $CH_3CN/H_2O$+0.1% TFA gradient to provide the title compound as a white solid (9.1 mg, 56% yield).

LC/MS: Calc'd m/z=1234.4 for $C_{60}H_{67}FN_{10}O_{16}S$, found $[M+H]^+$=1235.8.

4.9: tert-butyl (2-((2-(((S)-1-((2-((4-(4-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)piperazin-1-yl)phenyl)amino)-2-oxoethyl)amino)-1-oxo-3-phenylpropan-2-yl)amino)-2-oxoethyl)amino)-2-oxoethyl)carbamate (Compound 4.9)

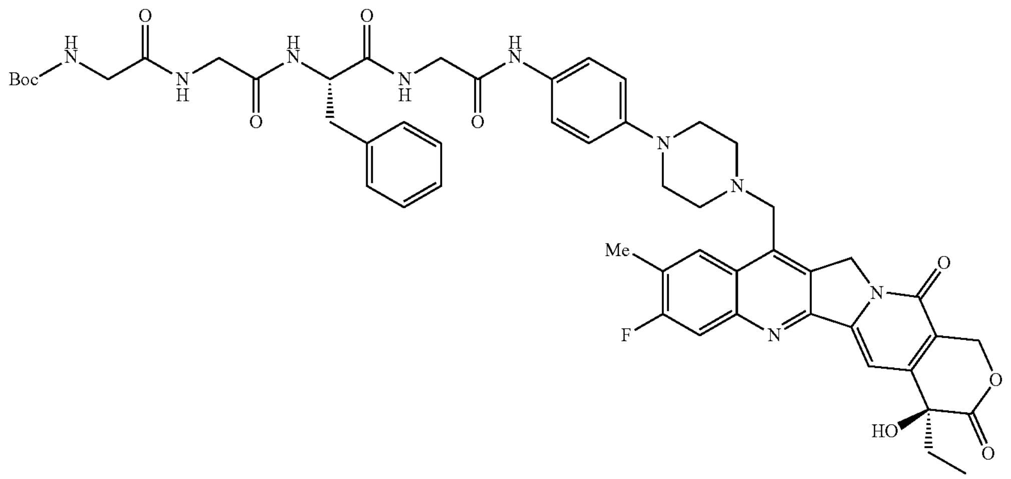 [SMILES: CC[C@@]1(O)C(=O)OCc2c1cc1n(c2=O)Cc2c-1nc1cc(F)c(C)cc1c2CN1CCN(c2ccc(NC(=O)CNC(=O)[C@H](Cc3ccccc3)NC(=O)CNC(=O)CNC(=O)OC(C)(C)C)cc2)CC1]

The title compound was prepared according to General Procedure 7 starting from Compound 108 (12 mg). Preparative HPLC purification was accomplished as described in General Procedure 9, eluting with a 10 to 60% $CH_3CN/H_2O$+0.1% TFA gradient to provide the title compound as a white solid (13 mg, 62% yield).

LC/MS: Calc'd m/z=987.4 for $C_{52}H_{58}N_9O_{10}$, found $[M+H]^+$=988.6.

4.10: (S)-2-(1-(2,5-dioxo-2,5-dihydro-1H-pyrrol-1-yl)-12,15-dioxo-3,6,9-trioxa-13,16-diazaoctadecan-18-amido)-N-(2-((4-(4-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)piperazin-1-yl)phenyl)amino)-2-oxoethyl)-3-phenylpropanamide (MT-GGFG-Compound 108)

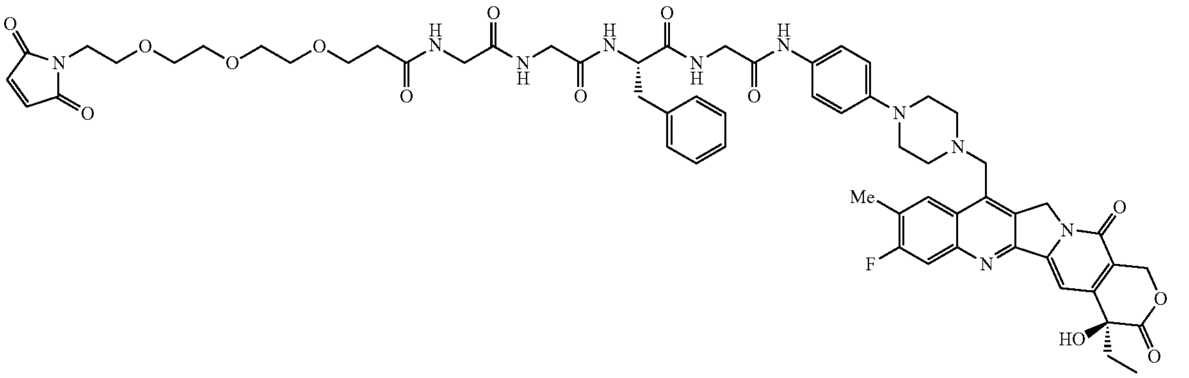 [SMILES: CC[C@@]1(O)C(=O)OCc2c1cc1n(c2=O)Cc2c-1nc1cc(F)c(C)cc1c2CN1CCN(c2ccc(NC(=O)CNC(=O)[C@H](Cc3ccccc3)NC(=O)CNC(=O)CNC(=O)CCOCCOCCOCCN3C(=O)C=CC3=O)cc2)CC1]

The title compound was prepared according to Procedure 6 followed by Procedure 8 starting from Compound 4.9 (13 mg). Preparative HPLC purification was accomplished as described in General Procedure 9, eluting with a 10 to 50% $CH_3CN/H_2O$+0.1% TFA gradient to provide the title compound as a white solid (3.1 mg, 20% yield).

LC/MS: Calc'd m/z=1170.5 for $C_{60}H_{67}FN_{10}O_{14}$, found $[M+H]^+$=1171.6.

4.11: (9H-fluoren-9-yl)methyl (S)-(1-(4-ethyl-8-fluoro-4-hydroxy-9-methyl-3,14-dioxo-3,4,12,14-tetrahydro-1H-pyrano[3',4':6,7]indolizino[1,2-b]quinolin-11-yl)-3,10-dioxo-7-oxa-2,4,9-triazaundecan-11-yl)carbamate (Compound 4.11)

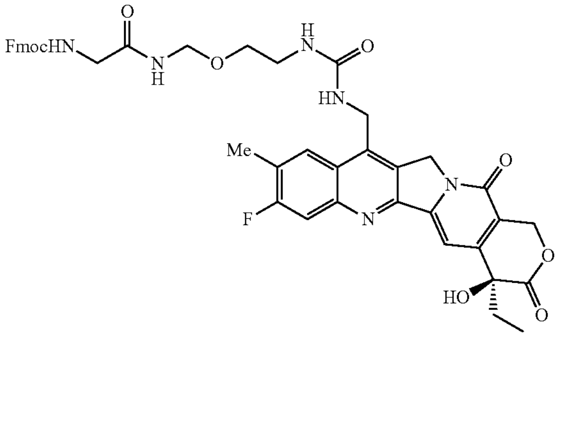

To a solution of Compound 1.2 (31 mg, 0.076 mmol) in DMF (750 uL) was added (9H-fluoren-9-yl)methyl (2-(((2-(((4-nitrophenoxy)carbonyl)amino)ethoxy)methyl)amino)-2-oxoethyl)carbamate (41 mg, 0.076 mmol) followed by $iPr_2NEt$ (26 uL, 0.15 mmol). This solution was stirred at room temperature for 2 h and then applied directly to 12 g C18 column. Purification was accomplished as described in General Procedure 9, eluting with a 10 to 100% $CH_3CN/H_2O$+0.1% TFA gradient to provide the title compound as a white solid (21 mg, 35% yield).

LC/MS: Calc'd m/z=804.87 for $C_{43}H_{41}FN_6O_9$, found $[M+H]^+$=805.6.

4.12: (S)-2-(1-(2,5-dioxo-2,5-dihydro-1H-pyrrol-1-yl)-12,15-dioxo-3,6,9-trioxa-13,16-diazaoctadecan-18-amido)-N-(1-((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)-3,10-dioxo-7-oxa-2,4,9-triazaundecan-11-yl)-3-phenylpropanamide (MT-GGFG-AM-Compound 136)

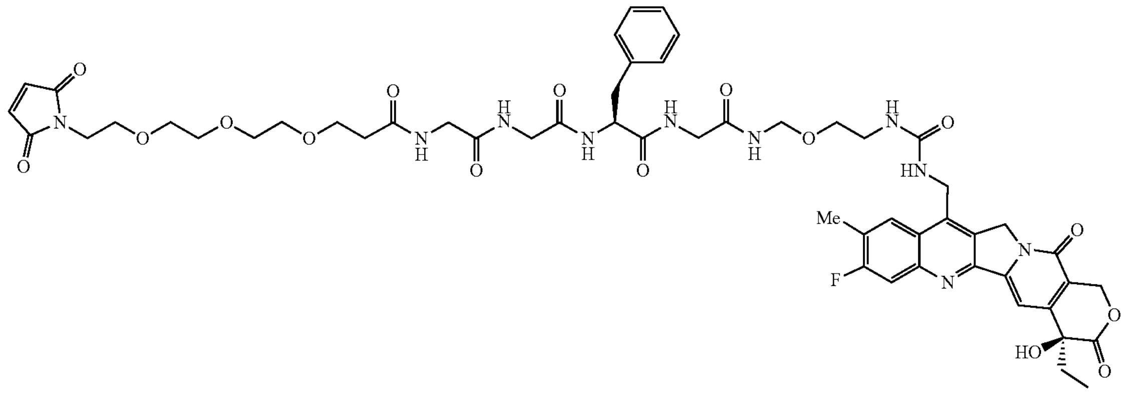 [SMILES: CC[C@@]1(O)C(=O)OCc2c1cc1n(c2=O)Cc2c-1nc1cc(F)c(C)cc1c2CNC(=O)NCCOCNC(=O)CNC(=O)[C@H](Cc1ccccc1)NC(=O)CNC(=O)CNC(=O)CCOCCOCCOCCN1C(=O)C=CC1=O]

Compound 4.11 (21 mg, 0.026 mmol) was taken up in a 10% solution of piperidine in DMF (1 mL) and stirred for 10 min. The piperidine solution was evaporated, the resulting residue was redissolved in DMF (5 mL), and then evaporated to dryness once more. To this residue was added DMF (50 uL) and DCM (450 uL) followed by Compound 4.4 (15 mg, 0.026 mmol), NMM (10 uL) and HATU (10 mg, 0.026 mmol). Preparative HPLC purification was accomplished as described in General Procedure 9, eluting with a 30 to 60% $CH_3CN/H_2O$+0.1% TFA gradient to provide the title compound as a yellow solid (7.6 mg, 26% yield).

LC/MS: Calc'd m/z=1127.1 for $C_{54}H_{63}FN_{10}O_{16}$, found $[M+H]^+$=1128.2.

4.13: (9H-fluoren-9-yl)methyl (2-(((2-(chlorosulfonyl)ethoxy)methyl)amino)-2-oxoethyl)carbamate (Compound 4.13)

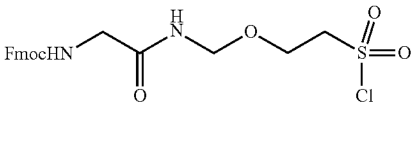

To a solution of Compound 4.5 (50 mg, 0.14 mmol), in DCM (800 uL) was added 2-hydroxyethane-1-sulfonyl chloride (100 mg, 0.7 mmol) followed by TFA (200 uL). This solution was stirred at room temperature for 30 min then evaporated to dryness. Purification was accomplished as described in General Procedure 9, using a 10 g silica column and eluting with a to 100% EtOAc/Hexanes gradient to provide the title compound as a clear film (31 mg, 50% yield).

LC/MS: Calc'd m/z=452.1 for $C_{20}H_{21}C_{1}N_{206}S$, found $[M+Na]^{+}$=472.9

4.14: (9H-fluoren-9-yl)methyl (S)-(2-(((2-(N-((4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)sulfamoyl)ethoxy)methyl)amino)-2-oxoethyl)carbamate (Compound 4.14)

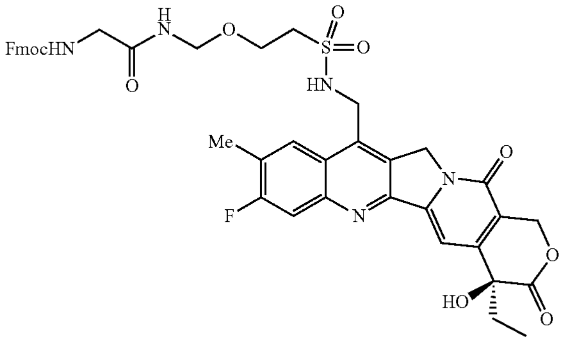

The title compound was prepared as described in General Procedure 3, using Compound 1.2 (28 mg, 0.07 mmol) and Compound 4.13 (31 mg, 0.07 mmol). Purification was accomplished as described in General Procedure 9, using a 12 g C18 column and eluting with a 10 to 100% $CH_3CN/H_2O$+0.1% TFA gradient to provide the title compound as a yellow solid (22 mg, 39% yield).

LC/MS: Calc'd m/z=825.9 for $C_{42}H_{40}FN_5O_{10}S$, found $[M+H]^{+}$=826.7.

4.15: (S)-2-(1-(2,5-dioxo-2,5-dihydro-1H-pyrrol-1-yl)-12,15-dioxo-3,6,9-trioxa-13,16-diazaoctadecan-18-amido)-N-(2-(((2-(N—(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)sulfamoyl) ethoxy)methyl)amino)-2-oxoethyl)-3-phenylpropanamide (MT-GGFG-AM-Compound 129)

Compound 4.14 (22 mg, 0.027 mmol) was taken up in a 10% solution of piperidine in DMF (1 mL) and stirred for 10 min. The piperidine solution was evaporated, the resulting residue was redissolved in DMF (5 mL), and then evaporated to dryness once more. To this residue was added DMF (50 uL) and DCM (450 uL) followed by Compound 4.4 (30 mg, 0.053 mmol), NMM (10 uL) and HATU (18 mg, 0.048 mmol). Preparative HPLC purification was accomplished as described in General Procedure 9, eluting with a 30 to 60% $CH_3CN/H_2O$+0.1% TFA gradient to provide the title compound as a yellow solid (6.4 mg, 21% yield).

LC/MS: Calc'd m/z=1148.2 for $C_{53}H_{62}FN_9O_{17}S$, found $[M+H]^{+}$=1148.6.

$^1$H NMR (300 MHz, MeOD) δ 8.60 (t, J=6.5 Hz, 1H), 8.36 (t, J=8.6 Hz, 2H), 8.13 (d, J=6.6 Hz, 1H), 7.77 (d, J=10.6 Hz, 1H), 7.65 (d, J=4.8 Hz, 1H), 7.28-7.00 (m, 6H), 6.80 (s, 2H), 5.69-5.50 (m, 3H), 5.45-5.33 (m, 2H), 4.44 (dd, J=8.7, 5.7 Hz, 1H), 3.96 (t, J=5.3 Hz, 2H), 3.90-3.76 (m, 5H), 3.76-3.57 (m, 7H), 3.09-2.81 (m, 3H), 2.61-2.45 (m, 5H), 2.04-1.90 (m, 2H), 1.03 (t, J=7.3 Hz, 3H).

4.16: (9H-fluoren-9-yl)methyl (S)-(2-(((morpholin-2-ylmethoxy)methyl)amino)-2-oxoethyl)carbamate (Compound 4.16)

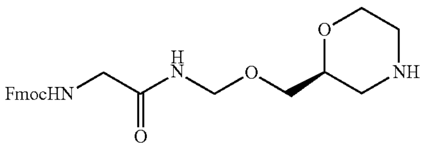

To a solution of Compound 4.5 (100 mg, 0.27 mmol) in DCM (800 uL) was added (S)-morpholin-2-ylmethanol (160 mg, 1.36 mmol) followed by TFA (200 uL). This solution was stirred at room temperature for 1 h then evaporated to dryness. Purification was accomplished as described in General Procedure 9, using a 12 g C18 flash column and eluting with a 10 to 90% $CH_3CN/H_2O$+0.1% TFA gradient to provide the title compound as a yellow solid (TFA salt, 105 mg, 72% yield).

LC/MS: Calc'd m/z=425.2 for $C_{23}H_{27}N_3O_5$, found $[M+Na]^{+}$=448.0.

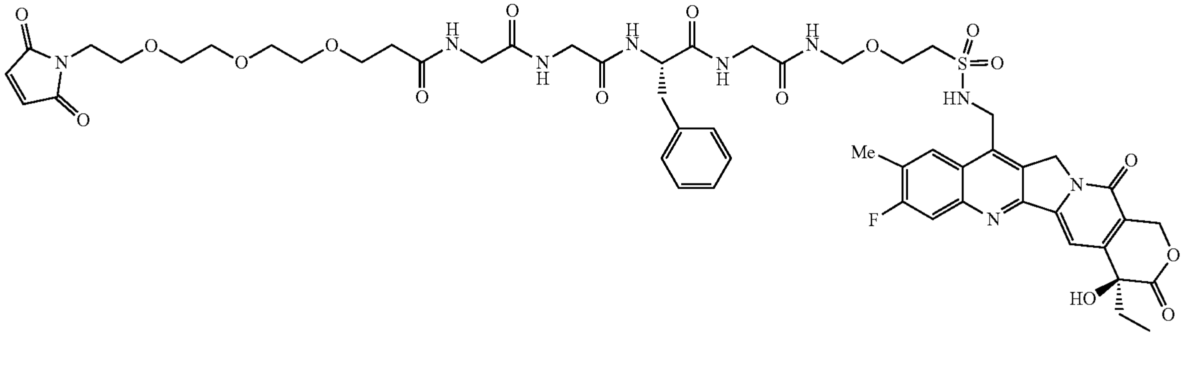 [SMILES: CC[C@@]1(O)C(=O)OCc2c1cc1n(c2=O)Cc2c-1nc1cc(F)c(C)cc1c2CNS(=O)(=O)CCOCNC(=O)CNC(=O)[C@H](Cc1ccccc1)NC(=O)CNC(=O)CNC(=O)CCOCCOCCOCCN1C(=O)C=CC1=O]

4.17: (9H-fluoren-9-yl)methyl (2-(((((S)-4-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)morpholin-2-yl)methoxy)methyl)amino)-2-oxoethyl)carbamate (Compound 4.17)

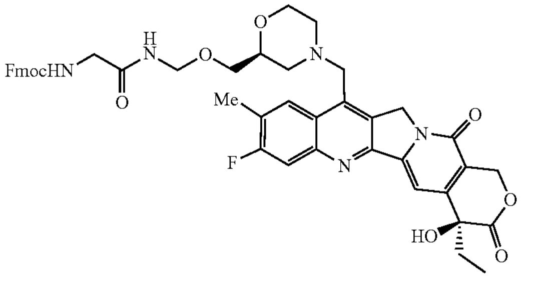

The title compound was prepared according to General Procedure 1 starting from Compound 1.1 (50 mg, 0.117 mmol) and Compound 4.16 (63 mg, 0.117 mmol). Preparative HPLC purification was accomplished as described in General Procedure 9, eluting with a 10 to 100% $CH_3CN/H_2O$+0.1% TFA gradient to give the title compound as an off-white solid (TFA salt, 33 mg, 35% yield).

LC/MS: Calc'd m/z=817.9 for $C_{45}H_{44}FN_5O_9$, found $[M+H]^+$=818.7.

4.18: (S)-2-(1-(2,5-dioxo-2,5-dihydro-1H-pyrrol-1-yl)-12,15-dioxo-3,6,9-trioxa-13,16-diazaoctadecan-18-amido)-N-(2-(((((S)-4-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)morpholin-2-yl)methoxy)methyl)amino)-2-oxoethyl)-3-phenylpropanamide (MT-GGFG-AM-Compound 113)

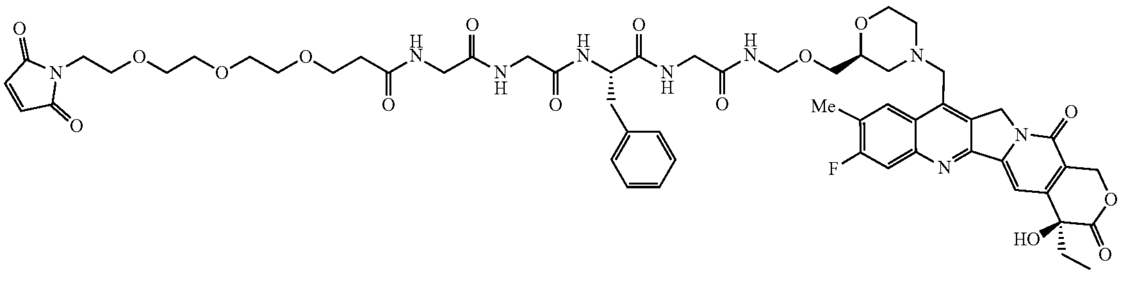 [SMILES: CC[C@@]1(O)C(=O)OCc2c1cc1n(c2=O)Cc2c-1nc1cc(F)c(C)cc1c2CN1CCO[C@H](COCNC(=O)CNC(=O)[C@H](Cc2ccccc2)NC(=O)CNC(=O)CNC(=O)CCOCCOCCOCCN2C(=O)C=CC2=O)C1]

Compound 4.17 (33 mg, 0.04 mmol) was taken up in a 10% solution of piperidine in DMF (1 mL) and stirred for 10 min. The piperidine solution was evaporated, the resulting residue was redissolved in DMF (5 mL), and then evaporated to dryness once more. To this residue was added DMF (100 uL) and DCM (900 uL) followed by Compound 4.4 (45 mg, 0.08 mmol), NMM (20 uL) and HATU (28 mg, 0.073 mmol). Preparative HPLC purification was accomplished as described in General Procedure 9, eluting with a 30 to 60% $CH_3CN/H_2O$+0.1% TFA gradient to provide the title compound as a yellow solid (22 mg, 48% yield).

LC/MS: Calc'd m/z=1140.2 for $C_{56}H_{66}FN_9O_{16}$, found $[M+H]^+$=1141.1.

$^1H$ NMR (300 MHz, MeOD) δ 8.35 (d, J=7.5 Hz, 2H), 7.74-7.61 (m, 1H), 7.53 (s, 1H), 7.34-7.10 (m, 6H), 6.81 (s, 2H), 5.65-5.30 (m, 4H), 4.64 (t, J=3.4 Hz, 2H), 4.42 (tt, J=6.3, 2.5 Hz, 1H), 4.09 (d, J=12.3 Hz, 1H), 3.98-3.76 (m, 8H), 3.72 (t, J=6.0 Hz, 2H), 3.69-3.44 (m, 17H), 3.21-2.85 (m, 3H), 2.64-2.42 (m, 5H), 2.03-1.84 (m, 2H), 0.98 (t, J=7.3 Hz, 3H).

4.19: (9H-fluoren-9-yl)methyl (S)-(2-((((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methoxy)methyl) amino)-2-oxoethyl) carbamate (Compound 4.19)

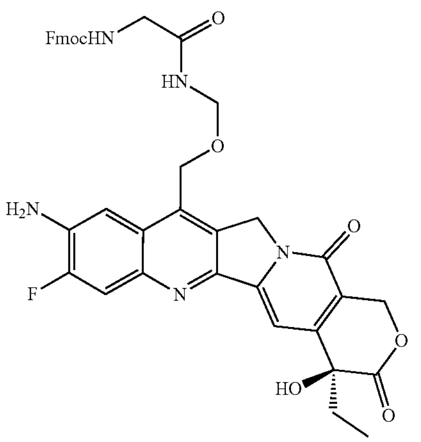

Compound 3.5 (55 mg, 0.11 mmol) was dissolved in TFA (500 uL) and stirred at room temperature for 20 min, then hexafluoroisopropanol (2 mL) was added followed by Compound 4.5 (40 mg, 0.11 mmol). This solution was stirred at room temperature for -16 h then concentrated to dryness. Purification was accomplished as described in General Procedure 9, using a 12 g C18 flash column and eluting with a 10 to 50% $CH_3CN/H_2O$+0.1% TFA gradient to provide the title compound as a yellow solid (11 mg, 14% yield).

LC/MS: Calc'd m/z=719.7 for $C_{39}H_{34}FN_5O_8$, found $[M+H]^+$=720.6.

4.20: (S)—N-(2-(((((S)-9-amino-4-ethyl-8-fluoro-4-hydroxy-3,14-dioxo-3,4,12,14-tetrahydro-1H-pyrano[3',4':6,7]indolizino[1,2-b]quinolin-11-yl)methoxy)methyl)amino)-2-oxoethyl)-2-(1-(2,5-dioxo-2,5-dihydro-1H-pyrrol-1-yl)-12,15-dioxo-3,6,9-trioxa-13,16-diazaoctadecan-18-amido)-3-phenylpropanamide (MT-GGFG-AM-Compound 141)

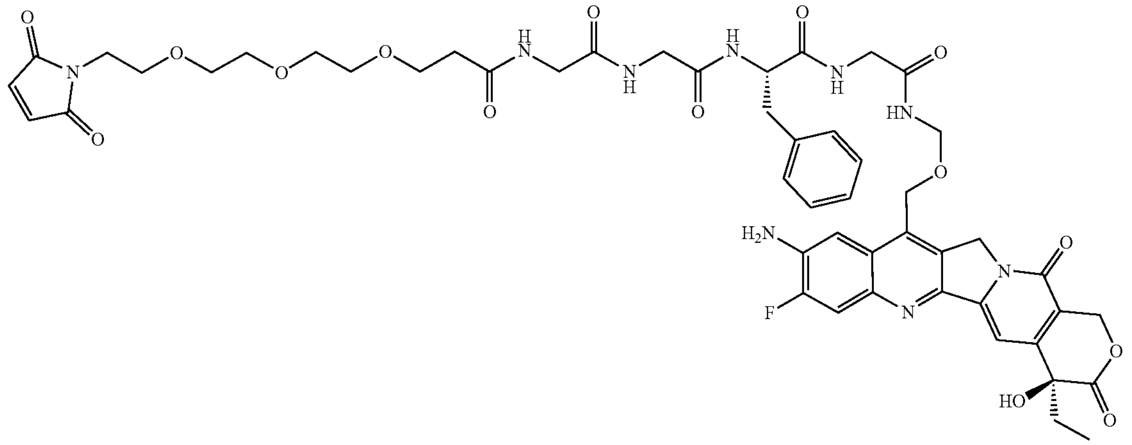 [SMILES: CC[C@@]1(O)C(=O)OCc2c1cc1n(c2=O)Cc2c-1nc1cc(F)c(N)cc1c2COCNC(=O)CNC(=O)[C@H](Cc1ccccc1)NC(=O)CNC(=O)CNC(=O)CCOCCOCCOCCN1C(=O)C=CC1=O]

Compound 4.19 (11 mg, 0.015 mmol) was taken up in a 10% solution of piperidine in DMF (1 mL) and stirred for 10 min. The piperidine solution was evaporated, the resulting residue was redissolved in DMF (5 mL), and then evaporated to dryness once more. To this residue was added DMF (50 uL) and DCM (450 uL) followed by Compound 4.4 (26 mg, 0.045 mmol), NMM (5 uL) and HATU (18 mg, 0.045 mmol). Preparative HPLC purification was accomplished as described in General Procedure 9, eluting with a 32 to 45% $CH_3CN/H_2O$+0.1% TFA gradient to provide the title compound as a yellow solid (4.6 mg, 29% yield).

LC/MS: Calc'd m/z=1142.0 for $C_{50}H_{56}FN_9O_{15}$, found $[M+H]^+$=1143.1.

$^1$H NMR (300 MHz, MeOD) δ 8.36 (s, 1H), 8.28 (d, J=6.1 Hz, 1H), 8.16 (dd, J=20.1, 6.8 Hz, 3H), 7.59-7.44 (m, 2H), 7.31-7.08 (m, 6H), 6.79 (s, 2H), 5.58 (d, J=16.1 Hz, 1H), 5.37 (d, J=16.1 Hz, 1H), 5.30-5.16 (m, 3H), 4.56-4.39 (m, 1H), 4.07-3.90 (m, 2H), 3.85 (dt, J=11.5, 5.4 Hz, 4H), 3.79-3.67 (m, 4H), 3.67-3.55 (m, 7H), 3.54 (d, J=6.5 Hz, 8H), 3.10 (dd, J=14.0, 6.1 Hz, 1H), 2.92 (dd, J=13.9, 9.1 Hz, 1H), 2.53 (t, J=6.0 Hz, 2H), 1.98 (q, J=7.2 Hz, 2H), 1.31 (s, 1H), 1.04 (t, J=7.3 Hz, 3H).

4.21: N—((S)-1-((S)-9-amino-4-ethyl-8-fluoro-4-hydroxy-3,14-dioxo-3,4,12,14-tetrahydro-1H-pyrano[3',4':6,7]indolizino[1,2-b]quinolin-11-yl)-9-benzyl-5,8,11,14-tetraoxo-2-oxa-4,7,10,13-tetraazapentadecan-15-yl)-6-(2,5-dioxo-2,5-dihydro-1H-pyrrol-1-yl)hexanamide (MC-GGFG-AM-Compound 141)

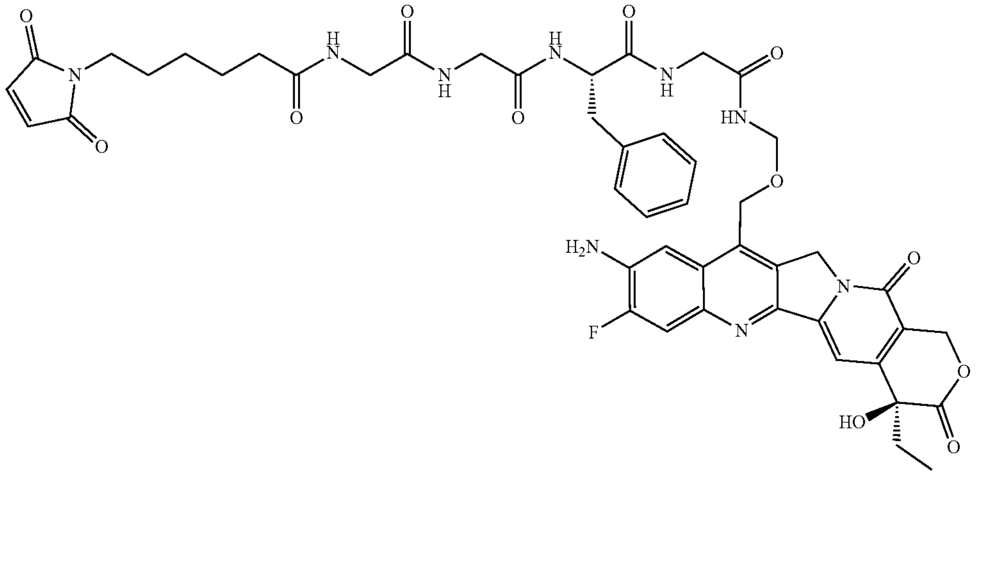 [SMILES: CC[C@@]1(O)C(=O)OCc2c1cc1n(c2=O)Cc2c-1nc1cc(F)c(N)cc1c2COCNC(=O)CNC(=O)[C@H](Cc1ccccc1)NC(=O)CNC(=O)CNC(=O)CCCCCN1C(=O)C=CC1=O]

Compound 4.19 (25 mg, 0.035 mmol) was taken up in a 10% solution of piperidine in DMF (1 mL) and stirred for 10 min. The piperidine solution was evaporated, the resulting residue was redissolved in DMF (5 mL), and then evaporated to dryness once more. To this residue was added DMF (50 uL) and DCM (450 uL), followed by MC-GGF-OH (33 mg, 0.07 mmol), NMM (20 uL) and HATU (25 mg, 0.066 mmol). Preparative HPLC purification was accomplished as described in General Procedure 9, eluting with a 30 to 50% $CH_3CN/H_2O$+0.1% TFA gradient to provide the title compound as a yellow solid (4.3 mg, 13% yield).

LC/MS: Calc'd m/z=952.0 for $C_{47}H_{50}FN_9O_{12}$, found $[M+H]^+$=952.9.

$^1H$ NMR (300 MHz, $CD_3CN$) 6 7.96-7.72 (m, 1H), 7.39-7.07 (m, 8H), 6.94 (d, J=9.1 Hz, 1H), 6.73 (s, 2H), 5.44 (d, J=16.2 Hz, 1H), 5.25 (d, J=16.2 Hz, 1H), 5.06 (d, J=4.4 Hz, 2H), 4.81 (d, J=26.1 Hz, 4H), 4.61 (s, 1H), 3.96 (s, 1H), 3.77 (d, J=8.1 Hz, 7H), 3.02 (d, J=5.6 Hz, 5H), 2.19 (t, J=7.7 Hz, 3H), 1.50 (dp, J=14.8, 7.4 Hz, 6H), 1.32-1.12 (m, 3H), 0.96 (t, J=7.2 Hz, 3H).

4.22: tert-butyl (2-((2-(((S)-1-((2-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-yl)amino)-2-oxoethyl)amino)-2-oxoethyl)carbamate (Compound 4.22)

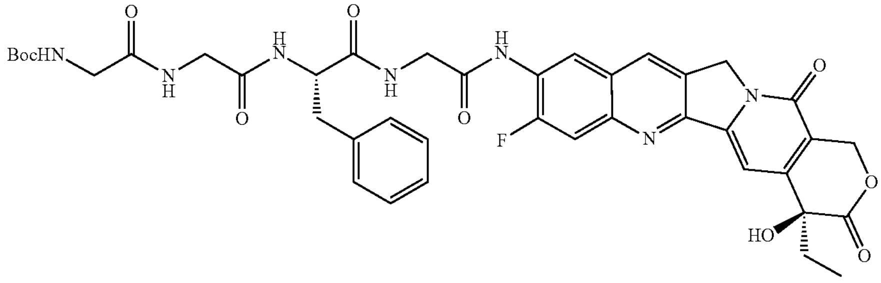 [SMILES: CC[C@@]1(O)C(=O)OCc2c1cc1n(c2=O)Cc2cc3cc(NC(=O)CNC(=O)[C@H](Cc4ccccc4)NC(=O)CNC(=O)CNC(=O)OC(C)(C)C)c(F)cc3nc2-1]

The title compound was prepared according to Procedure 7 starting from Compound 140 (28 mg). Preparative HPLC purification was accomplished as described in General Procedure 9, eluting with a 10 to 50% $CH_3CN/H_2O$+0.1% TFA gradient to provide the title compound as a white solid (10 mg, 17% yield).

LC/MS: Calc'd m/z=799.3 for $C_{40}H_{42}N_7O_{10}$, found $[M+H]^+$=800.6.

4.23: (S)-2-(1-(2,5-dioxo-2,5-dihydro-1H-pyrrol-1-yl)-12,15-dioxo-3,6,9-trioxa-13,16-diazaoctadecan-18-amido)-N-(2-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl)-3-phenylpropanamide (MT-GGFG-Compound 140)

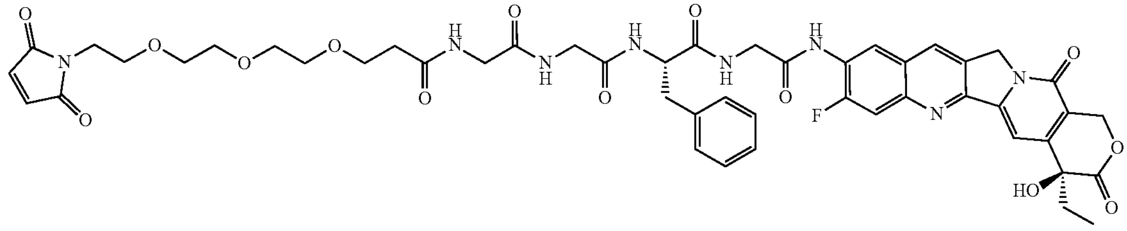 [SMILES: CC[C@@]1(O)C(=O)OCc2c1cc1n(c2=O)Cc2cc3cc(NC(=O)CNC(=O)[C@H](Cc4ccccc4)NC(=O)CNC(=O)CNC(=O)CCOCCOCCOCCN4C(=O)C=CC4=O)c(F)cc3nc2-1]

The title compound was prepared according to General Procedure 6 followed by General Procedure 8 starting from Compound 4.22 (10 mg). Preparative HPLC purification was accomplished as described in General Procedure 9, eluting with a 10 to 50% $CH_3CN/H_2O$+0.1% TFA gradient to provide the title compound as a white solid (6.8 mg, 55% yield).

LC/MS: Calc'd m/z=982.4 for $C_{48}H_{51}FN_8014$, found $[M+H]^+$=983.6.

4.24: tert-butyl (2-((2-(((S)-1-((2-(((S)-4-ethyl-8-fluoro-4-hydroxy-11-(morpholinomethyl)-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-yl)amino)-2-oxoethyl)amino)-2-oxoethyl)carbamate (Compound 4.24)

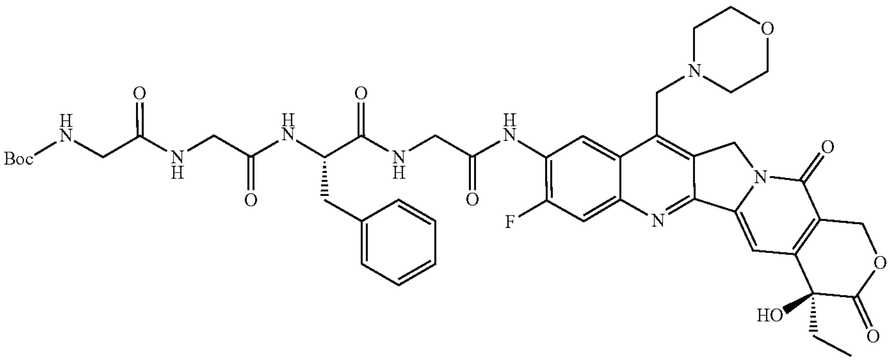 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)CNC(=O)OC(C)(C)C)cc1c2CN1CCOCC1]

The title compound was prepared according to General Procedure 7 starting from Compound 142 (TFA salt, 45 mg). Purification was accomplished as described in General Procedure 9, using a 12 g C18 flash column and eluting with a 10 to 50% $CH_3CN/H_2O$+0.1% TFA gradient to provide the title compound as a white solid (13 mg, 22% yield).

LC/MS: Calc'd m/z=898.4 for $C_{45}H_{51}N_8O_{11}$, found $[M+H]^+$=899.6.

4.25: (S)-2-(1-(2,5-dioxo-2,5-dihydro-1H-pyrrol-1-yl)-12,15-dioxo-3,6,9-trioxa-13,16-diazaoctadecan-18-amido)-N-(2-(((S)-4-ethyl-8-fluoro-4-hydroxy-11-(morpholinomethyl)-3,14-dioxo-3,4,12,14-tetrahydro-1H-pyrano[3',4':6,7]indolizino[1,2-b]quinolin-9-yl)amino)-2-oxoethyl)-3-phenylpropanamide (MT-GGFG-Compound 142)

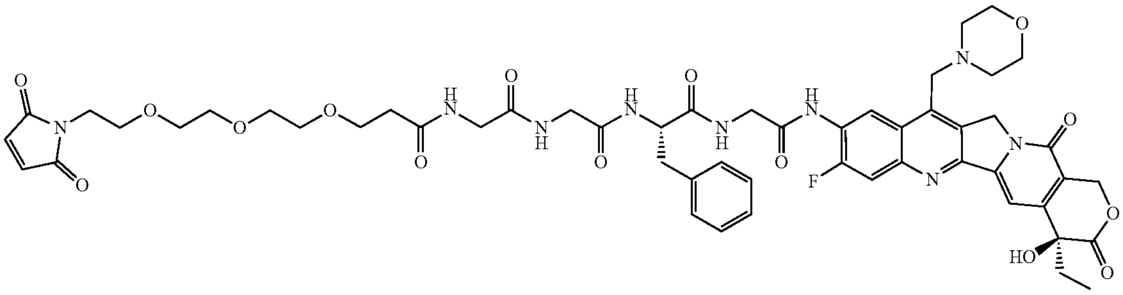 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)CNC(=O)CCOCCOCCOCCN3C(=O)C=CC3=O)cc1c2CN1CCOCC1]

The title compound was prepared according to General Procedure 6 followed by General Procedure 8 starting from Compound 4.24 (13 mg). Preparative HPLC purification was accomplished as described in General Procedure 9, eluting with a 10 to 50% $CH_3CN/H_2O$+0.1% TFA gradient to provide the title compound as a white solid (2.6 mg, 17% yield).

LC/MS: Calc'd m/z=1081.4 for $C_{53}H_{60}FN_9O_{15}$, found $[M+H]^+$=1082.6.

$^1$H NMR (300 MHz, MeOD) δ 9.34 (d, J=8.5 Hz, 1H), 7.87 (d, J=11.8 Hz, 1H), 7.62 (s, 1H), 7.33-7.19 (m, 5H), 6.80 (s, 2H), 5.62 (d, J=16.3 Hz, 1H), 5.51 (s, 2H), 5.47-5.35 (m, 3H), 4.73 (dd, J=9.6, 5.1 Hz, 1H), 4.61 (s, 3H), 4.30-4.15 (m, 2H), 4.11 (s, 2H), 4.00-3.82 (m, 4H), 3.82-3.70 (m, 7H), 3.70-3.50 (m, 13H), 3.18-3.04 (m, 1H), 2.88 (s, 1H), 2.64 (d, J=5.8 Hz, 4H), 2.54 (t, J=6.0 Hz, 2H), 2.09-1.92 (m, 2H), 1.03 (t, J=7.3 Hz, 3H).

4.26: (9H-fluoren-9-yl)methyl (S)-(12-benzyl-1-(4-nitrophenoxy)-1,8,11,14,17-pentaoxo-2,5-dioxa-7,10,13,16-tetraazaoctadecan-18-yl)carbamate (Compound 4.26)

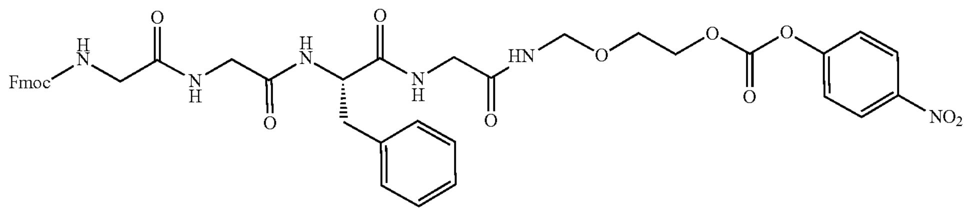

To a stirring solution of Compound 4.6 (60 mg) in dichloromethane (2 mL) was added ethylene glycol (100 uL) followed by trifluoracetic acid (0.4 mL). After 30 min the reaction was concentrated in vacuo. Purification of the intermediate compound was accomplished as described in General Procedure 9, using a 10 g flash column and eluting with a 0 to 20% dichloromethane/methanol gradient. To the purified intermediate in tetrahydrofuran (0.5 mL) was added bis-nitrophenol carbonate (58 mg) followed by DIPEA (50 uL). The solution was stirred for 16 h, quenched with acetic acid (~100 uL) then concentrated to dryness. Purification was accomplished as described in General Procedure 9, using a 10 g flash column and eluting with a 0 to 20% dichloromethane/methanol gradient to provide the title compound as a white solid (40 mg, 53% yield from Compound 4.6).

LC/MS: Calc'd m/z=796.3 for $C_{40}H_{40}N_6O_{12}$, found $[M+Na]^+$=819.4.

4.27: (S)-16-amino-10-benzyl-6,9,12,15-tetraoxo-3-oxa-5,8,11,14-tetraazahexadecyl (((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)carbamate (Compound 4.27)

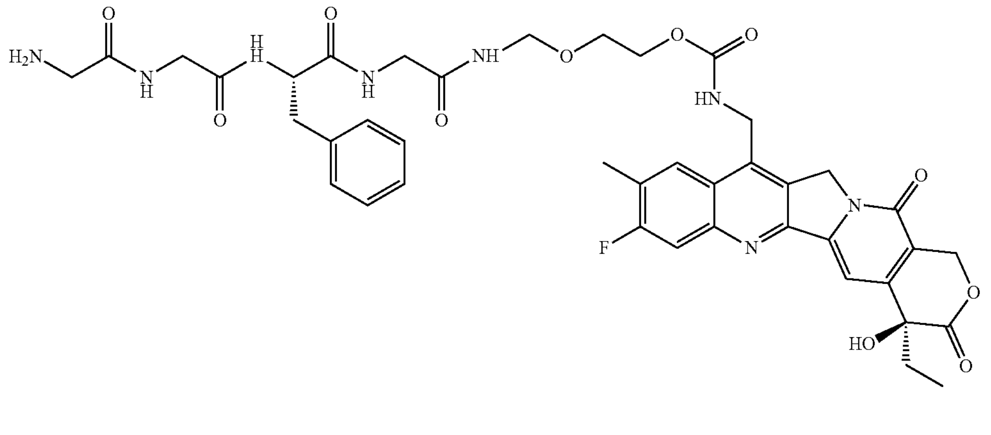

To a solution of Compound 4.26 (40 mg) in dimethylformamide (1 mL) was added DIPEA (26 uL) then a solution of Compound 1.2 (24 mg) in dimethylformamide (0.5 mL). This solution was stirred for 4 h at room temperature then quenched with a 20% piperidine in dimethylformamide solution (0.5 mL) and stirred for an additional 20 min. Purification was accomplished as described in General Procedure 9, using a 12 g C18 flash column and eluting with a 10 to 50% $CH_3CN/H_2O$+0.1% TFA gradient to provide the title compound as a white solid (TFA salt, 19 mg, 39% yield).

LC/MS: Calc'd m/z=844.3 for $C_{41}H_{45}FN_8011$, found $[M+H]^+$=845.6.

4.28: (S)-10-benzyl-29-(2,5-dioxo-2,5-dihydro-1H-pyrrol-1-yl)-6,9,12,15,18-pentaoxo-3,21,24,27-tetraoxa-5,8,11,14,17-pentaazanonacosyl (((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)carbamate (MT-GGFG-AM-Compound 139)

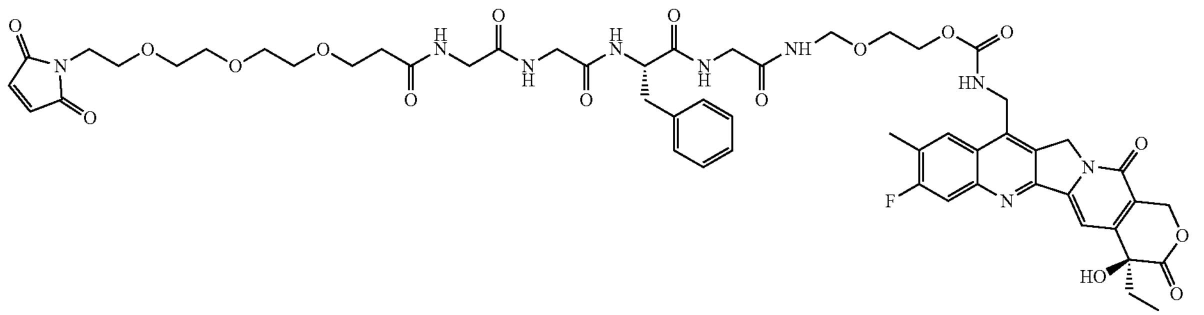 [SMILES: CC[C@@]1(O)C(=O)OCc2c1cc1n(c2=O)Cc2c-1nc1cc(F)c(C)cc1c2CNC(=O)OCCOCNC(=O)CNC(=O)[C@H](Cc1ccccc1)NC(=O)CNC(=O)CNC(=O)CCOCCOCCOCCN1C(=O)C=CC1=O]

The title compound was prepared according to General Procedure 8 starting from Compound 4.27 (10 mg). Preparative HPLC purification was accomplished as described in General Procedure 9, eluting with a 10 to 50% $CH_3CN/H_2O$+0.1% TFA gradient to provide the title compound as a white solid (8.8 mg, 75% yield).

LC/MS: Calc'd m/z=1127.4 for $C_{54}H_{62}FN_9O_{17}$, found $[M+H]^+$=1128.6.

$^1$H NMR (300 MHz, MeOD) δ 8.27 (d, J=8.1 Hz, 1H), 7.81 (d, J=10.7 Hz, 1H), 7.65 (s, 1H), 7.32-7.16 (m, 5H), 6.81 (s, 2H), 5.62 (d, J=16.4 Hz, 1H), 5.53 (s, 2H), 5.42 (d, J=16.4 Hz, 1H), 4.93 (s, 2H), 4.67 (s, 1H), 4.51 (dd, J=9.3, 5.6 Hz, 1H), 4.18 (t, J=4.7 Hz, 2H), 4.01-3.44 (m, 19H), 3.17 (dd, J=13.9, 5.8 Hz, 1H), 2.97 (dd, J=13.9, 9.0 Hz, 1H), 2.57 (s, 3H), 2.52 (t, J=6.0 Hz, 2H), 2.03-1.91 (m, 2H), 1.03 (t, J=7.4 Hz, 3H).

4.29: (S)-2-amino-N-(4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl)acetamide (Compound 4.29)

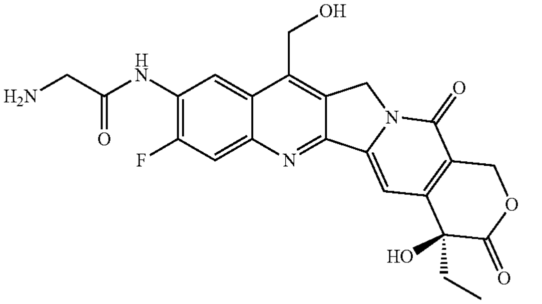 [SMILES: CC[C@@]1(O)C(=O)OCc2c1cc1n(c2=O)Cc2c-1nc1cc(F)c(NC(=O)CN)cc1c2CO]

To a stirring solution of Fmoc-glycine (217 mg) in dimethylformamide (2.5 mL) was added HATU (254 mg), HOAt (83 mg) then NMM (188 uL). This solution was stirred for 10 min then Compound 141 (50 mg) was added and the reaction was stirred at room temperature for 16 h. Lithium hydroxide (2.5 mL, 1 M in water) was added, and the reaction mixture was stirred for 2 h. This solution was partially concentrated, then a solution of 20% piperidine in dimethylformamide (0.5 mL) was added and was stirred for another 20 min. The reaction was then evaporated onto celite and purification was accomplished as described in General Procedure 9, using a 12 g C18 flash column and eluting with a 0 to 40% $CH_3CN/H_2O$+0.1% TFA gradient to provide the title compound as a white solid (TFA salt, 44 mg, 62% yield).

LC/MS: Calc'd m/z=468.1 for $C_{23}H_{21}FN_4O_6$, found $[M+H]^+$=469.4.

$^1H$ NMR (300 MHz, MeOD) δ 8.99 (d, J=8.3 Hz, 1H), 7.99 (s, 1H), 7.87 (d, J=12.0 Hz, 1H), 7.55 (s, 1H), 5.60 (d, J=16.3 Hz, 1H), 5.46-5.35 (m, 3H), 5.30 (s, 2H), 3.53-3.45 (m, 1H), 3.43-3.38 (m, 1H), 2.03-1.87 (m, 2H), 1.02 (t, J=7.3 Hz, 3H).

4.30: (S)-2-(1-(2,5-dioxo-2,5-dihydro-1H-pyrrol-1-yl)-12,15-dioxo-3,6,9-trioxa-13,16-diazaoctadecan-18-amido)-N-(2-(((S)-4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl)amino)-2-oxoethyl)-3-phenylpropanamide (MT-GGFG-Compound 141)

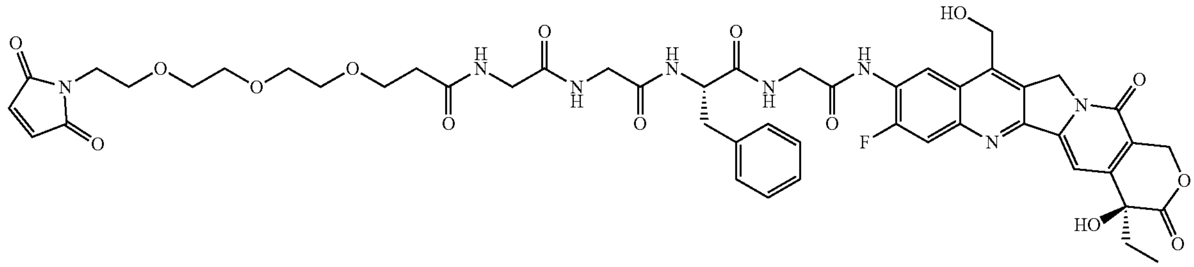 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)CNC(=O)CCOCCOCCOCCN3C(=O)C=CC3=O)cc1c2CO]

To a stirring solution of Compound 4.4 (23 mg) in a mixture of dimethylformamide (0.1 mL) and dichloromethane (0.9 mL) was added HATU (14 mg), a solution of Compound 4.29 (20 mg) in dimethyl formamide (0.1 mL) and dichloromethane (0.9 mL), and DIPEA (24 uL). The mixture was stirred for 15 min, then the reaction was partially concentrated. Preparative HPLC purification was accomplished as described in General Procedure 9, eluting with a 0 to 40% $CH_3CN/H_2O$+0.1% TFA gradient to provide the title compound as a white solid (7.1 mg, 20% yield).

LC/MS: Calc'd m/z=1012.4 for $C_{49}H_{53}FN_8015$, found $[M+H]^+$=1013.6.

$^1H$ NMR (300 MHz, MeOD) δ 9.89 (s, 1H), 8.75 (d, J=8.3 Hz, 1H), 8.44-8.32 (m, 1H), 8.27-8.14 (m, 2H), 7.78 (d, J=11.9 Hz, 1H), 7.53 (s, 1H), 7.39-7.20 (m, 5H), 6.82 (s, 2H), 5.57 (d, J=16.3 Hz, 1H), 5.39 (d, J=16.3 Hz, 1H), 5.34-5.25 (m, 2H), 5.22 (s, 2H), 4.32-4.09 (m, 2H), 3.96-3.83 (m, 3H), 3.76 (t, J=6.0 Hz, 2H), 3.69-3.62 (m, 2H), 3.62-3.47 (m, 9H), 3.40-3.33 (m, 1H), 3.08 (dd, J=14.0, 9.6 Hz, 1H), 2.56 (t, J=6.1 Hz, 2H), 2.03-1.91 (m, 2H), 1.04 (t, J=7.3 Hz, 3H).

4.31: tert-butyl (S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl) carbamate (Compound 4.31)

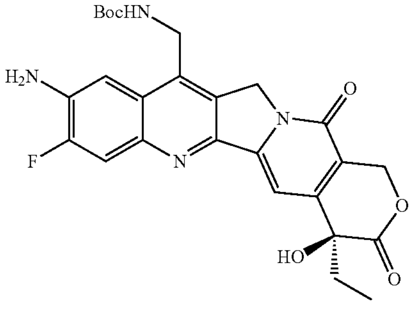 [SMILES: CC[C@@]1(O)C(=O)OCc2c1cc1n(c2=O)Cc2c-1nc1cc(F)c(N)cc1c2CNC(=O)OC(C)(C)C]

To a stirring solution of Compound 145 (32 mg) in dichloromethane (2 mL) and acetonitrile (0.5 mL) was added di-tert-butyl dicarbonate (20 uL) followed by DIPEA (42 uL). The reaction mixture was stirred at room temperature for 3 h then concentrated to dryness to provide the title compound as a red solid (34 mg, 87%).

LC/MS: Calc'd m/z=510.2 for $C_{26}H_{27}FN_4O_6$, found $[M+H]^+$=511.2.

4.32: tert-butyl (S)-((9-(2-aminoacetamido)-4-ethyl-8-fluoro-4-hydroxy-3,14-dioxo-3,4,12,14-tetrahydro-1H-pyrano[3',4':6,7]indolizino[1,2-b]quinolin-11-yl) methyl)carbamate (Compound 4.32)

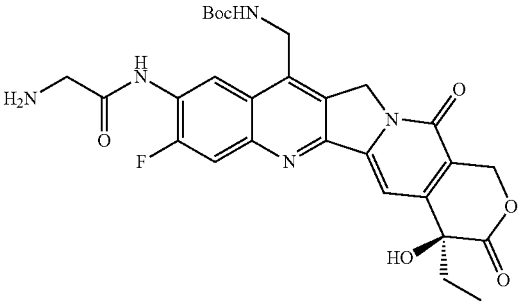 [SMILES: CC[C@@]1(O)C(=O)OCc2c1cc1n(c2=O)Cc2c-1nc1cc(F)c(NC(=O)CN)cc1c2CNC(=O)OC(C)(C)C]

To a stirring solution of Fmoc-glycine (98 mg) in dimethylformamide (1 mL) was added HATU (115 mg), HOAt (37 mg) then NMM (85 μL). This solution was stirred for 10 min, then Compound 4.31 (28 mg) was added. The reaction was stirred at room temperature for 16 h then quenched with a solution of 20% piperidine in dimethylformamide (1 mL) and stirred for an additional 20 min. Purification was accomplished as described in General Procedure 9, using a 12 g C18 flash column and eluting with a 5 to 40% $CH_3CN/H_2O$+0.1% TFA gradient to provide the title compound as a white solid (TFA salt, 25 mg, 67% yield).

LC/MS: Calc'd m/z=567.2 for $C_{28}H_{30}FN_6O_7$, found $[M+H]^+$=568.4.

$^1$H NMR (300 MHz, MeOD) δ 9.01 (d, J=8.3 Hz, 1H), 7.83 (d, J=11.9 Hz, 1H), 7.52 (s, 1H), 5.57 (d, J=16.4 Hz, 1H), 5.38 (d, J=16.3 Hz, 1H), 5.27 (d, J=3.1 Hz, 2H), 4.80 (s, 2H), 4.10 (s, 2H), 1.97 (q, J=7.4 Hz, 2H), 1.50 (s, 9H), 1.02 (t, J=7.3 Hz, 3H).

4.33: tert-butyl (((S)-9-(2-((S)-2-(2-(2-aminoacetamido)acetamido)-3-phenylpropanamido)acetamido)-4-ethyl-8-fluoro-4-hydroxy-3,14-dioxo-3,4,12,14-tetrahydro-1H-pyrano[3',4':6,7]indolizino[1,2-b]quinolin-11-yl)methyl)carbamate (Compound 4.33)

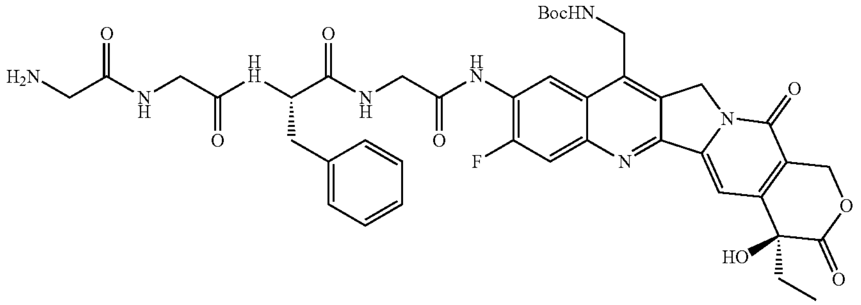

To a stirring solution of Fmoc-GGF-OH (28 mg) and HATU (20 mg) in a mixture of DMF (0.2 mL) and dichloromethane (1.8 mL) was added Compound 4.32 (25 mg) followed by DIPEA (32 uL). This solution was stirred for 15 min at room temperature, quenched with a solution of 20% piperidine in dimethylformamide (0.250 mL), stirred for an additional 20 min, then partially concentrated in vacuo. Purification was accomplished as described in General Procedure 9, using a 12 g C18 flash column and eluting with a 10 to 45% $CH_3CN/H_2O$+0.1% TFA gradient to provide the title compound as a white solid (TFA salt, 22 mg, 64% yield).

LC/MS: Calc'd m/z=828.3 for $C_{41}H_{45}FN_8010$, found $[M+H]^+$=829.6.

4.34: (S)—N-(2-(((S)-11-(aminomethyl)-4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl)-2-(1-(2,5-dioxo-2,5-dihydro-1H-pyrrol-1-yl)-12,15-dioxo-3,6,9-trioxa-13,16-diazaoctadecan-18-amido)-3-phenylpropanamide (MT-GGFG-Compound 145)

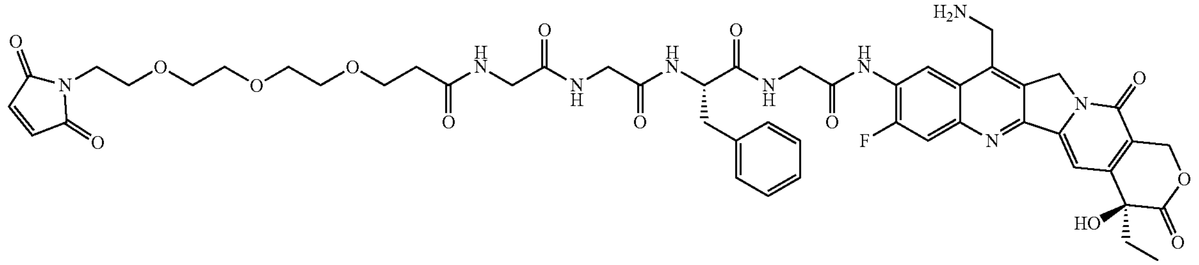 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)CNC(=O)CCOCCOCCOCCN3C(=O)C=CC3=O)cc1c2CN]

The title compound was prepared according to Procedure 6 followed by Procedure 8 starting from Compound 4.33 (15 mg). Preparative HPLC purification of the intermediate Boc-protected compound was accomplished as described in General Procedure 9, eluting with a 10 to 50% $CH_3CN/H_2O$+0.1% TFA gradient. The title compound was obtained post Boc-deprotection as a white-solid (TFA salt, 8.5 mg, 52% yield).

LC/MS: Calc'd m/z=1011.4 for $C_{49}H_{53}FN_8015$, found $[M+H]^+$=1012.6.

$^1$H NMR (300 MHz, MeOD) δ 9.04 (d, J=8.0 Hz, 1H), 8.40 (d, J=5.7 Hz, 1H), 8.21 (d, J=7.7 Hz, 1H), 8.05 (d, J=11.5 Hz, 1H), 7.67 (s, 1H), 7.42-7.03 (m, 5H), 6.81 (s, 2H), 5.63 (d, J=16.4 Hz, 1H), 5.51 (s, 1H), 5.43 (d, J=16.5 Hz, 1H), 4.81 (s, 2H), 4.75-4.58 (m, 1H), 4.29-4.10 (m, 2H), 3.98-3.81 (m, 4H), 3.78-3.71 (m, 2H), 3.71-3.63 (m, 2H), 3.62-3.53 (m, 9H), 3.14-2.98 (m, 1H), 2.54 (t, J=6.0 Hz, 2H), 2.08-1.93 (m, 2H), 1.03 (t, J=7.3 Hz, 3H).

4.35: (9H-fluoren-9-yl)methyl(S)-(2-((4-ethyl-8-fluoro-4-hydroxy-3,14-dioxo-11-(piperidin-1-ylmethyl)-3,4,12,14-tetrahydro-1H-pyrano[3',4':6,7]indolizino[1,2-b]quinolin-9-yl)amino)-2-oxoethyl) carbamate (Compound 4.35)

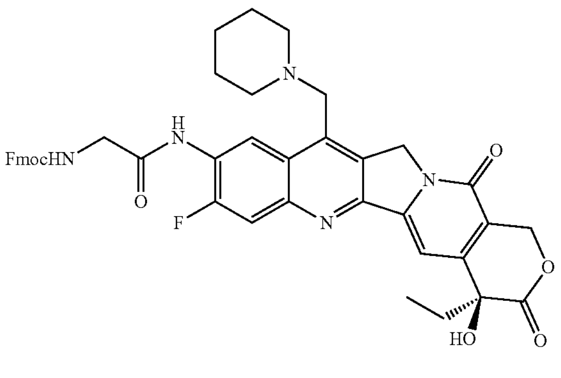

To a solution of Fmoc-Gly-OH (100.9 mg, 0.34 mmol) in dimethylformamide (550 uL) was added NMM (0.112 mL,1.02 mmol) and HATU (0.103 μg, 0.272 mmol). This solution was stirred at room temperature for 20 min, then a solution of Compound 148 (32.5 mg, 0.068 mmol) in DMF (250 uL) was added, and the reaction mixture was stirred for 16 h. Purification was accomplished as described in General Procedure 9, using a 12 g C18 flash column and eluting with a 5 to 40% $CH_3CN/H_2O$+0.1% TFA gradient. The obtained residue was re-purified according to General Procedure 9, using a 10 g flash column and eluting with a 0 to 10% MeOH/DCM gradient to provide the title compound as a yellow powder (15.3 mg, 30% yield).

LC/MS: Calc'd m/z=757.3 for $C_{43}H_{40}FN_5O_7$, found $[M+H]^+$=758.6.

4.36: (S)-2-(1-(2,5-dioxo-2,5-dihydro-1H-pyrrol-1-yl)-12,15-dioxo-3,6,9-trioxa-13,16-diazaoctadecan-18-amido)-N-(2-(((S)-4-ethyl-8-fluoro-4-hydroxy-3,14-dioxo-11-(piperidin-1-ylmethyl)-3,4,12,14-tetrahydro-1H-pyrano[3',4':6,7]indolizino[1,2-b]quinolin-9-yl)amino)-2-oxoethyl)-3-phenylpropanamide (MT-GGFG-Compound 148)

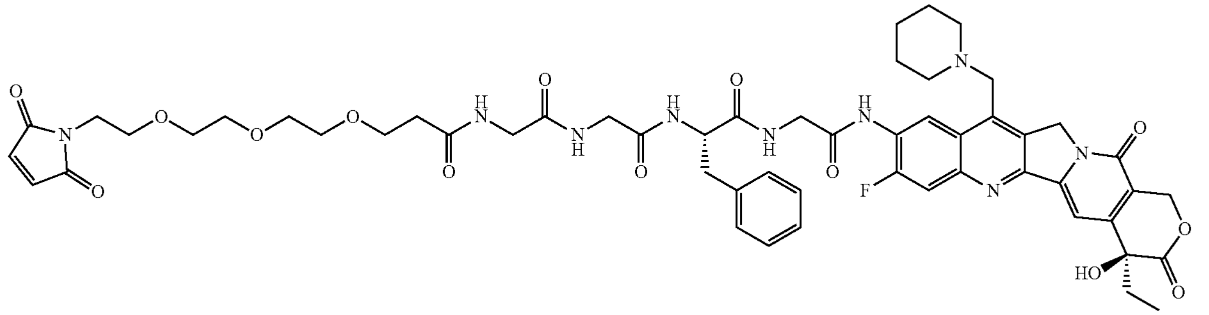 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)CNC(=O)CCOCCOCCOCCN3C(=O)C=CC3=O)cc1c2CN1CCCCC1]

To a 50 mL flask containing Compound 4.35 (15.3 mg, 0.02 mmol) was added a solution of 20% piperidine in DMF (2.0 mL). This solution was stirred at room temperature for 5 min then evaporated to dryness. The obtained residue was then dissolved in 10% DMF/DCM (1.0 mL), then NMM (5.50 μL, 0.05 mmol), Compound 4.4 (11.2 mg, 0.02 mmol) and HATU (8.7 mg, 0.02 mmol) were added. This solution was stirred for 45 min, then partially evaporated. Preparative HPLC purification was accomplished as described in General Procedure 9, eluting with a 15 to 45% $CH_3CN/H_2O$+0.1% TFA gradient to give the title product as a yellow powder (7.8 mg, 33% yield).

LC/MS: Calc'd m/z=1079.4 for $C_{54}H_{62}FN_9O_{14}$, found $[M+H]^+$=1080.8.

$^1$H NMR (300 MHz, MeOD) δ 8.99 (d, J=8.2 Hz, 1H), 7.52 (d, J=12.3 Hz, 1H), 7.39-7.25 (m, 5H), 7.25-7.17 (m, 1H), 6.79 (s, 2H), 5.53 (d, J=16.4 Hz, 1H), 5.33 (d, J=16.5 Hz, 1H), 4.80-4.72 (m, 1H), 4.32-4.11 (m, 2H), 3.98-3.79 (m, 6H), 3.76 (t, J=6.0 Hz, 2H), 3.66-3.60 (m, 2H), 3.62-3.49 (m, I0H), 3.15-3.03 (m, 1H), 2.65-2.47 (m, 6H), 1.96 (q, J=7.4 Hz, 2H), 1.72-1.57 (m, 4H), 1.57-1.42 (m, 2H), 1.03 (t, J=7.4 Hz, 3H).

4.37: tert-butyl (2-((2-(((S)-1-((2-((4-(N—(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)sulfamoyl)phenyl)amino)-2-oxoethyl)amino)-1-oxo-3-phenylpropan-2-yl)amino)-2-oxoethyl)amino)-2-oxoethyl)carbamate (Compound 4.37)

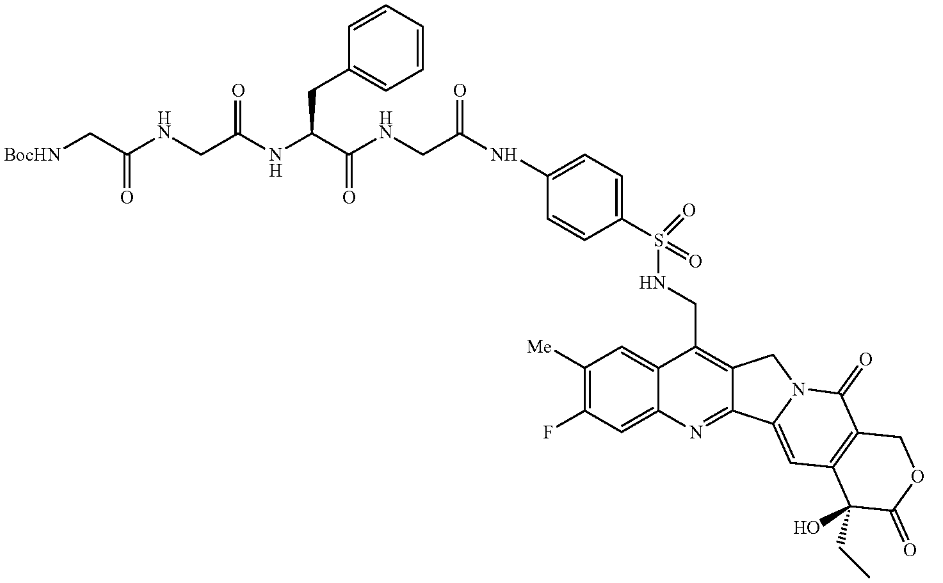 [SMILES: CC[C@@]1(O)C(=O)OCc2c1cc1n(c2=O)Cc2c-1nc1cc(F)c(C)cc1c2CNS(=O)(=O)c1ccc(NC(=O)CNC(=O)[C@H](Cc2ccccc2)NC(=O)CNC(=O)CNC(=O)OC(C)(C)C)cc1]

The title compound was prepared according to General Procedure 7 starting from Compound 127 (46 mg). Preparative HPLC purification was accomplished as described in General Procedure 9, eluting with a 10 to 60% $CH_3CN/H_2O$+0.1% TFA gradient to provide the title compound as a white solid (7.2 mg, 21% yield).

LC/MS: Calc'd m/z=983.0 for $C_{48}H_{51}N_8O_{12}S$, found $[M+H]^+$=983.9.

4.38: (S)-2-(1-(2,5-dioxo-2,5-dihydro-1H-pyrrol-1-yl)-12,15-dioxo-3,6,9-trioxa-13,16-diazaoctadecan-18-amido)-N-(2-((4-(N—(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)sulfamoyl) phenyl)amino)-2-oxoethyl)-3-phenylpropanamide (MT-GGFG-Compound 127)

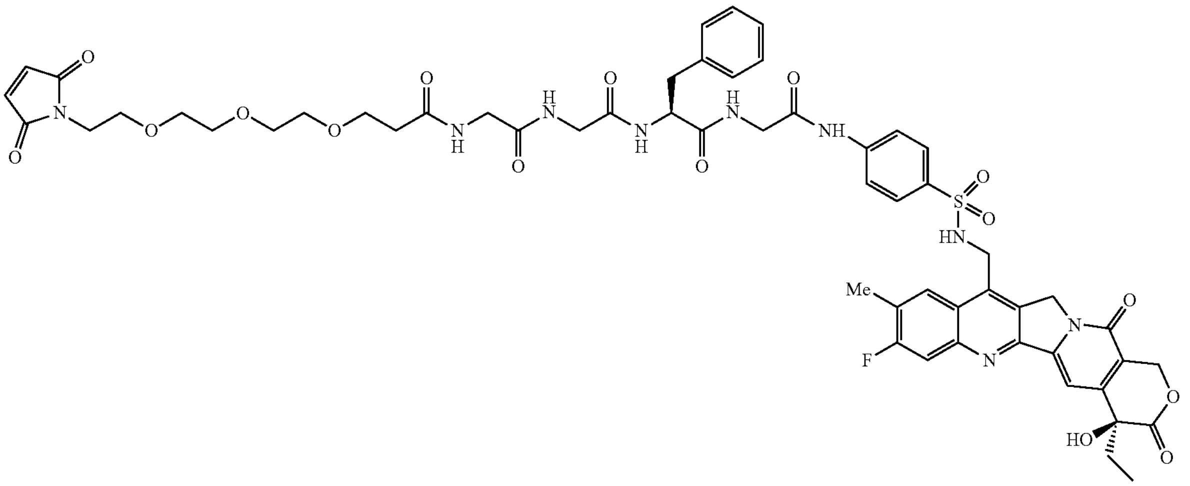 [SMILES: CC[C@@]1(O)C(=O)OCc2c1cc1n(c2=O)Cc2c-1nc1cc(F)c(C)cc1c2CNS(=O)(=O)c1ccc(NC(=O)CNC(=O)[C@H](Cc2ccccc2)NC(=O)CNC(=O)CNC(=O)CCOCCOCCOCCN2C(=O)C=CC2=O)cc1]

The title compound was prepared according to Procedure 6 followed by Procedure 8 starting from Compound 4.37 (7.2 mg). Preparative HPLC purification was accomplished as described in General Procedure 9, eluting with a 10 to 50% $CH_3CN/H_2O$+0.1% TFA gradient to provide the title compound as a white solid (1 mg, 12% yield).

LC/MS: Calc'd m/z=1166.2 for $C_{56}H_{60}FN_9O_{16}$, found $[M+H]^+$=1167.1

4.39: (9H-fluoren-9-yl)methyl ((7S)-1-((3-azabicyclo[3.1.1]heptan-6-yl)oxy)-7-benzyl-3,6,9,12-tetraoxo-2,5,8,11-tetraazatridecan-13-yl)carbamate (Compound 4.39)

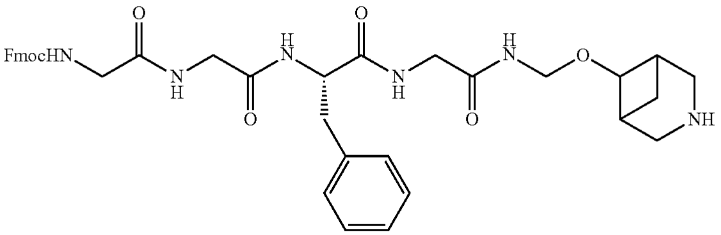

To a stirring solution of Compound 4.6 (44 mg) in dichloromethane (2 mL) was added 3-azabicyclo[3.1.1]heptan-6-ol (5.3 mg) followed by trifluoracetic acid (0.4 mL). After 30 min the reaction was concentrated in vacuo. Purification was accomplished as described in General Procedure 9, using a 10 g flash column and eluting with a 0 to 20% dichloromethane/methanol gradient to provide the title compound as a white solid (14.7 mg, 46% yield).

LC/MS: Calc'd m/z=682.8 for $C_{37}H_{42}N_6O_7$, found $[M+H]^+$=683.6.

4.40: (2S)-2-(2-(2-aminoacetamido)acetamido)-N-(2-((((3-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-azabicyclo[3.1.1]heptan-6-yl)oxy)methyl)amino)-2-oxoethyl)-3-phenylpropanamide (Compound 4.40)

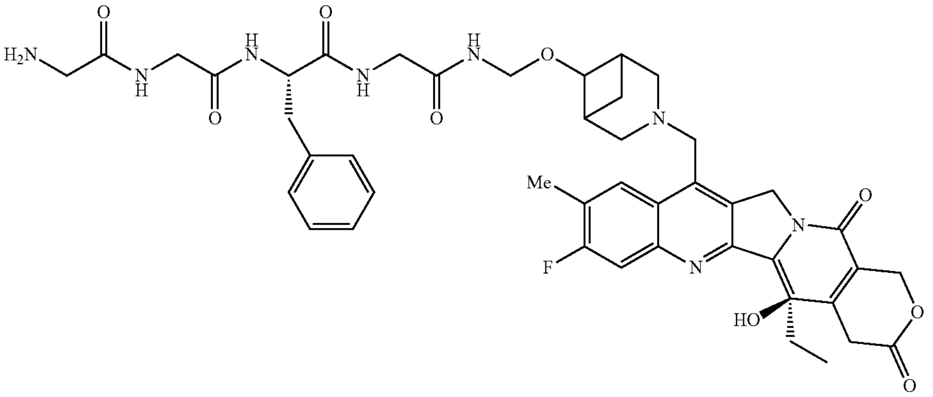

The title compound was prepared according to General Procedure 1 starting from Compound 1.1 (3 mg, 0.007 mmol) and Compound 4.39 (14.7 mg, 0.022 mmol) and utilizing 200 uL DMF. Following complete consumption of Compound 1.1, a solution of 20% piperidine in DMF (200 uL) was added and this solution was stirred at room temperature for 10 min. Preparative HPLC purification was accomplished as described in General Procedure 9, eluting with a 20 to 37% $CH_3CN/H_2O$+0.1% TFA gradient to give the title compound as an off-white solid (TFA salt, 1.8 mg, 29% yield).

LC/MS: Calc'd m/z=852.9 for $C_{44}H_{49}FNsO_9$, found $[M+H]^+$=853.7.

4.41: (2S)-2-(1-(2,5-dioxo-2,5-dihydro-1H-pyrrol-1-yl)-12,15-dioxo-3,6,9-trioxa-13,16-diazaoctadecan-18-amido)-N-(2-((((3-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-azabicyclo[3.1.1]heptan-6-yl)oxy)methyl)amino)-2-oxoethyl)-3-phenylpropanamide (MT-GGFG-AM-Compound 117)

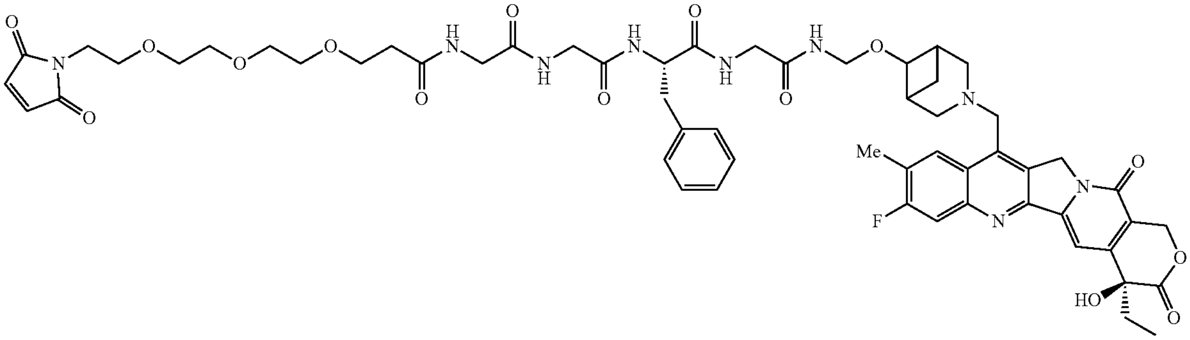 [SMILES: CC[C@@]1(O)C(=O)OCc2c1cc1n(c2=O)Cc2c-1nc1cc(F)c(C)cc1c2CN1CC2CC(C1)C2OCNC(=O)CNC(=O)[C@H](Cc1ccccc1)NC(=O)CNC(=O)CNC(=O)CCOCCOCCOCCN1C(=O)C=CC1=O]

The title compound was prepared according to Procedure 8 starting from Compound 4.40 (1.8 mg). Preparative HPLC purification was accomplished as described in General Procedure 9, eluting with a 25 to 45% $CH_3CN/H_2O$+0.1% TFA gradient to provide the title compound as a white-solid (TFA salt, 0.5 mg, 22% yield).

LC/MS: Calc'd m/z=1135.5 for $C_{57}H_{66}FN_9O_{15}$, found $[M+H]^+$=1136.3.

4.42: (9H-fluoren-9-yl)methyl (S)-(9-benzyl-1-(3-fluoroazetidin-3-yl)-5,8,11,14-tetraoxo-2-oxa-4,7,10,13-tetraazapentadecan-15-yl)carbamate (Compound 4.42)

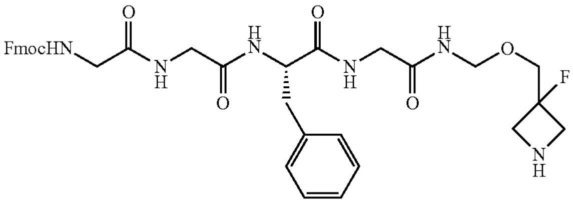

To a stirring solution of Compound 4.6 (144 mg) in dichloromethane (2 mL) was added (3-fluoroazetidin-3-yl) methanol (16 mg) followed by trifluoracetic acid (0.4 mL). After 30 min the reaction was concentrated in vacuo. Purification was accomplished as described in General Procedure 9, using a 10 g flash column and eluting with a 0 to 20% dichloromethane/methanol gradient to provide the title compound as a white solid (55 mg, 54% yield).

LC/MS: Calc'd m/z=674.7 for $C_{35}H_{39}N_6FO_7$, found $[M+H]^+$=675.6.

4.43: (S)-2-(2-(2-aminoacetamido)acetamido)-N-(2-((((1-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-fluoroazetidin-3-yl)methoxy)methyl)amino)-2-oxoethyl)-3-phenylpropanamide (Compound 4.43)

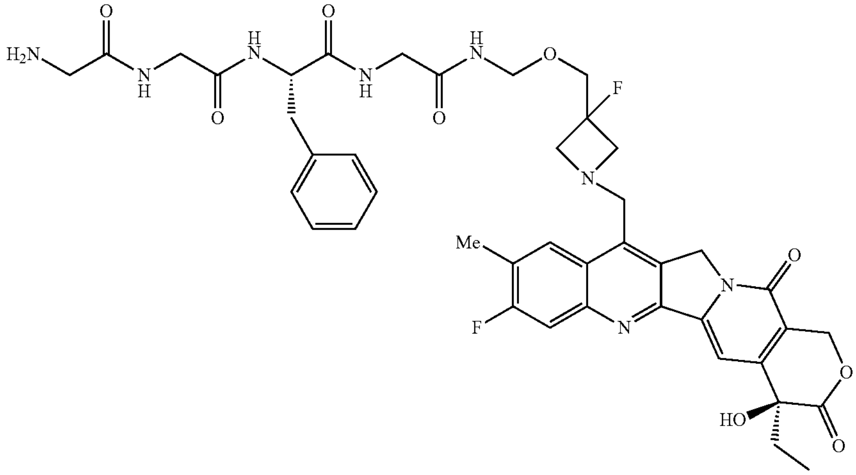 [SMILES: CC[C@@]1(O)C(=O)OCc2c1cc1n(c2=O)Cc2c-1nc1cc(F)c(C)cc1c2CN1CC(F)(COCNC(=O)CNC(=O)[C@H](Cc2ccccc2)NC(=O)CNC(=O)CN)C1]

The title compound was prepared according to General Procedure 1 starting from Compound 1.1 (11.6 mg, 0.027 mmol) and Compound 4.42 (55 mg, 0.082 mmol) and utilizing 500 uL DMF. Following complete consumption of Compound 1.1, a solution of 20% piperidine in DMF (500 uL) was added and this solution was stirred at room temperature for 10 min.

Preparative HPLC purification was accomplished as described in General Procedure 9, eluting with a 25 to 32% $CH_3CN/H_2O$+0.1% TFA gradient to give the title compound as an off-white solid (TFA salt, 8.1 mg, 28% yield).

LC/MS: Calc'd m/z=844.3 for $C_{42}H_{46}F_2N_809$, found $[M+H]^+$=845.3

4.44: (S)-2-(1-(2,5-dioxo-2,5-dihydro-1H-pyrrol-1-yl)-12,15-dioxo-3,6,9-trioxa-13,16-diazaoctadecan-18-amido)-N-(2-((((1-(((S)-4-ethyl-8-fluoro-4-hydroxy-9-methyl-3,14-dioxo-3,4,12,14-tetrahydro-1H-pyrano[3',4':6,7]indolizino[1,2-b]quinolin-11-yl)methyl)-3-fluoroazetidin-3-yl)methoxy)methyl)amino)-2-oxoethyl)-3-phenylpropanamide (MT-GGFG-AM-Compound 118)

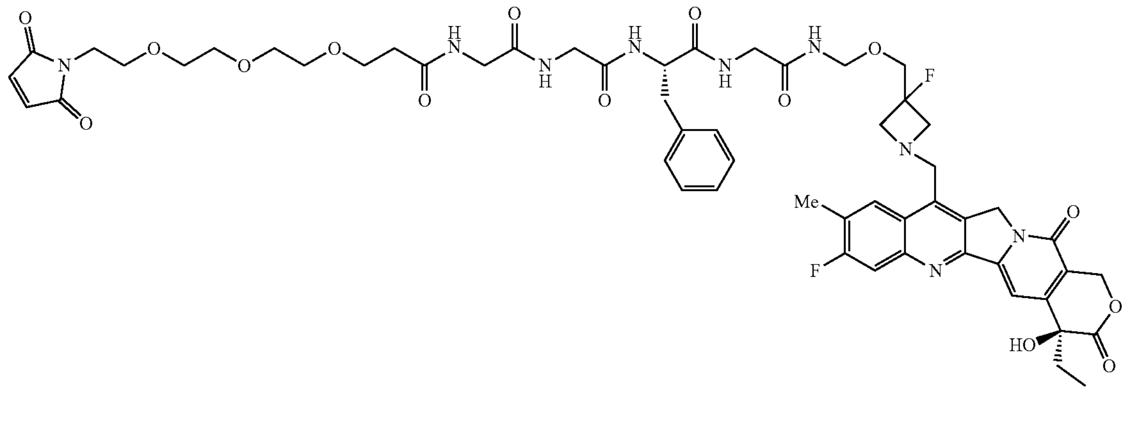 [SMILES: CC[C@@]1(O)C(=O)OCc2c1cc1n(c2=O)Cc2c-1nc1cc(F)c(C)cc1c2CN1CC(F)(COCNC(=O)CNC(=O)[C@H](Cc2ccccc2)NC(=O)CNC(=O)CNC(=O)CCOCCOCCOCCN2C(=O)C=CC2=O)C1]

The title compound was prepared according to Procedure 8 starting from Compound 4.43 (8.1 mg). Preparative HPLC purification was accomplished as described in General Procedure 9, eluting with a 25 to 45% $CH_3CN/H_2O$+0.1% TFA gradient to provide the title compound as a white-solid (TFA salt, 2.9 mg, 28% yield).

LC/MS: Calc'd m/z=1127.4 for $C_{55}H_{63}F_2N_9O_{15}$, found $[M+H]^+$=1128.8.

4.45: (S)-10-BENZYL-23-(2,5-DIOXO-2,5-DIHYDRO-1H-PYRROL-1-YL)-6,9,12,15,18-PENTAOXO-3-OXA-5,8,11,14,7-PENTAAZATRICOSYL (((S)-4-ETHYL-8-FLUORO-4-HYDROXY-9-METHYL-3,14-DIOXO-3,4,12,14-TETRAHYDRO-1H-PYRANO[3',4':6,7]INDOLIZINO[1,2-B]QUINOLIN-11-YL)METHYL)CARBAMATE (MC-GGFG-AM-COMPOUND 139)

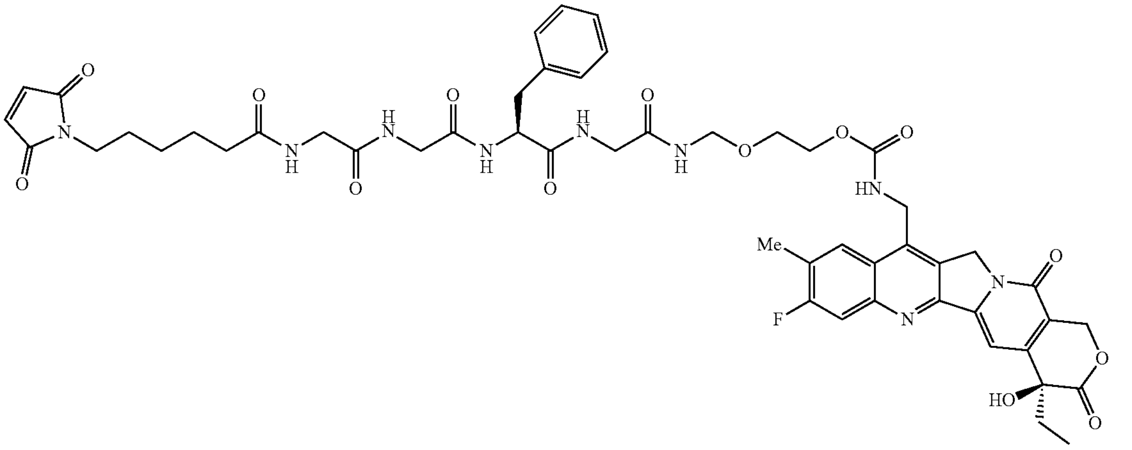 [SMILES: CC[C@@]1(O)C(=O)OCc2c1cc1n(c2=O)Cc2c-1nc1cc(F)c(C)cc1c2CNC(=O)OCCOCNC(=O)CNC(=O)[C@H](Cc1ccccc1)NC(=O)CNC(=O)CNC(=O)CCCCCN1C(=O)C=CC1=O]

To Compound 4.27 (450 mg) was added a solution of 2,5-dioxopyrrolidin-1-yl 6-(2,5-dioxopyrrol-1-yl)hexanoate (130 mg) and N-ethyldiisopropylamine (250 uL) in DMF (10 mL). This solution was stirred at room temperature for 30 min then concentrated to −1 mL volume. Purification was accomplished as described in General Procedure 9 first using a 60 g C18 flash column and eluting with a 10 to 60% $CH_3CN/H_2O$+0.1% TFA gradient followed by preparative HPLC of impure fractions using a 20 to 50% $CH_3CN/H_2O$+0.1% TFA gradient to provide the title compound as a white solid (320 mg, 66% yield).

LC/MS: Calc'd m/z=1037.4 for $C_{51}H_{56}FN_9O_{14}$, found $[M+H]^+$=1038.6.

$^1$H NMR (300 MHz, MeOD) δ 8.10 (d, J=8.1 Hz, 2H), 8.01 (s, 1H), 7.95 (d, J=7.0 Hz, 1H), 7.74 (d, J=10.4 Hz, 1H), 7.66 (s, 1H), 7.56 (s, 1H), 7.32-7.10 (m, 5H), 6.69 (s, 2H), 5.63 (d, J=16.4 Hz, 1H), 5.46 (s, 2H), 5.32 (s, 1H), 5.28 (d, J=16.5 Hz, 1H), 4.88 (s, 2H), 4.67 (d, J=6.4 Hz, 2H), 4.48 (d, J=7.1 Hz, 2H), 4.15 (t, J=4.2 Hz, 2H), 3.92 (dd, J=17.1, 6.2 Hz, 2H), 3.83-3.57 (m, 6H), 3.46 (t, J=7.1 Hz, 2H), 3.16 (dd, J=14.0, 5.9 Hz, 1H), 2.95 (dd, J=13.9, 8.9 Hz, 1H), 2.53 (s, 3H), 2.21 (t, J=7.6 Hz, 2H), 1.97-1.79 (m, 2H), 1.58 (dp, J=15.0, 7.6 Hz, 4H), 1.29 (dd, J=16.6, 9.3 Hz, 3H), 1.01 (t, J=7.3 Hz, 3H).

4.46: tert-butyl (S)-(2-((4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl) carbamate (Compound 4.46)

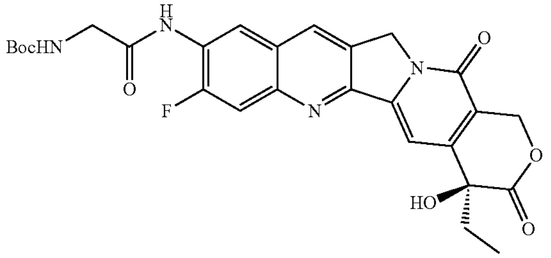 [SMILES: CC[C@@]1(O)C(=O)OCc2c1cc1n(c2=O)Cc2cc3cc(NC(=O)CNC(=O)OC(C)(C)C)c(F)cc3nc2-1]

A solution of Compound 140 (860 mg, 1.7 mmol, TFA salt), Boc-Gly-OH (760 mg, 4.3 mmol), HATU (1.6 μg, 4.1 mmol), and N-ethyldiisopropylamine (0.6 mL) in DMF (4 mL) was stirred at room temperature for 24 h then poured into water (50 mL). The resulting solid was collected by filtration, redissolved in 10% MeOH/DCM and purification was accomplished as described in General Procedure 9, using a 30 g silica column and eluting with a 0 to 10% MeOH/DCM to provide the title compound as a yellow solid (750 mg, 80% yield).

LC/MS: Calc'd m/z=538.5 for $C_{27}H_{27}FN_4O_7$, found $[M+H]^+$=539.4.

$^1$H NMR (300 MHz, MeOD) δ 8.84 (d, J=8.4 Hz, 1H), 8.52 (s, 1H), 8.00 (s, 1H), 7.87 (d, J=12.1 Hz, 1H), 7.62 (s, 1H), 5.60 (d, J=16.3 Hz, 1H), 5.40 (d, J=16.4 Hz, 1H), 5.27 (s, 2H), 4.02 (s, 2H), 1.99 (dt, J=8.7, 6.7 Hz, 2H), 1.52 (s, 9H), 1.03 (t, J=7.4 Hz, 3H).

4.47: (S)-1-((2-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-aminium (Compound 4.47)

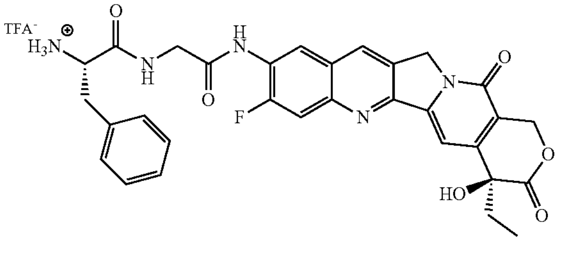 [SMILES: CC[C@@]1(O)C(=O)OCc2c1cc1n(c2=O)Cc2cc3cc(NC(=O)CNC(=O)[C@@H]([NH3+])Cc4ccccc4)c(F)cc3nc2-1]

The title compound was prepared in three steps from Compound 4.46 (750 mg). The Boc protecting group was cleaved in neat TFA (2 mL) followed by precipitation in $Et_2O$ (50 mL). The solid was collected by filtration and added to a solution of 2,5-dioxopyrrolidin-1-yl (2S)-2-[(tert-butoxycarbonyl)amino]-3-phenylpropanoate (340 mg, 1.1 equiv) and N-ethyldiisopropylamine (300 uL) in DMF (1.7 mL). This solution was stirred at room temperature for 30 min then pipetted into $Et_2O$ (50 mL). The precipitate was collected by filtration, dried under vacuum then dissolved in neat TFA (2 mL). After 20 min, $Et_2O$ (50 mL) was added and the precipitate collected by filtration to provide the title compound as a yellow solid (531 mg, 54% yield).

LC/MS: Calc'd m/z=585.2 for $C_{31}H_{28}FN_5O_6$, found $[M+H]^+$=586.1.

4.48: 2-((2-(((S)-1-((2-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-yl)amino)-2-oxoethyl)amino)-2-oxoethan-1-aminium (Compound 4.48)

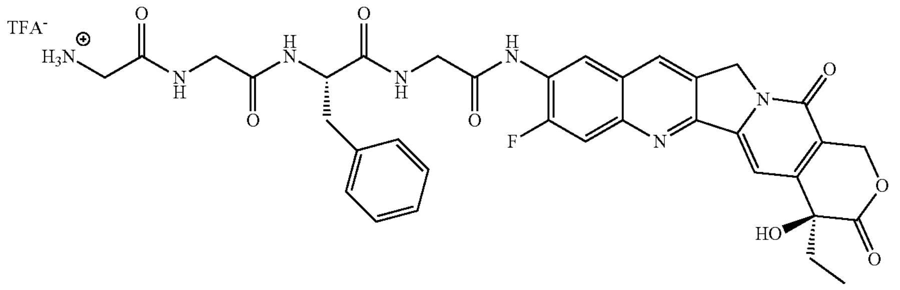 [SMILES: CC[C@@]1(O)C(=O)OCc2c1cc1n(c2=O)Cc2cc3cc(NC(=O)CNC(=O)[C@H](Cc4ccccc4)NC(=O)CNC(=O)C[NH3+])c(F)cc3nc2-1]

To Compound 4.47 (490 mg) was added a solution of Boc-gly-gly-NHS (250 mg, 1.1 equiv) and N-ethyldiisopropylamine (250 uL) in DMF (3 mL). This solution was stirred at room temperature for 30 min then pipetted into $Et_2O$ (50 mL). The precipitate was collected by filtration then dissolved in neat TFA (2 mL). After 20 min, $Et_2O$ (50 mL) was added and the precipitate collected by filtration to provide the title compound as a yellow solid (500 mg, 88% yield).

LC/MS: Calc'd m/z=699.2 for $C_{35}H_{34}FN_708$, found $[M+H]^+$=700.4.

4.49: 6-(2,5-dioxo-2,5-dihydro-1H-pyrrol-1-yl)-N-(2-((2-(((S)-1-((2-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-yl)amino)-2-oxoethyl)amino)-2-oxoethyl)hexanamide (MC-GGFG-Compound 140)

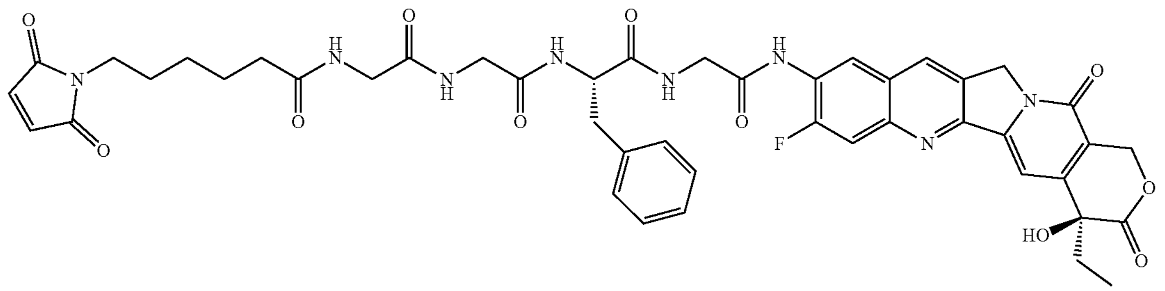 [SMILES: CC[C@@]1(O)C(=O)OCc2c1cc1n(c2=O)Cc2cc3cc(NC(=O)CNC(=O)[C@H](Cc4ccccc4)NC(=O)CNC(=O)CNC(=O)CCCCCN4C(=O)C=CC4=O)c(F)cc3nc2-1]

To Compound 4.48 (500 mg) was added a solution of 2,5-dioxocyclopentyl 6-(2,5-dioxopyrrol-1-yl)hexanoate (210 mg, 1.1 equiv) and N-ethyldiisopropylamine (215 uL) in DMF (4 mL). This solution was stirred at room temperature for 30 min then pipetted into $Et_2O$ (50 mL).

The precipitate was collected by filtration then dissolved in DMF (2 mL). Preparative HPLC purification was accomplished as described in General Procedure 9, eluting with a 24 to 38% $CH_3CN/H_2O$+0.1% TFA gradient to provide the title compound as a yellow solid (190 mg, 40% yield).

LC/MS: Calc'd m/z=892.9 for $C_{45}H_{45}FN_8011$, found $[M+H]^+$=893.6.

$^1H$ NMR (300 MHz, $CD_3CN$) 6 8.67 (d, J=8.4 Hz, 1H), 8.44 (s, 1H), 7.78 (d, J=12.1 Hz, 1H), 7.41 (s, 1H), 7.30 (d, J=4.3 Hz, 4H), 7.26-7.16 (m, 1H), 6.72 (s, 2H), 5.52 (d, J=16.4 Hz, 1H), 5.31 (d, J=16.4 Hz, 1H), 5.12 (s, 2H), 4.64 (dd, J=9.7, 5.0 Hz, 1H), 4.11 (d, J=3.2 Hz, 2H), 3.87-3.68 (m, 4H), 3.37 (t, J=7.1 Hz, 2H), 3.00 (dd, J=14.0, 9.7 Hz, 1H), 2.20 (t, J=7.6 Hz, 2H), 1.49 (dq, J=19.5, 7.4 Hz, 4H), 1.22 (p, J=7.6, 7.1 Hz, 2H), 0.94 (t, J=7.3 Hz, 3H).

4.50: tert-butyl (S)-(2-((4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl)amino)-2-oxoethyl)carbamate (Compound 4.50)

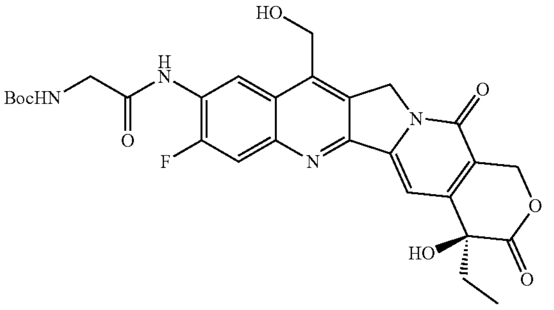 [SMILES: CC[C@@]1(O)C(=O)OCc2c1cc1n(c2=O)Cc2c-1nc1cc(F)c(NC(=O)CNC(=O)OC(C)(C)C)cc1c2CO]

A solution of Compound 4.46 (1.8 g), iron (II) sulfate heptahydrate (1.4 µg, 1.5 equiv), and sulfuric acid (450 uL, 2.5 equiv) in MeOH (33 mL) was heated to 60° C. and hydrogen peroxide (1.25 mL, 12 equiv) was added dropwise over 10 min. This solution was heated for another 20 min then cooled to room temperature and poured into ice water (~200 mL). The brown precipitate was collected by filtration and the filtrate was quenched with saturated aqueous $Na_2S203$. MeOH was evaporated and the solution allowed to stand for 2 h while a second brown precipitate formed.

This precipitate was collected by filtration and the combined precipitates were purified as described in General Procedure 9 using a 50 g silica column and eluting with a 0 to 15% MeOH/DCM gradient to provide the title compound as a yellow solid (860 mg, 45% yield).

LC/MS: Calc'd m/z=568.5 for $C_{28}H_{29}FN_4O_8$, found $[M+H]^+$=569.7.

4.51: (S)-1-((2-(((S)-4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-aminium (Compound 4.51)

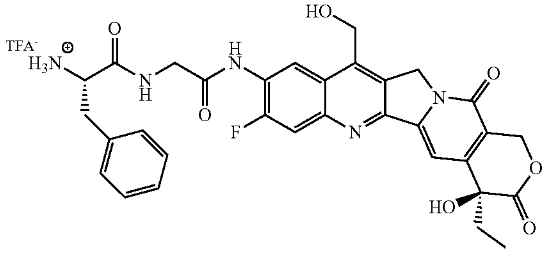 [SMILES: CC[C@@]1(O)C(=O)OCc2c1cc1n(c2=O)Cc2c-1nc1cc(F)c(NC(=O)CNC(=O)[C@@H]([NH3+])Cc3ccccc3)cc1c2CO]

The title compound was prepared in three steps from Compound 4.50 (750 mg). The Boc protecting group was cleaved in neat TFA (2 mL) followed by precipitation in $Et_2O$ (100 mL).

The solid was collected by filtration and added to a solution of 2,5-dioxopyrrolidin-1-yl (2S)-2-[(tert-butoxycarbonyl)amino]-3-phenylpropanoate (600 mg, 1.1 equiv) and N-ethyldiisopropylamine (300 uL) in DMF (7 mL). This solution was stirred at room temperature for 30 min then pipetted into $Et_2O$ (100 mL). The precipitate was collected by filtration, dried under vacuum then dissolved in neat TFA (2 mL). After 20 min, $Et_2O$ (100 mL) was added and the precipitate collected by filtration to provide the title compound as a yellow solid (756 mg, 78% yield).

LC/MS: Calc'd m/z=615.2 for $C_{32}H_{30}FN_5O_7$, found $[M+H]^+$=616.3.

4.52: 2-((2-(((S)-1-((2-(((S)-4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-yl)amino)-2-oxoethyl)amino)-2-oxoethan-1-aminium (Compound 4.52)

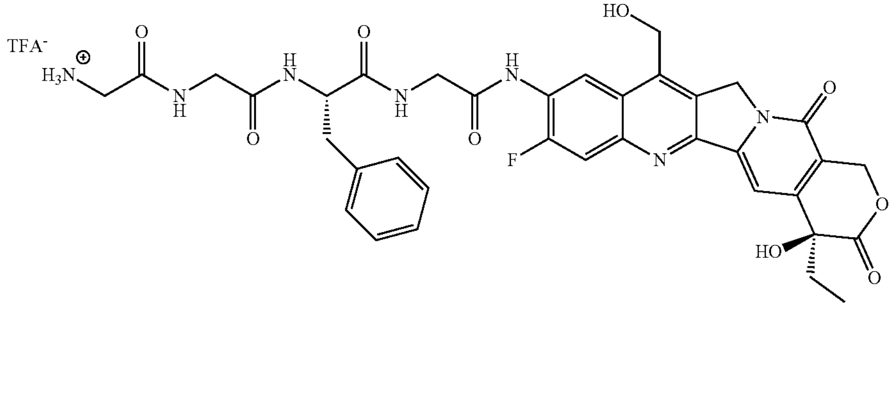 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)C[NH3+])cc1c2CO]

To Compound 4.51 (756 mg) was added a solution of Boc-gly-gly-NHS (375 mg, 1.1 equiv) and N-ethyldiisopropylamine (400 uL) in DMF (5 mL). This solution was stirred at room temperature for 30 min then pipetted into $Et_2O$ (75 mL). The precipitate was collected by filtration then dissolved in neat TFA (4 mL). After 20 min, $Et_2O$ (100 mL) was added and the precipitate collected by filtration to provide the title compound as a yellow solid (826 mg, 95% yield).

LC/MS: Calc'd m/z=729.2 for $C_{36}H_{36}FN_{7}09$, found $[M+H]^{+}$=730.2.

4.53: 6-(2,5-dioxo-2,5-dihydro-1H-pyrrol-1-yl)-N-(2-((2-(((S)-1-((2-(((S)-4-ethyl-8-fluoro-4-hydroxy-11-(hydroxymethyl)-3,14-dioxo-3,4,12,14-tetrahydro-1H-pyrano[3',4':6,7]indolizino[1,2-b]quinolin-9-yl)amino)-2-oxoethyl)amino)-1-oxo-3-phenylpropan-2-yl)amino)-2-oxoethyl)amino)-2-oxoethyl)hexanamide (MC-GGFG-Compound 141)

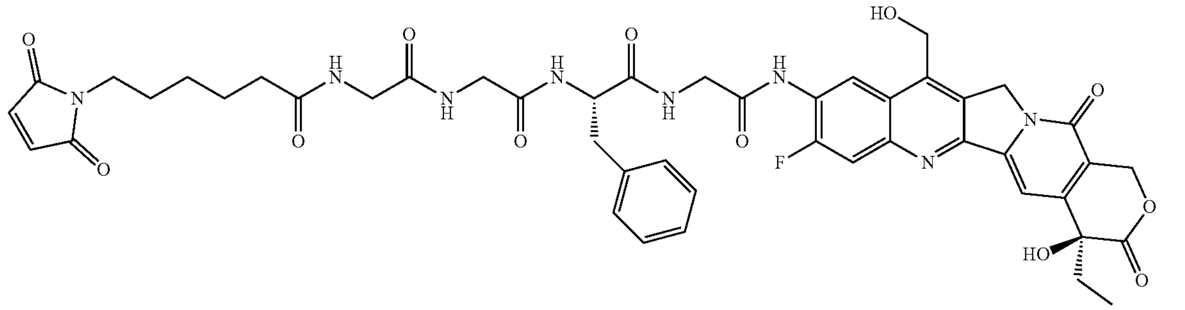 [SMILES: CC[C@@]1(O)C(=O)OCc2c1cc1n(c2=O)Cc2c-1nc1cc(F)c(NC(=O)CNC(=O)[C@H](Cc3ccccc3)NC(=O)CNC(=O)CNC(=O)CCCCCN3C(=O)C=CC3=O)cc1c2CO]

To Compound 4.52 (826 mg) was added a solution of 2,5-dioxocyclopentyl 6-(2,5-dioxopyrrol-1-yl)hexanoate (382 mg, 1.1 equiv) and N-ethyldiisopropylamine (300 uL) in DMF (5.5 mL). This solution was stirred at room temperature for 30 min then pipetted into $Et_2O$ (100 mL). The precipitate was collected by filtration then dissolved in DMF (2 mL). Preparative HPLC purification was accomplished as described in General Procedure 9, eluting with a 25 to 40% $CH_3CN/H_2O$+0.1% TFA gradient to provide the title compound as a yellow solid (370 mg, 35% yield).

LC/MS: Calc'd m/z=922.9 for $C_{46}H_{47}FN_{8}012$, found $[M+H]^{+}$=923.8.

$^1$H NMR (300 MHz, $CD_3CN$) 6 8.63 (d, J=8.4 Hz, 1H), 7.67 (d, J=11.9 Hz, 1H), 7.38-7.27 (m, 5H), 7.24 (d, J=4.3 Hz, 1H), 6.72 (s, 2H), 5.48 (d, J=16.4 Hz, 1H), 5.28 (d, J=16.3 Hz, 1H), 5.24-5.01 (m, 4H), 4.65 (dd, J=9.7, 4.9 Hz, 1H), 4.13 (s, 2H), 3.85-3.75 (m, 3H), 3.37 (t, J=7.1 Hz, 2H), 3.00 (dd, J=14.0, 9.8 Hz, 1H), 2.21 (t, J=7.6 Hz, 2H), 1.51 (dp, J=22.0, 7.4 Hz, 4H), 1.22 (p, J=7.4, 7.0 Hz, 2H), 0.94 (t, J=7.3 Hz, 3H).

4.54: tert-butyl ((S)-1-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-1-oxopropan-2-yl)carbamate (Compound 4.54)

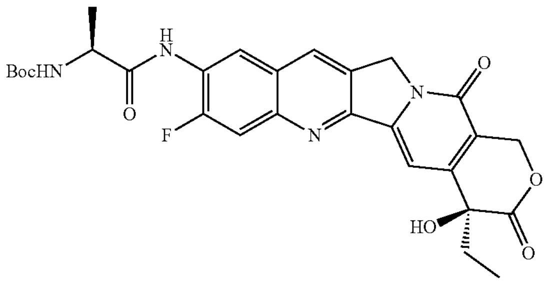 [SMILES: CC[C@@]1(O)C(=O)OCc2c1cc1n(c2=O)Cc2cc3cc(NC(=O)[C@H](C)NC(=O)OC(C)(C)C)c(F)cc3nc2-1]

To Compound 3.4 (500 mg, 1.0 mmol) was added TFA (4 mL) and this solution was allowed to stand at rt for 1 h, then $Et_2O$ (100 mL) was added, and the precipitate was collected by filtration. This solid was taken up in DMF (3.4 mL) and Boc-Ala-OH (590 mg, 3.1 mmol, 3 equiv) and HATU (1.2 µg, 3.1 mmol, 3 equiv) were added followed by N-ethyldiisopropylamine (0.9 mL, 5.2 mmol, 5 equiv). This solution was stirred at rt for 3 days then poured into ice water (50 mL) and the precipitate was collected by filtration to give the title compound as a brown solid (125 mg, 22% yield).

LC/MS: Calc'd m/z=552.6 for $C_{28}H_{29}FN_{4}O_{7}$, found $[M+H]^{+}$=553.7.

4.55: (S)-2-amino-N—((S)-1-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-1-oxopropan-2-yl)-3-methylbutanamide (Compound 4.55)

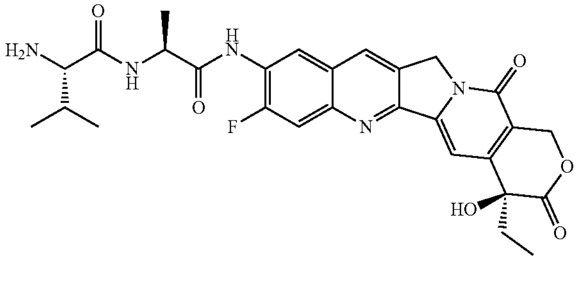 [SMILES: CC[C@@]1(O)C(=O)OCc2c1cc1n(c2=O)Cc2cc3cc(NC(=O)[C@H](C)NC(=O)[C@@H](N)C(C)C)c(F)cc3nc2-1]

To Compound 4.54 (125 mg, 0.225 mmol) in a 100 mL round bottom flask was added TFA (2 mL). This solution was allowed to stand for 10 min, then $Et_2O$ (50 mL) was added, and the precipitate collected by filtration. The resulting orange solid was added to a solution of Boc-Val-NHS (78 mg, 0.25 mmol, 1.1 equiv) and N-ethyldiisopropylamine (80 uL, 0.45 mmol, 2 equiv) in DMF (2 mL). This solution was stirred at rt for 30 min, then pipetted into $Et_2O$ (40 mL) in a 50 mL falcon tube and the precipitate was collected by centrifugation and decanting of the $Et_2O$. The pellet was dissolved in TFA (2 mL) and allowed to stand for 10 min prior to the addition of $Et_2O$ (40 mL). The precipitate was collected by centrifugation and decanting the $Et_2O$. The pellet was dried under high vacuum to give the title compound as an orange solid (135 mg, 90% yield over 3 steps).

LC/MS: Calc'd m/z=551.2 for $C_{28}H_{30}FN_5O_6$, found $[M+H]^+$=552.2.

4.56: 6-(2,5-dioxo-2,5-dihydro-1H-pyrrol-1-yl)-N—((S)-1-(((S)-1-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-1-oxopropan-2-yl)amino)-3-methyl-1-oxobutan-2-yl)hexanamide (MC-VA-Compound 140)

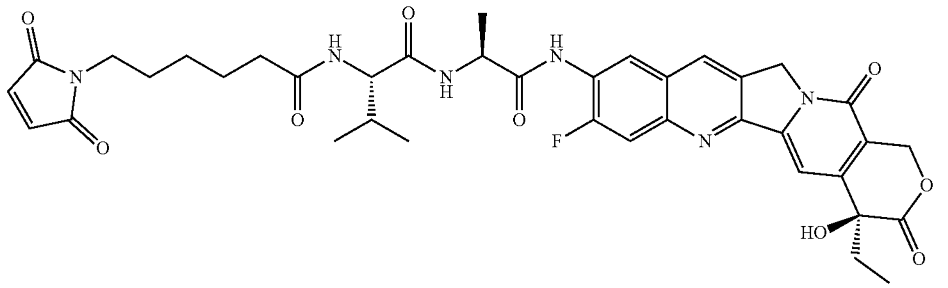 [SMILES: CC[C@@]1(O)C(=O)OCc2c1cc1n(c2=O)Cc2cc3cc(NC(=O)[C@H](C)NC(=O)[C@@H](NC(=O)CCCCCN4C(=O)C=CC4=O)C(C)C)c(F)cc3nc2-1]

To Compound 4.55 (20 mg, 0.03 mmol) was added a solution of 2,5-dioxopyrrolidin-1-yl 6-(2,5-dioxopyrrol-1-yl)hexanoate (11 mg, 0.036 mmol) and N-ethyldiisopropylamine (10 uL) in DMF (1 mL). This solution was stirred at rt for 30 min then purified directly. Preparative HPLC purification was accomplished as described in General Procedure 9, eluting with a 20 to 60% $CH_3CN/H_2O$+0.1% TFA gradient to provide the title compound as a yellow solid (8.8 mg, 40% yield).

LC/MS: Calc'd m/z=744.8 for $C_{38}H_{41}FN_6O_9$, found $[M+H]^+$=745.6.

$^1H$ NMR (300 MHz, 10% $D_2O/CD_3CN$) 6 8.60 (d, J=8.5 Hz, 1H), 8.31 (s, 1H), 7.96 (d, J=6.5 Hz, 1H), 7.65 (d, J=12.0 Hz, 1H), 7.37-7.26 (m, 2H), 6.75 (s, 2H), 5.45 (d, J=16.6 Hz, 1H), 5.25 (d, J=16.3 Hz, 1H), 5.04 (d, J=4.0 Hz, 2H), 4.78-4.58 (m, 1H), 4.30-4.13 (m, 1H), 2.32-2.16 (m, 2H), 2.10 (dt, J=13.6, 6.8 Hz, 1H), 1.88 (q, J=7.4 Hz, 2H), 1.57 (dq, J=15.5, 7.6 Hz, 4H), 1.45 (d, J=7.1 Hz, 3H), 1.26 (tt, J=10.1, 6.1 Hz, 2H), 1.05-0.83 (m, 9H).

4.57: 2,5-dioxopyrrolidin-1-yl 6-(((S)-1-(((S)-1-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-1-oxopropan-2-yl)amino)-3-methyl-1-oxobutan-2-yl)amino)-6-oxohexanoate (NHC—C-VA-Compound 140)

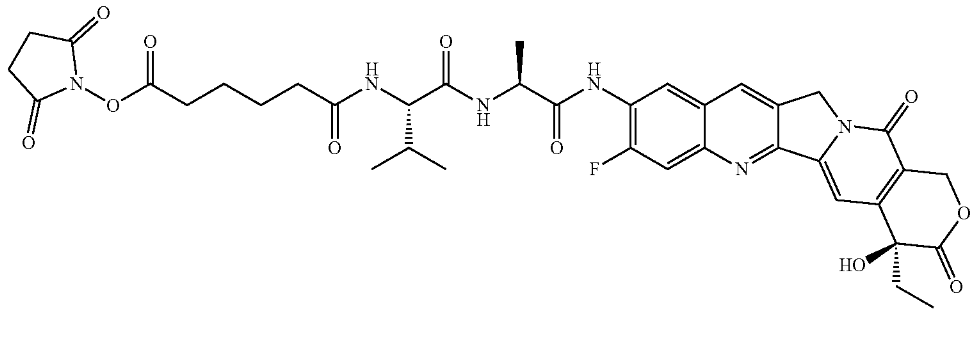 [SMILES: CC[C@@]1(O)C(=O)OCc2c1cc1n(c2=O)Cc2cc3cc(NC(=O)[C@H](C)NC(=O)[C@@H](NC(=O)CCCCC(=O)ON4C(=O)CCC4=O)C(C)C)c(F)cc3nc2-1]

To Compound 4.55 (20 mg, 0.03 mmol) was added a solution of bis(2,5-dioxopyrrolidin-1-yl) adipate (30 mg, 0.09 mmol, 3 equiv) and N-ethyldiisopropylamine (10 uL) in DMF (1 mL). This solution was stirred at rt for 30 min then purified directly. Preparative HPLC purification was accomplished as described in General Procedure 9, eluting with a 25 to 35% $CH_3CN/H_2O$+0.1% TFA gradient to provide the title compound as a yellow solid (4.1 mg, 18% yield).

LC/MS: Calc'd m/z=776.8 for $C_{38}H_{41}FN_6O_{11}$, found $[M+H]^+$=777.6.

$^1$H NMR (300 MHz, 10% $D_2O/CD_3CN$) 6 8.65 (dd, J=8.4, 2.3 Hz, 1H), 8.38 (s, 1H), 7.95 (d, J=6.5 Hz, 1H), 7.72 (d, J=12.0 Hz, 1H), 7.37 (d, J=11.8 Hz, 2H), 5.58-5.19 (m, 2H), 5.10 (s, 2H), 4.78-4.56 (m, 1H), 4.23 (dd, J=8.4, 7.0 Hz, 1H), 2.80 (s, 4H), 2.65 (t, J=6.9 Hz, 2H), 2.39-2.22 (m, 2H), 2.11 (q, J=6.8 Hz, 1H), 1.94-1.81 (m, 2H), 1.79-1.57 (m, 4H), 1.45 (d, J=7.1 Hz, 3H), 1.10-0.78 (m, 9H).

4.58: (S)-2-(32-azido-5-oxo-3,9,12,15,18,21,24,27,30-nonaoxa-6-azadotriacontanamido)-N—((S)-1-(((S)-4-ethyl-8-fluoro-4-hydroxy-3,14-dioxo-3,4,12,14-tetrahydro-1H-pyrano[3',4':6,7]indolizino[1,2-b]quinolin-9-yl)amino)-1-oxopropan-2-yl)-3-methylbutanamide (2-((Azido-PEG8-carbamoyl)methoxy)acetamido-VA-Compound 140)

The title compound was prepared as described in Wang, et al., *Nano Lett.*, 2014, 14(10):5577-5583.

4.59: tert-butyl (2-((2-hydroxyethyl)disulfaneyl)ethyl)carbamate (Compound 4.59)

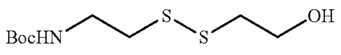

To a solution of Compound 4.58 (200 mg, 0.7 mmol) in DCM (1.4 mL) was added p-mercaptoethanol (50 μL, 0.7 mmol) and this solution was stirred at rt for 5 h. The solution was diluted with DCM (10 mL), washed with a water (3×10 mL), dried over $Na_2SO_4$, and concentrated to an oil. Purification was accomplished as described in General Procedure 9, using a 10 g silica column, and eluting with a 0 to 10% MeOH/DCM to give the title compound as a colorless solid (212 mg, 82% yield).

LC/MS: Calc'd m/z=253.1 for $C_{11}H_{23}NO_3S_2$, found $[M+H,-Boc]^+$=154.0.

$^1$H NMR (300 MHz, Chloroform-d) δ 4.94 (s, 1H), 3.91 (t, J=5.7 Hz, 2H), 3.49 (q, J=6.4 Hz, 2H), 2.86 (dt, J=23.7, 6.1 Hz, 4H), 2.15 (s, 2H), 1.47 (s, 9H).

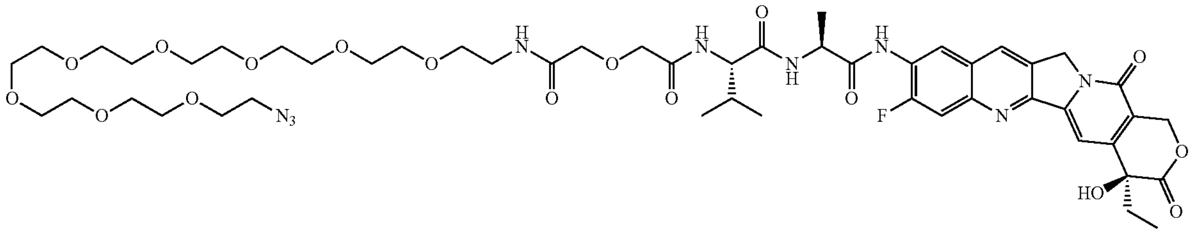 [SMILES: CC[C@@]1(O)C(=O)OCc2c1cc1n(c2=O)Cc2cc3cc(NC(=O)[C@H](C)NC(=O)[C@@H](NC(=O)COCC(=O)NCCOCCOCCOCCOCCOCCOCCOCCOCCN=[N+]=[N-])C(C)C)c(F)cc3nc2-1]

A solution of Compound 4.55 (20 mg, 0.03 mmol), 32-azido-5-oxo-3,9,12,15,18,21,24,27,30-nonaoxa-6-azadotriacontanoic acid (17 mg, 0.03 mmol), and HATU (13 mg, 0.03 mmol) in DMF (300 uL) was cooled to 0° C. and N-ethyldiisopropylamine (16 uL, 0.09 mmol) was added. This solution was stirred for 30 min the purified directly. Preparative HPLC purification was accomplished as described in General Procedure 9, eluting with a 20 to 50% $CH_3CN/H_2O$+0.1% TFA gradient to provide the title compound as a yellow solid (13.7 mg, 42% yield).

LC/MS: Calc'd m/z=1088.2 for $C_{50}H_{70}FN_9O_{17}$, found $[M+H]^+$=1088.8.

$^1$H NMR (300 MHz, 10% $D_2O/CD_3CN$) 6 8.62 (d, J=8.5 Hz, 1H), 8.33 (s, 1H), 7.66 (d, J=12.2 Hz, 1H), 7.35 (s, 1H), 5.52-5.18 (m, 2H), 5.04 (s, 2H), 4.72 (q, J=7.1 Hz, 1H), 4.32 (d, J=7.3 Hz, 1H), 4.15-3.98 (m, 4H), 3.68-3.48 (m, 35H), 3.41-3.34 (m, 6H), 2.18 (h, J=6.8 Hz, 1H), 1.88 (q, J=7.4 Hz, 2H), 1.47 (d, J=7.1 Hz, 3H), 1.13-0.84 (m, 9H).

4.58: tert-butyl (2-(pyridin-2-yldisulfaneyl)ethyl)carbamate (Compound 4.58)

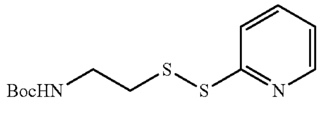 [SMILES: CC(C)(C)OC(=O)NCCSSc1ccccn1]

4.60: 2-((2-(3-(2,5-dioxo-2,5-dihydro-1H-pyrrol-1-yl)propanamido)ethyl)disulfaneyl)ethyl (4-nitrophenyl) carbonate (Compound 4.60)

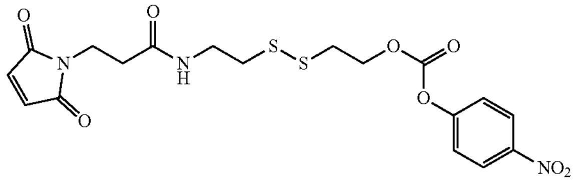 [SMILES: O=C(CCN1C(=O)C=CC1=O)NCCSSCCOC(=O)Oc1ccc([N+](=O)[O-])cc1]

To Compound 4.59 (212 mg, 0.837 mmol) in a 25 mL round bottom flask was added a 4M HCl/dioxane solution (5 mL) and the solution was stirred at rt for 30 min, then evaporated to dryness. The residue was suspended in EtOAc (10 mL) and evaporated to dryness to give the amine as the HCl salt and as a white powder. To this solid was added a solution of 2,5-dioxopyrrolidin-1-yl 3-(2,5-dioxopyrrol-1-yl)propanoate (245 mg, 0.92 mmol, 1.1 equiv.) and N-ethyldiisopropylamine (0.438 mL, 2.51 mmol) in DMF (1.7 mL). This solution was stirred at rt for 20 min then 4-nitrophenyl carbonate (280 mg, 0.92 mmol) was added and the reaction was then left to stir overnight. Purification of the crude reaction mixture was accomplished as described in General Procedure 9, using a 12 g C18 flash column, and eluting with a 10 to 100% $CH_3CN/H_2O$+0.1% TFA gradient to provide the title compound as a white solid (141 mg, 36% yield).

LC/MS: Calc'd m/z=469.5 for $C18H_{19}N_3O_8S_2$, found $[M+H]^+$=470.2.

$^1H$ NMR (300 MHz, Chloroform-d) δ 8.37-8.25 (m, 2H), 7.46-7.35 (m, 2H), 6.71 (d, J=2.1 Hz, 2H), 6.32 (s, 1H), 4.55 (t, J=6.6 Hz, 2H), 3.83 (t, J=7.0 Hz, 2H), 3.65-3.50 (m, 2H), 3.09-2.99 (m, 2H), 2.84 (q, J=6.1 Hz, 2H), 2.52 (td, J=7.1, 3.1 Hz, 2H).

4.61: 2-((2-(3-(2,5-dioxo-2,5-dihydro-1H-pyrrol-1-yl)propanamido)ethyl)disulfaneyl)ethyl (S)-((9-amino-4-ethyl-8-fluoro-4-hydroxy-3,14-dioxo-3,4,12,14-tetrahydro-1H-pyrano[3',4':6,7]indolizino[1,2-b]quinolin-11-yl)methyl)carbamate (DiS-Compound 145)

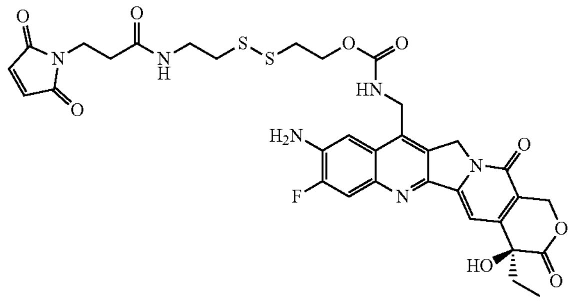 [SMILES: CC[C@@]1(O)C(=O)OCc2c1cc1n(c2=O)Cc2c-1nc1cc(F)c(N)cc1c2CNC(=O)OCCSSCCNC(=O)CCN1C(=O)C=CC1=O]

A solution of Compound 4.60 (18 mg, 0.038 mmol) and N-ethyldiisopropylamine (15 uL, 0.087 mmol) in DMF (300 uL) was added to Compound 145 (13 mg, 0.029 mmol) and this solution was stirred at rt for 20 min. The solution was acidified with an aqueous 1M HCl solution (100 uL) and purified directly. Preparative HPLC purification was accomplished as described in General Procedure 9, eluting with a 20 to 45% $CH_3CN/H_2O$+0.1% TFA gradient to provide the title compound as a yellow solid (6.8 mg, 32% yield).

LC/MS: Calc'd m/z=740.8 for $C_{33}H_{33}FN_6O_9S_2$, found $[M+H]^+$=741.5.

$^1H$ NMR (300 MHz, 10% $D_2O/CD_3CN$) 6 7.63 (d, J=12.1 Hz, 1H), 7.39-7.22 (m, 2H), 6.74 (d, J=6.7 Hz, 2H), 5.50 (d, J=16.2 Hz, 1H), 5.26 (d, J=16.2 Hz, 1H), 5.20 (s, 2H) 4.69 (s, 2H), 4.28 (t, J=6.3 Hz, 2H), 3.62 (t, J=7.0 Hz, 2H), 3.31 (t, J=6.6 Hz, 2H), 2.74-2.64 (m, 2H), 2.35 (t, J=7.0 Hz, 2H), 1.90 (dd, J=15.5, 8.1 Hz, 2H), 1.23-1.04 (m, 6H), 0.93 (t, J=7.4 Hz, 3H).

Example 5: In Vitro Cytotoxicity of Camptothecin Analogues

Cytotoxicity of the camptothecin analogues was assessed in vitro as follows.

In vitro potency was assessed on multiple cancer cell lines: SK-BR-3 (breast cancer), SKOV-3 (ovarian cancer), Calu-3 (lung cancer), ZR-75-1 (breast cancer) and MDA-MB-468 (breast cancer). Serial dilutions of camptothecin analogues were prepared in RPMI 1640+10% FBS, and 20 μL of each dilution was added to 384-well plates. Cells cultured in log-phase growth were detached by brief incubation in 0.05% Trypsin and resuspended in respective culturing media at 20,000 cells/mL (with the exception of ZR-75 cells, which were resuspended at 10,000 cells/mL). 50 μL of cell suspension was then added to the plates containing test articles. Cells were incubated with test articles for 4 d at 37° C. (with the exception of ZR-75 cells, which were incubated for 5 d). Growth inhibition was assessed by CellTiter-Glo® (Promega Corporation, Madison, WI) and luminescence was measured on a plate reader. IC50 values were determined by GraphPad Prism (GraphPad Software, San Diego CA).

The results are shown in Table 5.1.

TABLE 5.1

In vitro Cytotoxicity of Camptothecin Analogues (pIC50)

| Camptothecin | pIC50 | | | | |
|---|---|---|---|---|---|
| Analogue | Calu-3 | SKBR-3 | SKOV-3 | ZR-75 | MDA-MB-468 |
| Compound 100 | 8.95 | 8.96 | 8.64 | 8.91 | 8.60 |
| Compound 102 | ND* | 9.03 | 8.67 | 9.10 | 8.63 |
| Compound 104 | 8.28 | 8.57 | 8.11 | 8.59 | 8.58 |
| Compound 122 | 8.43 | 8.95 | 8.04 | 8.89 | 8.96 |
| Compound 132 | 7.29 | 7.64 | 6.98 | 7.81 | 7.57 |
| Compound 106 | 8.34 | 8.47 | 8.13 | 8.42 | 8.03 |
| Compound 108 | 7.39 | 7.53 | 7.26 | 7.73 | 7.32 |
| Compound 101 | ND | 8.97 | 8.80 | 8.97 | 8.59 |
| Compound 103 | 8.63 | 8.77 | 8.36 | 8.62 | 8.33 |
| Compound 105 | 8.35 | 8.44 | 7.97 | 8.51 | 8.56 |
| Compound 107 | 8.39 | 8.51 | ND | 8.56 | 8.41 |
| Compound 109 | ND | 8.24 | 8.15 | 8.30 | 8.09 |
| Compound 134 | 7.61 | 8.02 | 7.11 | 7.92 | 7.94 |
| Compound 138 | 9.41 | 9.32 | 9.21 | 9.71 | 9.06 |
| Compound 124 | 8.77 | 8.92 | ND | 8.64 | 8.46 |
| Compound 136 | 7.58 | 8.40 | 7.29 | 8.30 | 8.20 |
| Compound 133 | 7.92 | 8.17 | 7.13 | 8.01 | 7.97 |
| Compound 135 | 7.60 | 7.91 | ND | 7.88 | 7.97 |
| Compound 137 | 7.20 | 7.77 | ND | 7.73 | 7.55 |
| Compound 123 | 8.43 | 8.72 | 7.71 | 8.61 | 8.70 |
| Compound 125 | 8.55 | 8.88 | 8.15 | 8.88 | 8.42 |
| Compound 128 | ND | 8.28 | 7.74 | 8.37 | 8.08 |
| Compound 126 | 8.53 | 8.96 | 8.20 | 9.14 | 8.71 |
| Compound 130 | 8.78 | 7.83 | 7.62 | ND | 8.19 |
| Compound 129 | 8.28 | 8.51 | 7.69 | 8.58 | 8.40 |
| Compound 127 | 8.03 | 8.48 | 7.84 | 8.28 | 8.42 |
| Compound 110 | 9.09 | 8.88 | 9.03 | 9.07 | 8.81 |
| Compound 111 | 7.71 | 8.07 | 7.78 | 8.04 | 7.54 |
| Compound 112 | 7.76 | 8.18 | 7.70 | 7.92 | 7.87 |
| Compound 113 | 8.52 | 8.71 | 8.37 | 8.66 | 8.47 |
| Compound 139 | 8.15 | 8.92 | 8.30 | 8.97 | 8.82 |
| Compound 140 | 9.51 | 9.50 | 9.34 | 9.48 | 9.15 |
| Compound 141 | 8.99 | 9.46 | 8.55 | 9.51 | 8.84 |
| Compound 142 | 8.89 | 9.20 | 8.89 | 9.12 | 8.89 |
| Compound 143 | 9.15 | 9.41 | 8.55 | 9.07 | 9.15 |
| Compound 144 | 7.65 | 9.10 | 7.16 | 7.88 | 7.65 |
| Compound 145 | 9.57 | 9.45 | 9.03 | 9.42 | 9.57 |
| Compound 146 | 8.36 | 8.76 | 7.95 | 8.22 | 8.36 |
| Compound 147 | 7.67 | 8.29 | 7.36 | ND | 7.67 |
| Compound 148 | 9.69 | 9.49 | ND | 9.66 | 9.69 |
| Compound 131 | 8.04 | 8.98 | ND | 9.02 | 8.04 |
| Compound 149 | 8.20 | 8.50 | 8.00 | 8.74 | 8.20 |
| Compound 150 | ND | 8.10 | 7.20 | 8.19 | ND |
| Compound 151 | 7.94 | 8.57 | 7.34 | 8.23 | 7.94 |
| Compound 152 | 8.83 | 8.49 | 8.54 | ND | 8.30 |
| Compound 153 | 9.94 | 9.29 | 9.03 | ND | ND |
| Compound 114 | 10.03 | 9.97 | 9.75 | ND | 9.38 |
| Compound 115 | 8.89 | 8.59 | 8.42 | ND | 8.38 |
| Compound 117 | 9.79 | 10.02 | 9.77 | ND | 9.33 |
| Compound 118 | 9.03 | 8.82 | 8.84 | ND | 8.73 |
| Compound 119 | 8.93 | 8.38 | 8.43 | ND | 8.56 |
| Compound 120 | 10.00 | 8.96 | 9.60 | ND | 9.72 |
| Compound 121 | 9.84 | 9.83 | 9.71 | ND | 9.57 |
| Compound 116 | 9.10 | 8.15 | 7.90 | ND | 8.03 |

*ND = not determined

Example 6: Preparation of Anti-Folate Receptor Alpha Antibodies

Antibodies that specifically bind folate receptor alpha (FRα) were generated by immunizing rabbits with human FRα antigen, isolated and sequenced as described below.

6.1 Immunizations

Antibodies to FRα were raised in rabbits immunized with soluble HIS-tagged human folate receptor 1 antigen (FRα-HIS) (ACROBiosystems, Newark, DE; Cat #FO1-H82E2). Briefly, two New Zealand White rabbits were immunized with a primary boost consisting of 200 g of FRα-HIS antigen mixed with Alum (5 mg/injection)/CpG (10 μg/injection) administered subcutaneously at 3 sites (0.333 mL/site) along the rabbit's dorsal body. These were followed by 4 immunizations with 100 g of FRα-HIS antigen mixed with Alum (5 mg/injection)/CpG (10 g/injection). Each of the immunizations were separated by 14 days. The animals were bled prior to the fourth immunization for serology.

6.2 Selection of Animals for Harvest

Anti-human FRca antibody titers were determined by flow cytometry using CHO cells expressing human FRα. Briefly, CHO cells were transiently transfected with a pTT5-based expression plasmid (National Research Council of Canada) encoding human FRα according to manufacturer's instructions for Lipofectamine™ 2000 (Thermo Fisher Scientific Corp., Waltham, MA). A dilution of immunized rabbit sera starting at 1:400 and serially diluted 1:2 over 11 points was incubated with 50,000 CHO cells transiently expressing human FRα for 30 minutes. Samples were then washed, and antibody binding was detected with a goat anti-rabbit secondary antibody conjugated to Alexa Fluor-647 (Jackson Immuno Research Labs, West Grove, PA) by flow cytometry. Titers were determined by identifying the highest dilution sample that showed at least 2 times fluorescent signal above background.

6.3 Recovery of B Cells and Discovery of Anti-Human FR aAntibodies

Immunized rabbits with desired titers above 100,000 were sacrificed, and the spleens harvested. The lymphoid cells were dissociated by grinding in FACS buffer (PBS, 2% v/v FBS) to release the cells from the tissues. The cells were pelleted and then suspended for 1 minute in 5 mL of Pharm Lyse™ (Becton, Dickinson & Co., Franklin Lakes, NJ) to lyse red blood cells. Equal volume of FACS buffer was added to neutralize the Pharm Lyse™ and the resultant lymphocyte sample was pelleted and resuspended in FACS buffer.

The lymphocyte suspension was then stained with goat anti-rabbit IgG Alexa Fluor-647 (Jackson Immuno Research Labs, West Grove, PA) to identify IgG+B cells. After 30 minutes of staining, IgG+B cells were sorted on a FACSAria™ (Becton, Dickinson & Co., Franklin Lakes, NJ) and counted. Using the Selected Lymphocyte Antibody Method (SLAM) (Babcook et al., 1996, *Proc Natl Acad Sci USA,* 93(15):7843-7848), B cells were plated at different densities ranging from single cell up to 50 cells in a 384 well plate, expanded in culture for 7 days and the supernatants harvested for detection of anti-human FRα antibodies. The 384 well plates were stored at −80° C.

Supernatants were screened for human FRα specific monoclonal antibodies by ELISA. 384 well ELISA plates were coated with 25 μL/well of human FRca-HIS (2 μg/mL) in PBS, then incubated at 4° C. overnight. After incubation, the plates were washed twice with water, 90 μL/well Blocking Buffer (2% skim milk, PBS) was added and the plates incubated at room temperature for 1 hour. After incubation, the plates were washed and 12.5 μL/well of antibody-containing supernatants+12.5 μL Blocking Buffer, and positive and negative controls were added and the plates incubated at room temperature for 2 hours.

After incubation, the plates were washed, 25 μL of 0.4 μg/mL goat anti-rabbit IgG Fc-HRP detection antibody (Jackson Immuno Research Labs, West Grove, PA) was added to each well and the plates were incubated at room temperature for 1 hour. After the incubation, the plates were washed and 25 μL of tetramethylbenzidine (TMB) was added and the plates allowed to develop for about 10 minutes (until negative control wells started to show signal). Then 25 L stop solution (1 N HCL) was added to each well and the plates read on a Synergy™ $H_1$ microplate (BioTek Instruments, Winooski, VT) at wavelength 450 nm.

6.4 Sequencing Anti-Human FRα Antibodies

Total RNA was extracted from wells containing antibodies having desired characteristics using RNeasy (Qiagen, Hilden, Germany) according to manufacturer's protocols. Resulting total RNA was used as template with SuperScript™ III (Thermo Fisher Scientific Corp., Waltham, MA) and oligo-dT20 (Integrated DNA Technologies, Inc., Coralville, IA) to transcribe cDNA from mRNA. cDNA was subsequently treated with RNaseH (New England Biolabs, Ipswich, MA). Initial PCR of heavy and light chain antibody-coding sequences was performed using primers and methods modified from Babcook et al., 1996*, Proc Natl Acad Sci USA,* 93(15):7843-7848 and von Boehmer et al., 2016*, Nat Protoc.,* 11(10):1908, with cDNA as the nucleic acid template. PCR products were cloned into pCRTOPO4 using the Zero Blunt™ TOPO™ PCR Cloning kit (Thermo Fisher Scientific Corp., Waltham, MA) and transformed into E. cloni® cells (Lucigen Corporation, Middleton, WI). Antibiotic-resistant clones were Sanger sequenced and analyzed for unique antibody-coding sequences.

A subsequent PCR reaction was then performed on these unique sequences using V-segment family and J-segment family-specific primers. The resulting amplicons were cloned into pTT5-based expression plasmids (National Research Council of Canada). Unique heavy chain sequences and light chain sequences emerging from a single well sample were co-expressed in HEK293-6E cells (National Research Council of Canada) in all possible combinations to determine the correct heavy and light chain pairing. Antibodies produced were assayed for binding to antigen that was transiently expressed on HEK293 cells.

6.5 Generation of Chimeric Antibodies

Coding sequences for antibody variable regions were cloned in frame into a huIgG1 expression and a huCK expression vector (based on the pTT5 vector). The huIgG1 constant region starts at alanine Kabat-118 and huCK constant region starts at arginine Kabat-108. The activities of the resultant recombinant chimeric antibodies were confirmed in specificity binding assays and were found comparable to the parental ones.

Example 7: Humanization of Anti-Frα Antibody

One of the chimeric anti-human FRα (anti-hFRα), variant v23924, generated as described in Example 6, was selected for humanization. The CDR sequences of v23924 are provided in Table 7.1, and the VH and VL sequences are provided in Table 7.2. Humanization was conducted as described below.

TABLE 7.1

CDR Sequences of the Anti-hFRα Antibody v23924

| Numbering System | Heavy Chain CDR1 | SEQ ID NO | Heavy Chain CDR2 | SEQ ID NO | Heavy Chain CDR3 | SEQ ID NO |
|---|---|---|---|---|---|---|
| IMGT | GFSLSSYG | 20 | VNSGGSA | 21 | ARSGSGY PMDYLAI | 22 |
| Kabat | SYGVS | 26 | AVNSGGSA YYANWAKS | 27 | SGSGYPM DYLAI | 25 |
| Chothia | GFSLSSY | 23 | NSGGS | 24 | SGSGYPM DYLAI | 25 |
| AbM | GFSLSS YGVS | 31 | AVNSG GSAY | 32 | SGSGYPM DYLAI | 25 |
| Contact | SSYGVS | 28 | WIGAVN SGGSAY | 29 | ARSGSGY PMDYLA | 30 |
| | Light Chain CDR1 | SEQ ID NO | Light Chain CDR2 | SEQ ID NO | Light Chain CDR3 | SEQ ID NO |
| IMGT | QSIGDW | 40 | EAS | 41 | QQGYGRS NVDNI | 42 |
| Kabat | QASQSI GDWLA | 43 | EASTLAS | 44 | QQGYGRS NVDNI | 42 |
| Chothia | QASQSI GDWLA | 43 | EASTLAS | 44 | QQGYGRS NVDNI | 42 |
| AbM | QASQSI GDWLA | 43 | EASTLAS | 44 | QQGYGRS NVDNI | 42 |
| Contact | GDWLAWY | 45 | LLIYEASTLA | 46 | QQGYGR SNVDN | 47 |

TABLE 7.2

VH and VL Sequences of the Anti-hFRα Antibody v23924

| | Sequence | SEQ ID NO |
|---|---|---|
| VH | QSVKESEGGLFKPTDTLTLTCT VSGFSLSSYGVSWVRQAPGNGL EWIGAVNSGGSAYYANWAKSRS TITRNTNLFTVTLKMTSLAVAD TATYFCARSGSGYPMDYLAIWG PGTLVTVSS | 19 |
| VL | AYDMTQTPASVEVAVGGTVTIK CQASQSIGDWLAWYQQKPGQPP RLLIYEASTLASGVPSRFSGSG SGTQFTLTISGVECADAATYYC QQGYGRSNVDNIFGGGTEVVVK | 39 |

7.1 Humanization

Sequence alignment of the rabbit VH and VL sequences of v23924 to respective human germline sequences identified IGHV3-23*01 and IGKVI-39*01 as the closest, as well as most frequent, human germline sequences. CDR sequences according to the AbM definition (see Table 2.1) were ported onto the framework of these selected human germline sequences as shown in FIG. 1. Back mutations to rabbit residues in the resultant sequences at positions judged likely to be important for the retention of binding affinity to antigen, hFRα, were included creating several humanized sequences in which generated sequences for the most part built on the previous sequence, and where the first humanized sequence contained the minimal number of back mutations. None of the variants modified the CDRs of the parent antibody as defined by the AbM method.

This process was carried out in two cycles, in which the first cycle ("cycle one") resulted in six variable heavy chain humanized sequences and five variable light chain humanized sequences. The second cycle ("cycle two") expanded to an additional 5 variable heavy chain humanized sequences in pursuit of more closer parental-like affinity of the humanized antibody to hFRα. Full heavy chain sequences containing humanized heavy chain variable domain (VH) and hIgG1 heavy chain constant domains ($CH_1$, hinge, $CH_2$, $CH_3$), and full light chain sequence containing humanized light chain variable domain (VL) and human kappa light chain constant domain (kappa CL) were assembled. Monoclonal antibody (mAb) variants were then assembled such that in cycle one, each of the humanized heavy chains was paired with each of the humanized light chains to provide 30 humanized variants and in cycle two, additional humanized heavy chains were paired with select humanized light chains to give an additional 15 humanized variants, for a total of 45 humanized variants to be evaluated experimentally.

7.2 Production of Humanized Antibodies

Each of the 45 humanized mAb constructs, as well as the parental v23924 mAb construct, were produced in full-size antibody (FSA) format containing either two identical full-length heavy chains (parental v23924 and 15 humanized variants) resulting in a homodimeric Fc region (HomoFc), or heterodimeric full-length heavy chains comprising complementary mutations in $CH_3$ region to drive exclusive heavy chain pairing (30 humanized variants) resulting in a heterodimeric Fc region (HetFc). A version of v23924 that contained a HetFc instead of a HomoFc was also produced (variant v30618). All constructs included two identical kappa light chains.

The two identical full-length heavy chains comprised by the HomoFc region contained the human $CH_1$-hinge-$CH_2$—$CH_3$ domain sequence of IGHG1*01 (SEQ ID NO:146; see Table 7.3). The heterodimeric full-length heavy chains comprised by the HetFc region (HetFc-A and HetFc-B) contained the human $CH_1$-hinge-$CH_2$—$CH_3$ domain sequence of IGHG1*01 with the following mutations in the Fc region:

HetFc-A: T350V_L351Y_$F_{405}$A_Y407V

HetFc-B: T350V_T366L_K392L_T394W

The sequences of HetFc-A (SEQ ID NO:148) and HetFc-B (SEQ ID NO:149) are provided in Table 7.3. The human kappa CL sequence of IGKC*01 (SEQ ID NO:147; see Table 7.3) was used for all constructs.

TABLE 7.3

HomoFc and HetFc Sequences

| | Sequence | SEQ ID NO |
|---|---|---|
| CH1-hinge-CH2-CH3 (IGHG1*01) | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK | 146 |

TABLE 7.3-continued

HomoFc and HetFc Sequences

| | Sequence | SEQ ID NO |
|---|---|---|
| | EYKCKVSNKALPAPIEKTIS KAKGQPREPQVYTLPPSRDE LTKNQVSLTCLVKGFYPSDI AVEWESNGQPENNYKTTPPV LDSDGSFFLYSKLTVDKSRW QQGNVFSCSVMHEALHNHYT QKSLSLSPG | |
| CL (kappa) (IGKC*01) | RTVAAPSVFIFPPSDEQLKS GTASVVCLLNNFYPREAKVQ WKVDNALQSGNSQESVTEQD SKDSTYSLSSTLTLSKADYE KHKVYACEVTHQGLSSPVTK SFNRGEC | 147 |
| CH1-hinge-CH2-CH3 (HetFc-A) (IGHG1*01) | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYVYPPSRDE LTKNQVSLTCLVKGFYPSDI AVEWESNGQPENNYKTTPPV LDSDGSFALVSKLTVDKSRW QQGNVFSCSVMHEALHNHYT QKSLSLSPG | 148 |
| CH1-hinge-CH2-CH3 (HetFc-B) (IGHG1*01) | ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN STYRVVSVLTVLHQDWLNGK EYKCKVSNKALPAPIEKTIS KAKGQPREPQVYVLPPSRDE LTKNQVSLLCLVKGFYPSDI AVEWESNGQPENNYLTWPPV LDSDGSFFLYSKLTVDKSRW QQGNVFSCSVMHEALHNHYT QKSLSLSPG | 149 |

Each of the humanized VH domain sequences from cycle one was appended to the human CH1-hinge-CH2-CH3 (HetFc-A and HetFc-B) domain sequence of IGHG1*01 to provide twelve humanized full heavy chain sequences (six humanized VH x2). Rabbit VH and each of the additional five humanized VH domain sequences from cycle two were appended to the human CH1-hinge-CH2-CH3 domain sequence of IGHG1*01, to provide the parental rabbit-human chimeric full heavy chain sequence and five additional humanized full heavy chain sequences. Each of the VL domain sequences was appended to the human kappa CL sequence of IGKC*01 to provide five humanized light chain sequences. All sequences were reverse translated to DNA, codon optimized for mammalian expression and gene synthesized.

Heavy chain vector inserts comprising a signal peptide (artificially designed sequence: MRPTWAWWLFLVLLLA-LWAPARG (SEQ ID NO:150) (Barash et al., 2002, *Biochem and Biophys Res. Comm.,* 294:835-842)) and the heavy chain clone terminating at residue G446 (EU numbering) of the CH3 domain were ligated into a pTT5 vector to produce heavy chain expression vectors. Light chain vector inserts comprising the same signal peptide were ligated into a pTT5 vector to produce light chain expression vectors. The resulting heavy and light chain expression vectors were sequenced to confirm correct reading frame and sequence of the coding DNA.

The heavy and light chains of each of the humanized antibody variants were expressed in 200 ml cultures of CHO-3E7 cells. Briefly, CHO-3E7 cells, at a density of $1.7\text{-}2\times10^6$ cells/ml, viability >95%, were cultured at 37° C. in FreeStyle™ F17 medium (Thermo Fisher Scientific, Waltham, MA) supplemented with 4 mM glutamine (GE Life Sciences, Marlborough, MA) and 0.1% Pluronic® F-68 (Gibco/Thermo Fisher Scientific, Waltham, MA). A total volume of 200 ml CHO-3E7 cells +1× antibiotic/antimycotics (GE Life Sciences, Marlborough, MA) was transfected with a total of 200 ug DNA (100 ug of antibody DNA and 100 µg of GFP/AKT/stuffer DNA) using PEI-MAX® (Polyscience, Inc., Philadelphia, PA) at a DNA:PEI ratio of 1:4 (w/w). Twenty-four hours after the addition of the DNA-PEI mixture, 0.5 mM valproic acid (final concentration)+1% w/v Tryptone (final concentration) were added to the cells, which were then transferred to 32° C. and incubated for 6 more days prior to harvesting.

Protein A purification was performed in batch mode or using 1 mL HiTrap™ MabSelect™ SuRe™ columns (Cytiva, Marlborough, MA). In batch mode, clarified supernatant samples were incubated in batch with mAb Select SuRe™ resin (GE Healthcare, Chicago, IL) cleaned-in-place (CIP'd) with NaOH and equilibrated in Dulbecco's PBS (DPBS). Resin was poured into CIP'd columns, the columns were washed with DPBS. In both purification modes, protein was eluted with 100 mM sodium citrate buffer pH 3.0. The eluted fractions were pH adjusted by adding 10% (v/v) 1M HEPES (pH -10.6-10.7) to yield a final pH of 6-7. Samples were buffer exchanged into DPBS. Protein was quantitated based on absorbance at 280 nm (A280 nm). Parental rabbit-human antibody chimera variants (v23924 and v30618) were further purified by preparatory SEC chromatography on a Superdex 200 Increase 10/30 column (GE Healthcare, Chicago, IL) in DPBS mobile phase following Protein A purification.

Following purification, purity of samples was assessed by electrophoresis under non-reducing and reducing conditions using the High Throughput Protein Express assay and Caliper LabChip® GXII or GXII Touch HT (Perkin Elmer, Waltham, MA). Procedures were carried out according to HT Protein Express LabChip® User Guide version 2 with the following modifications. Antibody samples, at either 2 µl or 5 µl (concentration range 5-2000 ng/µl), were added to separate wells in 96 well plates (BioRad, Hercules, CA) along with 7 µl of HT Protein Express Sample Buffer (Perkin Elmer, Cat #760328). Antibody samples were then denatured at 70° C. for 15 mins. The LabChip® instrument was operated using the HT Protein Express Chip (Perkin Elmer, Waltham, MA) and the Ab-200 assay setting.

The yield (post protein-A purification) across the forty-five humanized antibody variants and the parental chimeric antibody, v23924, ranged from~9-17 mg (or 45-85 mg/L). FIGS. 2A and 2C show the Caliper electrophoresis results for the parental chimeric antibody v23924 and a representative humanized variant, v30384, As can be seen from FIG. 2, for the representative humanized antibody sample, non-reducing (NR) and reducing (R) Caliper reflected a single species corresponding to full-size antibody and intact heavy and light chains. This was also the case for the other humanized variants.

7.3 Quality Assessment of Humanized Antibodies

Species homogeneity of the humanized antibody variants was assessed by UPLC-SEC after Protein A purification and after preparatory SEC purification for the parental chimera antibody, v23924.

UPLC-SEC was performed using a Waters Acquity BEH200 SEC column (2.5 mL, 4.6×150 mm, stainless steel, 1.7 m particles) (Waters LTD, Mississauga, ON) set to 30° C. and mounted on a Waters Acquity UPLC™ H-Class Bio system with a photodiode array (PDA) detector. The mobile phase was Dulbecco's phosphate buffered saline (DPBS) with 0.02% Tween 20 pH 7.4 and the flow rate was 0.4 ml/min. Total run time for each injection was 7 min with a total mobile phase volume of 2.8 mL. Elution was monitored by UV absorbance in the range 210-500 nm, and chromatograms were extracted at 280 nm. Peak integration was performed using Waters Empower®3 software employing the Apex Track™ and detect shoulders features.

Figure 2B:
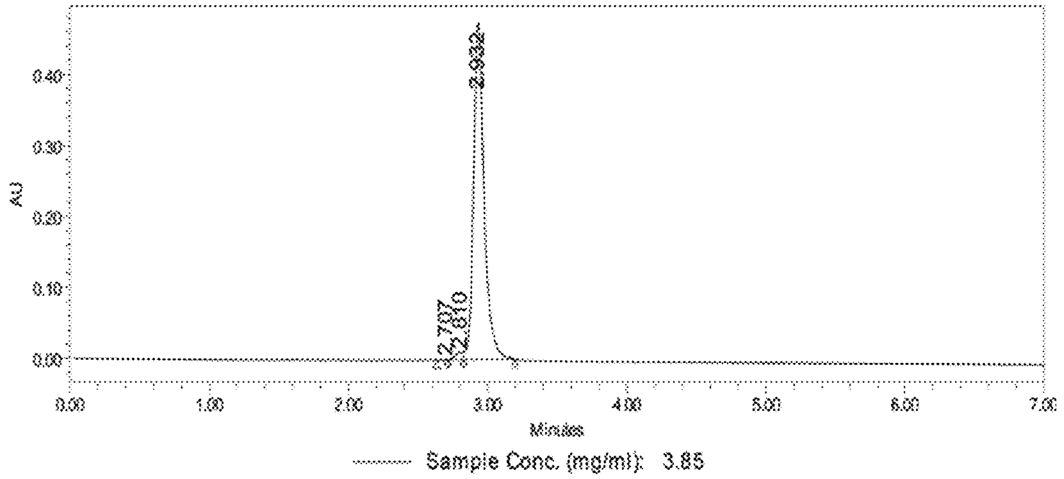
Figure 2C:
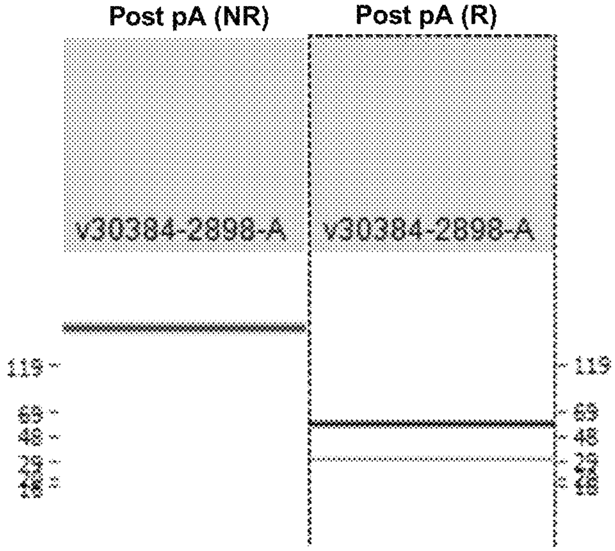
Figure 2D:
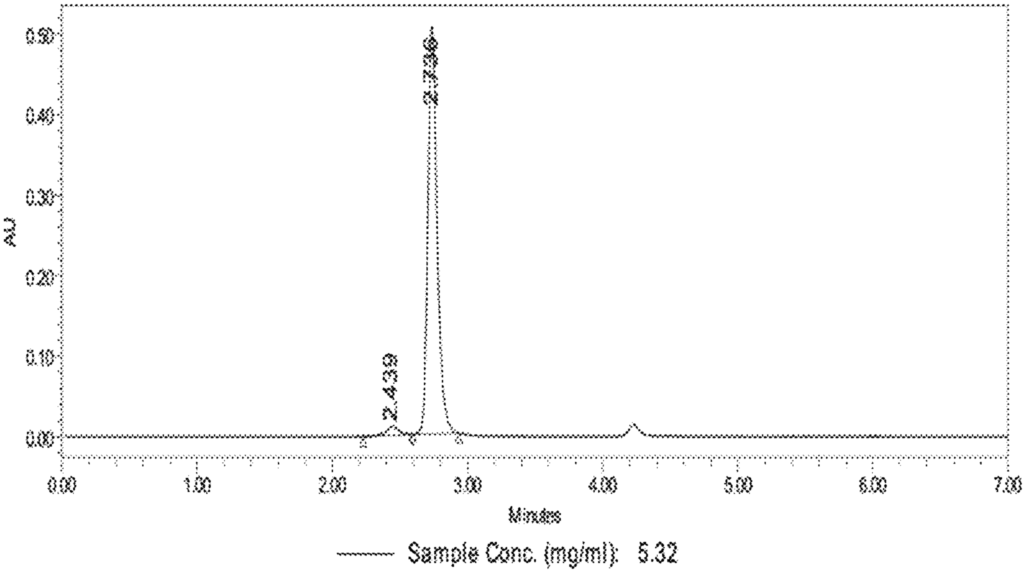

FIGS. 2B and 2D show the UPLC-SEC profiles for the parental chimeric antibody v23924 (post SEC purification) and for a representative humanized antibody v30384 (post Protein A purification, respectively. The UPLC-SEC profile for the representative humanized antibody sample reflected high species homogeneity, comparable to the parental chimeric antibody sample. The samples from the remaining humanized antibody variants had similar profiles to that shown for the representative humanized antibody sample.

Example 8: Binding of Humanized Antibodies to hFRα

8.1 Affinity Assessment of the Humanized Antibodies for hFRα

To determine whether the humanization process affected the affinity of the humanized variants for their target, the ability of the 45 purified humanized antibody variants to bind the hFRα antigen was assessed by Bio-layer interferometry (BLI) as follows.

hFRα antigen binding was assessed using the Octet® RED96 system (ForteBio, Fremont, CA) by cycling through the following steps: loading of antibodies (0.9 μg/mL) onto anti-human IgG Fc capture (AHC) biosensors over 200s; stabilization of baseline for 60s; association to recombinant His-tagged human FRα (ACROBiosystems, Newark, DE) at multiple relevant concentrations spanning the expected $K_D$ for 400-500s; recordation of dissociation for 500-1000s; and regeneration performed by cycling 3 times between 10 mM glycine pH 1.5 (15s) and the assay buffer (is) before proceeding to the next antibody. The assay buffer used was KB buffer (kinetics buffer, composed of PBS pH 7.4, 0.1% BSA, 0.02% Tween 20, 0.05% sodium azide) supplemented with 0.06% Tween 20 and in some instances also with 1% BSA. The experiment was conducted at 30° C. with a shake speed of 1000 rpm.

Data analysis was performed using Data Analysis Software 9.0 (ForteBio, Fremont CA). The reference-subtracted binding curves were globally fitted to the 1:1 interaction model to generate the binding kinetic parameters $k_{on}$, $k_{off}$, and the dissociation constant $K_D$.

Figure 3A:
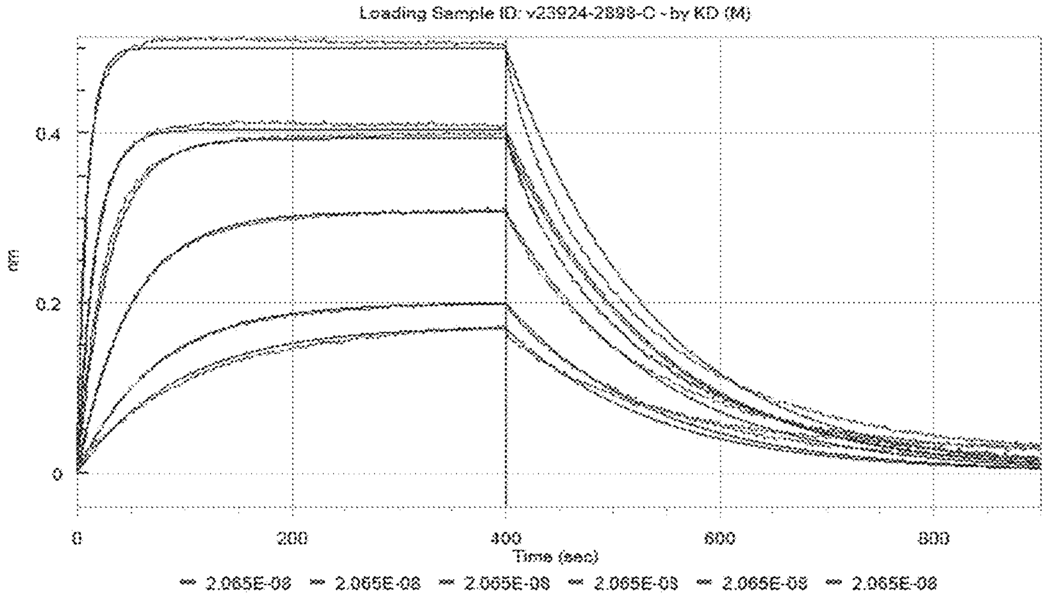
FIG. 3A & B depict the bio-layer interferometry (BLI) sensorgrams of parental chimeric anti-FRα antibody v23924 (3A) and purified representative humanized variant v30384 (3B).
Figure 3B:
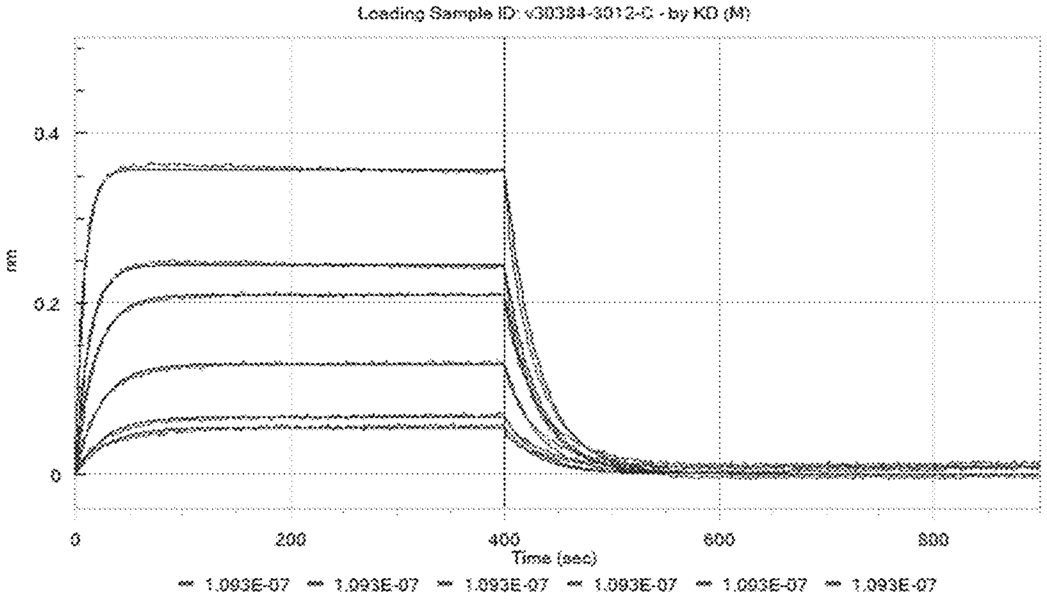
Figure 4A:
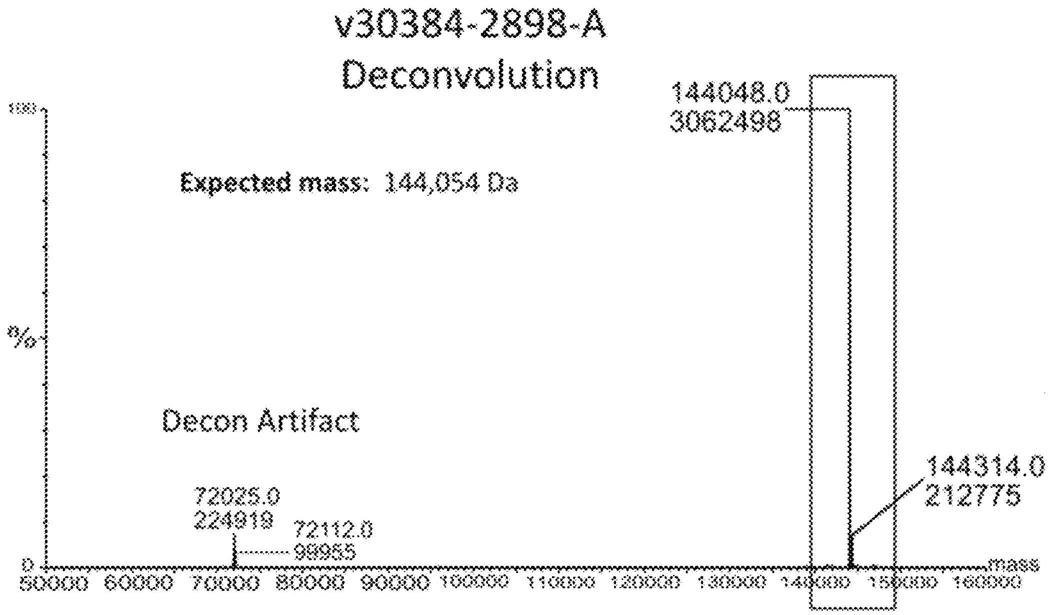
FIG. 4A, 4B, 4C, & 4D depict the intact LC/MS profiles for representative humanized variants v30384 (4A, with an expanded view of the main peak in 4B) and v31422 (4C, with an expanded view of the main peak in 4D).
Figure 4B:
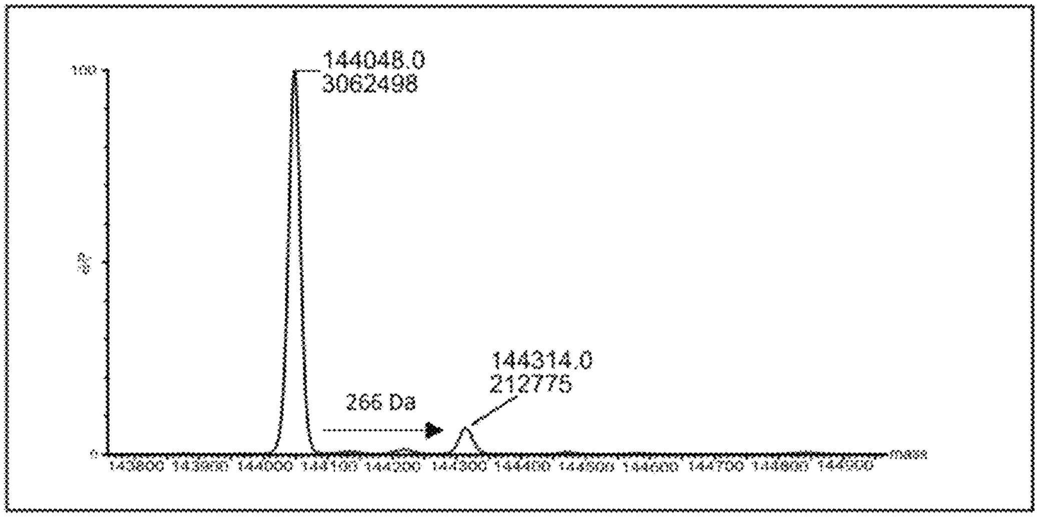
Figure 4C:
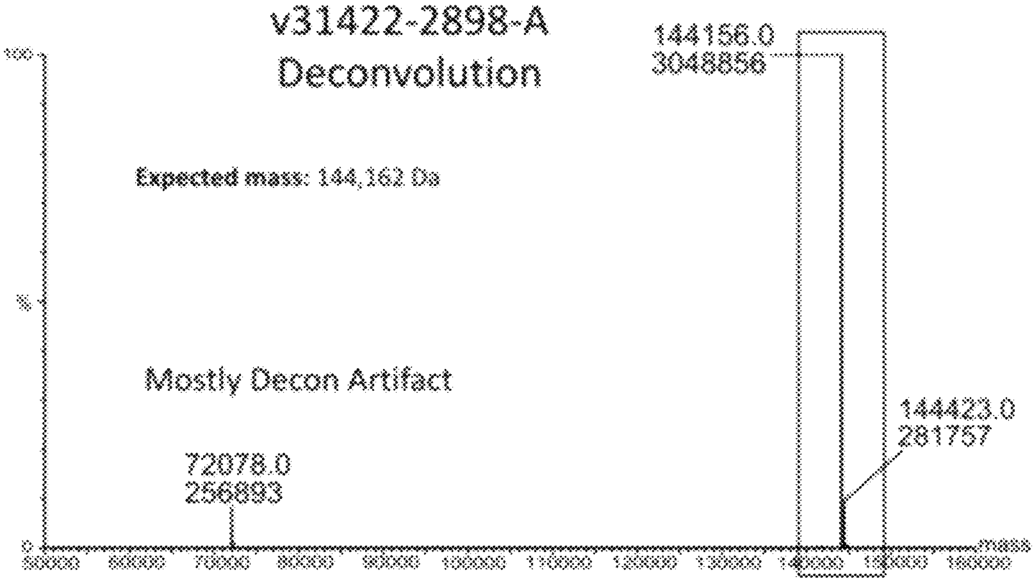
Figure 4D:
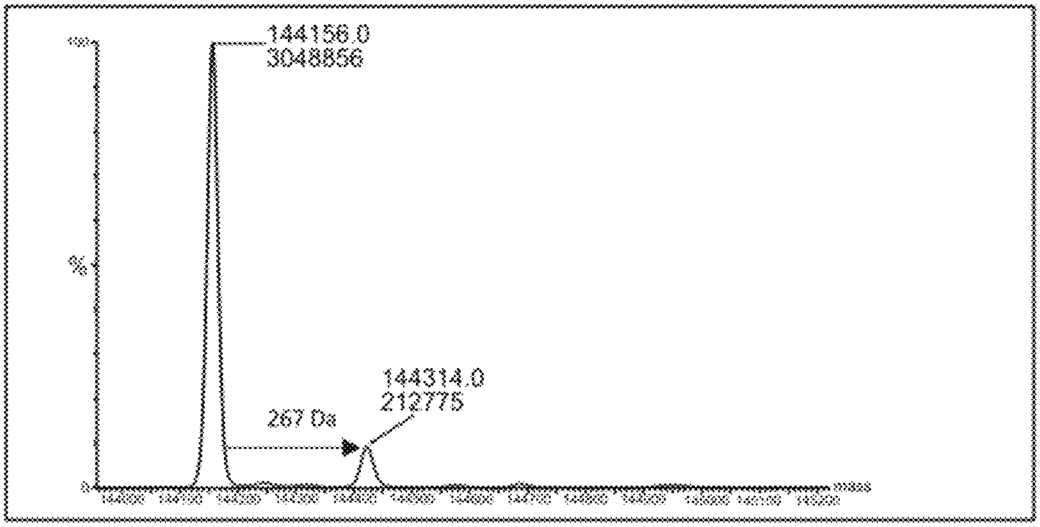

Nine of the 45 humanized antibody variants were found to bind hFRα with $K_D$ values ranging from ~63 nM to 210 nM (see Table 8.1). The $K_D$ of the parental chimera antibody (v23924) was determined to be 27 nM. Humanized antibody variants that exhibited binding to hFRα were characterized by an ~2-fold to ~8-fold reduced affinity compared to that of the parental chimera antibody. As can be seen from Table 8.1, all successful humanized variants shared the same variable light chain (4L) but differed in variable heavy chain composition. The sequences of light chain and heavy chains of the successful humanized variants are provided in Table 8.2. FIG. 3 shows the BLI sensorgrams for the parental chimeric antibody v23924, and a representative humanized antibody v30384.

TABLE 8.1

Antigen Binding Assessment of Humanized Variants by Octet ®

| Variant | Composition (VH + VL) | Fc Region[1] | Mean $K_D$ (M)[2] | Std Dev $K_D$ (M) |
|---|---|---|---|---|
| v23924 (parental) | — | HomoFc | 2.7E−08 | 8.4E−09 |
| Cycle One Variants | | | | |
| v30384 | 3H4L | HetFc | 1.1E−07 | 4.2E−09 |
| v30389 | 3bH4L | HetFc | 1.0E−07 | 1.4E−09 |
| v30394 | 4H4L | HetFc | 6.3E−08 | 7.1E−11 |
| v30399 | 4bH4L | HetFc | 6.9E−08 | 2.5E−09 |
| Cycle Two Variants | | | | |
| v31422 | 3cH4L | HomoFc | 1.8E−07 | 2.8E−08 |
| v31423 | 3dH4L | HomoFc | 1.1E−07 | 1.2E−08 |
| v31424 | 3eH4L | HomoFc | 1.1E−07 | 1.9E−08 |
| v31425 | 3fH4L | HomoFc | 1.6E−07 | 4.2E−10 |
| v31426 | 3gH4L | HomoFc | 2.1E−07 | 3.5E−10 |

[1]HetFc = heterodimeric Fc region; HomoFc = homodimeric Fc region (see Example 2)
[2]n = 2

TABLE 8.2

Amino Acid Sequences of Humanized VH and VL Chains

| Name | Amino Acid Sequence | SEQ ID NO |
|---|---|---|
| 3H_VH | EVQLLESGGGLVQPGGSLRL SCAVSGFSLSSYGVSWVRQA PGKGLEWIGAVNSGGSAYYA DSVKGRSTISRDNSKNTVYL QMNSLRAEDTAVYYCARSGS GYPMDYLAIWGQGTLVTVSS | 50 |
| 3bH_VH | EVQVLESGGGLVQPGGSLRL SCAVSGFSLSSYGVSWVRQA PGKGLEWIGAVNSGGSAYYA DSVKGRSTISRDNSKNTVYL QMNSLRAEDTAVYYCARSGS GYPMDYLAIWGQGTLVTVSS | 54 |
| 3cH_VH | EVQLLESGGGLFQPGGSLRL SCAVSGFSLSSYGVSWVRQA PGKGLEWIGAVNSGGSAYYA DSVKGRSTISRDNSKNTVYL QMNSLRAEDTAVYYCARSGS GYPMDYLAIWGQGTLVTVSS | 76 |
| 3dH_VH | EVQLLESGGGLVQPGGSLRL SCAVSGFSLSSYGVSWVRQA PGKGLEWIGAVNSGGSAYYA DSVKGRSTISRDTSKNTVYL QMNSLRAEDTAVYYCARSGS GYPMDYLAIWGQGTLVTVSS | 79 |
| 3eH_VH | EVQLLESGGGLVQPGGSLRL SCAVSGFSLSSYGVSWVRQA PGKGLEWIGAVNSGGSAYYA DSVKGRSTISRDTSKFTVYL QMNSLRAEDTAVYYCARSGS GYPMDYLAIWGQGTLVTVSS | 82 |

TABLE 8.2-continued

| Amino Acid Sequences of Humanized VH and VL Chains | | |
|---|---|---|
| Name | Amino Acid Sequence | SEQ ID NO |
| 3fH_VH | EVQLLESGGGLFQPGGSLRL SCAVSGFSLSSYGVSWVRQA PGKGLEWIGAVNSGGSAYYA DSVKGRSTISRDTSKFTVYL QMNSLRAEDTAVYYCARSGS GYPMDYLAIWGQGTLVTVSS | 85 |
| 3gH_VH | QQLLESGGGLFQPGGSLRLS CAVSGFSLSSYGVSWVRQAP GKGLEWIGAVNSGGSAYYAD SVKGRSTISRDTSKFTVYLQ MNSLRAEDTAVYYCARSGSG YPMDYLAIWGQGTLVTVSS | 88 |
| 4H_VH | EVQLLESGGGLVQPGGSLRL SCAVSGFSLSSYGVSWVRQA PGKGLEWIGAVNSGGSAYYA DWAKGRSTISRDNSKNTVYL QMNSLRAEDTAVYYCARSGS GYPMDYLAIWGQGTLVTVSS | 57 |
| 4bH_VH | EVQVLESGGGLVQPGGSLRL SCAVSGFSLSSYGVSWVRQA PGKGLEWIGAVNSGGSAYYA DWAKGRSTISRDNSKNTVYL QMNSLRAEDTAVYYCARSGS GYPMDYLAIWGQGTLVTVSS | 61 |
| 4L_VL | DYQMTQSPSSVSASVGDRVT ITCRASQSIGDWLAWYQQKP GKAPKLLIYEASTLASGVPS RFSGSGSGTDFTLTISSVQP EDAATYYCQQGYGRSNVDNI FGGGTKVEVK | 64 |

8.2 Avidity Assessment of the Humanized Antibodies for hFRα

The avidity of antigen binding for parental and selected humanized variants in FSA format was assessed by surface plasmon resonance (SPR) as described below.

The SPR assay for determination of hFRα affinity and avidity of the parental chimeric antibody (v23924) and the humanized variants was carried out on a Biacore™ T200 SPR system with PBS-T (PBS+0.05% (v/v) Tween 20) running buffer (with 0.5 M EDTA stock solution added to 3.4 mM final concentration) at a temperature of 25'C. CM5 Series S sensor chip, Biacore™ amine coupling kit (NHS, EDC and 1 M ethanolamine), and 10 mM sodium acetate buffers were purchased from GE Healthcare Life Science (Mississauga, ON, Canada). PBS running buffer with 0.05% Tween20 (PBST) was purchased from Teknova Inc. (Hollister, CA). Recombinant human FRα was purchased from ACRObiosystems (Newark, DE).

Screening of the variants for binding to hFRα antigen was conducted in two steps: capture of hFRα onto surface, followed by injection of three to five concentrations of variant. The hFRα surface was prepared on a CM5 Series S sensor chip by standard amine coupling methods as described by the manufacturer (GE Healthcare Life Science, Mississauga, ON, Canada). The immobilization of the hFRα was performed using Biacore™ T200 immobilization wizard with an amine coupling method aiming for resonance units (RUs) ranging from 5 to 200 RUs. Using multi-cycle kinetics, three to five concentrations of a two-fold dilution series of samples starting at 300 nM with a blank buffer control were injected at 50 uL/min for 180s with a 600s dissociation phase, resulting in a set of sensorgrams with a buffer blank reference. The hFRα surface was regenerated to prepare for the next injection cycle by one pulse of 10 mM glycine/HCl pH 1.5 for 30s at 30 uL/min. Blank-subtracted sensorgrams were analyzed using Biacore™ T200 Evaluation Software v3.0. The blank-subtracted sensorgrams were then fit to the 1:1 *Langmuir* binding model.

The results are shown in Table 8.3. Both parental antibody (v23924) and the two humanized variants (v30384 and v30399) in the regular bivalent antibody format (FSA) demonstrated avidity in binding to the hFRα antigen. Namely, -17-fold lower $K_D$ values in the case of parental and -27-39-fold in the case of humanized samples were obtained in FSA compared to one-armed antibody (OAA) format at medium-low antigen density, which further decreased to -108-fold and -116-181-fold respectively, at high antigen density.

TABLE 8.3

Avidity Assessment of Selected Humanized Variants by SPR

| Variant | Format[1] | Mean $K_D$ (M)[2] High Antigen Density | Medium Antigen Density | Medium-Low Antigen Density |
|---|---|---|---|---|
| v23924 | FSA | 2.78E−10 | 1.37E−09 | 2.29E−09 |
| v32596 | OAA v23924 equivalent | 3E−08 | 3.03E−08 | 3.79E−08 |
| v30384 | FSA | 7.9E−10 | 2.58E−09 | 3.76E−09 |
| v32597 | OAA v30384 equivalent | 1.43E−07 | 1.39E−07 | 1.46E−07 |
| v30399 | FSA | 7.09E−10 | 2.67E−09 | 3.71E−09 |
| v32598 | OAA v30399 equivalent | 8.2E−08 | 8.08E−08 | 9.15E−08 |

[1]OAA = one armed antibody, FSA = full size antibody; OAA antibody samples are equivalents of respective FSA samples and were produced in the similar manner to FSA samples described in Example 2.
[2] n = 2

Example 9: Purity of Humanized Anti-Frα Antibodies

The apparent purity of the humanized antibody variants from Example 8 was assessed using mass spectrometry after Protein A purification (Example 7) and non-denaturating deglycosylation.

As the antibody variant samples contained Fc N-linked glycans only, the samples were treated with N-glycosidase F (PNGase-F) only. The purified samples were de-glycosylated with PNGaseF as follows: 0.1U PNGaseF/g of antibody in 50 mM Tris-HCl pH 7.0, overnight incubation at 37° C., final protein concentration of 0.48 mg/mL. After deglycosylation, the samples were stored at 4° C. prior to LC-MS analysis.

The deglycosylated protein samples were analyzed by intact LC-MS using an Agilent 1100 HPLC system coupled to an LTQ-Orbitrap™ XL mass spectrometer (ThermoFisher, Waltham, MA) (tuned for optimal detection of larger proteins (>50 kDa)) via an Ion Max electrospray source. The samples were injected onto a 2.1×30 mm Poros $R^2$ reverse phase column (Applied Biosystems Corp., Waltham, MA) and resolved using a 0.1% formic acid aq/acetonitrile (degassed) linear gradient consisting of increasing concentration (20-90%) of acetonitrile. The column was heated to 82.5° C. and solvents were heated pre-column to 80° C. to improve protein peak shape. The cone voltage (source fragmentation setting) was approximately 40 V, the FT resolution setting was 7,500 and the scan range was m/z 400-4,000. The LC-MS system was evaluated for IgG sample analysis using a deglycosylated IgG standard (Waters IgG standard) as well as a deglycosylated mAb standard mix (25:75 half:full sized antibody). For each LC-MS analysis, the mass spectra acquired across the antibody peak (typically 3.6-4.1 minutes) were summed and the entire multiply charged ion envelope (m/z 1,200-4,000) was deconvoluted into a molecular weight profile using the MaxEnt 1 module of MassLynx™ data analysis software (Waters, Milford, MA). The apparent amount of each antibody species in each sample was determined from peak heights in the resulting molecular weight profiles.

The results are shown in Table 9.1. Almost all humanized variants were of high purity, ranging from ~89-100% desired species, with only v30389 showing a lower purity (82.6%). The slightly lower purity of four variants, v30384, v30389, v30394 and v30399, compared to that of the remaining variants is due to these variants comprising a heterodimeric CH3 region (see Example 7) which results in the presence of some half-antibodies. FIG. 4 depicts LC/MS profile for two representative humanized variants, v30384 and v31422. In the LC/MS profiles of all samples, a side peak of ~+266 Da was observed, which is likely an artifact of the analysis.

TABLE 9.1

Purity of Humanized Variants Determined by LC/MS

| Variant | % Desired Species |
|---|---|
| v30384 | 93.2 |
| v30389 | 82.6 |
| v30394 | 89.1 |
| v30399 | 91.8 |
| v31422 | 100 |
| v31423 | 100 |
| v31424 | 100 |
| v31425 | 100 |
| v31426 | 100 |

Example 10: Thermal Stability of Humanized Anti-FRα Antibodies

The thermal stability of the humanized antibody variants was assessed by differential scanning calorimetry (DSC) as described below.

400 μL of purified samples primarily at concentrations of 0.4 mg/mL in PBS were used for DSC analysis with a VP-Capillary DSC (GE Healthcare, Chicago, IL). At the start of each DSC run, 5 buffer blank injections were performed to stabilize the baseline, and a buffer injection was placed before each sample injection for referencing. Each sample was scanned from 20° C. to 100° C. at a 60° C./hr rate, with low feedback, 8 sec filter, 3 min pre-scan thermostat, and 70 psi nitrogen pressure. The resulting thermograms were referenced and analyzed using Origin 7 software (OriginLab Corporation, Northampton, MA) to determine melting temperature (Tm) as an indicator of thermal stability.

The Fab Tm values determined for the humanized variants are shown in Table 10.1. All humanized variants exhibited increased thermal stability compared to the parental antibody, v23924 (Fab Tm of ~72° C.), with Fab Tm values ranging from ~81-84° C. Of the humanized variants, v30394 showed the highest thermal stability.

TABLE 10.1

Thermal Stability of Humanized Variants

| Variant | Fab Tm (° C.) |
|---|---|
| v23924 (parental) | 72.1 |
| v30384 | 81.7 |
| v30389 | 80.7 |
| v30394 | 84.4 |
| v30399 | 83.4 |
| v31422 | 82.6 |
| v31423 | 83.0 |
| v31424 | 81.3 |
| v31425 | 82.4 |
| v31426 | 81.9 |

Example 11: Determination of Isoelectric Point for Humanized Anti-FRα Antibodies The isoelectric point of the humanized antibody variants was determined by capillary isoelectric focusing (cIEF) as described below.

cIEF was carried out using CE-UV Agilent 7100 Capillary Electrophoresis (CE) system. 5 ug (or maximal 2.5 uL) of sample was applied to the capillary (ampholytes range of 3.0-10.0). pI markers mix, 4.1, 4.22, 5.5, 7.0 and 10.0 for system suitability tests and 4.1 and 10.0 for sample analyses were used. The Agilent 7100 CE system equipped with an external water bath set to 6° C., the detector filter assembly (280 nm) and 9 bar external pressure were used for all CE runs. The neutral coated capillary (fluorocarbon) was cut at both ends at a distance of 8.5 cm and 24.5 cm from the detection window, respectively, equipped with a green alignment interface and fitted into the Agilent capillary cassette. Once a day, capillaries were conditioned as follows: high pressure flush at 3.5 bar with 350 mM acetic acid for 5 minutes, with water for 2 minutes and with cIEF gel for 5 minutes. Prior to every run, capillaries were conditioned as follows: high pressure flush at 3.5 bar with 4.3 M urea solution for 3 minutes and with water for 2 minutes. Samples were injected by applying 2 bar high pressure for 100 seconds, followed by a water dip of both inlet and outlet electrode. Focusing was performed for 10 minutes at 25 kV with 200 mM phosphoric acid as anolyte and 300 mM NaOH as catholyte. Using chemical mobilization, the outlet vial was exchanged for 350 mM acetic acid and 30 kV was applied for 30 minutes. After each run, a high pressure flush at 3.5 bar with water was performed for 2 minutes. Manual integration for peaks RT and electropherograms were obtained using Agilent OpenLAB Intelligent Reporting A.01.06.111 software. Raw data (signal vs retention time) were exported to a CVS file and main isoform pI, pI range and pI at the center of mass were calculated (based on the internal pI markers) in Microsoft Excel.

The results are shown in Table 11.1. The pI values determined for the main isoform for the majority of the humanized variants ranged from 7.78 to 7.97, with one variant having pI of 8.25 (v31426), which all fall within the typical range for therapeutic antibodies and are relatively comparable to that of the parental chimeric antibody v23924 (pI of 7.65).

TABLE 11.1

| Isoelectric Point for Humanized Variants | |
|---|---|
| Variant | pI (main isoform) |
| v23924 (parental) | 7.65 |
| v30384 | 7.79 |
| v30389 | 7.78 |
| v30394 | 7.89 |
| v30399 | 7.89 |
| v31422 | 7.93 |
| v31423 | 7.94 |
| v31424 | 7.97 |
| v31425 | 7.93 |
| v31426 | 8.25 |

Example 12: Chromatographic Analysis of Anti-FRα Antibodies

Parental and humanized variants were analyzed by hydrophobic interaction chromatography (HIC) and size exclusion chromatography (SEC) as described below.

12.1 HIC Analysis

The hydrophobicity/hydrophilicity of the antibodies were assessed by HIC as described in Antibody Drug Conjugates, Methods in Molecular Biology, 2013, vol. 1045, pp. 275-284. L. Ducry, Ed. The experiments were performed on an Agilent Infinity II 1290 HPLC using a TSKgel® Butyl-NPR column (2.5 μm, 4.6×35 mm, TOSOH Bioscience GmbH, Griesheim, Germany) pre-equilibrated with 5 column volumes of Buffer A (1.5 M $(NH_4)_2SO_4$, 25 mM $NaH_2PO_4$, pH=6.95) at room temperature. Typically, 20-30 g of sample at 2-3 mg/mL concentration was loaded on the column with 95% Buffer A and 5% Buffer B (75% 25 mM P043-plus 25% isopropanol, pH 6.95) and run for 15 mins at 0.5 mL/min using the gradient shown in Table 12.1. HIC chromatograms were integrated using appropriate parameters that provided complete, baseline-to-baseline integration.

TABLE 12.1

| HIC Solvent Gradient | | |
|---|---|---|
| Time (min) | % Buffer A | % Buffer B |
| 0 | 95 | 5 |
| 0.1 | 95 | 5 |
| 5 | 80 | 20 |
| 9.5 | 65 | 35 |
| 11.5 | 50 | 50 |
| 12.5 | 5 | 95 |
| 13.5 | 5 | 95 |
| 12.6 | 95 | 5 |
| 15 | 95 | 5 |

12.2 SEC Analysis

Analytical SEC was performed using an Agilent Infinity II 1260 HPLC with Advance Bio SEC column (300 Å, 2.7 μm, 7.8×150 mm) equilibrated with 5 column volumes of Mobile Phase A (150 mM $Na_2PO_4$, pH 6.95) at room temperature. Typically, 20-30 g of sample at 2-3 mg/mL concentration was eluted isostatically for 7 mins at 1 mL/min and absorbance was monitored at A280. Chromatograms were integrated to provide complete, baseline-to-baseline integration of each peak, with reasonably placed separation between partially resolved peaks. The peak corresponding to the major component for IgG (approximate retention time 3.3 min) was reported as the monomer based on the SEC profile of control trastuzumab. Any peak occurring prior to 3.3 min was designated as high molecular weight species (HMWS), and any peak occurring after 3.3 min was designated as low molecular weight species (LMWS), excluding solvent peaks (over 5.2 min).

12.3 Results

The summary of HIC retention time (HIC-RT) and SEC monomer % of parental and humanized variants are provided in Table 12.2. Overall, HIC and SEC showed favourable biophysical behaviour of all humanized variants. Parental chimeric antibody v23924 eluted at 6.5 mins on HIC gradient, whereas all humanized variants eluted between 6.0-6.7 mins. SEC profiles showed >90% monomer for all humanized variants, with variant v30389 having the lowest monomer % (94%). All these variants had <5% HMWS and <5% LMWS.

TABLE 12.2

| HIC and SEC Analysis of Parental and Humanized Anti-FRα Antibodies | | | | | |
|---|---|---|---|---|---|
| | | | SEC | | |
| Variant | Antibody | HIC-RT (min) | Monomer % | HMWS % | LMWS % |
| v23924 | Chimeric (parental) | 6.5 | 100 | 0 | 0 |
| v30618 | Chimeric (HetFc) | 6.7 | 94 | 6 | 0 |
| v30384 | Humanized | 6.2 | 97 | 3 | 0 |
| v30389 | Cycle one* | 6.2 | 94 | 3 | 4 |
| v30394 | | 6.0 | 95 | 4 | 2 |
| v30399 | | 6.1 | 96 | 4 | 0 |
| v31422 | Humanized | 6.0 | 100 | 0 | 0 |
| v31423 | Cycle two | 6.0 | 100 | 0 | 0 |
| v31424 | | 6.1 | 100 | 0 | 0 |
| v31425 | | 6.2 | 100 | 0 | 0 |
| v31426 | | 6.5 | 100 | 0 | 0 |

*No previous Prep-SEC

Example 13: Additional Stability Studies

In order to further investigate the stability of the humanized antibody variants, 40° C. stability and acid stability studies were performed in which samples were characterized at specific timepoints by Caliper and UPLC-SEC, as described in Example 7 and in the case of 40° C. stability study additionally by cIEF and Octet antigen binding, as described in Examples 11 and 8, respectively. Trastuzumab was used as a control in these studies.

Selected humanized variants (v30389, v30394, v30399, v31423 and v31424) underwent a 40° C. stability study for a duration of 14 days at -1 mg/ml sample concentration in PBS pH 7.4 buffer. Samples were characterized at timepoints 0, 5, 7, 11 and 14 days. An acid stability study was performed upon buffer exchange of the sample into acetate buffer of pH 3.6 at varied sample concentrations for a duration of 1 hr at 25° C., with characterization at timepoints 0, 15, 30 and 60 min. Additionally, freeze-thaw (from −80° C. to room temperature) constituting three cycles of 30 min per cycle was performed at −1 mg/ml sample concentration in PBS pH7.4.

The results are shown in Table 13.1. No significant issues with the stability of the humanized variants were identified in the studies. Freeze-thaw and acid stability studies did not reveal any change in sample composition over the course of the study, as determined by Caliper and UPLC-SEC. The 40° C. stability study showed minor changes in Caliper and UPLC-SEC profiles as the study progressed (specifically, the appearance of some amounts of lower molecular weight species, ranging from $-10^{-17}$%). No changes to the antigen-binding affinity were observed. cIEF revealed expected minor increases in more acidic species to relative to the main isoform.

TABLE 13.1

Stability Assessment of Humanized Variants in 40° C., Acid Stability and Freeze-Thaw Studies

| | % Monomer by UPLC-SEC | | |
|---|---|---|---|
| Variant | 40° C. Study Day 0/7/14 | Acid Stability Study 0/30/60 min | Freeze-Thaw Study |
| v6738[1] | 99.93/99.71/99.43 | Err[2]/100/100 | ND |
| v30389 | 92.75/87.64/82.02 | Err/94.91/93.83 | ND |
| v30394 | 95.49/89.01/83.51 | 95.12/95.53/95.49 | ND |
| v30399 | 96.13/89.25/81.68 | Err/100/100 | ND |
| v31423 | 100/90.92/82.58 | Err/100/100 | 99.22 |
| v31424 | 100/90.96 | 100/100/100 | 99.36 |

[1]Trastuzumab control
[2]Err = Erroneous baseline

Example 14: Functional Characterization of Anti-FRα Antibodies -FRα Specificity The binding cross-reactivity of parental chimeric antibody v23924 to FRα (FOLR1), FOLR2, FOLR3 and FOLR4 was assessed by flow cytometry and ELISA. FRα, FOLR2 and FOLR4 binding was assessed through flow cytometry using HEK293 transfected cells. FOLR3 binding was assessed through ELISA as FOLR3 is a soluble protein. Control anti-FOLR2 (mouse anti-human FOLR2; Nordic BioSite AB, Taby, Sweden; Cat. No. AFC-4544-2), anti-FOLR3 (mouse anti-human FOLR3; LS Bio, Seattle, WA; Cat. No. LS-$C_{125621}$) and anti-FOLR4 (mouse anti-His DyLight™ 650; Novus Biologicals, Littleton, CO; Cat. No. NBP2-31055C) antibodies were included in these experiments.

FRα, FOLR2 and FOLR4 binding: Briefly, HEK293-6e cells were transfected for ~24 hours to transiently express human FRα (Cat. No. 13420), FOLR2 (Cat. No. 13481) and FOLR4 (Cat. No. 13483) (all from GenScript Biotech, Piscataway, NJ), 1 ug DNA per 1 million cells. Following transfection, 50,000 cells were seeded in V-bottom 96-well plates and incubated with 50 nM primary antibody for 45 min under standard culturing conditions. Following incubation, cells were washed and stained with anti-Human IgG Fc AF647 conjugate (Jackson Immuno Research Labs, West Grove, PA; Cat. No. 109-605-098) at RT for 45 min. Following incubation and washing, fluorescence was detected by flow cytometry on a BD LSRFortessa™ Cell Analyzer (BD Biosciences, Franklin Lake, NJ) with 1,000 minimum events collected per well.

FOLR3 binding: ELISA 96-well plate was coated with commercial purified FOLR3 protein (R&D Systems, Inc., Minneapolis, MN; Cat. No. 5319-FR) for 1 hr at 37° C. The plate was blocked with 1% milk in PBS pH 7.4 for 1 hr at RT. Following blocking, primary antibodies were added at 7 nM for 1 hr at RT. HRP-conjugated secondary antibody (Jackson Immuno Research Labs, West Grove, PA; Cat. No. 109-035-098) was then added at 0.4 μg/ml, for 1 hr at RT. Plates were developed using tetramethylbenzidine (TMB) and HCl was used to stop reaction. Absorbance was read at 450 nm using a Synergy™ H1 microplate reader (BioTek Instruments, Winooski, VT).

Results

The results are shown in Tables 14.1 and 14.2. Anti-FRα, anti-FOLR2, anti-FOLR3 and anti-FOLR4 control antibodies showed expected binding to the respective target proteins by flow cytometry or ELISA. By flow cytometry, live singlet cell population was gated using FlowJo™ v8 software (BD Biosciences, Franklin Lake, NJ), and AF647 GeoMean and % positive binding was determined in this population for each antibody. For ELISA, % positive binding of anti-FOLR3 and v23924 antibodies was determined using raw absorbance values compared to negative control absorbance signal. v23924 showed expected binding to human FRα, and did not exhibit binding cross reactivity to FOLR2, FOLR3 or FOLR4, indicating FRα specificity.

TABLE 14.1

Binding to FRα, FOLR2 and FOLR4 Assessed by Flow Cytometry

| | AF647/DyLight650 GeoMean Singlet Population | | | % Positive Binding Singlet Population | | |
|---|---|---|---|---|---|---|
| Antibody | FRα | FOLR2 | FOLR4 | FRα | FOLR2 | FOLR4 |
| v23924 | 7663 | 7 | 27 | 71 | 0 | 0 |
| anti-FRα Control | 17971 | 227 | 188 | 86 | 1 | 0 |
| anti-FOLR2 Control | 17 | 4267 | 15 | 1 | 87 | 0 |
| anti-FOLR4 Control | 32 | 32 | 164 | 1 | 1 | 48 |
| Human IgG | 59 | 20 | 23 | 0 | 0 | 0 |

TABLE 14.2

Binding to FOLR3 Assessed by ELISA

| Antibody | Absorbance 450 nm | % Binding |
|---|---|---|
| v23924 | 0.29 | 8.9 |
| anti-FRα Control | 0.24 | 7.4 |
| anti-FOLR3 Control | 3.27 | 100.0 |
| Human IgG | 0.15 | 4.5 |

Example 15: Functional Characterization of Anti-FRα Antibodies -Binding to Cynomolgus FRα

The cross-reactivity of parental chimeric antibody v23924 to human and cynomolgus monkey FRα was assessed by flow cytometry using transfected CHO—S cells as described below. Palivizumab (anti-RSV) (v22277) was used as a negative control.

Briefly, CHO—S cells were transfected for ~24 hours to transiently express human or cynomolgus monkey FRα, 1 ug DNA per 1 million cells. Following transfection, cells were seeded at 50,000 cells/well in V-bottom 96-well plates and treated with antibody for 24 hours at 4° C. to prevent internalization. Following incubation, cells were washed and stained with anti-human IgG Fc AF647 conjugate (Jackson Immuno Research Labs, West Grove, PA; Cat. No. 109-605-098) at 4° C. for 30 min. Following incubation and washing, fluorescence was detected by flow cytometry on a BD LSRFortessa™ Cell Analyzer (BD Biosciences, Franklin Lake, NJ).

The results are shown in Table 15.1. v23924 showed comparable binding to human and cynomolgus FRα on CHO—S transfected cells, with apparent Kd values of 83.89 μM and 121.60 pM on human FRα and cynomolgus monkey FRα transfected cells, respectively. No binding by control v22277 was observed, as expected.

TABLE 15.1

| Binding to Cynomolgus Monkey FRα | | | |
|---|---|---|---|
| Antibody | Cells | Bmax | Apparent Kd (nM) |
| v23924 | CHO-S | 398.90 | 0.08 |
| v22277 | Human FRα | 6.94 | >50 |
| v23924 | CHO-S | 7626 | 0.12 |
| v22277 | Cyno FRα | 79.62 | >50 |

Example 16: Functional Characterization of Anti-FRα Antibodies -Cellular Binding The on-cell binding capabilities of the parental chimeric antibody v23924 and a representative humanized variant v30384 were assessed on JEG-3 and HEC-1-A endogenous FRα-expressing cell lines by flow cytometry as described below.

Briefly, cells were seeded at 50,000 cells/well in V-bottom 96-well plates and treated with antibody for 24 hours at 4° C. to prevent internalization. Following incubation, cells were washed and stained with anti-Human IgG Fc AF647 conjugate (Jackson Immuno Research Labs, West Grove, PA; Cat. No. 109-605-098) at 4° C. for 30 min. Following incubation and washing, fluorescence was detected by flow cytometry on a BD LSRFortessa™ Cell Analyzer (BD Biosciences, Franklin Lake, NJ) with 1,000 minimum events collected per well. AF647/APC-A GeoMean (fluorescence signal geometric mean, proportional to anti-Human AF647 binding) in live cell population was plotted using GraphPad Prism Version 9 (GraphPad Software, San Diego, CA).

The results are shown in Table 16.1. Both the chimeric (v23924) and humanized (v30384) antibodies yielded comparable apparent Kd and Bmax values in both JEG-3 and HEC-1-A cell lines (high and moderate endogenous FRα expression, respectively).

TABLE 16.1

| Cellular Binding | | | | | | |
|---|---|---|---|---|---|---|
| | JEG-3 | | | HEC-1-A | | |
| Antibody | Bmax | Curve Hill Slope (h) | Kd (nM) | Bmax | Curve Hill Slope (h) | Kd (nM) |
| v23924 | 20337 | 1.18 | 0.32 | 2490 | 1.38 | 0.05 |
| v30384 | 18299 | 1.73 | 0.31 | 2125 | 1.31 | 0.07 |
| Human IgG | NA | NA | NA | NA | NA | NA |

Example 17: Functional Characterization of Anti-FRα Antibodies -INTERNALIZATION The receptor-mediated internalization capabilities of the chimeric antibody v23924 and a representative humanized variant, v30384, in FRα-expressing cell lines (IGROV-1 and OVCAR-3) were determined by high content imaging as described below. The FRα-targeting antibodies mirvetuximab and farletuzumab were used as positive controls, and palivizumab (anti-RSV) (v22277) was used as a negative control.

Briefly, antibodies were fluorescently labeled by coupling to an anti-human IgG Fc Fab fragment pHAb dye conjugate (Promega Corporation, Madison, WI; Cat. No. G9841) (~3 dye molecules per Fab fragment) at a 5:1 molar excess for 24 hours at 4° C. Cells were seeded and incubated overnight at 37° C. in 5% $C_{02}$ in 96-well plates. Coupled antibodies were added to cells the following day and incubated at 37° C. for 6-24 hours to allow for internalization. Following incubation, cells were stained with Dye Cycle Violet (ThermoFisher Scientific Corporation, Waltham, MA; Cat. No. V35003) for viable cell identification and internalized fluorescence in live cells was analyzed by high content imaging using the CellInsight™ CX5 High Content Screening (HCS) Platform (ThermoFisher Scientific Corporation, Waltham, MA). Fold-over fluorescence of the chimeric antibody v23924 was plotted using GraphPad Prism, Version 9 (GraphPad Software, San Diego, CA).

Results

Figure 5A:
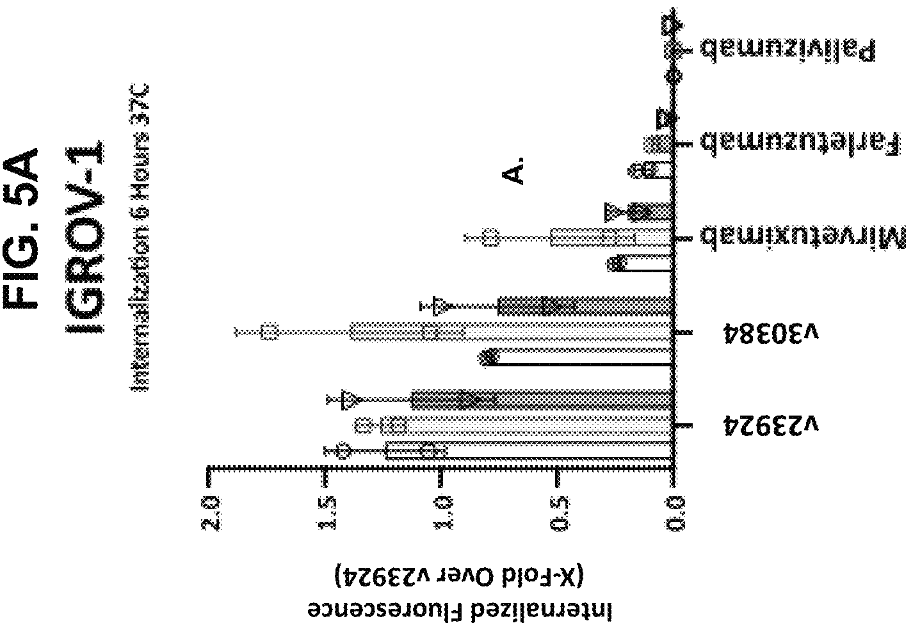
FIG. 5A & 5B shows the receptor-mediated internalization capabilities of the chimeric anti-FRα antibody v23924, a representative humanized variant, v30384, and the FRα-targeting antibodies mirvetuximab and farletuzumab at various concentrations in the FRα-expressing cell line IGROV-1 as determined by flow cytometry after a 6-hour incubation (5A) and a 24-hour incubation (5B). The anti-RSV antibody, palivizumab, was included as a negative control.
Figure 5B:
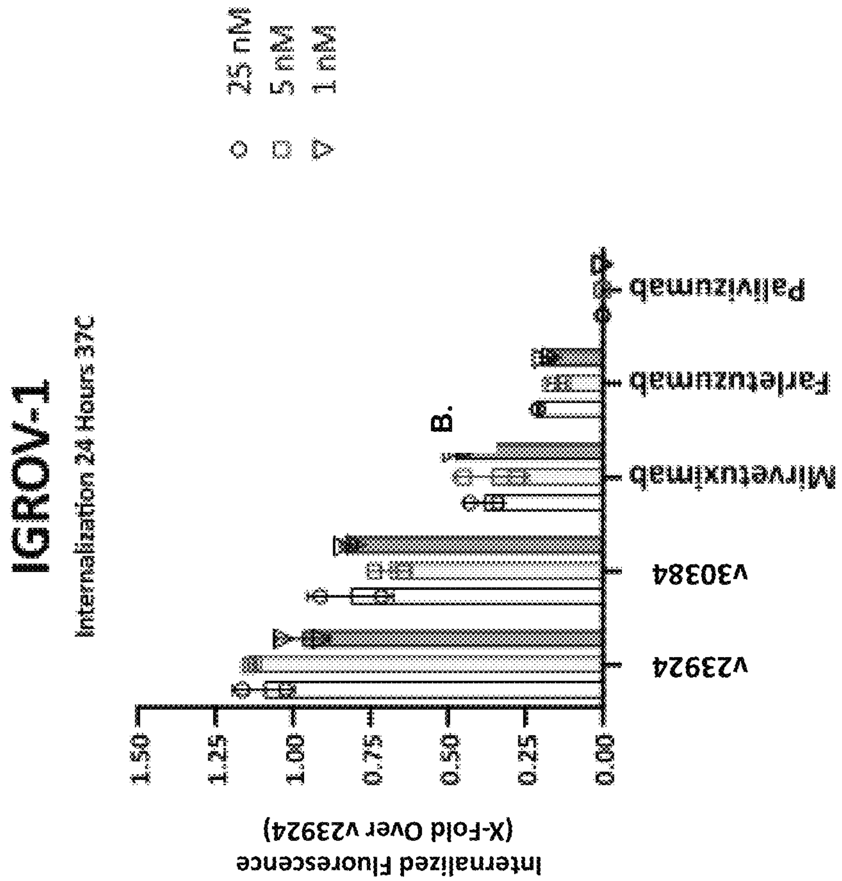
Figure 6B:
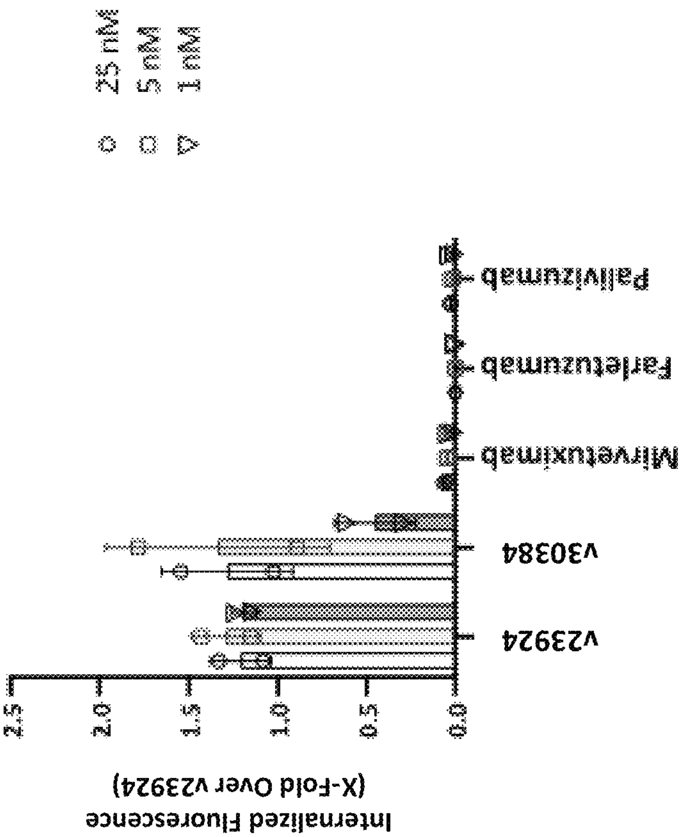
FIG. 6A & 6B show the receptor-mediated internalization capabilities of the chimeric anti-FRα antibody v23924, a representative humanized variant, v30384, and the FRα-targeting antibodies mirvetuximab and farletuzumab at various concentrations in the FRα-expressing cell line OVCAR-3 as determined by flow cytometry after a 6-hour incubation (6A) and a 24-hour incubation (6B). The anti-RSV antibody, palivizumab, was included as a negative control.
Figure 6A:
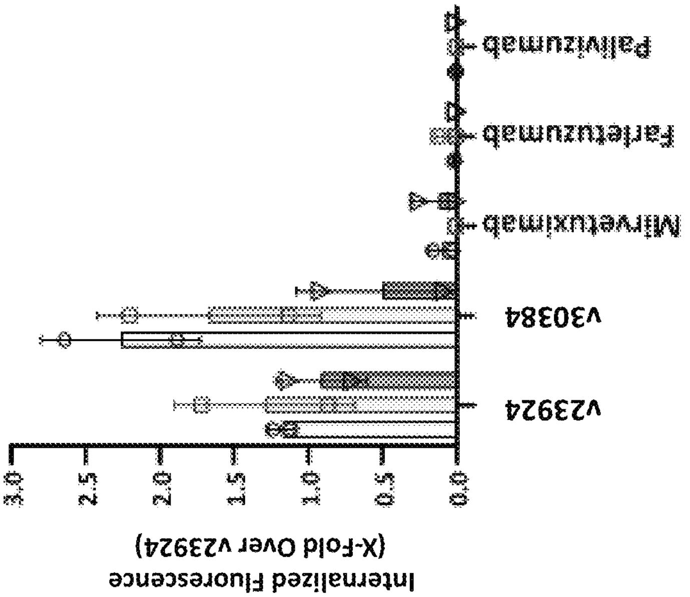

The results are shown in FIG. 5A & 5B (IGROV-1 cells) and FIG. 6A & 6B (OVCAR-3 cells). Chimeric antibody v23924 showed comparable levels of internalization to the humanized variant v30384 in both IGROV-1 cells (high FRα) and OVCAR-3 cells (moderate FRα). In both IGROV-1 and OVCAR cells, the chimeric antibody v23924 and the humanized variant v30384 showed increased internalization compared to mirvetuximab and farletuzumab positive controls across all tested concentrations (25 to 1 nM) and time points (6-24 hours). For example, following a 6-hour incubation in IGROV-1 cells, humanized variant v30384 showed 3.3 and 6.1-fold increase in internalized fluorescence compared to mirvetuximab and farletuzumab, respectively, at 25 nM, and 2.6 and 19.1-fold increase in internalized fluorescence compared to mirvetuximab and farletuzumab, respectively, at 5 nM (FIG. 5A). Similarly, following a 24-hour incubation in IGROV-1 cells, humanized variant v30384 showed 2.1 and 3.9-fold increase in internalized fluorescence compared to mirvetuximab and farletuzumab, respectively, at 25 nM, and 1.9 and 4.7-fold increase in internalized fluorescence compared to mirvetuximab and farletuzumab, respectively, at 5 nM (FIG. 5B).

Example 18: Epitope Mapping

High resolution epitope mapping of the parental chimeric antibody v23924 on human FRα antigen (hFRα) was conducted by hydrogen/deuterium exchange mass spectrometry (HDX-MS) at NovoAb Bioanalytics Inc. (Victoria, BC. Canada) as described below.

18.1 Sample Preparation for HDX-MS

Lyophilized hFRα was purchased from ACROBiosystems (Newark, DE; Catalogue no: FO1-H5229) and dissolved to a concentration of 2.5 mg/ml. The antigen-antibody complex was prepared by mixing hFRα with the parental chimeric antibody v23924 at a molar ratio of 2:1. All samples had a pH of 7.4 and were clear (no precipitation was observed). For peptide identification, hFRα at a concentration of 10 M was reduced with 100 mM of tris-(2-carboxyethyl) phosphine (TCEP) in the presence of 2 M guanidine at pH 2.4, and then digested with pepsin at an enzyme-to-protein molar ratio of 1:1. HDX was initiated by mixing the protein samples with $D_{20}$ buffer at a ratio of 2:8 (v/v). The resulting solutions were incubated at 26° C., and aliquots were taken at 20 s, 7 min, 1 h and 4 h, and instantly quenched by adding a 200 mM TCEP solution containing 4 M guanidine. These samples were flash frozen in liquid nitrogen and stored at −80° C. During LC-MS experiments, the protein aliquots were quickly thawed and kept on ice for the reduction to proceed for 2 min, and then digested at 0° C. with pepsin for 2 min.

18.2 LC-MS and LC-MS/MS

In the LC-MS experiments, 20 μL aliquots of each sample were instantly injected into a C18 analytical column and separated by reversed-phase liquid chromatography using a Dionex UHPLC system (Thermo Fisher Scientific, Bremen, Germany) at a flow rate of 100 μL/min. The UHPLC system was coupled to a Thermo Scientific Orbitrap Fusion™ mass spectrometer equipped with a heated electrospray ionization (HESI) II source. The column, accessories, injector and solvent delivery lines were embedded in an ice bucket to minimize H/D back-exchange. The syringe used for injection was chilled on ice. The mobile phase was 0.1% formic acid (A) and 100% acetonitrile/0.1% formic acid (B), and the peptides were separated by a 13-minute gradient.

The MS survey scan was carried out within m/z 300-1600 range, with a mass resolution of 120,000 FWHM. The Orbitrap detector was calibrated to be ≤3 ppm error by using Calibration Mix (Calmix; ThermoFisher Scientific Corporation, Waltham, MA). In the electron transfer dissociation (ETD) experiments, fluoranthene radical anions were introduced into the ion trap over 50 ms. Collision induced dissociation (CID) and ETD fragment ions were detected in the Orbitrap using a scan range of 150-2000 m/z.

For data analysis, raw bottom-up LC-MS/MS data were processed using the Proteome Discoverer™ software suite (Thermo Fisher Scientific). The generated peak lists were submitted to the Mascot 2.2 server in-house and searched against the sequence of hFRα. The peptides thus identified were used for HDX data analysis. ETD data were processed using Xcalibur™ software (ThermoFisher Scientific Corporation, Waltham, MA) and the generated ETD peak lists were searched against the sequence of hFRα using Protein Prospector (available online from the University of California, San Francisco website; http://prospector.ucsf.edu). Matched ions were also checked and confirmed by manual inspection. The mass shift of the peptides and the deuteration status of individual amides were determined based on their centroid m/z values before and after H/D exchange. All HDX data were normalized to 100% $D_{20}$ content (80% D exchange-in buffer for all the time points). Percent deuterium incorporation values were obtained by comparing the number of acquired deuterium to the total number of amide hydrogens contained in each peptide. The amide level deuteration information was calculated based on the deuterium uptake of the ETD fragments.

18.3 Results

Protein Sequence Coverage and Peptide Identification

The presence of protein disulfide bonds has a significant impact on the pepsin digestion pattern and efficiency in the peptide-based HDX-MS analysis. Since both hFRα and the antibody v23924 contain multiple disulfide bridges, an optimized protocol for rapid protein disulfide reduction and pepsin digestion was first developed. The reduction time and digestion time was optimized to be 2 min for each, and these conditions were applicable to both hFRα and the hFRα-v23924 complex. The peptides thus identified covered 100% of the antigen sequence (see FIG. 7).

Peptide Level HDX Comparison

Figure 8A:
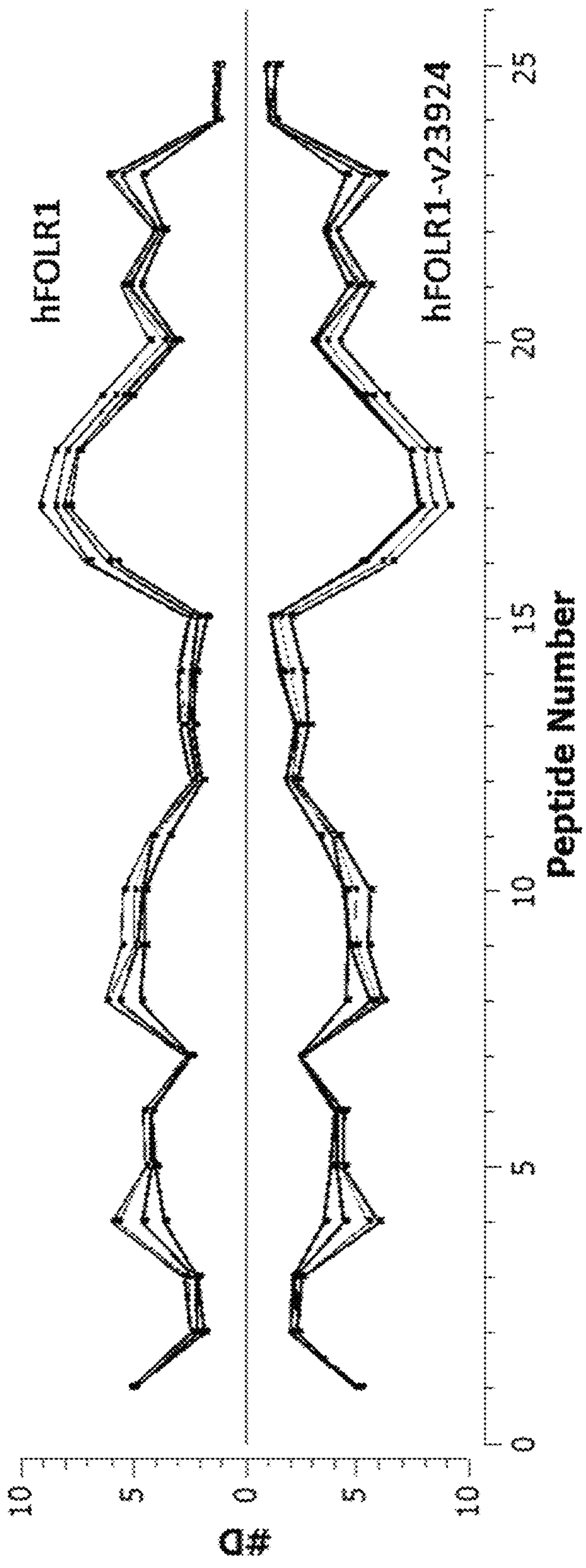
FIG. 8A & 8B show a summary plot (8A) and a differential plot (8B) of the hydrogen/deuterium exchange mass spectrometry (HDX-MS) kinetics of the peptides generated by pepsin digestion of hFRα: hFOLR1 (hFRα) vs. hFOLR1-v23924 complex.
Figure 8B:
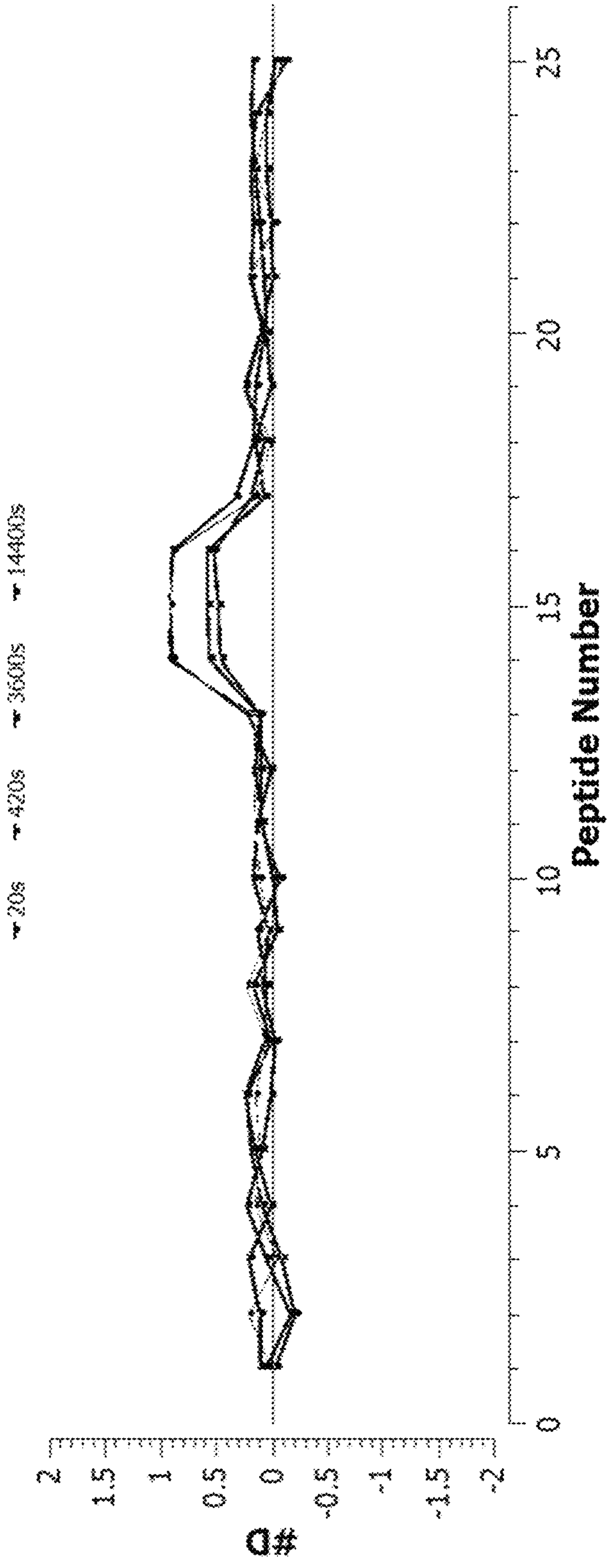

The deuterium incorporation levels of peptides from hFRα and the v23924 complex were plotted versus HDX time (20s, 7 min, 1 h, and 4 h). The results are summarized and shown in FIG. 8. Most of the peptides have the same deuterium uptake behavior before and after antibody binding (FIG. 8A), suggesting the binding site (epitope) of the v23924 antibody is quite localized. In the differential plot shown in FIG. 8B, three peptides (numbers 14, 15 and 16) showed significant lowering in deuterium uptake after v23924 binding, indicating they are in the epitope region. The sequences of these peptides are WWEDCRTSY (118-126) (SEQ ID NO:151), WEDCRTSY (119-126) (SEQ ID NO:152), and WEDCRTSYTCKSNWHKGWNWTSGF (119-142) (SEQ ID NO:153), respectively.

Epitope Determination at Amino Acid Level

Figures 9A, 9B, 9C:
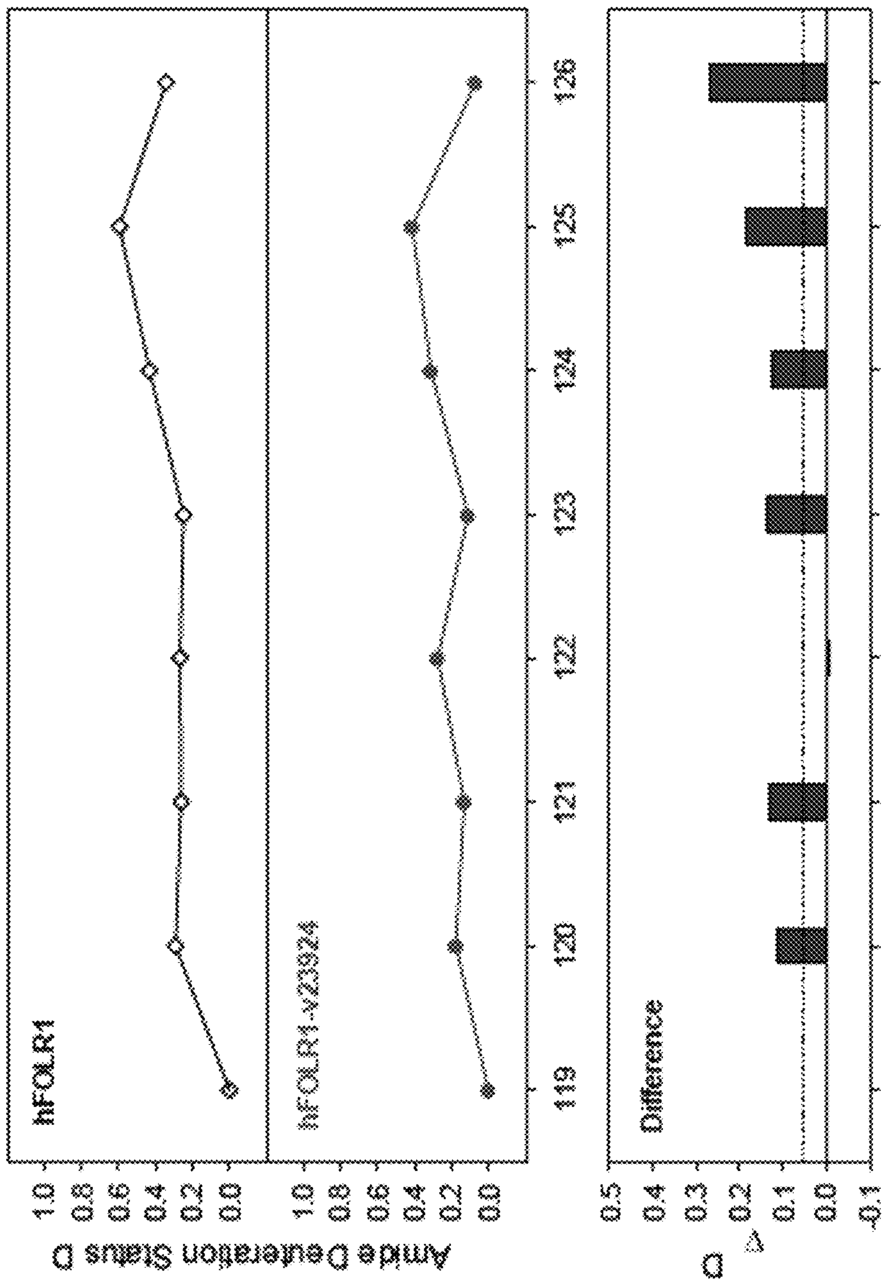
FIG. 9A 9B, & 9C show the amide deuteration level of peptide 119-126 (WEDCRTSY) (SEQ ID NO: 152) after hydrogen/deuterium exchange mass spectrometry (HDX-MS) for 1 h: hFOLR1 (9A) vs. hFOLR1-v23924 complex (9B), and the differential plot (9C).

Although the three epitope peptides differ in sequence, their HDX differences are the same (FIG. 8), and they all contain the sequence WEDCRTSY (119-126) (SEQ ID NO:152). This indicates that all the epitope residues are included in the shortest peptide 119-126. The observation of multiple differential peptides in the same region provides additional confirmation that this region of the protein is the binding site of the v23924 antibody. To further locate the HDX differences and pinpoint the epitope down to individual amino acids, MSMS was carried out on the peptide 119-126 using ETD. The HDX time point of 1 h was selected as this gave the largest difference. The ETD fragments provided single-residue resolution. The deuteration level of each amino acid was calculated and compared between hFRα and the v23924 complex (FIG. 9). Based on the results of the difference plot, the epitope residues were determined to be E120, D121, R123, T124, S125, and Y126 of SEQ ID NO: 15 (i.e. the epitope sequence is: EDRTSY; SEQ ID NO: 154).

Example 19: Affinity Maturation of Anti-Frα Antibody

The humanized antibody v30384 (see Example 8) was affinity matured using the HuTarg™ system (Innovative Targeting Solutions, Vancouver, BC, Canada). Genetic recombination was applied to the variable regions of the humanized variant v30384, and high affinity mutants were identified using next-generation sequencing (NGS).

19.1 Design of Library Plasmid Pool

The CDR loops of the humanized variant v30384 variable domains were interspersed with RAG1/2 recombination signal sequences (RSS). These variable domains were synthesized at Integrated DNA Technologies, Inc. (Coralville, IA) and cloned into plasmid E951 (Innovative Targeting Solutions, Vancouver, BC, Canada).

19.2 HuTarg™ Library Generation

The following steps were performed in accordance with Innovative Targeting System's protocols. E951-based plasmid pools were integrated into HuTarg™ cells, and RAG1/2 expression induced for 48 hours. HuTarg™ cells displaying successfully recombined antibodies, shown after staining with PE-conjugated goat anti-human kappa light chain antibody (Bio-Rad Laboratories, Hercules, CA; cat #206009) were then selected for further interrogation.

19.3 FACS-Based Selection of Affinity Mutants

HuTarg™ cells were subjected to multiple rounds of FACS-based sorting on a BD FACSAria™ Flow Cytometer (BD Biosciences, Franklin Lakes, NJ), with each round using a reduced amount of biotinylated soluble HIS-tagged FRα antigen (FRα-HIS, ACROBiosystems Newark, DE; cat #FO1-$H_{82}$E2), detected with streptavidin conjugated to AlexaFluor-647 (Thermo Fisher Scientific Corp., Waltham, MA; cat #S11223). HuTarg™ cells that exhibited increased binding to biotinylated FRα-HIS were sorted directly to RNAzol RT (Sigma-Aldrich, St. Louis, MI; cat #$R^{4533}$) in preparation for next-generation sequencing.

19.4 Next-Generation Sequencing of Affinity Mutants

Total RNA from cells lysed in RNAzol was isolated as per manufacturer's instructions. RNA was then digested with ezDNase™ (Thermo Fisher Scientific Corp., Waltham, MA;

cat #11766051), and cDNA transcribed using Superscript™ IV (Thermo Fisher Scientific Corp., Waltham, MA; cat #18090010) and a gene-specific primer. VH and VK domains were targeted for PCR amplification, and molecularly barcoded with NEBNext® Ultra™ DNA Library Prep Kit (New England Biolabs, Ipswich, MA; cat #E7370L). Samples were pooled and run on an Illumina MiSeq™ sequencer with a 500-cycle kit using v2 chemistry (Illumina, San Diego, CA; cat #MS-102-2003). Sequence analysis was performed to identify mutations within VH and VK sequences that exhibited high likelihood of conferring affinity increase.

19.5 Recombinant Expression of Affinity Mutants

DNA sequences encoding mutated VH and VK domains were synthesized as "MiniGenes" (Integrated Technologies, Inc., Coralville, IA) and cloned into expression vectors to provide expression plasmids coding for complete human IgG1 heavy chains and human kappa light chains, respectively. Expression plasmids were matrixed with one another to pair every heavy chain plasmid with every light chain plasmid. This matrix was recombinantly expressed in Expi293™ cells (Thermo Fisher Scientific Corp., Waltham, MA; cat #A14635) according to manufacturer's instructions to create 64 samples.

19.6 Evaluation of Affinity Mutants

Protein G particles (Spherotech Inc., Lake Forest, IL) were coated with the humanized variant v30384 or affinity matured antibodies at a normalized concentration. Soluble human FRα was diluted to a limiting antigen concentration and incubated with antibody coated beads. FRα antigen binding and antibody capture was detected using AlexaFluor-647 conjugated streptavidin and AlexaFluor-488 conjugated goat anti-human IgG Fcγ (both from Jackson Laboratories, Bar Harbor, ME), respectively. Samples were analyzed by flow cytometry on a BD LSRFortessa™ Cell Analyzer (BD Biosciences, Franklin Lakes, NJ). Geometric mean for FRα binding and antibody capture was analyzed for each sample. Antibody capture was normalized to FRα binding to affinity rank humanized variant v30384 against affinity matured antibodies.

Single point affinity ranking was performed by measuring the ratio of antibody captured on beads to the amount of antigen captured by antibody. Variant v30384 binding was minimal (3× over background) using a human FRα concentration of 1.9 nM, while the majority of mutated variants exhibited higher binding ratios. Of 64 mutated variants, 3 variants showed a 4-fold increase in binding ratio, and 10 showed an equivalent binding ratio.

Example 20: Assessment of Affinity of Affinity Matured Antibodies for FRα

Ten of the affinity matured variants described in Example 19 were produced in full size antibody (FSA) format at WuXi Biologics (Hong Kong) Limited, China, via transient transfection in CHO-K1 cells and affinity capture purification with a subsequent polishing step (where necessary) involving primarily preparatory SEC or CEX chromatography, yielding greater than 97% sample purity by HPLC-SEC. The FSA format was similar to that of parental humanized variant v30384 except these variants comprised a HomoFc rather than HetFc. The ten affinity matured variants were characterized for binding to hFRα using the Octet® RED96 system as described in Example 8.

Results

The results are shown in Table 20.1. Affinity maturation was successful in obtaining humanized variants with affinities to hFRα substantially higher than the parental humanized antibody v30384 ($K_D$ 1.27E-07 M), ranging from ~12 to 58-fold improvement. The lowest $K_D$ of 2.2E-09 M was observed for variant v35348. The gain in affinity was determined to be primarily achieved by lowering of the dissociation constant.

TABLE 20.1

Affinity Assessment of Affinity Matured Variants

| Variant | Mean $K_D$ (M)* | Std Dev $K_D$ (M) |
|---|---|---|
| v30384 (parental humanized) | 1.27E−07 | 2.49E−08 |
| v35305 | 1.08E−08 | 9.12E−10 |
| v35342 | 4.1E−09 | 1.3E−10 |
| v35347 | 8.65E−09 | 9.18E−10 |
| v35348 | 2.2E−09 | 1.8E−10 |
| v35350 | 3.55E−09 | 2.89E−10 |
| v35354 | 3.13E−09 | 7.64E−11 |
| v35356 | 4.98E−09 | 1.8E−10 |
| v35358 | 7.22E−09 | 4.21E−10 |
| v36167 | 7.29E−09 | 1E−10 |
| v36168 | 4.97E−09 | 2.64E−10 |

*n = 2

Example 21: Chromatographic Analysis of Affinity Matured Antibodies

The ten affinity matured variants from Example 20 were analyzed by hydrophobic interaction chromatography (HIC) and size exclusion chromatography (SEC) as described in Example 12. The results are shown in Table 21.1. Affinity maturation of the antibody resulted in changes to the hydrophobicity/hydrophilicity as demonstrated by the variable HIC-RT. Antibody monomer content was above 97% in all cases and did not correlate with HIC-RT.

TABLE 21.1

HIC and SEC Analysis of Affinity Matured Anti-FRα Antibodies

| | HIC-RT | SEC | | |
|---|---|---|---|---|
| Variant | (min) | Monomer % | HMWS % | LMWS % |
| v30384 (parental humanized) | 6.2 | 97 | 3 | 0 |
| v36167 | 8.4 | 98.8 | 1.2 | 0 |
| v36168 | 10.0 | 99.4 | 0.6 | 0 |
| v35305 | 9.2 | 100.0 | 0.0 | 0 |
| v35342 | 10.1 | 100.0 | 0.0 | 0 |
| v35347 | 4.9 | 97.3 | 2.7 | 0 |
| v35348 | 5.6 | 98.4 | 1.6 | 0 |
| v35350 | 9.9 | 100.0 | 0.0 | 0 |
| v35354 | 9.6 | 100.0 | 0.0 | 0 |
| v35356 | 5.0 | 98.7 | 1.3 | 0 |
| v35358 | 8.7 | 98.7 | 1.3 | 0 |

Example 22: Functional Characterization of Affinity Matured Antibodies—Cellular Binding The on-cell binding capabilities of a representative affinity matured variant v35356 were assessed on IGROV-1 and JEG-3 endogenous FRO-expressing cell lines by flow cytometry as described in Example 16.

Results

The results are shown in Table 22.1. Parental humanized variant v30384 and affinity matured variant v35356 yielded comparable apparent Kd and Bmax values in both IGROV-1 and JEG-3 cell lines (high and moderate endogenous FRα expression, respectively).

TABLE 22.1

| Cellular Binding | | | | | | |
|---|---|---|---|---|---|---|
| | IGROV-1 | | | JEG-3 | | |
| Antibody | Bmax | Curve Hill Slope (h) | Kd (nM) | Bmax | Curve Hill Slope (h) | Kd (nM) |
| v30384 (parental humanized) | 42,611 | 1.442 | 1.38 | 35,942 | 1.598 | 0.50 |
| v35356 (affinity matured) | 43,842 | 1.537 | 1.31 | 40,110 | 2.119 | 0.44 |
| Human IgG | 208 | NA | NA | 144 | NA | NA |

Example 23: Functional Characterization of Affinity Matured Antibodies—Internalization The receptor-mediated internalization capabilities of the parental humanized variant, v30384, and a representative affinity matured variant, v35356, in FRα-expressing cell lines (IGROV-1 and JEG-3) were determined by flow cytometry as described below. Palivizumab (anti-RSV) (v22277) was used as a negative control.

Briefly, antibodies were fluorescently labeled by coupling to Fab-AF488 anti-Human IgG Fc labelling reagent (Jackson Immuno Research Labs, West Grove, PA; Cat. No. 109-547-008) at a 1:1 molar ratio for 24 hours at 4° C. Cells were seeded and incubated overnight at 37° C. in 5% $CO_2$in 48-well plates. Coupled antibodies were added to cells the following day and incubated at 37° C. for 24 hours to allow for internalization. Following incubation, cells were dissociated, washed and surface AF488 fluorescence was quenched using an anti-488 antibody at 100 nM incubated at 4° C. for 45 min. Quenched AF488 fluorescence (internalized fluorescence) was analyzed by flow cytometry for all samples on a BD LSRFortessa™ Cell Analyzer (BD Biosciences, Franklin Lake, NJ), with 1,000 minimum events collected per well. AF488/FITC-A GeoMean in live cell population was plotted using GraphPad Prism Version 9 (GraphPad Software, San Diego, CA).

Results

Figure 10A:
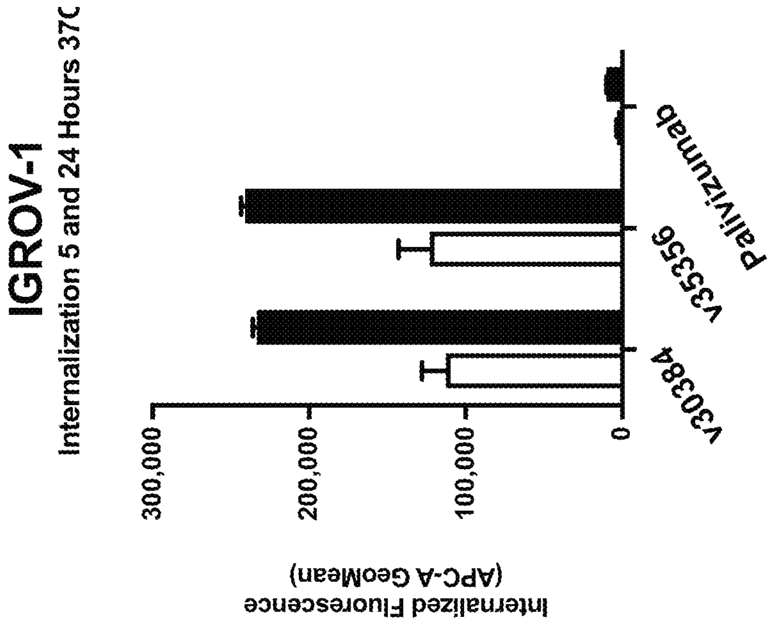
FIG. 10A & 10B show the receptor-mediated internalization capabilities of a parental anti-FRα humanized antibody variant, v30384, and a representative affinity matured variant, v35356, in FRα-expressing cell lines IGROV-1 (10A) and JEG-3 (10B) as determined by flow cytometry after 5 h and 24 h incubation periods. Palivizumab was included as a non-targeted control.
Figure 10B:
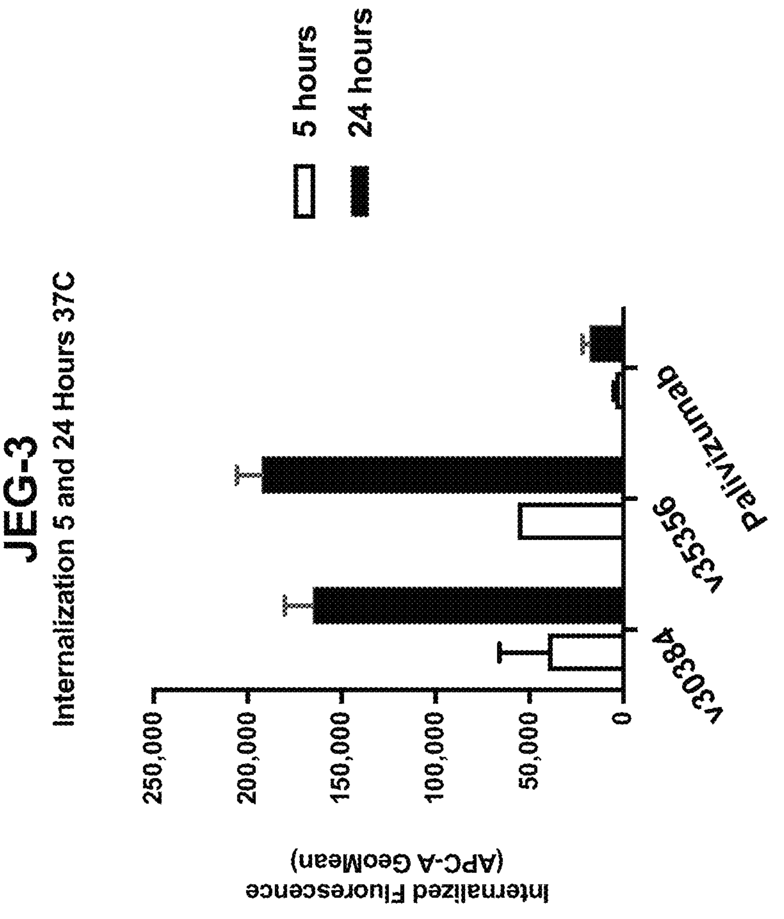

The results are shown in FIG. 10. Parental humanized variant v30384 and the affinity matured variant v35356 showed comparable internalization in IGROV-1 (FIG. 10(A)) and JEG-3 (FIG. 10(B)) cells, when administered at 20 nM, at both 5 hour and 24 hour exposure.

Example 24: Preparation of Antibody-Drug Conjugates

Antibody-drug conjugates shown in Table 24.1 were prepared. Exemplary protocols are provided below. Variant v36675 comprises the same paratopes as variant v30384 but has a HomoFc Fc region rather than a HetFe region.

v36675-MC-GGFG-AM-DXd1: A solution (83.5 mL) of the humanized variant v36675 (1.5 g) in PBS, pH 7.4 was reduced by addition of 5 mM diethylenetriamine pentaacetic acid (DTPA) (24 mL in PBS, pH adjusted to 7.4) and 10 mM of an aqueous tris(2-carboxyethyl)phosphine (TCEP) solution (12.5 mL, 12 eq.). After 3 hours at 37° C., the reduced antibody was diluted to 125 mL with PBS and purified using a Pellicon® XL Ultrafiltration Module (Ultracel 30 kDa 0.005 $m^2$; MilliporeSigma, Burlington, MA; $PXC030C_{50}$) with approximately 5 diavolumes of 10 mM NaOAc, pH 5.5. The purified antibody (1133 mg) was diluted to a final volume of 211 mL using 10 mM NaOAc, pH 5.5. To the antibody solution was added 6.4 mL of DMSO and an excess of drug-linker MC-GGFG-AM-DXd1 (9.43 mL; 12 eq.) from a 10 mM DMSO stock solution. The conjugation reaction proceeded at room temperature with mixing for 75 minutes. An excess of a 10 mM N-acetyl-L-cysteine solution (4.72 mL, 6 eq.) was added to quench the conjugation reaction.

v36675-MC-GGFG-AM-Compound 141, v36675-MC-GGFG-AM-Compound 139 & v36675-MC-GGFG-Compound 141: A solution (2.95 mL) of humanized variant v36675 (60 mg) in PBS, pH 7.4 was reduced by addition of 5 mM diethylenetriamine pentaacetic acid (DTPA) (0.96 mL in PBS, pH adjusted to 7.4) and 1 mM of an aqueous tris(2-carboxyethyl)phosphine (TCEP) solution (0.9 mL, 2.15 eq.). After 100 minutes at 37° C., 1.6 mL of the reduced antibody was diluted with 0.92 mL of PBS, pH 7.4 and 1.08 mL of 100 mM NaOAc, pH 5.5. To the antibody solution was added 289 μL of DMSO and an excess of MC-GGFG-AM-Compound 141, MC-GGFG-AM-Compound 139 or MC-GGFG-Compound 141 (111 uL; 8 eq.) from a 10 mM DMSO stock solution. The conjugation reaction proceeded at room temperature with mixing for 60 minutes. An excess of 10 mM cysteamine-HCl solution (444 uL, 32 eq.) was added to quench each conjugation reaction.

TABLE 24.1

| Antibody-Drug Conjugates | | | | |
|---|---|---|---|---|
| Variant | Antibody | Fc | Drug-Linker | DAR |
| v36675 | Humanized | HomoFc | MC-GGFG-AM-DXd1[3] | 8 |
| | | | MC-GGFG-AM-Compound 141[1] | 8 |
| | | | MC-GGFG-AM-Compound 139[1] | 8 |
| | | | MC-GGFG-Compound 141[1] | 8 |
| | | | MC-GGFG-Compound 140[1] | 8 |
| | | | MC-GGFG-AM-Compound 141 | 4 |
| | | | MC-GGFG-AM-Compound 139 | 4 |
| | | | MC-GGFG-Compound 141 | 4 |
| v30384 | Humanized | HetFc | MC-GGFG-AM-DXd1 | 8 |
| | | | MC-GGFG-AM-Compound 141 | 8 |
| | | | MT-GGFG-AM-Compound 139[1] | 8 |
| | | | MT-GGFG-Compound 141[1] | 8 |
| | | | MT-GGFG-Compound 140[1] | 8 |
| | | | MT-GGFG-Compound 148[1] | 8 |
| | | | MC-GGFG-Compound 140 | 8 |
| | | | MT-GGFG-AM-Compound 141[1] | 8 |
| | | | Controls | |
| v21995[2] | — | HomoFc | MT-GGFG-AM-DXd1[3] | 8 |
| | | | MC-GGFG-AM-DXd1 | 8 |
| | | | MT-GGFG-Compound 140 | 8 |
| | | | MT-GGFG-AM-Compound 141 | 8 |
| | | | MT-GGFG-Compound 141 | 8 |
| | | | MC-GGFG-Compound 140 | 8 |
| | | | MT-GGFG-AM-Compound 139 | 8 |

[1]See Tables 8 & 9 for structures

[2]Palivizumab (anti-RSV)

[3]Structures shown below. The abbreviations DXd1 and DXd are used interchangeably to refer to the same payload.

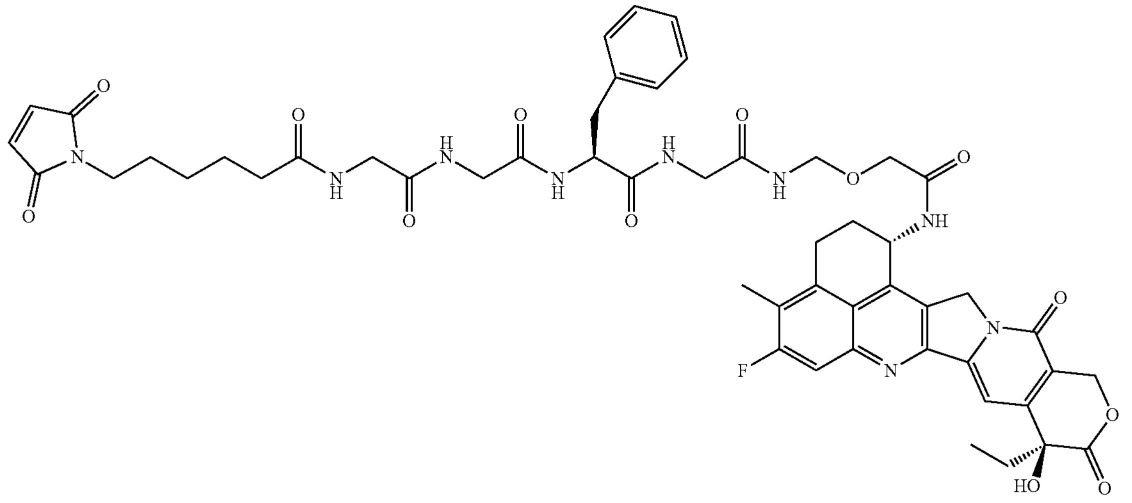

MC-GGFG-AM-DXd1

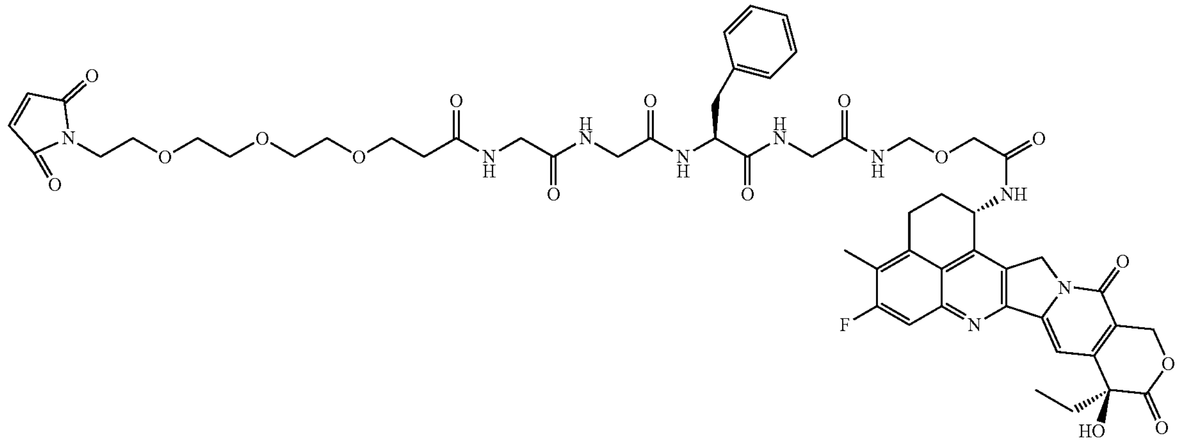

MT-GGFG-AM-DXd1

Example 25: Purification and Characterization of Antibody-Drug Conjugates

ADCs prepared at a large scale as described in Example 24 were purified using a Pellicon® XL Ultrafiltration Module (MilliporeSigma, Burlington, MA) and sterile filtered (0.22 m). An exemplary protocol is provided below.

The quenched ADC solution from Example 24 was diluted to approximately 5 mg/mL with 10 mM NaOAc, pH 5.5 and purified using a Pellicon® XL Ultrafiltration Module (Ultracel kDa 0.005 $m^2$; MilliporeSigma, Burlington, MA; PXC030C50) with 11 diavolumes of 10 mM NaOAc, pH 4.5, followed by 4 diavolumes of 10 mM NaOAc, pH 4.5 with 9% (v/v) sucrose. The purified ADC was then sterile filtered (0.2 m).

ADCs prepared at a small scale as described in Example 24 were purified on an AKTA™ pure chromatography system (Cytiva Life Sciences, Marlborough, MA) using a 53 mL HiPrep 26/10 Desalting column (Cytiva Life Sciences, Marlborough, MA) and a mobile phase consisting of 10 mM NaOAc, pH 4.5 with 150 mM NaCl and a flow rate of 10 mL/min.

Following purification, the concentration of the ADCs was determined by a BCA assay with reference to a standard curve generated using the humanized variant v36675. Alternatively, concentrations were estimated by measurement of absorption at 280 nm using extinction coefficients taken from the literature (European Patent No. 3 342 785, for MC-GGFG-AM-DXd1) or determined experimentally (for the remaining drug-linkers). ADCs were also characterized by hydrophobic interaction chromatography (HIC) and size exclusion chromatography (SEC) as described below.

25.1 Hydrophobic Interaction Chromatography

Antibodies and ADCs were analyzed by HIC to estimate the drug-to-antibody ratio (DAR). Chromatography was performed on an Agilent Infinity II 1290 HPLC (Agilent Technologies, Santa Clara, CA) using a TSKgel® Butyl-NPR column (2.5 μm, 4.6x35 mm; TOSOH Bioscience GmbH, Griesheim, Germany) and employing a gradient of 95/5% MPA/MPB to 5/95% MPA/MPB over a period of 12 minutes at a flow rate of 0.5 mL/min (MPA=1.5 M $(NH_4)_2SO_4$, 25 mM $NaxPO_4$, pH 7 and MPB=75% 25 mM $Na_xPO_4$, pH 7, 25% isopropanol). Detection was by absorbance at 280 nm.

25.2 Size Exclusion Chromatography

The extent of aggregation of antibodies and ADCs (~15-150 μg, 5 μL injection volume) was assessed by SEC on an Agilent Infinity II 1260 HPLC (Agilent Technologies, Santa Clara, CA) using an AdvanceBio SEC column (300 angstroms, 2.7 μm, 7.8×150 mm) (Agilent, Santa Clara, California) and a mobile phase consisting of 150 mM phosphate, pH 6.95 and a flow rate of 1 mL/min. Detection was by absorbance at 280 nm.

Results

The individual contributions of the DARO, DAR2, DAR4, DAR6 and DAR8 species to the average DAR of the purified ADCs were assessed by integration of the HPLC-HIC chromatogram. The average drug to antibody ratio (DAR) of each ADC was determined by the weighted average of each DAR species. The average DAR for each ADC, when rounded to the nearest integer, was the same as the target DAR shown in Table 25.1.

The extent of aggregation and monomer content was assessed by integration of the HPLC-SEC chromatogram. The monomer peak of each ADC was identified as the peak with the same retention time as the unconjugated antibody from which each ADC was derived from. All peaks with an earlier retention time relative to the monomer species was determined to be aggregated species. Percent monomer species determined for each ADC is shown in Table 25.1. All ADC preparations showed >95% monomer species.

TABLE 25.1

| Variant | Drug-Linker | Target DAR | % Monomer |
|---|---|---|---|
| v36675 | MC-GGFG-AM-DXd1 | 8 | 99.1% |
| | MC-GGFG-AM-Compound 141 | 8 | 98.3% |
| | MC-GGFG-AM-Compound 139 | 8 | 98.1% |
| | MC-GGFG-Compound 141 | 8 | 98.1% |
| | MC-GGFG-Compound 140 | 8 | 97.7% |
| | MC-GGFG-AM-Compound 141 | 4 | 98.6% |
| | MC-GGFG-AM-Compound 139 | 4 | 98.4% |
| | MC-GGFG-Compound 141 | 4 | 98.4% |
| v30384 | MC-GGFG-AM-DXd1 | 8 | 96.2% |
| | MC-GGFG-AM-Compound 141 | 8 | 96.7% |
| | MT-GGFG-AM-Compound 139 | 8 | 99.5% |
| | MT-GGFG-Compound 141 | 8 | 99.7% |
| | MT-GGFG-Compound 140 | 8 | 97.3% |
| | MT-GGFG-Compound 148 | 8 | 95.8% |
| | MC-GGFG-Compound 140 | 8 | 97.8% |
| | MT-GGFG-AM-Compound 141 | 8 | 99.6% |
| v21995 | MT-GGFG-AM-DXd1 | 8 | 100% |
| | MC-GGFG-AM-DXd1 | 8 | 100% |
| | MT-GGFG-Compound 140 | 8 | 98.8% |
| | MT-GGFG-AM-Compound 141 | 8 | 98.6% |
| | MT-GGFG-Compound 141 | 8 | 100% |
| | MC-GGFG-Compound 140 | 8 | 100% |
| | MT-GGFG-AM-Compound 139 | 8 | 100% |

Example 26: In Vitro Cytotoxicity of Antibody-Drug Conjugates—2D Monolayer

The cell growth inhibition (cytotoxicity) capabilities of the humanized variant v30384 conjugated to various drug-linkers were assessed in a panel of FRα-expressing cell lines as described below. Cell lines used were KB—HeLa (endocervical carcinoma), JEG-3 (choriocarcinoma), T-47D (breast carcinoma) and MDA-MB-468 (breast adenocarcinoma; FRα-negative). ADCs comprising the antibody palivizumab (v21995) were used as non-targeted controls.

Briefly, cells were seeded in 384-well plates and treated with a titration of test article, generated in cell growth medium. Cells were incubated for 4 days under standard culturing conditions. After incubation, CellTiter-Glo® reagent (Promega Corporation, Madison, WI) was spiked in all wells and luminescence corresponding to ATP present in each well was measured using a Synergy™ $H_1$ plate reader (BioTek Instruments, Winooski, VT). Based on blank wells (no test article added), % cytotoxicity values were calculated and plotted against test article concentration using GraphPad Prism 9 software (GraphPad Software, San Diego, CA).

Results

The results are shown in Table 26.1. All v30384 ADCs displayed significant cytotoxicity in the FRα-expressing cell lines KB-HeLa, JEG-3 and T-47D, yielding single-digit nM or lower EC50 values after the 4-day treatment. In the FRα-negative cell line, MDA-MB-468, the ADCs did not show target-dependent cytotoxicity. Both v30384 and control (palivizumab) ADCs showed comparable potency in this cell line.

TABLE 26.1

In vitro Cytotoxicity—2D Monolayer

| ADC | DAR | EC50 (nM) KB-HeLa | JEG-3 | T-47D | MDA-MB-468 |
|---|---|---|---|---|---|
| v30384-MC-GGFG-AM-DXd1 | 8 | 0.52 | 0.54 | 2.08 | 22.13 |
| v30384-MT-GGFG-AM-Compound 139 | 8 | 0.72 | 1.14 | 1.12 | 36.70 |
| v30384-MT-GGFG-Compound 140 | 8 | 3.75 | 1.29 | 12.43 | 23.33 |
| v30384-MC-GGFG-AM-Compound 141 | 8 | 0.77 | 3.45 | 0.43 | 83.19 |
| v30384-MT-GGFG-Compound 141 | 8 | 0.81 | 1.68 | 0.44 | 25.68 |
| v30384-MT-GGFG-Compound 148 | 8 | 0.73 | 0.54 | 3.45 | 21.20 |
| Controls | | | | | |
| v21995-MT-GGFG-DXd1 | 8 | 19.45 | 15.02 | 11.26 | 17.95 |
| v21995-MT-GGFG-Compound 140 | 8 | >100 | IC* | IC* | 20.05 |
| v21995-MT-GGFG-AM-Compound 141 | 8 | >100 | >100 | 17.71 | 34.28 |
| v21995-MT-GGFG-Compound 141 | 8 | >100 | >100 | 21.80 | 38.06 |

*Incomplete curve

Example 27: In Vitro Cytotoxicity of Antibody-Drug Conjugates—3D Spheroids

The 3D cytotoxicity capabilities of the humanized variant v30384 conjugated to various drug-linkers as shown in Table 27.1 were assessed in a panel of FRα-expressing cell line spheroids as described below. Spheroids provide a three-dimensional organization of cells with layers of distinct cell populations and the formation of different gradients from the outer to the inner regions. Cell signaling is more complex in spheroids than in two-dimensional cell cultures. As a result of these features, spheroids have the potential to recapitulate drug resistance and metabolic adaptation.

Cell lines used were IGROV-1 (ovarian adenocarcinoma), T-47D (breast carcinoma), OVCAR-3 (ovarian adenocarcinoma), HEC-1-A (uterine adenocarcinoma) and EBC-1 (lung carcinoma; FRα-negative). ADCs comprising the antibody palivizumab (v21995) were used as non-targeted controls.

Briefly, cells were seeded in Ultra-Low Attachment 384-well plates, centrifuged and incubated under standard culturing conditions to allow for spheroid formation and growth. Monoculture cell line spheroids were then treated with a titration of test article, generated in cell growth medium. Spheroids were incubated for 6 days under standard culturing conditions. After incubation, CellTiter-Glo® 3D reagent (Promega Corporation, Madison, WI) was spiked in all wells. Plates were incubated in the dark at room temperature for 1 hour and luminescence was quantified using a BioTek Cytation 5 Cell Imaging Multi-Mode Reader (Agilent Technologies, Inc., Santa Clara, CA). Based on blank wells (no test article added), percent cytotoxicity values were calculated and plotted against test article concentration using GraphPad Prism 9 software (GraphPad Software, San Diego, CA).

Results

The results are shown in Table 27.1. All v30384 ADCs displayed significant cytotoxicity in the FRα-expressing monoculture spheroids (IGROV-1, T-47D, OVCAR-3 and HEC-1-A) yielding single-digit nM EC50 values in spheroids after 6-day treatment. In the FRα-negative cell line spheroids, EBC-1, v30384 ADCs did not show target-dependent cytotoxicity. Both v30384 and control (palivizumab) ADCs showed comparable potency in this cell line spheroid.

TABLE 27.1

In vitro Cytotoxicity—3D Spheroids

| ADC | DAR | 3D EC50 (nM) IGROV-1 | T-47D | OVCAR-3 | HEC-1-A | EBC-1 |
|---|---|---|---|---|---|---|
| v30384-MC-GGFG-AM-DXd | 8 | 0.5 | 0.9 | 8.2 | 1.1 | 10.3 |
| v30384-MC-GGFG-Compound 140 | 8 | 0.2 | 1.6 | 20.5 | 6.7 | 7.6 |
| v30384-MT-GGFG-AM-Compound 139 | 8 | 1.0 | 1.1 | 1.5 | 3.9 | 23.0 |
| v30384-MT-GGFG-Compound 141 | 8 | 1.0 | 0.4 | 1.6 | 5.0 | 22.5 |
| v30384-MC-GGFG-AM-Compound 141 | 8 | 0.6 | 0.4 | 1.8 | 8.5 | 12.8 |
| Controls | | | | | | |
| v21995-MC-GGFG-DXd | 8 | 16.7 | 17.8 | 46.0 | 27.6 | 24.4 |
| v21995-MC-GGFG-Compound 140 | 8 | 7.0 | 9.0 | 28.6 | 45.7 | 8.3 |
| v21995-MT-GGFG-AM-Compound 139 | 8 | 33.1 | 32.8 | 150.0 | 145.3 | 36.2 |
| v21995-MT-GGFG-Compound 141 | 8 | 79.2 | 15.3 | 36.6 | 150.0 | 35.6 |

Example 28: In Vivo Efficacy Studies #1

The in vivo anti-tumor activities of humanized variant v30384 conjugated to various drug-linkers were assessed in a numberofxenograft models as describedbelow. In some models, ADCs comprising the antibody palivizumab (v21995) were used as non-targeted controls.

The ADCs, xenograft models, dosages and study durations employed in each xenograft study are summarized in Table 28.1. All ADCs were DAR 8. For each xenograft study, tumor volume and body weight of the animals were measured twice weekly.

TABLE 28.1

Study Parameters

| Xenograft Model | Cancer Type | FRα Expression | ADC | Dose (mg/kg) | Study Duration (days) |
|---|---|---|---|---|---|
| OV90 #1 | Ovarian | Mid | v30384-MC-GGFG-AM-DXd1 | 3 | 60 |
| | | | v30384-MT-GGFG-AM-Compound 139 | 3 | |
| | | | v30384-MT-GGFG-AM-Compound 141 | 3 | |
| | | | v30384-MT-GGFG-Compound 141 | 3 | |
| OV90 #2 | Ovarian | Mid | v30384-MC-GGFG-AM-DXd1 | 3 | 60 |
| | | | v30384-MT-GGFG-Compound 140 | 3 | |
| | | | v30384-MT-GGFG-AM-Compound 141 | 3 | |
| | | | v30384-MC-GGFG-AM-Compound 141 | 3 | |
| | | | v21995-MC-GGFG-AM-DXd1 | 3 | |
| | | | v21995-MT-GGFG-AM-Compound 141 | 3 | |
| | | | v21995-MT-GGFG-Compound 140 | 3 | |
| NCI-H2110 | Lung | Mid/Low | v30384-MC-GGFG-AM-DXd1 | 6 | 28 |
| | | | v30384-MC-GGFG-AM-Compound 141 | 6 | |
| | | | v30384-MT-GGFG-AM-Compound 141 | 6 | |
| | | | v30384-MC-GGFG-Compound 140 | 6 | |
| | | | v30384-MT-GGFG-Compound 140 | 6 | |
| | | | v30384-MT-GGFG-Compound 148 | 6 | |
| | | | v30384-MT-GGFG-AM-Compound 139 | 6 | |
| | | | v21995-MC-GGFG-AM-DXd1 | 6 | |
| | | | v21995-MT-GGFG-AM-Compound 141 | 6 | |
| | | | v21995-MT-GGFG-Compound 140 | 6 | |

For the OV90 model studies #1 and #2, tumor cell suspensions ($1\times10^7$ cells in 0.1 ml 50% Matrigel®) were implanted subcutaneously into female CB. 17 SCID mice. When mean tumor volume reached 100-150 $mm^3$, the animals were randomly assigned to groups (n=6 per group for study #1, and n=8 per group for study #2) and treated on study day 1 with a single IV dose of test article as shown in Table 28.1. Serum was collected at a number of timepoints for PK analysis.

For the NCI-H21 10 CDX model study, tumor cell suspensions ($1\times10^7$ cells in 0.1 ml 50% Matrigel®) were implanted subcutaneously into CB. 17 SCID mice. When mean tumor volume reached ~140 $mm^3$ the animals were randomly assigned to groups (n=6 per group) and treated with a single IV dose of test article on study day 0 as shown in Table 28.1.

Results

Figure 19A:
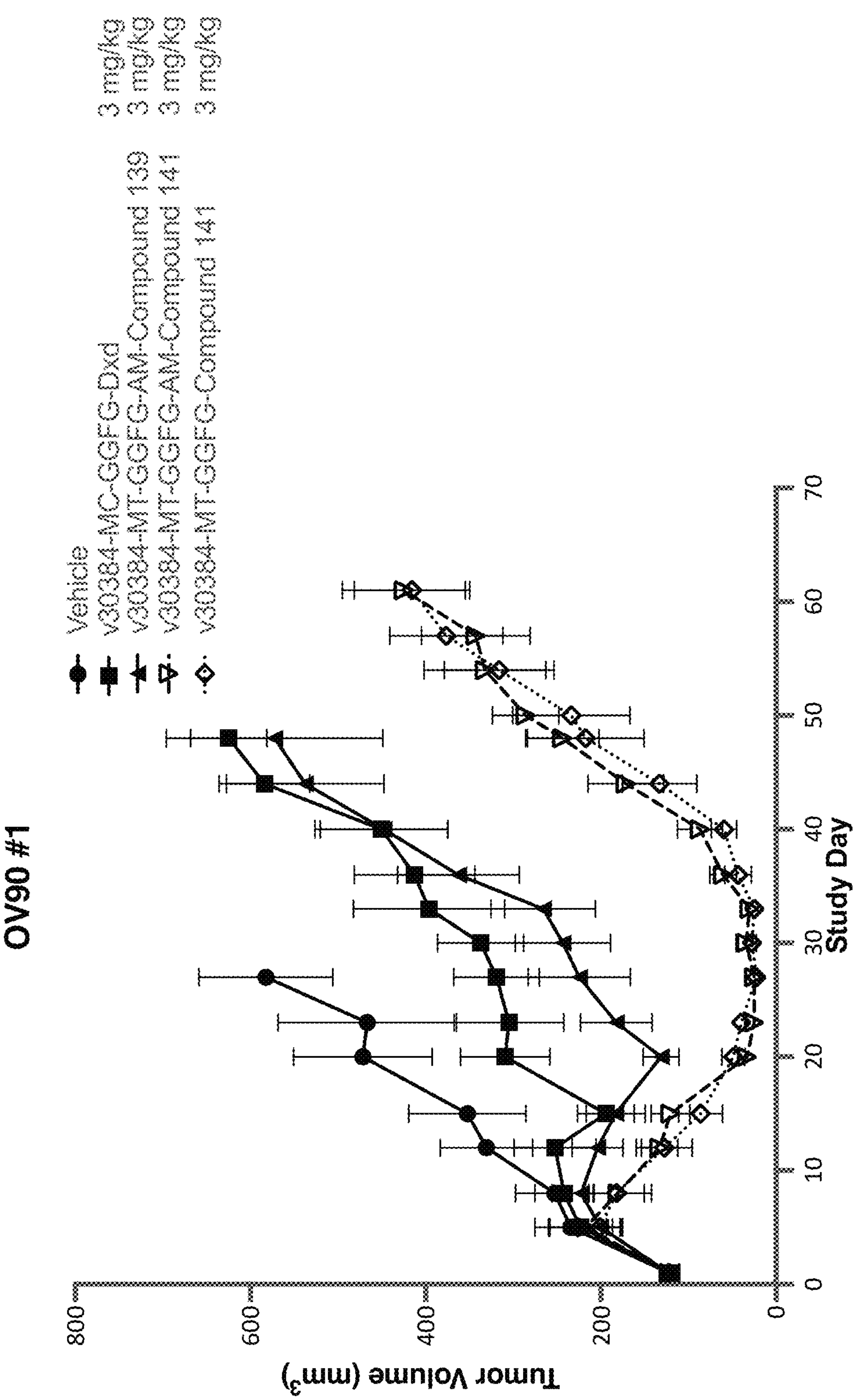
FIG. 19A, 19B, &19C shows the in vivo anti-tumor activities of ADCs comprising the anti-FRα humanized antibody variant v30384 conjugated to the camptothecin analogues Compound 139 or Compound 141, at DAR 8 in an OV90 xenograft model (19A & 19B), and conjugated to the camptothecin analogues Compound 139, Compound 140, Compound 141 or Compound 148, at DAR 8 in a H2110 xenograft model (19C). ADCs comprising palivizumab (v21995) were included as controls.
Figure 19B:
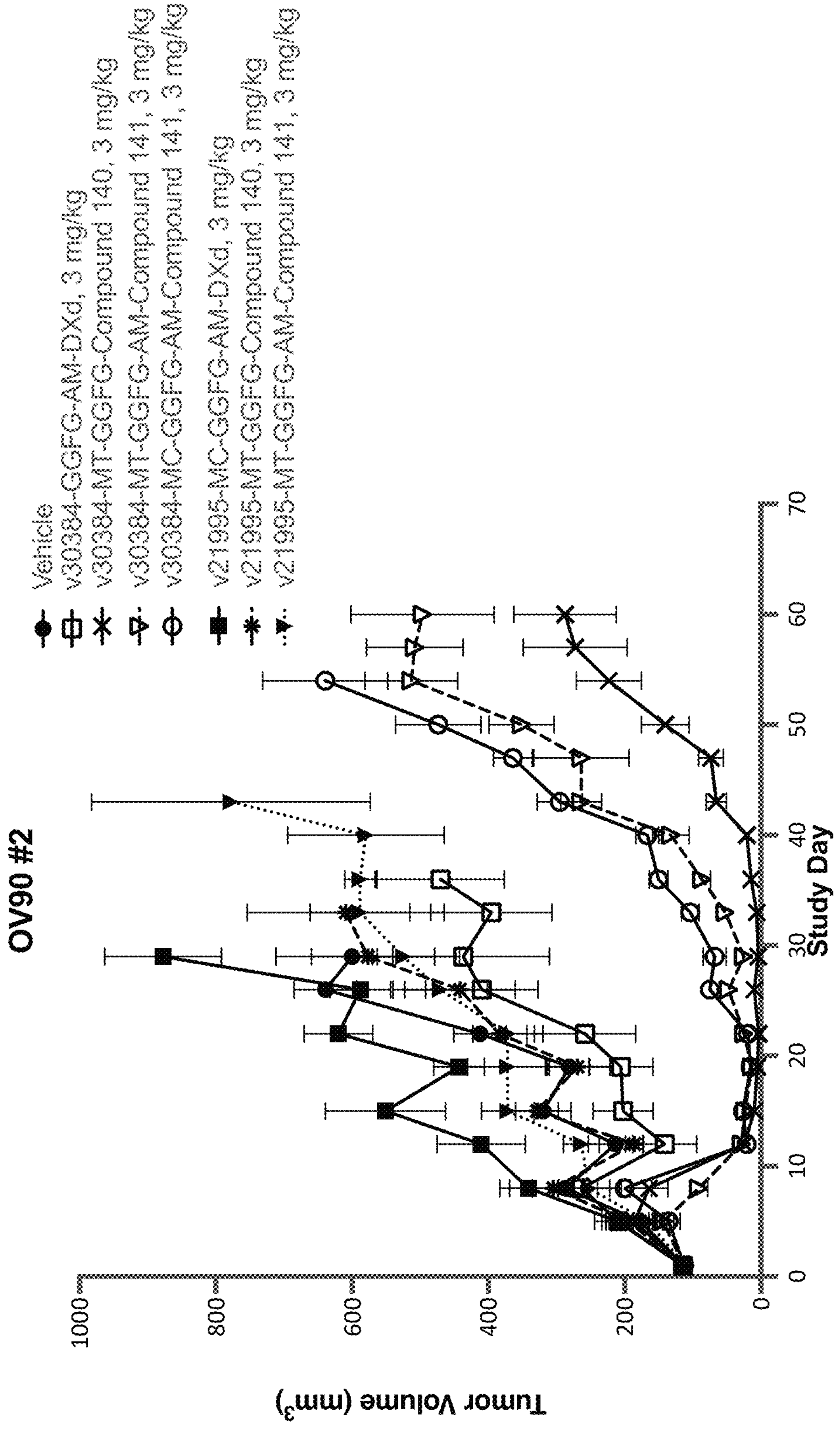
Figure 19C:
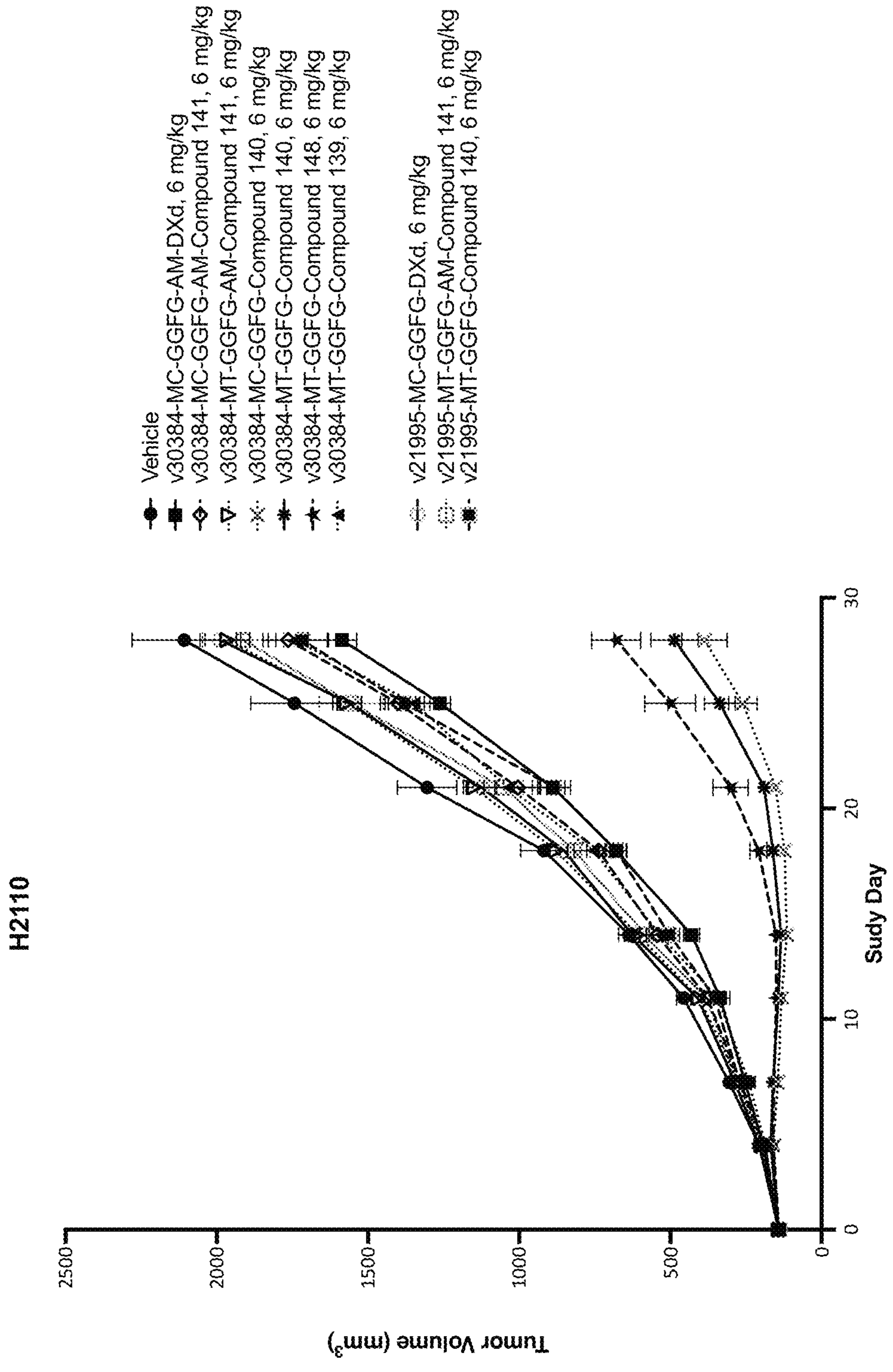

The results are shown in FIG. 19. In the OV90 model study #1 (see FIG. 19A), when dosed at 3 mg/kg, all ADCs resulted in a statistically significant reduction in the tumor growth rate compared to control (p<0.02). The ADCs v30384-MT-GGFG-AM-Compound 139, v30384-MT-GGFG-AM-Compound 141 and v30384-MT-GGFG-Compound 141 all resulted in superior inhibition of tumor growth rate compared to v30384-MC-GGFG-AM-DXd (p<0.01).

Similarly, in the OV90 model study #2 (see FIG. 19B), when dosed at 3 mg/kg, v30384-MT-GGFG-Compound 140, v30384-MT-GGFG-AM-Compound 141 and v30384-MC-GGFG-AM-Compound 141 all resulted in tumor regressions, while v30384-MC-GGFG-AM-DXd had a marginal effect on tumor growth compared to control. Non-targeted v21995 ADCs did not substantially affect tumor growth.

In the NCI-H2110 CDX model study (see FIG. 19C), when dosed at 6 mg/kg, v30384-MT-GGFG-Compound 140, v30384-MC-GGFG-Compound 140 and v30384-MT-GGFG-Compound 148 all resulted in stasis of tumor growth for approximately 2 weeks post-dose, which represented a statistically significant inhibition of tumor growth rate compared to each of control, v30384-MC-GGFG-AM-DXd and non-targeted v21995 ADCs ($p<0.01$). v30384-GGFG-AM-DXd, v30384-MC-GGFG-AM-Compound 141, v30384-MT-GGFG-AM-Compound 141 and v30384-MT-GGFG-AM-Compound 139 did not result in significant tumor growth rate inhibition in this model.

Example 29: Pharmacokinetics of ADCs in In Vivo Efficacy Models

Serum was collected from the xenograft studies described in Example 28, as noted, and analyzed for the pharmacokinetics (PK) of the ADCs as described below. ADCs comprising the antibody palivizumab (v21995) were included as non-targeted controls.

Test article concentrations were measured in mouse serum by sandwich ELISA utilizing an anti-human IgG1 Fc capture antibody (Jackson Immuno Research Labs, West Grove, PA; Cat. 709-005-098) and a HRP-conjugated anti-IgG1 Fab detection antibody (Jackson Immuno Research Labs; Cat. 109-035-097) for total IgG levels. Absorbance at 450 nM was measured using a Synergy™ H1 Hybrid Multi-Mode Plate Reader (BioTek Instruments, Winooski, VT). Pharmacokinetics parameters were calculated from non-compartmental analysis using Phoenix WinNonlin™ software (Certara, Princeton, NJ).

Overall, the OV90 studies in immunocompromised tumor-bearing mice demonstrate that v30384 ADCs utilizing payloads Compound 141, Compound 139 and Compound 140 have favorable PK properties shown by longer or comparable elimination half-life compared to v30384-MC-GGFG-AM-DXd1 (control). Shorter elimination half-lives were observed for all v30384 ADCs, including DXd1 control, in the NCI-H2110 model compared to OV90 models. Elimination half-lives for non-targeting control v21995 ADCs were comparable in OV90 and NCI-H2110 models (Table 29.1)

TABLE 29.1

Elimination Half-life of ADCs

| Xenograft Model | ADC | Dose (mg/kg) | Half-life (day) |
|---|---|---|---|
| OV90 #1 | v30384-MC-GGFG-AM-DXd1 | 3 | 4.42 |
| | v30384-MT-GGFG-AM-Compound 139 | 3 | 8.27 |
| | v30384-MT-GGFG-AM-Compound 141 | 3 | 6.57 |
| | v30384-MT-GGFG-Compound 141 | 3 | 5.63 |
| OV90 #2 | v30384-MC-GGFG-AM-DXd1 | 3 | 4.26 |
| | v30384-MT-GGFG-Compound 140 | 3 | 5.88 |
| | v30384-MT-GGFG-AM-Compound 141 | 3 | 4.62 |
| | v30384-MC-GGFG-AM-Compound 141 | 3 | 5.17 |
| | v21995-MC-GGFG-AM-DXd1 | 3 | 4.68 |
| | v21995-MT-GGFG-AM-Compound 141 | 3 | 7.90 |
| | v21995-MT-GGFG-Compound 140 | 3 | 4.01 |

TABLE 29.1-continued

Elimination Half-life of ADCs

| Xenograft Model | ADC | Dose (mg/kg) | Half-life (day) |
|---|---|---|---|
| NCI-H2110 | v30384-MC-GGFG-AM-DXd1 | 6 | 2.35 |
| | v30384-MC-GGFG-AM-Compound 141 | 6 | 1.87 |
| | v30384-MT-GGFG-AM-Compound 141 | 6 | 2.13 |
| | v30384-MC-GGFG-Compound 140 | 6 | 2.70 |
| | v30384-MT-GGFG-Compound 140 | 6 | 4.80 |
| | v30384-MT-GGFG-Compound 148 | 6 | 3.64 |
| | v30384-MT-GGFG-AM-Compound 139 | 6 | 2.39 |
| | v21995-MC-GGFG-AM-DXd1 | 6 | 4.00 |
| | v21995-MT-GGFG-AM-Compound 141 | 6 | 5.60 |
| | v21995-MT-GGFG-Compound 140 | 6 | 4.94 |

Example 30: Murine Tolerability Study

ADCs comprising humanized variant v30384 conjugated to various drug-linkers as shown in Table 30.1 were assessed for tolerability in mice at single doses of 60 and 200 mg/kg as described below.

Test articles were administered to mice (Balb/c, female, 6-8 weeks old, -20g) via 20 ml/kg intraperitoneal injections at 60 and 200 mg/kg. From each dose group, 3 mice were subject to planned observation for 3 weeks post-dose. An additional 3 mice were subject to planned observation for 1 week post-dose, followed by termination and examination of formalin-fixed, paraffin-embedded organs. Mice were euthanized if body weight fell by ≥20% from pre-dose levels. Serum collection was planned for all mice at 24 hr and 7 day post-dose for pharmacokinetic analysis.

TABLE 30.1

ADCs, Doses and Unscheduled Deaths in Murine Tolerability Study

| Group No. | ADC | Dose level (mg/kg) | Number of females: Dosing phase | Number of females: Recovery Phase | Unscheduled deaths—days post dose |
|---|---|---|---|---|---|
| 1 | Vehicle Control | 0 | 6 | 6 | — |
| 2 | v30384-MC-GGFG-AM-DXd1 | 60 | 3 | 3 | — |
| | | 200 | 3 | 3 | — |
| 3 | v30384-MT-GGFG-AM-Compound 139 | 60 | 3 | 3 | — |
| | | 200 | 3 | 3 | — |
| 4 | v30384-MT-GGFG-AM-Compound 141 | 60 | 3 | 3 | — |
| | | 200 | 3 | 3 | — |
| 5 | v30384-MT-GGFG-Compound 141 | 60 | 3 | 3 | — |
| | | 200 | 3 | 3 | — |
| 6 | v30384-MT-GGFG-Compound 140 | 60 | 3 | 3 | 4, 5, 5, 5, 6, 6 |
| | | 200 | 3 | 3 | 4, 4, 4, 5, 5, 5 |
| 7 | v30384-MT-GGFG-Compound 148 | 60 | 3 | 3 | 4, 5, 5, 5, 6, 6 |
| | | 200 | 3 | 3 | 4, 4, 4, 5, 5, 5 |
| 8 | v30384-MC-GGFG-Compound 140 | 60 | 3 | 3 | 3, 4, 5, 5, 6, 6 |
| | | 200 | 3 | 3 | 3, 3, 3, 4, 4, 4 |
| 9 | v30384-MC-GGFG-Compound 141 | 60 | 3 | 3 | — |

Results

The ADCs 30384-MC-GGFG-AM-DXd1, v30384-MT-GGFG-AM-Compound 139, v30384-MT-GGFG-AM-Compound 141, v30384-MT-GGFG-Compound 141 and v30384-MC-GGFG-Compound 141 were well tolerated at both 60 and 200 mg/kg, with no substantial body weight loss observed over 21 days, similar to mice administered vehicle control. ADCs v30384-MT-GGFG-Compound 140, v30384-MT-GGFG-Compound 148 and v30384-MC-GGFG-Compound 140 resulted in rapid body weight loss, mortality or sacrifice due to moribund condition between 3-6 days post dose (see Table 30.1).

No treatment-related macroscopic changes were observed in mice treated with the ADCs 30384-MC-GGFG-AM-DXd1, v30384-MT-GGFG-AM-Compound 139, v30384-MT-GGFG-AM-Compound 141, v30384-MT-GGFG-Compound 141 and v30384-MC-GGFG-Compound 141 at 60 or 200 mg/kg. Macroscopic changes considered related to the ADCs were present in preterminal animals treated with 60 and/or 200 mg/kg of v30384-MT-GGFG-Compound 140, v30384-MT-GGFG-Compound 148 and v30384-MC-GGFG-Compound 140.

The different macroscopic findings included watery/reduced/discolored intestinal contents, reduced size of thymus and spleen. Watery intestinal contents were correlated microscopically with degeneration/necrosis of the crypt/gland epithelium and associated atrophy of the villi or mucosa of the small and large intestine. Reduced size of thymus and spleen correlated microscopically with decreased cellularity in these organs.

No treatment related microscopic findings were present in mice administered the ADCs v30384-MC-GGFG-AM-DXd1, v30384-MT-GGFG-AM-Compound 139 and v30384-MC-GGFG-Compound 141. Microscopic changes considered related to administration of ADCs v30384-MT-GGFG-Compound 140, v30384-MT-GGFG-Compound 148 and v30384-MC-GGFG-Compound 140 at ≥60 mg/kg dose were present in intestine, bone marrow, thymus, spleen and mesenteric lymph node.

Example 31: Pharmacokinetic Study in Tg32 Mice

The pharmacokinetics of the humanized antibody v36675 and four ADCs comprising v36675 were assessed in hFcRn Tg32 mice as described below. The ADCs were: v36675-MC-GGFG-AM-Dxd (control); v36675-MC-GGFG-AM-Compound 141; v36675-MC-GGFG-Compound 141, and v36675-MC-GGFG-AM-Compound 139. All ADCs were DAR 8.

Antibody v36675 and each of the four ADCs were administered at 5 mg/kg to hFcRn Tg32 mice (The Jackson Laboratory, Bar Harbor, ME; Stock #014565) by intravenous injection. For each test article, blood was collected from n=4 animals by retro-orbital bleed at 1, 3, and 6 hours and 1, 3, 7, 10, 14 and 21 days post-dose. Blood was processed to serum and stored frozen at −80° C. in 96-well storage plates prior to pharmacokinetics analysis.

Test article concentrations were measured in mouse serum by sandwich ELISA utilizing an anti-human IgG1 Fc capture antibody (Jackson Immuno Research Labs, West Grove, PA; Cat. 709-005-098) and a HRP-conjugated anti-IgG1 Fab detection antibody (Jackson Immuno Research Labs; Cat. 109-035-097) for total IgG levels. Absorbance at 450 nM was measured using a Synergy™ H1 Hybrid Multi-Mode Plate Reader (BioTek Instruments, Winooski, VT). Pharmacokinetics parameters were calculated from non-compartmental analysis using Phoenix WinNonlin™ software (Certara, Princeton, NJ).

Results

Figure 20:
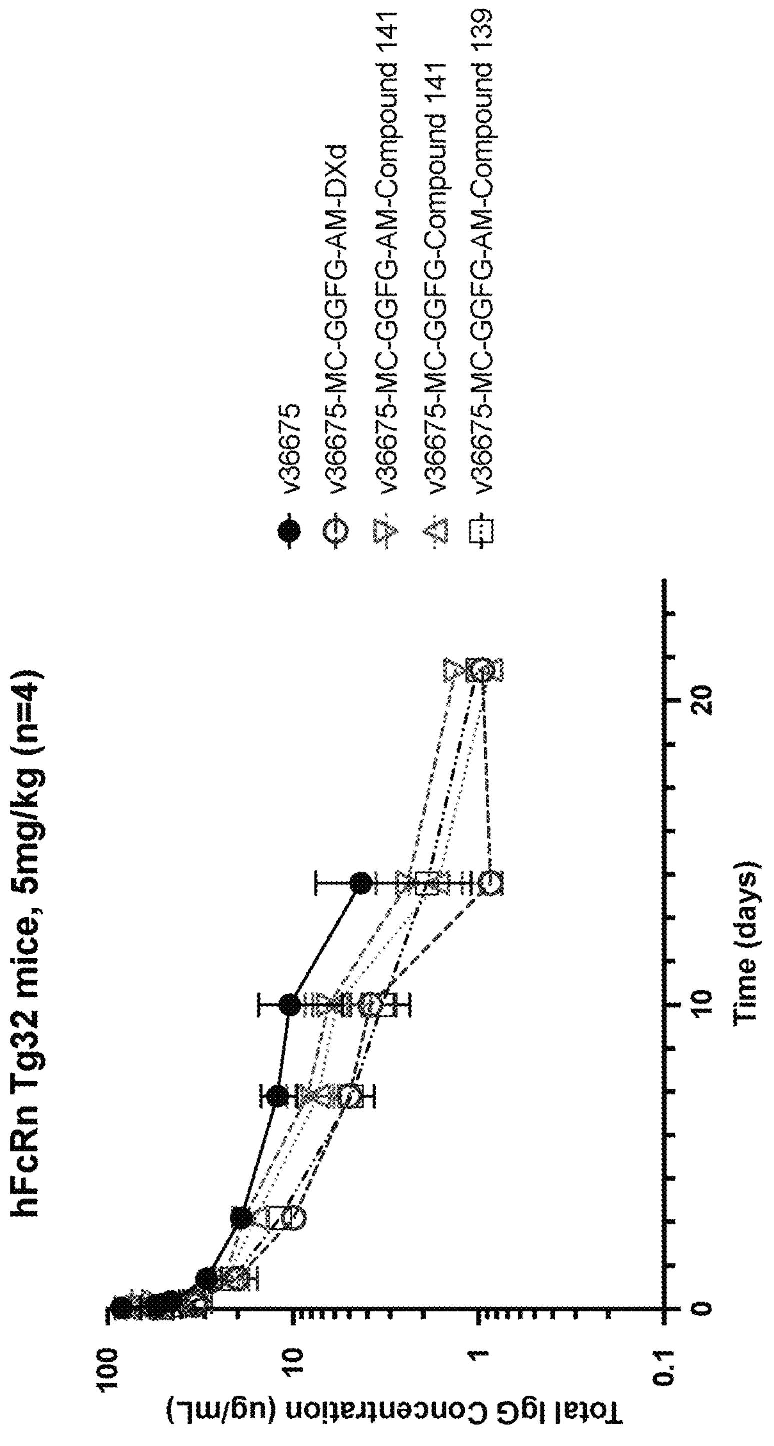
FIG. 20 shows the pharmacokinetics of the anti-FRα humanized antibody v36675 and four ADCs comprising v36675 conjugated to DXd or the camptothecin analogues Compound 139 or Compound 141 at DAR8 assessed in hFcRn Tg32 mice (n=4). The average serum concentration at some time points was calculated using n<4 animals (as some samples were below detection limit).

The results are shown in FIG. 20. Analysis in hFcRn Tg32 mice demonstrated the total IgG PK of the four ADCs was comparable with the naked antibody, with typical antibody-like prolonged exposures. Elimination half-life of the v36675 antibody was determined to be 5.2 days; elimination half-lives of ADCs were determined to be 4.36 days for v36675-MC-GGFG-AM-Dxd (control), 4.61 days for v36675-MC-GGFG-AM-Compound 141, 6.20 days for v36675-MC-GGFG-Compound 141, and 4.09 days for v36675-MC-GGFG-AM-Compound 139 by non-compartmental analysis.

Example 32: In Vivo Stability

The in vivo stability of four ADCs comprising the humanized variant v36675 in Tg32 mice was assessed using immunoprecipitation/mass spectrometry as described below. The ADCs assessed were: v36675-MC-GGFG-AM-Dxd (control); v36675-MC-GGFG-AM-Compound 141; v36675-MC-GGFG-Compound 141, and v36675-MC-GGFG-AM-Compound 139. All ADCs were DAR 8. Serum samples taken from Tg32 mice as noted in Example 31 at various time points in circulation (1 hr to 10 days) were employed for the immunoprecipitation/mass spectrometry. For all groups, mouse serum samples from each time point (1 hr to 10 days post-dose) were pooled between animals (n=4) and tested.

Briefly, biotinylated anti-human IgG F(ab')$_2$ antibody was coupled to magnetic beads coated with streptavidin (15 ug antibody per sample) for 30 min at room temperature. Following coupling, the beads were incubated with test sample for 1.5 hrs at room temperature to allow for immunocapture. Following incubation and washing using DynaMag™-2 magnet (ThermoFisher Scientific Corporation, Waltham, MA), immunocaptured sample was reduced using dithiothreitol (DTT) in PBS, pH 7.4, for 1 hr at room temperature. After reduction, sample was eluted by incubating with pH 3.0 buffer (distilled water containing 20% acetonitrile and 1% formic acid) for 1 hr at room temperature. Purified ADC samples were then analyzed by mass spectrometry to quantify DAR or drug loading, or kept frozen at −80° C. until further analysis.

Drug loading and % maleimide ring opening of purified ADC samples were assessed using an Agilent 1290 Infinity II HPLC system coupled to an Agilent 6545 Quadrupole Time of Flight Mass Spectrometer (Agilent Technologies, Santa Clara, CA). Extent of drug loading and % maleimide ring opening at each time point was graphed using GraphPad Prism software (GraphPad Software, San Diego, CA).

Results

Figure 21:
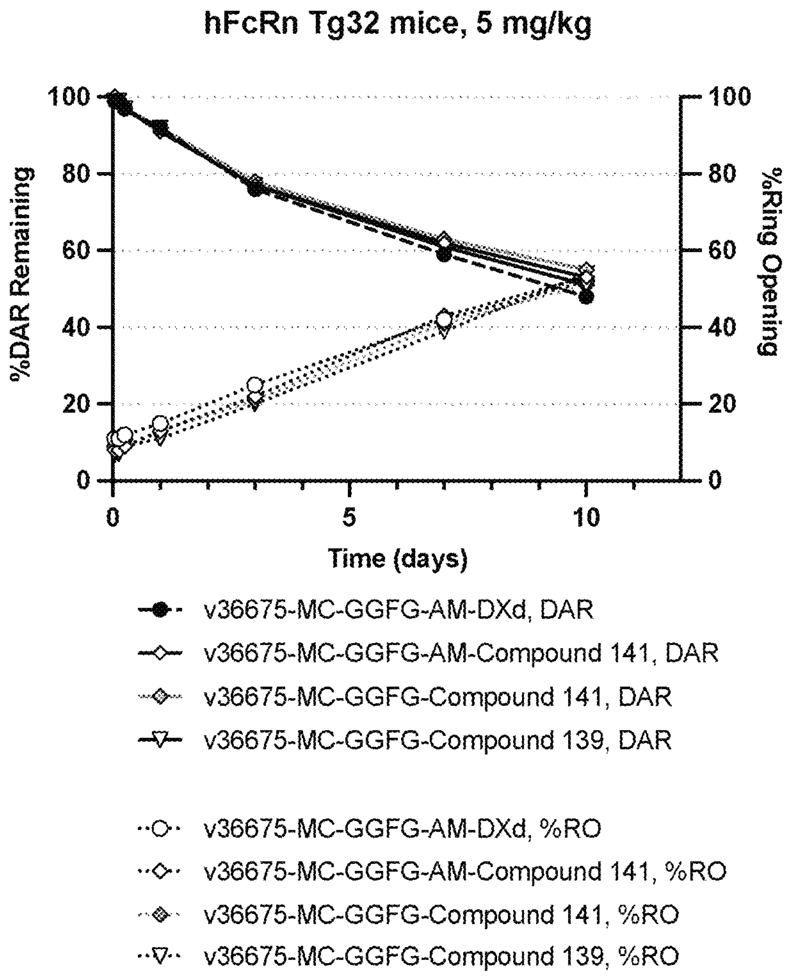
FIG. 21 shows the in vivo stability of four ADCs comprising the humanized variant v36675 conjugated to DXd or the camptothecin analogues Compound 139 or Compound 141 at DAR8 in Tg32 mice serum. Solid lines show % DAR remaining (left axis) and dotted lines show % maleimide ring opening (right axis).
Figure 22A:
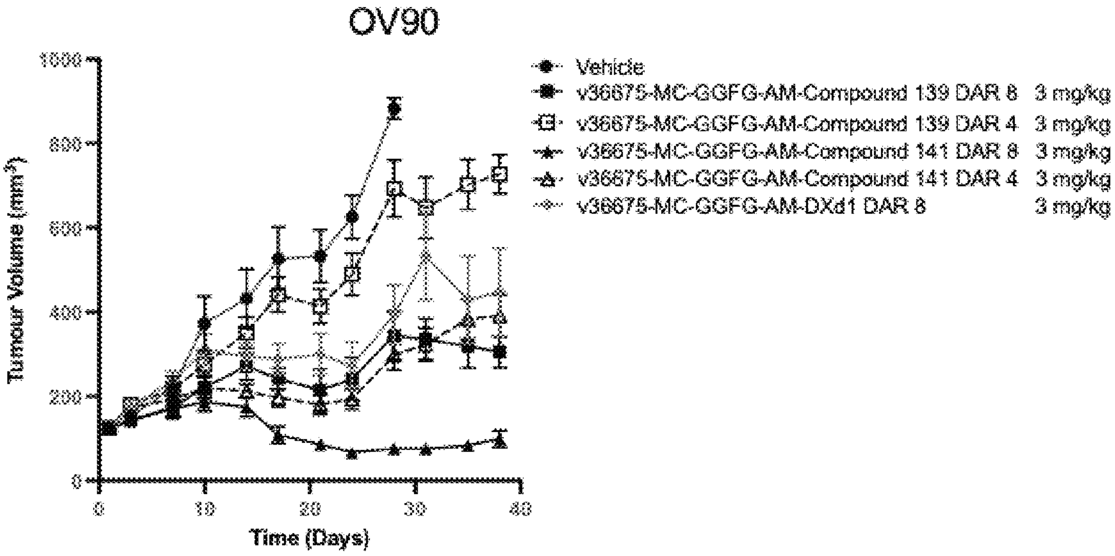
Figure 22B:
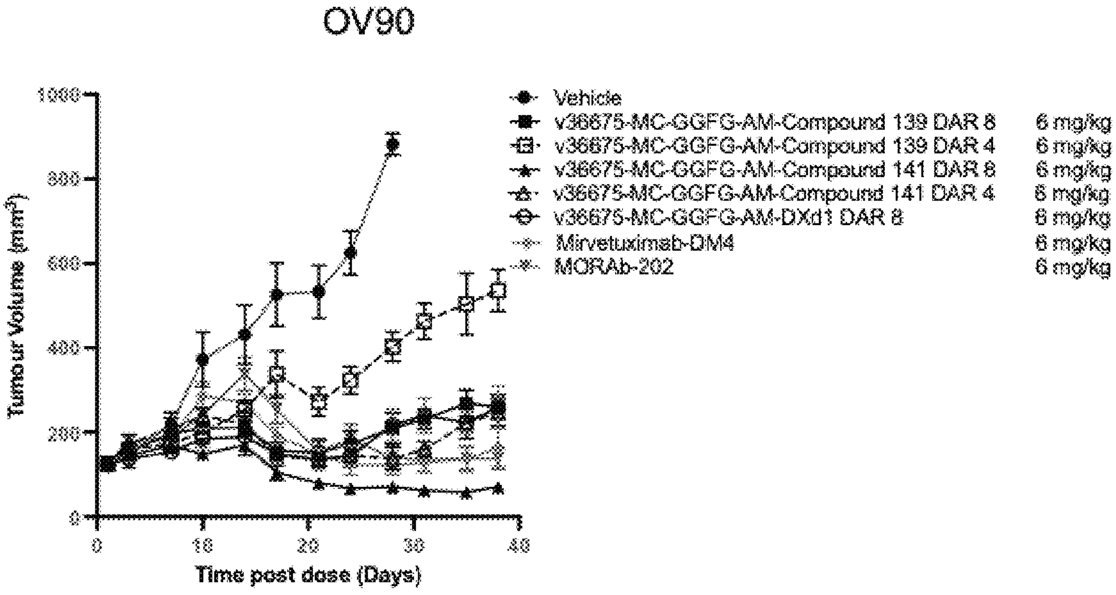
Figure 22C:
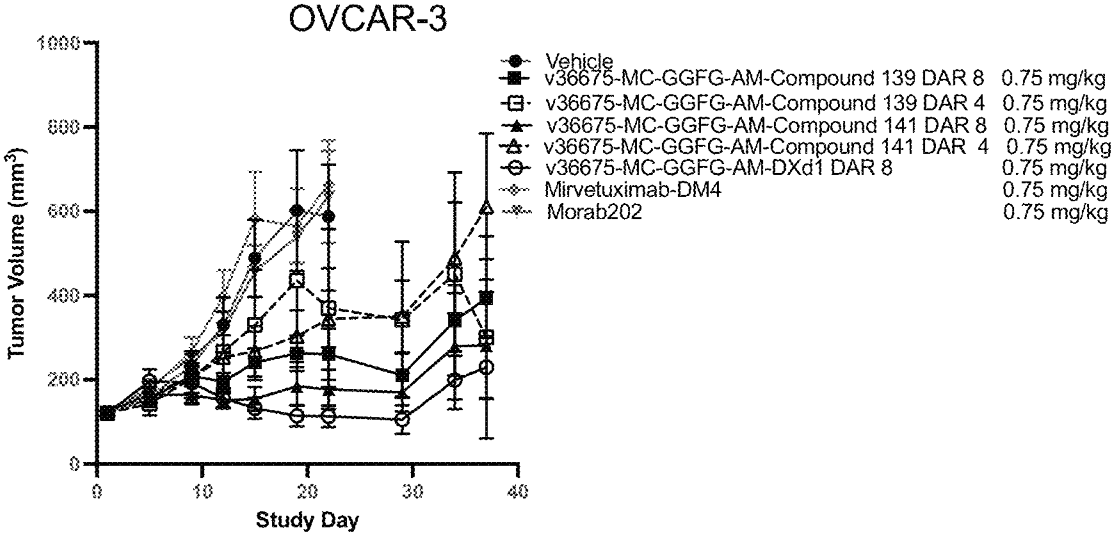
Figure 22D:
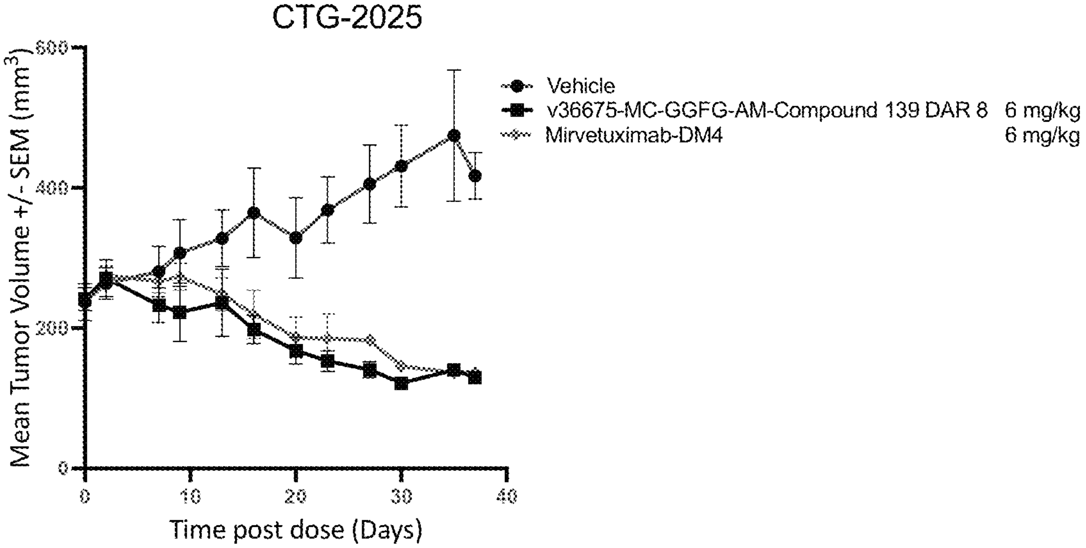
Figure 22E:
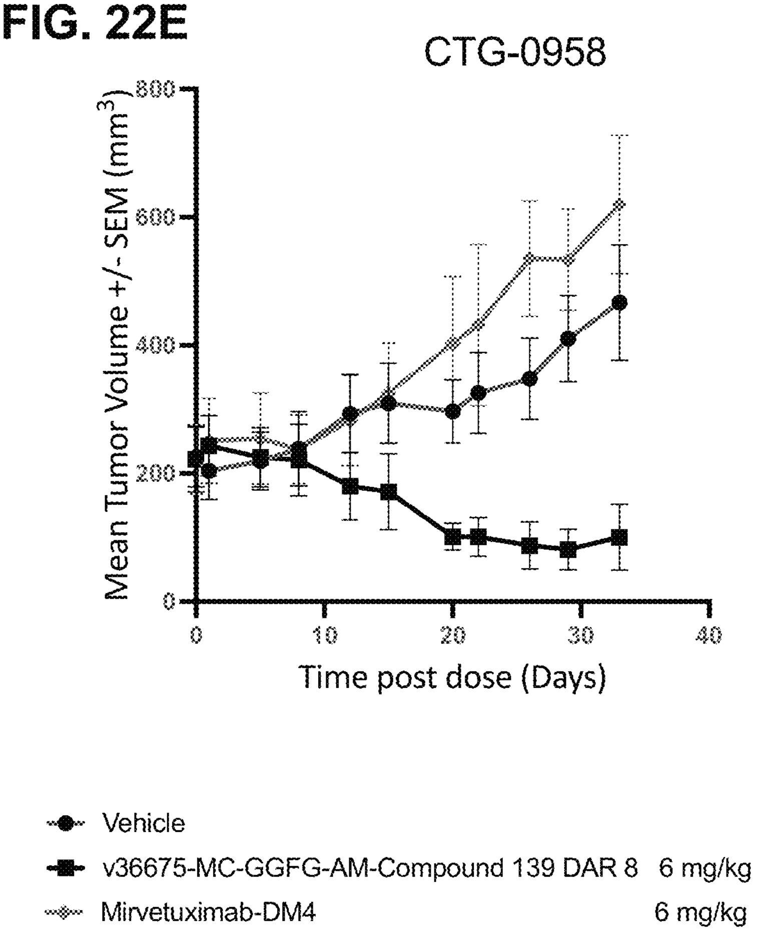
Figure 23A:
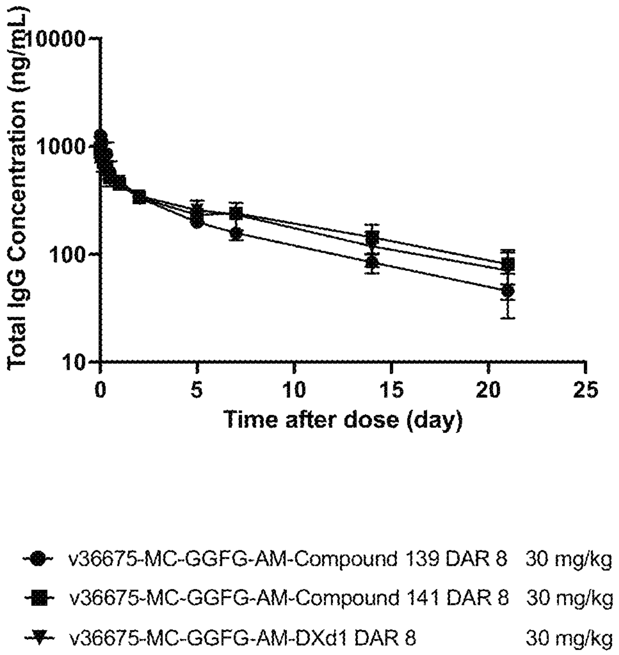
Figure 23B:
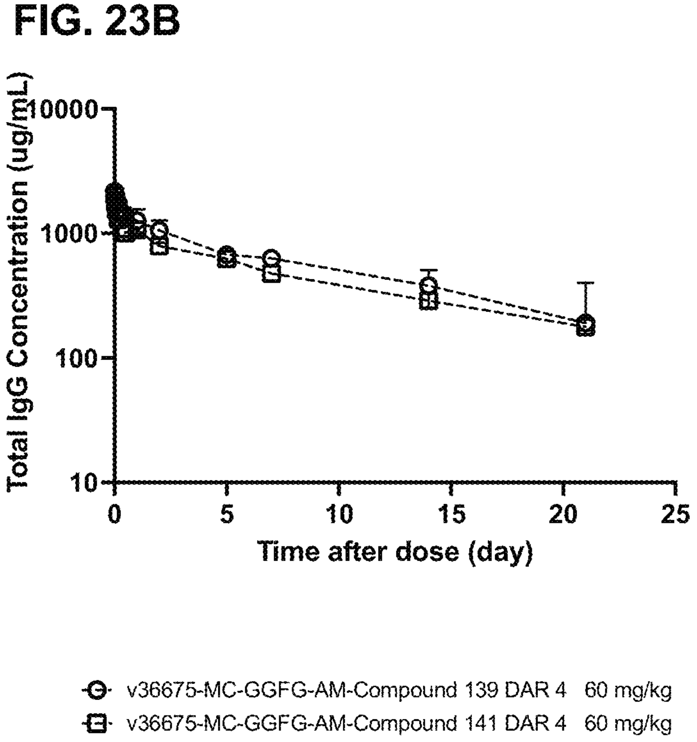
Figure 23C:
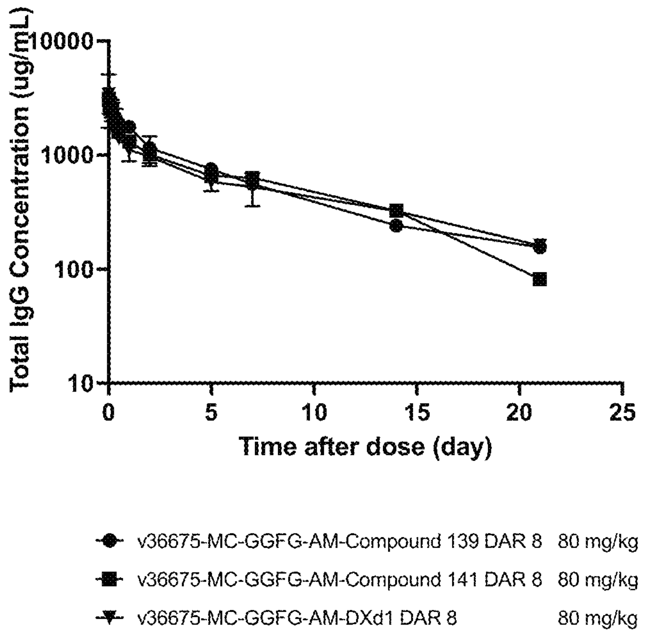
Figure 23D:
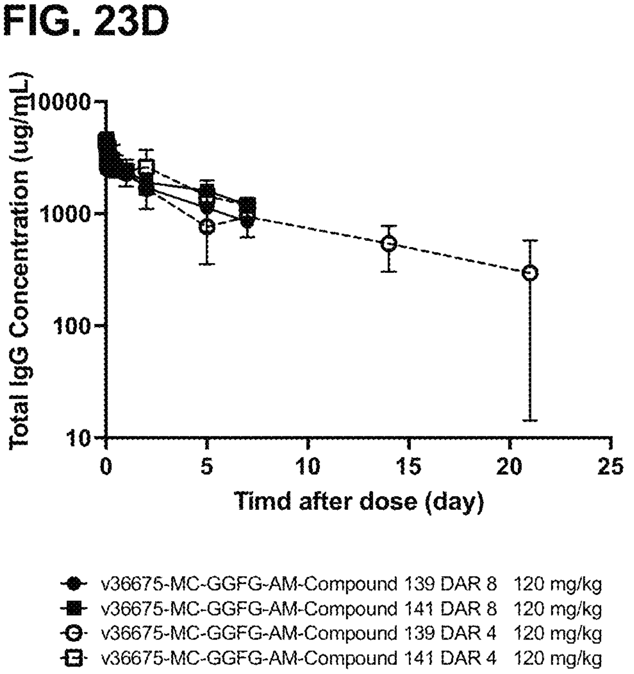

The results are shown in FIG. 21 and Table 32.1. Overall, all four ADCs showed highly similar results for DAR loss over time and extent of maleimide ring opening. All ADCs showed 48-55% DAR loss and 51-54% maleimide ring opening over 10 days. No significant linker drug decomposition was observed in any ADC tested.

TABLE 32.1

DAR Loss and % Maleimide Ring Opening (Changes over 10 days)

| ADC | % DAR Loss | % Maleimide Ring Opening |
|---|---|---|
| v36675-MC-GGFG-AM-DXd1 | 52 | 52 |
| v36675-MC-GGFG-AM-Compound 141 | 47 | 53 |
| v36675-MC-GGFG-Compound 141 | 45 | 51 |
| v36675-MC-GGFG-AM-Compound 139 | 50 | 54 |

Example 33: Rat Toxicity Study

A 2-dose (once every 3 weeks) intravenous exploratory toxicity and toxicokinetics study of the ADCs shown in Table 33.1 in Sprague Dawley rats was conducted as described below. The objective of this study was to determine the potential toxicity of the ADCs when administered twice to female Sprague Dawley (SD) rats, as well as to assess the reversibility, persistence, or delayed occurrence of toxic effects following a 4-week recovery period and to determine toxicokinetics (TK) of the ADCs following first dose. Sprague Dawley rat was selected as non-cross reactive rodent species to evaluate target independent toxic effects of these ADCs.

In this study, vehicle or test article ADCs, as shown in Table 33.1, were administered via slow intravenous injection over 10 minutes on Day 1 and Day 22 at the dose levels of 30, 60 and 200 mg/kg (6 animals/dose level). All the animals were evaluated for morbidity/mortality, clinical signs, body weight, food consumption, ophthalmic examinations, clinical pathology (hematology, serum chemistry, coagulation and urinalyses), changes in organ weight, and macroscopic and microscopic changes in organs/tissues. Blood samples were collected for toxicokinetic analysis of total antibody following first dose. The test article concentrations in all dose formulations were analyzed using bicinchoninic acid (BCA) assay. Scheduled complete necropsy was conducted at the end of dosing phase (on study Day 29) and recovery phase (on study Day 51). The study design is presented in the Table 33.1.

TABLE 33.1

Study Design

| Group No. | Test Article | Doses: Dose (mg/kg/dose) | Doses: Volume (mL/kg) | Doses: Conc. (mg/mL) | Number of Animals: Dosing Phase | Number of Animals: Recovery Phase |
|---|---|---|---|---|---|---|
| 1 | Vehicle | 0 | 20 | 0 | 3 | 3 |
| 2 | v36675-MC-GGFG-AM-DXd1 | 30 | 20 | 1.5 | 3 | 3 |
| 3 | v36675-MC-GGFG-AM- DXd1 | 60 | 20 | 3 | 3 | 3 |
| 4 | v36675-MC-GGFG-AM- DXd1 | 200 | 20 | 10 | 3 | 3 |
| 5 | v36675-MC-GGFG-AM-Compound 141 | 30 | 20 | 1.5 | 3 | 3 |
| 6 | v36675-MC-GGFG-AM-Compound 141 | 60 | 20 | 3 | 3 | 3 |
| 7 | v36675-MC-GGFG-AM-Compound 141 | 200 | 20 | 10 | 3 | 3 |
| 8 | v36675-MC-GGFG-Compound 140 | 30 | 20 | 1.5 | 3 | 3 |
| 9 | v36675-MC-GGFG-Compound 140 | 60 | 20 | 3 | 3 | 3 |
| 10 | v36675-MC-GGFG-Compound 140 | 200 | 20 | 10 | 3 | 3 |
| 11 | v36675-MC-GGFG-Compound 141 | 30 | 20 | 1.5 | 3 | 3 |
| 12 | v36675-MC-GGFG-Compound 141 | 60 | 20 | 3 | 3 | 3 |
| 13 | v36675-MC-GGFG-Compound 141 | 200 | 20 | 10 | 3 | 3 |
| 14 | v36675-MC-GGFG-AM-Compound 139 | 30 | 20 | 1.5 | 3 | 3 |
| 15 | v36675-MC-GGFG-AM-Compound 139 | 60 | 20 | 3 | 3 | 3 |
| 16 | v36675-MC-GGFG-AM-Compound 139 | 200 | 20 | 10 | 3 | 3 |

Conc. = Concentration

Results v36675-MC-GGFG-AM-DXd1 (control): After 1$^{st}$ dose administration of v36675-MC-GGFG-AM-Dxd the systematic exposure increased approximately dose-proportionally as the dosage increased from 30 to 200 mg/kg/dose There was no mortality, no test article related changes in clinical signs, ophthalmic examinations, coagulation/serum chemistry parameters; macroscopic examination at terminal and/or recovery sacrifice.

At terminal sacrifice, test article related hematological changes included decreased lymphocyte counts (at ≥60 mg/kg/dose) and erythrocyte counts (at 200 mg/kg/dose). These changes were reversed during recovery phase. Presence of urine protein was noted in one animal at 200 mg/kg/dose at the end of both dosing and recovery phases. At terminal sacrifice, test article related microscopic changes were present in lymphoid organs (at ≥60 mg/kg/dose) and bone marrow (at 200 mg/kg/dose). These changes were reversed during recovery phase.

v36675-MC-GGFG-AM-Compound 141: After 1$^{st}$ dose administration of v36675-MC-GGFG-AM-Compound 141, the systemic exposure increased approximately dose-proportionally as the dosage increased from 30 to 200 mg/kg/dose.

Test article related mortality was noted on Day 7 in one animal at 200 mg/kg/dose. The cause of the moribund condition was attributed to the mucosal atrophy and/or crypt dilation in the gastrointestinal (GI) tract. Clinical signs in the moribund animal included unkempt, decreased activity, thinness (correlated with 31% body weight loss during Days -1 to 7), hunched posture, and yellow soiled coat. Before death, changes in hematology and clinical chemistry parameters were noted. The test article-related microscopic findings were observed in the GI tract, lymphoid organs, pancreas, salivary gland and ovaries.

There was no test article related changes in ophthalmic examinations, coagulation/serum chemistry parameters at terminal and/or recovery sacrifice.

Test article related clinical signs (decreased activity, soiled coat, hunched posture, thinness and unkempt), significant body weight loss (12% or 14%, in the first week post each dose) and decreased food consumption (up to 44.1% decrease) was present at 200 mg/kg/dose only. At terminal sacrifice, test article related hematology changes included increased neutrophil/monocyte counts and decreased lymphocyte counts at 200 mg/kg/dose. These changes were reversed during recovery phase. Presence of urine protein was noted in one animal at ≥60 mg/kg/dose at the end of dosing and/or recovery phase. At terminal sacrifice, test article related changes included reduced thymus size (200 mg/kg/dose), decreased thymus weight (at ≥60 mg/kg/dose) and microscopic changes in the bone marrow (at ≥60 mg/kg/dose), GI tract (at ≥30 mg/kg/dose) and lymphoid organs (at ≥30 mg/kg/dose). All these changes were reversed during recovery phase.

v36675-MC-GGFG-Compound 140: Test article related mortalities were noted at ≥60 mg/kg/dose in all animals on Day 5 or 6. The cause of the moribund condition was attributed to mucosal atrophy and/or crypt dilation in the GI tract. Clinical signs in the moribund animals included soiled coat, hunched posture, thinness (correlated with up to 23% body weight loss after one dose administration), unkempt, red/brown material around nose, mucoid and soft stool, pale skin of ears, and yellow tooth. In the moribund animals, test article-related microscopic findings were observed in the bone marrow, GI tract, lymphoid organs, pancreas, salivary gland, ovaries and adrenal gland.

There were no test article related changes in ophthalmic examinations, coagulation/serum chemistry/urinalysis parameters and macroscopic examination at terminal and/or recovery sacrifice in the surviving 30 mg/kg/dose animals.

Test article related clinical signs (thinness and unkempt), body weight loss (9% or 8% in the first week post each dose administration) and decreased in food consumption (up to 31.7% J) were present at 30 mg/kg/dose. At terminal sacrifice, test article related hematology changes included decreased erythrocyte count, hemoglobin, hematocrit and reticulocyte counts. These changes were reversed during recovery phase. At terminal sacrifice, test article related changes at 30 mg/kg/dose included decreased thymus/ovary weight; microscopic changes in the bone marrow, GI tract and lymphoid organs. All these changes were reversed during recovery phase.

v36675-MC-GGFG-Compound 141: After 1st dose administration of v36675-MC-GGFG-Compound 141, the systemic exposure increased dose-proportionally as the dosage increased from 30 to 200 mg/kg/dose.

Test article related mortality was noted in one animal on Day 6. The cause of the moribund condition was attributed to mucosal atrophy and/or crypt dilation in the GI tract. Clinical signs in the animal on days before death included thinness, soiled coat, hunched posture, and abnormal gait. In the found dead animal the size of the spleen/thymus was reduced, and test article-related microscopic findings were present in the bone marrow, GI tract, lymphoid organs, pancreas, salivary gland and adrenal gland.

There was no test article related changes in ophthalmic examinations, coagulation/serum chemistry parameters at terminal sacrifice and/or recovery sacrifice.

Test article related clinical signs (hunched posture, thinness and unkempt), body weight loss (3.3% or 2.3% in the first week post each dose administration) and decreased food consumption (up to 36.3% decrease) were present at 200 mg/kg/dose. At terminal sacrifice, test article related hematology changes included decreased lymphocyte counts (at 60 and 200 mg/kg/dose) and increased neutrophil/reticulocyte/platelet counts (at 200 mg/kg/dose). These changes were reversed during recovery phase. Urinary protein was noted in one animal at ≥60 mg/kg/dose at the end of dosing and/or recovery phase. At terminal sacrifice, test article related changes included reduced thymus size (at 200 mg/kg/dose); decreased thymus weight (at ≥60 mg/kg/dose); microscopic changes in the bone marrow (at 200 mg/kg/dose), lymphoid organs (at ≥60 mg/kg/dose) and pancreas/salivary gland (at ≥60 mg/kg/dose). All these changes were reversed during recovery phase.

v36675-MC-GGFG-AM-Compound 139: After 1st dose administration of v36675-MC-GGFG-AM-Compound 139, the systemic exposure increased approximately dose-proportionally as the dosage increased from 30 to 200 mg/kg/dose.

There was no mortality and no test article related changes in clinical signs, ophthalmic examinations, clinical pathology parameters and macroscopic examination at terminal and/or recovery sacrifice.

Test article related body weight loss (1.35% or 6.15%) and decreased food consumption (up to 11.8%) was present at 200 mg/kg/dose in the first week post each dose administration. At terminal sacrifice test article related microscopic changes were present in lymphoid organs at ≥30 mg/kg/dose and these changes were reversed during recovery phase.

Conclusions

This study demonstrated that two intravenous injections of v36675-MC-GGFG-AM-Dxdl (control) and v36675-MC-GGFG-AM-Compound 139 to female SD rats on Days 1 and 22 at 30, 60, and 200 mg/kg/dose followed by a 4-week recovery was well tolerated, resulting in a Maximum Tolerated Dose (MTD) of 200 mg/kg.

Two intravenous injections of v36675-MC-GGFG-AM-Compound 141 and v36675-MC-GGFG-Compound 141 to female SD rats on Days 1 and 22 at 30, 60, and 200 mg/kg/dose followed by a 4-week recovery caused mortality at 200 mg/kg/dose, resulting in a MTD of 60 mg/kg.

Two intravenous injections of v36675-MC-GGFG-Compound 140 to female SD rats on Days 1 and 22 at 30, 60, and 200 mg/kg/dose followed by a 4-week recovery caused mortality at 60 and 200 mg/kg/dose, resulting in a MTD of 30 mg/kg.

Example 34: In Vivo Efficacy Studies #2

The in vivo anti-tumor activities of humanized variant v36675 conjugated to various drug-linkers at DAR 4 or DAR 8 were assessed in a number of cell-line derived xenograft (CDX) and patient derived xenograft (PDX) models as described below. In some models, ADCs including v32603 (Mirvetuzimab-DM4), v32385 (MORAb-202) and v36675 conjugated to DXd were assessed for comparison. The OVCAR-3 model included unconjugated v36675 mAb for comparison.

The ADCs, DARs, xenograft models and dosages employed in each xenograft study are summarized in Table 34.1. For each xenograft study, tumor volume and body weight of the animals were measured twice weekly.

TABLE 34.1

| Study Parameters | | | | | |
|---|---|---|---|---|---|
| Xenograft Model | Cancer Type | FRα Expression | Test Article | DAR | Dose (mg/kg) |
| OV90 #3 | Ovarian | Mid | v36675-MC-GGFG-AM-DXd | 8 | 3, 6 |
| | | | v36675-MC-GGFG-AM-Compound 139 | 8 | 3, 6 |
| | | | v36675-MC-GGFG-AM-Compound 141 | 8 | 3, 6 |
| | | | v36675-MC-GGFG-AM-Compound 139 | 4 | 3, 6 |
| | | | v36675-MC-GGFG-AM-Compound 141 | 4 | 3, 6 |
| | | | v17716-DM4 (mirvetuximab-DM4) | 4 | 6 |
| | | | v31629-eribulin (MORAb-202) | 4 | 6 |
| OVCAR-3 | Ovarian | Mid | v36675-MC-GGFG-AM-DXd1 (36690) | 8 | 0.75 |
| | | | v36675-MC-GGFG-AM-Compound 139 | 8 | 0.75 |
| | | | v36675-MC-GGFG-AM-Compound 141 | 8 | 0.75 |
| | | | v36675-MC-GGFG-AM-Compound 139 | 4 | 0.75 |
| | | | v36675-MC-GGFG-AM-Compound 141 | 4 | 0.75 |
| | | | v17716-DM4 (mirvetuximab-DM4) | 4 | 0.75 |
| | | | v31629-eribulin (MORAb-202) | 4 | 0.75 |
| | | | v36675 mAb | / | 0.75 |
| CTG-2025 | Ovarian | High | v36675-MC-GGFG-AM-Compound 139 | 8 | 6 |
| | | | v17716-DM4 (mirvetuximab-DM4) | 4 | 6 |
| CTG-0958 | Ovarian | Mid | v36675-MC-GGFG-AM-Compound 139 | 8 | 6 |
| | | | v17716-DM4 (mirvetuximab-DM4) | 4 | 6 |

For the OV90 CDX model study #3, tumor cell suspensions ($1\times10^7$ cells in 0.1 ml 50% Matrigel®) were implanted subcutaneously into female CB. 17 SCID mice, and for the OVCAR3 CDX model study, tumor fragments (~1 $mm^3$) were implanted subcutaneously into female CB. 17 SCID mice. When mean tumor volume reached 100-150 $mm^3$, the animals were randomly assigned to groups (n=6 per group in each study) and treated on study day 1 with a single IV dose of test article as shown in Table 34.1.

For the ovarian cancer PDX models CTG-2025 and CTG-0958, tumor fragments were implanted subcutaneously into female athymic Nude-Foxnlnu mice. When mean tumor volume reached ~240 $mm^3$ (for CTG-2025) or −220 $mm^3$ (for CTG-0958), the animals were assigned to groups (n=3 per group for each study) and treated on study day 1 with a single IV dose of test articles as shown in Table 34.1.

Results

The results are summarized in FIG. 22. In the OV90 CDX model, when dosed at 3 mg/kg, v36675-MC-GGFG-AM-Compound 139 DAR8 resulted in moderate inhibition of tumor growth, similar to v36675-MC-GGFG-AM-DXd (FIG. 22A). When dosed at 6 mg/kg, v36675-MC-GGFG-AM-Compound 139 resulted in moderate and strong inhibition of tumor growth as DAR4 and DAR8 ADCs, respectively (FIG. 22B). At 3 mg/kg, v36675-MC-GGFG-AM-Compound 141 resulted in moderate and strong inhibition of tumor growth as DAR4 and DAR8 ADCs, respectively (FIG. 22A). When dosed at 6 mg/kg, v36675-MC-GGFG-AM-Compound 141 resulted in strong tumor growth inhibition as a DAR4 ADC and superior activity as a DAR8 ADC (FIG. 22B).

In the OVCAR3 CDX model (see FIG. 22C), when dosed at 0.75 mg/kg, v36675-MC-GGFG-AM-Compound 139 and v36675-MC-GGFG-AM-Compound 141 both showed a trend towards superior inhibition of tumor growth as DAR8 ADCs than as DAR4 ADCs. At both DARs, v36675-MC-GGFG-AM-Compound 141 showed a trend towards superior inhibition of tumor growth to v36675-MC-GGFG-AM-Compound 139. v36675-MC-GGFG-AM-Compound 141 DAR8 resulted in comparable inhibition of tumor growth to the v36675-MC-GGFG-AM-DXd control ADC. When dosed at 0.75 mg/kg, the control ADCs mirvetuximb-DM4 and MORAb-202 were both inactive.

In the CTG-2025 PDX model (see FIG. 22D), when dosed at 6 mg/kg, v36675-MC-GGFG-AM-Compound 139 DAR8 and mirvetuximab-DM4 both resulted in strong inhibition of tumor growth.

In the CTG-0958 PDX model (see FIG. 22E), when dosed at 6 mg/kg, v36675-MC-GGFG-AM-Compound 139 DAR8 resulted in strong inhibition of tumor growth, while mirvetuximab-DM4 was inactive.

Example 35: Cynomolgus Monkey Toxicity Study

The objective of this study was to determine the maximum tolerated dose (MTD) and potential toxicity of four ADCs comprising the humanized variant v36675 conjugated to various drug-linkers when administered twice to male cynomolgus monkeys. Cynomolgus monkey was selected as a cross-reactive species to evaluate toxic effects of these ADCs. The ADCs tested were v36675-MC-GGFG-AM-Compound 139 (DAR8), v36675-MC-GGFG-AM-Compound 141 (DAR8), v36675-MC-GGFG-AM-Compound 139 (DAR4) and v36675-MC-GGFG-AM-Compound 141 (DAR4), together with an ADC comprising variant v36675 conjugated to Dxd (v36675-MC-GGFG-AM-DXd, DAR8).

Materials and Methods

In this study, vehicle and test article ADCs were administered by slow intravenous injection over 3 minutes on Day 1 and Day 22 to male cynomolgus monkeys (n=2/group). Study design, dose levels and dose volume details are summarized in the Table 35.1. All the animals were evaluated for moribundity/mortality, clinical signs, body weight, food consumption, clinical pathology (hematology, serum chemistry and coagulation), changes in organ weight, and macroscopic and microscopic changes in organs/tissues. Blood samples were collected for toxicokinetic analysis following the first dose (see Example 36). The test article concentrations in all dose formulations were analyzed using UV-Vis or bicinchoninic acid (BCA) assay. Scheduled necropsy was conducted on study Day 29.

TABLE 35.1

Study Design

| Group | Treatment | DAR | Dose level (mg/kg/dose) | Dose volume (mL/kg) | Concentration (mg/mL) | Number of animals |
|---|---|---|---|---|---|---|
| 1 | Vehicle | | 0 | 5 | 0 | 2 |
| 2 | v36675-MC-GGFG- | 8 | 30 | 5 | 6 | 2 |
| 3 | AM-Compound 139 | | 80 | 5 | 16 | 2 |
| 4 | | | 120 | 5 | 24 | 2 |
| 5 | v36675-MC-GGFG- | 8 | 30 | 5 | 6 | 2 |
| 6 | AM-Compound 141 | | 80 | 5 | 16 | 2 |
| 7 | | | 120 | 5 | 24 | 2 |
| 8 | v36675-MC-GGFG- | 4 | 60 | 5 | 12 | 2 |
| 9 | AM-Compound 139 | | 120 | 5 | 24 | 2 |
| 10 | v36675-MC-GGFG- | 4 | 60 | 5 | 12 | 2 |
| 11 | AM-Compound 141 | | 120 | 5 | 24 | 2 |
| 12 | v36675-MC-GGFG- | 8 | 30 | 5 | 6 | 2 |
| 13 | AM-DXd | | 80 | 5 | 16 | 2 |

Results v36675-MC-GGFG-AM-Compound 139, DAR8: Test article related mortality was noted in one animal (on Day 7) at 80 mg/kg/dose and 2 animals (on day 8 and day 10) at 120 mg/kg/dose. Both the animals treated at 30 mg/kg/dose and one animal treated with 80 mg/kg/dose survived until terminal necropsy.

Preterminal animals: As compared to their own baselines, substantial increase in values for alanine aminotransferase (ALT), aspartate aminotransferase (AST), alkaline phosphatase (ALP), total bilirubin (TBIL), blood urea (BU), and glucose (GLU); substantial decrease in reticulocyte (ABRETIC) and lymphocyte (ABLYMP) counts; substantial shortened prothrombin time (PT) were observed.

Terminal animals: As compared to the mean of control group and their own baseline values, at 30 and 80 mg/kg/dose, substantial increases in value for ALT, AST, and BU; substantial decrease in ABRETIC counts, and relatively low PT value were observed. At 80 mg/kg/dose, substantial decrease in ABLYMP count was observed. Microscopic findings were present in thymus, stomach, kidneys, the meninges of the brain and testis.

v36675-MC-GGFG-AM-Compound 141, DAR8: Test article related mortality was noted in one animal (on Day 11) at 80 mg/kg dose and 2 animals (on day 7 and day 8) at 120 mg/kg/dose. Both the animals treated at 30 mg/kg/dose and one animal treated with 80 mg/kg/dose survived until terminal necropsy.

Preterminal animals: As compared to their own baselines, substantial increase in values for ALT, AST, creatine kinase (CK), lactate dehydrogenase (LDH), TBIL, BU, creatinine (CRE), and GLU; substantial decrease in ABRETIC and ABLYMP counts; substantial increase in fibrinogen (FIB) level were observed.

Terminal animals: As compared to the mean of control group and their own baseline values, at 30 and 80 mg/kg/dose, substantial increases in values for ALT, AST, CK, LDH, and TBIL, and substantial decrease in ABRETIC and ABLYMP count were observed. Animals administered at 80 mg/kg/day showed low activated partial thromboplastin time (APTT), low PT and relatively high FIB levels. Microscopic findings were present in thymus, liver, spleen, pancreas, gastrointestinal tract, adrenal glands, kidneys, the meninges of the brain and mesenteric lymph node.

v36675-MC-GGFG-AM-Compound 139, DAR4: There was no mortality up to 120 mg/kg/dose level and all the animals survived until terminal necropsy.

Terminal animals: At 60 and 120 mg/kg/dose, no substantial value changes for serum chemistry parameters; substantial decrease in ABRETIC and neutrophil (ABNEUT) counts were noted. Microscopic findings were present in thymus, spleen, stomach, adrenal glands, testis, prostate gland, meninges of the brain and mesenteric lymph node.

v36675-MC-GGFG-AM-Compound 141, DAR4: Test article related mortality was noted in both animals (on day 7 and day 8) at 120 mg/kg/dose. Both the animals treated at 60 mg/kg/dose survived until terminal necropsy.

Preterminal animals: as compared to their own baselines, substantial increase in values for AST, CK, LDH, TBIL, BU, CRE, GLU, phosphorus (P), and BUN/C; substantial decrease in albumin/globulin ratio (A/G); substantial decrease in ABRETIC counts were noted.

Terminal animals: As compared to the mean of control group and their own baseline values, at 60 mg/kg/dose, substantial and dose-dependent increase in values for AST, CK, and LDH; substantial decrease in ABRETIC and leukocyte (WBC) counts were noted. Microscopic findings were present in thymus, kidneys, prostate gland, meninges of the brain and mesenteric lymph node.

v36675-MC-GGFG-AM-DXd, DAR8: Test article related mortality was noted in one animal (on Day 8) at 80 mg/kg/dose. Both the animals treated at 30 mg/kg/dose and one animal treated with 80 mg/kg/dose survived until terminal necropsy.

Preterminal animal: As compared to baseline, substantial increase in values for ALT, CK, LDH, TBIL, CRE, BUN/C, and BU; substantial decrease in ABRETIC counts; substantial shortened PT were observed. Target organs in the preterminal animals include thymus, esophagus, liver, spleen, gastrointestinal tract, pancreas, adrenal glands, kidney, mesenteric and mandibular lymph node nodes, bone marrow, skin, and the femur.

Terminal animals: As compared to the mean of control group and their own baseline values, at 80 mg/kg/dose level, substantial increases in value for ALT, CK, TBIL, and LDH were observed. At 30 and 80 mg/kg/dose, substantial decrease in ABRETIC, WBC and ABLYMP counts were observed. At 30 mg/kg/dose relatively high APTT was observed. Microscopic findings were present in thymus, spleen, large intestine, kidneys, testis, meninges of the brain, mandibular and mesenteric lymph nodes, bone marrow of the sternum and the femur.

Conclusions

This study demonstrated that in male cynomolgus monkeys, two intravenous administrations (on Days 1 and 22) of the ADC v36675-MC-GGFG-AM-Compound 139 (DAR4) was well tolerated up to 120 mg/kg/dose; the ADC v36675-MC-GGFG-AM-Compound 141 (DAR4) was well tolerated at 60 mg/kg/dose; the ADCs v36675-MC-GGFG-AM-Compound 139 (DAR8), v36675-MC-GGFG-AM-Compound 141 (DAR8) and v36675-MC-GGFG-AM-DXd (DAR8) were well tolerated at 30 mg/kg/dose.

The ADCs v36675-MC-GGFG-AM-Compound 139 (DAR8) and v36675-MC-GGFG-AM-Compound 141 (DAR8) at 80 and 120 mg/kg/dose, the ADC V36675-MC-GGFG-AM-Compound 141 (DAR4) at 120 mg/kg/dose and the ADC v36675-MC-GGFG-AM-DXd (DAR8) at 80 mg/kg/dose resulted in moribundity/mortality in one or both the monkeys. The cause of moribundity/mortality of these monkeys was related to the test article administration.

Example 36: Toxicokinetic Analysis

Total antibody serum concentrations of ADCs in the blood samples collected after the first dose in the toxicity study described in Example 35 were analyzed using an ELISA. ADCs from serum were captured onto a 384-well plate coated with mouse anti-human IgG Fc antibody (Abcam plc, Cambridge, UK; catalogue #ab124055). Total anti-IgG antibody was detected with a secondary goat anti-human IgG (H+L) horseradish peroxidase (HRP) antibody (Novus Biologicals, LLC, Centennial, CO; NB7489). After addition of 3,3',5,5''-tetramethylbenzidine (TMB) substrate and reaction quenching by the addition of hydrochloric acid, 1N solution, absorbance at 450 nm was read. Sample data were analyzed using SoftMax® Pro 7.1 (Molecular Devices, San Jose, CA).

Results

The results are shown in FIG. 23A-D. All ADCs demonstrated a typical antibody-like exposure, with approximate dose proportionality across the dose levels administered. Pharmacokinetic profiles were comparable between the different ADCs at each dose level.

Example 37: Bystander Activity of Antibody Drug Conjugates

The ability of the humanized variant v30384 conjugated to various drug-linkers to exert a bystander killing effect on cancer cells was assessed according to the method described below. Bystander killing most commonly occurs after target-specific uptake of an ADC into an antigen-positive cell. Trafficking and degradation of the ADC results in release of active catabolite free drug, which then crosses the cell membrane of nearby cells to elicit cell death.

The following ADCs were tested in JEG-3 cells (high FRα expression) and MDA-MB-468 cells (negative FRα expression): v30384-MT-GGFG-AM-Compound 139, v30384-MT-GGFG-Compound 141, v30384-MT-GGFG-AM-Compound 141, v30384-MT-GGFG-Compound 140, v30384-MT-GGFG-Compound 148 (all DAR 8). Positive controls v30384-MC-GGFG-AM-DXd1 (DAR 8) and v30384-MCvcPABC-MMAE (DAR 4), whose drug linkers are known have bystander activity, and negative controls palivizumab (anti-RSV) (v22277) conjugated to MC-GGFG-AM-DXd1 (DAR 8) and MCvcPABC-MMAE (DAR 4), were included.

FRα-positive JEG-3 and FRα-negative MDA-MB-468 cells were seeded either as mono-cultures or co-cultures in a 48-well plate at 20,000 cells and 10,000 cells, respectively, in 100 μL assay media (Minimum Essential Media supplemented with 10% Fetal Bovine Serum (both from Thermo Fisher Scientific, Waltham, MA)). ADCs were diluted to 4 nM in assay media and 100 μL was added to the cell-containing plates (2 nM final ADC concentration). Cells were incubated with ADCs for 4 days under standard culturing conditions (37° C./5% $C_{O2}$). Following incubation, cells were dissociated, washed, and stained using a viability dye, YO—PRO®-1 (ThermoFisher Scientific, Waltham, MA), and an anti-FRα antibody, mirvetuximab (v17716), conjugated to Alexa Fluor®647, for 20 minutes at 4° C. After incubation, cells were washed in FACS buffer (phosphate buffered saline pH 7.4 (ThermoFisher Scientific, Waltham, MA) supplemented with 2% FBS), resuspended in 70 μL FACS buffer per well, and 35 μL per well were analyzed on a BD LSRFortessa™ Cell Analyzer (BD Biosciences, Franklin Lake, NJ). Dead cells were excluded by gating on YO—PRO®-1 staining. The number of JEG-3 and MDA-MB-468 cells were determined by the number of events in the Alexa Fluor®647 positive (FRα-positive) and Alexa Fluor®647 negative (FRα-negative) gates, respectively. Percent viability was calculated as the number of cells in treatment condition divided by the number of cells in the no-treatment condition.

Results

Figure 24:
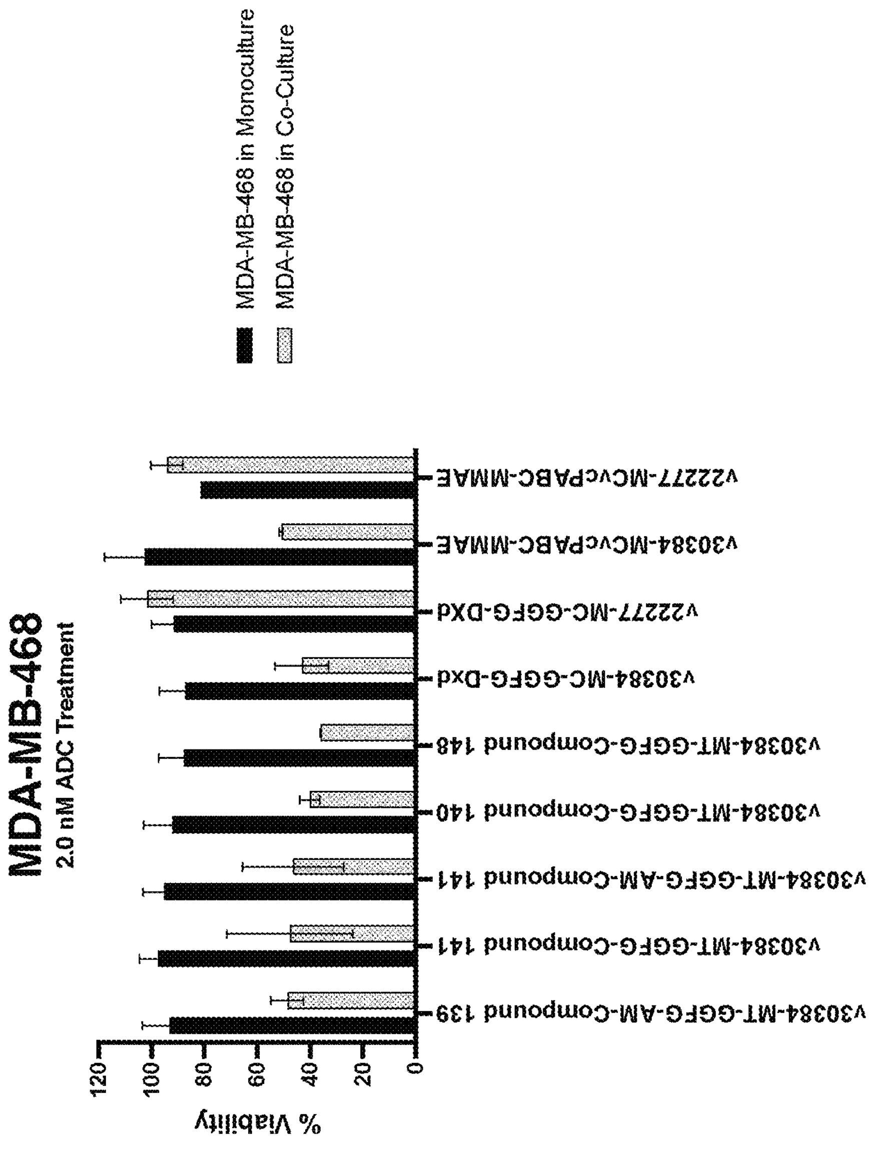
FIG. 24 shows the in vitro bystander activity of ADCs comprising the anti-FRα humanized antibody variant v30384 conjugated to various camptothecin analogues against the FRα-negative MDA-MB-468 cell line. The ADCs v30384-MC-GGFG-AM-DXd1 and v30384-MCvcPABC-MMAE were included as positive controls and ADCs comprising palivizumab (v22277) conjugated to MC-GGFG-AM-DXd1 and MCvcPABC-MMAE were included as negative controls.
Figure 25A:
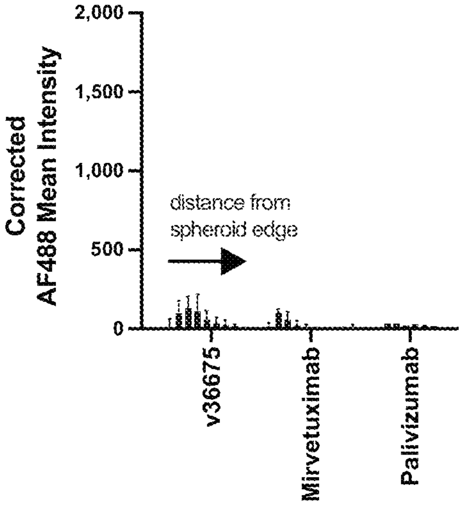
Figure 25B:
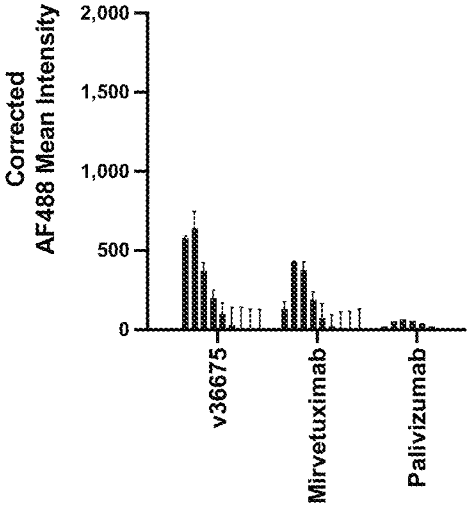
Figure 25C:
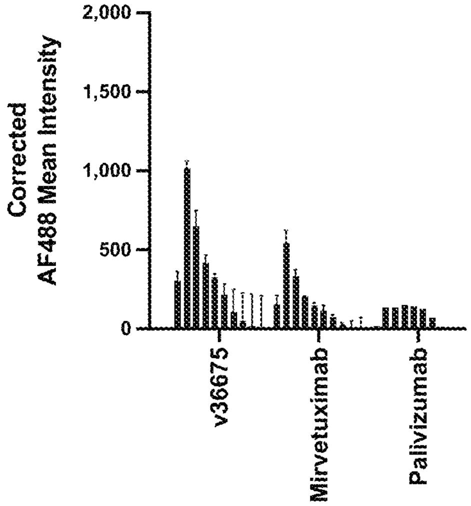
Figure 25D:
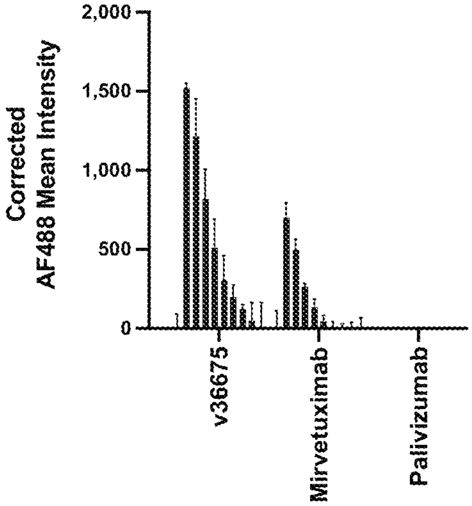

The results are provided in Table 37.1 below and in FIG. 24. Bystander effect was calculated by comparing the viability of FRα-negative MDA-MB-468 cells treated as monoculture (black bars) with that of the cells treated as a co-culture with FRα-positive JEG-3 cells (grey bars) (see FIG. 24). A greater decrease in viability in co-culture compared with mono-culture indicated a greater bystander effect. FRα-targeted camptothecin analogue ADCs all showed bystander capability to varying degrees. Positive controls v30384-MC-GGFG-AM-DXd1 and v30384-MCvcPABC-MMAE showed positive bystander activity, as expected. Negative controls palivizumab MC-GGFG-AM-DXd1 and palivizumab MCvcPABC-MMAE showed negative bystander activity, as expected.

TABLE 37.1

Bystander Activity of anti-FRα ADCs against FRα-negative MDA-MB-468 cells

| ADC | DAR | Average MDA-MB-468 Viability (%) Mono-culture* | Co-culture* | % Bystander Activity |
|---|---|---|---|---|
| v30384-MT-GGFG-AM-Compound 139 | 8 | 93.2 | 48.7 | 44.6 |
| v30384-MT-GGFG-Compound 141 | 8 | 97.5 | 47.7 | 49.7 |
| v30384-MT-GGFG-AM-Compound 141 | 8 | 95.3 | 46.5 | 48.8 |
| v30384-MT-GGFG-Compound 140 | 8 | 92.0 | 40.2 | 51.8 |
| v30384-MT-GGFG-Compound 148 | 8 | 87.6 | 36.0 | 51.7 |
| v30384-MC-GGFG-AM-DXd1 | 8 | 87.5 | 43.2 | 44.3 |
| v22277-MC-GGFG-AM-DXd1 | 8 | 91.6 | 101.8 | −10.2 |
| v30384-MCvcPABC-MMAE | 4 | 102.4 | 50.9 | 51.5 |
| v22277-MCvcPABC-MMAE | 4 | 81.3 | 94.2 | −12.9 |

*Relative to untreated blank

Example 38: Penetration of Anti-Frα Antibodies in Multicellular Tumor Spheroids The ability of anti-FRα antibodies to penetrate FRα-expressing cell line spheroids was assessed according to the method described below. Spheroids provide a three-dimensional organization of cells with layers of distinct cell populations and the formation of different gradients from the outer to the inner regions. Cell signaling is more complex in spheroids than in two-dimensional cell cultures. As a result of these features, spheroids have the potential to recapitulate drug resistance and metabolic adaptation.

The spheroid penetration capability of humanized variant v36675 was compared to mirvetuximab (v17716) and non-FRα targeting control palivizumab (anti-RSV) (v22277). Variant v36675 is the same as variant v30384 but comprises HomoFc rather than HetFc. The cell line used was high FRα-expressing JEG-3 (placental choriocarcinoma).

Antibodies were fluorescently labeled by coupling to a Fab fragment AF488 conjugate targeting anti-Human IgG Fc (Jackson Immuno Research Labs, West Grove, PA; Cat. No. 109-547-008) at a 1:1 molar ratio in PBS pH 7.4 (Thermo Fisher Scientific, Waltham, MA; Cat. No. 10010-023), for 24 hours at 4° C.

JEG-3 cells were detached from culture vessels with TrypLE™ Express Enzyme (IX) (Thermo Fisher Scientific, Waltham, MA) and counted using the Cellaca® MX high-throughput automated cell counter (Nexcelom Bioscience LLC, Lawrence, MA). Cells were diluted in complete growth medium (Minimum Essential Media supplemented with 10% Fetal Bovine Serum (both from Thermo Fisher Scientific, Waltham, MA)) and seeded at 3,000 cells/well into 96-well CellCarrier Spheroid ultra-low attachment plates (Perkin Elmer, Waltham, MA), centrifuged, and incubated for 3 days under standard culturing conditions to allow for spheroid formation and growth.

After spheroid formation, Fab-AF488 coupled antibodies were added to spheroids at a final concentration of 25 nM and incubated under standard culturing conditions for 4-96 hours. Following incubation, excess antibody was removed by adding 100 μL complete growth medium and removing 100 μL medium from the well, to a total three washes. Spheroids were treated with a solution of 1 μM Hoechst 33342 (Thermo Fisher Scientific, Waltham, MA) and 100 nM anti-Alexa Fluor 488 antibody (Thermo Fisher Scientific, Waltham, MA; Cat. No. A-11094), and incubated at 37° C./5% $CO_2$ for 2 hours.

Imaging was performed using an Operetta CLS™ high content analysis system (Perkin Elmer, Waltham, MA) with confocal acquisition and 10× magnification air objective. A Z stack of planes separated by 15 μm was acquired and the slice with greatest diameter representing the spheroid center slice was selected for 2D analysis. Image analysis was performed using Harmony®4.5 software (Perkin Elmer, Waltham, MA). Briefly, spheroid identification was performed by applying a mask around Hoechst 33342 positive objects to one spheroid per well. The spheroid region was divided into subregions of concentric bands, each representing 10% area of the spheroid region. Mean AF488 fluorescence within each subregion band was quantified, corrected by subtracting the inner 10% mean AF488 fluorescence, and plotted using GraphPad Prism Version 9 (GraphPad Software, San Diego, CA).

Results

The results are summarized in Table 38.1 and FIG. 25. The humanized antibody variant v36675 showed a greater degree of penetration than mirvetuximab into JEG-3 spheroids by AF488 intensity at each subregion band and by distance from spheroid edge to which AF488 fluorescence was detectable at all time points assessed. Non-binding control palivizumab showed lesser AF488 signal throughout the spheroid compared to both anti-FRα antibodies at all time points assessed.

TABLE 38.1

Penetration of Anti-FRa Antibodies in JEG-3 Spheroids

| | | Average Corrected AF488 Mean Intensity | | | | | | | | | |
|---|---|---|---|---|---|---|---|---|---|---|---|
| Time (h) | Sample | Band 1 | Band 2 | Band 3 | Band 4 | Band 5 | Band 6 | Band 7 | Band 8 | Band 9 | Spheroid Center |
| 4 | v36675 | −11.2 | 97.5 | 129.6 | 107.1 | 56.1 | 33.0 | 23.9 | 14.6 | 7.8 | 0.0 |
| | Mirvetuximab | 9.8 | 100.1 | 57.1 | 17.0 | 0.1 | −13.5 | −15.9 | −13.7 | −7.1 | 0.0 |
| | Palivizumab | −16.0 | 5.1 | 31.7 | 31.2 | 21.6 | 25.4 | 23.5 | 14.8 | 7.5 | 0.0 |
| 24 | v36675 | −133.1 | 576.7 | 643.2 | 370.2 | 199.2 | 95.3 | 25.7 | 6.4 | −1.7 | 0.0 |
| | Mirvetuximab | −134.5 | 129.0 | 427.8 | 374.6 | 187.3 | 71.3 | 17.9 | 10.1 | 0.3 | 0.0 |
| | Palivizumab | −18.2 | 18.0 | 50.9 | 62.1 | 53.5 | 37.4 | 21.5 | 7.3 | 1.8 | 0.0 |
| 48 | v36675 | 303.6 | 1017.6 | 648.1 | 418.6 | 324.6 | 214.1 | 106.6 | 47.2 | 17.5 | 0.0 |
| | Mirvetuximab | 153.2 | 542.7 | 332.1 | 206.6 | 146.2 | 112.5 | 71.7 | 28.9 | 4.2 | 0.0 |
| | Palivizumab | 17.8 | 136.1 | 133.9 | 148.9 | 141.8 | 125.0 | 69.6 | 12.8 | 4.0 | 0.0 |
| 96 | v36675 | −60.5 | 1519.5 | 1213.0 | 815.5 | 507.5 | 305.5 | 196.5 | 121.5 | 48.5 | 0.0 |
| | Mirvetuximab | −24.8 | 698.9 | 495.9 | 261.9 | 134.9 | 44.7 | 5.8 | −12.1 | −11.6 | 0.0 |
| | Palivizumab | −147.8 | −25.7 | −0.1 | −20.1 | −28.2 | −18.8 | −13.6 | −9.9 | −5.3 | 0.0 |

Example 39: Intracellular Payload Release and Quantitation

The intracellular and extracellular payload delivery capabilities of the humanized variant v36675 conjugated to Compound 139 at DAR 8 (v36675-MC-GGFG-AM-Compound 139; v36789) were assessed using mass spectrometry as follows. Palivizumab (v21995) conjugated to Compound 139 at DAR 8 was used as a non-targeted control.

Briefly, adherent IGROV-1 tumor cells were seeded in 12-well plates at 200,000 cells/well and treated with ADC for 24, 48, and 72 hours under standard culturing conditions. After incubation, supernatant was transferred to a 96-well plate for extracellular payload quantitation. Remainder cells were washed using PBS pH 7.4, collected, counted, transferred to a separate 96-well plate and frozen down at −80° C. for intracellular payload quantitation. After thawing, cells were lysed using pure acetonitrile. Initial supernatant and cell lysate supernatants were injected into an LC/MS instrument (Agilent 6545 Quadrupole Time-of-Flight (Q-TOF) liquid chromatography/mass spectrometer, Agilent Technologies, Santa Clara, CA), 15 μL/injection, and free Compound 139 in samples was quantified using Compound 139 standards of known concentration. MassHunter software (Agilent Technologies, Santa Clara, CA) was employed for deconvolution and data analysis.

Results

Figure 26A:
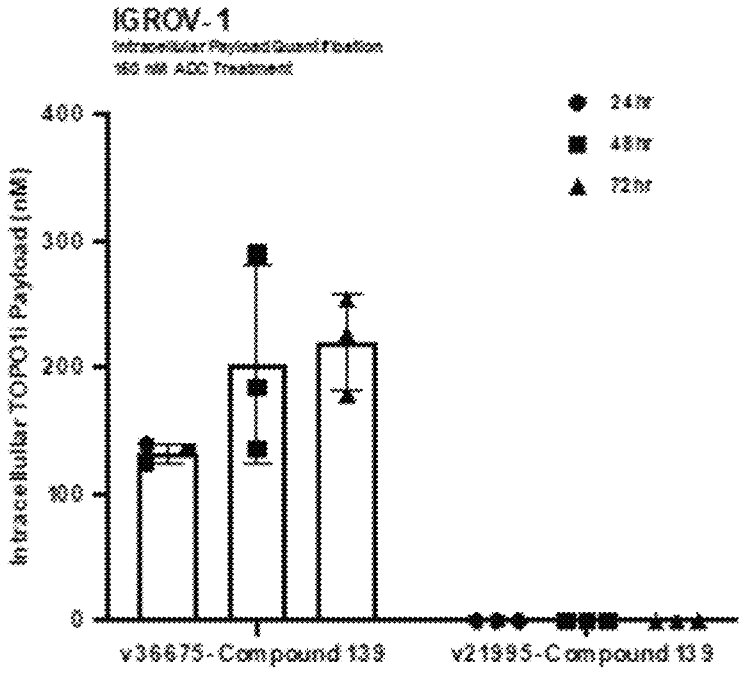
FIG. 26A & 26B show intracellular (26A) and extracellular (26B) payload release from an ADC comprising anti-FRα humanized antibody variant v36675 conjugated to Compound 139 at DAR 8 (v36675-MC-GGFG-AM-Compound 139) and an ADC comprising non-targeted control palivizumab (v21995) conjugated to Compound 139 at DAR 8 in the high FRα-expressing cell line IGROV-1.
Figure 26B:
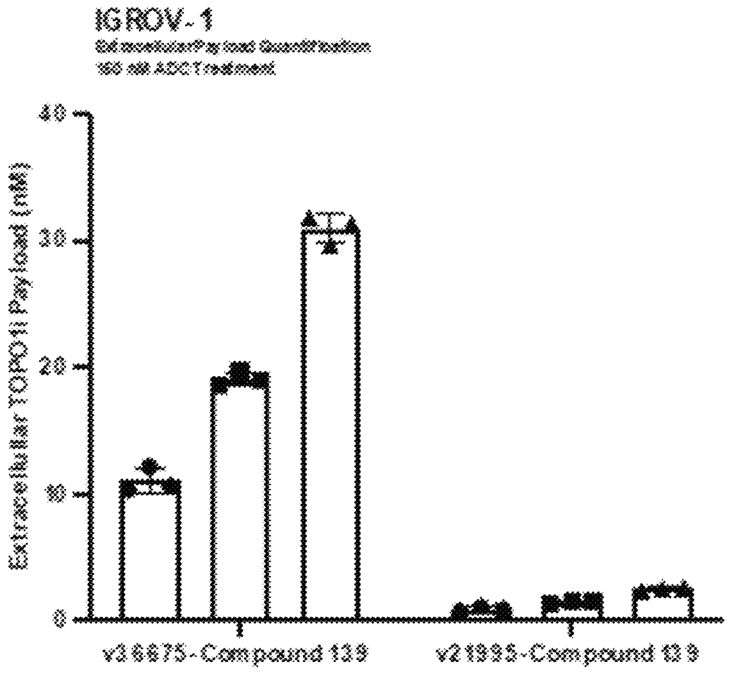
Figure 27A:
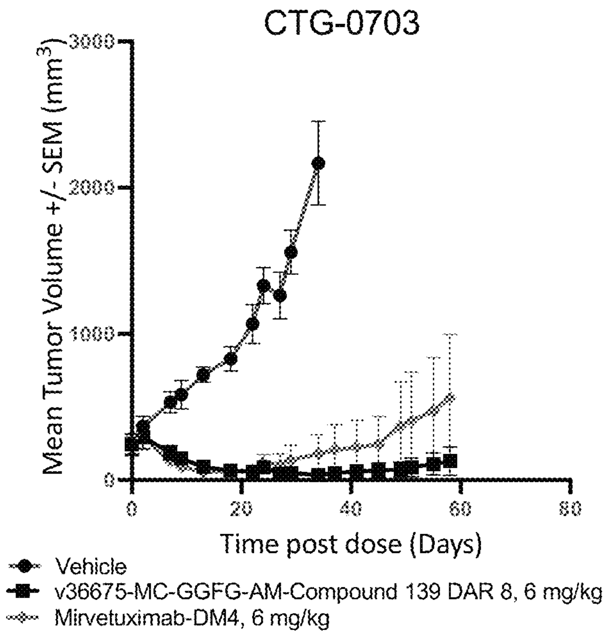
Figure 27B:
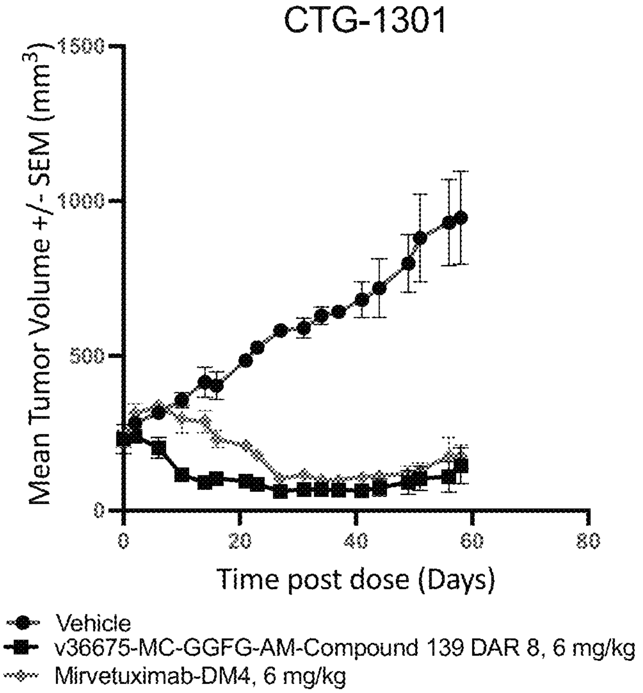
Figure 27C:
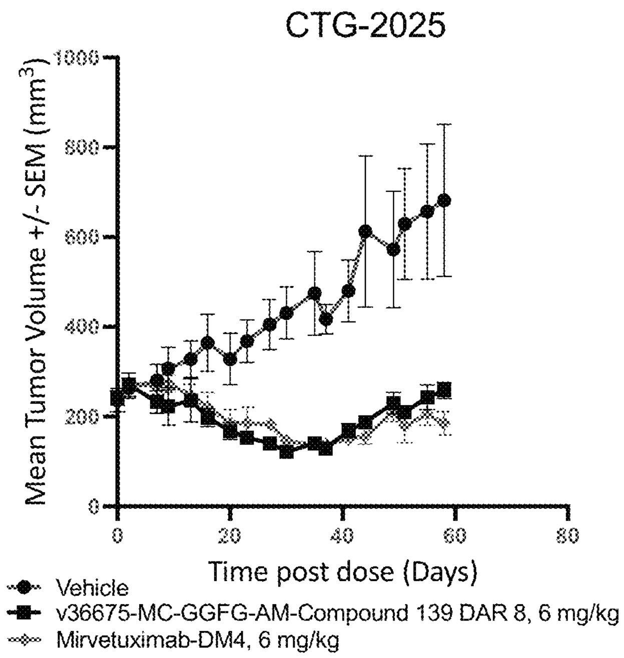
Figure 27D:
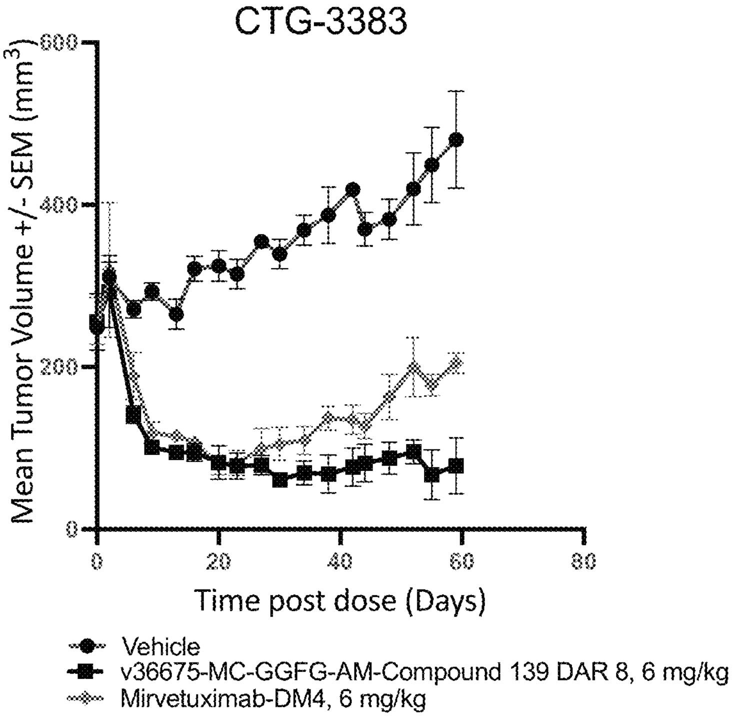
Figure 27E:
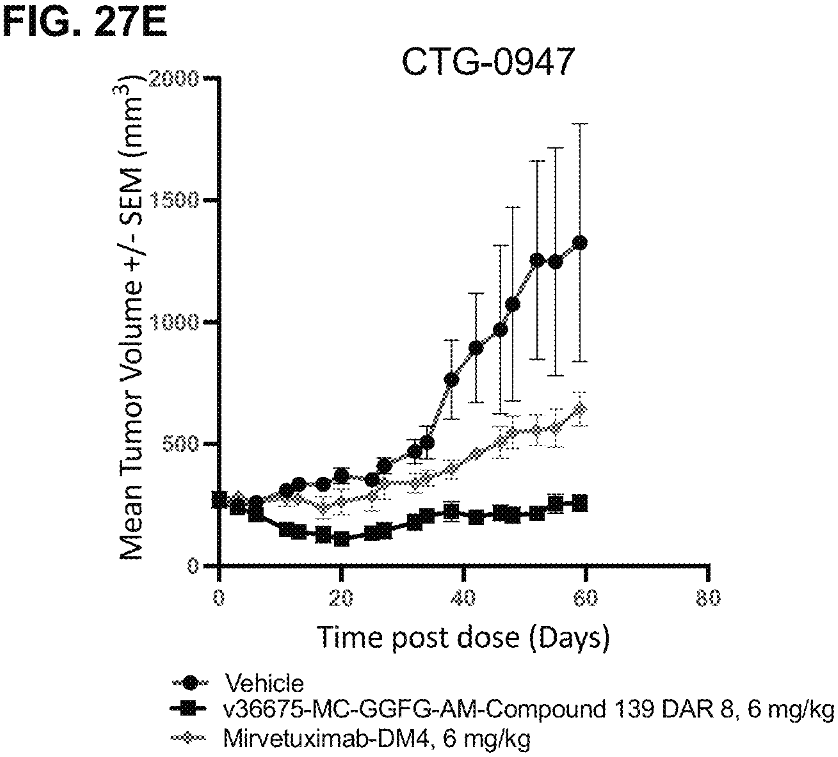
Figure 27F:
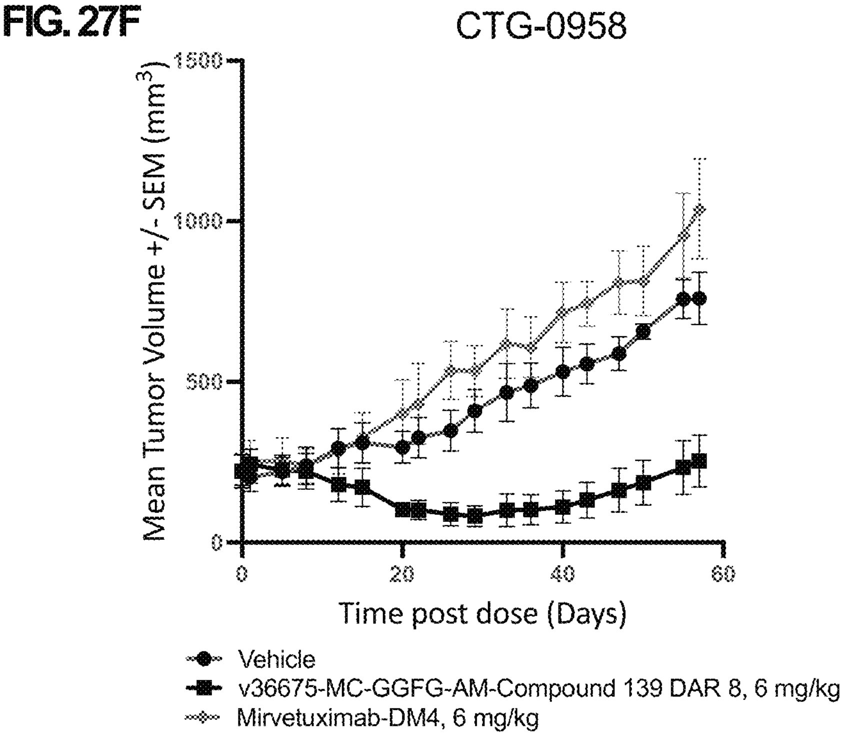
Figure 27G:
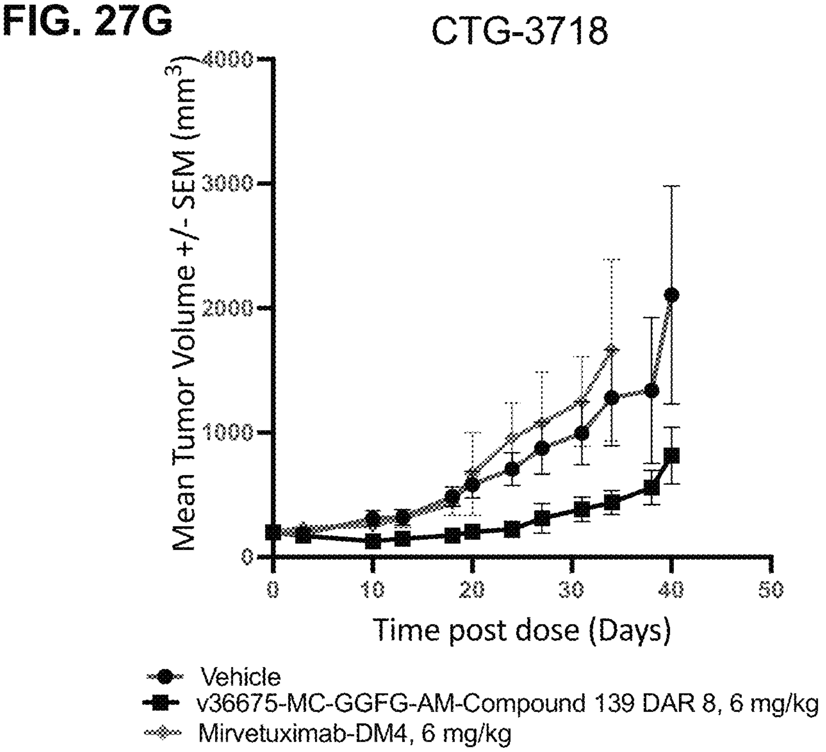
Figure 27H:
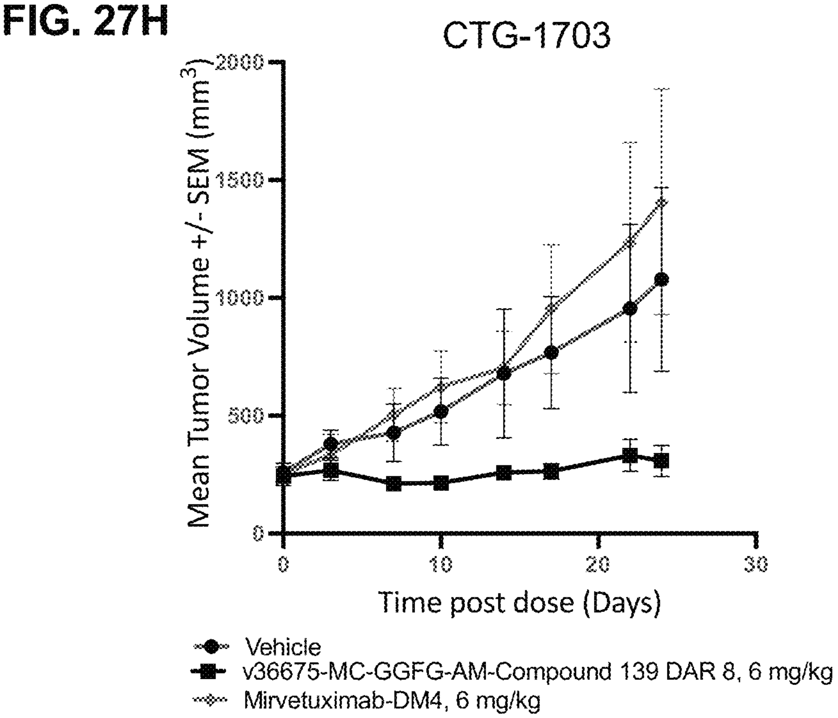
Figure 27I:
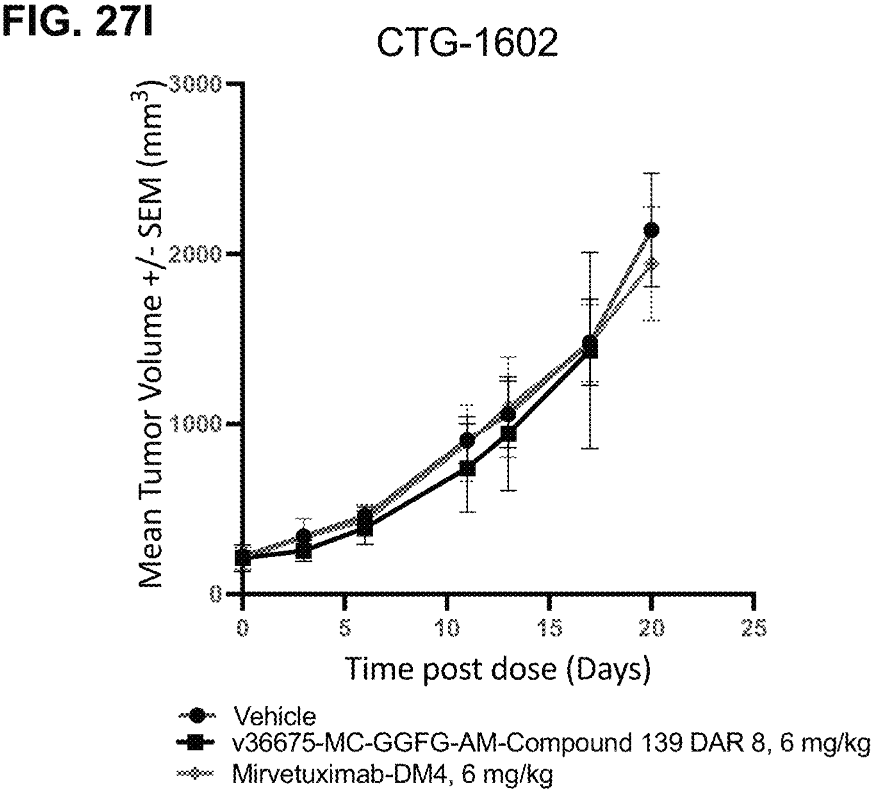

The results are shown in FIG. 26. Humanized variant v36675 conjugated to Compound 139 (v36789 ADC) showed a high degree of intracellular payload (Compound 139) delivery in the high FRα-expressing cell line IGROV-1. The intracellular payload delivery was time-dependent, showing an increase from 24 to 72 hours (FIG. 26A). The extracellular payload release from the ADC was much lower than intracellular concentrations, but was also time-dependent, also showing an increase from 24 to 72 hours (FIG. 26B). The non-targeting control palivizumab (v21995) conjugated to Compound 139 did not display intracellular payload delivery (FIG. 26A), and yielded low levels of extracellular payload release (FIG. 26B).

Example 40: In Vivo Efficacy Studies #3

The in vivo anti-tumor activity of humanized variant v36675 conjugated to Compound 139 at DAR 8 (v36789) was assessed in a number of patient derived xenograft (PDX) models of ovarian cancer as described below. The ADC v32603 (mirvetuximab-DM4 DAR 4) was assessed for comparison.

The ADCs, DARs, xenograft models and dosages employed in each xenograft study are summarized in Table 40.1. For each xenograft study, tumor volume and body weight of the animals were measured twice weekly.

TABLE 40.1

Study Parameters

| Xenograft Model | Cancer Type | FRα Expression | Test Article | DAR | Dose (mg/kg) |
|---|---|---|---|---|---|
| CTG-0703 | Ovarian | Strong | v36675-MC-GGFG-AM-Compound 139 | 8 | 6 |
| | | | v17716-DM4 (mirvetuximab-DM4) | 4 | 6 |
| CTG-1301 | Ovarian | Strong | v36675-MC-GGFG-AM-Compound 139 | 8 | 6 |
| | | | v17716-DM4 (mirvetuximab-DM4) | 4 | 6 |
| CTG-2025 | Ovarian | Moderate/ Strong | v36675-MC-GGFG-AM-Compound 139 | 8 | 6 |
| | | | v17716-DM4 (mirvetuximab-DM4) | 4 | 6 |
| CTG-3383 | Ovarian | Moderate | v36675-MC-GGFG-AM-Compound 139 | 8 | 6 |
| | | | v17716-DM4 (mirvetuximab-DM4) | 4 | 6 |
| CTG-0947 | Ovarian | Moderate/ Weak | v36675-MC-GGFG-AM-Compound 139 | 8 | 6 |
| | | | v17716-DM4 (mirvetuximab-DM4) | 4 | 6 |
| CTG-0958 | Ovarian | Moderate/ Weak | v36675-MC-GGFG-AM-Compound 139 | 8 | 6 |
| | | | v17716-DM4 (mirvetuximab-DM4) | 4 | 6 |
| CTG-3718 | Ovarian | Moderate/ Weak | v36675-MC-GGFG-AM-Compound 139 | 8 | 6 |
| | | | v17716-DM4 (mirvetuximab-DM4) | 4 | 6 |
| CTG-1703 | Ovarian | Weak | v36675-MC-GGFG-AM-Compound 139 | 8 | 6 |
| | | | v17716-DM4 (mirvetuximab-DM4) | 4 | 6 |
| CTG-1602 | Ovarian | Weak | v36675-MC-GGFG-AM-Compound 139 | 8 | 6 |
| | | | v17716-DM4 (mirvetuximab-DM4) | 4 | 6 |

Tumor fragments were implanted subcutaneously into female athymic Nude-Foxnlnu mice. When mean tumor volume reached -200-250 $mm^3$, the animals were assigned to groups (n=3 per group) and treated on study day 1 with a single IV dose of test article as shown in Table 40.1.

Results

The results are shown in FIG. 27A-I. In the CTG-0703, CTG-1301, CTG-2025 and CTG-3383 PDX models (FIG. 27A, B, C & D, respectively), when dosed at 6 mg/kg, v36675-MC-GGFG-AM-Compound 139 DAR8 and mirvetuximab-DM4 both resulted in strong inhibition of tumor growth.

In the CTG-0947 PDX model (FIG. 27E), when dosed at 6 mg/kg, v36675-MC-GGFG-AM-Compound 139 DAR8 resulted in strong inhibition of tumor growth, whereas mirvetuximab-DM4 resulted in moderate inhibition of tumor growth.

In the CTG-0958, CTG-3718 and CTG-1703 PDX models (FIG. 27F, G & H, respectively), when dosed at 6 mg/kg, v36675-MC-GGFG-AM-Compound 139 DAR8 resulted in strong inhibition of tumor growth, while mirvetuximab-DM4 was inactive.

In the CTG-1602 PDX model (FIG. 27I), when dosed at 6 mg/kg, both v36675-MC-GGFG-AM-Compound 139 DAR8 and mirvetuximab-DM4 were inactive.

Together, these data demonstrate that while both v36675-MC-GGFG-AM-Compound 139 DAR8 and mirvetuximab-DM4 are active in PDX models assessed to express strong levels of FRα, only v36675-MC-GGFG-AM-Compound 139 DAR8 was strongly active in PDX models expressing moderate/weak levels of FRα.

Example 41: Specificity Assessment of Anti-FRα Antibodies

The Retrogenix Cell Microarray Technology (Charles River Laboratories, Wilmington, MA) was used to screen for any specific off-target binding interactions of the following anti-FRα antibodies: humanized variant v36675 and affinity matured variant v35356.

Retrogenix Cell Microarray Technology identifies interactions both with cell surface receptors and secreted proteins by screening test ligands for binding against a library of cDNA clones representing over 6,300 human proteins. These proteins include plasma membrane monomers, heterodimers (formed by co-expression of the separate subunits) and secreted proteins (expressed with an inert cell membrane tether). Each cDNA is spotted in duplicate onto specialized slides and overlaid with HEK293 cells. These cells become reverse-transfected, resulting in clusters of cells each overexpressing a different, individual protein (or heterodimeric complex).

The study was carried out at Charles River Laboratories consisted of three phases: pre-screen, library screen and confirmation screen. A pre-screen was first performed to determine a suitable concentration of the test antibodies for the library screen (i.e. the concentration at which a low level of background binding to fixed untransfected HEK293 cells and strong binding to cells over-expressing FRα was observed). In the library screen phase, the test antibodies were screened as a pool against fixed HEK293 cells, individually expressing the -6,300 human proteins. In the confirmation screen phase, each library hit was re-expressed and re-tested with each test antibody individually using both fixed and live HEK293 cells.

In all three phases, slides were individually spotted with expression vectors encoding both ZsGreen1 (for assessing transfection efficiency) and (1) in the pre-screen phase: human FRα or control receptors (EGFR and CD20); (2) in the library screen phase: the above described protein library individually arrayed in duplicate across a number of microarray slides ("slide sets") with two replicate slides screened for each of the slide sets; or (3) in the confirmation screen phase: protein hits identified in the library screen or control receptors (EGFR and CD20) arrayed in duplicate.

In the pre-screen phase, each of the selected antibodies at 2, 5 or 20 μg/mL, control antibody (Rituximab biosimilar, which binds CD20) at 1 μg/mL or PBS were added to the slides after cell fixation. In the library screen phase, a pool of the two antibodies (variant v36675 at 20 μg/mL and variant v35356 at 5 μg/mL) was added to each slide after cell fixation. In the confirmation screen phase, slides were treated with individual antibodies: variant v36675 at 20 μg/mL, variant v35356 at 5 μg/mL or control antibody (Rituximab biosimilar) at 1 μg/mL, or no test article, in the absence of fixation (live cells; n=1 slide per treatment) and after cell fixation (n=2 slides per treatment).

Binding was detected using an AlexaFluor® 647 labelled anti-human IgG H+L (AF647 anti-hIgG H+L), followed by fluorescence imaging. Fluorescent images were analysed and quantitated (for transfection) using ImageQuant™ software (Version 8.2; GE Healthcare, Chicago, IL). A protein hit was defined as a duplicate spot showing an increased signal compared to background levels and was identified by visual inspection using the images gridded on the ImageQuant™ software. Hits were classified as strong, medium, weak or very weak by visual inspection by two experienced scientists based on the intensity of the duplicate spots.

Results

The majority of the initial hits identified in the library screen, with spot intensities ranging from very weak to strong, were confirmed to be hits in the confirmation screens for both variant v36675 and variant v35356. However, aside from hits that were reflective of the expected strong interactions with FRα, the other hits were deemed to be non-specific as these hits were either 1) also observed for the control antibody (Rituximab biosimilar) as they included FcgR receptors (signal due to Fc-domain mediated interactions) or 2) included various immunoglobulins that were recognized by the detection antibody.

Figure 28A:
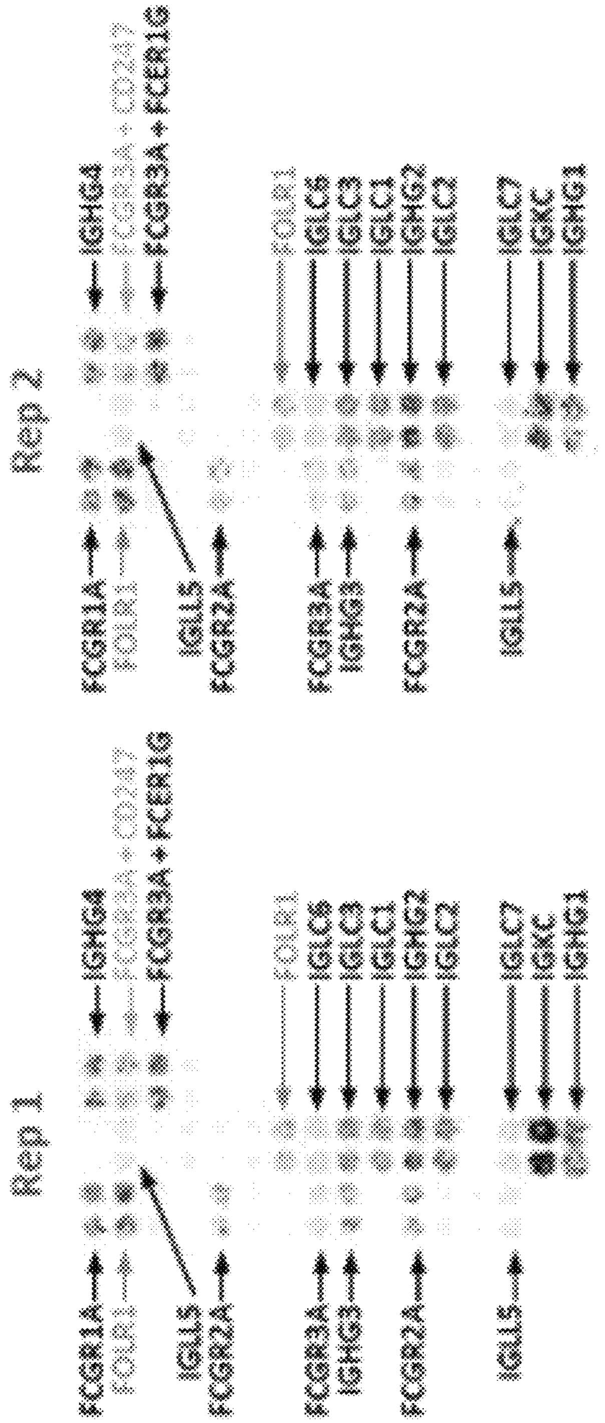
FIG. 28A & 28B show fixed cell confirmation screen images from a screen for specific off-target binding interactions using Retrogenix Cell Microarray Technology for the anti-FRα humanized antibody variant v36675 at 20 mg/mL (28A) and control antibody (rituximab biosimilar) at 1 mg/mL (28B).
Figure 28B:
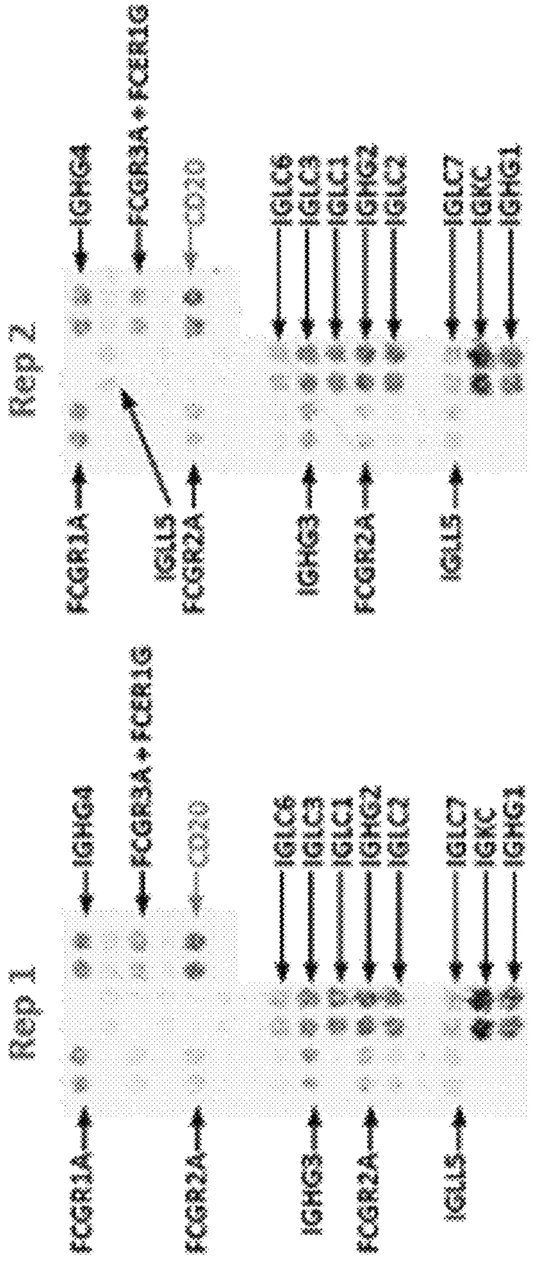

For the humanized variant v36675, no other interactions were identified (see FIG. 28), indicating the high specificity of variant v36675 for its primary target, FRα. The weak interaction observed for this variant with the heterodimer FCGR3A+CD247, which was not observed in the control (compare FIG. 28A & B), was not considered strong enough to be a hit.

For the affinity matured variant v35356, a signal of weak intensity was detected for the protein COL6A2 isoform $2C_2A$ in the library screen. This "hit" was confirmed in the fixed cell screen but not in the live cell screen, indicating that observed discrepancy was likely due to a fixation artifact.

Example 42: Competition Assay

Competition binding to the FRα target between the parental chimeric antibody v23924 and the anti-FRα antibodies mirvetuximab (v17716) and farletuzumab (v31629) was assessed in the moderate FRα-expressing tumor cell line H2110 by flow cytometry as follows.

Briefly, antibodies were fluorescently labelled with Alexa Fluor 647 (AF647; ThermoFisher Scientific, Waltham, MA; Cat. No. A20006) according to manufacturer's specifications prior to cell treatment. Tumor cells were seeded at 50,000 cells/well in V-bottom 96-well plates and treated with unlabelled antibodies for 1 hour at 4° C. to prevent internalization. Following incubation, cells were washed and fluorescently labelled antibodies were added for 1 hour at 4° C. Following incubation and washing, fluorescence was detected by flow cytometry on a BD LSRFortessa™ Cell Analyzer (BD Biosciences, Franklin Lake, NJ), with 1,000 minimum events collected per well. AF647/APC-A GeoMean (fluorescence signal geometric mean, proportional to anti-Human AF647 binding) in live cell population was used to calculate % competition binding relative to untreated control and data was plotted using GraphPad Prism Version 9 (GraphPad Software, San Diego, CA).

Results

Figure 29:
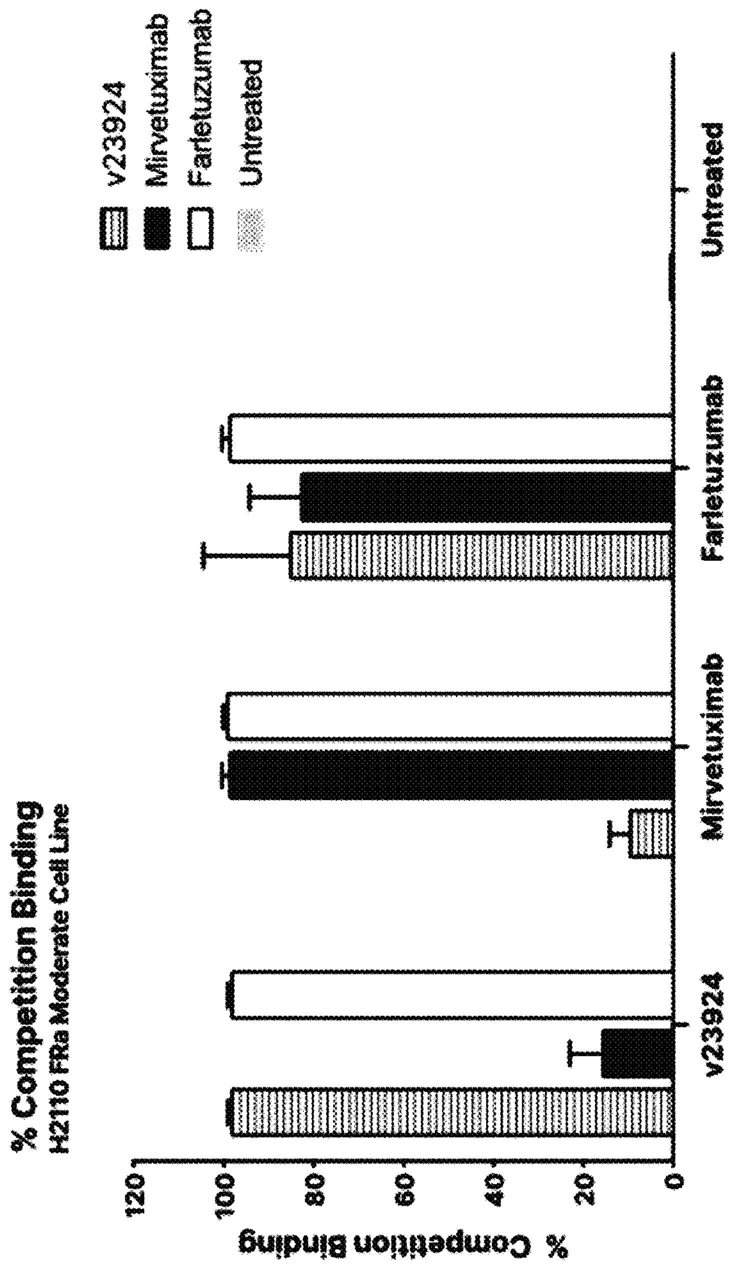
FIG. 29 shows competition binding between the chimeric anti-FRα antibody v23294 and the anti-FRα antibodies mirvetuximab and farletuzumab assessed in H2110 cells.

The results are shown in FIG. 29 and Table 42.1. Chimeric antibody v23924 was found to compete with farletuzumab for FRα binding in the H2110 cell line, yielding close to 100% competition binding in both binding orientations (primary antibody farletuzumab and secondary fluorescently labelled antibody variant v23924, and primary antibody variant v23924 and secondary fluorescently labelled antibody farletuzumab). Chimeric antibody v23924 was found not to compete for FRα binding with mirvetuximab in the H2110 cell line. These antibodies showed low levels of % competition in both binding orientations. In contrast, farletuzumab showed competition binding with mirvetuximab. Chimeric antibody v23924 thus demonstrates a binding profile that is distinct from both mirvetuximab and farletuzumab.

TABLE 42.1

Competition Binding with Farletuzumab and Mirvetuximab on H2110 Cells

| | % Competition Binding | | | | | | | |
|---|---|---|---|---|---|---|---|---|
| | v23924 | | Mirvetuximab | | Farletuzumab | | Untreated | |
| v23924 | 98 | 99 | 11 | 21 | 99 | 98 | 0 | 0 |
| Mirvetuximab | 13 | 7 | 100 | 98 | 99 | 100 | 0 | 0 |
| Farletuzumab | 99 | 72 | 91 | 75 | 98 | 100 | 0 | 0 |
| Untreated | 1 | 1 | 0 | 0 | 0 | 0 | 0 | 0 |

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Modifications of the specific embodiments described herein that would be apparent to those skilled in the art are intended to be included within the scope of the following claims.

Sequence Tables

TABLE A

Clone Numbers for Variants

| Variant | Clone Numbers H1 | H2 | L1 | L2 |
|---|---|---|---|---|
| 23924 | 18894 | 18894 | 18915 | 18915 |
| 30618 | 18908 | 18901 | 18915 | 18915 |
| 30384 | 22046 | 22057 | 22054 | 22054 |
| 30389 | 22047 | 22058 | 22054 | 22054 |
| 30394 | 22048 | 22059 | 22054 | 22054 |

TABLE A-continued

Clone Numbers for Variants

| Variant | Clone Numbers H1 | H2 | L1 | L2 |
|---|---|---|---|---|
| 30399 | 22049 | 22060 | 22054 | 22054 |
| 31422 | 22874 | 22874 | 22054 | 22054 |
| 31423 | 22875 | 22875 | 22054 | 22054 |
| 31424 | 22876 | 22876 | 22054 | 22054 |
| 31425 | 22877 | 22877 | 22054 | 22054 |
| 31426 | 22878 | 22878 | 22054 | 22054 |
| 35305 | 26434 | 26434 | 26449 | 26449 |
| 35342 | 26443 | 26443 | 26450 | 26450 |
| 35347 | 26445 | 26445 | 27276 | 27276 |
| 35348 | 26445 | 26445 | 26448 | 26448 |
| 35350 | 26445 | 26445 | 26450 | 26450 |
| 35354 | 26446 | 26446 | 26450 | 26450 |
| 35356 | 26447 | 26447 | 26448 | 26448 |
| 35358 | 26447 | 26447 | 26450 | 26450 |
| 36167 | 27272 | 27272 | 27274 | 27274 |
| 36168 | 27273 | 27273 | 27274 | 27274 |
| 36675 | 27275 | 27275 | 22054 | 22054 |

TABLE B

Clone Sequences

| Clone ID | Region | Sequence | SEQ ID NO |
|---|---|---|---|
| 18894 | Full | QSVKESEGGLFKPTDTLTLTCTVSGFSLSS<br>YGVSWVRQAPGNGLEWIGAVNSGGSAYYAN<br>WAKSRSTITRNTNLFTVTLKMTSLAVADTA<br>TYFCARSGSGYPMDYLAIWGPGTLVTVSSA<br>STKGPSVFPLAPSSKSTSGGTAALGCLVKD<br>YFPEPVTVSWNSGALTSGVHTFPAVLQSSG<br>LYSLSSVVTVPSSSLGTQTYICNVNHKPSN<br>TKVDKKVEPKSCDKTHTCPPCPAPELLGGP<br>SVFLFPPKPKDTLMISRTPEVTCVVVDVSH<br>EDPEVKFNWYVDGVEVHNAKTKPREEQYNS<br>TYRVVSVLTVLHQDWLNGKEYKCKVSNKAL<br>PAPIEKTISKAKGQPREPQVYTLPPSRDEL<br>TKNQVSLTCLVKGFYPSDIAVEWESNGQPE<br>NNYKTTPPVLDSDGSFFLYSKLTVDKSRWQ<br>QGNVFSCSVMHEALHNHYTQKSLSLSPG | 17 |
| | Full | CAGAGCGTGAAGGAGTCCGAGGGCGGCCTG<br>TTCAAGCCCACCGACACACTGACCCTGACA<br>TGCACCGTGTCTGGCTTTAGCCTGAGCTCC<br>TACGGCGTGTCTTGGGTGCGGCAGGCCCCC<br>GGAAACGGACTGGAGTGGATCGGAGCCGTG<br>AACAGCGGCGGCTCTGCCTACTATGCCAAC<br>TGGGCCAAGTCCCGGTCTACAATCACCAGA<br>AACACAAATCTGTTCACAGTGACCCTGAAG<br>ATGACCTCCCTGGCCGTGGCAGACACAGCA<br>ACCTATTTTTGTGCAAGGAGCGGCTCCGGA<br>TACCCAATGGATTATCTGGCCATCTGGGGC<br>CCTGGCACACTGGTGACCGTGTCTAGCGCT<br>AGCACTAAGGGGCCTTCCGTGTTTCCACTG<br>GCTCCCTCTAGTAAATCCACCTCTGGAGGC<br>ACAGCTGCACTGGGATGTCTGGTGAAGGAT<br>TACTTCCCTGAACCAGTCACAGTGAGTTGG<br>AACTCAGGGGCTCTGACAAGTGGAGTCCAT<br>ACTTTTCCCGCAGTGCTGCAGTCAAGCGGA<br>CTGTACTCCCTGTCCTCTGTGGTCACCGTG<br>CCTAGTTCAAGCCTGGGCACCCAGACATAT<br>ATCTGCAACGTGAATCACAAGCCATCAAAT<br>ACAAAAGTCGACAAGAAAGTGGAGCCCAAG<br>AGCTGTGATAAAACTCATACCTGCCCACCT<br>TGTCCGGCGCCAGAACTGCTGGGAGGACCA<br>AGCGTGTTCCTGTTTCCACCCAAGCCTAAA<br>GACACCCTGATGATTTCCCGGACTCCTGAG<br>GTCACCTGCGTGGTCGTGGACGTGTCTCAC<br>GAGGACCCCGAAGTCAAGTTCAACTGGTAC<br>GTGGATGGCGTCGAAGTGCATAATGCCAAG | 18 |

TABLE B-continued

Clone Sequences

| Clone ID | Region | Sequence | SEQ ID NO |
|---|---|---|---|
| | | ACCAAACCCCGGGAGGAACAGTACAACTCT ACCTATAGAGTCGTGAGTGTCCTGACAGTG CTGCACCAGGACTGGCTGAATGGGAAGGAG TATAAGTGTAAAGTGAGCAACAAAGCCCTG CCCGCCCCAATCGAAAAAACAATCTCTAAA GCAAAAGGACAGCCTCGCGAACCACAGGTG TACACTCTGCCTCCATCTCGGGACGAGCTG ACTAAGAACCAGGTCAGTCTGACCTGTCTG GTGAAAGGATTCTATCCCAGCGATATCGCT GTGGAGTGGGAATCCAATGGCCAGCCTGAG AACAATTACAAGACCACACCCCCTGTGCTG GACTCTGATGGCAGTTTCTTTCTGTATAGT AAGCTGACCGTCGATAAATCACGATGGCAG CAGGGGAACGTGTTCAGCTGTTCAGTGATG CACGAAGCCCTGCACAACCATTACACCCAG AAGAGCCTGAGCCTGTCTCCCGGC | |
| | VH | QSVKESEGGLFKPTDTLTLTCTVSGFSLSS YGVSWVRQAPGNGLEWIGAVNSGGSAYYAN WAKSRSTITRNTNLFTVTLKMTSLAVADTA TYFCARSGSGYPMDYLAIWGPGTLVTVSS | 19 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYANWAKS | 27 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 18901 | Full | QSVKESEGGLFKPTDTLTLTCTVSGFSLSS YGVSWVRQAPGNGLEWIGAVNSGGSAYYAN WAKSRSTITRNTNLFTVTLKMTSLAVADTA TYFCARSGSGYPMDYLAIWGPGTLVTVSSA STKGPSVFPLAPSSKSTSGGTAALGCLVKD YFPEPVTVSWNSGALTSGVHTFPAVLQSSG LYSLSSVVTVPSSSLGTQTYICNVNHKPSN | 33 |

TABLE B-continued

Clone Sequences

| Clone ID | Region | Sequence | SEQ ID NO |
|---|---|---|---|
| | | TKVDKKVEPKSCDKTHTCPPCPAPELLGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL PAPIEKTISKAKGQPREPQVYVYPPSRDEL TKNQVSLTCLVKGFYPSDIAVEWESNGQPE NNYKTTPPVLDSDGSFALVSKLTVDKSRWQ QGNVFSCSVMHEALHNHYTQKSLSLSPG | |
| | Full | CAGAGCGTGAAGGAGTCCGAGGGCGGCCTG TTCAAGCCCACCGACACACTGACCCTGACA TGCACCGTGTCTGGCTTTAGCCTGAGCTCC TACGGCGTGTCTTGGGTGCGGCAGGCCCCC GGAAACGGACTGGAGTGGATCGGAGCCGTG AACAGCGGCGGCTCTGCCTACTATGCCAAC TGGGCCAAGTCCCGGTCTACAATCACCAGA AACACAAATCTGTTCACAGTGACCCTGAAG ATGACCTCCCTGGCCGTGGCAGACACAGCA ACCTATTTTTGTGCAAGGAGCGGCTCCGGA TACCCAATGGATTATCTGGCCATCTGGGGC CCTGGCACACTGGTGACCGTGTCTAGCGCT AGCACTAAGGGGCCTTCCGTGTTTCCACTG GCTCCCTCTAGTAAATCCACCTCTGGAGGC ACAGCTGCACTGGGATGTCTGGTGAAGGAT TACTTCCCTGAACCAGTCACAGTGAGTTGG AACTCAGGGGCTCTGACAAGTGGAGTCCAT ACTTTTCCCGCAGTGCTGCAGTCAAGCGGA CTGTACTCCCTGTCCTCTGTGGTCACCGTG CCTAGTTCAAGCCTGGGCACCCAGACATAT ATCTGCAACGTGAATCACAAGCCATCAAAT ACAAAAGTCGACAAGAAAGTGGAGCCCAAG AGCTGTGATAAAACTCATACCTGCCCACCT TGTCCGGCGCCAGAACTGCTGGGAGGACCA AGCGTGTTCCTGTTTCCACCCAAGCCTAAA GACACCCTGATGATTTCCCGGACTCCTGAG GTCACCTGCGTGGTCGTGGACGTGTCTCAC GAGGACCCCGAAGTCAAGTTCAACTGGTAC GTGGATGGCGTCGAAGTGCATAATGCCAAG ACCAAACCCCGGGAGGAACAGTACAACTCT ACCTATAGAGTCGTGAGTGTCCTGACAGTG CTGCACCAGGACTGGCTGAATGGGAAGGAG TATAAGTGTAAAGTGAGCAACAAAGCCCTG CCCGCCCCAATCGAAAAAACAATCTCTAAA GCAAAAGGACAGCCTCGCGAACCACAGGTC TACGTCTACCCCCCATCAAGAGATGAACTG ACAAAAAATCAGGTCTCTCTGACATGCCTG GTCAAAGGATTCTACCCTTCCGACATCGCC GTGGAGTGGGAAAGTAACGGCCAGCCCGAG AACAATTACAAGACCACACCCCCTGTCCTG GACTCTGATGGGAGTTTCGCTCTGGTGTCA AAGCTGACCGTCGATAAAAGCCGGTGGCAG CAGGGCAATGTGTTTAGCTGCTCCGTCATG CACGAAGCCCTGCACAATCACTACACACAG AAGTCCCTGAGCCTGAGCCCTGGC | 34 |
| | VH | QSVKESEGGLFKPTDTLTLTCTVSGFSLSS YGVSWVRQAPGNGLEWIGAVNSGGSAYYAN WAKSRSTITRNTNLFTVTLKMTSLAVADTA TYFCARSGSGYPMDYLAIWGPGTLVTVSS | 19 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |

TABLE B-continued

Clone Sequences

| Clone ID | Region | Sequence | SEQ ID NO |
|---|---|---|---|
| | Chothia CDR3 | SGSGYPMDYLAI | 25 |
| | Kabat CDR1 | SYGVS | 26 |
| | Kabat CDR2 | AVNSGGSAYYANWAKS | 27 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 18908 | Full | QSVKESEGGLFKPTDTLTLTCTVSGFSLSS<br>YGVSWVRQAPGNGLEWIGAVNSGGSAYYAN<br>WAKSRSTITRNTNLFTVTLKMTSLAVADTA<br>TYFCARSGSGYPMDYLAIWGPGTLVTVSSA<br>STKGPSVFPLAPSSKSTSGGTAALGCLVKD<br>YFPEPVTVSWNSGALTSGVHTFPAVLQSSG<br>LYSLSSVVTVPSSSLGTQTYICNVNHKPSN<br>TKVDKKVEPKSCDKTHTCPPCPAPELLGGP<br>SVFLFPPKPKDTLMISRTPEVTCVVVDVSH<br>EDPEVKFNWYVDGVEVHNAKTKPREEQYNS<br>TYRVVSVLTVLHQDWLNGKEYKCKVSNKAL<br>PAPIEKTISKAKGQPREPQVYVLPPSRDEL<br>TKNQVSLLCLVKGFYPSDIAVEWESNGQPE<br>NNYLTWPPVLDSDGSFFLYSKLTVDKSRWQ<br>QGNVFSCSVMHEALHNHYTQKSLSLSPG | 35 |
| | Full | CAGAGCGTGAAGGAGTCCGAGGGCGGCCT<br>GTTCAAGCCCACCGACACA<br>CTGACCCTGACATG<br>CACCGTGTCTGGCTTTAGCCTGAGCTCCTA<br>CGGCGTGTCTTGGGTGCGGCAGGCCCCCGG<br>AAACGGACTGGAGTGGATCGGAGCCGTGAA<br>CAGCGGCGGCTCTGCCTACTATGCCAACTG<br>GGCCAAGTCCCGGTCTACAATCACCAGAAA<br>CACAAATCTGTTCACAGTGACCCTGAAGAT<br>GACCTCCCTGGCCGTGGCAGACACAGCAAC<br>CTATTTTTGTGCAAGGAGCGGCTCCGGATA<br>CCCAATGGATTATCTGGCCATCTGGGGCCC<br>TGGCACACTGGTGACCGTGTCTAGCGCTAG<br>CACTAAGGGGCCTTCCGTGTTTCCACTGGC<br>TCCCTCTAGTAAATCCACCTCTGGAGGCAC<br>AGCTGCACTGGGATGTCTGGTGAAGGATTA<br>CTTCCCTGAACCAGTCACAGTGAGTTGGAA<br>CTCAGGGGCTCTGACAAGTGGAGTCCATAC<br>TTTTCCCGCAGTGCTGCAGTCAAGCGGACT<br>GTACTCCCTGTCCTCTGTGGTCACCGTGCC<br>TAGTTCAAGCCTGGGCACCCAGACATATAT<br>CTGCAACGTGAATCACAAGCCATCAAATAC<br>AAAAGTCGACAAGAAAGTGGAGCCCAAGAG<br>CTGTGATAAAACTCATACCTGCCCACCTTG<br>TCCGGCGCCAGAACTGCTGGGAGGACCAAG<br>CGTGTTCCTGTTTCCACCCAAGCCTAAAGA<br>CACCCTGATGATTTCCCGGACTCCTGAGGT | 36 |
| | | CACCTGCGTGGTCGTGGACGTGTCTCACGA<br>GGACCCCGAAGTCAAGTTCAACTGGTACGT<br>GGATGGCGTCGAAGTGCATAATGCCAAGAC<br>CAAACCCCGGGAGGAACAGTACAACTCTAC<br>CTATAGAGTCGTGAGTGTCCTGACAGTGCT<br>GCACCAGGACTGGCTGAATGGGAAGGAGTA<br>TAAGTGTAAAGTGAGCAACAAAGCCCTGCC<br>CGCCCCAATCGAAAAAACAATCTCTAAAGC<br>AAAAGGACAGCCTCGCGAACCACAGGTCTA<br>CGTGCTGCCCCCTAGCCGCGACGAACTGAC<br>TAAAAATCAGGTCTCTCTGCTGTGTCTGGT<br>CAAAGGATTCTACCCTTCCGACATCGCCGT<br>GGAGTGGGAAAGTAACGGCCAGCCCGAGAA<br>CAATTACCTGACCTGGCCCCCTGTGCTGGA<br>CTCTGATGGGAGTTTCTTTCTGTATTCAAA<br>GCTGACAGTCGATAAAAGCCGGTGGCAGCA<br>GGGCAATGTGTTCAGCTGCTCCGTCATGCA<br>CGAAGCACTGCACAACCATTACACTCAGAA<br>GTCCCTGTCCCTGTCACCTGGC | |
| | VH | QSVKESEGGLFKPTDTLTLTCTVSGFSLSS<br>YGVSWVRQAPGNGLEWIGAVNSGGSAYYAN<br>WAKSRSTITRNTNLFTVTLKMTSLAVADTA<br>TYFCARSGSGYPMDYLAIWGPGTLVTVSS | 19 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYANWAKS | 27 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 18915 | Full | AYDMTQTPASVEVAVGGTVTIKCQASQSIG<br>DWLAWYQQKPGQPPRLLIYEASTLASGVPS<br>RFSGSGSGTQFTLTISGVECADAATYYCQQ<br>GYGRSNVDNIFGGGTEVVVKRTVAAPSVFI | 37 |

TABLE B-continued

Clone Sequences

| Clone ID | Region | Sequence | SEQ ID NO |
|---|---|---|---|
| | | FPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | |
| | Full | GCCTACGACATGACCCAGACACCCGCCTCCGTGGAGGTGGCAGTGGGAGGAACCGTGACAATCAAGTGCCAGGCCAGCCAGTCCATCGGCGATTGGCTGGCCTGGTACCAGCAGAAGCCTGGACAGCCACCTCGGCTGCTGATCTATGAGGCCTCTACCCTGGCCAGCGGAGTGCCATCCAGATTCTCTGGCAGCGGCTCCGGCACACAGTTTACCCTGACAATCTCTGGAGTGGAGTGCGCAGACGCAGCAACCTACTATTGTCAGCAGGGCTATGGCAGGAGCAACGTGGATAATATCTTTGGAGGAGGAACCGAGGTGGTGGTGAAGAGGACAGTGGCGGCGCCCAGTGTCTTCATTTTCCCCCCTAGCGACGAACAGCTGAAGTCTGGGACAGCCAGTGTGGTCTGTCTGCTGAACAACTTCTACCCTAGAGAGGCTAAAGTGCAGTGGAAGGTCGATAACGCACTGCAGTCCGGAAATTCTCAGGAGAGTGTGACTGAACAGGACTCAAAAGATAGCACCTATTCCCTGTCAAGCACACTGACTCTGAGCAAGGCCGACTACGAGAAGCATAAAGTGTATGCTTGTGAAGTCACCCACCAGGGGCTGAGTTCACCAGTCACAAAATCATTCAACAGAGGGGAGTGC | 38 |
| | VL | AYDMTQTPASVEVAVGGTVTIKCQASQSIGDWLAWYQQKPGQPPRLLIYEASTLASGVPSRFSGSGSGTQFTLTISGVECADAATYYCQQGYGRSNVDNIFGGGTEVVVK | 39 |
| | IMGT CDR1 | QSIGDW | 40 |
| | IMGT CDR2 | EAS | 41 |
| | IMGT CDR3 | QQGYGRSNVDNI | 42 |
| | Chothia CDR1 | QASQSIGDWLA | 43 |
| | Chothia CDR2 | EASTLAS | 44 |
| | Chothia CDR3 | QQGYGRSNVDNI | 42 |
| | Kabat CDR1 | QASQSIGDWLA | 43 |
| | Kabat CDR2 | EASTLAS | 44 |
| | Kabat CDR3 | QQGYGRSNVDNI | 42 |
| | Contact CDR1 | GDWLAWY | 45 |
| | Contact CDR2 | LLIYEASTLA | 46 |
| | Contact CDR3 | QQGYGRSNVDN | 47 |
| | AbM CDR1 | QASQSIGDWLA | 43 |
| | AbM CDR2 | EASTLAS | 44 |
| | AbM CDR3 | QQGYGRSNVDNI | 42 |
| 22046 | Full | EVQLLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVYPPSRDELTKNQVSLTCLVKGFYPSDIAVEWESNGQPENNYKTTPPVLDSDGSFALVSKLTVDKSRWQQGNVFSCSVMHEALHNHYTQKSLSLSPG | 48 |
| | Full | GAGGTGCAGCTGCTGGAGAGCGGAGGAGGACTGGTGCAGCCAGGAGGCAGCCTGCGGCTGTCCTGCGCCGTGAGCGGCTTTTCCCTGAGCTCCTACGGCGTGTCCTGGGTGAGACAGGCCCCCGGCAAGGGACTGGAGTGGATCGGAGCCGTGAACTCTGGCGGCAGCGCCTACTATGCCGACTCTGTGAAGGGCCGGTCCACCATCTCTAGAGATAACTCTAAGAATACAGTGTATCTGCAGATGAATAGCCTGAGGGCCGAGGACACAGCCGTGTACTATTGTGCACGCTCCGGCTCTGGCTACCCCATGGATTATCTGGCCATCTGGGGACAGGGCACCCTGGTGACAGTGTCTAGCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCGCCAGAACTGCTGGGAGGACCAAGCGTGTTCCTGTTTCCACCCAAGCCTAAAGACACCCTGATGATTTCCCGGACTCCTGAGGTCACCTGCGTGGTCGTGGACGTGTCTCACGAGGACCCCGAAGTCAAGTTCAACTGGTACGTGGATGGCGTCGAAGTGCATAATGCCAAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTCTACGTCTACCCCCCATCAAGAGATGAACTGACAAAAAATCAGGTCTCTCTGACATGCCTGGTCAAAGGATTCTACCCTTCCGACATCGCCGTGGAGTGGGAAAGTAACGGCCAGCCCGAGAACAATTACAAGACCACACCCCCTGTCCTGGACTCTGATGGGAGTTTCGCTCTGGTGTCAAAGCTGACCGTCGATAAAAGCCGGTGGCAGCAGGGCAATGTGTTTAGCTGCTCCGTCATGCACGAAGCCCTGCACAATCACTACACACAGAAGTCCCTGAGCCTGAGCCCTGGC | 49 |
| | VH | EVQLLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSS | 50 |
| | IMGT CDR1 | GFSLSSYG | 20 |

TABLE B-continued

Clone Sequences

| Clone ID | Region | Sequence | SEQ ID NO |
|---|---|---|---|
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22047 | Full | EVQVLESGGGLVQPGGSLRLSCAVSGFSLS SYGVSWVRQAPGKGLEWIGAVNSGGSAYYA DSVKGRSTISRDNSKNTVYLQMNSLRAEDT AVYYCARSGSGYPMDYLAIWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYVYPPSRDE LTKNQVSLTCLVKGFYPSDIAVEWESNGQP ENNYKTTPPVLDSDGSFALVS KLTVDKSRWQQGNVFSCSVMHEALHNHYTQ KSLSLSPG | 52 |
| | Full | GAGGTGCAGGTGCTGGAGAGCGGAGGAGGA CTGGTGCAGCCAGGAGGCAGCCTGCGGCTG TCCTGCGCCGTGAGCGGCTTTTCCCTGAGC TCCTACGGCGTGTCCTGGGTGAGACAGGCC CCCGGCAAGGGACTGGAGTGGATCGGAGCC GTGAACTCTGGCGGCAGCGCCTACTATGCC GACTCTGTGAAGGGCCGGTCCACCATCTCT AGAGATAACTCTAAGAATACAGTGTATCTG CAGATGAATAGCCTGAGGGCCGAGGACACA GCCGTGTACTATTGTGCACGCTCCGGCTCT GGCTACCCCATGGATTATCTGGCCATCTGG GGACAGGGCACCCTGGTGACAGTGTCTAGC GCTAGCACTAAGGGGCCTTCCGTGTTTCCA CTGGCTCCCTCTAGTAAATCCACCTCTGGA GGCACAGCTGCACTGGGATGTCTGGTGAAG GATTACTTCCCTGAACCAGTCACAGTGAGT TGGAACTCAGGGGCTCTGACAAGTGGAGTC CATACTTTTCCCGCAGTGCTGCAGTCAAGC GGACTGTACTCCCTGTCCTCTGTGGTCACC GTGCCTAGTTCAAGCCTGGGCACCCAGACA TATATCTGCAACGTGAATCACAAGCCATCA AATACAAAAGTCGACAAGAAAGTGGAGCCC AAGAGCTGTGATAAAACTCATACCTGCCCA CCTTGTCCGGCGCCAGAACTGCTGGGAGGA CCAAGCGTGTTCCTGTTTCCACCCAAGCCT AAAGACACCCTGATGATTTCCCGGACTCCT GAGGTCACCTGCGTGGTCGTGGACGTGTCT CACGAGGACCCCGAAGTCAAGTTCAACTGG TACGTGGATGGCGTCGAAGTGCATAATGCC AAGACCAAACCCCGGGAGGAACAGTACAAC TCTACCTATAGAGTCGTGAGTGTCCTGACA GTGCTGCACCAGGACTGGCTGAATGGGAAG GAGTATAAGTGTAAAGTGAGCAACAAAGCC CTGCCCGCCCCAATCGAAAAAACAATCTCT AAAGCAAAAGGACAGCCTCGCGAACCACAG GTCTACGTCTACCCCCCATCAAGAGATGAA CTGACAAAAAATCAGGTCTCTCTGACATGC CTGGTCAAAGGATTCTACCCTTCCGACATC GCCGTGGAGTGGGAAAGTAACGGCCAGCCC GAGAACAATTACAAGACCACACCCCCTGTC CTGGACTCTGATGGGAGTTTCGCTCTGGTG TCAAAGCTGACCGTCGATAAAAGCCGGTGG CAGCAGGGCAATGTGTTTAGCTGCTCCGTC ATGCACGAAGCCCTGCACAATCACTACACA CAGAAGTCCCTGAGCCTGAGCCCTGGC | 53 |
| | VH | EVQVLESGGGLVQPGGSLRLSCAVSGFSLS SYGVSWVRQAPGKGLEWIGAVNSGGSAYYA DSVKGRSTISRDNSKNTVYLQMNSLRAEDT AVYYCARSGSGYPMDYLAIWGQGTLVTVSS | 54 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |

TABLE B-continued

| Clone Sequences | | | |
|---|---|---|---|
| Clone ID | Region | Sequence | SEQ ID NO |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22048 | Full | EVQLLESGGGLVQPGGSLRLSCAVSGFSLS SYGVSWVRQAPGKGLEWIGAVNSGGSAYYA DWAKGRSTISRDNSKNTVYLQMNSLRAEDT AVYYCARSGSGYPMDYLAIWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYVYPPSRDE LTKNQVSLTCLVKGFYPSDIAVEWESNGQ PENNYKTTPPVLDSDGSFALVS KLTVDKSRWQQGNVFSCSVMHEALHNHYTQ KSLSLSPG | 55 |
| | Full | GAGGTGCAGCTGCTGGAGTCCGGAGGAGGA CTGGTGCAGCCAGGAGGCAGCCTGCGGCTG TCCTGCGCCGTGAGCGGCTTTTCCCTGAGC TCCTACGGCGTGTCTTGGGTGAGACAGGCC CCCGGCAAGGGACTGGAGTGGATCGGAGCC GTGAACTCTGGAGGCAGCGCCTACTATGCA GACTGGGCAAAGGGCCGGTCCACCATCTCT AGAGATAACTCTAAGAATACAGTGTATCTG CAGATGAATAGCCTGAGGGCCGAGGACACA GCCGTGTACTATTGTGCACGCTCCGGCTCT GGCTACCCCATGGATTATCTGGCCATCTGG GGACAGGGCACCCTGGTGACAGTGTCTAGC GCTAGCACTAAGGGGCCTTCCGTGTTTCCA CTGGCTCCCTCTAGTAAATCCACCTCTGGA GGCACAGCTGCACTGGGATGTCTGGTGAAG GATTACTTCCCTGAACCAGTCACAGTGAGT TGGAACTCAGGGGCTCTGACAAGTGGAGTC CATACTTTTCCCGCAGTGCTGCAGTCAAGC GGACTGTACTCCCTGTCCTCTGTGGTCACC GTGCCTAGTTCAAGCCTGGGCACCCAGACA TATATCTGCAACGTGAATCACAAGCCATCA AATACAAAAGTCGACAAGAAAGTGGAGCCC AAGAGCTGTGATAAAACTCATACCTGCCCA CCTTGTCCGGCGCCAGAACTGCTGGGAGGA CCAAGCGTGTTCCTGTTTCCACCCAAGCCT AAAGACACCCTGATGATTTCCCGGACTCCT GAGGTCACCTGCGTGGTCGTGGACGTGTCT CACGAGGACCCCGAAGTCAAGTTCAACTGG TACGTGGATGGCGTCGAAGTGCATAATGCC AAGACCAAACCCCGGGAGGAACAGTACAAC TCTACCTATAGAGTCGTGAGTGTCCTGACA GTGCTGCACCAGGACTGGCTGAATGGGAAG GAGTATAAGTGTAAAGTGAGCAACAAAGCC CTGCCCGCCCCAATCGAAAAAACAATCTCT AAAGCAAAAGGACAGCCTCGCGAACCACAG GTCTACGTCTACCCCCCATCAAGAGATGAA CTGACAAAAAATCAGGTCTCTCTGACATGC CTGGTCAAAGGATTCTACCCTTCCGACATC GCCGTGGAGTGGGAAAGTAACGGCCAGCCC GAGAACAATTACAAGACCACACCCCCTGTC CTGGACTCTGATGGGAGTTTCGCTCTGGTG TCAAAGCTGACCGTCGATAAAAGCCGGTGG CAGCAGGGCAATGTGTTTAGCTGCTCCGTC ATGCACGAAGCCCTGCACAATCACTACACA CAGAAGTCCCTGAGCCTGAGCCCTGGC | 56 |

TABLE B-continued

| Clone Sequences | | | |
|---|---|---|---|
| Clone ID | Region | Sequence | SEQ ID NO |
| | VH | EVQLLESGGGLVQPGGSLRLSCAVSGFSLS SYGVSWVRQAPGKGLEWIGAVNSGGSAYYA DWAKGRSTISRDNSKNTVYLQMNSLRAEDT AVYYCARSGSGYPMDYLAIWGQGTLVTVSS | 57 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADWAKG | 58 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22049 | Full | EVQVLESGGGLVQPGGSLRLSCAVSGFSLS SYGVSWVRQAPGKGLEWIGAVNSGGSAYYA DWAKGRSTISRDNSKNTVYLQMNSLRAEDT AVYYCARSGSGYPMDYLAIWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYVYPPSRDE LTKNQVSLTCLVKGFYPSDIAVEWESNGQP ENNYKTTPPVLDSDGSFALVSKLTVDKSRW QQGNVFSCSVMHEALHNHYTQKSLSLSPG | 59 |
| | Full | GAGGTGCAGGTGCTGGAGTCCG GAGGAGGACTGGTGCAGCCAGGAGGCAGCC TGCGGCTGTCCTGCGCCGTGAGCGGCTTTT CCCTGAGCTCCTACGGCGTGTCTTGGGTGA GACAGGCCCCCGGCAAGGGACTGGAGTGGA TCGGAGCCGTGAACTCTGGAGGCAGCGCCT ACTATGCAGACTGGGCAAAGGGCCGGTCCA | 60 |

TABLE B-continued

Clone Sequences

| Clone ID | Region | Sequence | SEQ ID NO |
|---|---|---|---|
| | | CCATCTCTAGAGATAACTCTAAGAATACAGTGTATCTGCAGATGAATAGCCTGAGGGCCGAGGACACAGCCGTGTACTATTGTGCACGCTCCGGCTCTGGCTACCCCATGGATTATCTGGCCATCTGGGGACAGGGCACCCTGGTGACAGTGTCTAGCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCGCCAGAACTGCTGGGAGGACCAAGCGTGTTCCTGTTTCCACCCAAGCCTAAAGACACCCTGATGATTTCCCGGACTCCTGAGGTCACCTGCGTGGTCGTGGACGTGTCTCACGAGGACCCCGAAGTCAAGTTCAACTGGTACGTGGATGGCGTCGAAGTGCATAATGCCAAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTCTACGTCTACCCCCCATCAAGAGATGAACTGACAAAAAATCAGGTCTCTCTGACATGCCTGGTCAAAGGATTCTACCCTTCCGACATCGCCGTGGAGTGGGAAAGTAACGGCCAGCCCGAGAACAATTACAAGACCACACCCCCTGTCCTGGACTCTGATGGGAGTTTCGCTCTGGTGTCAAAGCTGACCGTCGATAAAAGCCGGTGGCAGCAGGGCAATGTGTTTAGCTGCTCCGTCATGCACGAAGCCCTGCACAATCACTACACACAGAAGTCCCTGAGCCTGAGCCCTGGC | |
| | VH | EVQVLESGGGLVQPGGSLRLSCAVSGFSLSSYGVSWVRQAPGKGLEWIGAVNSGGSAYYADWAKGRSTISRDNSKNTVYLQMNSLRAEDTAVYYCARSGSGYPMDYLAIWGQGTLVTVSS | 61 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADWAKG | 58 |
| | Kabat CDR3 | SGSGYPMDYLAI | 25 |
| | Contact CDR1 | SSYGVS | 28 |

TABLE B-continued

Clone Sequences

| Clone ID | Region | Sequence | SEQ ID NO |
|---|---|---|---|
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22054 | Full | DYQMTQSPSSVSASVGDRVTITCRASQSIGDWLAWYQQKPGKAPKLLIYEASTLASGVPSRFSGSGSGTDFTLTISSVQPEDAATYYCQQGYGRSNVDNIFGGGTKVEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 62 |
| | Full | GACTACCAGATGACCCAGTCTCCAAGCTCCGTGTCCGCCTCTGTGGGCGACAGGGTGACCATCACATGCAGAGCCAGCCAGTCCATCGGCGATTGGCTGGCCTGGTATCAGCAGAAGCCCGGCAAGGCCCCTAAGCTGCTGATCTATGAGGCCTCTACCCTGGCCAGCGGCGTGCCTTCCCGGTTCTCTGGCAGCGGCTCCGGCACAGACTTTACCCTGACAATCTCTAGCGTGCAGCCAGAGGATGCCGCCACCTACTATTGTCAGCAGGGCTATGGCAGGTCCAACGTGGATAATATCTTTGGAGGAGGCACCAAGGTGGAGGTGAAGAGGACAGTGGCGGCGCCCAGTGTCTTCATTTTTCCCCCTAGCGACGAACAGCTGAAGTCTGGGACAGCCAGTGTGGTCTGTCTGCTGAACAACTTCTACCCTAGAGAGGCTAAAGTGCAGTGGAAGGTCGATAACGCACTGCAGTCCGGAAATTCTCAGGAGAGTGTGACTGAACAGGACTCAAAAGATAGCACCTATTCCCTGTCAAGCACACTGACTCTGAGCAAGGCCGACTACGAGAAGCATAAAGTGTATGCTTGTGAAGTCACCCACCAGGGGCTGAGTTCACCAGTCACAAAATCATTCAACAGAGGGGAGTGC | 63 |
| | VL | DYQMTQSPSSVSASVGDRVTITCRASQSIGDWLAWYQQKPGKAPKLLIYEASTLASGVPSRFSGSGSGTDFTLTISSVQPEDAATYYCQQGYGRSNVDNIFGGGTKVEVK | 64 |
| | IMGT CDR1 | QSIGDW | 40 |
| | IMGT CDR2 | EAS | 41 |
| | IMGT CDR3 | QQGYGRSNVDNI | 42 |
| | Chothia CDR1 | RASQSIGDWLA | 65 |
| | Chothia CDR2 | EASTLAS | 44 |
| | Chothia CDR3 | QQGYGRSNVDNI | 42 |
| | Kabat CDR1 | RASQSIGDWLA | 65 |

TABLE B-continued

Clone Sequences

| Clone ID | Region | Sequence | SEQ ID NO |
|---|---|---|---|
| | Kabat CDR2 | EASTLAS | 44 |
| | Kabat CDR3 | QQGYGRSNVDNI | 42 |
| | Contact CDR1 | GDWLAWY | 45 |
| | Contact CDR2 | LLIYEASTLA | 46 |
| | Contact CDR3 | QQGYGRSNVDN | 47 |
| | AbM CDR1 | RASQSIGDWLA | 65 |
| | AbM CDR2 | EASTLAS | 44 |
| | AbM CDR3 | QQGYGRSNVDNI | 42 |
| 22057 | Full | EVQLLESGGGLVQPGGSLRLSCAVSGFSLS<br>SYGVSWVRQAPGKGLEWIGAVNSGGSAYYA<br>DSVKGRSTISRDNSKNTVYLQMNSLRAEDT<br>AVYYCARSGSGYPMDYLAIWGQGTLVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYVLPPSRDE<br>LTKNQVSLLCLVKGFYPSDIAVEWESNGQP<br>ENNYLTWPPVLDSDGSFFLYS<br>KLTVDKSRWQQGNVFSCSVMHEALHNHYTQ<br>KSLSLSPG | 66 |
| | Full | GAGGTGCAGCTGCTGGAGAGCGGAGGAGGA<br>CTGGTGCAGCCAGGAGGCAGCCTGCGGCTG<br>TCCTGCGCCGTGAGCGGCTTTTCCCTGAGC<br>TCCTACGGCGTGTCCTGGGTGAGACAGGCC<br>CCCGGCAAGGGACTGGAGTGGATCGGAGCC<br>GTGAACTCTGGCGGCAGCGCCTACTATGCC<br>GACTCTGTGAAGGGCCGGTCCACCATCTCT<br>AGAGATAACTCTAAGAATACAGTGTATCTG<br>CAGATGAATAGCCTGAGGGCCGAGGACACA<br>GCCGTGTACTATTGTGCACGCTCCGGCTCT<br>GGCTACCCCATGGATTATCTGGCCATCTGG<br>GGACAGGGCACCCTGGTGACAGTGTCTAGC<br>GCTAGCACTAAGGGGCCTTCCGTGTTTCCA<br>CTGGCTCCCTCTAGTAAATCCACCTCTGGA<br>GGCACAGCTGCACTGGGATGTCTGGTGAAG<br>GATTACTTCCCTGAACCAGTCACAGTGAGT<br>TGGAACTCAGGGGCTCTGACAAGTGGAGTC<br>CATACTTTTCCCGCAGTGCTGCAGTCAAGC<br>GGACTGTACTCCCTGTCCTCTGTGGTCACC<br>GTGCCTAGTTCAAGCCTGGGCACCCAGACA<br>TATATCTGCAACGTGAATCACAAGCCATCA<br>AATACAAAAGTCGACAAGAAAGTGGAGCCC<br>AAGAGCTGTGATAAAACTCATACCTGCCCA<br>CCTTGTCCGGCGCCAGAACTGCTGGGAGGA<br>CCAAGCGTGTTCCTGTTTCCACCCAAGCCT<br>AAAGACACCCTGATGATTTCCCGGACTCCT<br>GAGGTCACCTGCGTGGTCGTGGACGTGTCT<br>CACGAGGACCCCGAAGTCAAGTTCAACTGG<br>TACGTGGATGGCGTCGAAGTGCATAATGCC<br>AAGACCAAACCCCGGGAGGAACAGTACAAC<br>TCTACCTATAGAGTCGTGAGTGTCCTGACA<br>GTGCTGCACCAGGACTGGCTGAATGGGAAG<br>GAGTATAAGTGTAAAGTGAGCAACAAAGCC | 67 |

TABLE B-continued

Clone Sequences

| Clone ID | Region | Sequence | SEQ ID NO |
|---|---|---|---|
| | | CTGCCCGCCCCAATCGAAAAAACAATCTCT<br>AAAGCAAAAGGACAGCCTCGCGAACCACAG<br>GTCTACGTGCTGCCCCCTAGCCGCGACGAA<br>CTGACTAAAAATCAGGTCTCTCTGCTGTGT<br>CTGGTCAAAGGATTCTACCCTTCCGACATC<br>GCCGTGGAGTGGGAAAGTAACGGCCAGCCC<br>GAGAACAATTACCTGACCTGGCCCCCTGTG<br>CTGGACTCTGATGGGAGTTTCTTTCTGTAT<br>TCAAAGCTGACAGTCGATAAAAGCCGGTGG<br>CAGCAGGGCAATGTGTTCAGCTGCTCCGTC<br>ATGCACGAAGCACTGCACAACCATTACACT<br>CAGAAGTCCCTGTCCCTGTCACCTGGC | |
| | VH | EVQLLESGGGLVQPGGSLRLSCAVSGFSLS<br>SYGVSWVRQAPGKGLEWIGAVNSGGSAYYA<br>DSVKGRSTISRDNSKNTVYLQMNSLRAEDT<br>AVYYCARSGSGYPMDYLAIWGQGTLVTVSS | 50 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22058 | Full | EVQVLESGGGLVQPGGSLRLSCAVSGFSLS<br>SYGVSWVRQAPGKGLEWIGAVNSGGSAYYA<br>DSVKGRSTISRDNSKNTVYLQMNSLRAEDT<br>AVYYCARSGSGYPMDYLAIWGQGTLVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA | 68 |

TABLE B-continued

Clone Sequences

| Clone ID | Region | Sequence | SEQ ID NO |
|---|---|---|---|
| | | LPAPIEKTISKAKGQPREPQVYVLPPSRDE LTKNQVSLLCLVKGFYPSDIAVEWESNGQP ENNYLTWPPVLDSDGSFFLYSKLTVDKSRW QQGNVFSCSVMHEALHNHYTQKSLSLSPG | |
| | Full | GAGGTGCAGGTGCTGGAGAGCGGAGGAGGA CTGGTGCAGCCAGGAGGCAGCCTGCGGCTG TCCTGCGCCGTGAGCGGCTTTTCCCTGAGC TCCTACGGCGTGTCCTGGGTGAGACAGGCC CCCGGCAAGGGACTGGAGTGGATCGGAGCC GTGAACTCTGGCGGCAGCGCCTACTATGCC GACTCTGTGAAGGGCCGGTCCACCATCTCT AGAGATAACTCTAAGAATACAGTGTATCTG CAGATGAATAGCCTGAGGGCCGAGGACACA GCCGTGTACTATTGTGCACGCTCCGGCTCT GGCTACCCCATGGATTATCTGGCCATCTGG GGACAGGGCACCCTGGTGACAGTGTCTAGC GCTAGCACTAAGGGGCCTTCCGTGTTTCCA CTGGCTCCCTCTAGTAAATCCACCTCTGGA GGCACAGCTGCACTGGGATGTCTGGTGAAG GATTACTTCCCTGAACCAGTCACAGTGAGT TGGAACTCAGGGGCTCTGACAAGTGGAGTC CATACTTTTCCCGCAGTGCTGCAGTCAAGC GGACTGTACTCCCTGTCCTCTGTGGTCACC GTGCCTAGTTCAAGCCTGGGCACCCAGACA TATATCTGCAACGTGAATCACAAGCCATCA AATACAAAAGTCGACAAGAAAGTGGAGCCC AAGAGCTGTGATAAAACTCATACCTGCCCA CCTTGTCCGGCGCCAGAACTGCTGGGAGGA CCAAGCGTGTTCCTGTTTCCACCCAAGCCT AAAGACACCCTGATGATTTCCCGGACTCCT GAGGTCACCTGCGTGGTCGTGGACGTGTCT CACGAGGACCCCGAAGTCAAGTTCAACTGG TACGTGGATGGCGTCGAAGTGCATAATGCC AAGACCAAACCCCGGGAGGAACAGTACAAC TCTACCTATAGAGTCGTGAGTGTCCTGACA GTGCTGCACCAGGACTGGCTGAATGGGAAG GAGTATAAGTGTAAAGTGAGCAACAAAGCC CTGCCCGCCCCAATCGAAAAAACAATCTCT AAAGCAAAAGGACAGCCTCGCGAACCACAG GTCTACGTGCTGCCCCCTAGCCGCGACGAA CTGACTAAAAATCAGGTCTCTCTGCTGTGT CTGGTCAAAGGATTCTACCCTTCCGACATC GCCGTGGAGTGGGAAAGTAACGGCCAGCCC GAGAACAATTACCTGACCTGGCCCCCTGTG CTGGACTCTGATGGGAGTTTCTTTCTGTAT TCAAAGCTGACAGTCGATAAAAGCCGGTGG CAGCAGGGCAATGTGTTCAGCTGCTCCGTC ATGCACGAAGCACTGCACAACCATTACACT CAGAAGTCCCTGTCCCTGTCACCTGGC | 69 |
| | VH | EVQVLESGGGLVQPGGSLRLSCAVSGFSLS SYGVSWVRQAPGKGLEWIGAVNSGGSAYYA DSVKGRSTISRDNSKNTVYLQMNSLRAEDT AVYYCARSGSGYPMDYLAIWGQGTL VTVSS | 54 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22059 | Full | EVQLLESGGGLVQPGGSLRLSCAVSGFSLS SYGVSWVRQAPGKGLEWIGAVNSGGSAYYA DWAKGRSTISRDNSKNTVYLQMNSLRAEDT AVYYCARSGSGYPMDYLAIWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYVLPPSRDE LTKNQVSLLCLVKGFYPSDIAVEWESNGQP ENNYLTWPPVLDSDGSFFLYS KLTVDKSRWQQGNVFSCSVMHEALHNHYTQ KSLSLSPG | 70 |
| | Full | GAGGTGCAGCTGCTGGAGTCCGGAGGAGGA CTGGTGCAGCCAGGAGGCAGCCTGCGGCTG TCCTGCGCCGTGAGCGGCTTTTCCCTGAGC TCCTACGGCGTGTCTTGGGTGAGACAGGCC CCCGGCAAGGGACTGGAGTGGATCGGAGCC GTGAACTCTGGAGGCAGCGCCTACTATGCA GACTGGGCAAAGGGCCGGTCCACCATCTCT AGAGATAACTCTAAGAATACAGTGTATCTG CAGATGAATAGCCTGAGGGCCGAGGACACA GCCGTGTACTATTGTGCACGCTCCGGCTCT GGCTACCCCATGGATTATCTGGCCATCTGG GGACAGGGCACCCTGGTGACAGTGTCTAGC GCTAGCACTAAGGGGCCTTCCGTGTTTCCA CTGGCTCCCTCTAGTAAATCCACCTCTGGA GGCACAGCTGCACTGGGATGTCTGGTGAAG GATTACTTCCCTGAACCAGTCACAGTGAGT TGGAACTCAGGGGCTCTGACAAGTGGAGTC CATACTTTTCCCGCAGTGCTGCAGTCAAGC GGACTGTACTCCCTGTCCTCTGTGGTCACC GTGCCTAGTTCAAGCCTGGGCACCCAGACA TATATCTGCAACGTGAATCACAAGCCATCA AATACAAAAGTCGACAAGAAAGTGGAGCCC AAGAGCTGTGATAAAACTCATACCTGCCCA CCTTGTCCGGCGCCAGAACTGCTGGGAGGA CCAAGCGTGTTCCTGTTTCCACCCAAGCCT AAAGACACCCTGATGATTTCCCGGACTCCT GAGGTCACCTGCGTGGTCGTGGACGTGTCT CACGAGGACCCCGAAGTCAAGTTCAACTGG TACGTGGATGGCGTCGAAGTGCATAATGCC | 71 |

TABLE B-continued

Clone Sequences

| Clone ID | Region | Sequence | SEQ ID NO |
|---|---|---|---|
| | | AAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTCTACGTGCTGCCCCCTAGCCGCGACGAACTGACTAAAAATCAGGTCTCTCTGCTGTGTCTGGTCAAAGGATTCTACCCTTCCGACATCGCCGTGGAGTGGGAAAGTAACGGCCAGCCCGAGAACAATTACCTGACCTGGCCCCCTGTGCTGGACTCTGATGGGAGTTTCTTTCTGTATTCAAAGCTGACAGTCGATAAAAGCCGGTGGCAGCAGGGCAATGTGTTCAGCTGCTCCGTCATGCACGAAGCACTGCACAACCATTACACTCAGAAGTCCCTGTCCCTGTCACCTGGC | |
| | VH | EVQLLESGGGLVQPGGSLRLSCAVSGFSLSSYGVSWVRQAPGKGLEWIGAVNSGGSAYYADWAKGRSTISRDNSKNTVYLQMNSLRAEDTAVYYCARSGSGYPMDYLAIWGQGTLVTVSS | 57 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADWAKG | 58 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22060 | Full | EVQVLESGGGLVQPGGSLRLSCAVSGFSLSSYGVSWVRQAPGKGLEWIGAVNSGGSAYYADWAKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVLPPSRDELTKNQVSLLCLVKGFYPSDIAVEWESNGQPENNYLTWPPVLDSDGSFFLYSKLTVDKSRWQQGNVFSCSVMHEALHNHYTQKSLSLSPG | 72 |
| | Full | GAGGTGCAGGTGCTGGAGTCCGGAGGAGGACTGGTGCAGCCAGGAGGCAGCCTGCGGCTGTCCTGCGCCGTGAGCGGCTTTTCCCTGAGCTCCTACGGCGTGTCTTGGGTGAGACAGGCCCCCGGCAAGGGACTGGAGTGGATCGGAGCCGTGAACTCTGGAGGCAGCGCCTACTATGCAGACTGGGCAAAGGGCCGGTCCACCATCTCTAGAGATAACTCTAAGAATACAGTGTATCTGCAGATGAATAGCCTGAGGGCCGAGGACACAGCCGTGTACTATTGTGCACGCTCCGGCTCTGGCTACCCCATGGATTATCTGGCCATCTGGGGACAGGGCACCCTGGTGACAGTGTCTAGCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCGCCAGAACTGCTGGGAGGACCAAGCGTGTTCCTGTTTCCACCCAAGCCTAAAGACACCCTGATGATTTCCCGGACTCCTGAGGTCACCTGCGTGGTCGTGGACGTGTCTCACGAGGACCCCGAAGTCAAGTTCAACTGGTACGTGGATGGCGTCGAAGTGCATAATGCCAAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTCTACGTGCTGCCCCCTAGCCGCGACGAACTGACTAAAAATCAGGTCTCTCTGCTGTGTCTGGTCAAAGGATTCTACCCTTCCGACATCGCCGTGGAGTGGGAAAGTAACGGCCAGCCCGAGAACAATTACCTGACCTGGCCCCCTGTGCTGGACTCTGATGGGAGTTTCTTTCTGTATTCAAAGCTGACAGTCGATAAAAGCCGGTGGCAGCAGGGCAATGTGTTCAGCTGCTCCGTCATGCACGAAGCACTGCACAACCATTACACTCAGAAGTCCCTGTCCCTGTCACCTGGC | 73 |
| | VH | EVQVLESGGGLVQPGGSLRLSCAVSGFSLSSYGVSWVRQAPGKGLEWIGAVNSGGSAYYADWAKGRSTISRDNSKNTVYLQMNSLRAEDTAVYYCARSGSGYPMDYLAIWGQGTLVTVSS | 61 |
| | IMGT CDR1 | GFSLSSYG | 20 |
| | IMGT CDR2 | VNSGGSA | 21 |
| | IMGT CDR3 | ARSGSGYPMDYLAI | 22 |

TABLE B-continued

Clone Sequences

| Clone ID | Region | Sequence | SEQ ID NO |
|---|---|---|---|
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADWAKG | 58 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22874 | Full | EVQLLESGGGLFQPGGSLRLSCAVSGFSLS SYGVSWVRQAPGKGLEWIGAVNSGGSAYYA DSVKGRSTISRDNSKNTVYLQMNSLRAEDT AVYYCARSGSGYPMDYLAIWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPG | 74 |
| | Full | GAGGTGCAGCTGCTGGAGAGCGGAGGAGGA CTGTTCCAGCCAGGAGGCAGCCTGCGGCTG TCCTGCGCCGTGAGCGGCTTTTCCCTGAGC TCCTACGGCGTGTCCTGGGTGAGACAGGCC CCCGGCAAGGGACTGGAGTGGATCGGAGCC GTGAACTCTGGCGGCAGCGCCTACTATGCC GACTCTGTGAAGGGCCGGTCCACCATCTCT AGAGATAACTCTAAGAATACAGTGTATCTG CAGATGAATAGCCTGAGGGCCGAGGACACA GCCGTGTACTATTGTGCACGCTCCGGCTCT GGCTACCCCATGGATTATCTGGCCATCTGG GGACAGGGCACCCTGGTGACAGTGTCTAGC GCTAGCACTAAGGGGCCTTCCGTGTTTCCA CTGGCTCCCTCTAGTAAATCCACCTCTGGA GGCACAGCTGCACTGGGATGTCTGGTGAAG GATTACTTCCCTGAACCAGTCACAGTGAGT TGGAACTCAGGGGCTCTGACAAGTGGAGTC CATACTTTTCCCGCAGTGCTGCAGTCAAGC GGACTGTACTCCCTGTCCTCTGTGGTCACC GTGCCTAGTTCAAGCCTGGGCACCCAGACA TATATCTGCAACGTGAATCACAAGCCATCA AATACAAAAGTCGACAAGAAAGTGGAGCCC AAGAGCTGTGATAAAACTCATACCTGCCCA CCTTGTCCGGCGCCAGAACTGCTGGGAGGA CCAAGCGTGTTCCTGTTTCCACCCAAGCCT AAAGACACCCTGATGATTTCCCGGACTCCT GAGGTCACCTGCGTGGTCGTGGACGTGTCT CACGAGGACCCCGAAGTCAAGTTCAACTGG TACGTGGATGGCGTCGAAGTGCATAATGCC AAGACCAAACCCCGGGAGGAACAGTACAAC TCTACCTATAGAGTCGTGAGTGTCCTGACA GTGCTGCACCAGGACTGGCTGAATGGGAAG GAGTATAAGTGTAAAGTGAGCAACAAAGCC CTGCCCGCCCCAATCGAAAAAACAATCTCT AAAGCAAAAGGACAGCCTCGCGAACCACAG GTGTACACTCTGCCTCCATCTCGGGACGAG CTGACTAAGAACCAGGTCAGTCTGACCTGT CTGGTGAAAGGATTCTATCCCAGCGATATC GCTGTGGAGTGGGAATCCAATGGCCAGCCT GAGAACAATTACAAGACCACACCCCCTGTG CTGGACTCTGATGGCAGTTTCTTTCTGTAT AGTAAGCTGACCGTCGATAAATCACGATGG CAGCAGGGGAACGTGTTCAGCTGTTCAGTG ATGCACGAAGCCCTGCACAACCATTACACC CAGAAGAGCCTGAGCCTGTCTCCCGGC | 75 |
| | VH | EVQLLESGGGLFQPGGSLRLSCAVSGFSLS SYGVSWVRQAPGKGLEWIGAVNSGGSAYYA DSVKGRSTISRDNSKNTVYLQMNSLRAEDT AVYYCARSGSGYPMDYLAIWGQGTL VTVSS | 76 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |

TABLE B-continued

Clone Sequences

| Clone ID | Region | Sequence | SEQ ID NO |
|---|---|---|---|
| 22875 | Full | EVQLLESGGGLVQPGGSLRLSCAVSGFSLSSYGVSWVRQAPGKGLEWIGAVNSGGSAYYADSVKGRSTISRDTSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 77 |
| | Full | GAGGTGCAGCTGCTGGAGAGCGGAGGAGGACTGGTGCAGCCAGGAGGCAGCCTGCGGCTGTCCTGCGCCGTGAGCGGCTTTTCCCTGAGCTCCTACGGCGTGTCCTGGGTGAGACAGGCCCCCGGCAAGGGACTGGAGTGGATCGGAGCCGTGAACTCTGGCGGCAGCGCCTACTATGCCGACTCTGTGAAGGGCCGGTCCACCATCTCTAGAGATACCTCTAAGAACACAGTGTATCTGCAGATGAATAGCCTGAGGGCCGAGGACACAGCCGTGTACTATTGTGCACGCTCCGGCTCTGGCTACCCCATGGATTATCTGGCCATCTGGGGACAGGGCACCCTGGTGACAGTGTCTAGCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCGCCAGAACTGCTGGGAGGACCAAGCGTGTTCCTGTTTCCACCCAAGCCTAAAGACACCCTGATGATTTCCCGGACTCCTGAGGTCACCTGCGTGGTCGTGGACGTGTCTCACGAGGACCCCGAAGTCAAGTTCAACTGGTACGTGGATGGCGTCGAAGTGCATAATGCCAAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTGTACACTCTGCCTCCATCTCGGGACGAGCTGACTAAGAACCAGGTCAGTCTGACCTGTCTGGTGAAAGGATTCTATCCCAGCGATATCGCTGTGGAGTGGGAATCCAATGGCCAGCCTGAGAACAATTACAAGACCACACCCCCTGTGCTGGACTCTGATGGCAGTTTCTTTCTGTATAGTAAGCTGACCGTCGATAAATCACGATGGCAGCAGGGGAACGTGTTCAGCTGTTCAGTGATGCACGAAGCCCTGCACAACCATTACACCCAGAAGAGCCTGAGCCTGTCTCCCGGC | 78 |
| | VH | EVQLLESGGGLVQPGGSLRLSCAVSGFSLSSYGVSWVRQAPGKGLEWIGAVNSGGSAYYADSVKGRSTISRDTSKNTVYLQMNSLRAEDTAVYYCARSGSGYPMDYLAIWGQGTLVTVSS | 79 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22876 | Full | EVQLLESGGGLVQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 80 |
| | Full | GAGGTGCAGCTGCTGGAGAGCGGAGGAGGACTGGTGCAGCCAGGAGGCAGCCTGCGGCTGTCCTGCGCCGTGAGCGGCTTTTCCCTGAGCTCCTACGGCGTGTCCTGGGTGAGACAGGCCCCCGGCAAGGGACTGGAGTGGATCGGAGCCGTGAACTCTGGCGGCAGCGCCTACTATGCCGACTCTGTGAAGGGCCGGTCCACCATCTCTAGAGATACCTCTAAGTTCACAGTGTATCTGCAGATGAATAGCCTGAGGGCCGAGGACACAGCCGTGTACTATTGTGCACGCTCCGGCTCTGGCTACCCCATGGATTATCTGGCCATCTGGGGACAGGGCACCCTGGTGACAGTGTCTAGCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGC | 81 |

TABLE B-continued

Clone Sequences

| Clone ID | Region | Sequence | SEQ ID NO |
|---|---|---|---|
| | | GGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCGCCAGAACTGCTGGGAGGACCAAGCGTGTTCCTGTTTCCACCCAAGCCTAAAGACACCCTGATGATTTCCCGGACTCCTGAGGTCACCTGCGTGGTCGTGGACGTGTCTCACGAGGACCCCGAAGTCAAGTTCAACTGGTACGTGGATGGCGTCGAAGTGCATAATGCCAAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTGTACACTCTGCCTCCATCTCGGGACGAGCTGACTAAGAACCAGGTCAGTCTGACCTGTCTGGTGAAAGGATTCTATCCCAGCGATATCGCTGTGGAGTGGGAATCCAATGGCCAGCCTGAGAACAATTACAAGACCACACCCCCTGTGCTGGACTCTGATGGCAGTTTCTTTCTGTATAGTAAGCTGACCGTCGATAAATCACGATGGCAGCAGGGGAACGTGTTCAGCTGTTCAGTGATGCACGAAGCCCTGCACAACCATTACACCCAGAAGAGCCTGAGCCTGTCTCCCGGC | |
| | VH | EVQLLESGGGLVQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSS | 82 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |

TABLE B-continued

Clone Sequences

| Clone ID | Region | Sequence | SEQ ID NO |
|---|---|---|---|
| | AbM CDR3 | SGSGYPMDYLAI | 25 |
| 22877 | Full | EVQLLESGGGLFQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 83 |
| | Full | GAGGTGCAGCTGCTGGAGAGCGGAGGAGGACTGTTCCAGCCAGGAGGCAGCCTGCGGCTGTCCTGCGCCGTGAGCGGCTTTTCCCTGAGCTCCTACGGCGTGTCCTGGGTGAGACAGGCCCCCGGCAAGGGACTGGAGTGGATCGGAGCCGTGAACTCTGGCGGCAGCGCCTACTATGCCGACTCTGTGAAGGGCCGGTCCACCATCTCTAGAGATACCTCTAAGTTTACAGTGTATCTGCAGATGAATAGCCTGAGGGCCGAGGACACAGCCGTGTACTATTGTGCACGCTCCGGCTCTGGCTACCCCATGGATTATCTGGCCATCTGGGGACAGGGCACCCTGGTGACAGTGTCTAGCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCGCCAGAACTGCTGGGAGGACCAAGCGTGTTCCTGTTTCCACCCAAGCCTAAAGACACCCTGATGATTTCCCGGACTCCTGAGGTCACCTGCGTGGTCGTGGACGTGTCTCACGAGGACCCCGAAGTCAAGTTCAACTGGTACGTGGATGGCGTCGAAGTGCATAATGCCAAGACCAAACCCCGGGAGGAACAGTACAACTCTACCTATAGAGTCGTGAGTGTCCTGACAGTGCTGCACCAGGACTGGCTGAATGGGAAGGAGTATAAGTGTAAAGTGAGCAACAAAGCCCTGCCCGCCCCAATCGAAAAAACAATCTCTAAAGCAAAAGGACAGCCTCGCGAACCACAGGTGTACACTCTGCCTCCATCTCGGGACGAGCTGACTAAGAACCAGGTCAGTCTGACCTGTCTGGTGAAAGGATTCTATCCCAGCGATATCGCTGTGGAGTGGGAATCCAATGGCCAGCCTGAGAACAATTACAAGACCACACCCCCTGTGCTGGACTCTGATGGCAGTTTCTTTCTGTATAGTAAGCTGACCGTCGATAAATCACGATGGCAGCAGGGGAACGTGTTCAGCTGTTCAGTGATGCACGAAGCCCTGCACAACCATTACACCCAGAAGAGCCTGAGCCTGTCTCCCGGC | 84 |
| | VH | EVQLLESGGGLFQPGGSLRLSCAVSGFSLSSYGVSWVRQAPGKGLEWIGAVNSGGSAYYADSVKGRSTISRDTSKFTVYLQMNSLRAEDTAVYYCARSGSGYPMDYLAIWGQGTLVTVSS | 85 |
| | IMGT CDR1 | GFSLSSYG | 20 |

TABLE B-continued

Clone Sequences

| Clone ID | Region | Sequence | SEQ ID NO |
|---|---|---|---|
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 22878 | Full | QQLLESGGGLFQPGGSLRLSCAVSGFSLSS YGVSWVRQAPGKGLEWIGAVNSGGSAYYAD SVKGRSTISRDTSKFTVYLQMNSLRAEDTA VYYCARSGSGYPMDYLAIWGQGTLVTVSSA STKGPSVFPLAPSSKSTSGGTAALGCLVKD YFPEPVTVSWNSGALTSGVHTFPAVLQSSG LYSLSSVVTVPSSSLGTQTYICNVNHKPSN TKVDKKVEPKSCDKTHTCPPCPAPELLGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL PAPIEKTISKAKGQPREPQVYTLPPSRDEL TKNQVSLTCLVKGFYPSDIAVEWESNGQPE NNYKTTPPVLDSDGSFFLYSKLTVDKSRWQ QGNVFSCSVMHEALHNHYTQKSLSLSPG | 86 |
| | Full | CAGCAGCTGCTGGAGAGCGGCGGCGGCCTG TTCCAGCCTGGAGGCAGCCTGAGACTGTCC TGCGCCGTGAGCGGCTTTTCCCTGAGCTCC TACGGCGTGTCCTGGGTGAGGCAGGCCCCC GGCAAGGGCCTGGAGTGGATCGGAGCCGTG AACTCTGGCGGCAGCGCCTACTATGCCGAC TCTGTGAAGGGCCGGTCCACCATCTCTAGA GATACCTCTAAGTTTACAGTGTATCTGCAG ATGAATAGCCTGAGGGCCGAGGACACAGCC GTGTACTATTGTGCACGCTCCGGCTCTGGC TACCCCATGGATTATCTGGCCATCTGGGGA CAGGGCACCCTGGTGACAGTGTCTAGCGCT AGCACTAAGGGGCCTTCCGTGTTTCCACTG GCTCCCTCTAGTAAATCCACCTCTGGAGGC ACAGCTGCACTGGGATGTCTGGTGAAGGAT TACTTCCCTGAACCAGTCACAGTGAGTTGG AACTCAGGGGCTCTGACAAGTGGAGTCCAT ACTTTTCCCGCAGTGCTGCAGTCAAGCGGA CTGTACTCCCTGTCCTCTGTGGTCACCGTG CCTAGTTCAAGCCTGGGCACCCAGACATAT ATCTGCAACGTGAATCACAAGCCATCAAAT ACAAAAGTCGACAAGAAAGTGGAGCCCAAG AGCTGTGATAAAACTCATACCTGCCCACCT TGTCCGGCGCCAGAACTGCTGGGAGGACCA AGCGTGTTCCTGTTTCCACCCAAGCCTAAA GACACCCTGATGATTTCCCGGACTCCTGAG GTCACCTGCGTGGTCGTGGACGTGTCTCAC GAGGACCCCGAAGTCAAGTTCAACTGGTAC GTGGATGGCGTCGAAGTGCATAATGCCAAG ACCAAACCCCGGGAGGAACAGTACAACTCT ACCTATAGAGTCGTGAGTGTCCTGACAGTG CTGCACCAGGACTGGCTGAATGGGAAGGAG TATAAGTGTAAAGTGAGCAACAAAGCCCTG CCCGCCCCAATCGAAAAAACAATCTCTAAA GCAAAAGGACAGCCTCGCGAACCACAGGTG TACACTCTGCCTCCATCTCGGGACGAGCTG ACTAAGAACCAGGTCAGTCTGACCTGTCTG GTGAAAGGATTCTATCCCAGCGATATCGCT GTGGAGTGGGAATCCAATGGCCAGCCTGAG AACAATTACAAGACCACACCCCCTGTGCTG GACTCTGATGGCAGTTTCTTTCTGTATAGT AAGCTGACCGTCGATAAATCACGATGGCAG CAGGGGAACGTGTTCAGCTGTTCAGTGATG CACGAAGCCCTGCACAACCATTACACCCAG AAGAGCCTGAGCCTGTCTCCCGGC | 87 |
| | VH | QQLLESGGGLFQPGGSLRLSCAVSGFSLSS YGVSWVRQAPGKGLEWIGAVNSGGSAYYAD SVKGRSTISRDTSKFTVYLQMNSLRAEDTA VYYCARSGSGYPMDYLAIWGQGTLVTVSS | 88 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |

TABLE B-continued

Clone Sequences

| Clone ID | Region | Sequence | SEQ ID NO |
|---|---|---|---|
| | AbM CDR2 | AVNSGGSAY | 32 |
| | AbM CDR3 | SGSGYPMDYLAI | 25 |
| 26434 | Full | EVQLLESGGGLVQPGGSLRLSCAVSGFSLSLYGVSWVRQAPGKGLEWIGAVNSGGSAYYADSVKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 89 |
| | Full | GAGGTCCAGTTGCTGGAATCAGGAGGTGGACTCGTGCAGCCTGGGGGTTCCCTGCGCTTGTCTTGCGCTGTCAGCGGTTTTAGCTTATCTTTATACGGTGTAAGTTGGGTTCGGCAGGCTCCTGGCAAAGGTCTGGAATGGATCGGGGCTGTAAACAGCGGGGGGTCCGCCTACTATGCTGATTCTGTTAAGGGGAGGTCCACCATTAGCAGAGATAATTCCAAGAACACCGTTTATCTCCAGATGAACTCCTTGAGGGCGGAGGACACTGCTGTCTATTATTGTGCGCGGTCAGGCAGCGGATACCCGATGGACTATCTGGCGATCTGGGGCCAGGGAACCCTTGTGACAGTCTCTTCCGCTAGCACCAAGGGACCTAGCGTATTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCTCCAGAGCTGCTCGGCGGACCATCCGTGTTCCTGTTTCCTCCAAAGCCTAAAGATACACTGATGATTAGCCGCACTCCCGAAGTCACCTGTGTGGTCGTGGACGTGTCCCACGAGGACCCCGAAGTCAAGTTCAACTGGTACGTGGACGGCGTCGAGGTGCATAATGCCAAGACTAAACCAAGAGAGGAACAGTACAATTCAACCTATAGGGTCGTGAGCGTCCTGACAGTGCTGCATCAGGATTGGCTGAACGGCAAGGAGTATAAGTGCAAAGTGTCTAACAAGGCCCTGCCCGCTCCTATCGAGAAGACTATTAGCAAGGCAAAAGGGCAGCCACGGGAACCCCAGGTCTACACTCTGCCCCCTAGCAGAGACGAGCTGACCAAAAACCAGGTGTCCCTGACTTGTCTGGTGAAGGGCTTTTATCCTAGTGATATCGCTGTGGAGTGGGAATCAAATGGGCAGCCAGAAAACAATTACAAAACAACTCCACCCGTGCTGGACAGCGATGGGTCCTTCTTTCTGTATTCCAAACTGACTGTGGACAAGTCCAGATGGCAGCAGGGAAACGTCTTCAGCTGTTCCGTGATGCACGAGGCCCTGCACAATCATTACACCCAGAAGTCTCTGAGTCTGTCACCCGGC | 90 |
| | VH | EVQLLESGGGLVQPGGSLRLSCAVSGFSLSLYGVSWVRQAPGKGLEWIGAVNSGGSAYYADSVKGRSTISRDNSKNTVYLQMNSLRAEDTAVYYCARSGSGYPMDYLAIWGQGTLVTVSS | 91 |
| | IMGT CDR1 | GFSLSLYG | 92 |
| | IMGT CDR2 | VNSGGSA | 21 |
| | IMGT CDR3 | ARSGSGYPMDYLAI | 22 |
| | Chothia CDR1 | GFSLSLY | 93 |
| | Chothia CDR2 | NSGGS | 24 |
| | Chothia CDR3 | SGSGYPMDYLAI | 25 |
| | Kabat CDR1 | LYGVS | 94 |
| | Kabat CDR2 | AVNSGGSAYYADSVKG | 51 |
| | Kabat CDR3 | SGSGYPMDYLAI | 25 |
| | Contact CDR1 | SLYGVS | 95 |
| | Contact CDR2 | WIGAVNSGGSAY | 29 |
| | Contact CDR3 | ARSGSGYPMDYLA | 30 |
| | AbM CDR1 | GFSLSLYGVS | 96 |
| | AbM CDR2 | AVNSGGSAY | 32 |
| | AbM CDR3 | SGSGYPMDYLAI | 25 |
| 26443 | Full | EVQLLESGGGLVQPGGSLRLSCAVSGFSLSLYGVSWVRQAPGKGLEWIGSLNSGGSAYYADSVKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 97 |
| | Full | GAGGTTCAGTTGCTTGAGTCTGGAGGTGGGTTGGTACAACCAGGTGGATCTCTCCGCCTTTCTTGTGCAGTCTCAGGCTTCTCTCTCAGCCTGTACGGCGTGTCATGGGTTAGACAAGCTCCGGGTAAAGGCCTTGAGTGGATTGGAAGTCTTAATAGTGGGGGAAGCGCCTACTATGCAGATAGCGTAAAAGGAAGATCAACTATATCCAGAGACAATTCTAAGAATACCGTCTACTTGCAGATGAACTCTCTGCGGGCAGAGGATACTGCGGTTTACTATTGTGCGCGAAGCGGTAGTGGATACCCTATGGATTATCTTGCTATTTGG | 98 |

TABLE B-continued

Clone Sequences

| Clone ID | Region | Sequence | SEQ ID NO |
|---|---|---|---|
| | | GGTCAAGGTACCCTCGTAACGGTCTCTAGTGCTAGCACCAAGGGACCTAGCGTATTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCTCCAGAGCTGCTCGGCGGACCATCCGTGTTCCTGTTTCCTCCAAAGCCTAAAGATACACTGATGATTAGCCGCACTCCCGAAGTCACCTGTGTGGTCGTGGACGTGTCCCACGAGGACCCCGAAGTCAAGTTCAACTGGTACGTGGACGGCGTCGAGGTGCATAATGCCAAGACTAAACCAAGAGAGGAACAGTACAATTCAACCTATAGGGTCGTGAGCGTCCTGACAGTGCTGCATCAGGATTGGCTGAACGGCAAGGAGTATAAGTGCAAAGTGTCTAACAAGGCCCTGCCCGCTCCTATCGAGAAGACTATTAGCAAGGCAAAAGGGCAGCCACGGGAACCCCAGGTCTACACTCTGCCCCCTAGCAGAGACGAGCTGACCAAAAACCAGGTGTCCCTGACTTGTCTGGTGAAGGGCTTTTATCCTAGTGATATCGCTGTGGAGTGGGAATCAAATGGGCAGCCAGAAAACAATTACAAAACAACTCCACCCGTGCTGGACAGCGATGGGTCCTTCTTTCTGTATTCCAAACTGACTGTGGACAAGTCCAGATGGCAGCAGGGAAACGTCTTCAGCTGTTCCGTGATGCACGAGGCCCTGCACAATCATTACACCCAGAAGTCTCTGAGTCTGTCACCCGGC | |
| | VH | EVQLLESGGGLVQPGGSLRLSCAVSGFSLSLYGVSWVRQAPGKGLEWIGSLNSGGSAYYADSVKGRSTISRDNSKNTVYLQMNSLRAEDTAVYYCARSGSGYPMDYLAIWGQGTLVTVSS | 99 |
| | IMGT CDR1 | GFSLSLYG | 92 |
| | IMGT CDR2 | LNSGGSA | 100 |
| | IMGT CDR3 | ARSGSGYPMDYLAI | 22 |
| | Chothia CDR1 | GFSLSLY | 93 |
| | Chothia CDR2 | NSGGS | 24 |
| | Chothia CDR3 | SGSGYPMDYLAI | 25 |
| | Kabat CDR1 | LYGVS | 94 |
| | Kabat CDR2 | SLNSGGSAYYADSVKG | 101 |
| | Kabat CDR3 | SGSGYPMDYLAI | 25 |
| | Contact CDR1 | SLYGVS | 95 |
| | Contact CDR2 | WIGSLNSGGSAY | 102 |
| | Contact CDR3 | ARSGSGYPMDYLA | 30 |
| | AbM CDR1 | GFSLSLYGVS | 96 |
| | AbM CDR2 | SLNSGGSAY | 103 |
| | AbM CDR3 | SGSGYPMDYLAI | 25 |
| 26445 | Full | EVQLLESGGGLVQPGGSLRLSCAVSGFSLSLYGVSWVRQAPGKGLEWIGAVNSGGSAYYADSFKGRSTISRDNSKNTVYLQMNSLRAEDTAVYYCARSGSGYPMDYHPIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGG | 104 |
| | Full | AGGTCCAGCTCTTGGAGTCAGGAGGCGGCCTGGTTCAGCCGGGGGGTTCACTCAGACTTAGTTGTGCGGTAAGCGGGTTCAGCCTTAGTCTGTATGGCGTATCATGGGTCCGGCAAGCGCCTGGTAAGGGCCTGGAGTGGATAGGTGCTGTCAATAGCGGTGGCTCCGCATACTACGCGGACTCTTTTAAGGGCAGATCCACCATCAGCCGGGACAACAGCAAGAACACTGTATATCTTCAGATGAACTCACTCAGGGCGGAGGATACTGCGGTATACTACTGTGCACGAAGTGGTAGTGGTTACCCAATGGATTACCATCCCATTTGGGGGCAAGGGACACTCGTTACAGTGAGTAGTGCTAGCACCAAGGGACCTAGCGTATTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCTCCAGAGCTGCTCGGCGGACCATCCGTGTTCCTGTTTCCTCCAAAGCCTAAAGATACACTGATGATTAGCCGCACTCCCGAAGTCACCTGTGTGGTCGTGGACGTGTCCCACGAGGACCCCGAAGTCAAGTTCAACTGGTACGTGGACGGCGTCGAGGTGCATAATGCCAAGACTAAACCAAGAGAGGAACAGTACAATTCAACCTATAGGGTCGTGAGCGTCCTGACAGTGCTGCATCAGGATTGGCTGAACGGCAAGGAGTATAAGTGCAAAGTGTCTAACAAGGCCCTGCCCGCTCCTATCGAGAAGACTATTAGCAAGGCAAAAGGGCAGCCACGGGAACCCCAGGTCTACACTCTGCCCCCTAGCAGAGACGAGCTGACCAAAAACCAGGTGTCCCTGACTTGTCTGGTGAAGGGCTTTTATCCTAGTGATATCGCTGTGGAGTGGGAATCAAATGGGCAGCCAGAAAACAATTACAAAACAACTCCACCCGTGCTGGACAGCGATGGGTCCTTCTTTCTGTATTCCAAACTGACTGTGGACAAGTCCAGATGGCAGCAGGGAAACGTCTTCAGCTGTTCCGTGATGCACGAGGCCCTGCACAATCATTACACCCAGAAGTCTCTGAGTCTGTCACCCGGC | 105 |

TABLE B-continued

Clone Sequences

| Clone ID | Region | Sequence | SEQ ID NO |
|---|---|---|---|
| | VH | EVQLLESGGGLVQPGGSLRLSCAVSGFSLS LYGVSWVRQAPGKGLEWIGAVNSGGSAYYA DSFKGRSTISRDNSKNTVYLQMNSLRAEDT AVYYCARSGSGYPMDYHPIWGQGTLVTVSS | 106 |
| | IMGT CDR1 | GFSLSLYG | 92 |
| | IMGT CDR2 | VNSGGSA | 21 |
| | IMGT CDR3 | ARSGSGYPMDYHPI | 107 |
| | Chothia CDR1 | GFSLSLY | 93 |
| | Chothia CDR2 | NSGGS | 24 |
| | Chothia CDR3 | SGSGYPMDYHPI | 108 |
| | Kabat CDR1 | LYGVS | 94 |
| | Kabat CDR2 | AVNSGGSAYYADSFKG | 109 |
| | Kabat CDR3 | SGSGYPMDYHPI | 108 |
| | Contact CDR1 | SLYGVS | 95 |
| | Contact CDR2 | WIGAVNSGGSAY | 29 |
| | Contact CDR3 | ARSGSGYPMDYHP | 110 |
| | AbM CDR1 | GFSLSLYGVS | 96 |
| | AbM CDR2 | AVNSGGSAY | 32 |
| | AbM CDR3 | SGSGYPMDYHPI | 108 |
| 26446 | Full | EVQLLESGGGLVQPGGSLRLSCAVSGFSLS LYGVSWVRQAPGKGLEWIGAVNSGGSAYYA DSFKGRSTISRDNSKNTVYLQMNSLRAEDT AVYYCARSGSGYPMDYLAIWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPG | 111 |
| | Full | GAGGTACAGCTTCTGGAAAGTGGTGGCGGT CTTGTCCAGCCTGGAGGAAGTCTCAGGTTG TCATGTGCAGTCTCTGGTTTTTCCCTCTCA TTGTACGGCGTGAGTTGGGTTAGACAAGCG CCAGGTAAGGGGTTGGAGTGGATCGGGGCG GTCAATTCCGGCGGTTCTGCCTATTACGCC GACTCATTCAAAGGCCGCTCCACGATTAGT CGAGATAATTCCAAAAATACTGTGTATCTC CAAATGAATAGTCTCCGCGCGGAGGACACA GCTGTTTATTATTGTGCCCGGTCCGGAAGT GGCTATCCAATGGACTATCTCGCCATCTGG GGTCAGGGCACGTTGGTAACGGTGTCCTCC GCTAGCACCAAGGGACCTAGCGTATTTCCA CTGGCTCCCTCTAGTAAATCCACCTCTGGA GGCACAGCTGCACTGGGATGTCTGGTGAAG GATTACTTCCCTGAACCAGTCACAGTGAGT TGGAACTCAGGGGCTCTGACAAGTGGAGTC CATACTTTTCCCGCAGTGCTGCAGTCAAGC GGACTGTACTCCCTGTCCTCTGTGGTCACC GTGCCTAGTTCAAGCCTGGGCACCCAGACA TATATCTGCAACGTGAATCACAAGCCATCA AATACAAAAGTCGACAAGAAAGTGGAGCCC AAGAGCTGTGATAAAACTCATACCTGCCCA CCTTGTCCGGCTCCAGAGCTGCTCGGCGGA CCATCCGTGTTCCTGTTTCCTCCAAAGCCT AAAGATACACTGATGATTAGCCGCACTCCC GAAGTCACCTGTGTGGTCGTGGACGTGTCC CACGAGGACCCCGAAGTCAAGTTCAACTGG TACGTGGACGGCGTCGAGGTGCATAATGCC AAGACTAAACCAAGAGAGGAACAGTACAAT TCAACCTATAGGGTCGTGAGCGTCCTGACA GTGCTGCATCAGGATTGGCTGAACGGCAAG GAGTATAAGTGCAAAGTGTCTAACAAGGCC CTGCCCGCTCCTATCGAGAAGACTATTAGC AAGGCAAAAGGGCAGCCACGGGAACCCCAG GTCTACACTCTGCCCCCTAGCAGAGACGAG CTGACCAAAAACCAGGTGTCCCTGACTTGT CTGGTGAAGGGCTTTTATCCTAGTGATATC GCTGTGGAGTGGGAATCAAATGGGCAGCCA GAAAACAATTACAAAACAACTCCACCCGTG CTGGACAGCGATGGGTCCTTCTTTCTGTAT TCCAAACTGACTGTGGACAAGTCCAGATGG CAGCAGGGAAACGTCTTCAGCTGTTCCGTG ATGCACGAGGCCCTGCACAATCATTACACC CAGAAGTCTCTGAGTCTGTCACCCGGC | 112 |
| | VH | EVQLLESGGGLVQPGGSLRLSCAVSGFSLS LYGVSWVRQAPGKGLEWIGAVNSGGSAYYA DSFKGRSTISRDNSKNTVYLQMNSLRAEDT AVYYCARSGSGYPMDYLAIWGQGTL VTVSS | 113 |
| | IMGT CDR1 | GFSLSLYG | 92 |
| | IMGT CDR2 | VNSGGSA | 21 |
| | IMGT CDR3 | ARSGSGYPMDYLAI | 22 |
| | Chothia CDR1 | GFSLSLY | 93 |
| | Chothia CDR2 | NSGGS | 24 |
| | Chothia CDR3 | SGSGYPMDYLAI | 25 |
| | Kabat CDR1 | LYGVS | 94 |
| | Kabat CDR2 | AVNSGGSAYYADSFKG | 109 |
| | Kabat CDR3 | SGSGYPMDYLAI | 25 |
| | Contact CDR1 | SLYGVS | 95 |

TABLE B-continued

Clone Sequences

| Clone ID | Region | Sequence | SEQ ID NO |
|---|---|---|---|
| | Contact CDR2 | WIGAVNSGGSAY | 29 |
| | Contact CDR3 | ARSGSGYPMDYLA | 30 |
| | AbM CDR1 | GFSLSLYGVS | 96 |
| | AbM CDR2 | AVNSGGSAY | 32 |
| | AbM CDR3 | SGSGYPMDYLAI | 25 |
| 26447 | Full | EVQLLESGGGLVQPGGSLRLSCAVSGFSLSSYGVSWVRQAPGKGLEWIGAVNSGGSAYYADSFKGRSTISRDNSKNTVYLQMNSLRAEDTAVYYCARSGSGYPMDYHPIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 114 |
| | Full | GAGGTGCAACTGTTGGAATCCGGAGGTGGTTTGGTGCAGCCTGGCGGTAGTCTGCGGCTTAGTTGCGCTGTTTCAGGCTTTTCTCTCTCATCATACGGGGTATCATGGGTGAGACAGGCACCAGGAAAGGGTCTTGAATGGATTGGGGCCGTAAATTCCGGAGGTAGTGCATACTATGCTGACTCATTCAAGGGCAGGTCCACCATTAGTCGAGATAACTCAAAGAACACGGTTTATCTGCAGATGAATAGCCTTAGAGCGGAGGACACGGCAGTATATTATTGCGCGAGAAGCGGGTCTGGATATCCGATGGACTACCATCCAATCTGGGGCCAGGGAACACTCGTAACGGTGAGCAGCGCTAGCACCAAGGGACCTAGCGTATTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCCAAGAGCTGTGATAAAACTCATACCTGCCCACCTTGTCCGGCTCCAGAGCTGCTCGGCGGACCATCCGTGTTCCTGTTTCCTCCAAAGCCTAAAGATACACTGATGATTAGCCGCACTCCCGAAGTCACCTGTGTGGTCGTGGACGTGTCCCACGAGGACCCCGAAGTCAAGTTCAACTGGTACGTGGACGGCGTCGAGGTGCATAATGCCAAGACTAAACCAAGAGAGGAACAGTACAATTCAACCTATAGGGTCGTGAGCGTCCTGACAGTGCTGCATCAGGATTGGCTGAACGGCAAGGAGTATAAGTGCAAAGTGTCTAACAAGGCCCTGCCCGCTCCTATCGAGAAGACTATTAGCAAGGCAAAAGGGCAGCCACGGGAACCCCAGGTCTACACTCTGCCCCCTAGCAGAGACGAGCTGACCAAAAACCAGGTGTCCCTGACTTGTCTGGTGAAGGGCTTTTATCCTAGTGATATCGCTGTGGAGTGGGAATCAAATGGGCAGCCAGAAAACAATTACAAAACAACTCCACCCGTGCTGGACAGCGATGGGTCCTTCTTTCTGTATTCCAAACTGACTGTGGACAAGTCCAGATGGCAGCAGGGAAACGT | 115 |

TABLE B-continued

Clone Sequences

| Clone ID | Region | Sequence | SEQ ID NO |
|---|---|---|---|
| | | CTTCAGCTGTTCCGTGATGCACGAGGCCCTGCACAATCATTACACCCAGAAGTCTCTGAGTCTGTCACCCGGC | |
| | VH | EVQLLESGGGLVQPGGSLRLSCAVSGFSLSSYGVSWVRQAPGKGLEWIGAVNSGGSAYYADSFKGRSTISRDNSKNTVYLQMNSLRAEDTAVYYCARSGSGYPMDYHPIWGQGTLVTVSS | 116 |
| | IMGT CDR1 | GFSLSSYG | 20 |
| | IMGT CDR2 | VNSGGSA | 21 |
| | IMGT CDR3 | ARSGSGYPMDYHPI | 107 |
| | Chothia CDR1 | GFSLSSY | 23 |
| | Chothia CDR2 | NSGGS | 24 |
| | Chothia CDR3 | SGSGYPMDYHPI | 108 |
| | Kabat CDR1 | SYGVS | 26 |
| | Kabat CDR2 | AVNSGGSAYYADSFKG | 109 |
| | Kabat CDR3 | SGSGYPMDYHPI | 108 |
| | Contact CDR1 | SSYGVS | 28 |
| | Contact CDR2 | WIGAVNSGGSAY | 29 |
| | Contact CDR3 | ARSGSGYPMDYHP | 110 |
| | AbM CDR1 | GFSLSSYGVS | 31 |
| | AbM CDR2 | AVNSGGSAY | 32 |
| | AbM CDR3 | SGSGYPMDYHPI | 108 |
| 26448 | Full | DYQMTQSPSSVSASVGDRVTITCRASQSIGDWLAWYQQKPGKAPKLLIYEASTLASGVPSRFSGSGSGTDFTLTISSVQPEDAATYYCQQGYGRWHILNIFGGGTKVEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 117 |
| | Full | GACTATCAAATGACGCAGTCCCCGTCCTCCGTTTCCGCCTCAGTTGGTGACCGGGTTACAATCACTTGCAGAGCATCTCAGTCTATTGGTGATTGGCTGGCGTGGTATCAACAGAAGCCCGGCAAAGCCCCTAAACTCCTGATATACGAAGCATCAACGCTTGCTTCTGGAGTACCCTCCCGGTTTTCTGGGTCAGGAAGCGGCACGGATTTTACCCTGACTATCTCTTCTGTTCAGCCTGAGGATGCCGCAACCTATTATTGCCAACAGGGGTATGGCAGATGGCATATCCTAAATATTTTCGGTGGCGGGACCAAAGTTGAGGTTAAA | 118 |

TABLE B-continued

Clone Sequences

| Clone ID | Region | Sequence | SEQ ID NO |
|---|---|---|---|
| | | CGTACGGTAGCAGCTCCCAGCGTATTTATTTTTCCCCCTAGCGACGAACAGCTGAAGTCTGGGACAGCCAGTGTGGTCTGTCTGCTGAACAACTTCTACCCTAGAGAGGCTAAAGTGCAGTGGAAGGTCGATAACGCACTGCAGTCCGGAAATTCTCAGGAGAGTGTGACTGAACAGGACTCAAAAGATAGCACCTATTCCCTGTCAAGCACACTGACTCTGAGCAAGGCCGACTACGAGAAGCATAAAGTGTATGCTTGTGAAGTCACCCACCAGGGGCTGAGTTCACCAGTCACAAAATCATTCAACAGAGGGGAGTGC | |
| | VL | DYQMTQSPSSVSASVGDRVTITCRASQSIGDWLAWYQQKPGKAPKLLIYEASTLASGVPSRFSGSGSGTDFTLTISSVQPEDAATYYCQQGYGRWHILNIFGGGTKVEVK | 119 |
| | IMGT CDR1 | QSIGDW | 40 |
| | IMGT CDR2 | EAS | 41 |
| | IMGT CDR3 | QQGYGRWHILNI | 120 |
| | Chothia CDR1 | RASQSIGDWLA | 65 |
| | Chothia CDR2 | EASTLAS | 44 |
| | Chothia CDR3 | QQGYGR WHILNI | 120 |
| | Kabat CDR1 | RASQSIGDWLA | 65 |
| | Kabat CDR2 | EASTLAS | 44 |
| | Kabat CDR3 | QQGYGR WHILNI | 120 |
| | Contact CDR1 | GDWLAWY | 45 |
| | Contact CDR2 | LLIYEASTLA | 46 |
| | Contact CDR3 | QQGYGRWHILN | 121 |
| | AbM CDR1 | RASQSIGDWLA | 65 |
| | AbM CDR2 | EASTLAS | 44 |
| | AbM CDR3 | QQGYGRWHILNI | 120 |
| 26449 | Full | DYQMTQSPSSVSASVGDRVTITCRASQSIWYWLAWYQQKPGKAPKLLIYEASTLASGVPSRFSGSGSGTDFTLTISSVQPEDAATYYCQQGYGRSNVDNIFGGGTKVEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 122 |
| | Full | GACTATCAAATGACGCAGTCCCCGTCCTCCGTTTCCGCCTCAGTTGGTGACCGGGTTACAATCACTTGCAGAGCATCTCAGTCTATTTGGTATTGGCTGGCGTGGTATCAACAGAAGCCCGGCAAAGCCCCTAAACTCCTGATATACGAAGCATCAACGCTTGCTTCTGGAGTACCCTCCCGGTTTTCTGGGTCAGGAAGCGGCACGGATTTTACCCTGACTATCTCTTCTGTTCAGCCTGAGGATGCCGCAACCTATTATTGCCAACAGGGGTATGGCAGATCAAACGTGGATAATATTTTCGGTGGCGGGACCAAAGTTGAGGTTAAACGTACGGTAGCAGCTCCCAGCGTATTTATTTTTCCCCCTAGCGACGAACAGCTGAAGTCTGGGACAGCCAGTGTGGTCTGTCTGCTGAACAACTTCTACCCTAGAGAGGCTAAAGTGCAGTGGAAGGTCGATAACGCACTGCAGTCCGGAAATTCTCAGGAGAGTGTGACTGAACAGGACTCAAAAGATAGCACCTATTCCCTGTCAAGCACACTGACTCTGAGCAAGGCCGACTACGAGAAGCATAAAGTGTATGCTTGTGAAGTCACCCACCAGGGGCTGAGTTCACCAGTCACAAAATCATTCAACAGAGGGGAGTGC | 123 |
| | VL | DYQMTQSPSSVSASVGDRVTITCRASQSIWYWLAWYQQKPGKAPKLLIYEASTLASGVPSRFSGSGSGTDFTLTISSVQPEDAATYYCQQGYGRSNVDNIFGGGTKVEVK | 124 |
| | IMGT CDR1 | QSIWYW | 125 |
| | IMGT CDR2 | EAS | 41 |
| | IMGT CDR3 | QQGYGRSNVDNI | 42 |
| | Chothia CDR1 | RASQSIWYWLA | 126 |
| | Chothia CDR2 | EASTLAS | 44 |
| | Chothia CDR3 | QQGYGRSNVDNI | 42 |
| | Kabat CDR1 | RASQSIWYWLA | 126 |
| | Kabat CDR2 | EASTLAS | 44 |
| | Kabat CDR3 | QQGYGRSNVDNI | 42 |
| | Contact CDR1 | WYWLAWY | 127 |
| | Contact CDR2 | LLIYEASTLA | 46 |
| | Contact CDR3 | QQGYGRSNVDN | 47 |
| | AbM CDR1 | RASQSIWYWLA | 126 |
| | AbM CDR2 | EASTLAS | 44 |
| | AbM CDR3 | QQGYGRSNVDNI | 42 |
| 26450 | Full | DYQMTQSPSSVSASVGDRVTITCRASQSIWYWLAWYQQKPGKAPKLLIYEASTLASGVPSRFSGSGSGTDFTLTISSVQPEDAATYYCQQGYGRWHILNIFGGGTKVEVKRTVAAPSVFI | 128 |

TABLE B-continued

Clone Sequences

| Clone ID | Region | Sequence | SEQ ID NO |
|---|---|---|---|
| | | FPPSDEQLKSGTASVVCLLNNFYPREAKVQ WKVDNALQSGNSQESVTEQDSKDSTYSLSS TLTLSKADYEKHKVYACEVTHQGLSSPVTK SFNRGEC | |
| | Full | GATTATCAGATGACACAGAGTCCTTCCTCA GTCAGCGCATCTGTGGGAGATCGGGTTACA ATTACCTGCCGAGCATCTCAATCAATCTGG TATTGGCTGGCCTGGTACCAGCAAAAACCA GGAAAAGCACCTAAACTGTTGATTTATGAG GCCAGCACTCTTGCTAGTGGGGTCCCAAGT AGGTTCAGCGGCAGCGGTTCAGGGACGGAT TTTACCTTGACCATAAGTTCCGTTCAGCCA GAAGACGCGGCGACCTATTATTGCCAACAA GGGTACGGTAGATGGCACATTTTGAACATA TTCGGTGGAGGTACTAAGGTCGAGGTGAAG CGTACGGTAGCAGCTCCCAGCGTATTTATT TTTCCCCCTAGCGACGAACAGCTGAAGTCT GGGACAGCCAGTGTGGTCTGTCTGCTGAAC AACTTCTACCCTAGAGAGGCTAAAGTGCAG TGGAAGGTCGATAACGCACTGCAGTCCGGA AATTCTCAGGAGAGTGTGACTGAACAGGAC TCAAAAGATAGCACCTATTCCCTGTCAAGC ACACTGACTCTGAGCAAGGCCGACTACGAG AAGCATAAAGTGTATGCTTGTGAAGTCACC CACCAGGGGCTGAGTTCACCAGTCACAAAA TCATTCAACAGAGGGGAGTGC | 129 |
| | VL | DYQMTQSPSSVSASVGDRVTITCRASQSIW YWLAWYQQKPGKAPKLLIYEASTLASGVPS RFSGSGSGTDFTLTISSVQPEDAATYYCQQ GYGRWHILNIFGGGTKVEVK | 130 |
| | IMGT CDR1 | QSIWYW | 125 |
| | IMGT CDR2 | EAS | 41 |
| | IMGT CDR3 | QQGYGR WHILNI | 120 |
| | Chothia CDR1 | RASQSIWYWLA | 126 |
| | Chothia CDR2 | EASTLAS | 44 |
| | Chothia CDR3 | QQGYGR WHILNI | 120 |
| | Kabat CDR1 | RASQSIWYWLA | 126 |
| | Kabat CDR2 | EASTLAS | 44 |
| | Kabat CDR3 | QQGYGRWHILNI | 120 |
| | Contact CDR1 | WYWLAWY | 127 |
| | Contact CDR2 | LLIYEASTLA | 46 |
| | Contact CDR3 | QQGYGRWHILN | 121 |
| | AbM CDR1 | RASQSIWYWLA | 126 |
| | AbM CDR2 | EASTLAS | 44 |
| | AbM CDR3 | QQGYGRWHILNI | 120 |
| 27272 | Full | EVQLLESGGGLVQPGGSLRLSCAVSGFSLS SYGVSWVRQAPGKGLEWIGAVNSGGSAYYA DSFKGRSTISRDNSKNTVYLQMNSLRAEDT AVYYCARSGSGYPMDYLAIWGQGTLVTVSS ASTKGPSVFPLAPSSKSTSGGTAAL GCLVKDYFPEPVTVSWNSGALTSGVHTFPA VLQSSGLYSLSSVVTVPSSSLGTQTYICNV NHKPSNTKVDKKVEPKSCDKTHTCPPCPAP ELLGGPSVFLFPPKPKDTLMISRTPEVTCV VVDVSHEDPEVKFNWYVDGVEVHNAKTKPR EEQYNSTYRVVSVLTVLHQDWLNGKEYKCK VSNKALPAPIEKTISKAKGQPREPQVYTLP PSRDELTKNQVSLTCLVKGFYPSDIAVEWE SNGQPENNYKTTPPVLDSDGSFFLYS KLTVDKSRWQQGNVFSCSVMHEALHNHYTQ KSLSLSPGK | 131 |
| | Full | GAAGTGCAGCTCCTGGAGAGTGGAGGCGGC CTAGTCCAACCCGGTGGATCTCTGAGGCTC TCCTGTGCTGTTAGTGGTTTTTCACTCTCT TCCTATGGAGTCAGCTGGGTTAGACAGGCA CCCGGCAAGGGCTTGGAGTGGATCGGCGCT GTTAATTCCGGCGGTTCCGCCTACTATGCT GACTCTTTCAAAGGAAGAAGTACTATTTCC CGCGACAACTCTAAGAACACAGTGTATCTC CAAATGAACTCCCTGCGTGCCGAGGACACC GCCGTCTACTACTGCGCCCGGAGCGGCTCT GGCTATCCAATGGATTACCTGGCCATCTGG GGCCAAGGTACCCTGGTGACAGTCTCAAGC GCTAGCACCAAGGGCCCATCGGTCTTCCCC CTGGCACCCTCCTCCAAGAGCACCTCTGGG GGCACAGCGGCCCTGGGCTGCCTGGTCAAG GACTACTTCCCCGAACCGGTGACGGTGTCG TGGAACTCAGGCGCCCTGACCAGCGGCGTG CACACCTTCCCGGCCGTCCTACAGTCCTCA GGACTCTACTCCCTCAGCAGCGTGGTGACC GTGCCCTCCAGCAGCTTGGGCACCCAGACC TACATCTGCAACGTGAATCACAAGCCCAGC AACACCAAGGTGGACAAGAAGGTTGAGCCC AAATCTTGTGACAAAACTCACACATGCCCA CCGTGCCCAGCACCTGAACTCCTGGGGGGA CCGTCAGTCTTCCTCTTCCCCCCAAAACCC AAGGACACCCTCATGATCTCCCGGACCCCT GAGGTCACATGCGTGGTGGTGGACGTGAGC CACGAAGACCCTGAGGTCAAGTTCAACTGG TACGTGGACGGCGTGGAGGTGCATAATGCC AAGACAAAGCCGCGGGAGGAGCAGTACAAC AGCACGTACCGTGTGGTCAGCGTCCTCACC GTCCTGCACCAGGACTGGCTGAATGGCAAG GAGTACAAGTGCAAGGTCTCCAACAAAGCC CTCCCAGCCCCCATCGAGAAAACCATCTCC AAAGCCAAAGGGCAGCCCCGAGAACCACAG GTGTACACCCTGCCCCCATCCCGGGACGAG CTGACCAAGAACCAGGTCAGCCTGACCTGC CTGGTCAAAGGCTTCTATCCCAGCGACATC GCCGTGGAGTGGGAGAGCAATGGGCAGCCG GAGAACAACTACAAGACCACGCCTCCCGTG CTGGACTCCGACGGCTCCTTCTTCCTCTAC AGCAAGCTCACCGTGGACAAGAGCAGGTGG CAGCAGGGGAACGTCTTCTCATGCTCCGTG ATGCATGAGGCTCTGCACAACCACTACACG CAGAAGAGCCTCTCCCTGTCTCCGGGCAAA | 132 |
| | VH | EVQLLESGGGLVQPGGSLRLSCAVSGFSLS SYGVSWVRQAPGKGLEWIGAVNSGGSAYYA DSFKGRSTISRDNSKNTVYLQMNSLRAEDT AVYYCARSGSGYPMDYLAIWGQGTL VTVSS | 133 |

TABLE B-continued

Clone Sequences

| Clone ID | Region | Sequence | SEQ ID NO |
|---|---|---|---|
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSFKG | 109 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |
| 27273 | Full | EVQLLESGGGLVQPGGSLRLSCAVSGFSLSLYGVSWVRQAPGKGLEWIGSVNSGGSAYYADSVKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 134 |
| | Full | GAGGTTCAGCTTCTCGAGTCTGGCGGTGGCCTGGTTCAACCTGGTGGTAGTCTCCGACTGAGCTGTGCTGTTTCGGGCTTCAGCCTGAGCCTTTACGGCGTGTCCTGGGTCAGGCAGGCTCCAGGCAAGGGCCTGGAGTGGATCGGCTCCGTGAACAGCGGTGGAAGTGCCTACTATGCTGATTCTGTGAAGGGCCGAAGCACGATTTCTCGCGATAACAGCAAGAATACTGTGTATTTGCAAATGAACTCTCTGCGTGCCGAGGATACCGCTGTGTACTACTGCGCTCGATCGGGGTCCGGTTACCCTATGGATTACCTGGCCATCTGGGGTCAGGGTACCCTTGTTACTGTATCCTCTGCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCCGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAGGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGACGAGCTGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGCAAA | 135 |
| | VH | EVQLLESGGGLVQPGGSLRLSCAVSGFSLSLYGVSWVRQAPGKGLEWIGSVNSGGSAYYADSVKGRSTISRDNSKNTVYLQMNSLRAEDTAVYYCARSGSGYPMDYLAIWGQGTLVTVSS | 136 |
| | IMGT CDR1 | GFSLSLYG | 92 |
| | IMGT CDR2 | VNSGGSA | 21 |
| | IMGT CDR3 | ARSGSGYPMDYLAI | 22 |
| | Chothia CDR1 | GFSLSLY | 93 |
| | Chothia CDR2 | NSGGS | 24 |
| | Chothia CDR3 | SGSGYPMDYLAI | 25 |
| | Kabat CDR1 | LYGVS | 94 |
| | Kabat CDR2 | SVNSGGSAYYADSVKG | 137 |
| | Kabat CDR3 | SGSGYPMDYLAI | 25 |
| | Contact CDR1 | SLYGVS | 95 |
| | Contact CDR2 | WIGSVNSGGSAY | 138 |
| | Contact CDR3 | ARSGSGYPMDYLA | 30 |

TABLE B-continued

Clone Sequences

| Clone ID | Region | Sequence | SEQ ID NO |
|---|---|---|---|
| | AbM CDR1 | GFSLSLYGVS | 96 |
| | AbM CDR2 | SVNSGGSAY | 139 |
| | AbM CDR3 | SGSGYPMDYLAI | 25 |
| 27274 | Full | DYQMTQSPSSVSASVGDRVTITCRASQSIWYWLAWYQQKPGKAPKLLIYEASTLASGVPSRFSGSGSGTDFTLTISSVQPEDAATYYCQQGYGRWHILNIFGGGTKVEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 140 |
| | Full | GACTACCAGATGACCCAGAGCCCAAGTTCAGTATCGGCCTCCGTTGGTGACAGAGTCACCATCACCTGCCGGGCCAGCCAATCCATCTGGTACTGGCTGGCCTGGTATCAACAAAAGCCGGGCAAAGCACCCAAGCTCCTCATCTACGAGGCTAGCACACTGGCCTCCGGCGTTCCTTCGCGATTCAGTGGTTCCGGGTCTGGAACAGACTTCACTTTGACCATTTCTTCTGTGCAACCCGAGGATGCTGCAACATATTACTGCCAACAAGGCTATGGCCGGTGGCACATTCTGAACATCTTTGGCGGCGGAACTAAGGTTGAAGTCAAACGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT | 141 |
| | VL | DYQMTQSPSSVSASVGDRVTITCRASQSIWYWLAWYQQKPGKAPKLLIYEASTLASGVPSRFSGSGSGTDFTLTISSVQPEDAATYYCQQGYGRWHILNIFGGGTKVEVK | 130 |
| | IMGT CDR1 | QSIWYW | 125 |
| | IMGT CDR2 | EAS | 41 |
| | IMGT CDR3 | QQGYGRWHILNI | 120 |
| | Chothia CDR1 | RASQSIWYWLA | 126 |
| | Chothia CDR2 | EASTLAS | 44 |
| | Chothia CDR3 | QQGYGRWHILNI | 120 |
| | Kabat CDR1 | RASQSIWYWLA | 126 |
| | Kabat CDR2 | EASTLAS | 44 |
| | Kabat CDR3 | QQGYGRWHILNI | 120 |

TABLE B-continued

Clone Sequences

| Clone ID | Region | Sequence | SEQ ID NO |
|---|---|---|---|
| | Contact CDR1 | WYWLAWY | 127 |
| | Contact CDR2 | LLIYEASTLA | 46 |
| | Contact CDR3 | QQGYGRWHILN | 121 |
| | AbM CDR1 | RASQSIWYWLA | 126 |
| | AbM CDR2 | EASTLAS | 44 |
| | AbM CDR3 | QQGYGRWHILNI | 120 |
| 27275 | Full | EVQLLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 142 |
| | Full + C-terminal Lys | EVQLLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 157 |
| | Full | GAGGTCCAGTTGCTGGAATCAGGAGGTGGACTCGTGCAGCCTGGGGGTTCCCTGCGCTTGTCTTGCGCTGTCAGCGGTTTTAGCTTATCTTCATACGGTGTAAGTTGGGTTCGGCAGGCTCCTGGCAAAGGTCTGGAATGGATCGGGGCTGTAAACAGCGGGGGGTCCGCCTACTATGCTGATTCTGTTAAGGGGAGGTCCACCATTAGCAGAGATAATTCCAAGAACACCGTTTATCTCCAGATGAACTCCTTGAGGGCGGAGGACACTGCTGTCTATTATTGTGCGCGGTCAGGCAGCGGATACCCGATGGACTATCTGGCGATCTGGGGCCAGGGAACCCTTGTGACAGTCTCTTCCGCTAGCACTAAGGGGCCTTCCGTGTTTCCACTGGCTCCCTCTAGTAAATCCACCTCTGGAGGCACAGCTGCACTGGGATGTCTGGTGAAGGATTACTTCCCTGAACCAGTCACAGTGAGTTGGAACTCAGGGGCTCTGACAAGTGGAGTCCATACTTTTCCCGCAGTGCTGCAGTCAAGCGGACTGTACTCCCTGTCCTCTGTGGTCACCGTGCCTAGTTCAAGCCTGGGCACCCAGACATATATCTGCAACGTGAATCACAAGCCATCAAATACAAAAGTCGACAAGAAAGTGGAGCCC | 143 |

TABLE B-continued

Clone Sequences

| Clone ID | Region | Sequence | SEQ ID NO |
|---|---|---|---|
| | | AAGAGCTGTGATAAAACTCATACCTGCCCACCTTGTCCGGCTCCAGAGCTGCTCGGCGGACCATCCGTGTTCCTGTTTCCTCCAAAGCCTAAAGATACACTGATGATTAGCCGCACTCCCGAAGTCACCTGTGTGGTCGTGGACGTGTCCCACGAGGACCCCGAAGTCAAGTTCAACTGGTACGTGGACGGCGTCGAGGTGCATAATGCCAAGACTAAACCAAGAGAGGAACAGTACAATTCAACCTATAGGGTCGTGAGCGTCCTGACAGTGCTGCATCAGGATTGGCTGAACGGCAAGGAGTATAAGTGCAAAGTGTCTAACAAGGCCCTGCCCGCTCCTATCGAGAAGACTATTAGCAAGGCAAAAGGGCAGCCACGGGAACCCCAGGTCTACACTCTGCCCCCTAGCAGAGACGAGCTGACCAAAAACCAGGTGTCCCTGACTTGTCTGGTGAAGGGCTTTTATCCTAGTGATATCGCTGTGGAGTGGGAATCAAATGGGCAGCCAGAAAACAATTACAAAACAACTCCACCCGTGCTGGACAGCGATGGGTCCTTCTTTCTGTATTCCAAACTGACTGTGGACAAGTCCAGATGGCAGCAGGGAAACGTCTTCAGCTGTTCCGTGATGCACGAGGCCCTGCACAATCATTACACCCAGAAGTCTCTGAGTCTGTCACCCGGC | |
| | VH | EVQLLESGGGLVQPGGSLRLSCAVSGFSLSSYGVSWVRQAPGKGLEWIGAVNSGGSAYYADSVKGRSTISRDNSKNTVYLQMNSLRAEDTAVYYCARSGSGYPMDYLAIWGQGTLVTVSS | 50 |
| | IMGT CDR1 | GFSLSSYG | 20 |
| | IMGT CDR2 | VNSGGSA | 21 |
| | IMGT CDR3 | ARSGSGYPMDYLAI | 22 |
| | Chothia CDR1 | GFSLSSY | 23 |
| | Chothia CDR2 | NSGGS | 24 |
| | Chothia CDR3 | SGSGYPMDYLAI | 25 |
| | Kabat CDR1 | SYGVS | 26 |
| | Kabat CDR2 | AVNSGGSAYYADSVKG | 51 |
| | Kabat CDR3 | SGSGYPMDYLAI | 25 |
| | Contact CDR1 | SSYGVS | 28 |
| | Contact CDR2 | WIGAVNSGGSAY | 29 |
| | Contact CDR3 | ARSGSGYPMDYLA | 30 |
| | AbM CDR1 | GFSLSSYGVS | 31 |
| | AbM CDR2 | AVNSGGSAY | 32 |
| | AbM CDR3 | SGSGYPMDYLAI | 25 |

TABLE B-continued

Clone Sequences

| Clone ID | Region | Sequence | SEQ ID NO |
|---|---|---|---|
| 27276 | Full | DYQMTQSPSSVSASVGDRVTITCRASQSIGDWLAWYQQKPGKAPKLLIYEASTLASGVPSRFSGSGSGTDFTLTISSVQPEDAATYYCQQGYGRSNVDNIFGGGTKVEVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 144 |
| | Full | GACTATCAAATGACGCAGTCCCCGTCCTCCGTTTCCGCCTCAGTTGGTGACCGGGTTACAATCACTTGCAGAGCATCTCAGTCTATTGGTGATTGGCTGGCGTGGTATCAACAGAAGCCCGGCAAAGCCCCTAAACTCCTGATATACGAAGCATCAACGCTTGCTTCTGGAGTACCCTCCCGGTTTTCTGGGTCAGGAAGCGGCACGGATTTTACCCTGACTATCTCTTCTGTTCAGCCTGAGGATGCCGCAACCTATTATTGCCAACAGGGGTATGGCAGATCAAACGTGGATAATATTTTCGGTGGCGGGACCAAAGTTGAGGTTAAACGTACGGTGGCGGCGCCCAGTGTCTTCATTTTTCCCCCTAGCGACGAACAGCTGAAGTCTGGGACAGCCAGTGTGGTCTGTCTGCTGAACAACTTCTACCCTAGAGAGGCTAAAGTGCAGTGGAAGGTCGATAACGCACTGCAGTCCGGAAATTCTCAGGAGAGTGTGACTGAACAGGACTCAAAAGATAGCACCTATTCCCTGTCAAGCACACTGACTCTGAGCAAGGCCGACTACGAGAAGCATAAAGTGTATGCTTGTGAAGTCACCCACCGGAGTGCAGGGGCTGAGTTCACCAGTCACAAAATCATTCAACAGAGG | 145 |
| | VL | DYQMTQSPSSVSASVGDRVTITCRASQSIGDWLAWYQQKPGKAPKLLIYEASTLASGVPSRFSGSGSGTDFTLTISSVQPEDAATYYCQQGYGRSNVDNIFGGGTKVEVK | 64 |
| | IMGT CDR1 | QSIGDW | 40 |
| | IMGT CDR2 | EAS | 41 |
| | IMGT CDR3 | QQGYGRSNVDNI | 42 |
| | Chothia CDR1 | RASQSIGDWLA | 65 |
| | Chothia CDR2 | EASTLAS | 44 |
| | Chothia CDR3 | QQGYGRSNVDNI | 42 |
| | Kabat CDR1 | RASQSIGDWLA | 65 |
| | Kabat CDR2 | EASTLAS | 44 |
| | Kabat CDR3 | QQGYGRSNVDNI | 42 |
| | Contact CDR1 | GDWLAWY | 45 |
| | Contact CDR2 | LLIYEASTLA | 46 |
| | Contact CDR3 | QQGYGRSNVDN | 47 |

TABLE B-continued

Clone Sequences

| Clone ID | Region | Sequence | SEQ ID NO |
|---|---|---|---|
| | AbM CDR1 | RASQSIGDWLA | 65 |
| | AbM CDR2 | EASTLAS | 44 |
| | AbM CDR3 | QQGYGRSNVDNI | 42 |

SEQUENCE LISTING

```
Sequence total quantity: 161
SEQ ID NO: 1            moltype = AA  length = 257
FEATURE                 Location/Qualifiers
source                  1..257
                        mol_type = protein
                        organism = Homo sapiens
SEQUENCE: 1
MAQRMTTQLL LLLVWVAVVG EAQTRIAWAR TELLNVCMNA KHHKEKPGPE DKLHEQCRPW  60
RKNACCSTNT SQEAHKDVSY LYRFNWNHCG EMAPACKRHF IQDTCLYECS PNLGPWIQQV  120
DQSWRKERVL NVPLCKEDCE QWWEDCRTSY TCKSNWHKGW NWTSGFNKCA VGAACQPFHF  180
YFPTPTVLCN EIWTHSYKVS NYSRGSGRCI QMWFDPAQGN PNEEVARFYA AAMSGAGPWA  240
AWPFLLSLAL MLLWLLS                                                 257

SEQ ID NO: 2            moltype = AA  length = 257
FEATURE                 Location/Qualifiers
source                  1..257
                        mol_type = protein
                        organism = Macaca fascicularis
SEQUENCE: 2
MAQRMTTQLL LLLVWVAVVG EAQTRTTRAR TELLNVCMNA KHHKEKPGPE DKLHEQCRPW  60
KKNACCSTNT SQEAHKDVSY LYRFNWNHCG EMAPACKRHF IQDTCLYECS PNLGPWIQQV  120
DQSWRKERVL NVPLCKEDCE QWWEDCRTSY TCKSNWHKGW NWTSGFNKCP VGAACQPFHF  180
YFPTPTVLCN EIWTYSYKVS NYSRGSGRCI QMWFDPAQGN PNEEVARFYA AAMSGAGPWA  240
AWPLLLSLAL TLLWLLS                                                 257

SEQ ID NO: 3            moltype = AA  length = 5
FEATURE                 Location/Qualifiers
source                  1..5
                        mol_type = protein
                        note = HCDR1
                        organism = synthetic construct
VARIANT                 1
                        note = X is S or L
SEQUENCE: 3
XYGVS                                                              5

SEQ ID NO: 4            moltype = AA  length = 5
FEATURE                 Location/Qualifiers
source                  1..5
                        mol_type = protein
                        note = HCDR2
                        organism = synthetic construct
SEQUENCE: 4
NSGGS                                                              5

SEQ ID NO: 5            moltype = AA  length = 12
FEATURE                 Location/Qualifiers
source                  1..12
                        mol_type = protein
                        note = HCDR3
                        organism = synthetic construct
VARIANT                 10
                        note = X is L or H
VARIANT                 11
                        note = X is A or P
SEQUENCE: 5
SGSGYPMDYX XI                                                      12

SEQ ID NO: 6            moltype = AA  length = 6
FEATURE                 Location/Qualifiers
source                  1..6
                        mol_type = protein
```

```
                        note = LCDR1
                        organism = synthetic construct
VARIANT                 4
                        note = X is G or W
VARIANT                 5
                        note = X is D or Y
SEQUENCE: 6
QSIXXW                                                                    6

SEQ ID NO: 7            moltype =   length =
SEQUENCE: 7
000

SEQ ID NO: 8            moltype = AA  length = 11
FEATURE                 Location/Qualifiers
source                  1..11
                        mol_type = protein
                        note = LCDR3
                        organism = synthetic construct
VARIANT                 7
                        note = X is S or W
VARIANT                 8
                        note = X is N or H
VARIANT                 9
                        note = X is V or I
VARIANT                 10
                        note = X is D or L
SEQUENCE: 8
QQGYGRXXXX N                                                              11

SEQ ID NO: 9            moltype = AA  length = 10
FEATURE                 Location/Qualifiers
source                  1..10
                        mol_type = protein
                        note = HCDR1
                        organism = synthetic construct
VARIANT                 6
                        note = X is S or L
SEQUENCE: 9
GFSLSXYGVS                                                                10

SEQ ID NO: 10           moltype = AA  length = 9
FEATURE                 Location/Qualifiers
source                  1..9
                        mol_type = protein
                        note = HCDR2
                        organism = synthetic construct
VARIANT                 1
                        note = X is S or A
VARIANT                 2
                        note = X is V or L
SEQUENCE: 10
XXNSGGSAY                                                                 9

SEQ ID NO: 11           moltype = AA  length = 12
FEATURE                 Location/Qualifiers
source                  1..12
                        mol_type = protein
                        note = HCDR3
                        organism = synthetic construct
VARIANT                 10
                        note = X is L or H
VARIANT                 11
                        note = X is A or P
SEQUENCE: 11
SGSGYPMDYX XI                                                             12

SEQ ID NO: 12           moltype = AA  length = 11
FEATURE                 Location/Qualifiers
source                  1..11
                        mol_type = protein
                        note = LCDR1
                        organism = synthetic construct
VARIANT                 1
                        note = X is R or Q
VARIANT                 7
                        note = X is G or W
VARIANT                 8
                        note = X is D or Y
```

```
SEQUENCE: 12
XASQSIXXWL A                                                11

SEQ ID NO: 13          moltype = AA  length = 7
FEATURE                Location/Qualifiers
source                 1..7
                       mol_type = protein
                       note = LCDR2
                       organism = synthetic construct
SEQUENCE: 13
EASTLAS                                                     7

SEQ ID NO: 14          moltype = AA  length = 12
FEATURE                Location/Qualifiers
source                 1..12
                       mol_type = protein
                       note = LCDR3
                       organism = synthetic construct
VARIANT                7
                       note = X is S or W
VARIANT                8
                       note = X is N or H
VARIANT                9
                       note = X is V or I
VARIANT                10
                       note = X is D or L
SEQUENCE: 14
QQGYGRXXXX NI                                               12

SEQ ID NO: 15          moltype = AA  length = 227
FEATURE                Location/Qualifiers
source                 1..227
                       mol_type = protein
                       note = Human FRa
                       organism = synthetic construct
SEQUENCE: 15
RIAWARTELL NVCMNAKHHK EKPGPEDKLH EQCRPWRKNA CCSTNTSQEA HKDVSYLYRF  60
NWNHCGEMAP ACKRHFIQDT CLYECSPNLG PWIQQVDQSW RKERVLNVPL CKEDCEQWWE  120
DCRTSYTCKS NWHKGWNWTS GFNKCAVGAA CQPFHFYFPT PTVLCNEIWT HSYKVSNYSR  180
GSGRCIQMWF DPAQGNPNEE VARFYAAAMG GGSGGGSHHH HHHHHHH             227

SEQ ID NO: 16          moltype = AA  length = 217
FEATURE                Location/Qualifiers
source                 1..217
                       mol_type = protein
                       note = Human IgG1 Fc Sequence
                       organism = Homo sapiens
SEQUENCE: 16
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPGK                       217

SEQ ID NO: 17          moltype = AA  length = 448
FEATURE                Location/Qualifiers
source                 1..448
                       mol_type = protein
                       note = Clone ID 18894 Full
                       organism = synthetic construct
SEQUENCE: 17
QSVKESEGGL FKPTDTLTLT CTVSGFSLSS YGVSWVRQAP GNGLEWIGAV NSGGSAYYAN  60
WAKSRSTITR NTNLFTVTLK MTSLAVADTA TYFCARSGSG YPMDYLAIWG PGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                  448

SEQ ID NO: 18          moltype = DNA  length = 1344
FEATURE                Location/Qualifiers
source                 1..1344
                       mol_type = other DNA
                       note = Clone ID 18894 Full
                       organism = synthetic construct
SEQUENCE: 18
cagagcgtga aggagtccga gggcggcctg ttcaagccca ccgacacact gaccctgaca  60
tgcaccgtgt ctggctttag cctgagctcc tacggcgtgt cttgggtgcg gcaggccccc  120
ggaaacggac tggagtggat cggagccgtg aacagcggcg gctctgccta ctatgccaac  180
```

```
tgggccaagt cccggtctac aatcaccaga aacacaaatc tgttcacagt gaccctgaag  240
atgacctccc tggccgtggc agacacagca acctattttt gtgcaaggag cggctccgga  300
tacccaatgg attatctggc catctggggc cctggcacac tggtgaccgt gtctagcgct  360
agcactaagg ggccttccgt gtttccactg gctccctcta gtaaatccac ctctggaggc  420
acagctgcac tgggatgtct ggtgaaggat tacttccctg aaccagtcac agtgagttgg  480
aactcagggg ctctgacaag tggagtccat acttttcccg cagtgctgca gtcaagcgga  540
ctgtactccc tgtcctctgt ggtcaccgtg cctagttcaa gcctgggcac ccagacatat  600
atctgcaacg tgaatcacaa gccatcaaat acaaaagtcg acaagaaagt ggagcccaag  660
agctgtgata aaactcatac ctgcccacct tgtccggcgc cagaactgct gggaggacca  720
agcgtgttcc tgtttccacc caagcctaaa gacaccctga tgatttcccg gactcctgag  780
gtcacctgcg tggtcgtgga cgtgtctcac gaggaccccg aagtcaagtt caactggtac  840
gtggatggcg tcgaagtgca taatgccaag accaaacccc gggaggaaca gtacaactct  900
acctatagag tcgtgagtgt cctgacagtg ctgcaccagg actggctgaa tgggaaggag  960
tataagtgta aagtgagcaa caaagccctg cccgccccaa tcgaaaaaac aatctctaaa  1020
gcaaaaggac agcctcgcga accacaggtg tacactctgc ctccatctcg ggacgagctg  1080
actaagaacc aggtcagtct gacctgtctg gtgaaaggat tctatcccag cgatatcgct  1140
gtggagtggg aatccaatgg ccagcctgag aacaattaca agaccacacc ccctgtgctg  1200
gactctgatg gcagtttctt tctgtatagt aagctgaccg tcgataaatc acgatggcag  1260
caggggaacg tgttcagctg ttcagtgatg cacgaagccc tgcacaacca ttacacccag  1320
aagagcctga gcctgtctcc cggc                                        1344

SEQ ID NO: 19          moltype = AA  length = 119
FEATURE                Location/Qualifiers
source                 1..119
                       mol_type = protein
                       note = Clone ID 18894, 18901, 18908 VH
                       organism = synthetic construct
SEQUENCE: 19
QSVKESEGGL FKPTDTLTLT CTVSGFSLSS YGVSWVRQAP GNGLEWIGAV NSGGSAYYAN  60
WAKSRSTITR NTNLFTVTLK MTSLAVADTA TYFCARSGSG YPMDYLAIWG PGTLVTVSS   119

SEQ ID NO: 20          moltype = AA  length = 8
FEATURE                Location/Qualifiers
source                 1..8
                       mol_type = protein
                       note = Clone ID 18894, 18901, 18908, 22046, 22047, 22048,
                        22049, 22057, 22058, 22059, 22060, 22874, 22875, 22876,
                        22877, 22878, 26447, 27272, 27275 IMGT CDR1
                       organism = synthetic construct
SEQUENCE: 20
GFSLSSYG                                                          8

SEQ ID NO: 21          moltype = AA  length = 7
FEATURE                Location/Qualifiers
source                 1..7
                       mol_type = protein
                       note = Clone ID 18894, 18901, 18908, 22046, 22047, 22048,
                        22049, 22057, 22058, 22059, 22060, 22874, 22875, 22876,
                        22877, 22878, 26434, 26445, 26446, 26447, 27272, 27273,
                        27275 IMGT CDR2
                       organism = synthetic construct
SEQUENCE: 21
VNSGGSA                                                           7

SEQ ID NO: 22          moltype = AA  length = 14
FEATURE                Location/Qualifiers
source                 1..14
                       mol_type = protein
                       note = 18894, 18901, 18908, 22046, 22047, 22048, 22049,
                        22057, 22058, 22059, 22060, 22874, 22875, 22876,  22877,
                        22878, 26434, 26443, 26446, 27272, 27273, 27275 IMGT CDR3
                       organism = synthetic construct
SEQUENCE: 22
ARSGSGYPMD YLAI                                                   14

SEQ ID NO: 23          moltype = AA  length = 7
FEATURE                Location/Qualifiers
source                 1..7
                       mol_type = protein
                       note = Clone ID 18894, 18901, 18908, 22046, 22047, 22048,
                        22049, 22057, 22058, 22059, 22060, 22874, 22875, 22876,
                        22877, 22878, 26447, 27272, 27275 Chothia CDR1
                       organism = synthetic construct
SEQUENCE: 23
GFSLSSY                                                           7

SEQ ID NO: 24          moltype = AA  length = 5
FEATURE                Location/Qualifiers
source                 1..5
```

-continued

```
                        mol_type = protein
                        note = Clone ID 18894, 18901, 18908,22046, 22047, 22048,
                         22049, 22057, 22058, 22059, 22060, 22874, 22875, 22876,
                         22877, 22878, 26434, 26443, 26445, 26446, 26447, 27272,
                         27273, 27275 Chothia CDR2
                        organism = synthetic construct
SEQUENCE: 24
NSGGS                                                               5

SEQ ID NO: 25           moltype = AA  length = 12
FEATURE                 Location/Qualifiers
source                  1..12
                        mol_type = protein
                        note = Clone ID 18894, 18901, 18908, 22046, 22047, 22048,
                         22049, 22057, 22058, 22059, 22060, 22874, 22875, 22876,   2
                         2877, 22878, 26434, 26443, 26446, 27272, 27273, 27275
                         Chothia, AbM and Kabat CDR3
                        organism = synthetic construct
SEQUENCE: 25
SGSGYPMDYL AI                                                       12

SEQ ID NO: 26           moltype = AA  length = 5
FEATURE                 Location/Qualifiers
source                  1..5
                        mol_type = protein
                        note = Clone ID 18894, 18901,18908,22046,22047, 22048,
                         22049, 22057, 22058, 22059, 22060, 22874, 22875, 22876,   2
                         2877, 22878, 26447, 27272, 27275 Kabat CDR1
                        organism = synthetic construct
SEQUENCE: 26
SYGVS                                                               5

SEQ ID NO: 27           moltype = AA  length = 16
FEATURE                 Location/Qualifiers
source                  1..16
                        mol_type = protein
                        note = Clone ID 18894, 18901, 18908 Kabat CDR2
                        organism = synthetic construct
SEQUENCE: 27
AVNSGGSAYY ANWAKS                                                   16

SEQ ID NO: 28           moltype = AA  length = 6
FEATURE                 Location/Qualifiers
source                  1..6
                        mol_type = protein
                        note = Clone ID 18894, 18901, 18908, 22046, 22047, 22048,
                         22049, 22057, 22058, 22059, 22060, 22874, 22875, 22876,
                         22877, 22878, 26447, 27272, 27275 Contact CDR1
                        organism = synthetic construct
SEQUENCE: 28
SSYGVS                                                              6

SEQ ID NO: 29           moltype = AA  length = 12
FEATURE                 Location/Qualifiers
source                  1..12
                        mol_type = protein
                        note = Clone ID 18894, 18901, 18908, 22046, 22047, 22048,
                         22049, 22057, 22058, 22059, 22060, 22874, 22875, 22876,
                         22877, 22878, 26434, 26445, 26446, 26447, 27272, 27275
                         Contact CDR2
                        organism = synthetic construct
SEQUENCE: 29
WIGAVNSGGS AY                                                       12

SEQ ID NO: 30           moltype = AA  length = 13
FEATURE                 Location/Qualifiers
source                  1..13
                        mol_type = protein
                        note = Clone ID 18894, 18901, 18908, 22046, 22047, 22048,
                         22049, 22057, 22058, 22059, 22060, 22874, 22875, 22876,
                         22877, 22878, 26434, 26445, 26446, 26447, 27272, 27275
                         Contact CDR3
                        organism = synthetic construct
SEQUENCE: 30
ARSGSGYPMD YLA                                                      13

SEQ ID NO: 31           moltype = AA  length = 10
FEATURE                 Location/Qualifiers
source                  1..10
```

```
                        mol_type = protein
                        note = Clone ID 18894, 18901, 18908, 22046, 22047, 22048,
                         22049, 22057, 22058, 22059, 22060, 22874, 22875, 22876,
                         22877, 22878, 26447, 27272, 27275 AbM CDR1
                        organism = synthetic construct
SEQUENCE: 31
GFSLSSYGVS                                                        10

SEQ ID NO: 32           moltype = AA  length = 9
FEATURE                 Location/Qualifiers
source                  1..9
                        mol_type = protein
                        note = Clone ID 18894, 18901, 18908, 22046, 22047, 22048,
                         22049, 22057, 22058, 22059, 22060, 22874, 22875, 22876,
                         22877, 22878, 26434, 26445, 26446, 26447, 27272, 27275 AbM
                         CDR2
                        organism = synthetic construct
SEQUENCE: 32
AVNSGGSAY                                                         9

SEQ ID NO: 33           moltype = AA  length = 448
FEATURE                 Location/Qualifiers
source                  1..448
                        mol_type = protein
                        note = Clone ID 18901 Full
                        organism = synthetic construct
SEQUENCE: 33
QSVKESEGGL FKPTDTLTLT CTVSGFSLSS YGVSWVRQAP GNGLEWIGAV NSGGSAYYAN  60
WAKSRSTITR NTNLFTVTLK MTSLAVADTA TYFCARSGSG YPMDYLAIWG PGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YVYPPSRDEL  360
TKNQVSLTCL VKGFYPSDIA VEWESNGQPE NNYKTTPPVL DSDGSFALVS KLTVDKSRWQ  420
QGNVFSCSVM HEALHNHYTQ KSLSLSPG                                    448

SEQ ID NO: 34           moltype = DNA  length = 1344
FEATURE                 Location/Qualifiers
source                  1..1344
                        mol_type = other DNA
                        note = Clone ID 18901 Full
                        organism = synthetic construct
SEQUENCE: 34
cagagcgtga aggagtccga gggcggcctg ttcaagccca ccgacacact gaccctgaca  60
tgcaccgtgt ctggctttag cctgagctcc tacggcgtgt cttgggtgcg gcaggccccc  120
ggaaacggac tggagtggat cggagccgtg aacagcggcg gctctgccta ctatgccaac  180
tgggccaagt cccggtctac aatcaccaga aacacaaatc tgttcacagt gaccctgaag  240
atgacctccc tggccgtggc agacacagca acctattttt gtgcaaggag cggctccgga  300
tacccaatgg attatctggc catctggggc cctggcacac tggtgaccgt gtctagcgct  360
agcactaagg ggccttccgt gtttccactg gctccctcta gtaaatccac ctctggaggc  420
acagctgcac tgggatgtct ggtgaaggat tacttccctg aaccagtcac agtgagttgg  480
aactcagggg ctctgacaag tggagtccat acttttcccg cagtgctgca gtcaagcgga  540
ctgtactccc tgtcctctgt ggtcaccgtg cctagttcaa gcctgggcac ccagacatat  600
atctgcaacg tgaatcacaa gccatcaaat acaaaagtcg acaagaaagt ggagcccaag  660
agctgtgata aaactcatac ctgcccacct tgtccggcgc cagaactgct gggaggacca  720
agcgtgttcc tgtttccacc caagcctaaa gacaccctga tgatttcccg gactcctgag  780
gtcacctgcg tggtcgtgga cgtgtctcac gaggaccccg aagtcaagtt caactggtac  840
gtggatggcg tcgaagtgca taatgccaag accaaacccc gggaggaaca gtacaactct  900
acctatagag tcgtgagtgt cctgacagtg ctgcaccagg actggctgaa tgggaaggag  960
tataagtgta aagtgagcaa caaagccctg cccgccccaa tcgaaaaaac aatctctaaa  1020
gcaaaaggac agcctcgcga accacaggtc tacgtctacc ccccatcaag agatgaactg  1080
acaaaaaatc aggtctctct gacatgcctg gtcaaaggat tctacccttc cgacatcgcc  1140
gtggagtggg aaagtaacgg ccagcccgag aacaattaca agaccacacc ccctgtcctg  1200
gactctgatg ggagtttcgc tctggtgtca aagctgaccg tcgataaaag ccggtggcag  1260
cagggcaatg tgtttagctg ctccgtcatg cacgaagccc tgcacaatca ctacacacag  1320
aagtccctga gcctgagccc tggc                                        1344

SEQ ID NO: 35           moltype = AA  length = 448
FEATURE                 Location/Qualifiers
source                  1..448
                        mol_type = protein
                        note = Clone ID 18908 Full
                        organism = synthetic construct
SEQUENCE: 35
QSVKESEGGL FKPTDTLTLT CTVSGFSLSS YGVSWVRQAP GNGLEWIGAV NSGGSAYYAN  60
WAKSRSTITR NTNLFTVTLK MTSLAVADTA TYFCARSGSG YPMDYLAIWG PGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
```

-continued

```
TYRVVSVLTV LHQDWLNGKE YKCKVSNKAL PAPIEKTISK AKGQPREPQV YVLPPSRDEL  360
TKNQVSLLCL VKGFYPSDIA VEWESNGQPE NNYLTWPPVL DSDGSFFLYS KLTVDKSRWQ  420
QGNVFSCSVM HEALHNHYTQ KSLSLSPG                                     448

SEQ ID NO: 36          moltype = DNA  length = 1344
FEATURE                Location/Qualifiers
source                 1..1344
                       mol_type = other DNA
                       note = Clone ID 18908 Full
                       organism = synthetic construct
SEQUENCE: 36
cagagcgtga aggagtccga gggcggcctg ttcaagccca ccgacacact gaccctgaca  60
tgcaccgtgt ctggctttag cctgagctcc tacggcgtgt cttgggtgcg gcaggccccc  120
ggaaacggac tggagtggat cggagccgtg aacagcggcg gctctgccta ctatgccaac  180
tgggccaagt cccggtctac aatcaccaga aacacaaatc tgttcacagt gaccctgaag  240
atgacctccc tggccgtggc agacacagca acctattttt gtgcaaggag cggctccgga  300
tacccaatgg attatctggc catctggggc cctggcacac tggtgaccgt gtctagcgct  360
agcactaagg ggccttccgt gtttccactg gctccctcta gtaaatccac ctctggaggc  420
acagctgcac tgggatgtct ggtgaaggat tacttccctg aaccagtcac agtgagttgg  480
aactcagggg ctctgacaag tggagtccat acttttcccg cagtgctgca gtcaagcgga  540
ctgtactccc tgtcctctgt ggtcaccgtg cctagttcaa gcctgggcac ccagacatat  600
atctgcaacg tgaatcacaa gccatcaaat acaaaagtcg acaagaaagt ggagcccaag  660
agctgtgata aaactcatac ctgcccacct tgtccggcgc cagaactgct gggaggacca  720
agcgtgttcc tgtttccacc caagcctaaa gacaccctga tgatttcccg gactcctgag  780
gtcacctgcg tggtcgtgga cgtgtctcac gaggaccccg aagtcaagtt caactggtac  840
gtggatggcg tcgaagtgca taatgccaag accaaacccc gggaggaaca gtacaactct  900
acctatagag tcgtgagtgt cctgacagtg ctgcaccagg actggctgaa tgggaaggag  960
tataagtgta aagtgagcaa caaagccctg cccgccccaa tcgaaaaaac aatctctaaa  1020
gcaaaaggac agcctcgcga accacaggtc tacgtgctgc cccctagccg cgacgaactg  1080
actaaaaatc aggtctctct gctgtgtctg gtcaaaggat tctacccttc cgacatcgcc  1140
gtggagtggg aaagtaacgg ccagcccgag aacaattacc tgacctggcc ccctgtgctg  1200
gactctgatg ggagtttctt tctgtattca aagctgacag tcgataaaag ccggtggcag  1260
cagggcaatg tgttcagctg ctccgtcatg cacgaagcac tgcacaacca ttacactcag  1320
aagtccctgt ccctgtcacc tggc                                         1344

SEQ ID NO: 37          moltype = AA  length = 217
FEATURE                Location/Qualifiers
source                 1..217
                       mol_type = protein
                       note = Clone ID 18915 Full
                       organism = synthetic construct
SEQUENCE: 37
AYDMTQTPAS VEVAVGGTVT IKCQASQSIG DWLAWYQQKP GQPPRLLIYE ASTLASGVPS  60
RFSGSGSGTQ FTLTISGVEC ADAATYYCQQ GYGRSNVDNI FGGGTEVVVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 38          moltype = DNA  length = 651
FEATURE                Location/Qualifiers
source                 1..651
                       mol_type = other DNA
                       note = Clone ID 18915 Full
                       organism = synthetic construct
SEQUENCE: 38
gcctacgaca tgacccagac acccgcctcc gtggaggtgg cagtgggagg aaccgtgaca  60
atcaagtgcc aggccagcca gtccatcggc gattggctgg cctggtacca gcagaagcct  120
ggacagccac ctcggctgct gatctatgag gcctctaccc tggccagcgg agtgccatcc  180
agattctctg gcagcggctc cggcacacag tttaccctga caatctctgg agtggagtgc  240
gcagacgcag caacctacta ttgtcagcag ggctatggca ggagcaacgt ggataatatc  300
tttggaggag gaaccgaggt ggtggtgaag aggacagtgg cggcgcccag tgtcttcatt  360
tttcccccta gcgacgaaca gctgaagtct gggacagcca gtgtggtctg tctgctgaac  420
aacttctacc ctagagaggc taaagtgcag tggaaggtcg ataacgcact gcagtccgga  480
aattctcagg agagtgtgac tgaacaggac tcaaaagata gcacctattc cctgtcaagc  540
acactgactc tgagcaaggc cgactacgag aagcataaag tgtatgcttg tgaagtcacc  600
caccaggggc tgagttcacc agtcacaaaa tcattcaaca gaggggagtg c           651

SEQ ID NO: 39          moltype = AA  length = 110
FEATURE                Location/Qualifiers
source                 1..110
                       mol_type = protein
                       note = Clone ID 18915 VL
                       organism = synthetic construct
SEQUENCE: 39
AYDMTQTPAS VEVAVGGTVT IKCQASQSIG DWLAWYQQKP GQPPRLLIYE ASTLASGVPS  60
RFSGSGSGTQ FTLTISGVEC ADAATYYCQQ GYGRSNVDNI FGGGTEVVVK             110

SEQ ID NO: 40          moltype = AA  length = 6
FEATURE                Location/Qualifiers
source                 1..6
```

```
                        mol_type = protein
                        note = Clone ID 18915, 22054, 26448, 27276 IMGT CDR1
                        organism = synthetic construct
SEQUENCE: 40
QSIGDW                                                                6

SEQ ID NO: 41           moltype =   length =
SEQUENCE: 41
000

SEQ ID NO: 42           moltype = AA  length = 12
FEATURE                 Location/Qualifiers
source                  1..12
                        mol_type = protein
                        note = Clone ID 18915, 22054, 26449, 27276 AbM, Chothia,
                         IMGT and Kabat CDR3
                        organism = synthetic construct
SEQUENCE: 42
QQGYGRSNVD NI                                                         12

SEQ ID NO: 43           moltype = AA  length = 11
FEATURE                 Location/Qualifiers
source                  1..11
                        mol_type = protein
                        note = Clone ID 18915 Chothia, Kabat and AbM CDR1
                        organism = synthetic construct
SEQUENCE: 43
QASQSIGDWL A                                                          11

SEQ ID NO: 44           moltype = AA  length = 7
FEATURE                 Location/Qualifiers
source                  1..7
                        mol_type = protein
                        note = Clone ID 18915, 22054, 26448, 26449, 26450, 27274,
                         27276 AbM, Chothia, Kabat CDR2
                        organism = synthetic construct
SEQUENCE: 44
EASTLAS                                                               7

SEQ ID NO: 45           moltype = AA  length = 7
FEATURE                 Location/Qualifiers
source                  1..7
                        mol_type = protein
                        note = Clone ID 18915, 22054, 26448, 27276 Contact CDR1
                        organism = synthetic construct
SEQUENCE: 45
GDWLAWY                                                               7

SEQ ID NO: 46           moltype = AA  length = 10
FEATURE                 Location/Qualifiers
source                  1..10
                        mol_type = protein
                        note = Clone ID 18915, 22054, 26448, 26449, 26450, 27274,
                         27276 Contact CDR2
                        organism = synthetic construct
SEQUENCE: 46
LLIYEASTLA                                                            10

SEQ ID NO: 47           moltype = AA  length = 11
FEATURE                 Location/Qualifiers
source                  1..11
                        mol_type = protein
                        note = Clone ID 18915, 22054, 26449, 27276 Contact CDR3
                        organism = synthetic construct
SEQUENCE: 47
QQGYGRSNVD N                                                          11

SEQ ID NO: 48           moltype = AA  length = 449
FEATURE                 Location/Qualifiers
source                  1..449
                        mol_type = protein
                        note = Clone ID 22046 Full
                        organism = synthetic construct
SEQUENCE: 48
EVQLLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
```

```
STYRVVSVLT VLHQDWLNGK EYKCKVSNKA LPAPIEKTIS KAKGQPREPQ VYVYPPSRDE  360
LTKNQVSLTC LVKGFYPSDI AVEWESNGQP ENNYKTTPPV LDSDGSFALV SKLTVDKSRW  420
QQGNVFSCSV MHEALHNHYT QKSLSLSPG                                    449

SEQ ID NO: 49          moltype = DNA  length = 1347
FEATURE                Location/Qualifiers
source                 1..1347
                       mol_type = other DNA
                       note = Clone ID 22046 Full
                       organism = synthetic construct
SEQUENCE: 49
gaggtgcagc tgctggagag cggaggagga ctggtgcagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtct accccccatc aagagatgaa  1080
ctgacaaaaa atcaggtctc tctgacatgc ctggtcaaag gattctaccc ttccgacatc  1140
gccgtggagt gggaaagtaa cggccagccc gagaacaatt acaagaccac accccctgtc  1200
ctggactctg atgggagttt cgctctggtg tcaaagctga ccgtcgataa aagccggtgg  1260
cagcagggca atgtgtttag ctgctccgtc atgcacgaag ccctgcacaa tcactacaca  1320
cagaagtccc tgagcctgag ccctggc                                      1347

SEQ ID NO: 50          moltype = AA  length = 120
FEATURE                Location/Qualifiers
source                 1..120
                       mol_type = protein
                       note = Clone ID 22046, 22057, 27275 VH
                       organism = synthetic construct
SEQUENCE: 50
EVQLLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120

SEQ ID NO: 51          moltype = AA  length = 16
FEATURE                Location/Qualifiers
source                 1..16
                       mol_type = protein
                       note = Clone ID 22046, 22047, 22057, 22058, 22874, 22875,
                        22876, 22877, 22878, 26434, 27275 Kabat CDR2
                       organism = synthetic construct
SEQUENCE: 51
AVNSGGSAYY ADSVKG                                                  16

SEQ ID NO: 52          moltype = AA  length = 449
FEATURE                Location/Qualifiers
source                 1..449
                       mol_type = protein
                       note = Clone ID 22047 Full
                       organism = synthetic construct
SEQUENCE: 52
EVQVLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVYPPSRDE  360
LTKNQVSLTC LVKGFYPSDI AVEWESNGQP ENNYKTTPPV LDSDGSFALV SKLTVDKSRW  420
QQGNVFSCSV MHEALHNHYT QKSLSLSPG                                    449

SEQ ID NO: 53          moltype = DNA  length = 1347
FEATURE                Location/Qualifiers
source                 1..1347
                       mol_type = other DNA
                       note = Clone ID 22047 Full
                       organism = synthetic construct
SEQUENCE: 53
gaggtgcagg tgctggagag cggaggagga ctggtgcagc caggaggcag cctgcggctg  60
```

```
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac ccgggaggga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtct acccccccatc aagagatgaa  1080
ctgacaaaaa atcaggtctc tctgacatgc ctggtcaaag gattctaccc ttccgacatc  1140
gccgtggagt gggaaagtaa cggccagccc gagaacaatt acaagaccac accccctgtc  1200
ctggactctg atgggagttt cgctctggtg tcaaagctga ccgtcgataa aagccggtgg  1260
cagcagggca atgtgtttag ctgctccgtc atgcacgaag ccctgcacaa tcactacaca  1320
cagaagtccc tgagcctgag ccctggc                                     1347

SEQ ID NO: 54          moltype = AA  length = 120
FEATURE                Location/Qualifiers
source                 1..120
                       mol_type = protein
                       note = Clone ID 22047, 22058 VH
                       organism = synthetic construct
SEQUENCE: 54
EVQVLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120

SEQ ID NO: 55          moltype = AA  length = 449
FEATURE                Location/Qualifiers
source                 1..449
                       mol_type = protein
                       note = Clone ID 22048 Full
                       organism = synthetic construct
SEQUENCE: 55
EVQLLESGGG LVQPGGSLRL SCAVSGFSLS SYGVSWVRQA PGKGLEWIGA VNSGGSAYYA  60
DWAKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVYPPSRDE  360
LTKNQVSLTC LVKGFYPSDI AVEWESNGQP ENNYKTTPPV LDSDGSFALV SKLTVDKSRW  420
QQGNVFSCSV MHEALHNHYT QKSLSLSPG                                   449

SEQ ID NO: 56          moltype = DNA  length = 1347
FEATURE                Location/Qualifiers
source                 1..1347
                       mol_type = other DNA
                       note = Clone ID 22048 Full
                       organism = synthetic construct
SEQUENCE: 56
gaggtgcagc tgctggagtc cggaggagga ctggtgcagc caggaggcag cctgcggctg  60
tcctgcgccg tgagcggctt ttccctgagc tcctacggcg tgtcttgggt gagacaggcc  120
cccggcaagg gactggagtg gatcggagcc gtgaactctg gaggcagcgc ctactatgca  180
gactgggcaa agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac ccgggaggga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtct acccccccatc aagagatgaa  1080
ctgacaaaaa atcaggtctc tctgacatgc ctggtcaaag gattctaccc ttccgacatc  1140
gccgtggagt gggaaagtaa cggccagccc gagaacaatt acaagaccac accccctgtc  1200
ctggactctg atgggagttt cgctctggtg tcaaagctga ccgtcgataa aagccggtgg  1260
cagcagggca atgtgtttag ctgctccgtc atgcacgaag ccctgcacaa tcactacaca  1320
cagaagtccc tgagcctgag ccctggc                                     1347
```

-continued

```
SEQ ID NO: 57          moltype = AA  length = 120
FEATURE                Location/Qualifiers
source                 1..120
                       mol_type = protein
                       note = Clone ID 22048, 22059 VH
                       organism = synthetic construct
SEQUENCE: 57
EVQLLESGGG LVQPGGSLRL SCAVSGFSLS SYGVSWVRQA PGKGLEWIGA VNSGGSAYYA  60
DWAKGRSTIS RDNSKNTVYL QMNSLRAEDT AVYYCARSGS GYPMDYLAIW GQGTLVTVSS  120

SEQ ID NO: 58          moltype = AA  length = 16
FEATURE                Location/Qualifiers
source                 1..16
                       mol_type = protein
                       note = Clone ID 22060, 22048, 22049, 22059 Kabat CDR2
                       organism = synthetic construct
SEQUENCE: 58
AVNSGGSAYY ADWAKG                                                  16

SEQ ID NO: 59          moltype = AA  length = 449
FEATURE                Location/Qualifiers
source                 1..449
                       mol_type = protein
                       note = Clone ID 22049 Full
                       organism = synthetic construct
SEQUENCE: 59
EVQVLESGGG LVQPGGSLRL SCAVSGFSLS SYGVSWVRQA PGKGLEWIGA VNSGGSAYYA  60
DWAKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVYPPSRDE  360
LTKNQVSLTC LVKGFYPSDI AVEWESNGQP ENNYKTTPPV LDSDGSFALV SKLTVDKSRW  420
QQGNVFSCSV MHEALHNHYT QKSLSLSPG                                    449

SEQ ID NO: 60          moltype = DNA  length = 1347
FEATURE                Location/Qualifiers
source                 1..1347
                       mol_type = other DNA
                       note = Clone ID 22049 Full
                       organism = synthetic construct
SEQUENCE: 60
gaggtgcagg tgctggagtc cggaggagga ctggtgcagc caggaggcag cctgcggctg  60
tcctgcgccg tgagcggctt ttccctgagc tcctacggcg tgtcttgggt gagacaggcc  120
cccggcaagg gactggagtg gatcggagcc gtgaactctg gaggcagcgc ctactatgca  180
gactgggcaa agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtct acccccccatc aagagatgaa  1080
ctgacaaaaa atcaggtctc tctgacatgc ctggtcaaag gattctaccc ttccgacatc  1140
gccgtggagt gggaaagtaa cggccagccc gagaacaatt acaagaccac accccctgtc  1200
ctggactctg atgggagttt cgctctggtg tcaaagctga ccgtcgataa aagccggtgg  1260
cagcagggca atgtgtttag ctgctccgtc atgcacgaag ccctgcacaa tcactacaca  1320
cagaagtccc tgagcctgag ccctggc                                      1347

SEQ ID NO: 61          moltype = AA  length = 120
FEATURE                Location/Qualifiers
source                 1..120
                       mol_type = protein
                       note = Clone ID 22049, 22060 VH
                       organism = synthetic construct
SEQUENCE: 61
EVQVLESGGG LVQPGGSLRL SCAVSGFSLS SYGVSWVRQA PGKGLEWIGA VNSGGSAYYA  60
DWAKGRSTIS RDNSKNTVYL QMNSLRAEDT AVYYCARSGS GYPMDYLAIW GQGTLVTVSS  120

SEQ ID NO: 62          moltype = AA  length = 217
FEATURE                Location/Qualifiers
```

-continued

```
source                  1..217
                        mol_type = protein
                        note = Clone ID 22054 Full
                        organism = synthetic construct
SEQUENCE: 62
DYQMTQSPSS VSASVGDRVT ITCRASQSIG DWLAWYQQKP GKAPKLLIYE ASTLASGVPS  60
RFSGSGSGTD FTLTISSVQP EDAATYYCQQ GYGRSNVDNI FGGGTKVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 63           moltype = DNA  length = 651
FEATURE                 Location/Qualifiers
source                  1..651
                        mol_type = other DNA
                        note = Clone ID 22054 Full
                        organism = synthetic construct
SEQUENCE: 63
gactaccaga tgacccagtc tccaagctcc gtgtccgcct ctgtgggcga cagggtgacc  60
atcacatgca gagccagcca gtccatcggc gattggctgg cctggtatca gcagaagccc  120
ggcaaggccc ctaagctgct gatctatgag gcctctaccc tggccagcgg cgtgccttcc  180
cggttctctg gcagcggctc cggcacagac tttaccctga caatctctag cgtgcagcca  240
gaggatgccg ccacctacta ttgtcagcag ggctatggca ggtccaacgt ggataatatc  300
tttggaggag gcaccaaggt ggaggtgaag aggacagtgg cggcgcccag tgtcttcatt  360
tttcccccta gcgacgaaca gctgaagtct gggacagcca gtgtggtctg tctgctgaac  420
aacttctacc ctagagaggc taaagtgcag tggaaggtcg ataacgcact gcagtccgga  480
aattctcagg agagtgtgac tgaacaggac tcaaaagata gcacctattc cctgtcaagc  540
acactgactc tgagcaaggc cgactacgag aagcataaag tgtatgcttg tgaagtcacc  600
caccaggggc tgagttcacc agtcacaaaa tcattcaaca gaggggagtg c           651

SEQ ID NO: 64           moltype = AA  length = 110
FEATURE                 Location/Qualifiers
source                  1..110
                        mol_type = protein
                        note = Clone ID 22054 VL
                        organism = synthetic construct
SEQUENCE: 64
DYQMTQSPSS VSASVGDRVT ITCRASQSIG DWLAWYQQKP GKAPKLLIYE ASTLASGVPS  60
RFSGSGSGTD FTLTISSVQP EDAATYYCQQ GYGRSNVDNI FGGGTKVEVK             110

SEQ ID NO: 65           moltype = AA  length = 11
FEATURE                 Location/Qualifiers
source                  1..11
                        mol_type = protein
                        note = Clone ID 22054, 26448, 27276 AbM, Kabat and Chothia
                         CDR1
                        organism = synthetic construct
SEQUENCE: 65
RASQSIGDWL A                                                       11

SEQ ID NO: 66           moltype = AA  length = 449
FEATURE                 Location/Qualifiers
source                  1..449
                        mol_type = protein
                        note = Clone ID 22057 Full
                        organism = synthetic construct
SEQUENCE: 66
EVQLLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVLPPSRDE  360
LTKNQVSLLC LVKGFYPSDI AVEWESNGQP ENNYLTWPPV LDSDGSFFLY SKLTVDKSRW  420
QQGNVFSCSV MHEALHNHYT QKSLSLSPG                                    449

SEQ ID NO: 67           moltype = DNA  length = 1347
FEATURE                 Location/Qualifiers
source                  1..1347
                        mol_type = other DNA
                        note = Clone ID 22057 Full
                        organism = synthetic construct
SEQUENCE: 67
gaggtgcagc tgctggagag cggaggagga ctggtgcagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
```

```
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtgc tgccccctag ccgcgacgaa  1080
ctgactaaaa atcaggtctc tctgctgtgt ctggtcaaag gattctaccc ttccgacatc  1140
gccgtggagt gggaaagtaa cggccagccc gagaacaatt acctgacctg gccccctgtg  1200
ctggactctg atgggagttt ctttctgtat tcaaagctga cagtcgataa aagccggtgg  1260
cagcagggca atgtgttcag ctgctccgtc atgcacgaag cactgcacaa ccattacact  1320
cagaagtccc tgtccctgtc acctggc                                     1347
```

```
SEQ ID NO: 68          moltype = AA  length = 449
FEATURE                Location/Qualifiers
source                 1..449
                       mol_type = protein
                       note = Clone ID 22058 Full
                       organism = synthetic construct
SEQUENCE: 68
EVQVLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVLPPSRDE  360
LTKNQVSLLC LVKGFYPSDI AVEWESNGQP ENNYLTWPPV LDSDGSFFLY SKLTVDKSRW  420
QQGNVFSCSV MHEALHNHYT QKSLSLSPG                                   449
```

```
SEQ ID NO: 69          moltype = DNA  length = 1347
FEATURE                Location/Qualifiers
source                 1..1347
                       mol_type = other DNA
                       note = Clone ID 22058 Full
                       organism = synthetic construct
SEQUENCE: 69
gaggtgcagg tgctggagag cggaggagga ctggtgcagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtgc tgccccctag ccgcgacgaa  1080
ctgactaaaa atcaggtctc tctgctgtgt ctggtcaaag gattctaccc ttccgacatc  1140
gccgtggagt gggaaagtaa cggccagccc gagaacaatt acctgacctg gccccctgtg  1200
ctggactctg atgggagttt ctttctgtat tcaaagctga cagtcgataa aagccggtgg  1260
cagcagggca atgtgttcag ctgctccgtc atgcacgaag cactgcacaa ccattacact  1320
cagaagtccc tgtccctgtc acctggc                                     1347
```

```
SEQ ID NO: 70          moltype = AA  length = 449
FEATURE                Location/Qualifiers
source                 1..449
                       mol_type = protein
                       note = Clone ID 22059 Full
                       organism = synthetic construct
SEQUENCE: 70
EVQLLESGGG LVQPGGSLRL SCAVSGFSLS SYGVSWVRQA PGKGLEWIGA VNSGGSAYYA  60
DWAKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVLPPSRDE  360
LTKNQVSLLC LVKGFYPSDI AVEWESNGQP ENNYLTWPPV LDSDGSFFLY SKLTVDKSRW  420
QQGNVFSCSV MHEALHNHYT QKSLSLSPG                                   449
```

```
SEQ ID NO: 71          moltype = DNA  length = 1347
FEATURE                Location/Qualifiers
source                 1..1347
                       mol_type = other DNA
                       note = Clone ID 22059 Full
                       organism = synthetic construct
SEQUENCE: 71
gaggtgcagc tgctggagtc cggaggagga ctggtgcagc caggaggcag cctgcggctg  60
tcctgcgccg tgagcggctt ttccctgagc tcctacggcg tgtcttgggt gagacaggcc  120
cccggcaagg gactggagtg gatcggagcc gtgaactctg gaggcagcgc ctactatgca  180
gactgggcaa agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtgc tgccccctag ccgcgacgaa  1080
ctgactaaaa atcaggtctc tctgctgtgt ctggtcaaag gattctaccc ttccgacatc  1140
gccgtggagt gggaaagtaa cggccagccc gagaacaatt acctgacctg gccccctgtg  1200
ctggactctg atgggagttt ctttctgtat tcaaagctga cagtcgataa aagccggtgg  1260
cagcagggca atgtgttcag ctgctccgtc atgcacgaag cactgcacaa ccattacact  1320
cagaagtccc tgtccctgtc acctggc                                     1347

SEQ ID NO: 72          moltype = AA  length = 449
FEATURE                Location/Qualifiers
source                 1..449
                       mol_type = protein
                       note = Clone ID 22060 Full
                       organism = synthetic construct
SEQUENCE: 72
EVQVLESGGG LVQPGGSLRL SCAVSGFSLS SYGVSWVRQA PGKGLEWIGA VNSGGSAYYA  60
DWAKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVLPPSRDE  360
LTKNQVSLLC LVKGFYPSDI AVEWESNGQP ENNYLTWPPV LDSDGSFFLY SKLTVDKSRW  420
QQGNVFSCSV MHEALHNHYT QKSLSLSPG                                   449

SEQ ID NO: 73          moltype = DNA  length = 1347
FEATURE                Location/Qualifiers
source                 1..1347
                       mol_type = other DNA
                       note = Clone ID 22060 Full
                       organism = synthetic construct
SEQUENCE: 73
gaggtgcagg tgctggagtc cggaggagga ctggtgcagc caggaggcag cctgcggctg  60
tcctgcgccg tgagcggctt ttccctgagc tcctacggcg tgtcttgggt gagacaggcc  120
cccggcaagg gactggagtg gatcggagcc gtgaactctg gaggcagcgc ctactatgca  180
gactgggcaa agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtctacgtgc tgccccctag ccgcgacgaa  1080
ctgactaaaa atcaggtctc tctgctgtgt ctggtcaaag gattctaccc ttccgacatc  1140
gccgtggagt gggaaagtaa cggccagccc gagaacaatt acctgacctg gccccctgtg  1200
ctggactctg atgggagttt ctttctgtat tcaaagctga cagtcgataa aagccggtgg  1260
cagcagggca atgtgttcag ctgctccgtc atgcacgaag cactgcacaa ccattacact  1320
cagaagtccc tgtccctgtc acctggc                                     1347
```

```
SEQ ID NO: 74           moltype = AA  length = 449
FEATURE                 Location/Qualifiers
source                  1..449
                        mol_type = protein
                        note = Clone ID 22874 Full
                        organism = synthetic construct
SEQUENCE: 74
EVQLLESGGG LFQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 75           moltype = DNA  length = 1347
FEATURE                 Location/Qualifiers
source                  1..1347
                        mol_type = other DNA
                        note = Clone ID 22874 Full
                        organism = synthetic construct
SEQUENCE: 75
gaggtgcagc tgctggagag cggaggagga ctgttccagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagataact ctaagaatac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtgtacactc tgcctccatc tcgggacgag  1080
ctgactaaga accaggtcag tctgacctgt ctggtgaaag gattctatcc cagcgatatc  1140
gctgtggagt gggaatccaa tggccagcct gagaacaatt acaagaccac accccctgtg  1200
ctggactctg atggcagttt ctttctgtat agtaagctga ccgtcgataa atcacgatgg  1260
cagcagggga acgtgttcag ctgttcagtg atgcacgaag ccctgcacaa ccattacacc  1320
cagaagagcc tgagcctgtc tcccggc                                    1347

SEQ ID NO: 76           moltype = AA  length = 120
FEATURE                 Location/Qualifiers
source                  1..120
                        mol_type = protein
                        note = Clone ID 22874 VH
                        organism = synthetic construct
SEQUENCE: 76
EVQLLESGGG LFQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120

SEQ ID NO: 77           moltype = AA  length = 449
FEATURE                 Location/Qualifiers
source                  1..449
                        mol_type = protein
                        note = Clone ID 22875 Full
                        organism = synthetic construct
SEQUENCE: 77
EVQLLESGGG LVQPGGSLRL SCAVSGFSLS SYGVSWVRQA PGKGLEWIGA VNSGGSAYYA  60
DSVKGRSTIS RDTSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 78           moltype = DNA  length = 1347
FEATURE                 Location/Qualifiers
source                  1..1347
                        mol_type = other DNA
                        note = Clone ID 22875 Full
                        organism = synthetic construct
```

```
SEQUENCE: 78
gaggtgcagc tgctggagag cggaggagga ctggtgcagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagatacct ctaagaacac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtgtacactc tgcctccatc tcgggacgag  1080
ctgactaaga accaggtcag tctgacctgt ctggtgaaag gattctatcc cagcgatatc  1140
gctgtggagt gggaatccaa tggccagcct gagaacaatt acaagaccac accccctgtg  1200
ctggactctg atggcagttt ctttctgtat agtaagctga ccgtcgataa atcacgatgg  1260
cagcagggga acgtgttcag ctgttcagtg atgcacgaag ccctgcacaa ccattacacc  1320
cagaagagcc tgagcctgtc tcccggc                                     1347

SEQ ID NO: 79           moltype = AA  length = 120
FEATURE                 Location/Qualifiers
source                  1..120
                        mol_type = protein
                        note = Clone ID 22875 VH
                        organism = synthetic construct
SEQUENCE: 79
EVQLLESGGG LVQPGGSLRL SCAVSGFSLS SYGVSWVRQA PGKGLEWIGA VNSGGSAYYA  60
DSVKGRSTIS RDTSKNTVYL QMNSLRAEDT AVYYCARSGS GYPMDYLAIW GQGTLVTVSS  120

SEQ ID NO: 80           moltype = AA  length = 449
FEATURE                 Location/Qualifiers
source                  1..449
                        mol_type = protein
                        note = Clone ID 22876 Full
                        organism = synthetic construct
SEQUENCE: 80
EVQLLESGGG LVQPGGSLRL SCAVSGFSLS SYGVSWVRQA PGKGLEWIGA VNSGGSAYYA  60
DSVKGRSTIS RDTSKFTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 81           moltype = DNA  length = 1347
FEATURE                 Location/Qualifiers
source                  1..1347
                        mol_type = other DNA
                        note = Clone ID 22876 Full
                        organism = synthetic construct
SEQUENCE: 81
gaggtgcagc tgctggagag cggaggagga ctggtgcagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagatacct ctaagttcac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtgtacactc tgcctccatc tcgggacgag  1080
ctgactaaga accaggtcag tctgacctgt ctggtgaaag gattctatcc cagcgatatc  1140
gctgtggagt gggaatccaa tggccagcct gagaacaatt acaagaccac accccctgtg  1200
ctggactctg atggcagttt ctttctgtat agtaagctga ccgtcgataa atcacgatgg  1260
```

-continued

```
cagcagggga acgtgttcag ctgttcagtg atgcacgaag ccctgcacaa ccattacacc  1320
cagaagagcc tgagcctgtc tcccggc                                      1347

SEQ ID NO: 82           moltype = AA  length = 120
FEATURE                 Location/Qualifiers
source                  1..120
                        mol_type = protein
                        note = Clone ID 22876 VH
                        organism = synthetic construct
SEQUENCE: 82
EVQLLESGGG LVQPGGSLRL SCAVSGFSLS SYGVSWVRQA PGKGLEWIGA VNSGGSAYYA  60
DSVKGRSTIS RDTSKFTVYL QMNSLRAEDT AVYYCARSGS GYPMDYLAIW GQGTLVTVSS  120

SEQ ID NO: 83           moltype = AA  length = 449
FEATURE                 Location/Qualifiers
source                  1..449
                        mol_type = protein
                        note = Clone ID 22877 Full
                        organism = synthetic construct
SEQUENCE: 83
EVQLLESGGG LFQPGGSLRL SCAVSGFSLS SYGVSWVRQA PGKGLEWIGA VNSGGSAYYA  60
DSVKGRSTIS RDTSKFTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 84           moltype = DNA  length = 1347
FEATURE                 Location/Qualifiers
source                  1..1347
                        mol_type = other DNA
                        note = Clone ID 22877 Full
                        organism = synthetic construct
SEQUENCE: 84
gaggtgcagc tgctggagag cggaggagga ctgttccagc caggaggcag cctgcggctg  60
tcctgcgccg tgagcggctt ttccctgagc tcctacggcg tgtcctgggt gagacaggcc  120
cccggcaagg gactggagtg gatcggagcc gtgaactctg gcggcagcgc ctactatgcc  180
gactctgtga agggccggtc caccatctct agagatacct ctaagtttac agtgtatctg  240
cagatgaata gcctgagggc cgaggacaca gccgtgtact attgtgcacg ctccggctct  300
ggctacccca tggattatct ggccatctgg ggacagggca ccctggtgac agtgtctagc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg cgccagaact gctgggagga  720
ccaagcgtgt tcctgtttcc acccaagcct aaagacaccc tgatgatttc ccggactcct  780
gaggtcacct gcgtggtcgt ggacgtgtct cacgaggacc ccgaagtcaa gttcaactgg  840
tacgtggatg gcgtcgaagt gcataatgcc aagaccaaac cccgggagga acagtacaac  900
tctacctata gagtcgtgag tgtcctgaca gtgctgcacc aggactggct gaatgggaag  960
gagtataagt gtaaagtgag caacaaagcc ctgcccgccc caatcgaaaa aacaatctct  1020
aaagcaaaag gacagcctcg cgaaccacag gtgtacactc tgcctccatc tcgggacgag  1080
ctgactaaga accaggtcag tctgacctgt ctggtgaaag gattctatcc cagcgatatc  1140
gctgtggagt gggaatccaa tggccagcct gagaacaatt acaagaccac accccctgtg  1200
ctggactctg atggcagttt ctttctgtat agtaagctga ccgtcgataa atcacgatgg  1260
cagcagggga acgtgttcag ctgttcagtg atgcacgaag ccctgcacaa ccattacacc  1320
cagaagagcc tgagcctgtc tcccggc                                      1347

SEQ ID NO: 85           moltype = AA  length = 120
FEATURE                 Location/Qualifiers
source                  1..120
                        mol_type = protein
                        note = Clone ID 22877 VH
                        organism = synthetic construct
SEQUENCE: 85
EVQLLESGGG LFQPGGSLRL SCAVSGFSLS SYGVSWVRQA PGKGLEWIGA VNSGGSAYYA  60
DSVKGRSTIS RDTSKFTVYL QMNSLRAEDT AVYYCARSGS GYPMDYLAIW GQGTLVTVSS  120

SEQ ID NO: 86           moltype = AA  length = 448
FEATURE                 Location/Qualifiers
source                  1..448
                        mol_type = protein
                        note = Clone ID 22878 Full
                        organism = synthetic construct
SEQUENCE: 86
QQLLESGGGL FQPGGSLRLS CAVSGFSLSS YGVSWVRQAP GKGLEWIGAV NSGGSAYYAD  60
SVKGRSTISR DTSKFTVYLQ MNSLRAEDTA VYYCARSGSG YPMDYLAIWG QGTLVTVSSA  120
```

-continued

```
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 87          moltype = DNA  length = 1344
FEATURE                Location/Qualifiers
source                 1..1344
                       mol_type = other DNA
                       note = Clone ID 22878 Full
                       organism = synthetic construct
SEQUENCE: 87
cagcagctgc tggagagcgg cggcggcctg ttccagcctg gaggcagcct gagactgtcc  60
tgcgccgtga gcggcttttc cctgagctcc tacggcgtgt cctgggtgag gcaggccccc  120
ggcaagggcc tggagtggat cggagccgtg aactctggcg gcagcgccta ctatgccgac  180
tctgtgaagg gccggtccac catctctaga gatacctcta agtttacagt gtatctgcag  240
atgaatagcc tgagggccga ggacacagcc gtgtactatt gtgcacgctc cggctctggc  300
taccccatgg attatctggc catctgggga cagggcaccc tggtgacagt gtctagcgct  360
agcactaagg ggccttccgt gtttccactg gctccctcta gtaaatccac ctctggaggc  420
acagctgcac tgggatgtct ggtgaaggat tacttccctg aaccagtcac agtgagttgg  480
aactcagggg ctctgacaag tggagtccat acttttcccg cagtgctgca gtcaagcgga  540
ctgtactccc tgtcctctgt ggtcaccgtg cctagttcaa gcctgggcac ccagacatat  600
atctgcaacg tgaatcacaa gccatcaaat acaaaagtcg acaagaaagt ggagcccaag  660
agctgtgata aaactcatac ctgcccacct tgtccggcgc cagaactgct gggaggacca  720
agcgtgttcc tgtttccacc caagcctaaa gacaccctga tgatttcccg gactcctgag  780
gtcacctgcg tggtcgtgga cgtgtctcac gaggaccccg aagtcaagtt caactggtac  840
gtggatggcg tcgaagtgca taatgccaag accaaacccc gggaggaaca gtacaactct  900
acctatagag tcgtgagtgt cctgacagtg ctgcaccagg actggctgaa tgggaaggag  960
tataagtgta aagtgagcaa caaagccctg cccgccccaa tcgaaaaaac aatctctaaa  1020
gcaaaaggac agcctcgcga accacaggtg tacactctgc ctccatctcg ggacgagctg  1080
actaagaacc aggtcagtct gacctgtctg gtgaaaggat tctatcccag cgatatcgct  1140
gtggagtggg aatccaatgg ccagcctgag aacaattaca agaccacacc ccctgtgctg  1200
gactctgatg gcagtttctt tctgtatagt aagctgaccg tcgataaatc acgatggcag  1260
caggggaacg tgttcagctg ttcagtgatg cacgaagccc tgcacaacca ttacacccag  1320
aagagcctga gcctgtctcc cggc                                         1344

SEQ ID NO: 88          moltype = AA  length = 119
FEATURE                Location/Qualifiers
source                 1..119
                       mol_type = protein
                       note = Clone ID 22878 VH
                       organism = synthetic construct
SEQUENCE: 88
QQLLESGGGL FQPGGSLRLS CAVSGFSLSS YGVSWVRQAP GKGLEWIGAV NSGGSAYYAD  60
SVKGRSTISR DTSKFTVYLQ MNSLRAEDTA VYYCARSGSG YPMDYLAIWG QGTLVTVSS   119

SEQ ID NO: 89          moltype = AA  length = 449
FEATURE                Location/Qualifiers
source                 1..449
                       mol_type = protein
                       note = Clone ID 26434 Full
                       organism = synthetic construct
SEQUENCE: 89
EVQLLESGGG LVQPGGSLRL SCAVSGFSLS LYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 90          moltype = DNA  length = 1347
FEATURE                Location/Qualifiers
source                 1..1347
                       mol_type = other DNA
                       note = Clone ID 26434 Full
                       organism = synthetic construct
SEQUENCE: 90
gaggtccagt tgctggaatc aggaggtgga ctcgtgcagc ctgggggttc cctgcgcttg  60
tcttgcgctg tcagcggttt tagcttatct ttatacggtg taagttgggt tcggcaggct  120
cctggcaaag gtctggaatg gatcggggct gtaaacagcg gggggtccgc ctactatgct  180
gattctgtta aggggaggtc caccattagc agagataatt ccaagaacac cgtttatctc  240
cagatgaact ccttgagggc ggaggacact gctgtctatt attgtgcgcg gtcaggcagc  300
ggatacccga tggactatct ggcgatctgg ggccagggaa cccttgtgac agtctcttcc  360
gctagcacca agggacctag cgtatttcca ctggctccct ctagtaaatc cacctctgga  420
ggcacagctg cactgggatg tctggtgaag gattacttcc ctgaaccagt cacagtgagt  480
```

```
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg ctccagagct gctcggcgga  720
ccatccgtgt tcctgtttcc tccaaagcct aaagatacac tgatgattag ccgcactccc  780
gaagtcacct gtgtggtcgt ggacgtgtcc cacgaggacc ccgaagtcaa gttcaactgg  840
tacgtggacg gcgtcgaggt gcataatgcc aagactaaac caagagagga acagtacaat  900
tcaacctata gggtcgtgag cgtcctgaca gtgctgcatc aggattggct gaacggcaag  960
gagtataagt gcaaagtgtc taacaaggcc ctgcccgctc ctatcgagaa gactattagc  1020
aaggcaaaag ggcagccacg ggaaccccag gtctacactc tgccccctag cagagacgag  1080
ctgaccaaaa accaggtgtc cctgacttgt ctggtgaagg gcttttatcc tagtgatatc  1140
gctgtggagt gggaatcaaa tgggcagcca gaaaacaatt acaaaacaac tccacccgtg  1200
ctggacagcg atgggtcctt ctttctgtat tccaaactga ctgtggacaa gtccagatgg  1260
cagcagggaa acgtcttcag ctgttccgtg atgcacgagg ccctgcacaa tcattacacc  1320
cagaagtctc tgagtctgtc acccggc                                     1347

SEQ ID NO: 91          moltype = AA  length = 120
FEATURE                Location/Qualifiers
source                 1..120
                       mol_type = protein
                       note = Clone ID 26434 VH
                       organism = synthetic construct
SEQUENCE: 91
EVQLLESGGG LVQPGGSLRL SCAVSGFSLS LYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120

SEQ ID NO: 92          moltype = AA  length = 8
FEATURE                Location/Qualifiers
source                 1..8
                       mol_type = protein
                       note = Clone ID 26446, 27273, 26434, 26443, 26445 IMGT CDR1
                       organism = synthetic construct
SEQUENCE: 92
GFSLSLYG                                                          8

SEQ ID NO: 93          moltype = AA  length = 7
FEATURE                Location/Qualifiers
source                 1..7
                       mol_type = protein
                       note = Clone ID 26434, 26443, 26445, 26446, 27273 Chothia
                        CDR1
                       organism = synthetic construct
SEQUENCE: 93
GFSLSLY                                                           7

SEQ ID NO: 94          moltype = AA  length = 5
FEATURE                Location/Qualifiers
source                 1..5
                       mol_type = protein
                       note = Clone ID 26434, 26443, 26445, 26446, 27273 Kabat CDR1
                       organism = synthetic construct
SEQUENCE: 94
LYGVS                                                             5

SEQ ID NO: 95          moltype = AA  length = 6
FEATURE                Location/Qualifiers
source                 1..6
                       mol_type = protein
                       note = Clone ID 26434, 26443, 26445, 26446, 27273 Contact
                        CDR1
                       organism = synthetic construct
SEQUENCE: 95
SLYGVS                                                            6

SEQ ID NO: 96          moltype = AA  length = 10
FEATURE                Location/Qualifiers
source                 1..10
                       mol_type = protein
                       note = Clone ID 26434, 26443, 26445, 26446, 27273 AbM CDR1
                       organism = synthetic construct
SEQUENCE: 96
GFSLSLYGVS                                                        10

SEQ ID NO: 97          moltype = AA  length = 449
FEATURE                Location/Qualifiers
source                 1..449
                       mol_type = protein
                       note = Clone ID 26443 Full
                       organism = synthetic construct
```

```
SEQUENCE: 97
EVQLLESGGG LVQPGGSLRL SCAVSGFSLS LYGVSWVRQA PGKGLEWIGS LNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 98           moltype = DNA  length = 1347
FEATURE                 Location/Qualifiers
source                  1..1347
                        mol_type = other DNA
                        note = Clone ID 26443 Full
                        organism = synthetic construct
SEQUENCE: 98
gaggttcagt tgcttgagtc tggaggtggg ttggtacaac caggtggatc tctccgcctt  60
tcttgtgcag tctcaggctt ctctctcagc ctgtacggcg tgtcatgggt tagacaagct  120
ccgggtaaag gccttgagtg gattggaagt cttaatagtg gggaagcgc ctactatgca  180
gatagcgtaa aaggaagatc aactatatcc agagacaatt ctaagaatac cgtctacttg  240
cagatgaact ctctgcgggc agaggatact gcggtttact attgtgcgcg aagcggtagt  300
ggatacccta tggattatct tgctatttgg ggtcaaggta ccctcgtaac ggtctctagt  360
gctagcacca agggacctag cgtatttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg ctccagagct gctcggcgga  720
ccatccgtgt tcctgtttcc tccaaagcct aaagatacac tgatgattag ccgcactccc  780
gaagtcacct gtgtggtcgt ggacgtgtcc cacgaggacc ccgaagtcaa gttcaactgg  840
tacgtggacg gcgtcgaggt gcataatgcc aagactaaac caagagagga acagtacaat  900
tcaacctata gggtcgtgag cgtcctgaca gtgctgcatc aggattggct gaacggcaag  960
gagtataagt gcaaagtgtc taacaaggcc ctgcccgctc ctatcgagaa gactattagc  1020
aaggcaaaag ggcagccacg ggaaccccag gtctacactc tgccccctag cagagacgag  1080
ctgaccaaaa accaggtgtc cctgacttgt ctggtgaagg gcttttatcc tagtgatatc  1140
gctgtggagt gggaatcaaa tggcagcca gaaaacaatt acaaaacaac tccacccgtg  1200
ctggacagcg atgggtcctt ctttctgtat tccaaactga ctgtggacaa gtccagatgg  1260
cagcagggaa acgtcttcag ctgttccgtg atgcacgagg ccctgcacaa tcattacacc  1320
cagaagtctc tgagtctgtc acccggc                                    1347

SEQ ID NO: 99           moltype = AA  length = 120
FEATURE                 Location/Qualifiers
source                  1..120
                        mol_type = protein
                        note = Clone ID 26443 VH
                        organism = synthetic construct
SEQUENCE: 99
EVQLLESGGG LVQPGGSLRL SCAVSGFSLS LYGVSWVRQA PGKGLEWIGS LNSGGSAYYA  60
DSVKGRSTIS RDNSKNTVYL QMNSLRAEDT AVYYCARSGS GYPMDYLAIW GQGTLVTVSS  120

SEQ ID NO: 100          moltype = AA  length = 7
FEATURE                 Location/Qualifiers
source                  1..7
                        mol_type = protein
                        note = Clone ID 26443 IMGT CDR2
                        organism = synthetic construct
SEQUENCE: 100
LNSGGSA                                                          7

SEQ ID NO: 101          moltype = AA  length = 16
FEATURE                 Location/Qualifiers
source                  1..16
                        mol_type = protein
                        note = Clone ID 26443 Kabat CDR2
                        organism = synthetic construct
SEQUENCE: 101
SLNSGGSAYY ADSVKG                                                16

SEQ ID NO: 102          moltype = AA  length = 12
FEATURE                 Location/Qualifiers
source                  1..12
                        mol_type = protein
                        note = Clone ID 26443 Contact CDR2
                        organism = synthetic construct
SEQUENCE: 102
WIGSLNSGGS AY                                                    12

SEQ ID NO: 103          moltype = AA  length = 9
```

```
FEATURE               Location/Qualifiers
source                1..9
                      mol_type = protein
                      note = Clone ID 26443 AbM CDR2
                      organism = synthetic construct
SEQUENCE: 103
SLNSGGSAY                                                  9

SEQ ID NO: 104        moltype = AA  length = 449
FEATURE               Location/Qualifiers
source                1..449
                      mol_type = protein
                      note = Clone ID 26445 Full
                      organism = synthetic construct
SEQUENCE: 104
EVQLLESGGG LVQPGGSLRL SCAVSGFSLS LYGVSWVRQA PGKGLEWIGA VNSGGSAYYA  60
DSFKGRSTIS RDNSKNTVYL QMNSLRAEDT AVYYCARSGS GYPMDYHPIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                              449

SEQ ID NO: 105        moltype = DNA  length = 1347
FEATURE               Location/Qualifiers
source                1..1347
                      mol_type = other DNA
                      note = Clone ID 26445 Full
                      organism = synthetic construct
SEQUENCE: 105
gaggtccagc tcttggagtc aggaggcggc ctggttcagc cggggggttc actcagactt  60
agttgtgcgg taagcgggtt cagccttagt ctgtatggcg tatcatgggt ccggcaagcg  120
cctggtaagg gcctggagtg gataggtgct gtcaatagcg gtggctccgc atactacgcg  180
gactctttta agggcagatc caccatcagc cgggacaaca gcaagaacac tgtatatctt  240
cagatgaact cactcagggc ggaggatact gcggtatact actgtgcacg aagtggtagt  300
ggttacccaa tggattacca tcccatttgg gggcaaggga cactcgttac agtgagtagt  360
gctagcacca agggacctag cgtatttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg ctccagagct gctcggcgga  720
ccatccgtgt tcctgtttcc tccaaagcct aaagatacac tgatgattag ccgcactccc  780
gaagtcacct gtgtggtcgt ggacgtgtcc cacgaggacc ccgaagtcaa gttcaactgg  840
tacgtggacg gcgtcgaggt gcataatgcc aagactaaac caagagagga acagtacaat  900
tcaacctata gggtcgtgag cgtcctgaca gtgctgcatc aggattggct gaacggcaag  960
gagtataagt gcaaagtgtc taacaaggcc ctgcccgctc ctatcgagaa gactattagc  1020
aaggcaaaag ggcagccacg ggaaccccag gtctacactc tgccccctag cagagacgag  1080
ctgaccaaaa accaggtgtc cctgacttgt ctggtgaagg gcttttatcc tagtgatatc  1140
gctgtggagt gggaatcaaa tgggcagcca gaaaacaatt acaaaacaac tccacccgtg  1200
ctggacagcg atgggtcctt ctttctgtat tccaaactga ctgtggacaa gtccagatgg  1260
cagcagggaa acgtcttcag ctgttccgtg atgcacgagg ccctgcacaa tcattacacc  1320
cagaagtctc tgagtctgtc acccggc                                1347

SEQ ID NO: 106        moltype = AA  length = 120
FEATURE               Location/Qualifiers
source                1..120
                      mol_type = protein
                      note = Clone ID 26445 VH
                      organism = synthetic construct
SEQUENCE: 106
EVQLLESGGG LVQPGGSLRL SCAVSGFSLS LYGVSWVRQA PGKGLEWIGA VNSGGSAYYA  60
DSFKGRSTIS RDNSKNTVYL QMNSLRAEDT AVYYCARSGS GYPMDYHPIW GQGTLVTVSS  120

SEQ ID NO: 107        moltype = AA  length = 14
FEATURE               Location/Qualifiers
source                1..14
                      mol_type = protein
                      note = Clone ID 26445, 26447 IMGT CDR3
                      organism = synthetic construct
SEQUENCE: 107
ARSGSGYPMD YHPI                                              14

SEQ ID NO: 108        moltype = AA  length = 12
FEATURE               Location/Qualifiers
source                1..12
                      mol_type = protein
                      note = Clone ID 26445, 26447 Chothia, Kabat and AbM CDR3
```

```
                        organism = synthetic construct
SEQUENCE: 108
SGSGYPMDYH PI                                                12

SEQ ID NO: 109          moltype = AA  length = 16
FEATURE                 Location/Qualifiers
source                  1..16
                        mol_type = protein
                        note = Clone ID 26445, 26446, 26447, 27272 Kabat CDR2
                        organism = synthetic construct
SEQUENCE: 109
AVNSGGSAYY ADSFKG                                            16

SEQ ID NO: 110          moltype = AA  length = 13
FEATURE                 Location/Qualifiers
source                  1..13
                        mol_type = protein
                        note = Clone ID 26445, 26447 Contact CDR3
                        organism = synthetic construct
SEQUENCE: 110
ARSGSGYPMD YHP                                               13

SEQ ID NO: 111          moltype = AA  length = 449
FEATURE                 Location/Qualifiers
source                  1..449
                        mol_type = protein
                        note = Clone ID 26446 Full
                        organism = synthetic construct
SEQUENCE: 111
EVQLLESGGG LVQPGGSLRL SCAVSGFSLS LYGVSWVRQA PGKGLEWIGA VNSGGSAYYA  60
DSFKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                              449

SEQ ID NO: 112          moltype = DNA  length = 1347
FEATURE                 Location/Qualifiers
source                  1..1347
                        mol_type = other DNA
                        note = Clone ID 26446 Full
                        organism = synthetic construct
SEQUENCE: 112
gaggtacagc ttctggaaag tggtggcggt cttgtccagc ctggaggaag tctcaggttg  60
tcatgtgcag tctctggttt ttccctctca ttgtacggcg tgagttgggt tagacaagcg  120
ccaggtaagg ggttggagtg gatcggggcg gtcaattccg gcggttctgc ctattacgcc  180
gactcattca aaggccgctc cacgattagt cgagataatt ccaaaaatac tgtgtatctc  240
caaatgaata gtctccgcgc ggaggacaca gctgtttatt attgtgcccg gtccggaagt  300
ggctatccaa tggactatct cgccatctgg ggtcagggca cgttggtaac ggtgtcctcc  360
gctagcacca agggacctag cgtatttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg ctccagagct gctcggcgga  720
ccatccgtgt tcctgtttcc tccaaagcct aaagatacac tgatgattag ccgcactccc  780
gaagtcacct gtgtggtcgt ggacgtgtcc cacgaggacc ccgaagtcaa gttcaactgg  840
tacgtggacg gcgtcgaggt gcataatgcc aagactaaac caagagagga acagtacaat  900
tcaacctata gggtcgtgag cgtcctgaca gtgctgcatc aggattggct gaacggcaag  960
gagtataagt gcaaagtgtc taacaaggcc ctgcccgctc ctatcgagaa gactattagc  1020
aaggcaaaag ggcagccacg ggaaccccag gtctacactc tgccccctag cagagacgag  1080
ctgaccaaaa accaggtgtc cctgacttgt ctggtgaagg gcttttatcc tagtgatatc  1140
gctgtggagt gggaatcaaa tggcagcca gaaaacaatt acaaaacaac tccacccgtg  1200
ctggacagcg atgggtcctt ctttctgtat tccaaactga ctgtggacaa gtccagatgg  1260
cagcagggaa acgtcttcag ctgttccgtg atgcacgagg ccctgcacaa tcattacacc  1320
cagaagtctc tgagtctgtc acccggc                                1347

SEQ ID NO: 113          moltype = AA  length = 120
FEATURE                 Location/Qualifiers
source                  1..120
                        mol_type = protein
                        note = Clone ID 26446 VH
                        organism = synthetic construct
SEQUENCE: 113
EVQLLESGGG LVQPGGSLRL SCAVSGFSLS LYGVSWVRQA PGKGLEWIGA VNSGGSAYYA  60
DSFKGRSTIS RDNSKNTVYL QMNSLRAEDT AVYYCARSGS GYPMDYLAIW GQGTLVTVSS  120
```

```
SEQ ID NO: 114         moltype = AA  length = 449
FEATURE                Location/Qualifiers
source                 1..449
                       mol_type = protein
                       note = Clone ID 26447 Full
                       organism = synthetic construct
SEQUENCE: 114
EVQLLESGGG LVQPGGSLRL SCAVSGFSLS SYGVSWVRQA PGKGLEWIGA VNSGGSAYYA  60
DSFKGRSTIS RDNSKNTVYL QMNSLRAEDT AVYYCARSGS GYPMDYHPIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 115         moltype = DNA  length = 1347
FEATURE                Location/Qualifiers
source                 1..1347
                       mol_type = other DNA
                       note = Clone ID 26447 Full
                       organism = synthetic construct
SEQUENCE: 115
gaggtgcaac tgttggaatc cggaggtggt ttggtgcagc ctggcggtag tctgcggctt  60
agttgcgctg tttcaggctt ttctctctca tcatacgggg tatcatgggt gagacaggca  120
ccaggaaagg gtcttgaatg gattggggcc gtaaattccg gaggtagtgc atactatgct  180
gactcattca agggcaggtc caccattagt cgagataact caaagaacac ggtttatctg  240
cagatgaata gccttagagc ggaggacacg gcagtatatt attgcgcgag aagcgggtct  300
ggatatccga tggactacca tccaatctgg ggccagggaa cactcgtaac ggtgagcagc  360
gctagcacca agggacctag cgtatttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg ctccagagct gctcggcgga  720
ccatccgtgt tcctgtttcc tccaaagcct aaagatacac tgatgattag ccgcactccc  780
gaagtcacct gtgtggtcgt ggacgtgtcc cacgaggacc ccgaagtcaa gttcaactgg  840
tacgtggacg gcgtcgaggt gcataatgcc aagactaaac caagagagga acagtacaat  900
tcaacctata gggtcgtgag cgtcctgaca gtgctgcatc aggattggct gaacggcaag  960
gagtataagt gcaaagtgtc taacaaggcc ctgcccgctc ctatcgagaa gactattagc  1020
aaggcaaaag ggcagccacg ggaaccccag gtctacactc tgccccctag cagagacgag  1080
ctgaccaaaa accaggtgtc cctgacttgt ctggtgaagg gcttttatcc tagtgatatc  1140
gctgtggagt gggaatcaaa tggcagccca gaaaacaatt acaaaaacaac tccacccgtg  1200
ctggacagcg atgggtcctt ctttctgtat tccaaactga ctgtggacaa gtccagatgg  1260
cagcagggaa acgtcttcag ctgttccgtg atgcacgagg ccctgcacaa tcattacacc  1320
cagaagtctc tgagtctgtc acccggc                                    1347

SEQ ID NO: 116         moltype = AA  length = 120
FEATURE                Location/Qualifiers
source                 1..120
                       mol_type = protein
                       note = Clone ID 26447 VH
                       organism = synthetic construct
SEQUENCE: 116
EVQLLESGGG LVQPGGSLRL SCAVSGFSLS SYGVSWVRQA PGKGLEWIGA VNSGGSAYYA  60
DSFKGRSTIS RDNSKNTVYL QMNSLRAEDT AVYYCARSGS GYPMDYHPIW GQGTLVTVSS  120

SEQ ID NO: 117         moltype = AA  length = 217
FEATURE                Location/Qualifiers
source                 1..217
                       mol_type = protein
                       note = Clone ID 26448 Full
                       organism = synthetic construct
SEQUENCE: 117
DYQMTQSPSS VSASVGDRVT ITCRASQSIG DWLAWYQQKP GKAPKLLIYE ASTLASGVPS  60
RFSGSGSGTD FTLTISSVQP EDAATYYCQQ GYGRWHILNI FGGGTKVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                          217

SEQ ID NO: 118         moltype = DNA  length = 651
FEATURE                Location/Qualifiers
source                 1..651
                       mol_type = other DNA
                       note = Clone ID 26448 Full
                       organism = synthetic construct
SEQUENCE: 118
gactatcaaa tgacgcagtc cccgtcctcc gtttccgcct cagttggtga ccgggttaca  60
atcacttgca gagcatctca gtctattggt gattggctgg cgtggtatca acagaagccc  120
ggcaaagccc ctaaactcct gatatacgaa gcatcaacgc ttgcttctgg agtaccctcc  180
```

```
cggttttctg ggtcaggaag cggcacggat tttaccctga ctatctcttc tgttcagcct  240
gaggatgccg caacctatta ttgccaacag gggtatggca gatggcatat cctaaatatt  300
ttcggtggcg ggaccaaagt tgaggttaaa cgtacggtag cagctcccag cgtatttatt  360
tttcccccta gcgacgaaca gctgaagtct gggacagcca gtgtggtctg tctgctgaac  420
aacttctacc ctagagaggc taaagtgcag tggaaggtcg ataacgcact gcagtccgga  480
aattctcagg agagtgtgac tgaacaggac tcaaaagata gcacctattc cctgtcaagc  540
acactgactc tgagcaaggc cgactacgag aagcataaag tgtatgcttg tgaagtcacc  600
caccaggggc tgagttcacc agtcacaaaa tcattcaaca gaggggagtg c           651

SEQ ID NO: 119          moltype = AA  length = 110
FEATURE                 Location/Qualifiers
source                  1..110
                        mol_type = protein
                        note = Clone ID 26448 VL
                        organism = synthetic construct
SEQUENCE: 119
DYQMTQSPSS VSASVGDRVT ITCRASQSIG DWLAWYQQKP GKAPKLLIYE ASTLASGVPS  60
RFSGSGSGTD FTLTISSVQP EDAATYYCQQ GYGRWHILNI FGGGTKVEVK             110

SEQ ID NO: 120          moltype = AA  length = 12
FEATURE                 Location/Qualifiers
source                  1..12
                        mol_type = protein
                        note = Clone ID 26448, 26450, 27274 Chothia, Kabat, AbM,
                         IMGT CDR3
                        organism = synthetic construct
SEQUENCE: 120
QQGYGRWHIL NI                                                      12

SEQ ID NO: 121          moltype = AA  length = 11
FEATURE                 Location/Qualifiers
source                  1..11
                        mol_type = protein
                        note = Clone ID 26448 Contact CD3
                        organism = synthetic construct
SEQUENCE: 121
QQGYGRWHIL N                                                       11

SEQ ID NO: 122          moltype = AA  length = 217
FEATURE                 Location/Qualifiers
source                  1..217
                        mol_type = protein
                        note = Clone ID 26449 Full
                        organism = synthetic construct
SEQUENCE: 122
DYQMTQSPSS VSASVGDRVT ITCRASQSIW YWLAWYQQKP GKAPKLLIYE ASTLASGVPS  60
RFSGSGSGTD FTLTISSVQP EDAATYYCQQ GYGRSNVDNI FGGGTKVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 123          moltype = DNA  length = 651
FEATURE                 Location/Qualifiers
source                  1..651
                        mol_type = other DNA
                        note = Clone ID 26449 Full
                        organism = synthetic construct
SEQUENCE: 123
gactatcaaa tgacgcagtc cccgtcctcc gtttccgcct cagttggtga ccgggttaca  60
atcacttgca gagcatctca gtctatttgg tattggctgg cgtggtatca acagaagccc  120
ggcaaagccc ctaaactcct gatatacgaa gcatcaacgc ttgcttctgg agtaccctcc  180
cggttttctg ggtcaggaag cggcacggat tttaccctga ctatctcttc tgttcagcct  240
gaggatgccg caacctatta ttgccaacag gggtatggca gatcaaacgt ggataatatt  300
ttcggtggcg ggaccaaagt tgaggttaaa cgtacggtag cagctcccag cgtatttatt  360
tttcccccta gcgacgaaca gctgaagtct gggacagcca gtgtggtctg tctgctgaac  420
aacttctacc ctagagaggc taaagtgcag tggaaggtcg ataacgcact gcagtccgga  480
aattctcagg agagtgtgac tgaacaggac tcaaaagata gcacctattc cctgtcaagc  540
acactgactc tgagcaaggc cgactacgag aagcataaag tgtatgcttg tgaagtcacc  600
caccaggggc tgagttcacc agtcacaaaa tcattcaaca gaggggagtg c           651

SEQ ID NO: 124          moltype = AA  length = 110
FEATURE                 Location/Qualifiers
source                  1..110
                        mol_type = protein
                        note = Clone ID 26449 VL
                        organism = synthetic construct
SEQUENCE: 124
DYQMTQSPSS VSASVGDRVT ITCRASQSIW YWLAWYQQKP GKAPKLLIYE ASTLASGVPS  60
RFSGSGSGTD FTLTISSVQP EDAATYYCQQ GYGRSNVDNI FGGGTKVEVK             110
```

-continued

```
SEQ ID NO: 125          moltype = AA  length = 6
FEATURE                 Location/Qualifiers
source                  1..6
                        mol_type = protein
                        note = Clone ID 26449, 26450, 27274 IMGT CDR1
                        organism = synthetic construct
SEQUENCE: 125
QSIWYW                                                            6

SEQ ID NO: 126          moltype = AA  length = 11
FEATURE                 Location/Qualifiers
source                  1..11
                        mol_type = protein
                        note = Clone ID 26449, 26450, 27274 Chothia, Kabat, AbM CDR1
                        organism = synthetic construct
SEQUENCE: 126
RASQSIWYWL A                                                      11

SEQ ID NO: 127          moltype = AA  length = 7
FEATURE                 Location/Qualifiers
source                  1..7
                        mol_type = protein
                        note = Clone ID 26449, 26450, 27274 Contact CDR1
                        organism = synthetic construct
SEQUENCE: 127
WYWLAWY                                                           7

SEQ ID NO: 128          moltype = AA  length = 217
FEATURE                 Location/Qualifiers
source                  1..217
                        mol_type = protein
                        note = Clone ID 26450 Full
                        organism = synthetic construct
SEQUENCE: 128
DYQMTQSPSS VSASVGDRVT ITCRASQSIW YWLAWYQQKP GKAPKLLIYE ASTLASGVPS  60
RFSGSGSGTD FTLTISSVQP EDAATYYCQQ GYGRWHILNI FGGGTKVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 129          moltype = DNA  length = 651
FEATURE                 Location/Qualifiers
source                  1..651
                        mol_type = other DNA
                        note = Clone ID 26450 Full
                        organism = synthetic construct
SEQUENCE: 129
gattatcaga tgacacagag tccttcctca gtcagcgcat ctgtgggaga tcgggttaca  60
attacctgcc gagcatctca atcaatctgg tattggctgg cctggtacca gcaaaaacca  120
ggaaaagcac ctaaactgtt gatttatgag gccagcactc ttgctagtgg ggtcccaagt  180
aggttcagcg gcagcggttc agggacggat tttaccttga ccataagttc cgttcagcca  240
gaagacgcgg cgacctatta ttgccaacaa gggtacggta gatggcacat tttgaacata  300
ttcggtggag gtactaaggt cgaggtgaag cgtacggtag cagctcccag cgtatttatt  360
tttcccccta gcgacgaaca gctgaagtct gggacagcca gtgtggtctg tctgctgaac  420
aacttctacc ctagagaggc taaagtgcag tggaaggtcg ataacgcact gcagtccgga  480
aattctcagg agagtgtgac tgaacaggac tcaaaagata gcacctattc cctgtcaagc  540
acactgactc tgagcaaggc cgactacgag aagcataaag tgtatgcttg tgaagtcacc  600
caccaggggc tgagttcacc agtcacaaaa tcattcaaca gaggggagtg c           651

SEQ ID NO: 130          moltype = AA  length = 110
FEATURE                 Location/Qualifiers
source                  1..110
                        mol_type = protein
                        note = Clone ID 26450, 27274 VL
                        organism = synthetic construct
SEQUENCE: 130
DYQMTQSPSS VSASVGDRVT ITCRASQSIW YWLAWYQQKP GKAPKLLIYE ASTLASGVPS  60
RFSGSGSGTD FTLTISSVQP EDAATYYCQQ GYGRWHILNI FGGGTKVEVK             110

SEQ ID NO: 131          moltype = AA  length = 450
FEATURE                 Location/Qualifiers
source                  1..450
                        mol_type = protein
                        note = Clone ID 27272 Full
                        organism = synthetic construct
SEQUENCE: 131
EVQLLESGGG LVQPGGSLRL SCAVSGFSLS SYGVSWVRQA PGKGLEWIGA VNSGGSAYYA  60
DSFKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
```

-continued

```
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 132          moltype = DNA  length = 1350
FEATURE                 Location/Qualifiers
source                  1..1350
                        mol_type = other DNA
                        note = Clone ID 27272 Full
                        organism = synthetic construct
SEQUENCE: 132
gaagtgcagc tcctggagag tggaggcggc ctagtccaac ccggtggatc tctgaggctc  60
tcctgtgctg ttagtggttt ttcactctct tcctatggag tcagctgggt tagacaggca  120
cccggcaagg gcttggagtg gatcggcgct gttaattccg gcggttccgc ctactatgct  180
gactctttca aggaagaag tactatttcc cgcgacaact ctaagaacac agtgtatctc  240
caaatgaact ccctgcgtgc cgaggacacc gccgtctact actgcgcccg gagcggctct  300
ggctatccaa tggattacct ggccatctgg ggccaaggta ccctggtgac agtctcaagc  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggccgtcct acagtcctca  540
ggactctact ccctcagcag cgtggtgacc gtgccctcca gcagcttggg cacccagacc  600
tacatctgca acgtgaatca caagcccagc aacaccaagg tggacaagaa ggttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggacgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggcaaa                                   1350

SEQ ID NO: 133          moltype = AA  length = 120
FEATURE                 Location/Qualifiers
source                  1..120
                        mol_type = protein
                        note = Clone ID 27272 VH
                        organism = synthetic construct
SEQUENCE: 133
EVQLLESGGG LVQPGGSLRL SCAVSGFSLS SYGVSWVRQA PGKGLEWIGA VNSGGSAYYA  60
DSFKGRSTIS RDNSKNTVYL QMNSLRAEDT AVYYCARSGS GYPMDYLAIW GQGTLVTVSS  120

SEQ ID NO: 134          moltype = AA  length = 450
FEATURE                 Location/Qualifiers
source                  1..450
                        mol_type = protein
                        note = Clone ID 27273 Full
                        organism = synthetic construct
SEQUENCE: 134
EVQLLESGGG LVQPGGSLRL SCAVSGFSLS LYGVSWVRQA PGKGLEWIGS VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 135          moltype = DNA  length = 1350
FEATURE                 Location/Qualifiers
source                  1..1350
                        mol_type = other DNA
                        note = Clone ID 27273 Full
                        organism = synthetic construct
SEQUENCE: 135
gaggttcagc ttctcgagtc tggcggtggc ctggttcaac ctggtggtag tctccgactg  60
agctgtgctg tttcgggctt cagcctgagc ctttacggcg tgtcctgggt caggcaggct  120
ccaggcaagg gcctggagtg gatcggctcc gtgaacagcg gtggaagtgc ctactatgct  180
gattctgtga agggccgaag cacgatttct cgcgataaca gcaagaatac tgtgtatttg  240
caaatgaact ctctgcgtgc cgaggatacc gctgtgtact actgcgctcg atcggggtcc  300
ggttacccta tggattacct ggccatctgg ggtcagggta cccttgttac tgtatcctct  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggccgtcct acagtcctca  540
ggactctact ccctcagcag cgtggtgacc gtgccctcca gcagcttggg cacccagacc  600
```

```
tacatctgca acgtgaatca caagcccagc aacaccaagg tggacaagaa ggttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggacgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagagcc tctccctgtc tccgggcaaa                                   1350

SEQ ID NO: 136          moltype = AA  length = 120
FEATURE                 Location/Qualifiers
source                  1..120
                        mol_type = protein
                        note = Clone ID 27273 VH
                        organism = synthetic construct
SEQUENCE: 136
EVQLLESGGG LVQPGGSLRL SCAVSGFSLS LYGVSWVRQA PGKGLEWIGS VNSGGSAYYA  60
DSVKGRSTIS RDNSKNTVYL QMNSLRAEDT AVYYCARSGS GYPMDYLAIW GQGTLVTVSS  120

SEQ ID NO: 137          moltype = AA  length = 16
FEATURE                 Location/Qualifiers
source                  1..16
                        mol_type = protein
                        note = Clone ID 27273 Kabat CDR2
                        organism = synthetic construct
SEQUENCE: 137
SVNSGGSAYY ADSVKG                                                  16

SEQ ID NO: 138          moltype = AA  length = 12
FEATURE                 Location/Qualifiers
source                  1..12
                        mol_type = protein
                        note = Clone ID 27273 Contact CDR2
                        organism = synthetic construct
SEQUENCE: 138
WIGSVNSGGS AY                                                      12

SEQ ID NO: 139          moltype = AA  length = 9
FEATURE                 Location/Qualifiers
source                  1..9
                        mol_type = protein
                        note = Clone ID 27273 AbM CDR2
                        organism = synthetic construct
SEQUENCE: 139
SVNSGGSAY                                                          9

SEQ ID NO: 140          moltype = AA  length = 217
FEATURE                 Location/Qualifiers
source                  1..217
                        mol_type = protein
                        note = Clone ID 27274 Full
                        organism = synthetic construct
SEQUENCE: 140
DYQMTQSPSS VSASVGDRVT ITCRASQSIW YWLAWYQQKP GKAPKLLIYE ASTLASGVPS  60
RFSGSGSGTD FTLTISSVQP EDAATYYCQQ GYGRWHILNI FGGGTKVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 141          moltype = DNA  length = 651
FEATURE                 Location/Qualifiers
source                  1..651
                        mol_type = other DNA
                        note = Clone ID 27274 Full
                        organism = synthetic construct
SEQUENCE: 141
gactaccaga tgacccagag cccaagttca gtatcggcct ccgttggtga cagagtcacc  60
atcacctgcc gggccagcca atccatctgg tactggctgg cctggtatca acaaaagccg  120
ggcaaagcac ccaagctcct catctacgag gctagcacac tggcctccgg cgttccttcg  180
cgattcagtg gttccgggtc tggaacagac ttcactttga ccatttcttc tgtgcaaccc  240
gaggatgctg caacatatta ctgccaacaa ggctatggcc ggtggcacat tctgaacatc  300
tttggcggcg gaactaaggt tgaagtcaaa cgtacggtgg ctgcaccatc tgtcttcatc  360
ttcccgccat ctgatgagca gttgaaatct ggaactgcct ctgttgtgtg cctgctgaat  420
aacttctatc ccagagaggc caaagtacag tggaaggtgg ataacgccct ccaatcgggt  480
aactcccagg agagtgtcac agagcaggac agcaaggaca gcacctacag cctcagcagc  540
```

-continued

```
accctgacgc tgagcaaagc agactacgag aaacacaaag tctacgcctg cgaagtcacc  600
catcagggcc tgagctcgcc cgtcacaaag agcttcaaca ggggagagtg t           651

SEQ ID NO: 142          moltype = AA  length = 449
FEATURE                 Location/Qualifiers
source                  1..449
                        mol_type = protein
                        note = Clone ID 27275 Full
                        organism = synthetic construct
SEQUENCE: 142
EVQLLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 143          moltype = DNA  length = 1347
FEATURE                 Location/Qualifiers
source                  1..1347
                        mol_type = other DNA
                        note = Clone ID 27275 Full
                        organism = synthetic construct
SEQUENCE: 143
gaggtccagt tgctggaatc aggaggtgga ctcgtgcagc ctggggggttc cctgcgcttg  60
tcttgcgctg tcagcggttt tagcttatct tcatacggtg taagttgggt tcggcaggct  120
cctggcaaag gtctggaatg gatcggggct gtaaacagcg gggggtccgc ctactatgct  180
gattctgtta aggggaggtc caccattagc agagataatt ccaagaacac cgtttatctc  240
cagatgaact ccttgagggc ggaggacact gctgtctatt attgtgcgcg gtcaggcagc  300
ggatacccga tggactatct ggcgatctgg ggccagggaa cccttgtgac agtctcttcc  360
gctagcacta aggggccttc cgtgtttcca ctggctccct ctagtaaatc cacctctgga  420
ggcacagctg cactgggatg tctggtgaag gattacttcc ctgaaccagt cacagtgagt  480
tggaactcag gggctctgac aagtggagtc catacttttc ccgcagtgct gcagtcaagc  540
ggactgtact ccctgtcctc tgtggtcacc gtgcctagtt caagcctggg cacccagaca  600
tatatctgca acgtgaatca caagccatca aatacaaaag tcgacaagaa agtggagccc  660
aagagctgtg ataaaactca tacctgccca ccttgtccgg ctccagagct gctcggcgga  720
ccatccgtgt tcctgtttcc tccaaagcct aaagatacac tgatgattag ccgcactccc  780
gaagtcacct gtgtggtcgt ggacgtgtcc cacgaggacc ccgaagtcaa gttcaactgg  840
tacgtggacg gcgtcgaggt gcataatgcc aagactaaac caagagagga acagtacaat  900
tcaacctata gggtcgtgag cgtcctgaca gtgctgcatc aggattggct gaacggcaag  960
gagtataagt gcaaagtgtc taacaaggcc ctgcccgctc ctatcgagaa gactattagc  1020
aaggcaaaag ggcagccacg ggaaccccag gtctacactc tgccccctag cagagacgag  1080
ctgaccaaaa accaggtgtc cctgacttgt ctggtgaagg gcttttatcc tagtgatatc  1140
gctgtggagt gggaatcaaa tgggcagcca gaaaacaatt acaaaaacaac tccacccgtg  1200
ctggacagcg atgggtcctt ctttctgtat tccaaactga ctgtggacaa gtccagatgg  1260
cagcagggaa acgtcttcag ctgttccgtg atgcacgagg ccctgcacaa tcattacacc  1320
cagaagtctc tgagtctgtc acccggc                                      1347

SEQ ID NO: 144          moltype = AA  length = 217
FEATURE                 Location/Qualifiers
source                  1..217
                        mol_type = protein
                        note = Clone ID 27276 Full
                        organism = synthetic construct
SEQUENCE: 144
DYQMTQSPSS VSASVGDRVT ITCRASQSIG DWLAWYQQKP GKAPKLLIYE ASTLASGVPS  60
RFSGSGSGTD FTLTISSVQP EDAATYYCQQ GYGRSNVDNI FGGGTKVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 145          moltype = DNA  length = 651
FEATURE                 Location/Qualifiers
source                  1..651
                        mol_type = other DNA
                        note = Clone ID 27276 Full
                        organism = synthetic construct
SEQUENCE: 145
gactatcaaa tgacgcagtc cccgtcctcc gtttccgcct cagttggtga ccgggttaca  60
atcacttgca gagcatctca gtctattggt gattggctgg cgtggtatca acagaagccc  120
ggcaaagccc ctaaactcct gatatacgaa gcatcaacgc ttgcttctgg agtaccctcc  180
cggttttctg ggtcaggaag cggcacggat tttaccctga ctatctcttc tgttcagcct  240
gaggatgccg caacctatta ttgccaacag gggtatggca gatcaaacgt ggataatatt  300
ttcggtggcg ggaccaaagt tgaggttaaa cgtacggtgg cggcgcccag tgtcttcatt  360
tttcccccta gcgacgaaca gctgaagtct gggacagcca gtgtggtctg tctgctgaac  420
aacttctacc ctagagaggc taaagtgcag tggaaggtcg ataacgcact gcagtccgga  480
aattctcagg agagtgtgac tgaacaggac tcaaaagata gcacctattc cctgtcaagc  540
acactgactc tgagcaaggc cgactacgag aagcataaag tgtatgcttg tgaagtcacc  600
```

```
caccaggggc tgagttcacc agtcacaaaa tcattcaaca gaggggagtg c          651

SEQ ID NO: 146         moltype = AA  length = 329
FEATURE                Location/Qualifiers
source                 1..329
                       mol_type = protein
                       note = CH1-hinge-CH2-CH3 (IGHG1*01)
                       organism = Homo sapiens
SEQUENCE: 146
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 147         moltype = AA  length = 107
FEATURE                Location/Qualifiers
source                 1..107
                       mol_type = protein
                       note = CL (kappa) (IGKC*01)
                       organism = Homo sapiens
SEQUENCE: 147
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 148         moltype = AA  length = 329
FEATURE                Location/Qualifiers
source                 1..329
                       mol_type = protein
                       note = CH1-hinge-CH2-CH3 (HetFc-A) (IGHG1*01)
                       organism = synthetic construct
SEQUENCE: 148
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYVYPPSRDE  240
LTKNQVSLTC LVKGFYPSDI AVEWESNGQP ENNYKTTPPV LDSDGSFALV SKLTVDKSRW  300
QQGNVFSCSV MHEALHNHYT QKSLSLSPG                                   329

SEQ ID NO: 149         moltype = AA  length = 329
FEATURE                Location/Qualifiers
source                 1..329
                       mol_type = protein
                       note = CH1-hinge-CH2-CH3 (HetFc-B) (IGHG1*01)
                       organism = synthetic construct
SEQUENCE: 149
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYVLPPSRDE  240
LTKNQVSLLC LVKGFYPSDI AVEWESNGQP ENNYLTWPPV LDSDGSFFLY SKLTVDKSRW  300
QQGNVFSCSV MHEALHNHYT QKSLSLSPG                                   329

SEQ ID NO: 150         moltype = AA  length = 23
FEATURE                Location/Qualifiers
source                 1..23
                       mol_type = protein
                       note = signal sequence
                       organism = synthetic construct
SEQUENCE: 150
MRPTWAWWLF LVLLLALWAP ARG                                         23

SEQ ID NO: 151         moltype = AA  length = 9
FEATURE                Location/Qualifiers
source                 1..9
                       mol_type = protein
                       note = Folate receptor alpha peptide
                       organism = synthetic construct
SEQUENCE: 151
WWEDCRTSY                                                         9

SEQ ID NO: 152         moltype = AA  length = 8
FEATURE                Location/Qualifiers
source                 1..8
                       mol_type = protein
                       note = Folate receptor alpha peptide
                       organism = synthetic construct
SEQUENCE: 152
```

```
WEDCRTSY                                                    8

SEQ ID NO: 153          moltype = AA  length = 24
FEATURE                 Location/Qualifiers
source                  1..24
                        mol_type = protein
                        note = Folate receptor alpha peptide
                        organism = synthetic construct
SEQUENCE: 153
WEDCRTSYTC KSNWHKGWNW TSGF                                  24

SEQ ID NO: 154          moltype = AA  length = 6
FEATURE                 Location/Qualifiers
source                  1..6
                        mol_type = protein
                        note = epitope sequence
                        organism = synthetic construct
SEQUENCE: 154
EDRTSY                                                      6

SEQ ID NO: 155          moltype = AA  length = 120
FEATURE                 Location/Qualifiers
source                  1..120
                        mol_type = protein
                        note = Rabbit heavy chain variable domain - framework
                         (IGHV3-23*01)
                        organism = synthetic construct
SEQUENCE: 155
EVQLLESGGG LVQPGGSLRL SCAASGFSLS SYGVSWVRQA PGKGLEWVSA VNSGGSAYYA  60
DSVKGRFTIS RDNSKNTLYL QMNSLRAEDT AVYYCAKSGS GYPMDYLAIW GQGTLVTVSS  120

SEQ ID NO: 156          moltype = AA  length = 110
FEATURE                 Location/Qualifiers
source                  1..110
                        mol_type = protein
                        note = Rabbit light chain variable domain CDRs of chimeric
                         antibody v23924 ported onto a human VL framework
                         (IGKVI-39*01)
                        organism = synthetic construct
SEQUENCE: 156
DIQMTQSPSS LSASVGDRVT ITCQASQSIG DWLAWYQQKP GKAPKLLIYE ASTLASGVPS  60
RFSGSGSGTD FTLTISSLQP EDFATYYCQQ GYGRSNVDNI FGGGTKVEIK           110

SEQ ID NO: 157          moltype = AA  length = 450
FEATURE                 Location/Qualifiers
source                  1..450
                        mol_type = protein
                        note = Clone ID 27275 Full + C-terminal Lys
                        organism = synthetic construct
SEQUENCE: 157
EVQLLESGGG LVQPGGSLRL SCAVSGFSLS SYGVSWVRQA PGKGLEWIGA VNSGGSAYYA  60
DSVKGRSTIS RDNSKNTVYL QMNSLRAEDT AVYYCARSGS GYPMDYLAIW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                450

SEQ ID NO: 158          moltype = AA  length = 4
FEATURE                 Location/Qualifiers
source                  1..4
                        mol_type = protein
                        note = linker
                        organism = synthetic construct
SEQUENCE: 158
ALAL                                                        4

SEQ ID NO: 159          moltype = AA  length = 4
FEATURE                 Location/Qualifiers
source                  1..4
                        mol_type = protein
                        note = linker
                        organism = synthetic construct
SEQUENCE: 159
GFLG                                                        4

SEQ ID NO: 160          moltype = AA  length = 4
FEATURE                 Location/Qualifiers
```

-continued

| | | |
|---|---|---|
| source | 1..4<br>mol_type = protein<br>note = linker<br>organism = synthetic construct | |
| SEQUENCE: 160 | | |
| GGFG | | 4 |
| SEQ ID NO: 161 | moltype = AA length = 4 | |
| FEATURE | Location/Qualifiers | |
| source | 1..4<br>mol_type = protein<br>note = linker<br>organism = synthetic construct | |
| SEQUENCE: 161 | | |
| GFGG | | 4 |

We claim:

1. An antibody-drug conjugate having a structure:

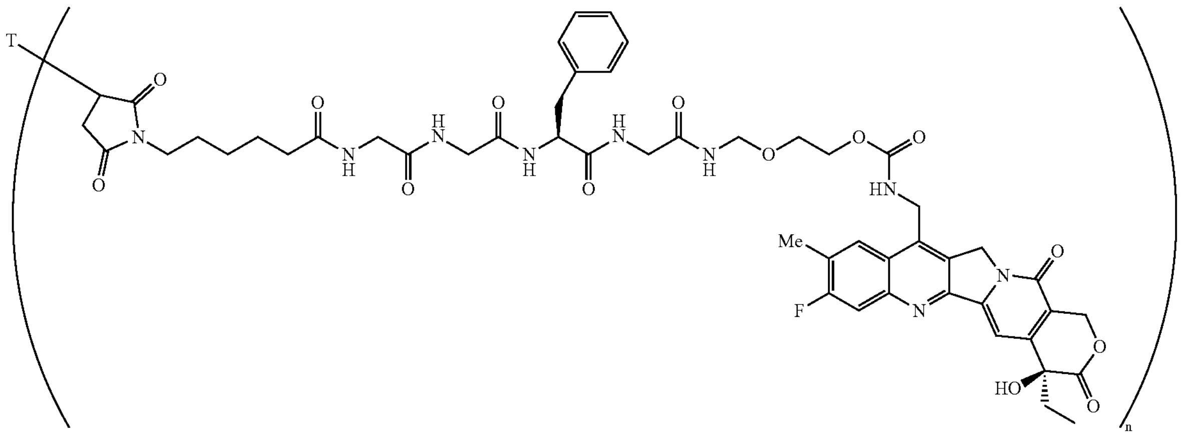

, wherein:

T is an anti-folate receptor alpha (anti-FRα) antibody construct comprising an antigen-binding domain operably linked to an IgG Fc region, the antigen-binding domain comprising three heavy chain complementarity determining regions (CDRs) (HCDR1, HCDR2, and HCDR3) and three light chain CDRs (LCDR1, LCDR2, and LCDR3), wherein:

(i) the HCDR1 amino acid sequence comprises a sequence as set forth in any one of SEQ ID NOs: 20, 23, 26, 28 or 31; the HCDR2 amino acid sequence comprises a sequence as set forth in any one of SEQ ID NOs: 21, 24, 29, 32 or 51, and the HCDR3 amino acid sequence comprises a sequence as set forth in any one of SEQ ID NOs: 22, 25 or 30, and (ii) the LCDR1 amino acid sequence comprises a sequence as set forth in any one of SEQ ID NOs: 40, 45 or 65; the LCDR2 amino acid sequence comprises a sequence as set forth in any one of SEQ ID NOs: 41, 44 or 46, and the LCDR3 amino acid sequence comprises a sequence as set forth in any one of SEQ ID NOs: 42 or 47, and wherein n is between about 4 and about 8.

2. The antibody-drug conjugate according to claim 1, wherein the antigen-binding domain comprises:

(i) the HCDR1 amino acid sequence comprising a sequence as set forth in SEQ ID NO: 20; the HCDR2 amino acid sequence comprising a sequence as set forth in SEQ ID NO: 21, and the HCDR3 amino acid sequence comprising a sequence as set forth in SEQ ID NOs: 22, and (ii) the LCDR1 amino acid sequence comprising a sequence as set forth in SEQ ID NO: 40; the LCDR2 amino acid sequence comprising a sequence as set forth in SEQ ID NO: 41, and the LCDR3 amino acid sequence comprising a sequence as set forth in SEQ ID NO: 42.

3. The antibody-drug conjugate according to claim 1, wherein the antigen-binding domain comprises:

(i) the HCDR1 amino acid sequence comprising a sequence as set forth in SEQ ID NO: 26; the HCDR2 amino acid sequence comprising a sequence as set forth in SEQ ID NO: 51, and the HCDR3 amino acid sequence comprising a sequence as set forth in SEQ ID NOs: 25, and (ii) the LCDR1 amino acid sequence comprising a sequence as set forth in SEQ ID NO: 65; the LCDR2 amino acid sequence comprising a sequence as set forth in SEQ ID NO: 44, and the LCDR3 amino acid sequence comprising a sequence as set forth in SEQ ID NO: 42.

4. The antibody-drug conjugate according to claim 1, wherein the antigen-binding domain comprises:

(i) the HCDR1 amino acid sequence comprising a sequence as set forth in SEQ ID NO: 23; the HCDR2 amino acid sequence comprising a sequence as set forth in SEQ ID NO: 24, and the HCDR3 amino acid sequence comprising a sequence as set forth in SEQ ID NOs: 25, and (ii) the LCDR1 amino acid sequence comprising a sequence as set forth in SEQ ID NO: 65; the LCDR2 amino acid sequence comprising a sequence as set forth in SEQ ID NO: 44, and the LCDR3 amino acid sequence comprising a sequence as set forth in SEQ ID NO: 42.

5. The antibody-drug conjugate according to claim 1, wherein the antigen-binding domain comprises:

(i) the HCDR1 amino acid sequence comprising a sequence as set forth in SEQ ID NO: 31; the HCDR2 amino acid sequence comprising a sequence as set forth in SEQ ID NO: 32, and the HCDR3 amino acid sequence comprising a sequence as set forth in SEQ ID NOs: 25, and (ii) the LCDR1 amino acid sequence comprising a sequence as set forth in SEQ ID NO: 65; the LCDR2 amino acid sequence comprising a sequence as set forth in SEQ ID NO: 44, and the LCDR3 amino acid sequence comprising a sequence as set forth in SEQ ID NO: 42.

6. The antibody-drug conjugate according to claim 1, wherein the antigen-binding domain comprises:

(i) the HCDR1 amino acid sequence comprising a sequence as set forth in SEQ ID NO: 28; the HCDR2 amino acid sequence comprising a sequence as set forth in SEQ ID NO: 29, and the HCDR3 amino acid sequence comprising a sequence as set forth in SEQ ID NOs: 30, and (ii) the LCDR1 amino acid sequence comprising a sequence as set forth in SEQ ID NO: 45; the LCDR2 amino acid sequence comprising a sequence as set forth in SEQ ID NO: 46, and the LCDR3 amino acid sequence comprising a sequence as set forth in SEQ ID NO: 47.

12. The antibody-drug conjugate according to claim 6, wherein n is about 8.

13. The antibody-drug conjugate according to claim 1, wherein the antigen-binding domain comprises a light chain variable domain (VL) amino acid sequence comprising a sequence as set forth in SEQ ID NO: 64 and a heavy chain variable domain (VH) amino acid sequence comprising a sequence as set forth in SEQ ID NO: 50.

14. The antibody-drug conjugate according to claim 1, wherein the antigen-binding domain comprises a light chain variable domain (VL) amino acid sequence consisting of a sequence as set forth in SEQ ID NO: 64 and a heavy chain variable domain (VH) amino acid sequence consisting of a sequence as set forth in SEQ ID NO: 50.

15. The antibody-drug conjugate according to claim 1, wherein the IgG Fc region is an IgG1 Fc region or a human IgG1 Fc region.

16. The antibody-drug conjugate according to claim 13, wherein the IgG Fc region is an IgG1 Fc region or a human IgG1 Fc region.

17. The antibody-drug conjugate according to claim 1, wherein the anti-FRαantibody construct comprises two heavy chains and two light chains, wherein each heavy chain comprises an amino acid sequence as set forth in SEQ ID NO: 142 or 157 and each light chain comprises an amino acid sequence as set forth in SEQ ID NO: 62.

18. The antibody-drug conjugate according to claim 1, wherein the anti-FRαantibody construct comprises two heavy chains and two light chains, wherein each heavy chain comprises an amino acid sequence as set forth in SEQ ID NO: 142 and each light chain comprises an amino acid sequence as set forth in SEQ ID NO: 62.

19. The antibody-drug conjugate according to claim 18, wherein n is about 8.

20. An antibody-drug conjugate having a structure:

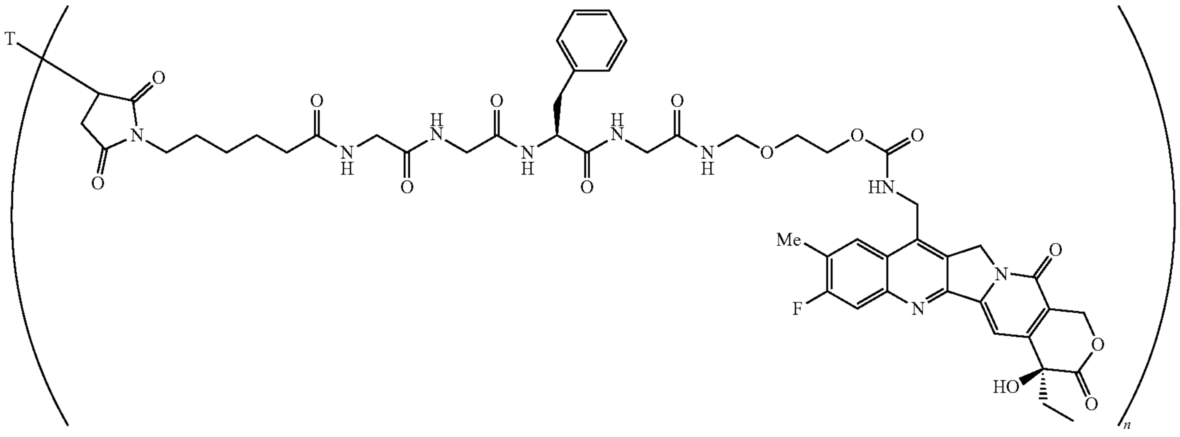

,

7. The antibody-drug conjugate according to claim 1, wherein n is about 8.

8. The antibody-drug conjugate according to claim 2, wherein n is about 8.

9. The antibody-drug conjugate according to claim 3, wherein n is about 8.

10. The antibody-drug conjugate according to claim 4, wherein n is about 8.

11. The antibody-drug conjugate according to claim 5, wherein n is about 8.

wherein:

T is an anti-folate receptor alpha (anti-FRα) antibody construct comprising two antigen-binding domains operably linked to an IgG Fc region, each of the antigen-binding domains comprising a light chain variable domain (VL) amino acid sequence comprising a sequence as set forth in SEQ ID NO: 64 and a heavy chain variable domain (VH) amino acid sequence comprising a sequence as set forth in SEQ ID NO: 50, wherein the IgG Fc region is a human IgG1 Fc region, and wherein n is about 8.

21. The antibody-drug conjugate according to claim 20, wherein the anti-FRαantibody construct comprises two heavy chains and two light chains, wherein each heavy chain comprises an amino acid sequence as set forth in SEQ ID NO: 142 or 157 and each light chain comprises an amino acid sequence as set forth in SEQ ID NO: 62.

22. The antibody-drug conjugate according to claim 20, wherein the anti-FRα antibody construct comprises two heavy chains and two light chains, wherein each heavy chain comprises an amino acid sequence as set forth in SEQ ID NO: 142 and each light chain comprises an amino acid sequence as set forth in SEQ ID NO: 62.

23. A pharmaceutical composition comprising an antibody-drug conjugate according to claim 1, and a pharmaceutically acceptable carrier or diluent.

24. A pharmaceutical composition comprising an antibody-drug conjugate according to claim 20, and a pharmaceutically acceptable carrier or diluent.

25. A pharmaceutical composition comprising an antibody-drug conjugate according to claim 22, and a pharmaceutically acceptable carrier or diluent.

26. The antibody-drug conjugate according to claim 1, wherein the anti-FRαantibody construct comprises a second antigen-binding domain operably linked to the IgG Fc region, the second antigen-binding domain comprising three heavy chain complementarity determining regions (CDRs) (HCDR1, HCDR2, and HCDR3) and three light chain CDRs (LCDR1, LCDR2, and LCDR3), wherein:

(i) the HCDR1 amino acid sequence comprises a sequence as set forth in any one of SEQ ID NOs: 20, 23, 26, 28 or 31; the HCDR2 amino acid sequence comprises a sequence as set forth in any one of SEQ ID NOs: 21, 24, 29, 32 or 51, and the HCDR3 amino acid sequence comprises a sequence as set forth in any one of SEQ ID NOs: 22, 25 or 30, and (ii) the LCDR1 amino acid sequence comprises a sequence as set forth in any one of SEQ ID NOs: 40, 45 or 65; the LCDR2 amino acid sequence comprises a sequence as set forth in any one of SEQ ID NOs: 41, 44 or 46, and the LCDR3 amino acid sequence comprises a sequence as set forth in any one of SEQ ID NOs: 42 or 47.

27. The antibody-drug conjugate according to claim 26, wherein the second antigen-binding domain comprises a light chain variable domain (VL) amino acid sequence comprising a sequence as set forth in SEQ ID NO: 64 and a heavy chain variable domain (VH) amino acid sequence comprising a sequence as set forth in SEQ ID NO: 50.

28. The antibody-drug conjugate according to claim 26, wherein the second antigen-binding domain comprises a light chain variable domain (VL) amino acid sequence consisting of a sequence as set forth in SEQ ID NO: 64 and a heavy chain variable domain (VH) amino acid sequence consisting of a sequence as set forth in SEQ ID NO: 50.

29. The antibody-drug conjugate according to claim 26, wherein the IgG Fc is a human IgG1 Fc.

30. The antibody-drug conjugate according to claim 26, wherein n is about 8.

* * * * *